(12) United States Patent
Gore et al.

(10) Patent No.: US 12,343,317 B2
(45) Date of Patent: Jul. 1, 2025

(54) COMPOSITIONS AND METHODS FOR TREATING BLEEDING AND BLEEDING DISORDERS

(71) Applicant: YewSavin, Inc., Fort Collins, CO (US)

(72) Inventors: Makarand Prabhakar Gore, Fort Collins, CO (US); Ashay Makarand Gore, Boulder, CO (US)

(73) Assignee: YewSavin, Inc., Fort Collins, CO (US)

( * ) Notice: Subject to any disclaimer, the term of this patent is extended or adjusted under 35 U.S.C. 154(b) by 0 days.

(21) Appl. No.: 17/983,844

(22) Filed: Nov. 9, 2022

(65) Prior Publication Data

US 2023/0190679 A1 Jun. 22, 2023

Related U.S. Application Data

(60) Provisional application No. 63/277,508, filed on Nov. 9, 2021.

(51) Int. Cl.
*A61K 31/12* (2006.01)
*A61P 7/04* (2006.01)

(52) U.S. Cl.
CPC .............. *A61K 31/12* (2013.01); *A61P 7/04* (2018.01)

(58) Field of Classification Search
CPC .................. A61K 31/12; A61P 7/04
See application file for complete search history.

(56) References Cited

U.S. PATENT DOCUMENTS

| | | |
|---|---|---|
| 2006/0276393 A1 | 12/2006 | Milburn et al. |
| 2007/0254859 A1* | 11/2007 | Wempe ................ A61K 31/352 540/114 |
| 2008/0188400 A1 | 8/2008 | Ropke et al. |
| 2014/0030247 A1* | 1/2014 | Madison .............. C12N 9/6432 435/320.1 |
| 2016/0176892 A1 | 6/2016 | Huang et al. |
| 2022/0347341 A1 | 11/2022 | Dowling et al. |
| 2023/0190679 A1 | 6/2023 | Gore et al. |

FOREIGN PATENT DOCUMENTS

| | | |
|---|---|---|
| CN | 115381899 A | 11/2022 |
| KR | 2002-0004236 A | 1/2002 |
| KR | 2002004236 | * 3/2003 |
| KR | 2015123477 A | 11/2015 |

OTHER PUBLICATIONS

Jackson et. al. (Blood (2007) 109:5067-5095) (Year: 2007).*
Gomes et. al. (The Netherlands Journal of Medicine (2003) 61:185-192) (Year: 2003).*
International Search Report and Written Opinion dated Mar. 30, 2023 issued in co-owned International Appl. No. PCT/US2022/049408.
Ohkura et al., Anti-platelet effects of chalconas from Angelica keiskel Koldzumi (Ashitaba) in vivo, Pharmazie, vol. 71, 2016 [retrieved on Feb. 23, 2023]. Retrieved from the internet: <URL: https://pubmed.ncbi.nlm.nih.gov/28441970/>, pp. 651-654.
Zeng et al., Isoliquiritigenin alleviates early brain injury after experimental intracerebral hemorrhage vis suppressing ROS- and/or NF-κβ-mediated NLRP3 inflammasome activation by promoting Nrf2 antioxidant pathway, Journal of Neuroinflammation, vol. 14, No. 119, Jun. 13, 2017 [retrieved on Feb. 23, 2023]. Retrieved from the internet: <URL: https://www.ncbi.nlm.nih.gov/pmc/articles/PMC5470182/>, pp. 1-19.
International Search Report and Written Opinion dated Aug. 13, 2024 issued in co-owned International Appl. No. PCT/US2024/028245.
Ohkura et al., Anti-platelet effects of chalconas from Angelica kelskel Koldzumi (Ashitaba) in vivo, Pharmazie, vol. 71, 2016 [retrieved on Feb. 23, 2023]. Retrieved from the internet: <URL: https://pubmed.ncbi.nlm.nih.gov/29441970/>. pp. 651-654.

* cited by examiner

*Primary Examiner* — Marcos L Sznaidman
(74) *Attorney, Agent, or Firm* — Toering Patents PLLC

(57) ABSTRACT

Various embodiments of the invention utilize chalcones to treat blood, bleeding, and/or bleeding disorders. As described herein, chalcones significantly reduce blood clotting time in normal/hemophilic blood and normal/hemophilic animal models. As also described herein, chalcones reduce blood clotting time and increase blood clotting efficiency without any apparent risk of immunogenicity or unwanted blood clots. As also described herein, chalcones reduce the inhibitory activity of antithrombin on thrombin-driven blood clotting, thereby increasing the effectiveness of the thrombin mechanism in clotting blood.

11 Claims, 21 Drawing Sheets

Chalcone Structure

Pharmacophore

2'-hydroxychalcone Structure

R or R' = -OCH3 or OH

R = Sugar (saccharide)

R = disaccharide

Rutoside

CAS 37620-38-5

Bakuchalcone

Xanthohumol

Flavokawain A

PubChem CID 6526201

PubChem CID 6123336

Sofalcone

Metochalcone

Isoliquiritigenin

Hesperidin Methyl Chalcone

COMPOSITIONS AND METHODS FOR TREATING BLEEDING AND BLEEDING DISORDERS

CROSS-REFERENCE TO RELATED APPLICATIONS

This application claims priority to U.S. Provisional Application No. 63/277,508, titled "Compositions and Methods for Treating Bleeding and Bleeding Disorders," filed on Nov. 9, 2021, which is incorporated herein by reference.

FIELD OF THE INVENTION

The invention is generally related to treating bleeding and bleeding disorders including hemophilia, and more specifically, to compositions and methods for treating bleeding and bleeding disorders, using compounds.

BACKGROUND OF THE INVENTION

Hemophilia A, B, C, and von Willebrand disease are bleeding disorders generally, and more particularly, blood clotting disorders, caused by the lack of, or insufficient activity of, clotting factor proteins involved in blood clotting mechanisms. Blood clotting, or "hemostasis," is initiated by two different pathways, an "intrinsic pathway" and an "extrinsic pathway," that converge downstream to form a "common pathway" as illustrated in FIG. 1. Within each of these pathways, the mechanisms of blood clotting involve a series of cascading reactions of various factor proteins, culminating in the formation of a stable fibrin clot at the end of the "common pathway." These mechanisms are regulated by anti-clotting proteins such as antithrombin, tissue factor pathway inhibitor ("TFPI"), and Protein C. In order for the body to effectively respond to bleeding, the overall process to stop blood from flowing (i.e., "hemostasis") and prevent uncontrolled bleeding from damaged blood vessels (i.e., "hemorrhage") must remain in balance with preventing the formation of unnecessary blood clots in healthy blood vessels (i.e., "thrombosis"). Excessive bleeding may occur in conditions such as thrombocytopenia, a disorder induced due to use of heparin during major surgery, dialysis or transfusion. Even in patients without a bleeding or blood clotting disorder, the control of blood clotting by use of medication in case of severe bleeding incidents such as accidents, wounds, other traumatic injuries, surgeries, and even viral hemorrhagic fevers may be necessary.

Existing therapies for treating blood clotting disorders can broadly be categorized into: 1) recombinant factor protein and factor protein concentrate therapies; 2) a bispecific antibody therapy; 3) experimental gene therapies; and 4) a small molecule therapy for select cases. Recombinant factor proteins and factor protein concentrates, such as Factor VIII ("FVIII") replacements for hemophilia A, Factor IX ("FIX") replacements for hemophilia B, Factor XI ("FXI") replacements for hemophilia C, and von Willebrand factor ("vWF") replacements for von Willebrand disease serve to emulate the role of missing or malfunctioning factor proteins in the body. These factor protein therapies are administered via injection either as prophylactics or during a bleeding episode. However, factor protein therapies can be rendered ineffective by the body's immune response after repeated administration, due to antibodies generated by the body to destroy these foreign proteins.

More recently, non-factor protein therapies such as the bispecific antibody emicizumab (marketed as HEMLIBRA®) have been developed to indirectly address the deficiencies of blood clotting disorders themselves. These non-factor protein therapies are also administered via injection prophylactically or at the time of injury, and boost the effectiveness of blood clotting mechanisms to compensate for the missing or malfunctioning proteins. However, these non-factor therapies can increase the risk of unwanted blood clotting, can be dangerous to use concurrently with other therapies, and just like factor protein therapies, can also be rendered ineffective by the body's immune response after repeated administration.

Gene therapies, which are currently pending U.S. Food and Drug Administration ("FDA") approval, attempt to replace the existing gene that is responsible for the missing or malfunctioning factor protein by delivering a new, working gene through a viral vector. While these therapies show promise, the full extent of their effectiveness is still being investigated, with several cases of severe side effects having already been observed in clinical trails.

A single small molecule therapy has also been approved to treat the minority of patients with mild cases of hemophilia A and von Willebrand disease. Desmopressin (marketed as DDAVP®), which is administered via injection, causes the release of von Willebrand's antigen, the protein that carries FVIII, from the platelets and the cells that line the blood vessels. This increase in von Willebrand's antigen and FVIII then helps to promote blood clotting. However, desmopressin's effectiveness is drastically reduced in moderate and severe cases of hemophilia A, with these types of cases comprising the majority of patients.

In addition to the specific concerns with all four types of existing therapies, these therapies need to be administered via injection which may require the assistance of a medical professional, thereby decreasing a patient's likelihood to comply with treatment.

Traditional medicines, such as plants and their extracts, are also known to enhance blood clotting. For example, the traditional Chinese herbal medicine *Pollen Typhae* contains a complex mixture of natural products and has historically been used to treat hemorrhagic disease. Traditional medicines, however, are not generally accepted as formal therapies due to their undefined compositions, unknown active components, unknown mechanisms of action, lack of standardization, and/or lack of systematic clinical studies.

Due to the aforementioned deficiencies in current therapies, there exists a need for an improved therapy for treating bleeding and bleeding disorders. Thus, the introduction of a therapy that is non-immunogenic, a small molecule, and/or carries a reduced risk of unwanted blood clotting will substantially increase the current standard of care for patients of bleeding and bleeding disorders.

SUMMARY OF THE INVENTION

Studies on naturally derived treatments for hemophilia have used separation and bioassay-guided fractionation methods as well as in vitro and in vivo assays. Furthermore, effective compounds have been prepared by synthetic methods, based on a molecular structural feature (i.e., "pharmacophore") found to be responsible for biological activity. A set of plant extracts known in traditional and modern literature for their blood clotting properties were investigated as potential bleeding and wound treatments. Extracts studied included those from *Chromolaena odorata, Eriodictyon californicum, Blumea balsamifera, Tridax procumbens, Achillea mollefolium, Oxytropis falcata,* and *Typha elephantina*. During the bioassay-guided fractionation process, blood clotting time was used as a screening parameter for active compounds, and a particular class of compounds known as "chalcones" (defined below) were found to promote blood clotting. Experiments using natural and synthetic single pure compounds demonstrated that chalcones significantly reduced blood clotting time in regular/hemophilic blood and in regular/hemophilic animal models. Furthermore, chalcones used as oral prophylactic agents in these animal models were found to to reduce blood clotting time and increase blood clotting efficiency without any apparent risks of immunogenicity or unwanted blood clots. Without subscribing to any particular theory, some experiments suggest that one of the mechanisms by which chalcones work is to reduce the inhibitory activity of antithrombin on thrombin-driven blood clotting, thereby increasing the effectiveness of the thrombin mechanism in blood clotting. This use of chalcones to treat blood clotting disorders, or to treat bleeding in any situation, and the discovery described herein that chalcones enhance thrombin generation and enhance blood clotting, and the mechanism by which chalcones enhance blood clotting were unknown prior to the invention.

In some aspects of invention, compounds of the general structure chalcones are identified as the pharmacophore of compounds and/or structural classes for reducing blood clotting time.

In some aspects of invention, compounds having the general structure of chalcones are identified as the core compounds and/or structural classes for increasing blood clotting efficiency by, for example, bringing clotting times within +/−20% of normal range for a given vertebrate model, and in some cases, within +/−50% of normal range for a given vertebrate model.

In some aspects of invention, compounds having the general structure of chalcones are provided to increase the effect of thrombin to reduce blood clotting time and/or increase blood clotting efficiency.

In some aspects of invention, chalcones are provided as an orally active compound(s) and/or structural class(es) to treat blood clotting disorders such as hemophilia and von Willebrand disease.

In some aspects of invention, chalcones are provided as a compound(s) and/or structural class(es) to treat post-surgical bleeding, particularly to reduce the effect of antithrombin, thereby increasing the effect of thrombin to reduce blood clotting time and/or increase blood clotting efficiency. For example, various invasive surgical procedures such as dialysis, open heart surgery, transplants, etc., use heparin treatment before, during, and after surgery (i.e., "perioperative") to avoid blood clotting from exposure to surfaces. The management of anticoagulation in patients undergoing such surgical procedures is challenging, since interrupting anticoagulation for a procedure transiently increases the risk of thromboembolism. At the same time, surgery and invasive procedures have associated bleeding risks that are increased by the anticoagulant(s) administered for thromboembolism prevention. If the patient bleeds from the procedure, their anticoagulant(s) may need to be discontinued for a longer period, resulting in a longer period of increased thromboembolic risk. A balance between reducing the risk of thromboembolism and preventing excessive bleeding may be reached in accordance with various aspects of the invention.

In some aspects of invention, chalcones are provided as a compound(s) and/or structural class(es) to treat bleeding during menstruation.

In some aspects of invention, chalcones are provided as a compound(s) and/or structural class(es) to treat bleeding during or after pregnancy.

In some aspects of invention, chalcones are provided as a compound(s) and/or structural class(es) to treat bleeding of non-compressible wounds.

In some aspects of invention, chalcones are provided as a compound(s) and/or structural class(es) to treat peptic ulcers.

In some aspects of invention, the method of contacting blood with chalcones is used to accelerate clotting in diseased (e.g., factor deficient) blood.

In some aspects of invention, the method of contacting blood with chalcones is used to accelerate clotting in healthy blood, including, for example, but not limited to, accidental or military wounds.

In some aspects of invention, the method of contacting blood with chalcones is used to induce clotting in diseased (e.g., viral hemorrhagic fever) blood.

In some aspects of invention, the method of contacting blood with chalcones is used to induce clotting in blood having an anticoagulant(s) and/or an anti-clotting agent(s) disposed therein.

In some aspects of invention, the method of contacting blood with chalcones is used to address viral hemorrhagic fever, and accompanying bleeding.

In some aspects of invention, the method of contacting blood with chalcones comprises intravenously administering chalcones to a patient. In some aspects of invention, the method of contacting blood with chalcones comprises intramuscularly administering chalcones to a patient. In some aspects of invention, the method of contacting blood with chalcones comprises subcutaneously administering chalcones to a patient. In some aspects of invention, the method of contacting blood with chalcones comprises orally administering chalcones to a patient, including, but not limited to controlled release capsules. In some aspects of invention, the method of contacting blood with chalcones comprises nasally administering chalcones to a patient, including, but not limited to, via a nasal spray. In some aspects of invention, the method of contacting blood with chalcones comprises introducing chalcones by topical application at a patient wound site, including, but not limited to, via a chalcone-impregnated dressing (e.g., bandages, gauze, etc.). In some aspects of invention, the method of contacting blood with chalcones comprises introducing chalcones topically at a patient wound site, including, but not limited to, via a chalcone spray, a chalcone liquid, a chalcone gel, a chalcone foam, a chalcone-impregnated dressing (i.e., bandages, gauze, etc.), or other topical applications. In some aspects of invention, the method of contacting blood with chalcones comprises transdermally administering chalcones to a skin surface of a patient.

In some aspects of invention, a method for treating bleeding disorders comprises administering a therapeutically effective amount of a composition comprising a chalcone to a subject in need thereof. In some aspects of invention, a method for treating bleeding disorders comprises administering a therapeutically effective amount of a composition comprising a chalcone to blood. In some aspects of invention, a method for treating bleeding comprises administering a therapeutically effective amount of a composition comprising a chalcone to a subject in need thereof. In some aspects of invention, a method for treating bleeding comprises administering a therapeutically effective amount of a composition comprising a chalcone to blood. In some aspects of invention, a method for treating vertebrate blood comprises administering a therapeutically effective amount of a composition comprising a chalcone to the blood.

In any of the aspects of the invention of the prior paragraph, wherein administering the therapeutically effective amount of the composition comprises prophylacticly administering the therapeutically effective amount of the chalcone composition. In any of the aspects of the invention of the prior paragraph, wherein the chalcone comprises a chalcone having the pharmacophore illustrated in FIG. 2B.

In any of the aspects of the invention of the prior paragraph, wherein the chalcone comprises a chalcone having a chalcone structure illustrated in FIG. 2A.

In any of the aspects of the invention of the prior paragraph, wherein the chalcone comprises a saccharide appendix. In any of the aspects of the invention of the prior paragraph, wherein the chalcone comprises a hydroxy appendix. In any of the aspects of the invention of the prior paragraph, wherein the chalcone comprises sofalcone. In any of the aspects of the invention of the prior paragraph, wherein the chalcone comprises metochalcone. In any of the aspects of the invention of the prior paragraph, wherein the chalcone comprises hesperidin methyl chalcone. In any of the aspects of the invention of the prior paragraph, wherein the chalcone comprises 1-(6-hydroxy-2,3,4-trimethoxyphenyl)-3-(4-hydroxy-phenyl)prop-2-en-1-one. In any of the aspects of the invention of the prior paragraph, wherein the chalcone comprises flavokawain A. In any of the aspects of the invention of the prior paragraph, wherein the chalcone comprises isoliquiritigenin. In any of the aspects of the invention of the prior paragraph, wherein the chalcone comprises naringenin chalcone. In any of the aspects of the invention of the prior paragraph, wherein the chalcone comprises 3-(1,3-benzodioxol-5-yl)-1-phenyl-2-propen-1-one. In any of the aspects of the invention of the prior paragraph, the administering of a chalcone comprises administering the chalcone to accelerate blood clotting. In any of the aspects of the invention of the prior paragraph, the administering of a chalcone comprises administering the chalcone to accelerate blood clotting. In any of the aspects of the invention of the prior paragraph, the administering of a chalcone comprises administering the chalcone to increase thrombin generation. In any of the aspects of the invention of the prior paragraph, the administering of a chalcone comprises administering the chalcone to enhance blood clotting. In any of the aspects of the invention of the prior paragraph, wherein at least two of the R' groups are hydrogen, and at least two of the R groups are hydrogen, and the chalcone has at least one carbohydrate group. In any of the aspects of the invention of the prior paragraph, wherein at least two of the R groups are hydrogen, and at least two of the R' groups are connected by a heteroatom(s). In any of the aspects of the invention of the prior paragraph, wherein at least two of the R' groups are hydrogen, at least two of the R groups are hydrogen, and at least one of the R' groups are connected by a heteroatom(s). In any of the aspects of the invention of the prior paragraph, wherein at least two of the R' groups are hydrogen, at least two of the R groups are hydrogen and at least one of the R groups or the R' groups is connected by a heteroatom(s). In any of the aspects of the invention of the prior paragraph, wherein at least two of the R' groups are hydrogen, and at least two of the R groups are hydrogen. In any of the aspects of the invention of the prior paragraph, wherein the chalcone comprises a prenyl group. In any of the aspects of the invention of the prior paragraph, wherein the chalcone comprises an isoprenyl group. In any of the aspects of the invention of the prior paragraph, wherein at least one of the R groups or one of the R' groups is a heteroatom connected group. In any of the aspects of the invention of the prior paragraph, wherein at least one of the R groups and one of the R' groups is an oxygen connected group. In any of the aspects of the invention of the prior paragraph, wherein at least one of the R groups or the R' groups is OH. In any of the aspects of the invention of the prior paragraph, wherein at least one of the R groups or the R' groups is a methoxy group. In any of the aspects of the invention of the prior paragraph, wherein at least one of the R groups or the R' groups is an alkyl group.

In any of the aspects of the invention, wherein the bleeding comprises menstrual bleeding. In any of the aspects of the invention, wherein the bleeding comprises bleeding associated with pregnancy. In any of the aspects of the invention, wherein the bleeding comprises bleeding associated with non-compressible wounds. In any of the aspects of the invention, wherein the bleeding comprises bleeding associated with peptic ulcers. In any of the aspects of the invention, wherein the bleeding comprises bleeding associated with viral hemorrhagic fever.

In any of the aspects of the invention, wherein the blood is diseased blood. In any of the aspects of the invention, wherein the blood is factor deficient blood. In any of the aspects of the invention, wherein the blood is healthy blood. In any of the aspects of the invention, wherein the blood comprises an anticoagulant(s) and/or anti-clotting agents.

These and other features of the invention are described in detail below.

DETAILED DESCRIPTION

Various embodiments of the invention utilize chalcones to treat bleeding, including, but not limited to, blood clotting disorders. As described below, chalcones significantly reduced clotting time of both hemophilic and regular blood in disease carrying and healthy animal models, respectively. As also described below, chalcones used as oral prophylactic agents reduced clotting time and increased clotting efficiency without any apparent immunogenicity or risk of unwanted blood clots. Experiments described below demonstrate that chalcones reduce the inhibitory activity of antithrombin on thrombin-driven blood clotting, thereby increasing the effectiveness of the thrombin mechanism in clotting blood. The discovery that chalcones act as coagulating agents runs counterintuitive to conventional knowledge, as the cyclized forms of chalcones, collectively called flavonoids, are known to be anticoagulant agents via the inhibition of thrombin and stimulation of TFPI.

Definitions

Unless otherwise indicated, the invention is not limited to specific methods, analogs, substituents, pharmaceutical formulations, formulation components, metabolites, or modes of administration, or the like, as such may vary. As would be appreciated, the terminology used herein is for the purpose of describing particular embodiments only and is not intended to be limiting.

As used in this Specification and the Claims, the singular forms "a," "an," and "the" include plural referents unless the context clearly indicates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

In this Specification and in the Claims that follow, reference will be made to a number of terms, which shall be defined to have the following meanings:

The phrase "having the formula" or "having the structure" is not intended to be limiting and is used in the same way that the term "comprising" is commonly used.

The term "pharmacophore" is an abstract description of molecular features that are necessary for molecular recognition of a ligand by a biological macromolecule.

Figure 2A:
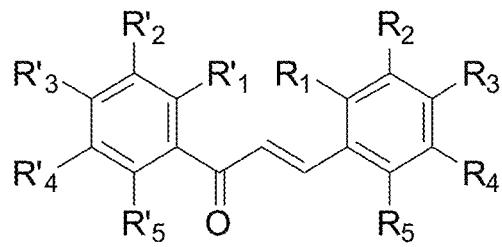
FIGS. 2A-2Q illustrate general and specific compound structures for chalcones in accordance with various embodiments of the invention.
Figure 2B:
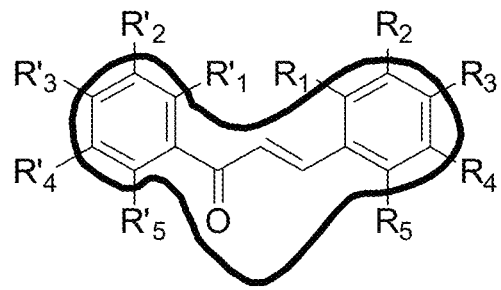
Figure 2C:
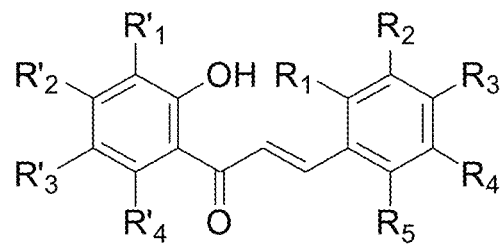

The term "chalcone" refers to any natural or synthetic compound that contains a 1,3-diaryl-2-propen-1-one (i.e., a conjugated ketone) substructure (for example, a chalcone structure illustrated in FIG. 2A) that forms the pharmacophore illustrated in FIG. 2B, which are known collectively as chalcones (sometimes also, chalconoids, chalcogenides, etc.). Alternative names for chalcone include benzylideneacetophenone, phenyl styryl ketone, benzalacetophenone, #-phenylacrylophenone, γ-oxo-α,γ-diphenyl-α-propylene, and α-phenyl-β-benzoylethylene, or 1,3-diaryl-2-propen-1-one derivative.

The term "hydroxychalcone" as used herein refers to any compound having a chalcone substructure with a hydroxyl group attached to a phenyl ring.

Figure 2D:
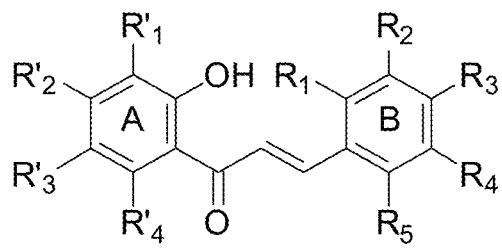
Figure 2E:
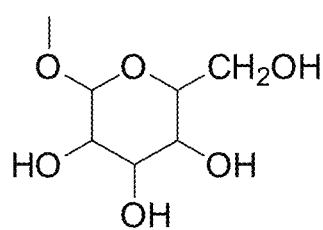
Figure 2F:
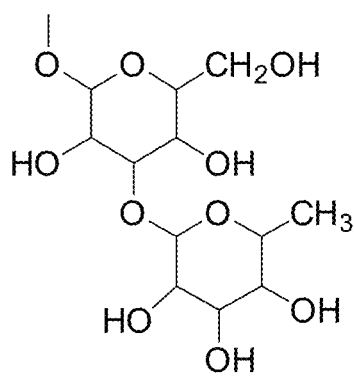
Figure 2G:
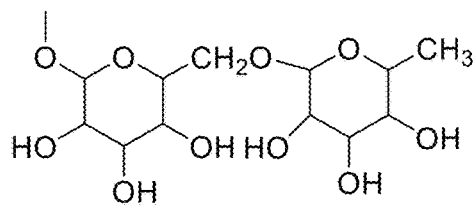
Figure 2H:
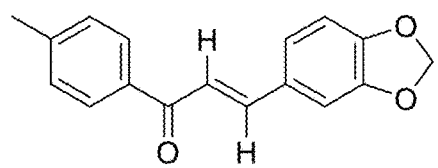

The term "R,R'-dihydroxychalcone" as used herein refers to any compound having a chalcone substructure consisting of at least one hydroxy group attached to each phenyl ring, A and B (see e.g., FIG. 2D).

The term "sugar" as used herein refers to any carbohydrate or saccharide residues attached to the phenyl rings of a chalcone substructure, such residues comprised of mono-saccharide, di-saccharide or poly-saccharide chains.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "$C_1$-$C_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail below. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to an alkenyl substituted with one or more substituent groups, and the terms "heteroatom-containing alkenyl" and "heteroalkenyl" refer to an alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkylene" refers to a difunctional linear, branched or cyclic alkyl group, where "alkyl" is as defined above. Alkylene linkages thus include —$CH_2$—$CH_2$— and —$CH_2$—$CH_2$—$CH_2$—, as well as substituted versions thereof wherein one or more hydrogen atoms is replaced with a nonhydrogen substituent. "Heteroalkylene" linkages refer to an alkylene moiety wherein one or more methylene units is replaced with a heteroatom(s).

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 12 carbon atoms. Exemplary aryl groups contain one aromatic ring or two fused or linked aromatic rings (e.g., phenyl, naphthyl, biphenyl, diphenylether, diphenylamine, benzophenone) and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom as described in further detail below. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Some aryloxy groups contain 5 to 20 carbon atoms, and some aryloxy groups contain 5 to 12 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "aralkyl" refers to an alkyl group with an aryl substituent, wherein "aryl" and "alkyl" are as defined above. Some aralkyl groups contain 5 to 20 carbon atoms, and some aralkyl groups contain 5 to 12 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "aralkyloxy" refers to an aralkyl group bound through a single, terminal ether linkage. As above, an "aralkyloxy" group may be represented as —O-Alk(Ar) wherein "Alk" is an alkyl group and "Ar" is an aryl substituent. Some aralkyloxy groups contain 5 to 20 carbon atoms, and some aralkyloxy groups contain 5 to 12 carbon atoms. Aralkyloxy substituents include, for example, benzyloxy, 2-phenoxy-ethyl, 3-phenoxy-propyl, 2-phenoxypropyl, 2-methyl-3-phenoxypropyl, 2-ethyl-3-phenoxypropyl, 4-phenoxy-butyl, 3-phenoxy-butyl, 2-methyl-4-phenoxybutyl, 4-phenoxycyclohexyl, 4-benzyloxycyclohexyl, 4-phenoxy-cyclohexylmethyl, 2-(4-phenoxy-cyclohexyl)-ethyl, and the like.

The term "cyclic" refers to alicyclic or aromatic substituents that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a compound, linkage or substituent in which one or more carbon atoms are replaced with an atom other than carbon (e.g., nitrogen, oxygen, sulfur, phosphorus or silicon, typically nitrogen, oxygen or sulfur). Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, alkoxy, alkenyloxy, alkynyloxy, aryloxy, acyl (including alkylcarbonyl (—CO-alkyl) and arylcarbonyl (—CO-aryl)), acyloxy (—O—(CO)—R where R=alkyl, aryl, alkaryl, etc.), alkoxycarbonyl (—(CO)—O-alkyl), aryloxycarbonyl (—(CO)—O-aryl), halocarbonyl (—CO)—X where X=halo), carboxy (—COOH), carboxylato (—COO$^-$), carbamoyl (—(CO)—NH$_2$), alkylcarbamoyl (—(CO)—NH-alkyl), arylcarbamoyl (—(CO)—NH-aryl), thiocarbamoyl (—(CS)—NH$_2$), carbamido (—NH—(CO)—NH$_2$), cyano(—C.ident.--N), isocyano (—N$^+$.ident.C$^-$), cyanato (—O—C.ident.N), isocyanato (—O—N$^+$.ident.C$^-$), isothiocyanato (—S—C.ident.N), azido (—N.dbd.N$^+$.dbd.N$^-$), formyl (—(CO)—H), thioformyl (—(CS)—H), primary amino (—NH$_2$), mono- and di-(alkyl)-substituted amino, mono- and di-(aryl)-substituted amino, alkylamido (—NH—(CO)-alkyl), arylamido (—NH—(CO)-aryl), imino (—CR.dbd.NH where R=hydrogen, alkyl, aryl, alkaryl, etc.), alkylimino (—CR.dbd.N(alkyl), where R=hydrogen, alkyl, aryl, alkaryl, etc.), arylimino (—CR.dbd.N(aryl), where R=hydrogen, alkyl, aryl, alkaryl, etc.), nitro (—NO$_2$), nitroso (—NO), sulfo (—SO$_2$—OH), sulfonato (—SO$_2$—O.sup.-), alkylsulfanyl (—S-alkyl; also termed "alkylthio"), arylsulfanyl (—S-aryl; also termed "arylthio"), alkylsulfinyl (—(SO)—O-alkyl), arylsulfinyl (—(SO)—O-aryl), boryl (—BH$_2$), borono (—B(OH)$_2$), phosphono (—P(O)(OH)$_2$), phosphonato (—P(O)(O.sup.-)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{18}$ alkyl, more preferably C$_1$-C$_{12}$ alkyl, most preferably C$_1$-C$_6$ alkyl), C$_2$-C$_{24}$ alkenyl (preferably C$_2$-C$_{18}$ alkenyl, more preferably C$_2$-C$_{12}$ alkenyl, most preferably C$_2$-C$_6$ alkenyl), C$_2$-C$_{24}$ alkynyl (preferably C$_2$-C$_{18}$ alkynyl, more preferably C$_2$-C$_{12}$ alkynyl, most preferably C$_2$-C$_6$ alkynyl), C$_5$-C$_{20}$ aryl (preferably C$_5$-C$_{12}$ aryl), and C$_5$-C$_{20}$ aralkyl (preferably C$_5$-C$_{12}$ aralkyl).

Figure 2I:
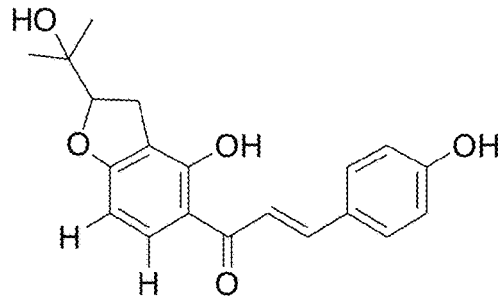
Figure 2J:
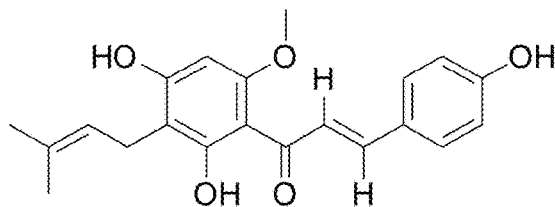
Figure 2K:
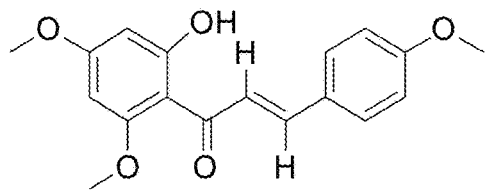
Figure 2L:
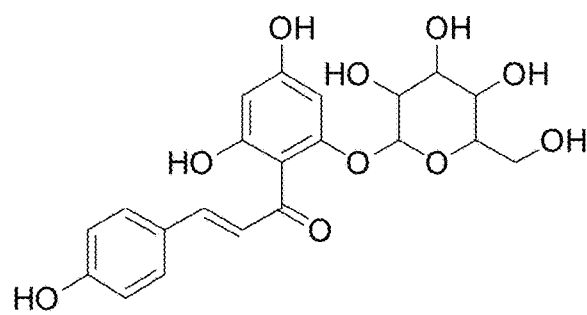
Figure 2M:
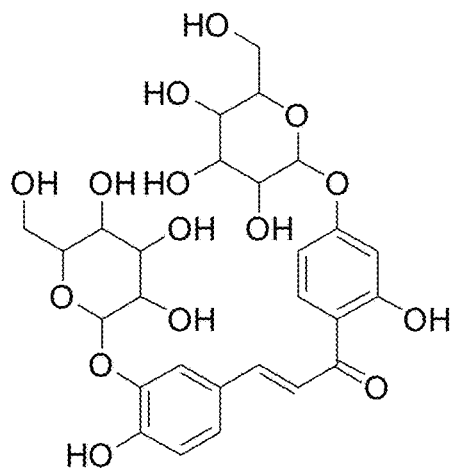
Figure 2O:
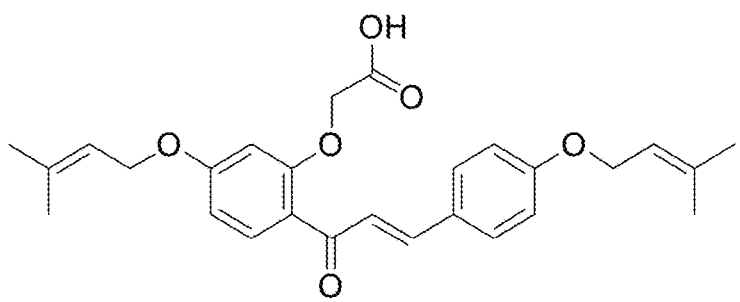

The term "prenylated" refers to a structural class of chalcones containing isoprene side chains and cyclized derivatives as (for example, the chalcones illustrated in FIGS. 2I-2J and 2O).

The term "appendix" refers to a group attached directly to phenyl rings A and/or B of the chalcone substructure, or connected to phenyl ring(s) A and/or B via a heteroatom(s).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

"Optional" or "optionally" means that the subsequently described circumstance(s) may or may not occur, so that the description includes instances where the circumstance(s) occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally present bond" as indicated by a dotted line ----- in the chemical formulas herein means that a bond may or may not be present.

In the molecular structures of the compounds herein, the use of bold and dashed lines to denote particular conformations of groups follows the conventions set forth by the International Union of Pure and Applied Chemistry ("IUPAC"). A bond indicated by a broken line indicates that the group in question is below the general plane of the molecular structure as drawn (i.e., the "beta" configuration), and a bond indicated by a bold line indicates that the group at the position in question is above the general plane of the molecular structure as drawn (i.e. the "alpha" configuration). Single bonds that are not indicated by broken or bold lines may be in either configuration; such bonds may also be indicated by simple or dotted straight lines. In some cases substructures are anticipated when there are no groups attached and the bonds are dotted lines.

When referring to a compound of the invention, Applicant intends the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs and related compounds.

The terms "treating" and "treatment" as used herein refer to reduction in severity and/or frequency of symptoms, elimination of symptoms and/or their underlying cause(s), prevention of the occurrence of symptoms and/or their underlying cause(s), and improvement or remediation of damage. Thus, "treating" a patient with a compound of the invention includes prevention of a particular disorder or adverse physiological event in a susceptible individual as well as treatment of a clinically symptomatic individual by inhibiting or causing regression of a disorder or disease.

By the terms "effective amount" or "therapeutically effective amount" of a compound of the invention is meant a non-toxic but sufficient amount of the drug or agent to provide the desired effect.

By "pharmaceutically acceptable" is meant a material that is not biologically, pharmaceutically, or otherwise undesirable, or in other words, the material may be incorporated into a pharmaceutical composition and administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the FDA. "Pharmacologically active" (or simply "active") as in a "pharmacologically active" derivative or analog, refers to a derivative or analog having the same type of pharmacological activity as the parent compound and approximately equivalent in degree.

Compositions

As discussed above, the term "chalcone" refers to any natural or synthetic compound that contains a 1,3-diaryl-2-propen-1-one (i.e., a conjugated ketone) substructure that forms the pharmacophore illustrated in FIG. 2B, which are known collectively as chalcones (sometimes also known as chalconoids, chalcogenides, etc.). The transected lines in FIG. 2B represent optional connections to bonds, rings, hydroxy, methoxy, iso-prenyl, O-SUG (where sugar is a glycoside, riboside, or chain of sugar residues, or a diasaccharide derivative), etc., as would be appreciated. Alternative names for chalcone may include, but may not be limited to, benzylideneacetophenone, phenyl styryl ketone, benzalacetophenone, #-phenylacrylophenone, γ-oxo-α,γ-diphenyl-α-propylene, or α-phenyl-β-benzoylethylene. Another description of the compounds of invention is: compounds containing a substructure (see e.g., FIG. 2A) or pharmacophore encircled by solid lines (see e.g., FIG. 2B) or compounds containing a 1,3-diaryl-2-propen-1-one substructure, where the R' and R groups are chains, rings, embedded or isolated rings, or a variety of groups such as ones described above.

Additional examples of compounds of the invention may be found by searching various databases such as SciFinder® and PubChem using representative pseudocode. An exemplary strategy to find some of these additional examples is through the use of substructure matching of functional groups (see e.g. FIG. 5). For example, the substructure matching of sugar and hydroxy derivatives yields the compounds that are described below.

Chalcones with Saccharide Substitution(s)

The following includes various exemplary chalcones with a saccharide substitution(s) (Numbers are PubChem Compound Identification (PubChem CID) numbers): 191628: 1-[2-Hydroxy-6-methoxy-4-[(3R,4S,5S,6R)-3,4,5-trihydroxy-6-(hydroxymethyl)oxan-2-yl]oxyphenyl]-3-(4-hydroxyphenyl)prop-2-en-1-one; 454264: 1-(2,4-Dihydroxyphenyl)-3-[4-[(2S,3R,4S,5S,6R)-3,4,5-trihydroxy-6-(hydroxymethyl)oxan-2-yl]oxyphenyl]prop-2-en-1-one; 480798: 3-[4-[3-[3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 636657: (2S,3R)-3-[5-[(E)-3-(2,4-Dihydroxyphenyl)-3-oxoprop-1-enyl]-2-hydroxy-phenyl]-5-hydroxy-2-(4-hydroxyphenyl)-7-[(2R,3R,4R,5R,6S)-3,4,5-trihydroxy-6-(hydroxy-methyl)oxan-2-yl]oxy-2,3-dihydrochromen-4-one; 2794965: [(2R,3R,4S,5R,6S)-3,4,5-Triacetyloxy-6-[4-(3-phenylprop-2-enoyl)phenoxy]oxan-2-yl]methyl acetate; 3577204: [3,4,5-Triacetyloxy-6-[4-(3-phenylprop-2-enoyl)phenoxy]oxan-2-yl]methyl acetate; 3769539: Hesperidin methyl chalcone; 3771190: [4,5-Diacetyloxy-6-[4-(3-phenylprop-2-enoyl)phenoxy]-3-[3,4,5-triacetyloxy-6-(acetyloxymethyl)oxan-2-yl]oxyoxan-2-yl]methyl acetate; 3787728: [3,4,5-Triacetyloxy-6-[4-(3-oxo-3-phenylprop-1-enyl)phenoxy]oxan-2-yl]methyl acetate; 3812135: [4,5-Diacetyloxy-6-[4-(3-oxo-3-phenylprop-1-enyl)phenoxy]-3-[3,4,5-triacetyloxy-6-(acetyloxymethyl)oxan-2-yl]oxyoxan-2-yl]methyl acetate; 3943170: 1-[4-[4,5-Dihydroxy-6-(hydroxymethyl)-3-(3,4,5-trihydroxy-6-methyloxan-2-yl)oxyoxan-2-yl]oxy-2,6-dihydroxyphenyl]-3-(3-hydroxy-4-methoxyphenyl)prop-2-en-1-one; 4398471: 1-[2,4-Dihydroxy-6-[3,4,5-trihydroxy-6-(hydroxymethyl)oxan-2-yl]oxyphenyl]-3-(4-hydroxyphenyl)prop-2-en-1-one; 4405834: 1-[2-Hydroxy-6-[3,4,5-trihydroxy-6-(hydroxymethyl)oxan-2-yl]oxyphenyl]-3-(4-nitro-phenyl)prop-2-en-1-one; 4481621: 1-[2-Hydroxy-4-[3,4,5-tri-hydroxy-6-(hydroxymethyl)oxan-2-yl]oxyphenyl]-3-[4-hydroxy-3-[3,4,5-trihydroxy-6-(hydroxymethyl)oxan-2-yl]oxyphenyl]prop-2-en-1-one; 4629641: 1-[4-[[2-(Furan-2-yl)-7,8-dihydroxy-4,4a,6,7,8,8a-hexahydropyrano[3,2-d][1,3]dioxin-6-yl]oxy]phenyl]-3-phenylprop-2-en-1-one; 4629986: N-[2-(Furan-2-yl)-8-hydroxy-6-[4-(3-phenylprop-2-enoyl)phenoxy]-4,4a,6,7,8,8a-hexahydropyrano[3,2-d][1,3]dioxin-7-yl]acetamide; 4691349: 3-(4-Chlorophenyl)-1-[2,4-dihydroxy-6-[3,4,5-trihydroxy-6-(hydroxymethyl)oxan-2-yl]oxyphenyl]prop-2-en-1-one; 5098942: 3-(4-Hydroxyphenyl)-1-[4-hydroxy-2-[3,4,5-trihydroxy-6-(hydroxymethyl)oxan-2-yl]oxyphenyl]prop-2-en-1-one; 5226098: [3,4-Bis(acetyloxy)-5-acetamido-6-[4-(3-phenyl-prop-2-enoyl)phenoxy]oxan-2-yl]methyl acetate; 5239685: 1-[2-Hydroxy-4-[3,4,5-trihydroxy-6-(hydroxymethyl)oxan-2-yl]oxyphenyl]-3-phenylprop-2-en-1-one; 5276742: (E)-1-[4-[(2S,3R,4S,5S,6R)-4,5-Dihydroxy-6-(hydroxymethyl)-3-[(2S,3R,4R,5R,6S)-3,4,5-trihydroxy-6-methyl-tetrahydropyran-2-yl]oxy-tetrahydropyran-2-yl]oxy-2,6-dihydroxy-phenyl]-3-(3-hydroxy-4-methoxy-phenyl)prop-2-en-1-one; 5281256: Isobutrin; 5318591: Isoliquiritin; 5318659: Isosalipuroside; 5320092: Neoisoliquiritin; 5712125: (E)-1-[4-[(2-O,3-O,4-O,6-O-Tetraacetyl-beta-D-gluco-pyranosyl)oxy]phenyl]-3-phenyl-2-propen-1-one; 5712126: 3-(Acetoxy)-6-[(acetoxy)methyl]-2-(4-cinnamoylphenoxy)-5-(3,4,5-tri (acetoxy)-6-[(acetoxy) methyl]THP2-yloxy)THP4-yl acetate; 5712127: (E)-1-Phenyl-3-[4-[(2-O,3-O,4-O,6-O-tetraacetyl-beta-D-gluco-pyranosyl)oxy]phenyl]-2-propen-1-one; 5712128: (E)-1-Phenyl-3-[4-[[4-O-(2-O,3-O,4-O,6-O-tetraacetyl-beta-D-gluco-pyranosyl)-2-O,3-O,6-O-triacetyl-beta-D-gluco-pyranosyl]oxy]phenyl]-2-propen-1-one; 5865563: 3,5-Di(acetyloxy)-2-[(acetyloxy) methyl]-6-(4-cinnamoylphenoxy)tetrahydro-2H-pyran-4-yl acetate; 5917946: (E)-3-(3-Hydroxy-4-methoxyphenyl)-1-[2-hydroxy-6-methoxy-4-[3,4,5-trihydroxy-6-[(3,4,5-trihydroxy-6-methyloxan-2-yl)oxymethyl]oxan-2-yl]oxyphenyl]prop-2-en-1-one; 5965043: (E)-1-[4-[4,5-Dihydroxy-6-(hydroxymethyl)-3-(3,4,5-trihydroxy-6-methyloxan-2-yl) oxyoxan-2-yl]oxy-2,6-dihydroxyphenyl]-3-(3-hydroxy-4-methoxyphenyl)prop-2-en-1-one; 6090017: (Z)-1-[2,4-Dihydroxy-6-[3,4,5-trihydroxy-6-(hydroxymethyl)oxan-2-yl]oxyphenyl]-3-(4-hydroxy-phenyl)prop-2-en-1-one; 6123336: (E)-1-[2-Hydroxy-4-[3,4,5-trihydroxy-6-(hydroxy-methyl)oxan-2-yl]oxyphenyl]-3-[4-hydroxy-3-[3,4, 5-tri hydroxy-6-(hydroxymethyl)oxan-2-yl]oxyphenyl]prop-2-en-1-one; 6168803: (E)-1-[4-[[2-(Furan-2-yl)-7,8-dihydroxy-4,4a,6,7,8,8a-hexahydropyrano[3,2-d][1,3] dioxin-6-yl]oxy]phenyl]-3-phenylprop-2-en-1-one; 6168899: N-[2-(Furan-2-yl)-8-hydroxy-6-[4-[(E)-3-phenylprop-2-enoyl]phenoxy]-4,4a,6,7,8,8a-hexahydropyrano[3,2-d][1,3]dioxin-7-yl]acetamide; 6306902: (E)-5-Acetamido-2-(acetoxymethyl)-6-(4-cinnamoylphenoxy) tetrahydro-2H-pyran-3,4-diyldiace-tate; 6310616: (E)-1-[2-Hydroxy-4-[3,4,5-trihydroxy-6-(hydroxymethyl)oxan-2-yl] oxyphenyl]-3-phenylprop-2-en-1-one; 6436550: Hesperidin methylchalcone; 6441309: Tomanil; 6442433: Isoliquiritin apioside; 6443577: 2',4,4'-Trihydroxy-6'-methoxychalcone 4'-beta-D-glucopyranoside; 6474973: (E)-1-[2,4-Dihydroxy-6-[[(2R,3S,4R,6R)-3,4,6-trihydroxy-oxan-2-yl] methoxy]phenyl]-3-(4-hydroxyphenyl)prop-2-en-1-one; 6475724: Licuroside; 6526201: (E)-1-[2,4-Dihydroxy-6-[3,4,5-trihydroxy-6-(hydroxymethyl)oxan-2-yl]oxyphenyl]-3-(4-hydroxyphenyl)prop-2-en-1-one; 6708743: 1-[2-Hydroxy-4-[(2S,3R,4S,5S,6R)-3,4,5-tri-hydroxy-6-(hydroxymethyl)oxan-2-yl]oxyphenyl]-3-phenylprop-2-en-1-one; 6857762: 2',4'-Dihydroxychalcone 4'-glucoside; 9933354: (E)-1-(2,4-Dihydroxyphenyl)-3-[4-[(3S,4R,5R,6S)-3,4,5-trihydroxy-3,6-bis(hydroxymethyl)oxan-2-yl]oxyphenyl]prop-2-en-1-one; 10095186: 2',4-Dihydroxy-4'-(beta-D-gluco-pyranosyloxy)-6'-methoxy-chalcone; 10227083: (E)-3-(1-Benzofuran-5-yl)-1-[2-hydroxy-4-methoxy-6-[[3,4,5-trihydroxy-6-(hydroxymethyl) oxan-2-yl]methyl]phenyl]prop-2-en-1-one; 10251436: (E)-1-[2,4-Dihydroxy-6-[(3S,4R,5R,6S)-3,4,5-trihydroxy-6-(hydroxymethyl)oxan-2-yl]oxyphenyl]-3-phenylprop-2-en-1-one; 10364694: Neoisoliquiritigenin; 10371291: (E)-1-[2-Hydroxy-4-[(2S,3R,4S,5S,6R)-3,4,5-trihydroxy-6-(hydroxymethyl)oxan-2-yl]oxyphenyl]-3-[4-hydroxy-3-[(2R,3S,4R,5R,6S)-3,4,5-trihydroxy-6-(hydroxymethyl) oxan-2-yl]oxyphenyl]prop-2-en-1-one; 10372091: (E)-3-(3, 4-Dimethoxyphenyl)-1-[2,6-dimethoxy-4-[(3R,4S,5S,6R)-3,4,5-trihydroxy-6-[[(2S,3R,4R,5R,6S)-3,4,5-trihydroxy-6-methyloxan-2-yl]oxymethyl]oxan-2-yl]oxyphenyl]prop-2-en-1-one; 10484055: (E)-3-(3-Hydroxy-4-methoxyphenyl)-1-[2-hydroxy-6-methoxy-4-[(2S,3R,4S,5S,6R)-3,4,5-trihydroxy-6-[[(2S,3R,4R,5R,6S)-3,4,5-trihydroxy-6-methyloxan-2-yl]oxymethyl]oxan-2-yl]oxyphenyl]prop-2-en-1-one; 10522436: (E)-3-(4-Chlorophenyl)-1-[2-hydroxy-4-(oxan-2-yloxy)phenyl]prop-2-en-1-one; 10526346: (E)-1-[2-Hydroxy-4-(oxan-2-yloxy)phenyl]-3-[3-(oxan-2-yloxy) phenyl]prop-2-en-1-one; 10575999: (E)-3-(3,4-Dimethoxyphenyl)-1-[2-hydroxy-6-[(2S,3R,4S,5S,6R)-3,4, 5-trihydroxy-6-(hydroxymethyl)oxan-2-yl]oxyphenyl]prop-2-en-1-one; 10595346: (E)-1-[2-Hydroxy-4-(oxan-2-yloxy) phenyl]-3-(4-methylsulfanylphenyl)prop-2-en-1-one; 10596175: Schembl21527700; 10625896: (e)-3-[3,4-Bis (tetra-hydro-2h-pyran-2-yloxy)phenyl]-1-[2-hydroxy-4-(tetrahydro-2h-pyran-2-yloxy)phenyl]prop-2-en-1-one; 10716790: (E)-3-(4-Methoxyphenyl)-1-[2-[(2S,3R,4S,5S, 6R)-3,4,5-trihydroxy-6-(hydroxymethyl)oxan-2-yl]oxyphenyl]prop-2-en-1-one; 10784314: (E)-1-[2-Hydroxy-4-(oxan-2-yloxy)phenyl]-3-(3-methoxyphenyl)prop-2-en-1-one; 10793864: (E)-3-[3,4-Bis(phenyl-methoxy)phenyl]-1-[2-hydroxy-6-[(2S,3R,4S,5S,6R)-3,4,5-trihydroxy-6-(hydroxymethyl) oxan-2-yl]oxyphenyl]prop-2-en-1-one; 10808037: (E)-1-[2-Hydroxy-4-(oxan-2-yloxy)phenyl]-3-(4-methoxyphenyl)prop-2-en-1-one; 10915319: (E)-3-Naphthalen-2-yl-1-[4-(oxan-2-yloxy)phenyl]prop-2-en-1-one; 10983454: (E)-1-[2,6-Dihydroxy-4-[(2S,3R,4S,5S, 6R)-3,4,5-trihydroxy-6-(hydroxymethyl)oxan-2-yl] oxyphenyl]-3-(3-hydroxy-4-methoxyphenyl)prop-2-en-1-one; 11070489: (E)-3-(1-Benzofuran-5-yl)-1-[2-hydroxy-4-methyl-6-[(2S,3R,4S,5S,6R)-3,4,5-trihydroxy-6-(hydroxymethyl)oxan-2-yl]oxyphenyl]prop-2-en-1-one; 11072502: (2S,3R)-3-[5-[(E)-3-(2,4-Dihydroxyphenyl)-3-oxoprop-1-enyl]-2-hydroxyphenyl]-5-hydroxy-2-(4-hydroxyphenyl)-7-[(2S,3R,4S,5S,6R)-3,4,5-trihydroxy-6-(hydroxymethyl)oxan-2-yl]oxy-2,3-dihydrochromen-4-one; 11271357: (E)-3-(1-Benzofuran-5-yl)-1-[2-hydroxy-4-methoxy-6-[[(2S,3R,4R,5S,6R)-3,4,5-trihydroxy-6-(hydroxymethyl)oxan-2-yl]methyl]phenyl]prop-2-en-1-one; 11532735: (E)-1-(2-Hydroxy-4,6-dimethoxyphenyl)-3-[4-[(2S,3R,4S,5S,6R)-3,4,5-trihydroxy-6-(hydroxymethyl) oxan-2-yl]oxyphenyl]prop-2-en-1-one; 11545988: (E)-1,3-Bis[4-(oxan-2-yloxy)phenyl]prop-2-en-1-one; 11547723: (E)-1-[2-Hydroxy-4-(oxan-2-yloxy)phenyl]-3-[3-(3-methylbut-2-enyl)-4-(oxan-2-yloxy)phenyl]prop-2-en-1-one; 11728217: (E)-3-(4-Butylphenyl)-1-[4-(oxan-2-yloxy)phenyl]prop-2-en-1-one; 11743626: (E)-1-[2,6-Dihydroxy-4-[3,4,5-trihydroxy-6-(hydroxymethyl)oxan-2-yl]oxyphenyl]-3-(4-hydroxyphenyl)prop-2-en-1-one; 11760601: (E)-1-(2, 4-Dichlorophenyl)-3-[4-(oxan-2-yloxy)phenyl]prop-2-en-1-one; 11799784: (E)-1-[2-Hydroxy-6-[(2S,3R,4S,5S,6R)-3, 4,5-trihydroxy-6-(hydroxymethyl)oxan-2-yl]oxyphenyl]-3-(4-phenylmethoxyphenyl)prop-2-en-1-one; 11972381: (E)-1-(2,4-Dihydroxyphenyl)-3-[4-[(2S,3R,4S,5R,6R)-3,4,5-trihydroxy-6-(hydroxymethyl)oxan-2-yl]oxyphenyl]prop-2-en-1-one; 12303942: Coreopsin; 12303943: Butein 4'-beta-D-glucoside; 12314458: 2',6'-Dihydroxy-4-methoxychalcone-4'-O-neohesperid; 12818405: (E)-1-[2,4-Dihydroxy-6-[(3R,4S,5S,6R)-3,4,5-trihydroxy-6-(hydroxymethyl)oxan-2-yl]oxyphenyl]-3-(4-hydroxyphenyl)prop-2-en-1-one; 13870531: 4,2'-Dihydroxy-4',6'-dimethoxychalcone 4-glucoside; 13870532: 4,2'-Dihydroxy-3,4',6'-trimethoxychalcone 4-glucoside; 13870533: (E)-1-(2-Hydroxy-4,6-dimethoxyphenyl)-3-[3-methoxy-4-[(2S,3R, 4S,5S,6R)-3,4,5-trihydroxy-6-(hydroxymethyl)oxan-2-yl] oxyphenyl]prop-2-en-1-one; 13870534: 4,2'-Dihydroxy-4', 6'-dimethoxychalcone 4-apiosyl-(1→2)-glucoside; 13870535: (E)-3-[4-[(2S,3R,4S,5S,6R)-3-[(2S,3R,4R)-3,4-Dihydroxy-4-(hydroxymethyl)oxolan-2-yl]oxy-4,5-dihydroxy-6-(hydroxymethyl)oxan-2-yl]oxyphenyl]-1-(2-hydroxy-4,6-dimethoxyphenyl)prop-2-en-1-one; 14187588: Isoliquiritoside; 14187589: (E)-1-(2,4-Dihydroxyphenyl)-3-[4-[(2R,3R,4S,5S,6R)-3,4,5-trihydroxy-6-(hydroxymethyl) oxan-2-yl]oxyphenyl]prop-2-en-1-one; 14282455: Licuraside; 14327425: (E)-3-(4-Hydroxyphenyl)-1-[2-hydroxy- 4-[3,4,5-trihydroxy-6-(hydroxymethyl)oxan-2-yl]oxyphenyl]prop-2-en-1-one; 14524443: Neosakuranin; 14524444: 2'-(beta-D-Glucopyranosyloxy)-4,6'-dihydroxy-4'-methoxychalcone; 14854161: Chalcononaringenin 2',4'-di-O-beta-D-glucoside; 15054625: (E)-1-[2-Methoxy-6-(oxan-2-yloxy)phenyl]-3-phenylprop-2-en-1-one; 15054630: (E)-1-[2-(Oxan-2-yloxy)-6-propan-2-yloxyphenyl]-3-phenylprop-2-en-1-one; 15054654: (E)-1-[2-Methoxy-4,6-bis(oxan-2-yloxy)phenyl]-3-phenylprop-2-en-1-one; 15054655: (E)-1-[4-Methoxy-2-(oxan-2-yloxy)phenyl]-3-phenylprop-2-en-1-one; 15054656: (E)-1-[2,4-Bis(oxan-2-yloxy)phenyl]-3-phenylprop-2-en-1-one; 15054657: (E)-1-[2,4-Dimethoxy-6-(oxan-2-yloxy)phenyl]-3-phenylprop-2-en-1-one; 15054658: (E)-1-[2,6-Bis(oxan-2-yloxy)phenyl]-3-phenylprop-2-en-1-one; 15680252: (e)-1-[2-Hydroxy-4-(tetrahydro-2h-pyran-2-yloxy)phenyl]-3-[4-(tetrahydro-2h-pyran-2-yloxy)phenyl]prop-2-en-1-one; 16398198: [(2R,3S,4R,5R,6S)-5-Acetamido-3,4-diacetyloxy-6-[4-[(E)-3-phenylprop-2-enoyl]phenoxy]oxan-2-yl]methyl acetate; 16757866: (E)-1-[2-Hydroxy-4-[(2R)-3,4,5-trihydroxy-6-(hydroxymethyl)oxan-2-yl]oxyphenyl]-3-phenylprop-2-en-1-one; 18888035: N-[8-Hydroxy-2,2-dimethyl-6-[4-[(E)-3-phenylprop-2-enoyl]phenoxy]-4,4a,6,7,8,8a-hexahydropyrano[3,2-d][1,3]dioxin-7-yl]acetamide; 18888036: N-[8-Hydroxy-2,2-dimethyl-6-[2-[(E)-3-phenylprop-2-enoyl]phenoxy]-4,4a,6,7,8,8a-hexahydropyrano[3,2-d][1,3]dioxin-7-yl]acetamide; 18888037: N-[8-Hydroxy-2,2-dimethyl-6-[4-[(E)-3-oxo-3-phenylprop-1-enyl]phenoxy]-4,4a,6,7,8,8a-hexahydropyrano[3,2-d][1,3]dioxin-7-yl]acetamide; 18888039: N-[6-[4-[(E)-3-(4-Chlorophenyl)-3-oxoprop-1-enyl]phenoxy]-8-hydroxy-2,2-dimethyl-4,4a,6,7,8,8a-hexahydropyrano[3,2-d][1,3]dioxin-7-yl]acetamide; 18888051: 4-[(2E)-3-Phenylprop-2-enoyl]phenyl 2-(acetylamino)-4,6-O-benzylidene-2-deoxyhexopyranoside; 18888052: N-[8-Hydroxy-2-phenyl-6-[2-[(E)-3-phenylprop-2-enoyl]phenoxy]-4,4a,6,7,8,8a-hexahydropyrano[3,2-d][1,3]dioxin-7-yl]acetamide; 18888053: 4-[(1 E)-3-Oxo-3-phenylprop-1-en-1-yl]phenyl 2-(acetylamino)-4,6-O-benzylidene-2-deoxyhexopyranoside; 18888055: N-[6-[4-[(E)-3-(4-Chlorophenyl)-3-oxoprop-1-enyl]phenoxy]-8-hydroxy-2-phenyl-4,4a,6,7,8,8a-hexahydropyrano[3,2-d][1,3]dioxin-7-yl]acetamide; 18888066: N-[2-(Furan-2-yl)-8-hydroxy-6-[2-[(E)-3-phenylprop-2-enoyl]phenoxy]-4,4a,6,7,8,8a-hexahydropyrano[3,2-d][1,3]dioxin-7-yl]acetamide; 18888067: N-[2-(Furan-2-yl)-8-hydroxy-6-[4-[(E)-3-oxo-3-phenylprop-1-enyl]phenoxy]-4,4a,6,7,8,8a-hexahydropyrano[3,2-d][1,3]dioxin-7-yl]acetamide; 18888069: N-[6-[4-[(E)-3-(4-Chlorophenyl)-3-oxoprop-1-enyl]phenoxy]-2-(furan-2-yl)-8-hydroxy-4,4a,6,7,8,8a-hexahydropyrano[3,2-d][1,3]dioxin-7-yl]acetamide; 18888092: 2-[[7-Acetamido-2,2-dimethyl-6-[4-[(E)-3-phenylprop-2-enoyl]phenoxy]-4,4a,6,7,8,8a-hexahydropyrano[3,2-d][1,3]dioxin-8-yl]oxy]propanoic acid; 18888093: 2-[[7-Acetamido-2,2-dimethyl-6-[2-[(E)-3-phenylprop-2-enoyl]phenoxy]-4,4a,6,7,8,8a-hexahydropyrano[3,2-d][1,3]dioxin-8-yl]oxy]propanoic acid; 18888094: 2-[[7-Acetamido-2,2-dimethyl-6-[4-[(E)-3-oxo-3-phenylprop-1-enyl]phenoxy]-4,4a,6,7,8,8a-hexahydropyrano[3,2-d][1,3]dioxin-8-yl]oxy]propanoic acid; 18888096: 2-[[7-Acetamido-6-[4-[(E)-3-(4-chlorophenyl)-3-oxoprop-1-enyl]phenoxy]-2,2-dimethyl-4,4a,6,7,8,8a-hexahydropyrano[3,2-d][1,3]dioxin-8-yl]oxy]propanoic acid; 18888119: 2-[[7-Acetamido-2-phenyl-6-[4-[(E)-3-phenylprop-2-enoyl]phenoxy]-4,4a,6,7,8,8a-hexahydropyrano[3,2-d][1,3]dioxin-8-yl]oxy]propanoic acid; 18888120: 2-[[7-Acetamido-2-phenyl-6-[2-[(E)-3-phenylprop-2-enoyl]phenoxy]-4,4a,6,7,8,8a-hexahydropyrano[3,2-d][1,3]dioxin-8-yl]oxy]propanoic acid; 18888121: 2-[[7-Acetamido-6-[4-[(E)-3-oxo-3-phenylprop-1-enyl]phenoxy]-2-phenyl-4,4a,6,7,8,8a-hexahydropyrano[3,2-d][1,3]dioxin-8-yl]oxy]propanoic acid; 18888123: 2-[[7-Acetamido-6-[4-[(E)-3-(4-chlorophenyl)-3-oxoprop-1-enyl]phenoxy]-2-phenyl-4,4a,6,7,8,8a-hexahydropyrano[3,2-d][1,3]dioxin-8-yl]oxy]propanoic acid; 18888146: 2-[[7-Acetamido-2-(furan-2-yl)-6-[4-[(E)-3-phenylprop-2-enoyl]phenoxy]-4,4a,6,7,8,8a-hexahydropyrano[3,2-d][1,3]dioxin-8-yl]oxy]propanoic acid; 18888147: 2-[[7-Acetamido-2-(furan-2-yl)-6-[2-[(E)-3-phenylprop-2-enoyl]phenoxy]-4,4a,6,7,8,8a-hexahydropyrano[3,2-d][1,3]dioxin-8-yl]oxy]propanoic acid; 18888148: 2-[[7-Acetamido-2-(furan-2-yl)-6-[4-[(E)-3-oxo-3-phenylprop-1-enyl]phenoxy]-4,4a,6,7,8,8a-hexahydropyrano[3,2-d][1,3]dioxin-8-yl]oxy]propanoic acid; 18888150: 2-[[7-Acetamido-6-[4-[(E)-3-(4-chlorophenyl)-3-oxoprop-1-enyl]phenoxy]-2-(furan-2-yl)-4,4a,6,7,8,8a-hexahydropyrano[3,2-d][1,3]dioxin-8-yl]oxy]propanoic acid; 18888173: 2-[[7-Acetamido-2,2-dimethyl-6-[4-[(E)-3-phenylprop-2-enoyl]phenoxy]-4,4a,6,7,8,8a-hexahydropyrano[3,2-d][1,3]dioxin-8-yl]oxy]acetic acid; 18888174: 2-[[7-Acetamido-2,2-dimethyl-6-[2-[(E)-3-phenylprop-2-enoyl]phenoxy]-4,4a,6,7,8,8a-hexahydropyrano[3,2-d][1,3]dioxin-8-yl]oxy]acetic acid; 18888175: 2-[[7-Acetamido-2,2-dimethyl-6-[4-[(E)-3-oxo-3-phenylprop-1-enyl]phenoxy]-4,4a,6,7,8,8a-hexahydropyrano[3,2-d][1,3]dioxin-8-yl]oxy]acetic acid; 18888177: 2-[[7-Acetamido-6-[4-[(E)-3-(4-chlorophenyl)-3-oxoprop-1-enyl]phenoxy]-2,2-dimethyl-4,4a,6,7,8,8a-hexahydropyrano[3,2-d][1,3]dioxin-8-yl]oxy]acetic acid; 18888200: 2-[[7-Acetamido-2-phenyl-6-[4-[(E)-3-phenylprop-2-enoyl]phenoxy]-4,4a,6,7,8,8a-hexahydropyrano[3,2-d][1,3]dioxin-8-yl]oxy]acetic acid; 18888201: 2-[[7-Acetamido-2-phenyl-6-[2-[(E)-3-phenylprop-2-enoyl]phenoxy]-4,4a,6,7,8,8a-hexahydropyrano[3,2-d][1,3]dioxin-8-yl]oxy]acetic acid; 18888202: 2-[[7-Acetamido-6-[4-[(E)-3-oxo-3-phenylprop-1-enyl]phenoxy]-2-phenyl-4,4a,6,7,8,8a-hexahydropyrano[3,2-d][1,3]dioxin-8-yl]oxy]acetic acid; 18888204: 2-[[7-Acetamido-6-[4-[(E)-3-(4-chlorophenyl)-3-oxoprop-1-enyl]phenoxy]-2-phenyl-4,4a,6,7,8,8a-hexahydropyrano[3,2-d][1,3]dioxin-8-yl]oxy]acetic acid; 18888227: 2-[[7-Acetamido-2-(furan-2-yl)-6-[4-[(E)-3-phenylprop-2-enoyl]phenoxy]-4,4a,6,7,8,8a-hexahydropyrano[3,2-d][1,3]dioxin-8-yl]oxy]acetic acid; 18888228: 2-[[7-Acetamido-2-(furan-2-yl)-6-[2-[(E)-3-phenylprop-2-enoyl]phenoxy]-4,4a,6,7,8,8a-hexahydropyrano[3,2-d][1,3]dioxin-8-yl]oxy]acetic acid; 18888229: 2-[[7-Acetamido-2-(furan-2-yl)-6-[4-[(E)-3-oxo-3-phenylprop-1-enyl]phenoxy]-4,4a,6,7,8,8a-hexahydropyrano[3,2-d][1,3]dioxin-8-yl]oxy]acetic acid; 18888231: 2-[[7-Acetamido-6-[4-[(E)-3-(4-chlorophenyl)-3-oxoprop-1-enyl]phenoxy]-2-(furan-2-yl)-4,4a,6,7,8,8a-hexahydropyrano[3,2-d][1,3]dioxin-8-yl]oxy]acetic acid; 19986357: (E)-1-[2-Hydroxy-4-(oxan-2-yloxy) phenyl]-3-phenylprop-2-en-1-one; 20838692: (Z)-3-(3-Hydroxy-4-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one; 21159083: 1-[2,4-Dihydroxy-6-[(2S,3R,4S,5S,6R)-3,4,5-trihydroxy-6-(hydroxymethyl)oxan-2-yl]oxyphenyl]-3-(4-hydroxyphenyl)propan-1-one; (E)-1,3-diphenylprop-2-en-1-one; 21362351: (E)-3-(1-Benzofuran-5-yl)-1-[2-[(6-ethyl-3,4,5-trimethyloxan-2-yl)methyl]-6-hydroxy-4-methylphenyl]prop-2-en-1-one; 21362356: (E)-3-(1-Benzofuran-5-yl)-1-[2-hydroxy-4-methyl-6-[[3,4,5-trihydroxy-6-(hydroxymethyl)oxan-2-yl]methyl]phenyl]prop-2-en-1-one; 21362358: (E)-3-(1-Benzofuran-5-yl)-1-[2-methoxy-4-methyl-6-[[3,4,5-trihydroxy- 6-(hydroxymethyl) oxan-2-yl]methyl]phenyl]prop-2-en-1-one; 21550846: (E)-1-(2,4-Dihydroxyphenyl)-3-[4-[(2S,3S,4S,5R,6S)-3,4,5-trihydroxy-6-(hydroxymethyl)oxan-2-yl]oxyphenyl]prop-2-en-1-one; 21726591: (E)-3-(4-Chlorophenyl)-1-[2-methoxy-6-(oxan-2-yloxy)phenyl]prop-2-en-1-one; 21726593: (E)-1-[2-Methoxy-6-(oxan-2-yloxy)phenyl]-3-(4-nitro-phenyl)prop-2-en-1-one; 21726596: (E)-1-[2-Methoxy-6-(oxan-2-yloxy)phenyl]-3-(4-methylphenyl)prop-2-en-1-one; 21729319: 4,2',4'-Trihydroxy-6'-methoxychalcone 4-glucoside; 22297302: (2R,3S)-3-[5-[(E)-3-(2,4-Dihydroxyphenyl)-3-oxoprop-1-enyl]-2-hydroxyphenyl]-5-hydroxy-2-(4-hydroxy-phenyl)-7-[3,4,5-trihydroxy-6-(hydroxymethyl)oxan-2-yl]oxy-2,3-dihydrochromen-4-one; 22297303: (2S,3R)-3-[5-[(E)-3-(2,4-Dihydroxyphenyl)-3-oxoprop-1-enyl]-2-hydroxyphenyl]-5-hydroxy-2-(4-hydroxyphenyl)-7-[3,4,5-trihydroxy-6-(hydroxymethyl)oxan-2-yl]oxy-2,3-dihydrochromen-4-one; 22524310: (E)-1-[2,4-Dihydroxy-6-[(2S,3R,4R,5S,6R)-3,4,5-trihydroxy-6-(hydroxymethyl)oxan-2-yl]oxyphenyl]-3-(4-hydroxyphenyl)prop-2-en-1-one; 22524410: CID 22524410; 22819972: [(2R,3S,4R,5R,6S)-5-Acetamido-3,4-diacetyloxy-6-[3,5-dimethoxy-2-[(E)-3-(4-methoxyphenyl)prop-2-enoyl]phenoxy]oxan-2-yl]methyl acetate; 22819973: N-[(2S,3R,4R,5S,6R)-2-[3,5-Dimethoxy-2-[(E)-3-(4-methoxyphenyl)prop-2-enoyl]phenoxy]-4,5-dihydroxy-6-(hydroxymethyl)oxan-3-yl]acetamide; 23144947: 4'-Hydroxychalcone 4'-glucoside; 23724744: Chalconaringenin 4'-glucoside; 23724745: 2',3,4,4',6'-Pentahydroxychalcone 4'-O-beta-D-glucoside; 23724747: Naringin chalcone; 23730416: 2'-Methoxy-4,4'-diacetoxy-6'-[[(S)-1-[4-(trifluoromethylsulfonyloxy)phenyl]-5-oxo-7-[4-(tetrahydro-2H-pyran-2-yloxy)phenyl]-3-heptenyl]oxy]chalcone; 23930387: [(2R,3R,4S,5R,6S)-3,4,5-Trihydroxy-6-[3-hydroxy-4-[(E)-3-phenylprop-2-enoyl]phenoxy]oxan-2-yl]methyl 3,4,5-trihydroxybenzoate; 24211943: (E)-1-[4-[(2S,4R,5S)-4,5-Dihydroxy-6-(hydroxymethyl)-3-[(2S,4S,5R)-3,4,5-trihydroxy-6-methyloxan-2-yl]oxyoxan-2-yl]oxy-2,6-dihydroxyphenyl]-3-(4-methoxyphenyl)prop-2-en-1-one; 24721139: (E)-3-(4-Hydroxy-phenyl)-1-[2-hydroxy-4-[(3R,4S,5S)-3,4,5-trihydroxy-6-(hydroxymethyl)oxan-2-yl]oxyphenyl]prop-2-en-1-one; 24777109: CID 24777109; 24777110: CID 24777110; 24777112: (E)-3-[4-[3-[Di(propan-2-yl)amino]prop-1-ynyl]phenyl]-1-[4-(oxan-2-yloxy)phenyl]prop-2-en-1-one; 24777245: (E)-1-[4-[3-[Di(propan-2-yl)amino]prop-1-ynyl]phenyl]-3-[4-(oxan-2-yloxy)phenyl]prop-2-en-1-one; 24777246: (E)-1-[4-(Oxan-2-yloxy)phenyl]-3-[4-[4-[(E)-3-[4-(oxan-2-yloxy)phenyl]-3-oxoprop-1-enyl]phenyl]buta-1,3-diynyl]phenyl]prop-2-en-1-one; 24777964: 4-(Tetrahydro-2H-pyran-2-yloxy)-4'-ethynylchalcone; 24777965: (E)-3-[4-(Oxan-2-yloxy)phenyl]-1-[4-[4-[(E)-3-[4-(oxan-2-yloxy)phenyl]prop-2-enoyl]phenyl]buta-1,3-diynyl]phenyl]prop-2-en-1-one; 25117344: (E)-3-[3-[(7-Chloroquinolin-4-yl)amino]phenyl]-1-[4-(oxan-2-yloxy)phenyl]prop-2-en-1-one; 42603440: Arenariumoside III; 42607522: Isoliquiritigenin 4,4'-diglucoside; 42607523: Isoliquiritigenin 2'-glucosyl-(1→4)-rhamnoside; 42607524: Monospermoside; 42607525: Isoliquiritigenin 4'-O-glucoside 4-O-apiofuranosyl-(1'''→2''')-glucoside; 42607526: Isoliquiritigenin 4-O-(5'''-O-p-coumaroyl)-apiofuranosyl-(1'''→2''')-glucoside; 42607527: Isoliquiritigenin 4-O-(5'''-O-feruloyl)-apio-furanosyl-(1'''→2''')-glucoside; 42607543: Butein 3,2'-diglucoside; 42607544: Butein 4'-arabinosyl-(1→4)-galactoside; 42607545: Homobutein 4-glucoside; 42607583: 4,2'-Dihydroxychalcone 4-glucoside; 42607585: 3,4-Dihydroxychalcone 4-beta-L-arabino-pyranosyl-(1→4)-galactoside; 42607601: Chalconaringenin 4-glucoside; 42607602: Chalconaringenin 2'-(6''-p-coumarylglucoside); 42607603: Chalconaringenin 2'-xyloside; 42607604: Chalconaringenin 2'-rhamnosyl-(1→4)-xyloside; 42607605: Chalconaringenin 2'-rhamnosyl-(1→4)-glucoside; 42607606: Chalconaringenin 2',4'-di-O-glucoside; 42607607: Chalconaringenin 2'-O-glucoside 4'-O-gentobioside; 42607611: 3,4,2',4',6'-Pentahydroxychalcone 2'-glucoside; 42607612: 3,4,2',4',6'-Pentahydroxychalcone 4'-glucoside; 42607615: Homoeriodictyolchalcone 2'-glucoside; 42607621: Helichrysin; 42607622: 4,2',4'-Trihydroxy-6'-methoxychalcone 4,4'-di-beta-glucoside; 42607623: Helichrysetin 4,4'-di-O-alpha-glucoside; 42607625: 3,4',6'-Trihydroxy-4,2'-dimethoxychalcone 4'-O-rutinoside; 42607627: 4,2'-Dihydroxy-4',6'-dimethoxychalcone 4-O-(5'''-O-p-cinnamoyl)-apiofuranosyl-(1'''→2'')-glucoside; 42637918: (E)-3-(4-Chlorophenyl)-1-[4-(oxan-2-yloxy)phenyl]prop-2-en-1-one; 44249754: (E)-3-(4-Bromophenyl)-1-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 44249790: (E)-3-(1,3-Benzodioxol-5-yl)-1-[4-[2-[[(1R,4S,5R,8S,9R,10S,12R,13R)-1,5,9-trimethyl-11,14,15,16-tetraoxatetracyclo[10.3.1.04,13.08,13] hexa-decan-10-yl]oxy]ethoxy]phenyl]prop-2-en-1-one; 44627063: (E)-3-(3,4-Dimethoxyphenyl)-1-[2-hydroxy-6-methoxy-4-[(2S,3R,4S,5S,6R)-3,4,5-trihydroxy-6-(hydroxymethyl)oxan-2-yl]oxyphenyl]prop-2-en-1-one; 45032251: 4-[(2E)-3-Phenylprop-2-enoyl]phenyl 2-(acetyl-amino)-2-deoxyhexopyranoside; 45047849: 3-(4-Hydroxy-phenyl)-1-(4-hydroxy-2-(gluco-pyranosyl)-phenyl)-propenone; 45047856: 1-(2-Hydroxy-6-(gluco-pyranosyl)-phenyl)-3-(4-nitro-phenyl)-propenone; 45050852: 2-[3-(4-Chlorophenyl)acryloyl]-3,5-dihydroxyphenyl alpha-L-glucopyranoside; 45267438: (E)-3-(3,4-Dimethoxyphenyl)-1-[4-[2-[[(1S,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 45267439: [(1S,4S,5R,8S,9R,10S,12R,13R)-1,5,9-Trimethyl-11,14,15,16-tetraoxatetracyclo[10.3.1.04,13.08,13]hexadecan-10-yl]2-[4-[(E)-3-(4-methoxyphenyl)prop-2-enoyl]phenoxy]acetate; 45268274: (E)-3-(4-Chlorophenyl)-1-[4-[2-[[(1S,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 45268275: (E)-3-(4-Methoxyphenyl)-1-[4-[2-[[(1S,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 45268276: (E)-3-Phenyl-1-[4-[2-[[(1S,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 45269155: (E)-3-(1,3-Benzodioxol-5-yl)-1-[4-[2-[[(1S,4S,5R,8S,9R,10S,12R,13R)-1,5,9-trimethyl-11,14,15,16-tetraoxatetracyclo[10.3.1.04, 13.08,13]hexadecan-10-yl]oxy]ethoxy]phenyl]prop-2-en-1-one; 45270851: [(1S,4S,5R,8S,9R,10S,12R,13R)-1,5,9-Trimethyl-11,14,15,16-tetraoxatetracyclo[10.3.1.04,13.08,13]hexadecan-10-yl] 2-[4-[(E)-3-(4-ethoxyphenyl)prop-2-enoyl]phenoxy]acetate; 45271694: [(1S,4S,5R,8S,9R,10S,12R,13R)-1,5,9-Trimethyl-11,14,15,16-tetraoxatetracyclo[10.3.1.04, 13.08,13]hexadecan-10-yl] 2-[4-[(E)-3-(4-chlorophenyl)prop-2-enoyl]phenoxy]acetate; 45271695: [(1S,4S,5R,8S,9R,10S,12R,13R)-1,5,9-Trimethyl-11,14,15,16-tetraoxatetracyclo[10.3.1.04,13.08,13]hexadecan-10-yl] 2-[4-[(E)-3-(4-bromophenyl)prop-2-enoyl]phenoxy]acetate; 45272571: (E)-3-(4-Bromophenyl)-1-[4-[2-[[(1S,4S,5R,8S,9R,10S,12R,13R)-1,5,9-trimethyl-11,14,15,16-tetraoxatetracyclo[10.3.1.04,13.08,13] hexadecan-10-yl]oxy]ethoxy]phenyl]prop-2-en-1-one;

45272572: (E)-3-(4-Ethoxyphenyl)-1-[4-[2-[[(1S,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 45783227: [(2R,3S,4S,5R,6S)-6-[4-[(E)-3-(2,4-Dihydroxyphenyl)-3-oxoprop-1-enyl]phenoxy]-3,4,5-trihydroxyoxan-2-yl]methyl (E)-3-(4-hydroxyphenyl)prop-2-enoate; 46232188: (E)-3-[4-[(2S,3R,4S,5S,6R)-3-[(2R,3S,4S)-3,4-Dihydroxy-4-(hydroxymethyl)oxolan-2-yl]oxy-4,5-dihydroxy-6-(hydroxy-methyl)oxan-2-yl]oxyphenyl]-1-(2,4-dihydroxyphenyl)prop-2-en-1-one; 46873245: (E)-1-(4-Nitrophenyl)-3-[4-[(2S,3R,4R,5S,6R)-3,4,5-trihydroxy-6-(hydroxymethyl)oxan-2-yl]oxyphenyl]prop-2-en-1-one; 52904993: N-[(2S,3R,4R,5S,6R)-4,5-Dihydroxy-6-(hydroxymethyl)-2-[4-[(E)-3-phenylprop-2-enoyl]phenoxy]oxan-3-yl]acetamide; 53253743: (E)-1-(4-Bromophenyl)-3-[4-[(2S,3R,4R,5S,6R)-3,4,5-trihydroxy-6-(hydroxymethyl)oxan-2-yl]oxyphenyl]prop-2-en-1-one; 53389715: 2-[4-[(E)-3-[4-(Trifluoromethoxy)phenyl]prop-2-enoyl]phenoxy]-N-[(1S,4S,5R,8S,9R,10S,12R,13R)-1,5,9-trimethyl-11,14,15,16-tetraoxatetracyclo[10.3.1.04,13.08,13]hexadecan-10-yl]acetamide; 53390085: 2-[4-[(E)-3-(4-Fluorophenyl)prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390087: 2-[4-[(E)-3-(4-Chlorophenyl)prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390088: 2-[4-[(E)-3-Phenylprop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390187: 2-[4-[(E)-3-(3-Methoxyphenyl)prop-2-enoyl]phenoxy]-N-[(1S,4S,5R,8S,9R,10R,12R,13R)-1,5,9-trimethyl-11,14,15,16-tetraoxatetracyclo[10.3.1.04, 13.08,13]hexadecan-10-yl]acetamide; 53390190: 2-[4-[(E)-3-(3,4-Difluorophenyl)prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390285: 2-[4-[(E)-3-(4-Methylsulfonylphenyl)prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390287: 2-[4-[(E)-3-[4-(Trifluoromethyl)phenyl]prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexa-decan-10-yl]acetamide; 53390376: 2-[4-[(Z)-3-(4-Chlorophenyl)prop-2-enoyl]phenoxy]-N-[(1S,4S,5R,8S,9R,10R,12R,13R)-1,5,9-trimethyl-11,14,15,16-tetraoxatetracyclo[10.3.1.04, 13.08,13]hexadecan-10-yl]acetamide; 53390377: 2-[4-[(Z)-3-[4-(Trifluoromethyl)phenyl]prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390378: 2-[4-[(Z)-3-(3-Methoxyphenyl)prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53390819: 2-[4-[(E)-3-[4-(Trifluoromethoxy)phenyl]prop-2-enoyl]phenoxy]-N-[(1S,4S,5R,8S,9R,10R,12R,13R)-1,5,9-trimethyl-11,14,15,16-tetraoxatetracyclo[10.3.1.04,13.08,13]hexadecan-10-yl]acetamide; 53391221: 2-[4-[(E)-3-[3-(Trifluoromethyl)phenyl]prop-2-enoyl]phenoxy]-N-[(1S,4S,5R,8S,9R,10S,12R,13R)-1,5,9-trimethyl-11,14,15,16-tetraoxatetracyclo[10.3.1.04,13.08,13]hexadecan-10-yl]acetamide; 53391304: 2-[4-[(E)-3-(4-Fluorophenyl)prop-2-enoyl]phenoxy]-N-[(1S,4S,5R,8S,9R,10S,12R,13R)-1,5,9-trimethyl-11,14,15,16-tetraoxatetracyclo[10.3.1.04,13.08,13]hexadecan-10-yl]acetamide; 53391305: 2-[4-[(E)-3-(4-Chlorophenyl)prop-2-enoyl]phenoxy]-N-[(1S,4S,5R,8S,9R,10S,12R,13R)-1,5,9-trimethyl-11,14,15,16-tetraoxatetracyclo[10.3.1.04,13.08,13]hexadecan-10-yl]acetamide; 53391394: 2-[4-[(E)-3-(3,4-Difluorophenyl)prop-2-enoyl]phenoxy]-N-[(1S,4S,5R,8S,9R,10S,12R,13R)-1,5,9-trimethyl-11,14,15,16-tetraoxatetracyclo[10.3.1.04,13.08,13]hexa-decan-10-yl]acetamide; 53391395: 2-[4-[(E)-3-(3-Methoxyphenyl)prop-2-enoyl]phenoxy]-N-[(1S,4S,5R,8S,9R,10S,12R,13R)-1,5,9-trimethyl-11,14,15,16-tetraoxatetracyclo[10.3.1.04, 13.08,13]hexadecan-10-yl]acetamide; 53391397: 2-[4-[(E)-3-Phenylprop-2-enoyl]phenoxy]-N-[(1S,4S,5R,8S,9R,10S,12R,13R)-1,5,9-trimethyl-11,14,15,16-tetraoxatetracyclo[10.3.1.04,13.08,13]hexadecan-10-yl]acetamide; 53493966: (3R,12Ar)-3,4,5,5aalpha,6,7,8,8aalpha,9,10-Decahydro-3,6alpha,9beta-trimethyl-3beta,12alpha-epoxy-10beta-[4-[(E)-4-(trifluoromethoxy)cinnamoyl]phenoxyacetylamino]pyrano[4,3-j]-1,2-benzodioxepin; 53493967: (3R,12Ar)-3,4,5,5aalpha,6,7,8,8aalpha,9,10-Decahydro-3,6alpha,9beta-trimethyl-3beta,12alpha-epoxy-10beta-[4-[(E)-3-(trifluoromethyl)cinnamoyl]phenoxyacetylamino]pyrano[4,3-j]-1,2-benzodioxepin; 53493968: (3R,12Ar)-3,4,5,5aalpha,6,7,8,8aalpha,9,10-Decahydro-3,6alpha,9beta-trimethyl-3beta,12alpha-epoxy-10beta-[4-[(E)-4-fluorocinnamoyl]phenoxyacetylamino]pyrano[4,3-j]-1,2-benzodioxepin; 53493969: 2-[4-[(E)-3-(4-Chlorophenyl)prop-2-enoyl]phenoxy]-N-[(1R,4S,5R,8S,9R,10S,12R,13R)-1,5,9-trimethyl-11,14,15,16-tetraoxatetracyclo[10.3.1.04, 13.08,13]hexadecan-10-yl]acetamide; 53494096: 2-[4-[(E)-3-(3-Methoxyphenyl)prop-2-enoyl]phenoxy]-N-[(1R,4S,5R,8S,9R,10S,12R,13R)-1,5,9-trimethyl-11,14,15,16-tetraoxatetracyclo[10.3.1.04,13.08,13]hexadecan-10-yl]acetamide; 53494097: (3R,12Ar)-3,4,5,5aalpha,6,7,8,8aalpha,9,10-Decahydro-3,6alpha,9beta-trimethyl-3beta,12alpha-epoxy-10beta-[4-[(E)-cinnamoyl]phenoxyacetylamino]pyrano[4,3-j]-1,2-benzodioxepin; 53494230: 2-[4-[(E)-3-(1,3-Benzodioxol-5-yl)prop-2-enoyl]phenoxy]-N-[(1R,4S,5R,8S,9R,10S,12R,13R)-1,5,9-trimethyl-11,14,15,16-tetraoxatetracyclo[10.3.1.04,13.08,13]hexa-decan-10-yl]acetamide; 53494371: 2-[4-[(E)-3-[4-(Trifluoromethoxy)phenyl]prop-2-enoyl]phenoxy]-N-[(1R,4S,5R,8S,9R,10R,12R,13R)-1,5,9-trimethyl-11,14,15,16-tetraoxatetracyclo[10.3.1.04,13.08,13]hexadecan-10-yl]acetamide; 53494372: 2-[4-[(E)-3-[3-(Trifluoromethyl)phenyl]prop-2-enoyl]phenoxy]-N-[(1R,4S,5R,8S,9R,10R,12R,13R)-1,5,9-trimethyl-11,14,15,16-tetraoxatetracyclo[10.3.1.04,13.08,13]hexadecan-10-yl]acetamide; 53494373: 2-[4-[(E)-3-(4-Fluorophenyl)prop-2-enoyl]phenoxy]-N-[(1R,4S,5R,8S,9R,10R,12R,13R)-1,5,9-trimethyl-11,14,15,16-tetraoxatetracyclo[10.3.1.04,13.08,13]hexadecan-10-yl]acetamide; 53494374: 2-[4-[(E)-3-(4-Chlorophenyl)prop-2-enoyl]phenoxy]-N-[(1R,4S,5R,8S,9R,10R,12R,13R)-1,5,9-trimethyl-11,14,15,16-tetraoxatetracyclo[10.3.1.04, 13.08, 13]hexadecan-10-yl]acetamide; 53494506: 2-[4-[(E)-3-(3-Methoxyphenyl)prop-2-enoyl]phenoxy]-N-[(1R,4S,5R,8S,9R,10R,12R,13R)-1,5,9-trimethyl-11,14,15,16-tetraoxatetracyclo[10.3.1.04,13.08,13]hexadecan-10-yl]acetamide; 53494507: 2-[4-[(E)-3-Phenylprop-2-enoyl]phenoxy]-N-[(1R,4S,5R,8S,9R,10R,12R,13R)-1,5,9-trimethyl-11,14,15,16-tetraoxatetracyclo[10.3.1.04,13.08, 13]hexadecan-10-yl]acetamide; 53494637: (3R,12Ar)-3,4,5,5aalpha,6,7,8,8aalpha,9,10-Decahydro-3,6alpha,9beta-trimethyl-3beta,12alpha-epoxy-10alpha-[4-[(E)-1-oxo-3-(1,3-benzodioxole-5-yl)-2-propenyl]phenoxyacetylamino]pyrano[4,3-j]-1,2-benzodioxepin; 53716400: [(2R,3S,4R,5R,6S)-5-Acetamido-3,4-diacetyloxy-6-[3,5-dimethoxy-2-[3-(4-methoxyphenyl)prop-2-enoyl]phenoxy]oxan-2-yl]

methyl acetate; 53770211: 1-[2-Hydroxy-4-(oxan-2-yloxy)phenyl]-3-phenylprop-2-en-1-one; 53999557: 3-[3,4-Bis(oxan-2-yloxy)phenyl]-1-[4-(oxan-2-yloxy)phenyl]prop-2-en-1-one; 54106084: 1-[2-Hydroxy-4-(oxan-2-yloxy)phenyl]-3-[4-methoxy-3-(oxan-2-yloxy)phenyl]prop-2-en-1-one; 54153200: 3-[3,4-Bis(oxan-2-yloxy)phenyl]-1-[2-hydroxy-4-(oxan-2-yloxy)phenyl]prop-2-en-1-one; 54155269: 1-[2-Hydroxy-4,6-bis(oxan-2-yloxy)phenyl]-3-[4-(oxan-2-yloxy)phenyl]prop-2-en-1-one; 54303977: 1-[2-Hydroxy-4-(oxan-2-yloxy)phenyl]-3-(4-methoxyphenyl)prop-2-en-1-one; 54348409: 2'-Hydroxy-4,4'-bis(tetrahydropyranyloxy) chalcone; 54398527: N-[(2S,3R,4R,5S,6R)-2-[3,5-Dimethoxy-2-[3-(4-methoxyphenyl)prop-2-enoyl]phenoxy]-4,5-dihydroxy-6-(hydroxymethyl)oxan-3-yl]acetamide; 54403936: 3-[3,4-Bis(oxan-2-yloxy)phenyl]-1-(2-hydroxyphenyl)prop-2-en-1-one; 54529107: 3-[3,4-Bis(oxan-2-yloxy)phenyl]-1-[2-hydroxy-4,6-bis(oxan-2-yloxy)phenyl]prop-2-en-1-one; 54538532: 1-[2-Hydroxy-4-(oxan-2-yloxy)phenyl]-3-[3-methoxy-4-(oxan-2-yloxy)phenyl]prop-2-en-1-one; 56650392: 2-[4-[(E)-3-(3,4-Difluorophenyl)prop-2-enoyl]phenoxy]-N-[(1R,4S,5R,8S,9R,10S,12R,13R)-1,5,9-trimethyl-11,14,15,16-tetraoxatetracyclo[10.3.1.04,13.08,13]hexadecan-10-yl]acetamide; 56650732: 2-[4-[(E)-3-(4-Methylsulfonylphenyl)prop-2-enoyl]phenoxy]-N-[(1R,4S,5R,8S,9R,10S,12R,13R)-1,5,9-trimethyl-11,14,15,16-tetraoxatetracyclo[10.3.1.04, 13.08,13]hexadecan-10-yl]acetamide; 56651073: 2-[4-[(E)-3-(3,4-Difluorophenyl)prop-2-enoyl]phenoxy]-N-[(1R,4S,5R,8S,9R,10R,12R,13R)-1,5,9-trimethyl-11,14,15,16-tetraoxatetracyclo[10.3.1.04,13.08,13]hexadecan-10-yl] acetamide; 56651407: 2-[4-[(E)-3-(4-Methylsulfonylphenyl)prop-2-enoyl]phenoxy]-N-[(1R,4S,5R,8S,9R,10R,12R,13R)-1,5,9-trimethyl-11,14,15,16-tetraoxatetracyclo[10.3.1.04,13.08,13]hexadecan-10-yl]acetamide; 56651410: 2-[4-[(E)-3-(4-Chlorophenyl)-3-oxoprop-1-enyl]phenoxy]-N-[(1R,4S,5R,8S,9R,10S,12R,13R)-1,5,9-trimethyl-11,14,15,16-tetraoxatetracyclo[10.3.1.04,13.08,13]hexa-decan-10-yl]acetamide; 56651744: 2-[4-[(E)-3-(4-Fluorophenyl)-3-oxoprop-1-enyl]phenoxy]-N-[(1R,4S,5R,8S,9R,10S,12R,13R)-1,5,9-trimethyl-11,14,15,16-tetraoxatetracyclo[10.3.1.04,13.08,13]hexadecan-10-yl]acetamide; 56651746: 2-[4-[(E)-3-Oxo-3-phenylprop-1-enyl]phenoxy]-N-[(1R,4S,5R,8S,9R,10S,12R,13R)-1,5,9-trimethyl-11,14,15,16-tetraoxatetracyclo[10.3.1.04,13.08,13]hexadecan-10-yl]acetamide; 56651747: 2-[4-[(E)-3-Oxo-3-[4-(trifluoromethyl)phenyl]prop-1-enyl]phenoxy]-N-[(1R,4S,5R,8S,9R,10S,12R,13R)-1,5,9-trimethyl-11,14,15,16-tetraoxatetracyclo[10.3.1.04,13.08,13]hexadecan-10-yl]acetamide; 56925805: (E)-3-[3,4-Bis(oxan-2-yloxy)phenyl]-1-[2,4,6-tris(oxan-2-yloxy)phenyl]prop-2-en-1-one; 57133872: N-[(2S,3S,4R,5S,6R)-2-[3,5-Dimethoxy-2-[3-(4-methoxyphenyl)prop-2-enoyl]phenoxy]-4,5-dihydroxy-6-(hydroxymethyl)oxan-3-yl]acetamide; 57168663: 3-(3,4-Dihydroxyphenyl)-1-[2-hydroxy-4-[3,4,5-trihydroxy-6-(hydroxymethyl)oxan-2-yl]oxyphenyl]prop-2-en-1-one; 58208350: (E)-N-(Oxan-2-yloxy)-3-[4-[(E)-3-oxo-3-phenylprop-1-enyl]phenyl]prop-2-enamide; 58208372: [4-[(E)-3-[4-[(E)-4-(Oxan-2-yloxy)-3-oxobut-1-enyl]phenyl]prop-2-enoyl]phenyl]methyl methanesulfonate; 58592127: (E)-1-[2,6-Dihydroxy-4-[(2S,4S,5R)-3,4,5-trihydroxy-6-[[(2R,4S,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 58769120: (E)-3-[3-Methoxy-4-(oxan-2-yloxy)phenyl]-1-phenylprop-2-en-1-one; 58833434: (E)-3-[3-Methyl-4-(oxan-2-yloxy)phenyl]-1-phenylprop-2-en-1-one; 58974313: N-(Oxan-2-yloxy)-4-[(E)-3-oxo-3-phenylprop-1-enyl]benzamide; 58975263: (E)-1-[2-Methyl-4-(oxan-2-yloxy)phenyl]-3-phenylprop-2-en-1-one; 58975272: 4'-(Tetrahydro-2H-pyran-2-yloxy)chalcone; 58975276: (E)-3-[3-(Oxan-2-yloxy)phenyl]-1-[4-(oxan-2-yloxy)phenyl]prop-2-en-1-one; 58981636: (E)-1-[2-[5-Fluoro-3,4-dihydroxy-6-(hydroxymethyl)oxan-2-yl]oxy-6-hydroxy-4-methylphenyl]-3-(4-methoxyphenyl)prop-2-en-1-one; 59312563: Methanesulfonic acid 4-((E)-3-4-[(E)-2-(tetrahydro-pyran-2-yloxycarbamoyl)-vinyl]-phenyl-acryloyl)-benzyl ester; 59349184: (E)-N-(3-Methyl-4-(3-(3-methyl-4-(tetrahydro-2H-pyran-2-yloxy)phenyl)acryloyl)phenyl)acetamide; 59408804: (E)-3-(3-Hydroxy-4-methoxyphenyl)-1-[2-hydroxy-6-methoxy-4-[(2S,4S,5R)-3,4,5-trihydroxy-6-[[(1R,3S,4S)-2,3,4-trihydroxy-5-methylcyclohexyl]oxymethyl]oxan-2-yl]oxyphenyl]prop-2-en-1-one; 59576450: (E)-1-[2-Hydroxy-4-(oxan-2-yloxy)phenyl]-3-[4-methoxy-3-(oxan-2-yloxy)phenyl]prop-2-en-1-one; 66607829: 1,3-Diphenylprop-2-en-1-one;(2S)-5-hydroxy-2-(3-hydroxy-4-methoxyphenyl)-7-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxy-2,3-dihydrochromen-4-one; 66912770: 4'-Glucosyloxychalkon; 67128,786: 3-[3-Hydroxy-4-[(2R,3R,4S,5S,6R)-3,4,5-trihydroxy-6-(hydroxymethyl)oxan-2-yl]oxyphenyl]-1-(2,4,6-trihydroxyphenyl)prop-2-en-1-one; 67566248: 2'-(beta-D-Glucopyranosyloxy)-6'-hydroxy-3-(5-benzo[b]furanyl)acrylophenone; 68498929: 3-Bromo-4'-(tetrahydropyranyloxy)chalcone; 68597153: N-[3-Methyl-4-[3-[3-methyl-4-(oxan-2-yloxy)phenyl]prop-2-enoyl]phenyl]acetamide; 68985794: 1-[2-Hydroxy-4-[(3R,4S,5S,6R)-3,4,5-trihydroxy-6-(hydroxymethyl)oxan-2-yl]oxyphenyl]-3-phenylprop-2-en-1-one; 69256468: 7-[(2S,3R,4S,5S,6R)-4,5-Dihydroxy-6-(hydroxymethyl)-3-[(2S,3R,4R,5R,6S)-3,4,5-trihydroxy-6-methyloxan-2-yl]oxyoxan-2-yl]oxy-5-hydroxy-2-(4-hydroxyphenyl)-2,3-dihydrochromen-4-one;1,3-diphenylprop-2-en-1-one; 69304756: [(3R,4Ar,5S,6S,6aS,10S,10aR,10bS)-3-ethenyl-6,10,10b-trihydroxy-3,4a,7,7,10a-pentamethyl-1-oxo-5,6,6a,8,9,10-hexahydro-2H-benzo[f]chromen-5-yl] acetate; (E)-1-(2,4-dihydroxyphenyl)-3-(4-hydroxyphenyl)prop-2-en-1-one; 69453837: (E)-3-[4-(Dimethyl-amino)phenyl]-1-[4-(oxan-2-yloxy)phenyl]prop-2-en-1-one; 69453838: 3-[4-(Dimethyl-amino)phenyl]-1-[4-(oxan-2-yloxy)phenyl]prop-2-en-1-one; 69507707: 3-[3-(Oxan-2-yloxy)phenyl]-1-[4-(oxan-2-yloxy)phenyl]prop-2-en-1-one; 69507714: 1,3-Bis4-[(oxan-2-yl)oxy]phenylprop-2-en-1-one; 69507855: 1-[4-(Oxan-2-yloxy)phenyl]-3-phenylprop-2-en-1-one; 69508058: 1-[2-Methyl-4-(oxan-2-yloxy)phenyl]-3-phenylprop-2-en-1-one; 69808174: 7-[(2S,3R,4S,5S,6R)-4,5-Dihydroxy-6-(hydroxymethyl)-3-[(2S,3R,4R,5R,6S)-3,4,5-trihydroxy-6-methyloxan-2-yl]oxyoxan-2-yl]oxy-5-hydroxy-2-(3-hydroxy-4-methoxyphenyl)-2,3-dihydrochromen-4-one;1,3-diphenylprop-2-en-1-one; 70681502: (Z)-1-[2,4-Dihydroxy-6-[(2S,3S,4S,5S,6S)-3,4,5-trihydroxy-6-(hydroxymethyl)oxan-2-yl]oxyphenyl]-3-(4-hydroxyphenyl)prop-2-en-1-one; 71299489: [(2R,3R,4S,5S,6R)-3,4,5-Triacetyloxy-6-[4-[(E)-3-phenylprop-2-enoyl]phenoxy]oxan-2-yl]methyl acetate; 71299490: [(2S,3S,4R,5S,6R)-4,5-Diacetyloxy-6-[4-[(E)-3-phenylprop-2-enoyl]phenoxy]-3-[(2R,3S,4S,5R,6R)-3,4,5-triacetyloxy-6-(acetyloxymethyl)oxan-2-yl]oxyoxan-2-yl]methyl acetate; 71299491: [(2R,3R,4S,5S,6R)-3,4,5-Triacetyloxy-6-[4-[(E)-3-oxo-3-phenylprop-1-enyl]phenoxy]oxan-2-yl]methyl acetate; 71299492: [(2S,3S,4R,5S,6R)-4,5-Diacetyloxy-6-[4-[(E)-3-oxo-3-phenyl-prop-1-enyl]phenoxy]-3-[(2R,3S,4S,5R,6R)-3,4,5-triacetyloxy-6-(acetyloxymethyl)oxan-2-yl]oxyoxan-2-yl]methyl acetate; 71963834: N-[(2S,3R,4R,5S,6R)-4,5-Dihydroxy-6-(hydroxymethyl)-2-[4-(3-phenylprop-2-enoyl)phenoxy]oxan-3-yl]acetamide; 71966162: [(2R,3S, 4R,5R,6S)-3,4-Bis(acetyloxy)-5-acetamido-6-[4-(3-phenylprop-2-enoyl)phenoxy]oxan-2-yl]methyl acetate; 72166725: N-[8-Hydroxy-6-[4-(3-oxo-3-phenylprop-1-enyl)phenoxy]-2-phenyl-4,4a,6,7,8,8a-hexahydropyrano[3,2-d][1,3]dioxin-7-yl]acetamide; 72166726: N-[8-Hydroxy-2-phenyl-6-[4-(3-phenylprop-2-enoyl)phenoxy]-4,4a,6,7,8,8a-hexahydropyrano[3,2-d][1,3]dioxin-7-yl]acetamide; 72166727: N-[4,5-Dihydroxy-6-(hydroxymethyl)-2-[4-(3-phenylprop-2-enoyl)phenoxy]oxan-3-yl]acetamide; 72253526: [4-[3-[4-[3-(Oxan-2-yloxyamino)-3-oxoprop-1-enyl]phenyl]prop-2-enoyl]phenyl]methyl methanesulfonate; 72418157: 3-[3-Methoxy-4-(oxan-2-yloxy)phenyl]-1-phenylprop-2-en-1-one; 72439016: 3-[3-Methyl-4-(oxan-2-yloxy)phenyl]-1-phenylprop-2-en-1-one; 72478364: N-(Oxan-2-yloxy)-4-(3-oxo-3-phenylprop-1-enyl)benzamide; 72480195: 1-[2-[5-Fluoro-3,4-dihydroxy-6-(hydroxymethyl)oxan-2-yl]oxy-6-hydroxy-4-methylphenyl]-3-(4-methoxyphenyl)prop-2-en-1-one; 72728334: 1-(2,4-Dihydroxyphenyl)-3-[4-[3,4,5-trihydroxy-6-(hydroxymethyl)oxan-2-yl]oxyphenyl]prop-2-en-1-one; 72729461: 1-[4-[3-[3,4-Dihydroxy-4-(hydroxymethyl)oxolan-2-yl]oxy-4,5-dihydroxy-6-(hydroxymethyl)oxan-2-yl]oxy-2-hydroxyphenyl]-3-(4-hydroxy-phenyl)prop-2-en-1-one; 72732169: 1-[2-Hydroxy-4-methoxy-6-[3,4,5-trihydroxy-6-(hydroxymethyl)oxan-2-yl]oxyphenyl]-3-(4-hydroxyphenyl)prop-2-en-1-one; 72777985: 3-(1-Benzofuran-5-yl)-1-[2-hydroxy-4-methoxy-6-[[3,4,5-trihydroxy-6-(hydroxymethyl)oxan-2-yl]methyl]phenyl]prop-2-en-1-one; 73441249: (E)-3-[4-(Methoxymethoxy)phenyl]-1-[2-methoxy-4-(oxan-2-yloxy)phenyl]prop-2-en-1-one; 73772601: 3-(1-Benzofuran-5-yl)-1-[2-hydroxy-4-methyl-6-[[3,4,5-trihydroxy-6-(hydroxymethyl)oxan-2-yl]methyl]phenyl]prop-2-en-1-one; 73772602: 3-(1-Benzofuran-5-yl)-1-[2-methoxy-4-methyl-6-[[3,4,5-trihydroxy-6-(hydroxymethyl)oxan-2-yl]methyl]phenyl]prop-2-en-1-one; 73981690: 3-(4-Hydroxyphenyl)-1-[2-hydroxy-4-[3,4,5-trihydroxy-6-(hydroxymethyl)oxan-2-yl]oxyphenyl]prop-2-en-1-one; 74259754: 1-[4-[4,5-Dihydroxy-6-(hydroxymethyl)-3-(3,4,5-trihydroxy-6-methyloxan-2-yl)oxyoxan-2-yl]oxy-2,6-dihydroxyphenyl]-3-(4-methoxyphenyl)prop-2-en-1-one; 76336275: [(3R,4S,5R)-5-[(2S,3R,4S,5S,6R)-2-[4-[(E)-3-(2,4-Dihydroxyphenyl)-3-oxoprop-1-enyl]phenoxy]-4,5-dihydroxy-6-(hydroxymethyl)oxan-3-yl]oxy-3,4-dihydroxyoxolan-3-yl]methyl (E)-3-(4-hydroxyphenyl)prop-2-enoate; 76844635: 3-(Acetyloxy)-6-[(acetyloxy)methyl]-2-(4-cinnamoylphenoxy)-5-(3,4,5-tri(acetyloxy)-6-[(acetyloxy)methyl]tetrahydro-2h-pyran-2-yloxy)tetrahydro-2h-pyran-4-ylacetate; 76844636: 3-(Acetyloxy)-6-[(acetyloxy)methyl]-2-[4-(3-oxo-3-phenylprop-1-enyl)phenoxy]-5-(3,4,5-tri(acetyloxy)-6-[(acetyloxy)methyl]tetrahydro-2h-pyran-2-yloxy)tetrahydro-2h-pyran-4-ylacetate; 77068272: 3,5-DI(Acetyloxy)-2-[(acetyl-oxy)methyl]-6-(4-cinnamoylphenoxy)tetrahydro-2H-pyran-4-ylacetate; 77068273: 2-[3,5-Diacetyloxy-2-(acetyloxymethyl)-6-[4-(3-phenylprop-2-enoyl)phenoxy]oxan-4-yl]acetic acid; 77068286: 2-[5-Acetyloxy-2-(acetyloxymethyl)-6-[4-(3-phenylprop-2-enoyl)phenoxy]-3-[3,4,5-triacetyloxy-6-(acetyloxymethyl)oxan-2-yl]oxyoxan-4-yl]acetate; 77068287: 2-[5-Acetyloxy-2-(acetyloxymethyl)-6-[4-(3-phenylprop-2-enoyl)phenoxy]-3-[3,4,5-triacetyloxy-6-(acetyloxymethyl)oxan-2-yl]oxyoxan-4-yl]acetic acid; 77230453: 2-[3,5-Diacetyloxy-2-(acetyloxymethyl)-6-[4-(3-oxo-3-phenylprop-1-enyl)phenoxy]oxan-4-yl]acetate; 77230454: 2-[3,5-Diacetyloxy-2-(acetyloxymethyl)-6-[4-(3-oxo-3-phenylprop-1-enyl)phenoxy]oxan-4-yl]acetic acid; 78319342: [(2R,4S,6S)-2-(4-Chlorophenyl)-6-[4-[(E)-3-(4-chlorophenyl)-3-oxoprop-1-enyl]phenyl]oxan-4-yl] 4-methylbenzenesulfonate; 85199098: Schembl21527701; 86289292: 2',3,4,4',6'-Pentahydroxychalcone 4'-O-beta-D-glucoside(1-); 86289435: 2',4,4',6'-Tetrahydroxychalcone 4'-O-beta-D-glucoside(1-); 86291910: (E)-3-(3,4-Dimethoxyphenyl)-1-[4-[(2S,3R,4S,5R,6R)-5-hydroxy-3,4-dimethoxy-6-[[(2R,3R,4R,5R,6S)-3,4,5-trihydroxy-6-methyloxan-2-yl]oxymethyl]oxan-2-yl]oxy-2,6-dimethoxyphenyl]prop-2-en-1-one; 86291911: (E)-1-[4-[(2S,3R,4S,5S,6R)-4,5-Dihydroxy-3-methoxy-6-[[(2R,3R,4R,5R,6S)-3,4,5-trihydroxy-6-methyloxan-2-yl]oxymethyl]oxan-2-yl]oxy-2-hydroxy-6-methoxyphenyl]-3-(3,4-dimethoxyphenyl)prop-2-en-1-one; 86291912: (E)-3-(3,4-Dimethoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one; 86641367: (E)-3-[4-[(E)-3-[4-(Hydroxymethyl)phenyl]-3-oxoprop-1-enyl]phenyl]-N-(oxan-2-yloxy)prop-2-enamide; 86641368: (E)-3-[4-[(E)-3-[4-(Chloromethyl)phenyl]-3-oxoprop-1-enyl]phenyl]-N-(oxan-2-yloxy)prop-2-enamide; 88249247: (E)-1-[2-[(2S,3R,4R,5S,6R)-3,4-Dihydroxy-6-(hydroxymethyl)-5-[(2S,3R,4S,5S,6R)-3,4,5-trihydroxy-6-(hydroxymethyl)oxan-2-yl]oxyoxan-2-yl]-6-hydroxyphenyl]-3-(4-methoxyphenyl)prop-2-en-1-one; 88250287: (Z)-1-[2-Hydroxy-6-[(2S,3R,4R,5S,6R)-3,4,5-trihydroxy-6-(hydroxymethyl) oxan-2-yl]phenyl]-3-(4-methylphenyl)prop-2-en-1-one; 88250935: (E)-3-(4-Hydroxyphenyl)-1-[2-phenylmethoxy-6-[(2S,3R,4R,5S,6R)-3,4,5-trihydroxy-6-(hydroxymethyl)oxan-2-yl]phenyl]prop-2-en-1-one; 88251175: Ethyl [4-[(Z)-3-oxo-3-[2-phenylmethoxy-6-[(2S,3R,4R,5S,6S)-3,4,5-trihydroxy-6-(hydroxymethyl)oxan-2-yl]phenyl]prop-1-enyl]phenyl] carbonate; 88753802: [(2R,3S,4R,5S,6S)-5-Acetamido-3,4-diacetyloxy-6-[3,5-dimethoxy-2-[(E)-3-(4-methoxyphenyl)prop-2-enoyl]phenoxy]oxan-2-yl]methyl acetate; 88754252: N-[(2S,3S,4R,5S,6R)-2-[3,5-Dimethoxy-2-[(E)-3-(4-methoxyphenyl)prop-2-enoyl]phenoxy]-4,5-dihydroxy-6-(hydroxymethyl)oxan-3-yl]acetamide; 89043374: (E)-3-(3-Hydroxy-4-methoxyphenyl)-1-[2-hydroxy-6-methoxy-4-[(2S,4R,5S)-3,4,5-trihydroxy-6-[[(1R,3S,4S)-2,3,4-trihydroxy-5-methylcyclohexyl]oxymethyl]oxan-2-yl]oxyphenyl]prop-2-en-1-one; 89050027: (E)-1-[4-[(2S,5S)-4,5-Dihydroxy-6-[[(5S)-5,6,7-trihydroxy-4-methylheptan-2-yl]oxymethyl]oxan-2-yl]oxy-2-hydroxy-6-methoxyphenyl]-3-(3-hydroxy-4-methoxyphenyl)prop-2-en-1-one; 89219370: (E)-3-(3-Hydroxy-4-methoxyphenyl)-1-[2-hydroxy-6-methoxy-4-[(2S,5S)-3,4,5-trihydroxy-6-[[(2R,5R)-3,4,5-trihydroxy-6-methyloxan-2-yl]oxymethyl]oxan-2-yl]oxyphenyl]prop-2-en-1-one; 89258670: Hesperidin chalcone; 90136149: (E)-3-(3-Hydroxy-4-methoxyphenyl)-1-[2-hydroxy-6-methoxy-4-[(2S,4R,5S)-3,4,5-trihydroxy-6-[[(2R,4S,5R)-3,4,5-trihydroxy-6-methyloxan-2-yl]oxymethyl]oxan-2-yl]oxyphenyl]prop-2-en-1-one; 90203356: 1,3-Diphenylprop-2-en-1-one;(3R,4S,5S,6R)-6-(hydroxymethyl)oxane-2,3,4,5-tetrol; 91193446: N-(Oxan-2-yl)-4-(3-oxo-3-phenylprop-1-enyl)benzamide; 91234996: 3-[4-[3-[4-(Chloromethyl)phenyl]-3-oxoprop-1-enyl]phenyl]-N-(oxan-2-yloxy)prop-2-enamide; 91259271: 3-[4-[3-[4-(Hydroxymethyl)phenyl]-3-oxoprop-1-enyl]phenyl]-N-(oxan-2-yloxy)prop-2-enamide; 91377096: 3-(3,4-Dihydroxyphenyl)-1-[4-hydroxy-2-[(2S,3R,4S,5S,6R)-3,4,5-trihydroxy-6-(hydroxymethyl)oxan-2-yl]peroxyphenyl]prop-2-en-1-one; 91435153: 3-(3-Hydroxy-4-methoxyphenyl)-1-[2-hydroxy-6-methoxy-4-[(2S,4R,5S)-3,4,5-trihydroxy-6-[[(1R,3S,4S)-2,3,4-trihydroxy-5-methylcyclohexyl]oxymethyl]oxan-2-yl]oxyphenyl]prop-2-en-1-one; 91435429: 1-(2-Hydroxy-4,6-dimethoxyphenyl)-

3-[4-[(2R,3R,4S,5S,6R)-3,4,5-trihydroxy-6-(hydroxymethyl)oxan-2-yl]oxyphenyl]prop-2-en-1-one; 91454387: 1-(2,4-Dihydroxyphenyl)-3-[4-hydroxy-3-[(2S,3R,4S,5S,6R)-3,4,5-trihydroxy-6-(hydroxymethyl)oxan-2-yl]oxyphenyl]prop-2-en-1-one; 91517295: (2S,6S)-2,6-Bis(2-chlorophenyl)oxan-4-one;(3S,5S)-3,5-bis(2-methoxyphenyl)cyclohexan-1-one;(E)-3-(3,4-dimethoxyphenyl)-1-phenylprop-2-en-1-one;2-(4-methoxyphenyl)-3,5-dimethyl-6-(4-methylphenyl)piperidin-4-one;(1E,4E)-1-(4-methoxyphenyl)-5-(4-methylphenyl)penta-1,4-dien-3-one; 91522557: 1-[2,6-Dihydroxy-4-[(2S,4R,5S)-3,4,5-trihydroxy-6-[[(2R,4S,5R)-3,4,5-trihydroxy-6-methyl-oxan-2-yl]oxymethyl]oxan-2-yl]oxyphenyl]-3-(3-hydroxy-4-methoxyphenyl)prop-2-en-1-one; 91525355: 3-(4-Hydroxyphenyl)-1-[2-hydroxy-4-[(2S,3R,4R,5S,6R)-3,4,5-trihydroxy-6-(hydroxymethyl)oxan-2-yl]oxyphenyl]prop-2-en-1-one; 91746158: 2',6'-Dihydroxy-4-methoxychalcone-4'-O-neohesperidoside; 92132543: (E)-1-[4-[(2S,3R,4S,5S,6R)-6-[[(2R,3R,4R,5R,6S)-3,5-Dihydroxy-4,6-dimethyloxan-2-yl]oxymethyl]-3,4,5-trihydroxyoxan-2-yl]oxy-2-hydroxy-6-methoxyphenyl]-3-(3-hydroxy-4-methoxyphenyl)prop-2-en-1-one; 92223797: (E)-3-(4-Hydroxyphenyl)-1-[4-hydroxy-2-[(2R,3R,4R,5S,6S)-3,4,5-trihydroxy-6-(hydroxymethyl)oxan-2-yl]oxyphenyl]prop-2-en-1-one; 92223798: (E)-3-(4-Hydroxyphenyl)-1-[4-hydroxy-2-[(2R,3S,4R,5S,6S)-3,4,5-trihydroxy-6-(hydroxymethyl)oxan-2-yl]oxyphenyl]prop-2-en-1-one; 92224287: (Z)-3-(4-Chlorophenyl)-1-[2,4-dihydroxy-6-[(2S,3R,4R,5S,6S)-3,4,5-trihydroxy-6-(hydroxymethyl)oxan-2-yl]oxyphenyl]prop-2-en-1-one; 92224296: (E)-1-[2-Hydroxy-6-[(2R,3R,4R,5S,6S)-3,4,5-trihydroxy-6-(hydroxymethyl)oxan-2-yl]oxyphenyl]-3-(4-nitro-phenyl)prop-2-en-1-one; 92224297: (E)-1-[2-Hydroxy-6-[(2R,3S,4R,5S,6S)-3,4,5-trihydroxy-6-(hydroxymethyl)oxan-2-yl]oxyphenyl]-3-(4-nitro-phenyl)prop-2-en-1-one; 92842624: (E)-3-(4-Hydroxyphenyl)-1-[4-hydroxy-2-[(2R,3S,4S,5S,6S)-3,4,5-trihydroxy-6-(hydroxymethyl)oxan-2-yl]oxyphenyl]prop-2-en-1-one; 92842626: (E)-3-(4-Hydroxyphenyl)-1-[4-hydroxy-2-[(2R,3R,4S,5S,6S)-3,4,5-trihydroxy-6-(hydroxymethyl)oxan-2-yl]oxyphenyl]prop-2-en-1-one; 92842678: (E)-1-[2-Hydroxy-6-[(2R,3S,4S,5S,6S)-3,4,5-trihydroxy-6-(hydroxymethyl)oxan-2-yl]oxyphenyl]-3-(4-nitro-phenyl)prop-2-en-1-one; 92842680: (E)-1-[2-Hydroxy-6-[(2R,3R,4S,5S,6S)-3,4,5-trihydroxy-6-(hydroxymethyl)oxan-2-yl]oxyphenyl]-3-(4-nitro-phenyl)prop-2-en-1-one; 93056580: (E)-3-(4-Chlorophenyl)-1-[2,4-dihydroxy-6-[(2S,3R,4R,5S,6S)-3,4,5-trihydroxy-6-(hydroxymethyl)oxan-2-yl]oxyphenyl]prop-2-en-1-one; 93286399: (Z)-3-(4-Chlorophenyl)-1-[2,4-dihydroxy-6-[(2S,3S,4R,5S,6S)-3,4,5-trihydroxy-6-(hydroxymethyl)oxan-2-yl]oxyphenyl]prop-2-en-1-one; 93286400: (E)-3-(4-Chlorophenyl)-1-[2,4-dihydroxy-6-[(2S,3S,4R,5S,6S)-3,4,5-trihydroxy-6-(hydroxymethyl)oxan-2-yl]oxyphenyl]prop-2-en-1-one; 97354055: [(2R,3S,4S,5S,6S)-3,4,5-Triacetyloxy-6-[4-[(E)-3-phenylprop-2-enoyl]phenoxy]oxan-2-yl]methyl acetate; 97354057: [(2S,3S,4S,5S,6S)-3,4,5-Triacetyloxy-6-[4-[(E)-3-phenylprop-2-enoyl]phenoxy]oxan-2-yl]methyl acetate; 98052074: (E)-3-(3-Hydroxy-4-methoxyphenyl)-1-[2-hydroxy-6-methoxy-4-[(2S,3S,4S,5R,6R)-3,4,5-trihydroxy-6-[[(2R,3S,4S,5R,6R)-3,4,5-trihydroxy-6-methyloxan-2-yl]oxymethyl]oxan-2-yl]oxyphenyl]prop-2-en-1-one; 98052075: (E)-3-(3-Hydroxy-4-methoxyphenyl)-1-[2-hydroxy-6-methoxy-4-[(2S,3S,4S,5R,6R)-3,4,5-trihydroxy-6-[[(2R,3S,4S,5R,6S)-3,4,5-trihydroxy-6-methyloxan-2-yl]oxymethyl]oxan-2-yl]oxyphenyl]prop-2-en-1-one; 98052076: (E)-3-(3-Hydroxy-4-methoxy-phenyl)-1-[2-hydroxy-6-methoxy-4-[(2S,3S,4S,5R,6R)-3,4,5-trihydroxy-6-[[(2R,3S,4S,5S,6R)-3,4,5-trihydroxy-6-methyloxan-2-yl]oxymethyl]oxan-2-yl]oxyphenyl]prop-2-en-1-one; 98052077: (E)-3-(3-Hydroxy-4-methoxyphenyl)-1-[2-hydroxy-6-methoxy-4-[(2S,3S,4S,5R,6R)-3,4,5-trihydroxy-6-[[(2R,3S,4S,5S,6S)-3,4,5-trihydroxy-6-methyloxan-2-yl]oxymethyl]oxan-2-yl]oxyphenyl]prop-2-en-1-one; 98072666: (E)-1-[4-[(2S,3R,4R,5S,6S)-4,5-Dihydroxy-6-(hydroxymethyl)-3-[(2S,3S,4S,5R,6R)-3,4,5-trihydroxy-6-methyloxan-2-yl]oxyoxan-2-yl]oxy-2,6-dihydroxyphenyl]-3-(4-methoxyphenyl)prop-2-en-1-one; 98072668: (E)-1-[4-[(2S,3R,4R,5S,6S)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(4-methoxyphenyl) prop-2-en-1-one; 98072669: (E)-1-[4-[(2S,3R,4R,5S,6S)-4,5-Dihydroxy-6-(hydroxymethyl)-3-[(2S,3R,4S,5R,6R)-3,4,5-trihydroxy-6-methyloxan-2-yl]oxyoxan-2-yl]oxy-2,6-dihydroxy-phenyl]-3-(4-methoxyphenyl)prop-2-en-1-one; 98072671: (E)-1-[4-[(2S,3R,4R,5S,6S)-4,5-Dihydroxy-6-(hydroxymethyl)-3-[(2S,3R,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 98116796: (E)-1-[4-[(2R,3R,4R,5S,6S)-4,5-Dihydroxy-6-(hydroxymethyl)-3-[(2S,3S,4S,5R,6R)-3,4,5-trihydroxy-6-methyloxan-2-yl]oxyoxan-2-yl]oxy-2,6-dihydroxyphenyl]-3-(3-hydroxy-4-methoxyphenyl)prop-2-en-1-one; 98116797: (E)-1-[4-[(2R,3R,4R,5S,6S)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(3-hydroxy-4-methoxyphenyl)prop-2-en-1-one; 98116798: (E)-1-[4-[(2R,3R,4R,5S,6S)-4,5-Dihydroxy-6-(hydroxymethyl)-3-[(2S,3S,4S,5S,6R)-3,4,5-trihydroxy-6-methyloxan-2-yl]oxyoxan-2-yl]oxy-2,6-dihydroxyphenyl]-3-(3-hydroxy-4-methoxyphenyl) prop-2-en-1-one; 98116799: (E)-1-[4-[(2R,3R,4R,5S,6S)-4,5-Dihydroxy-6-(hydroxymethyl)-3-[(2S,3S,4S,5S,6S)-3,4,5-trihydroxy-6-methyloxan-2-yl]oxyoxan-2-yl]oxy-2,6-dihydroxy-phenyl]-3-(3-hydroxy-4-methoxyphenyl)prop-2-en-1-one; 98144434: [(2S,3S,4S,5R,6R)-5-Acetamido-3,4-diacetyloxy-6-[4-[(E)-3-phenylprop-2-enoyl]phenoxy]oxan-2-yl]methyl acetate; 98144435: [(2S,3S,4S,5S,6R)-5-Acetamido-3,4-diacetyloxy-6-[4-[(E)-3-phenylprop-2-enoyl]phenoxy]oxan-2-yl]methyl acetate; 98144436: [(2S,3S,4R,5R,6R)-5-Acetamido-3,4-diacetyloxy-6-[4-[(E)-3-phenylprop-2-enoyl]phenoxy]oxan-2-yl]methyl acetate; 98144437: [(2S,3S,4R,5S,6R)-5-Acetamido-3,4-diacetyloxy-6-[4-[(E)-3-phenylprop-2-enoyl]phenoxy]oxan-2-yl]methyl acetate; 98144440: [(2R,3R,4S,5S,6S)-3,4,5-Triacetyloxy-6-[4-[(E)-3-phenylprop-2-enoyl]phenoxy]oxan-2-yl]methyl acetate; 98144441: [(2S,3R,4S,5S,6S)-3,4,5-Triacetyloxy-6-[4-[(E)-3-phenylprop-2-enoyl]phenoxy]oxan-2-yl]methyl acetate; 98527966: (E)-3-(3-Hydroxy-4-methoxyphenyl)-1-[2-hydroxy-6-methoxy-4-[(2R,3R,4R,5S,6S)-3,4,5-trihydroxy-6-[[(2R,5S)-5-hydroxyoxan-2-yl]oxymethyl]oxan-2-yl]oxyphenyl]prop-2-en-1-one; 98527968: (E)-3-(3-Hydroxy-4-methoxyphenyl)-1-[2-hydroxy-6-methoxy-4-[(2S,3R,4R,5S,6S)-3,4,5-trihydroxy-6-[[(2R,5S)-5-hydroxyoxan-2-yl]oxymethyl]oxan-2-yl]oxyphenyl]prop-2-en-1-one; 98527969: (E)-3-(3-Hydroxy-4-methoxyphenyl)-1-[2-hydroxy-6-methoxy-4-[(2R,3R,4R,5S,6S)-3,4,5-trihydroxy-6-[[(2R,5S)-5-hydroxyoxan-2-yl]oxymethyl]oxan-2-yl]oxyphenyl]prop-2-en-1-one; 98527970: (E)-3-(3-Hydroxy-4-methoxyphenyl)-1-[2-hydroxy-6-methoxy-4-[(2S,3R,4R,5S,6S)-3,4,5-trihydroxy-6-[[(2R,5S)-5-hydroxyoxan-2-yl]oxymethyl]oxan-2-yl]oxyphenyl]prop-2-en-1-one; 99844807: [(2S,3S,4R,5S,6S)-5-Acetamido-3,4-diacetyloxy-6-[4-[(E)-3-phenylprop-2-enoyl]phenoxy]oxan-2-yl]

methyl acetate; 99844808: [(2S,3S,4R,5R,6S)-5-Acetamido-3,4-diacetyloxy-6-[4-[(E)-3-phenylprop-2-enoyl]phenoxy]oxan-2-yl]methyl acetate; 99947316: (E)-3-(4-Hydroxyphenyl)-1-[4-hydroxy-2-[(2R,3S,4R,5R,6R)-3,4,5-trihydroxy-6-(hydroxymethyl)oxan-2-yl]oxyphenyl]prop-2-en-1-one; 99947328: (E)-1-[2-Hydroxy-6-[(2R,3S,4R,5R,6R)-3,4,5-trihydroxy-6-(hydroxymethyl)oxan-2-yl]oxyphenyl]-3-(4-nitro-phenyl)prop-2-en-1-one; 101406039: 6-(4-Cinnamoylphenoxy)hexyl 4-O-[4-O-(alpha-D-galactopyranosyl)-beta-D-galactopyranosyl]-beta-D-glucopyranoside; 101406040: 6-(4-Cinnamoylphenoxy)hexyl 4-O-[3-O-(alpha-D-galactopyranosyl)-beta-D-galactopyranosyl]-beta-D-glucopyranoside; 101423727: 4-[4-O-(p-Hydroxycinnamoyl)beta-D-gluco-pyranosyloxy]-2',4',6'-trihydroxychalcone; 101423795: 4,4'-Bis(beta-D-gluco-pyranosyloxy)-2'-hydroxychalcone; 101423796: 4'-Diglucosylisoliquiritigenin; 101526070: beta,beta'-[6,6'-Bis(tetrahydro-2H-pyran-2-yloxy)biphenyl-3,3'-diyl]bis[2'-hydroxy-4',6'-bis(tetrahydro-2H-pyran-2-yloxy)acrylophenone]; 101606231: Isoliquiritigenin 4'-O-apioglucoside; 101611732: 4'-[[6-O-(6-Deoxy-alpha-L-mannopyranosyl)-beta-D-gluco-pyranosyl]oxy]-3,6'-dihydroxy-4-methoxychalcone; 101611733: 4'-[[2-O,3-O,4-O-Trimethyl-6-O-(2-O,3-O,4-O-trimethyl-6-deoxy-alpha-L-mannopyranosyl)-beta-D-gluco-pyranosyl]oxy]-3,4,6'-trimethoxychalcone; 101614378: 2-[(E)-3-(4-Hydroxyphenyl)-1-oxo-2-propenyl]-3,5-dihydroxyphenyl 6-deoxy-beta-L-galactopyranoside; 101614379: 2-[(E)-3-(4-Hydroxy-phenyl)-1-oxo-2-propenyl]-3,5-dihydroxyphenyl 6-deoxy-beta-L-glucopyranoside; 101614380: 2-[(E)-3-(4-Hydroxyphenyl)-1-oxo-2-propenyl]-3,5-dihydroxyphenyl beta-L-glucopyranoside; 101643630: (E)-3-[4-(Benzoyloxy)phenyl]-1-[2-hydroxy-4-(6-deoxy-beta-L-gluco-pyranosyloxy)phenyl]-2-propen-1-one; 101643631: (E)-3-[4-(Benzoyloxy)phenyl]-1-[2-acetoxy-4-(6-deoxy-2-O-acetyl-beta-L-gluco-pyranosyloxy)phenyl]-2-propen-1-one; 101668463: 4'-(alpha-L-Rhamnopyranosyloxy)-2'-hydroxy-trans-chalcone; 101668464: 4'-(alpha-L-Rhamnopyranosyloxy)-2'-hydroxy-4-methoxy-trans-chalcone; 101678919: 2'-Hydroxy-4,4'-bis(beta-D-gluco-pyranosyloxy)-6'-methoxychalcone; 101938903: [(3S,4R,5S)-5-[(2S,3R,4S,5S,6R)-2-[4-[(E)-3-(2,4-Dihydroxyphenyl)-3-oxoprop-1-enyl]phenoxy]-4,5-dihydroxy-6-(hydroxymethyl)oxan-3-yl]oxy-3,4-dihydroxyoxolan-3-yl]methyl (E)-3-(4-hydroxy-3-methoxyphenyl)prop-2-enoate; 101938904: [(3S,4R,5S)-5-[(2S,3R,4S,5S,6R)-2-[4-[(E)-3-(2,4-Dihydroxyphenyl)-3-oxoprop-1-enyl]phenoxy]-4,5-dihydroxy-6-(hydroxymethyl) oxan-3-yl]oxy-3,4-dihydroxyoxolan-3-yl]methyl (E)-3-(4-hydroxyphenyl)prop-2-enoate; 102033205: 3-[[(2R,3S,4S,5R,6S)-6-[3-[(2S,3R,4S,5S,6R)-3-[(2S,3R,4S,5S,6R)-4,5-Dihydroxy-3-[3-(4-hydroxy-3-methoxyphenyl)prop-2-enoyloxy]-6-(hydroxymethyl)oxan-2-yl]oxy-4,5-dihydroxy-6-[[(E)-3-[4-[(2S,3R,4S,5S,6R)-3,4,5-trihydroxy-6-[3-[4-[3-(4- hydroxy-3-methoxyphenyl)prop-2-enoyl]-3-methoxyphenyl]prop-2-enoyloxymethyl]oxan-2-yl]oxyphenyl]prop-2-enoyl]oxymethyl]oxan-2-yl]oxy-2-(3,4-dihydroxyphenyl)-7-hydroxy-chromenylium-5-yl]oxy-3,4,5-trihydroxyoxan-2-yl]methoxy]-3-oxopropanoic acid; 102033209: 3-[2-O-(beta-D-Glucopyranosyl)-6-O-[(E)-3-[4-[6-O-[(E)-3-[3-methoxy-4-[(E)-3-(3-methoxy-4-hydroxyphenyl)propenoyl]phenyl]propenoyl]-beta-D-glucopyranosyloxy]phenyl]propenoyl]-beta-D-gluco-pyranosyloxy]-5-[6-O-(3-hydroxy-3-oxopropanoyl)-beta-D-glucopyranosyloxy]-7-hydroxy-2-(3,4-dihydroxyphenyl)-1-benzopyrylium; 102115846: 2'-Hydroxy-4,4'-bis(alpha-D-gluco-pyranosyloxy)-6'-methoxychalcone; 102121822: 1-[2-Hydroxy-4-(beta-D-gluco-pyranosyloxy)phenyl]-3-(4-hydroxy-3-methoxyphenyl)-2-propene-1-one; 102145742: 2',3-Bis(beta-D-gluco-pyranosyloxy)-4,4'-dihydroxychalcone; 102271454: 3-[[2-(4-Hydroxyphenyl)-4-oxo-5-hydroxy-7-(beta-D-gluco-pyranosyloxy)-3,4-dihydro-2H-1-benzopyran]-3-yl]-2',4,4'-trihydroxy-trans-chalcone; 102317735: Glucoisoquiritin apioside; 102320046: 1-[2-[6-O-(1-Oxo-8-hydroxy-5,6-octadiene-1-yl)-beta-D-glucopyranosyloxy]-4,6-dihydroxyphenyl]-3-(4-hydroxyphenyl)-2-propene-1-one; 102399253: (E)-2',3,4,6'-Tetra-methoxy-4'-[[6-O-(alpha-L-rhamnopyranosyl)-beta-D-gluco-pyranosyl]oxy]chalcone; 102399254: (E)-2',3,4,6'-Tetramethoxy-4'-[[2-O-methyl-6-O-(alpha-L-rhamnopyranosyl)-beta-D-gluco-pyranosyl]oxy]chalcone; 102467935: (Z)-4-(Tetrahydro-2H-pyran-2-yloxy) chalcone; 102500648: Tomoroside B; 102565358: 3-Hydroxy-4-[(2E)-3-(3-hydroxy-4-methoxyphenyl)prop-2-enoyl]-5-methoxyphenyl 6-O-(5-hydroxytetrahydro-2H-pyran-2-yl)hexopyranoside; 117590664: Sodium;2-[6-[6-[3-(5-ethyl-5-hydroxy-6-methyloxan-2-yl)-15-hydroxy-3,10,12-trimethyl-4,6,8-trioxadispiro[4.1.57.35]pentadec-13-en-9-yl]-3-hydroxy-4-methyl-5-oxooctan-2-yl]-5-methyloxan-2-yl]butanoate;1-(2-hydroxy-4,6-dimethoxyphenyl)-3-phenylprop-2-en-1-one; 117590676: [4-(Dimethylamino)-2-[[14-ethyl-7,12,13-trihydroxy-4-(5-hydroxy-4-methoxy-4,6-dimethyloxan-2-yl)oxy-3,5,7,9,11,13-hexamethyl-2,10-dioxo-oxacyclotetradec-6-yl]oxy]-6-methyloxan-3-yl]propanoate;dodecyl hydrogen sulfate;1-(2-hydroxy-4,6-dimethoxyphenyl)-3-phenylprop-2-en-1-one; 117590713: 2-Butan-2-yl-21',24'-dihydroxy-12'-[5-(5-hydroxy-4-methoxy-6-methyloxan-2-yl)oxy-4-methoxy-6-methyloxan-2-yl]oxy-3,11',13',22'-tetramethylspiro[2,3-dihydropyran-6,6'-3,7,19-trioxatetracyclo[15.6.1.14, 8.020,24]pentacosa-10,14,16,22-tetraene]-2'-one;1-(2-hydroxy-4,6-dimethoxyphenyl)-3-phenylprop-2-en-1-one; 117593260: 6-(Furan-3-yl)-17-hydroxy-1,7,11,15,15-pentamethyl-3-oxapentacyclo[8.8.0.02,4.02,7.011,16]octadeca-12,16-diene-14,18-dione;1-(2-hydroxy-4,6-dimethoxyphenyl)-3-phenylprop-2-en-1-one; 117593500: [6-(Furan-3-yl)-17-hydroxy-1,7,11,15,15-pentamethyl-14,18-dioxo-3-oxapentacyclo[8.8.0.02,4.02,7.011,16]octadeca-12,16-dien-9-yl] acetate;1-(2-hydroxy-4,6-dimethoxyphenyl)-3-phenylprop-2-en-1-one; 117596500: 1-(2-Hydroxy-4,6-dimethoxyphenyl)-3-phenylprop-2-en-1-one;5',7,9,13-tetramethylspiro[5-oxapentacyclo[10.8.0.02,9.04,8.013,18]icos-11-ene-6,2'-oxane]-16-ol; 117597750: [3-[3,4-Dihydroxy-6-methyl-5-[3,4,5-trihydroxy-6-(hydroxymethyl)oxan-2-yl]oxyoxan-2-yl]oxy-4,5-dihydroxyoxan-2-yl] 10-[3,4-dihydroxy-6-methyl-5-(3,4,5-trihydroxy-oxan-2-yl)oxyoxan-2-yl]oxy-5-hydroxy-2,2,6a,6b,9,9,12a-heptamethyl-1,3,4,5,6,6a,7,8,8a, 10,11,12,13,14b-tetradecahydropicene-4a-carboxylate;1-(2-hydroxy-4,6-dimethoxyphenyl)-3-phenylprop-2-en-1-one; 117597933: 1-(2-Hydroxy-4,6-dimethoxyphenyl)-3-phenylprop-2-en-1-one;[6-hydroxy-3,4,5-tris(3-nitropropanoyloxy)oxan-2-yl] methyl 3-nitropropanoate; 117718895: (E)-3-[3,4-Bis(oxan-2-yloxy)phenyl]-1-[4-(oxan-2-yloxy)phenyl]prop-2-en-1-one; 117957329: (E)-3-(3-Hydroxy-4-methoxyphenyl)-1-[2-hydroxy-6-methoxy-4-[(2S,3S,5S)-3,4,5-trihydroxy-6-[[(2R,4S,5R)-3,4,5-trihydroxy-6-methyloxan-2-yl]oxymethyl]oxan-2-yl]oxyphenyl]prop-2-en-1-one; 118726419: [(1S,4S,5R,8S,9R,12R,13R)-1,5,9-Trimethyl-11,14,15,16-tetraoxatetracyclo[10.3.1.04,13.08,13]hexadecan-10-yl] 4-[(E)-3-oxo-3-phenyl-prop-1-enyl]benzoate; 118726422: [(1S,4S,5R,8S,9R,12R,13R)-1,5,9-Trimethyl-11,14,15, 16-tetraoxatetracyclo[10.3.1.04,13.08,13]hexadecan-10-yl] 4-[(E)-3-(2,4-dimethoxyphenyl)-3-oxoprop-1-enyl]benzoate; 123514122: 3-[4-[3-(4-Methylphenyl)-3- oxoprop-1-enyl]phenyl]-N-(oxan-2-yloxy)prop-2-enamide; 123681995: 1-[2-[5-Fluoro-3,4-dihydroxy-6-(hydroxymethyl)oxan-2-yl]oxy-6-hydroxy-4-methylphenyl]-3-phenylprop-2-en-1-one; 124461562: (E)-3-(4-Hydroxyphenyl)-1-[2-hydroxy-4-[(2R,3S,4R,5R,6S)-3,4,5-trihydroxy-6-(hydroxymethyl) oxan-2-yl]oxyphenyl]prop-2-en-1-one; 124511253: Chembl4213562; 124771192: N-[(2S,3S,4S,5S,6R)-4,5-Dihydroxy-6-(hydroxymethyl)-2-[4-[(E)-3-phenylprop-2-enoyl]phenoxy]oxan-3-yl]acetamide; 124771193: N-[(2S,3S,4R,5R,6R)-4,5-Dihydroxy-6-(hydroxymethyl)-2-[4-[(E)-3-phenylprop-2-enoyl]phenoxy]oxan-3-yl]acetamide; 124771194: N-[(2S,3S,4S,5R,6R)-4,5-Dihydroxy-6-(hydroxymethyl)-2-[4-[(E)-3-phenylprop-2-enoyl]phenoxy]oxan-3-yl]acetamide; 124771195: N-[(2S,3S,4R,5S,6R)-4,5-Dihydroxy-6-(hydroxymethyl)-2-[4-[(E)-3-phenylprop-2-enoyl]phenoxy]oxan-3-yl]acetamide; 124772180: [(2R,3R,4S,5S,6S)-5-Acetamido-3,4-diacetyloxy-6-[4-[(E)-3-phenylprop-2-enoyl]phenoxy]oxan-2-yl]methyl acetate; 124772181: [(2R,3R,4R,5S,6S)-5-Acetamido-3,4-diacetyloxy-6-[4-[(E)-3-phenylprop-2-enoyl]phenoxy]oxan-2-yl] methyl acetate; 124833409: N-[(2S,4Ar,6S, 7S,8S,8aR)-8-hydroxy-6-[4-[(E)-3-oxo-3-phenylprop-1-enyl]phenoxy]-2-phenyl-4,4a,6,7,8, 8a-hexahydropyrano[3,2-d][1,3]dioxin-7-yl]acetamide; 124833410: N-[(2S,4Ar,6S,7S,8R,8aR)-8-hydroxy-6-[4-[(E)-3-oxo-3-phenylprop-1-enyl]phenoxy]-2-phenyl-4,4a,6,7,8,8a-hexahydropyrano[3,2-d][1,3]dioxin-7-yl]acetamide; 124833411: N-[(2S,4Ar,6S,7S,8R,8aS)-8-hydroxy-6-[4-[(E)-3-oxo-3-phenylprop-1-enyl]phenoxy]-2-phenyl-4,4a,6,7,8,8a-hexahydropyrano[3,2-d][1,3]dioxin-7-yl]acetamide; 124833412: N-[(2S,4Ar,6S,7S,8S,8aS)-8-hydroxy-6-[4-[(E)-3-oxo-3-phenylprop-1-enyl]phenoxy]-2-phenyl-4,4a,6,7,8,8a-hexahydropyrano[3,2-d][1,3]dioxin-7-yl]acetamide; 124833434: N-[(2S,4Ar,6S,7S,8S,8aR)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124833435: N-[(2S,4Ar,6S,7S,8R,8aR)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124833436: N-[(2S,4Ar,6S,7S,8R,8aS)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124833437: N-[(2S,4Ar,6S,7S,8S,8aS)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124837273: [(2R,3S,4R,5S,6S)-5-Acetamido-3,4-diacetyloxy-6-[4-[(E)-3-phenylprop-2-enoyl]phenoxy]oxan-2-yl]methyl acetate; 124837274: [(2R,3S,4S,5S,6S)-5-Acetamido-3,4-diacetyloxy-6-[4-[(E)-3-phenylprop-2-enoyl]phenoxy]oxan-2-yl]methyl acetate; 124897404: [(2S,3S,4R,5S,6S)-3,4,5-Triacetyloxy-6-[4-[(E)-3-phenylprop-2-enoyl]phenoxy]oxan-2-yl]methyl acetate; 124897405: [(2S,3S,4R,5S,6R)-3,4,5-Triacetyloxy-6-[4-[(E)-3-phenylprop-2-enoyl]phenoxy]oxan-2-yl]methyl acetate; 124906456: (E)-3-(3-Hydroxy-4-methoxy-phenyl)-1-[2-hydroxy-6-methoxy-4-[(2R,3S,4R,5R,6S)-3,4,5-trihydroxy-6-[[(2S,5R)-5-hydroxyoxan-2-yl]oxymethyl]oxan-2-yl]oxyphenyl]prop-2-en-1-one; 124906457: (E)-3-(3-Hydroxy-4-methoxyphenyl)-1-[2-hydroxy-6-methoxy-4-[(2R,3S,4R,5R,6S)-3,4,5-trihydroxy-6-[[(2S,5S)-5-hydroxyoxan-2-yl]oxymethyl]oxan-2-yl]oxyphenyl]prop-2-en-1-one; 124906458: (E)-3-(3-Hydroxy-4-methoxyphenyl)-1-[2-hydroxy-6-methoxy-4-[(2R,3S,4R,5R,6S)-3,4,5-trihydroxy-6-[[(2R,5R)-5-hydroxyoxan-2-yl]oxymethyl]oxan-2-yl]oxyphenyl]prop-2-en-1-one; 124906459: (E)-3-(3-Hydroxy-4-methoxyphenyl)-1-[2-hydroxy-6-methoxy-4-[(2R,3S,4R,5R,6S)-3,4,5-trihydroxy-6-[[(2R,5S)-5-hydroxyoxan-2-yl]oxymethyl]oxan-2-yl]oxyphenyl]prop-2-en-1-one; 124921909: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4S,5S,6R)-3,4,5-trihydroxy-6-methyloxan-2-yl]oxymethyl]oxan-2-yl]oxyphenyl]prop-2-en-1-one; 124921910: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4S,5R,6R)-3,4,5-trihydroxy-6-methyloxan-2-yl]oxymethyl]oxan-2-yl]oxyphenyl]prop-2-en-1-one; 124925164: 2-[(2S,3R,4R,5R,6R)-5-Acetyloxy-2-(acetyl-oxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 124925165: 2-[(2S,3R,4R,5R,6S)-5-Acetyloxy-2-(acetyloxymethyl)-6-[4-[(Z)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 124925166: 2-[(2S,3R,4R,5R,6S)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl) oxan-2-yl]oxyoxan-4-yl]acetic acid; 124925167: 2-[(2S,3R,4R,5R,6R)-5-Acetyloxy-2-(acetyloxymethyl)-6-[4-[(Z)-3-phenylprop-2-enoyl]phenoxy]-3-[(2S,3S,4R,5S,6S)-3,4,5-triacetyloxy-6-(acetyloxymethyl) oxan-2-yl]oxyoxan-4-yl]acetic acid; 124925172: 2-[(2S,3R,4R,5R,6R)-3,5-Diacetyloxy-2-(acetyloxymethyl)-6-[4-[(E)-3-oxo-3-phenylprop-1-enyl]phenoxy]oxan-4-yl]acetic acid; 124925173: 2-[(2S,3S,4R,5R,6R)-3,5-Diacetyloxy-2-(acetyloxymethyl)-6-[4-[(E)-3-oxo-3-phenylprop-1-enyl]phenoxy]oxan-4-yl]acetic acid; 124925174: 2-[(2S,3S,4R,5R,6R)-3,5-Diacetyloxy-2-(acetyloxymethyl)-6-[4-[(Z)-3-oxo-3-phenylprop-1-enyl]phenoxy]oxan-4-yl]acetic acid; 124925175: 2-[(2S,3R,4R,5R,6R)-3,5-Diacetyloxy-2-(acetyloxymethyl)-6-[4-[(Z)-3-oxo-3-phenylprop-1-enyl]phenoxy]oxan-4-yl]acetic acid; 124925242: 2-[(2S,3R,4R,5R,6R)-3,5-Diacetyloxy-2-(acetyloxymethyl)-6-[4-[(E)-3-phenylprop-2-enoyl]phenoxy]oxan-4-yl]acetic acid; 124925243: 2-[(2S,3R,4R,5R,6R)-3,5-Diacetyloxy-2-(acetyloxymethyl)-6-[4-[(Z)-3-phenylprop-2-enoyl]phenoxy]oxan-4-yl]acetic acid; 124925244: 2-[(2S,3S,4R,5R,6R)-3,5-Diacetyloxy-2-(acetyloxymethyl)-6-[4-[(Z)-3-phenylprop-2-enoyl]phenoxy]oxan-4-yl]acetic acid; 124925245: 2-[(2S,3S,4R,5R,6R)-3,5-Diacetyloxy-2-(acetyloxymethyl)-6-[4-[(E)-3-phenylprop-2-enoyl]phenoxy]oxan-4-yl]acetic acid; 125027357: (E)-1-[4-[(2S,3S,4R,5S,6R)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 125027358: (E)-1-[4-[(2S,3S,4R,5S,6R)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 125027359: (E)-1-[4-[(2S,3S,4R,5S,6R)-4,5-Dihydroxy-6-(hydroxymethyl)-3-[(2S,3S,4S,5R,6R)-3,4,5-trihydroxy-6-methyloxan-2-yl]oxyoxan-2-yl]oxy-2,6-dihydroxyphenyl]-3-(4-methoxyphenyl)prop-2-en-1-one; 125027360: (E)-1-[4-[(2S,3S,4R,5S,6R)-4,5-Dihydroxy-6-(hydroxymethyl)-3-[(2S,3R,4S,5R,6R)-3,4,5-trihydroxy-6-methyloxan-2-yl]oxyoxan-2-yl]oxy-2,6-dihydroxyphenyl]-3-(4-methoxyphenyl)prop-2-en-1-one; 125027596: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4R,5R,6R)-3,4,5-trihydroxy-6-methyloxan-2-yl]oxymethyl]oxan-2-yl]oxyphenyl]prop-2-en-1-one; 125027597: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4R,5S,6R)-3,4,5-trihydroxy-6-methyloxan-2-yl]oxymethyl]oxan-2-yl]oxyphenyl]prop-2-en-1-one; 125028931: (Z)-3-(4-

Chlorophenyl)-1-[2,4-dihydroxy-6-[(2S,3R,4S,5R,6R)-3,4,5-trihydroxy-6-(hydroxymethyl)oxan-2-yl]oxyphenyl]prop-2-en-1-one; 125028932: (E)-3-(4-Chlorophenyl)-1-[2,4-dihydroxy-6-[(2S,3S,4S,5R,6R)-3,4,5-trihydroxy-6-(hydroxymethyl) oxan-2-yl]oxyphenyl]prop-2-en-1-one; 125028933: (Z)-3-(4-Chlorophenyl)-1-[2,4-dihydroxy-6-[(2S,3S,4S,5R,6R)-3,4,5-trihydroxy-6-(hydroxymethyl) oxan-2-yl]oxyphenyl]prop-2-en-1-one; 125028934: (E)-3-(4-Chlorophenyl)-1-[2,4-dihydroxy-6-[(2S,3R,4S,5R,6R)-3,4,5-trihydroxy-6-(hydroxymethyl)oxan-2-yl]oxyphenyl] prop-2-en-1-one; 125029297: (E)-1-[2-Hydroxy-6-[(2R,3S,4S,5R,6R)-3,4,5-trihydroxy-6-(hydroxymethyl)oxan-2-yl]oxyphenyl]-3-(4-nitro-phenyl)prop-2-en-1-one; 125029298: (E)-1-[2-Hydroxy-6-[(2R,3R,4R,5R,6R)-3,4,5-trihydroxy-6-(hydroxymethyl)oxan-2-yl]oxyphenyl]-3-(4-nitro-phenyl) prop-2-en-1-one; 125029299: (E)-1-[2-Hydroxy-6-[(2R,3R,4S,5R,6R)-3,4,5-trihydroxy-6-(hydroxymethyl)oxan-2-yl] oxyphenyl]-3-(4-nitro-phenyl)prop-2-en-1-one; 125029365: (E)-3-(4-Hydroxyphenyl)-1-[4-hydroxy-2-[(2R,3S,4S,5R,6R)-3,4,5-trihydroxy-6-(hydroxymethyl)oxan-2-yl]oxyphenyl]prop-2-en-1-one; 125029366: (E)-3-(4-Hydroxyphenyl)-1-[4-hydroxy-2-[(2R,3R,4S,5R,6R)-3,4,5-trihydroxy-6-(hydroxymethyl)oxan-2-yl]oxyphenyl]prop-2-en-1-one; 125029367: (E)-3-(4-Hydroxyphenyl)-1-[4-hydroxy-2-[(2R,3R,4R,5R,6R)-3,4,5-trihydroxy-6-(hydroxymethyl) oxan-2-yl]oxyphenyl]prop-2-en-1-one; 125032725: 2-[(2S,3R,4R,5S,6S)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 125032726: 2-[(2S,3R,4R,5S,6R)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 125032834: 2-[(2S,3R,4R,5R,6S)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxymethyl) oxan-2-yl]oxyoxan-4-yl]acetic acid; 125032835: 2-[(2S,3R,4R,5R,6R)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxymethyl)oxan-2-yl]oxyoxan-4-yl]acetic acid; 125032836: 2-[(2S,3R,4R,5S,6S)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxymethyl)oxan-2-yl]oxyoxan-4-yl]acetic acid; 125032837: 2-[(2S,3R,4R,5S,6R)-5-Acetyloxy-2-(acetyloxy-methyl)-6-[4-[(E)-3-oxo-3-phenylprop-1-enyl]phenoxy]-3-[(2S,3S,4R,5S,6S)-3,4,5-triacetyloxy-6-(acetyloxymethyl)oxan-2-yl]oxyoxan-4-yl]acetic acid; 125040471: (E)-3-[4-[(2R,3S,4R,5R,6S)-3-[(2S,3R,4S)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125040472: (E)-3-[4-[(2R,3S,4R,5R,6S)-3-[(2S,3S,4S)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125040473: (E)-3-[4-[(2R,3S,4R,5R,6S)-3-[(2S,3S,4R)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125115470: (Z)-1-[2,4-Dihydroxy-6-[(2S,3R,4S,5R,6R)-3,4,5-trihydroxy-6-(hydroxymethyl)oxan-2-yl]oxyphenyl]-3-(4-hydroxy-phenyl)prop-2-en-1-one; 125115471: (E)-1-[2,4-Dihydroxy-6-[(2S,3S,4S,5R,6R)-3,4,5-trihydroxy-6-(hydroxymethyl)oxan-2-yl]oxyphenyl]-3-(4-hydroxyphenyl)prop-2-en-1-one; 125115472: (Z)-1-[2,4-Dihydroxy-6-[(2S,3S,4S,5R,6R)-3,4,5-trihydroxy-6-(hydroxymethyl) oxan-2-yl]oxyphenyl]-3-(4-hydroxyphenyl)prop-2-en-1-one; 125115473: (E)-1-[2,4-Di-hydroxy-6-[(2S,3R,4S,5R,6R)-3,4,5-trihydroxy-6-(hydroxymethyl)oxan-2-yl]oxyphenyl]-3-(4-hydroxyphenyl)prop-2-en-1-one; 125463410: (E)-3-[4-[(2R,3S,4R,5R,6S)-3-[(2R,3S,4S)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 126650039: 1-[2,4-Dihydroxy-6-[(2S,3R,4S,5S,6R)-3,4,5-trihydroxy-6-(hydroxymethyl)oxan-2-yl]oxyphenyl]-3-(4-hydroxyphenyl)propan-1-one;1,3-diphenylprop-2-en-1-one; methylsulfinylmethane; 129420712: [(2R,3R,4S,5S,6S)-5-Acetamido-3,4-diacetyloxy-6-[4-[(Z)-3-phenylprop-2-enoyl]phenoxy]oxan-2-yl]methyl acetate; 129420713: [(2R,3R,4R,5S,6S)-5-Acetamido-3,4-diacetyloxy-6-[4-[(Z)-3-phenylprop-2-enoyl]phenoxy]oxan-2-yl]methyl acetate; 129775442: 2'-Hydroxy-4'-methoxy-4-(tetrahydropyran-2-yloxy)chalcone; 129841726: (e)-3-[3,4-Bis(tetrahydro-2h-pyran-2-yloxy)phenyl]-1-(2-aminophenyl)prop-2-en-1-one; 129841964: (e)-1-(2-Amino-phenyl)-3-[4-(tetrahydro-2h-pyran-2-yloxy)phenyl]prop-2-en-1-one; 129900894: [(5R,9R,12R,13R)-1,5,9-Trimethyl-11,14,15,16-tetraoxatetracyclo[10.3.1.04,13.08,13]hexa-decan-10-yl] 4-[(E)-3-(2,4-dimethoxyphenyl)-3-oxoprop-1-enyl]benzoate; 129903062: [(5R,9R,12R,13R)-1,5,9-Trimethyl-11,14,15,16-tetraoxatetracyclo[10.3.1.04,13.08,13]hexa-decan-10-yl] 4-[(E)-3-oxo-3-phenylprop-1-enyl]benzoate; 130394862: (E)-1-[4-[(2S,3R,4R,5S,6R)-4,5-Dihydroxy-6-(hydroxymethyl)-3-methyloxan-2-yl]oxy-2,6-dihydroxyphenyl]-3-(4-hydroxyphenyl)prop-2-en-1-one; 131676039: 1-Propanone, 1-[4-[[6-O-(6-deoxy-alpha-L-mannopyranosyl)-beta-D-gluco-pyranosyl]oxy]-2,6-dihydroxyphenyl]-3-(4-methoxyphenyl)-; 131751237: Licorice glycoside B; 131751238: Licorice glycoside A; 131801300: (E)-3-(4-Hydroxy-3-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl] prop-2-en-1-one; 131834436: 6-3,5-Dihydroxy-2-[3-(3-hydroxy-4-methoxyphenyl)prop-2-enoyl]phenoxy-3,4,5-trihydroxyoxane-2-carboxylic acid; 131834437: 6-3,5-Dihydroxy-4-[3-(3-hydroxy-4-methoxyphenyl)prop-2-enoyl]phenoxy-3,4,5-trihydroxyoxane-2-carboxylic acid; 131834438: 3,4,5-Trihydroxy-6-2-methoxy-5-[3-oxo-3-(2,4,6-trihydroxyphenyl)prop-1-en-1-yl]phenoxyoxane-2-carboxylic acid; 131834447: 6-3,5-Dihydroxy-2-[3-(4-hydroxyphenyl) prop-2-enoyl]phenoxy-3,4,5-trihydroxyoxane-2-carboxylic acid; 131834448: 6-3,5-Dihydroxy-4-[3-(4-hydroxyphenyl)prop-2-enoyl]phenoxy-3,4,5-trihydroxyoxane-2-carboxylic acid; 131834449: 3,4,5-Trihydroxy-6-4-[3-oxo-3-(2,4,6-trihydroxyphenyl)prop-1-en-1-yl]phenoxyoxane-2-carboxylic acid; 131834453: 6-[3,5-Dihydroxy-2-(3-phenylprop-2-enoyl)phenoxy]-3,4,5-trihydroxyoxane-2-carboxylic acid; 131834454: 6-[3,5-Dihydroxy-4-(3-phenylprop-2-enoyl)phenoxy]-3,4,5-trihydroxyoxane-2-carboxylic acid; 131836668: 6-3,5-Dihydroxy-4-[3-(4-methoxyphenyl)prop-2-enoyl]phenoxy-3,4,5-trihydroxyoxane-2-carboxylic acid; 131837294: 6-2-[3-(3,4-Dihydroxyphenyl)prop-2-enoyl]-3,5-dihydroxyphenoxy-3,4,5-trihydroxyoxane-2-carboxylic acid; 131837295: 6-4-[3-(3,4-Dihydroxyphenyl)prop-2-enoyl]-3,5-dihydroxyphenoxy-3,4,5-trihydroxyoxane-2-carboxylic acid; 131837296: 3,4,5-Trihydroxy-6-2-hydroxy-5-[3-oxo-3-(2,4,6-trihydroxyphenyl)prop-1-en-1-yl] phenoxyoxane-2-carboxylic acid; 131837297: 3,4,5-Trihydroxy-6-2-hydroxy-4-[3-oxo-3-(2,4,6-trihydroxyphenyl)prop-1-en-1-yl]phenoxyoxane-2-carboxylic acid;

131838575: 6-4-[(1E)-3-(5-[(2-4-[3-(2,4-Dihydroxyphenyl)-3-oxoprop-1-en-1-yl]phenoxy-4,5-dihydroxy-6-(hydroxymethyl)oxan-3-yl)oxy]-3,4-dihydroxyoxolan-3-ylmethoxy)-3-oxoprop-1-en-1-yl]phenoxy-3,4,5-trihydroxyoxane-2-carboxylic acid; 131838576: 6-[4-(3-4-[(3-[3,4-Dihydroxy-4-([(2E)-3-(4-hydroxy-phenyl)prop-2-enoyl]oxymethyl)oxolan-2-yl]oxy-4,5-dihydroxy-6-(hydroxymethyl)oxan-2-yl)oxy]phenylprop-2-enoyl)-3-hydroxyphenoxy]-3,4,5-trihydroxyoxane-2-carboxylic acid; 131838577: 4-[(1 E)-3-(5-[(2-4-[3-(2,4-Dihydroxyphenyl)-3-oxoprop-1-en-1-yl]phenoxy-4,5-dihydroxy-6-(hydroxymethyl)oxan-3-yl)oxy]-3,4-dihydroxyoxolan-3-ylmethoxy)-3-oxoprop-1-en-1-yl]phenyloxidanesulfonic acid; 131838578: 2-[(2-4-[3-(2,4-Dihydroxyphenyl)-3-oxoprop-1-en-1-yl]phenoxy-4,5-dihydroxy-6-(hydroxymethyl)oxan-3-yl)oxy]-4-hydroxy-4-([(2E)-3-(4-hydroxyphenyl)prop-2-enoyl]oxymethyl)oxolan-3-yloxidanesulfonic acid; 131838579: 6-[4-(3-4-[(3-[3,4-Dihydroxy-4-(hydroxymethyl)oxolan-2-yl]oxy-4,5-dihydroxy-6-(hydroxymethyl)oxan-2-yl)oxy]phenylprop-2-enoyl)-3-hydroxyphenoxy]-3,4,5-tri hydroxy-oxane-2-carboxylic acid; 131838580: 6-[2-(3-4-[(3-[3,4-Dihydroxy-4-(hydroxymethyl)oxolan-2-yl]oxy-4,5-dihydroxy-6-(hydroxymethyl)oxan-2-yl)oxy]phenylprop-2-enoyl)-5-hydroxyphenoxy]-3,4,5-trihydroxyoxane-2-carboxylic acid; 131838581: (5-[(2-4-[3-(2,4-Dihydroxy-phenyl)-3-oxoprop-1-en-1-yl]phenoxy-4,5-dihydroxy-6-(hydroxymethyl)oxan-3-yl)oxy]-3,4-dihydroxyoxolan-3-ylmethoxy)sulfonic acid; 131838582: 2-[(2-4-[3-(2,4-Dihydroxyphenyl)-3-oxoprop-1-en-1-yl]phenoxy-4,5-dihydroxy-6-(hydroxymethyl)oxan-3-yl)oxy]-4-hydroxy-4-(hydroxymethyl)oxolan-3-yloxidanesulfonic acid; 131839144: 3,4,5-Trihydroxy-6-4-[(2E)-3-phenylprop-2-enoyl]phenoxyoxane-2-carboxylic acid; 131839146: 3,4,5-Trihydroxy-6-5-methoxy-2-[(2E)-3-phenylprop-2-enoyl]phenoxyoxane-2-carboxylic acid; 131839147: 3,4,5-Trihydroxy-6-4-[(1 E)-3-(4-methoxyphenyl)-3-oxoprop-1-en-1-yl]phenoxyoxane-2-carboxylic acid; 131839149: 3,4,5-Trihydroxy-6-3-[(1 E)-3-(4-methoxyphenyl)-3-oxoprop-1-en-1-yl]phenoxyoxane-2-carboxylic acid; 132277629: (2s,3s,4r,5s,6r)-2-(Acetoxymethyl)-6-(4-((e)-3-(4-((e)-3,3-dimethyltriaz-1-en-1-yl)phenyl)-3-oxoprop-1-en-1-yl)phenoxy)tetrahydro-2h-pyran-3,4,5-triyl triacetate; 132277736: (e)-1-(4-((e)-3,3-Dimethyltriaz-1-en-1-yl)phenyl)-3-(4-(((2r,3s,4r,5r,6s)-3,4,5-trihydroxy-6-(hydroxymethyl)tetrahydro-2h-pyran-2-yl)oxy)phenyl)prop-2-en-1-one; 132279066: (e)-1-(4-((e)-3,3-Dimethyltriaz-1-en-1-yl)phenyl)-3-(4-(((3s,4r,5r,6s)-3,4,5-trihydroxy-6-(hydroxymethyl)tetrahydro-2h-pyran-2-yl)oxy)phenyl)prop-2-en-1-one; 132279119: (2s,3s,4r,5s,6r)-2-(Acetoxymethyl)-6-(2-(4-((e)-3-(4-((e)-3,3-dimethyltriaz-1-en-1-yl)phenyl)-3-oxoprop-1-en-1-yl)phenoxy)acetoxy)tetrahydro-2h-pyran-3,4,5-triyl triacetate; 132280046: (e)-1-(4-((e)-3,3-Dimethyltriaz-1-en-1-yl)phenyl)-3-(3-methoxy-4-(((2r,3s,4r,5s)-3,4,5-trihydroxytetrahydro-2h-pyran-2-yl)oxy)phenyl)prop-2-en-1-one; 132280790: (2r,3s,5s)-2-(2-(4-((e)-3-(4-((e)-3,3-Dimethyltriaz-1-en-1-yl)phenyl)-3-oxoprop-1-en-1-yl)-2-methoxyphenoxy)acetoxy)tetrahydro-2h-pyran-3,4,5-triyl triacetate; 132281092: (e)-1-(4-((e)-3,3-Dimethyltriaz-1-en-1-yl)phenyl)-3-(3-methoxy-4-(((2r,3s,4r,5r, 6s)-3,4,5-trihydroxy-6-(hydroxymethyl)tetrahydro-2h-pyran-2-yl)oxy)phenyl)prop-2-en-1-one; 132281627: (e)-1-(4-((e)-3,3-Dimethyltriaz-1-en-1-yl)phenyl)-3-(4-(((2r,3s,4r,5s)-3,4,5-trihydroxytetrahydro-2h-pyran-2-yl)oxy)phenyl)prop-2-en-1-one; 132551953: 1-[2-(beta-D-Glucopyranosyloxy)-4,6-dihydroxyphenyl]-3-phenyl-2-propene-1-one; 132839041: 4'-(6-O-Galloyl-beta-D-gluco-pyranosyloxy)-2'-hydroxy-4-methoxychalcone; 132839042: 4'-(6-O-Galloyl-beta-D-gluco-pyranosyloxy)-2',4-dihydroxychalcone; 132839043: 4'-(beta-D-Glucopyranosyloxy)-2'-hydroxy-4-methoxychalcone; 132990990: 2'-Hydroxy-4-glucosyl-oxychalcone; 133556548: [(2S,3R,4R,5S,6R)-6-[4-[(E)-3-(2,4-Dihydroxyphenyl)-3-oxoprop-1-enyl]phenoxy]-3,4,5-trihydroxyoxan-2-yl]methyl (E)-3-(4-hydroxyphenyl)prop-2-enoate; 133577796: (E)-1-[2,4-Dihydroxy-6-[(2S)-3,4,5-trihydroxy-6-(hydroxymethyl)oxan-2-yl]oxyphenyl]-3-(4-hydroxyphenyl)prop-2-en-1-one; 134134040: (E)-1-(4-Hydroxyphenyl)-3-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134138288: (E)-3-(3-Ethoxy-4-hydroxyphenyl)-1-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134141177: (E)-1-(2,4-Dimethoxyphenyl)-3-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134141568: (E)-1,3-Bis[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134142186: (E)-1-(4-Chlorophenyl)-3-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134156241: (E)-1-(2-Chlorophenyl)-3-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134729052: (E)-3-(3-Hydroxy-4-methoxyphenyl)-1-[2-hydroxy-6-methoxy-4-[(2S,3R,4S,5S,6R)-3,4,5-trihydroxy-6-[[(2S,3S,4S,5S,6R)-3,4,5-trihydroxy-6-methyloxan-2-yl]oxymethyl]oxan-2-yl]oxyphenyl]prop-2-en-1-one; 134736870: (E)-1-[4-[(2S,3R,4S,5S,6R)-4,5-Dihydroxy-6-(hydroxymethyl)-3-[(2S,3R,4R,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 134833663: Schembl21527690; 135188495: (E)-1-(Hydroxy-4-methoxyphenyl)-3-[4-(oxan-2-yloxy)phenyl]prop-2-en-1-one; 137333808: (E)-1-[4-[(2R,3R,4R,5R,6R)-3,4-Dihydroxy-6-(hydroxy-methyl)-5-[(2S,3S,4R,5R)-3,4,5-trihydroxyoxan-2-yl]oxyoxan-2-yl]oxy-2-hydroxyphenyl]-3-(3,4-dihydroxyphenyl)prop-2-en-1-one; 138107319: (E)-1-(2,4-Dihydroxyphenyl)-3-[4-[(2R,3R,4R,5S,6R)-3,4,5-trihydroxy-6-(hydroxymethyl)oxan-2-yl]oxyphenyl]prop-2-en-1-one; 138114808: 3-[4-[3-[(4R)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 138454317: (E)-3-(3-Hydroxy-4-methoxyphenyl)-1-[2-hydroxy-6-methoxy-4-[(3R,4S,5S,6R)-3,4,5-trihydroxy-6-[[(2S,3R,4R,5R,6S)-3,4,5-trihydroxy-6-methyloxan-2-yl]oxymethyl]oxan-2-yl]oxyphenyl]prop-2-en-1-one; 139076079: E-4-(beta-D-Allopyranosyloxy)phenyl]-1-(4-chlorophenyl)prop-2-enone ethanol solvate; 139076080: (E)-1-(4-Chlorophenyl)-3-[4-[(2S,3R,4R,5R,6R)-3,4,5-trihydroxy-6-(hydroxymethyl)oxan-2-yl]oxyphenyl]prop-2-en-1-one; 139077109: (E)-4-(beta-D-Allopyranosyloxy)cinnamyl 4-bromophenyl ketone ethanol solvate; 139078358: (E)-1-(4-Chlorophenyl)-3-[4-(2,3,4,6-tetra-O-acetyl-beta-D-allopyrano-syloxy)phenyl]prop-2-en-1-one; 139078359: [(2R,3R,4R,5R,6S)-3,4,5-Triacetyloxy-6-[4-[(E)-3-(4-chlorophenyl)-3-oxoprop-1-enyl]phenoxy]oxan-2-yl]methyl acetate; 139234392: (E)-3-(4-Bromophenyl)-1-[4-(oxan-2-yloxy)phenyl]prop-2-en-1-one; 139234395: Schembl21527702; 139234397: (E)-3-(4-Methoxyphenyl)-1-[4-(oxan-2-yloxy)phenyl]prop-2-en-1- one; 139234399: (E)-3-(4-Methoxyphenyl)-1-[2-(oxan-2-yloxy)phenyl]prop-2-en-1-one; 139234402: (E)-1-(4-Fluorophenyl)-3-[4-(oxan-2-yloxy)phenyl]prop-2-en-1-one; 139234406: (E)-1-(4-Chlorophenyl)-3-[3-(oxan-2-yloxy)phenyl]prop-2-en-1-one; 139234414: (E)-1-(4-Chlorophenyl)-3-[4-(oxan-2-yloxy)phenyl]prop-2-en-1-one; 139234418: (E)-1-(4-Bromo-phenyl)-3-[4-(oxan-2-yloxy)phenyl]prop-2-en-1-one; 139234442: [2-(4-Chlorophenyl)-6-[4-[(E)-3-(4-fluorophenyl)-3-oxoprop-1-enyl]phenyl]oxan-4-yl] 4-methylbenzenesulfonate; 139234443: (E)-3-[4-[6-(4-Chlorophenyl)-4-hydroxyoxan-2-yl]phenyl]-1-(4-fluorophenyl) prop-2-en-1-one; 139234444: [2-(4-Bromophenyl)-6-[4-[(E)-3-(4-bromophenyl)-3-oxoprop-1-enyl]phenyl]oxan-4-yl] 4-methylbenzenesulfonate; 139234445: (E)-1-(4-Bromophenyl)-3-[4-[6-(4-bromophenyl)-4-hydroxyoxan-2-yl]phenyl]prop-2-en-1-one; 139234453: (E)-1-(2-Aminophenyl)-3-[4-methyl-3-(oxan-2-yloxy)phenyl]prop-2-en-1-one; 139675946: [(2R,3R,4S,5R,6S)-3,4,5-Triacetyloxy-6-[3-acetyloxy-2-[3-(4-methoxyphenyl)prop-2-enoyl]phenoxy]oxan-2-yl]methyl acetate; 139675949: 1-[2-Hydroxy-6-[(2S,3R,4S,5S,6R)-3,4,5-trihydroxy-6-(hydroxymethyl)oxan-2-yl]oxyphenyl]-3-(4-methoxyphenyl)prop-2-en-1-one; 139675959: Ethyl [4-[3-oxo-3-[2-phenylmethoxy-6-[(2S,3R,4S,5S,6R)-3,4,5-trihydroxy-6-(hydroxymethyl)oxan-2-yl]oxyphenyl]prop-1-enyl]phenyl] carbonate; 139675960: 3-(4-Hydroxyphenyl)-1-[2-phenylmethoxy-6-[(2S,3R,4S,5S,6R)-3,4,5-trihydroxy-6-(hydroxy-methyl)oxan-2-yl]oxyphenyl]prop-2-en-1-one; 139675966: 1-[2-[(2S,3R,4R,5S,6R)-3,4-Dihydroxy-6-(hydroxymethyl)-5-[(2R,3R,4S,5S,6R)-3,4,5-trihydroxy-6-(hydroxymethyl)oxan-2-yl]oxyoxan-2-yl]oxy-6-hydroxyphenyl]-3-(4-methoxyphenyl)prop-2-en-1-one; 139675975: 1-[2-Hydroxy-6-[(2S,3R,4S,5S,6R)-3,4,5-trihydroxy-6-(hydroxymethyl)oxan-2-yl]oxyphenyl]-3-(4-methylphenyl)prop-2-en-1-one; 139675977: 3-[4-(Oxan-2-yloxy)phenyl]-1-[2-phenylmethoxy-6-[(2S,3R,4S,5S,6R)-3,4,5-trihydroxy-6-(hydroxymethyl)oxan-2-yl]oxyphenyl]prop-2-en-1-one; 140426282: (E)-3-(1-Benzofuran-5-yl)-1-[2-hydroxy-4-methyl-6-[[3,4,5-tris(phenylmethoxy)-6-(phenylmethoxymethyl)oxan-2-yl]methyl]phenyl]prop-2-en-1-one; 140497894: (E)-1-[2,6-Dihydroxy-4-[(2S,4R,5S)-3,4,5-trihydroxy-6-[[(2R,4S,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 142905619: (E)-1-[2-[3,4-Dihydroxy-6-(hydroxymethyl)-5-methyloxan-2-yl]oxy-6-hydroxy-4-methylphenyl]-3-(4-methoxyphenyl) prop-2-en-1-one; 142905624: Ethane;(E)-1-[2-[5-fluoro-3,4-dihydroxy-6-(hydroxymethyl) oxan-2-yl]oxy-6-hydroxy-4-methylphenyl]-3-(4-methoxyphenyl)prop-2-en-1-one; 143186777: (E)-1-[2,6-Dihydroxy-4-[(2S,5S)-3,4,5-trihydroxy-6-[[(2R,5R)-5-hydroxy-6-methyloxan-2-yl]oxymethyl]oxan-2-yl]oxyphenyl]-3-(3-hydroxy-4-methoxyphenyl)prop-2-en-1-one; 145188916: (E)-3-[4-(Oxan-2-yloxy)phenyl]-1-phenylprop-2-en-1-one; 145188918: (E)-3-[4-(Oxan-2-yloxy)phenyl]-1-(4-phenylphenyl)prop-2-en-1-one; 145188947: (E)-1-(4-Cyclohexa-1,5-dien-1-ylphenyl)-3-[4-(oxan-2-yloxy)phenyl]prop-2-en-1-one; 145533558: (E)-1-[4-[3,4-Dihydroxy-6-[(1,2,3-trihydroxy-4-methoxypentoxy)methyl]oxan-2-yl]oxy-2-hydroxy-6-methoxyphenyl]-3-(3-hydroxy-4-methoxyphenyl)prop-2-en-1-one; 145847218: N-(Oxan-2-yl)-4-[(E)-3-oxo-3-phenylprop-1-enyl]benzamide; 146223484: Schembl21527686; 146223485: Schembl21527687; 146223486: Schembl21527691; 146223494: Schembl21527703; 146223495: Schembl21527704; 146223496: Schembl21527705; 146223501: Schembl21527712; 146223503: Schembl21527714; 146223504: Schembl21527715; 146223505: Schembl21527716; 146223507: Schembl21527718; 146223508: Schembl21527720; 146932022: (E)-1-Phenyl-3-[4-[3,4,5-trihydroxy-6-(hydroxymethyl)oxan-2-yl]oxyphenyl]prop-2-en-1-one; 147077786: (E)-1-[4-[(2S,5S)-4,5-Dihydroxy-6-[[(2R)-3,4,5-trihydroxy-6-methyl-3,6-dihydro-2H-pyran-2-yl]oxymethyl]oxan-2-yl]oxy-2,6-dihydroxyphenyl]-3-(3-hydroxy-4-methoxyphenyl)prop-2-en-1-one; 147583920: [4-[(E)-3-[4-[(2S,3R,4S,5S,6R)-3,5-Dihydroxy-6-(hydroxymethyl)-4-methyloxan-2-yl]oxyphenyl]prop-2-enoyl]-3-hydroxyphenyl] benzoate; 148266144: 1-Imino-1-[3-methyl-4-[(E)-3-[3-methyl-4-(oxan-2-yloxy)phenyl]prop-2-enoyl]phenyl]propan-2-one; 148307711: (E)-1-[4-[(2S,5S)-6-[[(2R,5R)-4,5-Dihydroxy-6-methyloxan-2-yl]oxymethyl]-3,4,5-trihydroxyoxan-2-yl]oxy-2,6-dihydroxyphenyl]-3-(3-hydroxy-4-methoxyphenyl)prop-2-en-1-one; 148479939: (E)-1-[2,6-Dihydroxy-4-[[(1R,4S)-1-hydroxy-2-[[3,4,5-trihydroxy-2-(iodomethyl)-2H-pyran-6-yl]oxymethyl]-3-oxabicyclo[4.1.0]heptan-4-yl]oxy]phenyl]-3-(3-hydroxy-4-methoxyphenyl) prop-2-en-1-one; 148896062: (E)-1-(2,4-Dihydroxyphenyl)-3-[4-(3,4,5,6-tetrahydroxyoxan-2-yl)oxyphenyl]prop-2-en-1-one; 149310647: (E)-1-[2-Ethoxy-4-(oxan-2-yloxy)phenyl]-3-[4-methoxy-3-(oxan-2-yloxy)phenyl]prop-2-en-1-one; 149916821: 2-[4-[(E)-3-[4-[(E)-3-(Oxan-2-yloxyamino)-3-oxoprop-1-enyl]phenyl]prop-2-enoyl]phenyl]ethanesulfonic acid; 150252462: (E)-3-[4-[(E)-3-[4-(Azidomethyl)phenyl]-3-oxoprop-1-enyl]phenyl]-N-(oxan-2-yloxy)prop-2-enamide; 151853930: (E)-3-[4-[(E)-3-[4-(Chloromethyl)phenyl]-3-oxoprop-1-enyl]phenyl]-N-(oxan-2-ylperoxy) prop-2-enamide; 152902528: (E)-1-(2-Hydroxy-4-methoxyphenyl)-3-[4-[(2S,3S,4S,6R)-3,4,5-trihydroxy-6-(hydroxymethyl)oxan-2-yl]oxyphenyl]prop-2-en-1-one; 152913097: (E)-1-[4-[(2S,5S)-6-[[(2R,5R)-4,5-Dihydroxy-6-methyloxan-2-yl]oxymethyl]-4,5-dihydroxyoxan-2-yl]oxy-2,6-dihydroxyphenyl]-3-(3-hydroxy-4-methoxyphenyl) prop-2-en-1-one; 153259545: (E)-1-[4-[(2S,5S)-4,5-Dihydroxy-6-[[(2R)-4-hydroxy-4-(hydroxymethyl)-6-methyloxan-2-yl]methoxymethyl]oxan-2-yl]oxy-2,6-dihydroxy-phenyl]-3-(3-hydroxy-4-methoxyphenyl)prop-2-en-1-one; 154441977: (E)-1-[2,6-Dihydroxy-4-[(2S,5S)-3,4,5-trihydroxy-6-[[(2R,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 154496376: (E)-3-(3,4-Dihydroxyphenyl)-1-[2-hydroxy-4-[(2S,3S,4S,5S,6S)-3,4,5-trihydroxy-6-(hydroxymethyl) oxan-2-yl]oxyphenyl] prop-2-en-1-one; 154496797: (E)-1-[2,4-Dihydroxy-6-[(2S,3S,4S,5S,6R)-3,4,5-trihydroxy-6-(hydroxymethyl)oxan-2-yl]oxyphenyl]-3-(4-hydroxyphenyl)prop-2-en-1-one; 154699691: (2S,3S,4S,5R,6S)-3,4,5-Trihydroxy-6-[2-[(E)-3-phenylprop-2-enoyl]phenoxy]oxane-2-carboxylic acid; 154699800: (2S,3S,4S,5R,6S)-3,4,5-Trihydroxy-6-[4-[(E)-3-phenylprop-2-enoyl]phenoxy]oxane-2-carboxylic acid; 154699814: (2S,3S,4S,5R,6S)-3,4,5-Trihydroxy-6-[4-[(E)-3-oxo-3-phenylprop-1-enyl]phenoxy]oxane-2-carboxylic acid; 154831693: (E)-3-(3-Hydroxy-4-methoxyphenyl)-1-[2-hydroxy-6-methoxy-4-[(2R,3S,4R,5R,6S)-3,4,5-trihydroxy-6-[[(2S,3S,4S,5S,6R)-3,4,5-trihydroxy-6-methyloxan-2-yl]oxymethyl]oxan-2-yl]oxyphenyl]prop-2-en-1-one; 155510974: Chembl4435309; 155520833: Chembl4449688; 155525409: Chembl4457806; 155527534: Chembl4459528; 155527687: Chembl4460121; 155529078: Chembl4462394; 155531903: Chembl4466811; 155536289: Chembl4473200; 155542903: Chembl4522036; 155543722: Chembl4522874; 155545633:

Chembl4529531; 155547171: Chembl4534640; 155563112: Chembl4573295; 155566202: Chembl4583837.

Chalcones with Hydroxy Substitution(s)

The following includes various exemplary chalcones with a hydroxy substitution(s) (Numbers are PubChem Compound Identification (PubChem CID) numbers): 425: GU17; ISL; Isoliquiritigen; 2483: 1-(2,4-Dihydroxyphenyl)-3-(3,4-dihydroxyphenyl)-2-propen-1-one; 2535: 3-(3,4-Dihydroxyphenyl)-1-(2-hydroxy-4-methoxyphenyl)prop-2-en-1-one; 5249: 2'-Carboxymethoxy-4,4'-bis(3-methyl-2-butenyloxy) chalcone; 14611: 1-(2-Hydroxyphenyl)-3-phenylprop-2-en-1-one; 25861: 1-(2-Hydroxyphenyl)-3-(4-hydroxyphenyl)prop-2-en-1-one; 25862: 2',4',3-Trihydroxy-4-methoxychalcone; 59787: 2-Carboxy-4-hydroxy-2-(hydroxy-methyl)-4-oxo-butanoate; dimethyl-[2-[2-[(E)-3-phenylprop-2-enoyl]phenoxy]ethyl]azanium; 89340: 3-(4-Hydroxyphenyl)-1-phenylprop-2-en-1-one; 94240: 1-(4-Hydroxyphenyl)-3-phenylprop-2-en-1-one; 95547: 2'-Hydroxy-4-methoxy-chalcone; 97766: CID 97766; 97793: 1-(4-Hydroxyphenyl)-3-(4-methoxyphenyl)prop-2-en-1-one; 97847: 1-(2-Hydroxyphenyl)-3-(4-dimethylaminophenyl)-2-propen-1-one; 98120: 2-Propen-1-one,1-(2-hydroxy-4-methoxy-phenyl)-3-(4-methoxyphenyl)-; 98239: CID 98239; 103608: 2',4,4',6'-Tetrahydroxy-3-methoxychalcone; 118586: 2',4',4-Trihydroxy-3-methoxychalcone; 125157: (E)-2',6'-Dihydroxy-4,4'-dimethoxychalcone; 127519: 4'-Ethoxy-2'-hydroxy-4,6'-dimethoxy chalcone; 134561: 2-Propen-1-one,1,3-bis(4-hydroxyphenyl)-, (2E)-; 146051: 3-(4-Hydroxy-3-methoxyphenyl)-1-phenylprop-2-en-1-one; 146817: 3-(3,4-Dihydroxyphenyl)-1-(4-hydroxy-2-methoxyphenyl)prop-2-en-1-one; 148236: 1-(2-Hydroxy-4,6-dimethoxyphenyl)-3-(3-hydroxy-4-methoxyphenyl) prop-2-en-1-one; 153145: 3-[3-Hydroxy-4-[3-(3-hydroxy-4-methoxyphenyl)prop-2-enoyl]phenoxy]propane-1-sulfonic acid; 153701: 1-(2-Hydroxy-4,6-dimethoxyphenyl)-3-(4-methylsulfanylphenyl)prop-2-en-1-one; 154102: 1-(2,4-Dihydroxy-6-methoxyphenyl)-3-phenylprop-2-en-1-one; 155802: 2-Propen-1-one, 3-(4-hydroxyphenyl)-1-(2,4,6-trihydroxyphenyl)-; 162957: 1-(2,4-Dihydroxy-6-methoxyphenyl)-3-(4-hydroxyphenyl) prop-2-en-1-one; 165210: 1-(2,4-Dihydroxyphenyl)-3-(3,4-dimethoxyphenyl)prop-2-en-1-one; 166795: 1-(2,4-Dihydroxyphenyl)-3-(4-methoxyphenyl)prop-2-en-1-one; 177052: CID 177052; 179278: 4-t-Butyl-2'-carboxymethoxy-4'-(3-methyl-2-butenyloxy)chalcone; 181323: 3-(3,4-Dimethoxyphenyl)-1-(4-hydroxyphenyl) prop-2-en-1-one; 184424: 2-[2-(3-Phenylprop-2-enoyl)phenyl]acetic acid; 185535: 1-(2,4-Dimethoxyphenyl)-3-(4-hydroxyphenyl)prop-2-en-1-one; 191628: 1-[2-Hydroxy-6-methoxy-4-[(3R,4S,5S,6R)-3,4,5-trihydroxy-6-(hydroxymethyl)oxan-2-yl]oxyphenyl]-3-(4-hydroxyphenyl)prop-2-en-1-one; 193980: 4-3-[4-(Carb-oxymethoxy)phenyl]-3-oxoprop-1-en-1-ylbenzoic acid; 215794: 4'-[Hydroxy-3-(4-phenylpiperazin-1-yl)-propoxy]-4-methoxy-chalcone; 217608: 2'-Hydroxy-4'-prenyloxychalcone; 235731: 3-(1,3-Benzodioxol-5-yl)-1-(2,4-dihydroxyphenyl)prop-2-en-1-one; 235736: 6'-Hydroxy-2',4,4'-trimethoxychalcone; 242589: 1-(2-Hydroxy-4,6-dimethoxy-phenyl)-3-phenyl-2-propen-1-one; 244230: 1-(4-Chlorophenyl)-3-(4-hydroxyphenyl)prop-2-en-1-one; 248019: 1-(2-Hydroxyphenyl)-3-(3-methoxyphenyl)prop-2-en-1-one; 252074: 1-(2-Hydroxyphenyl)-3-(3-hydroxyphenyl)prop-2-en-1-one; 261703: 1-(2-Hydroxyphenyl)-3-(3,4-methylenedioxyphenyl)-2-propen-1-one; 261706: 2',4-Dihydroxy-3-methoxychalcone; 265720: 1-(2-Hydroxy-4-methoxyphenyl)-3-phenylprop-2-en-1-one; 265725: 1-(2-Hydroxy-phenyl)-3-[4-[3-(2-hydroxyphenyl)-3-oxoprop-1-enyl]phenyl]prop-2-en-1-one; 284109: CID 284109; 308423: 3-(1,3-Benzodioxol-5-yl)-1-(2-hydroxy-4-methoxyphenyl)prop-2-en-1-one; 317158: 3-(3-Hydroxy-phenyl)-1-phenyl-prop-2-en-1-one; 321238: 1-[2-Hydroxy-4-(3-methylbut-2-enoxy)phenyl]-3-(4-hydroxyphenyl)prop-2-en-1-one; 344529: 4-Chloro-2'-hydroxychalcone; 344530: 2-Propen-1-one, 1-(2,4-dihydroxyphenyl)-3-phenyl-; 363394: 1-(2-Hydroxy-4,6-dimethoxyphenyl)-3-(4-methoxy-3-phenylmethoxyphenyl) prop-2-en-1-one; 380216: 4-[3-(3,4-Dihydroxyphenyl)prop-2-enoyl]benzonitrile; 380218: 3-[4-(Dimethylamino) phenyl]-1-(4-hydroxyphenyl)prop-2-en-1-one; 381076: 4'-Hydroxy-3,4-methylenedioxy-chalcone; 387385: 2-Propen-1-one, 3,3'-(1,4-phenylene)bis[1-(4-hydroxyphenyl)-; 387879: 2-[4-[3-(4-Methoxyphenyl)-3-oxoprop-1-enyl]phenoxy]acetic acid; 399426: 3-(3,4-Dihydroxy-phenyl)-1-(2,4-dimethoxyphenyl)prop-2-en-1-one; 403504: 3-(3,4-Dichlorophenyl)-1-(2-hydroxy-4,6-dimethoxyphenyl)prop-2-en-1-one; 404551: 3-[4-[4-Hydroxy-5-[3-(4-hydroxyphenyl)prop-2-enoyl]-2-methoxyphenoxy]phenyl]-1-(2-hydroxy-4-methoxyphenyl) prop-2-en-1-one; 404552: 1-(2,4-Dihydroxyphenyl)-3-[4-[4-hydroxy-5-[3-(4-hydroxyphenyl) prop-2-enoyl]-2-methoxyphenoxy]phenyl] prop-2-en-1-one; 404553: 1-[2-Hydroxy-4-[4-hydroxy-5-[3-(4-hydroxyphenyl)prop-2-enoyl]-2-methoxyphenoxy] phenyl]-3-(4-hydroxy-phenyl)prop-2-en-1-one; 404554: 3-[4-[2,4-Dihydroxy-5-[3-(4-hydroxyphenyl)prop-2-enoyl] phenoxy]phenyl]-1-(2,4-dihydroxyphenyl)prop-2-en-1-one; 404555: 1-[5-[5-[3-(2,4-Dihydroxyphenyl)-3-oxoprop-1-enyl]-2-hydroxyphenyl]-2,4-dihydroxyphenyl]-3-(4-hydroxy-phenyl)prop-2-en-1-one; 454264: 1-(2,4-Dihydroxyphenyl)-3-[4-[(2S,3R,4S,5S,6R)-3,4,5-trihydroxy-6-(hydroxymethyl)oxan-2-yl]oxyphenyl]prop-2-en-1-one; 460718: 3-Phenyl-1-(2,4,6-trihydroxyphenyl)prop-2-en-1-one; 466232: 2-Propen-1-one, 1-(2-hydroxy-6-methoxyphenyl)-3-(4-methoxyphenyl)-; 466233: 2-Propen-1-one, 1-(2,4-diethoxy-6-hydroxyphenyl)-3-phenyl-; 466245: CID 466245; 466246: 1-(4-Chloro-2-hydroxyphenyl)-3-(4-methoxyphenyl)prop-2-EN-1-one; 466257: 1-(2-Hydroxyphenyl)-3-(3-iodophenyl)prop-2-en-1-one; 466260: 1-(2-Hydroxyphenyl)-3-(4-iodophenyl)prop-2-en-1-one; 466266: 2-Propen-1-one, 3-(3-aminophenyl)-1-(2-hydroxyphenyl)-; 466337: 2-Propen-1-one, 3-(4-bromophenyl)-1-(2-hydroxyphenyl)-; 468135: 3-(3,4-Dihydroxyphenyl)-1-(4-hydroxyphenyl) prop-2-en-1-one; 468136: 2-Propen-1-one, 3-(3,4-dihydroxyphenyl)-1-phenyl-, (2E)-; 480789: 2',4'-Bis(methoxymethoxy)-6'-hydroxychalcone; 480790: 2'-Hydroxy-4,4',6'-tris(methoxymethoxy)chalcone; 480792: 2'-Hydroxy-3,4,4',6'-tetrakis(methoxymethoxy) chalcone; 480798: 3-[4-[3-[3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 563451: 3-(3-Hydroxyphenyl)-1-(2-phenylmethoxyphenyl)prop-2-en-1-one; 590378: 1-(2-Hydroxy-phenyl)-3-(4-nitro-phenyl)prop-2-en-1-one; 592132: 3-(3,4-Dimethoxyphenyl)-1-(2-hydroxy-4,6-dimethoxyphenyl)prop-2-en-1-one; 592216: 2-Propen-1-one, 1-(2-hydroxy-4-methoxy-phenyl)-3-(4-hydroxyphenyl)-; 606469: 2-Propen-1-one, 1-(2,6-dihydroxy-4-methoxy-phenyl)-3-phenyl-, (E)-; Chalcone, 2',6'-dihydroxy-4'-methoxy-; 2',6'-Dihydroxy-4'-methoxychalcone; 617249: CID 617249; 617944: 4-Hydroxyl-4'-fluorochalcone; 622978: 1-(4-Hydroxyphenyl)-3-(4-methylsulfanylphenyl)prop-2-en-1-one; 628474: 3-(2,3-Dihydro-1,4-benzodioxin-6-yl)-1-(2-hydroxy-4-methoxyphenyl)prop-2-en-1-one; 635448: 2-[4-[3-(4-Hydroxyphenyl)prop-2-enoyl]anilino]-3-piperidin-1-ylnaphthalene-1,4-dione; 636657: (2S,3R)-3-[5-[(E)-3-(2,4-Dihydroxyphenyl)-3-oxoprop-1-enyl]-2-hydroxyphenyl]-5-hydroxy-2-(4-hydroxyphenyl)-7-[(2R,3R,4R,5R,6S)-3,4,5-trihydroxy-6-(hydroxymethyl)oxan-2-yl]oxy-2,3-dihydrochromen-4-one; 638276: 2'-Hydroxychalcone; 638278: Isoliquiritigenin; 641785: Cardamonin; 2750015: 3-Hydroxy-4-[[3-(3-oxo-3-phenylprop-1-enyl)phenyl]diazenyl]naphthalene-2,7-disulfonic acid; 2750016: 5-Amino-4-hydroxy-3-[[3-(3-oxo-3-phenylprop-1-enyl)phenyl]diazenyl]naphthalene-2,7-disulfonic acid; 2750017: 3-Hydroxy-4-[[4-(3-oxo-3-phenylprop-1-enyl)phenyl]diazenyl]naphthalene-2,7-disulfonic acid; 2750018: 8-Hydroxy-7-[[4-(3-oxo-3-phenylprop-1-enyl)phenyl]diazenyl]naphthalene-1,3,6-trisulfonic acid; 2751345: 2-[4-(3-Oxo-3-phenylprop-1-enyl)phenoxy]acetic acid; 2764060: 1-(4-Chlorophenyl)-3-(3-hydroxyphenyl)prop-2-en-1-one; 2764545: Benzoic acid, 2-[3-(4-nitro-phenyl)-1-oxo-2-propenyl]-; 2775764: CID 2775764; 2775962: CID 2775962; 2777833: CID 2777833; 2777924: 2-Propen-1-one, 1-[2-hydroxy-4-(phenylmethoxy)phenyl]-3-phenyl-; 2778088: CID 2778088; 2778089: CID 2778089; 2778090: CID 2778090; 2779991: 1-(2-Hydroxy-4-phenylmethoxyphenyl)-3-(4-methoxyphenyl)prop-2-en-1-one; 2780497: 1-(2-Hydroxy-phenyl)-3-(4-isopropylphenyl)-prop-2-EN-1-one; 2780524: CID 2780524; 2780542: CID 2780542; 2780544: CID 2780544; 2780605: 3,2'-Dihydroxy-4,4'-dimethoxychalcone; 2780607: 1-(2-Hydroxy-4-methoxyphenyl)-3-(3-hydroxyphenyl)prop-2-en-1-one; 2780755: 4-Fluoro-2'-hydroxychalcone; 2780918: CID 2780918; 2780925: 6'-Methoxy-2',4-dihydroxychalcone; 2780956: 3-(3-Hydroxy-4-methoxyphenyl)-1-(2-phenylmethoxy-phenyl)prop-2-en-1-one; 2781383: 2'-Chloro 4-hydroxy chalcone; 2794956: 3-(3,4-Dimethoxyphenyl)-1-(2-hydroxyphenyl)prop-2-en-1-one; 2795162: 2-[4-(3-Phenylprop-2-enoyl)phenoxy]acetic Acid; 2795166: Acetic acid, [4-[3-(4-chlorophenyl)-1-oxo-2-propenyl]phenoxy]-; 2832510: 4-Oxo-4-[4-(3-oxo-3-phenylprop-1-enyl)anilino]but-2-enoic acid; 2832513: 1,3-Dioxo-2-[4-(3-oxo-3-phenylprop-1-enyl)phenyl]isoindole-5-carboxylic acid; 2840008: 1-(4-Hydroxyphenyl)-3-[4-(triazirin-1-yl)phenyl]prop-2-en-1-one; 2866770: 2-[2-[[4-(3-Oxo-3-phenylprop-1-enyl)phenyl]carbamoyl]phenyl]benzoic acid; 2867411: 1,3-Dioxo-2-[3-(3-oxo-3-phenylprop-1-enyl)phenyl]isoindole-5-carboxylic acid; 2886363: 3-(4-Fluoro-phenyl)-1-(4-hydroxyphenyl)prop-2-en-1-one; 2887832: 3-[3-(Benzotriazol-1-ylmethyl)-4-methoxyphenyl]-1-(4-hydroxyphenyl)prop-2-en-1-one; 2888194: 3-[3-[(4-Fluorophenoxy)methyl]-4-methoxyphenyl]-1-(4-hydroxyphenyl)prop-2-en-1-one; 2888197: 3-[4-[(2-Chlorophenyl)methoxy]-3-ethoxyphenyl]-1-(4-hydroxyphenyl)prop-2-en-1-one; 2888210: 2-Propen-1-one, 3-(4-bromophenyl)-1-(4-hydroxyphenyl)-; 2888668: 2-Propen-1-one, 1-(4-hydroxyphenyl)-3-(4-methylphenyl)-; 2888751: 3-[3-[(4-Chlorophenoxy)methyl]-4-methoxy-phenyl]-1-(4-hydroxyphenyl)prop-2-en-1-one; 2908747: 2-[3-(4-Fluorophenyl)prop-2-enoyl]benzoic acid; 2927306: 2-Propen-1-one, 1-(2-hydroxy-4-methoxyphenyl)-3-(4-methylphenyl)-; 2931258: 1-(2-Hydroxyphenyl)-3-[4-methoxy-3-[(4-nitrophenoxy)methyl]phenyl]prop-2-en-1-one; 2933051: N-[4-[[5-[3-(2-Hydroxyphenyl)-3-oxoprop-1-enyl]-2-methoxyphenyl]methoxy]phenyl]acetamide; 2933679: 1-(2-Hydroxyphenyl)-3-[4-methoxy-3-[(3-methyl-4-nitrophenoxy)methyl]phenyl]prop-2-en-1-one; 3090595: 1-(4-Chloro-2-hydroxy-phenyl)-3-(3,4-dihydro-2H-1,5-benzodioxepin-7-yl)prop-2-en-1-one; 3092393: 4-[1,3,5,7-Tetraoxo-2,6-bis[4-(3-oxo-3-phenylprop-1-enyl)phenyl]pyrrolo[3,4-f]isoindole-8-carbonyl]benzoic acid; 3142005: 1-(4-Hydroxyphenyl)-3-[4-methoxy-3-(morpholin-4-ylmethyl)phenyl]prop-2-en-1-one; 3279914: 2-[N-(Carboxymethyl)-4-[3-(2-hydroxyphenyl)-3-oxoprop-1-enyl]anilino]acetic acid; 3312978: 4-[3-(3-Ethoxy-4-hydroxyphenyl)prop-2-enoyl]benzonitrile; 3333641: 3-[4-(Dimethylamino)phenyl]-1-(2-hydroxy-4-methylphenyl)prop-2-en-1-one; 3334638: 1-(4-Hydroxyphenyl)-3-[4-(4-methylphenyl)sulfanyl-3-nitro-phenyl]prop-2-en-1-one; 3374656: 4-[3-(4-Bromophenyl)-3-oxoprop-1-en-1-yl]benzoic acid; 3387897: 2-[4-[3-(2-Fluoro-4-methoxyphenyl)-3-oxoprop-1-enyl]phenoxy]acetic acid; 3394884: 2-Propen-1-one, 3-(3-hydroxyphenyl)-1-(4-methoxyphenyl)-; 3399247: 2',4'-Dihydroxy-4-dimethylamino chalcone; 3403652: 3-(3,4-Dihydro-2H-1,5-benzodioxepin-7-yl)-1-(2-hydroxy-4-methylphenyl)prop-2-en-1-one; 3404361: 3-(4-Fluorophenyl)-1-(2-hydroxy-4,6-dimethoxyphenyl) prop-2-en-1-one; 3405030: 3-[4-(Dimethylamino)-3-nitro-phenyl]-1-(4-hydroxyphenyl)prop-2-en-1-one; 3425159: CID 3425159; 3425554: 2-Propen-1-one, 3-(4-chlorophenyl)-1-(2-hydroxy-4-methoxyphenyl)-; 3428008: 1-(4-Hydroxyphenyl)-3-(3-nitro-phenyl)prop-2-en-1-one; 3491388: 3-[3-[(2,3-Dimethylphenoxy)methyl]-4-methoxyphenyl]-1-(4-hydroxyphenyl) prop-2-en-1-one; 3516584: 1-[4-(5,6-Dimethyl-1,3-dihydroisoindol-2-yl)phenyl]-3-(4-hydroxyphenyl)prop-2-en-1-one; 3523081: 2-[4-[3-(4-Iodophenyl)-3-oxoprop-1-enyl]phenoxy]acetic acid; 3538741: 4-[3-(2,4-Dimethoxyphenyl)-3-oxoprop-1-enyl] benzoic acid; 3570892: (E)-3-(4-Hydroxyphenyl)-1-(4-morpholinophenyl)-2-propen-1-one; 3588264: 2-[4-[3-[4-(Difluoromethoxy)phenyl]-3-oxoprop-1-enyl]phenoxy]acetic acid; 3591885: 1-(2-Hydroxy-4-phenylmethoxyphenyl)-3-(4-phenylmethoxyphenyl)prop-2-en-1-one; 3596953: 2-[3,5-Dihydroxy-4-(3-phenylprop-2-enoyl)phenoxy]acetic acid; 3600196: 1-(4-Hydroxy-phenyl)-3-[4-(morpholin-4-yl)phenyl]prop-2-en-1-one; 3602610: 1-(4-Ethoxy-2-hydroxy-phenyl)-3-(3-ethoxy-4-methoxyphenyl)prop-2-en-1-one; 3605908: 3-[3-[(2-Cyclohexyl-phenoxy)methyl]-4-methoxyphenyl]-1-(4-hydroxyphenyl)prop-2-en-1-one; 3641048: 3-[3-(1H-Benzimidazol-2-ylsulfanylmethyl)-4-methoxyphenyl]-1-(4-hydroxyphenyl)prop-2-en-1-one; 3651078: 4-[3-[4-(Diethylsulfamoyl)phenyl]-3-oxoprop-1-enyl]benzoic acid; 3655026: [4-[3-(3,4-Dihydroxyphenyl) prop-2-enoyl]-3-hydroxyphenyl] acetate; 3677005: 2-[3-(5-Carboxy-1,3-dioxoisoindol-2-yl)-5-[[4-(3-oxo-3-phenylprop-1-enyl)phenyl]carbamoyl]phenyl]-1,3-dioxoisoindole-5-carboxylic acid; 3695632: CID 3695632; 3769539: Hesperidin methyl chalcone; 3773009: 1-(2-Hydroxy-4-methoxyphenyl)-3-(2,3,4,5-tetrahydro-1,6-benzodi-oxocin-8-yl)prop-2-en-1-one; 3797091: 3-(4-Azidophenyl)-1-(4-hydroxyphenyl)prop-2-en-1-one; 3889783: 2-[4-[3-(4-Bromophenyl)-3-oxoprop-1-enyl]phenoxy]acetic acid; 3895744: 1-(4-Cyclohexylphenyl)-3-(3-hydroxy-4-methoxyphenyl)prop-2-en-1-one; 3905786: 4-[3-Oxo-3-(4-phenylphenyl)prop-1-enyl]benzoic Acid; 3906441: 2-[4-[3-(4-Tert-butylphenyl)-3-oxoprop-1-enyl]phenoxy]acetic acid; 3912575: 1-(2-Hydroxy-4,6-dimethoxyphenyl)-3-(4-hydroxy-3-methoxyphenyl)prop-2-en-1-one; 3916296: 4-3-[4-(Morpholin-4-yl)phenyl]-3-oxoprop-1-en-1-ylbenzoic acid; 3919613: 3-[3-[(2,4-Dichlorophenoxy)methyl]-4-methoxy-phenyl]-1-(2-hydroxyphenyl)prop-2-en-1-one; 3923818: 3-(3-Hydroxyphenyl)-1-[4-(morpholin-4-yl)phenyl]prop-2-en-1-one; 3932496: 1-(2-Hydroxy-4,6-dimethoxyphenyl)-3-(4-methylphenyl)prop-2-en-1-one; 3935120: 1-(4-Hydroxyphenyl)-3-[3-methoxy-4-(pentyloxy) phenyl]prop-2-en-1-one; 3938424: 3-(4-Chlorophenyl)-1-(2-hydroxy-4,6-dimethoxyphenyl) prop-2-en-1-one; 3943170: 1-[4-[4,5-Dihydroxy-6-(hydroxymethyl)-3-(3,4,5-trihydroxy-6-methyloxan-2-yl)oxyoxan-2-yl]oxy-2,6-dihydroxyphenyl]-3-(3-hydroxy-4-methoxyphenyl) prop-2-en-1-one; 3947700: 2-[4-(3-[1,1'-Biphenyl]-4-yl-3-oxoprop-1- en-1-yl)phenoxy]acetic acid; 3954030: 3-(3-Bromophenyl)-1-(2-hydroxy-4,6-dimethoxyphenyl)prop-2-en-1-one; 3966823: 2-[4-[3-[4-(Dimethylsulfamoyl)phenyl]-3-oxoprop-1-enyl]phenoxy]acetic acid; 3967097: 4-[3-(4-Methoxyphenyl)-3-oxoprop-1-enyl]benzoic acid; 3971006: 3-[4-(Dimethyl-amino)phenyl]-1-(2-hydroxy-4,6-dimethoxyphenyl)prop-2-en-1-one; 3972708: 4-[3-(4-Methylphenyl)-3-oxoprop-1-enyl]benzoic acid; 3974953: 4-[3-[4-(Azepan-1-ylsulfonyl)phenyl]-3-oxoprop-1-enyl]benzoic acid; 3978835: 1-(2-Hydroxy-4,6-dimethoxyphenyl)-3-(3-methoxy-4-phenylmethoxyphenyl)prop-2-en-1-one; 3978982: 1-(4-Hydroxyphenyl)-3-[4-[[(4-methyl-1,2,4-triazol-3-yl)thio]-3-nitro-phenyl]-2-propen-1-one; 3982902: 3-[4-(Difluoro-methoxy)-3-methoxyphenyl]-1-(4-hydroxyphenyl)prop-2-en-1-one; 3995781: 4-Carboxychalcone; 4013485: 3-(4-Hydroxyphenyl)-1-(2,4,6-trimethoxyphenyl)prop-2-en-1-one; 4015531: 3-(3-Hydroxy-4-methoxyphenyl)-1-(2,4,6-trimethoxyphenyl)prop-2-en-1-one; 4020419: 2-[4-[3-(4-Chlorophenyl)-3-oxoprop-1-enyl]phenoxy]acetic acid; 4022274: 3-(3-Hydroxyphenyl)-1-[4-(pyrrolidine-1-sulfonyl)phenyl]prop-2-en-1-one; 4028467: 2-(4-3-[4-(Azepane-1-sulfonyl)phenyl]-3-oxoprop-1-en-1-ylphenoxy) acetic acid; 4031159: 1-(2-Chlorophenyl)-3-(3-hydroxy-4-methoxyphenyl)prop-2-en-1-one; 4036532: 1-[4-(Azepane-1-sulfonyl)phenyl]-3-(3,4-dihydroxyphenyl)prop-2-en-1-one; 4043064: 4-[3-(4-Chlorophenyl)-3-oxoprop-1-enyl]benzoic acid; 4092839: 2-[4-(3-Phenylprop-2-enoyl)phenyl]acetic Acid; 4134265: Methyl 4-(4-[3-(4-hydroxyphenyl)-3-oxoprop-1-en-1-yl]-2-methoxyphenoxymethyl)benzoate; 4144092: 3-(4-Hydroxyphenyl)-1-(2-methoxyphenyl)prop-2-en-1-one; 4171778: 3-(3-Fluorophenyl)-1-(2-hydroxyphenyl)prop-2-en-1-one; 4190507: 1-(2-Hydroxyphenyl)-3-[4-methoxy-3-(morpholin-4-ylmethyl)phenyl]prop-2-en-1-one; 4204739: 1-[3,5-Dihydroxy-2-(3-phenylprop-2-enoyl)phenyl]-3-phenylprop-2-en-1-one; 4206144: 3-(2,3-Dihydro-1,4-benzodioxin-6-yl)-1-[2-hydroxy-4,6-bis(methoxymethoxy)phenyl]prop-2-en-1-one; 4219708: 3-(2,3-Dihydro-1,4-benzodioxin-6-yl)-1-(2-hydroxy-4-methylphenyl)-2-propen-1-one; 4230875: 1-[2-Hydroxy-4-(2-hydroxyethoxy)phenyl]-3-(3-methoxyphenyl)prop-2-en-1-one; 4231699: 3-(3,4-Dimethoxyphenyl)-1-[2-hydroxy-4-(2-hydroxyethoxy)phenyl]prop-2-en-1-one; 4269080: 2-[4-[3-[4-(Diethylsulfamoyl)phenyl]-3-oxoprop-1-enyl]phenoxy]acetic acid; 4271076: 3-(3,4-Dihydro-2H-1,5-benzodioxepin-7-yl)-1-(2-hydroxy-4-methoxyphenyl)prop-2-en-1-one; 4272561: 4-[3-(4-Fluorophenyl)-3-oxoprop-1-enyl]benzoic acid; 4274430: 2-[4-[3-(4-Cyanophenyl)-3-oxoprop-1-enyl]phenoxy]acetic acid; 4305458: 1-(2-Hydroxy-4,6-dimethoxyphenyl)-3-(3-nitro-phenyl)prop-2-en-1-one; 4309547: 4-[3-Oxo-3-(4-pyrrolidin-1-ylsulfonylphenyl)prop-1-enyl]benzoic acid; 4310713: 3-(2,3-Dihydro-1,4-benzodioxin-6-yl)-1-(4-hydroxyphenyl)prop-2-en-1-one; 4328344: 2-[4-[3-(4-Morpholin-4-ylphenyl)-3-oxoprop-1-enyl]phenoxy]acetic acid; 4328732: 1-(2-Hydroxy-4-methoxyphenyl)-3-(3-methoxyphenyl)prop-2-en-1-one; 4336331: 3-(3-Hydroxy-4-methoxyphenyl)-1-[4-(morpholin-4-yl)phenyl]prop-2-en-1-one; 4375742: 4-3-[4-(Difluoromethoxy)phenyl]-3-oxoprop-1-en-1-ylbenzoic acid; 4398471: 1-[2,4-Dihydroxy-6-[3,4,5-trihydroxy-6-(hydroxymethyl)oxan-2-yl]oxyphenyl]-3-(4-hydroxyphenyl)prop-2-en-1-one; 4405834: 1-[2-Hydroxy-6-[3,4,5-trihydroxy-6-(hydroxy-methyl)oxan-2-yl]oxyphenyl]-3-(4-nitro-phenyl)prop-2-en-1-one; 4457529: 2-[4-[3-(2,4-Dichlorophenyl)-3-oxoprop-1-enyl]phenoxy]acetic acid; 4481621: 1-[2-Hydroxy-4-[3,4,5-trihydroxy-6-(hydroxymethyl)oxan-2-yl]oxyphenyl]-3-[4-hydroxy-3-[3,4,5-tri hydroxy-6-(hydroxymethyl)oxan-2-yl]oxyphenyl] prop-2-en-1-one; 4483656: 3-(3-Hydroxyphenyl)-1-(4-methylphenyl)prop-2-en-1-one; 4483657: 3-(4-Hydroxyphenyl)-1-(4-methylphenyl)prop-2-en-1-one; 4483659: 1-(4-Hydroxyphenyl)-3-(3-methoxyphenyl)prop-2-en-1-one; 4483660: 2-Propen-1-one, 3-(4-ethoxyphenyl)-1-(4-hydroxyphenyl)-; 4483662: 3-(4-Hydroxy-3-methoxyphenyl)-1-(4-methylphenyl)prop-2-en-1-one; 4525387: 4'-Amino-4-hydroxychalcone; 4528861: 3-[3-(1,3-Benzothiazol-2-ylsulfanylmethyl)-4-methoxyphenyl]-1-(4-hydroxyphenyl)prop-2-en-1-one; 4539530: 1-(4-Hydroxy-2-methylphenyl)-3-(4-methoxyphenyl)prop-2-en-1-one; 4541128: 1-(4-Hydroxyphenyl)-3-(4-propan-2-ylphenyl)prop-2-en-1-one; 4541971: 4-[3-(2-Bromophenyl)-3-oxoprop-1-enyl]benzoic acid; 4556985: 3-(4-Chloro-3-nitrophenyl)-1-(4-hydroxyphenyl)prop-2-en-1-one; 4563621: 2-[4-[3-(2,4-Dimethoxyphenyl)-3-oxoprop-1-enyl]phenoxy]acetic acid; 4573498: 4-[3-(3-Hydroxyphenyl)prop-2-enoyl]-N,N-dimethylbenzenesulfonamide; 4579060: 4-[3-(4-Nitrophenyl)-3-oxoprop-1-enyl]benzoic acid; 4619752: 2-[4-[3-Oxo-3-(4-pyrrolidin-1-ylsulfonylphenyl)prop-1-enyl]phenoxy]acetic acid; 4621396: 3-(4-Hydroxyphenyl)-1-[4-(morpholine-4-sulfonyl)phenyl]prop-2-en-1-one; 4625443: [5-[3-(2-Hydroxy-4-methoxy-phenyl)-3-oxoprop-1-enyl]-2-methoxyphenyl] acetate; 4629641: 1-[4-[[2-(Furan-2-yl)-7,8-dihydroxy-4,4a,6,7,8,8a-hexahydropyrano[3,2-d][1,3]dioxin-6-yl]oxy]phenyl]-3-phenylprop-2-en-1-one; 4629986: N-[2-(Furan-2-yl)-8-hydroxy-6-[4-(3-phenylprop-2-enoyl)phenoxy]-4,4a,6,7,8,8a-hexahydropyrano[3,2-d][1,3]dioxin-7-yl]acetamide; 4636781: Methyl 4-[3-(4-hydroxyphenyl)-3-oxoprop-1-en-1-yl]benzoate; 4636784: 1-(2,4-Dimethoxyphenyl)-3-(3-hydroxyphenyl)prop-2-en-1-one; 4636786: 3-(4-Hydroxy-3-methoxyphenyl)-1-(4-methoxy-phenyl)prop-2-en-1-one; 4636789: 3-(3-Hydroxyphenyl)-1-(4-phenylphenyl)prop-2-en-1-one; 4636790: 1-[1,1'-Biphenyl]-4-yl-3-(4-hydroxyphenyl)prop-2-en-1-one; 4636792: 1-(4-Bromophenyl)-3-(3-hydroxyphenyl)prop-2-en-1-one; 4636793: 1-(2,4-Dimethoxyphenyl)-3-(4-hydroxy-3-methoxyphenyl)prop-2-en-1-one; 4638791: 1-(2-Hydroxyphenyl)-3-(4-phenyl methoxyphenyl)prop-2-en-1-one; 4644633: 2-[2-[[3-(3-Oxo-3-phenylprop-1-enyl)phenyl]carbamoyl]phenyl]benzoic acid; 4670006: 4-[3-(2-Fluoro-4-methoxyphenyl)-3-oxoprop-1-enyl]benzoic acid; 4675668: 2'-Hydroxy-3,4-ethylenedioxychalcone; 4678311: 2-(3-Phenylprop-2-enoyl)benzoic Acid; 4691349: 3-(4-Chlorophenyl)-1-[2,4-dihydroxy-6-[3,4,5-trihydroxy-6-(hydroxymethyl)oxan-2-yl]oxyphenyl]prop-2-en-1-one; 4765797: 3-[3-[(3,5-Dimethyl-4-nitropyrazol-1-yl)methyl]-4-methoxyphenyl]-1-(2-hydroxyphenyl)prop-2-en-1-one; 4795644: 2-4-[3-(4-Bromophenyl)prop-2-enoyl]phenoxypropanoic acid; 4796352: 1-(2,4-Dichlorophenyl)-3-(4-hydroxy-3-nitrophenyl)prop-2-en-1-one; 4798244: 1-(4-Hydroxy-phenyl)-3-[3-methoxy-4-(2-methylpropoxy)phenyl]prop-2-en-1-one; 4798262: 2-4-[3-(4-Ethylphenyl)prop-2-enoyl]phenoxypropanoic acid; 4801009: 3-(4-Hydroxy-3-nitrophenyl)-1-(4-methoxyphenyl)prop-2-en-1-one; 4811008: 1-(4-Hydroxyphenyl)-3-(4-nitro-phenyl)prop-2-en-1-one; 4811011: 1-(4-Hydroxyphenyl)-3-[4-(trifluoromethyl)phenyl]prop-2-en-1-one; 4811012: 3-[4-(Difluoromethoxy)phenyl]-1-(4-hydroxyphenyl)prop-2-en-1-one; 4811013: 1-(4-Hydroxyphenyl)-3-[3-(trifluoromethyl)phenyl]prop-2-en-1-one; 4811015: 4-[3-(4-Hydroxy-phenyl)-3-oxoprop-1-enyl]benzonitrile; 4811016: 1-(4-Hydroxyphenyl)-3-(3-methylphenyl) prop-2-en-1-one; 4811019: 1-(4-Hydroxyphenyl)-3-(4-propoxyphenyl)prop-2-en-1-one; 4812865: 2-4-[3-(4-Hydroxyphenyl)-3-oxoprop-1-en-1-yl]-2-methoxyphenoxyacetonitrile; 4815851: (E)-3-(4-Hydroxy-3-nitro-phenyl)-1-(4-bromophenyl)-2-propene-1-one; 4815853: 3-(4-Hydroxy-3-nitro-phenyl)-1-(4-methylphenyl)prop-2-en-1-one; 4815906: 1-[4-(Difluoromethoxy)phenyl]-3-(4-hydroxy-3-nitro-phenyl)prop-2-en-1-one; 4815912: 3-(4-Hydroxy-3-nitro-phenyl)-1-(4-morpholin-4-ylphenyl)prop-2-en-1-one; 4815973: 3-(4-Hydroxy-3-nitro-phenyl)-1-(4-iodophenyl)prop-2-en-1-one; 4822612: 1-(4-Hydroxyphenyl)-3-(4-methoxy-3-propoxyphenyl)prop-2-en-1-one; 4826645: 3-(3-Ethoxy-4-hydroxyphenyl)-1-[4-(pyrrolidine-1-sulfonyl)phenyl]prop-2-en-1-one; 4829975: 4-[3-[4-(5,6-Dihydro-4H-1,3-thiazin-2-ylamino)phenyl]-3-oxoprop-1-enyl]benzoic acid; 4831854: 1-[4-(Azepan-1-yl)phenyl]-3-(3-hydroxy-4-methoxyphenyl)prop-2-en-1-one; 4839860: 4-[[4-[3-(4-Butoxyphenyl)prop-2-enoyl]phenyl]sulfonylamino]benzoic acid; 4848720: 1-(4-Tert-butylphenyl)-3-(4-hydroxy-phenyl)prop-2-en-1-one; 4851469: 3-(4-Hydroxy-3-nitro-phenyl)-1-[4-(3-methylbutoxy)phenyl]prop-2-en-1-one; 4851874: 1-(4-Hydroxyphenyl)-3-(3-phenoxyphenyl)prop-2-en-1-one; 4872711: 3-(2,3-Dihydro-1,4-benzodioxin-6-yl)-1-(2,4-dihydroxyphenyl)prop-2-en-1-one; 4876232: N,N-Diethyl-2-4-[3-(3-hydroxyphenyl)prop-2-enoyl]phenoxyacetamide; 4912782: 3-(4-Butoxyphenyl)-1-(4-hydroxyphenyl)prop-2-en-1-one; 4912783: 1-(4-Hydroxyphenyl)-3-(4-phenylmethoxyphenyl)prop-2-en-1-one; 4912784: 1-(4-Ethoxyphenyl)-3-(4-hydroxyphenyl)prop-2-en-1-one; 5029003: 1-(4-Bromophenyl)-3-(3-hydroxy-4-methoxy-phenyl)prop-2-en-1-one; 5036583: 2-(4-3-[4-(Methoxycarbonyl)phenyl]prop-2-enoylben-zenesulfonamido)propanoic acid; 5040378: 1-(4-Hydroxyphenyl)-3-(methoxy-4-phenyl-methoxyphenyl)prop-2-en-1-one; 5087802: 3-(4-Hydroxy-3-methoxyphenyl)-1-(4-phenylphenyl)prop-2-en-1-one; 5087803: 1-(4-Bromophenyl)-3-(4-hydroxy-3-methoxyphenyl)prop-2-en-1-one; 5095679: 1-(4-Hydroxyphenyl)-3-4-[methyl(phenyl)amino]-3-nitro-phenylprop-2-en-1-one; 5098942: 3-(4-Hydroxyphenyl)-1-[4-hydroxy-2-[3,4,5-trihydroxy-6-(hydroxymethyl)oxan-2-yl]oxyphenyl]prop-2-en-1-one; 5104225: 2-[4-[3-(2-Bromophenyl)-3-oxoprop-1-enyl]phenoxy]acetic acid; 5104737: 3-[3-[(4-Chloro-5-methyl-2-propan-2-ylphenoxy)methyl]-4-methoxyphenyl]-1-(2-hydroxyphenyl)prop-2-en-1-one; 5133115: 2-4-[3-(4-Nitrophenyl)-3-oxoprop-1-en-1-yl]phenoxyacetic acid; 5134310: 1-(4-Hydroxyphenyl)-3-[3-methoxy-4-[[3-(trifluoromethyl)phenyl]methoxy]phenyl]prop-2-en-1-one; 5152359: 1-(4-Hydroxyphenyl)-3-(3-nitro-4-piperidin-1-ylphenyl)prop-2-en-1-one; 5179897: 1-(2-Hydroxy-4,6-dimethoxyphenyl)-3-(4-hydroxyphenyl)prop-2-en-1-one; 5210470: 4-[3-[4-(Dimethylsulfamoyl)phenyl]-3-oxoprop-1-enyl]benzoic acid; 5218143: 2-4-[3-(4-Chlorophenyl)prop-2-enoyl]benzenesulfonamidopropanoic acid; 5227575: 4-[3-(2,4-Dichlorophenyl)-3-oxoprop-1-enyl]benzoic acid; 5237562: 2-[4-[3-(4-Methylphenyl)-3-oxoprop-1-enyl]phenoxy]acetic acid; 5239685: 1-[2-Hydroxy-4-[3,4,5-trihydroxy-6-(hydroxy-methyl)oxan-2-yl]oxyphenyl]-3-phenylprop-2-en-1-one; 5243500: Benzoic acid, 4-[3-(4-cyanophenyl)-3-oxo-1-propenyl]-; 5244220: 4-[3-(4-Tert-butylphenyl)-3-oxoprop-1-enyl]benzoic acid; 5270542: 3,2'-Dihydroxychalcone; 5272792: 4-[3-Oxo-3-(2-hydroxyphenyl)-1-propenyl]benzoic acid; 5276742: (E)-1-[4-[(2S,3R,4S,5S,6R)-4,5-Dihydroxy-6-(hydroxy-methyl)-3-[(2S,3R,4R,5R,6S)-3,4,5-trihydroxy-6-methyl-tetrahydropyran-2-yl]oxy-tetrahydro-pyran-2-yl]oxy-2,6-dihydroxyphenyl]-3-(3-hydroxy-4-methoxy-phenyl)prop-2-en-1-one; 5280960: Naringenin chalcone; 5281222: Butein; 5281256: Isobutrin; 5282219: Sofalcone; 5282361: 4-Hydroxychalcone; 5282362: 4'-Hydroxychalcone; 5285714: 2,2'-[5-(4-[(1 E)-3-Oxo-3-phenylprop-1-en-1-yl]phenylcarbamoyl) benzene-1,3-diyl]bis(1,3-dioxo-2,3-dihydro-1H-isoindole-5-carboxylic acid); 5315562: (Z)-1-(2,4-Dihydroxyphenyl)-3-(3,4-dihydroxy-phenyl)prop-2-en-1-one; 5316793: 2',6'-Dihydroxy-4'-methoxychalcone; 5318591: Isoliquiritin; 5318659: Isosalipurposide; 5319493: Sappanchalcone; 5319688: 2'-O-Methylisoliquiritigenin; 5320092: Neoisoliquiritin; 5331295: 2'-Hydroxy-4-methoxychalcone; 5331296: (2E)-3-[4-(Dimethylamino)phenyl]-1-(2-hydroxyphenyl)prop-2-en-1-one; 5337942: 3-(4-Fluorophenyl)-1-(2-hydroxyphenyl)prop-2-en-1-one; 5341375: 2-(4-[3-(4-Hydroxy-phenyl)acryloyl]phenylamino)-3-(1-piperidinyl)naphthoquinone; 5353470: Calythropsin; 5354702: (Z)-1-[4-[2-(Diethylamino)ethoxy]phenyl]-3-phenylprop-2-en-1-one;2-hydroxypropane-1,2,3-tricarboxylic acid; 5355468: (E)-3-(1,3-Benzodioxol-5-yl)-1-(2,4-dihydroxyphenyl)prop-2-en-1-one; 5355469: 2'-Hydroxy-4,4',6'-trimethoxychalcone; 5355594: 4'-Hydroxy-4-methoxychalcone; 5356121: Flavokawain b; 5356341: (E)-1-(4-Chlorophenyl)-3-(4-hydroxyphenyl)prop-2-en-1-one; 5357218: 2',4-Dihydroxychalcone; 5357488: 1-(2-Hydroxy-4-methoxyphenyl)-3-(4-methoxyphenyl)-2-propen-1-one; 5358381: 3-(3-Hydroxyphenyl)-1-phenylprop-2-en-1-one; 5368601: 1-[2-(Benzyloxy)phenyl]-3-(3-hydroxyphenyl)prop-2-en-1-one; 5372365: Acrylophenone, 2',4'-dihydroxy-3-(m-hydroxy-p-methoxyphenyl)-; 5372941: 3-(4-Bromophenyl)-1-(2-hydroxyphenyl)prop-2-en-1-one; 5372946: 3-(4-Chlorophenyl)-1-(2-hydroxyphenyl)prop-2-en-1-one; 5372977: 2-Propen-1-one, 1-(2-hydroxyphenyl)-3-(4-nitrophenyl)-; 5373259: 2'-Hydroxy-3,4,4',6'-tetramethoxychalcone; 5373269: 2-Hydroxy-alpha-(p-hydroxybenzylidene)-4-methoxyacetophenone; 5373273: 3-(3,4-Dimethoxyphenyl)-1-(2-hydroxy-4-methoxyphenyl)prop-2-en-1-one; 5376916: 2'-Hydroxy-4-methylchalcone; 5376979: 2',4'-Dihydroxychalcone; 5377024: 1-(4-Fluorophenyl)-3-(4-hydroxyphenyl)prop-2-en-1-one; 5377854: (E)-1-(4-Hydroxyphenyl)-3-(4-methylsulfanylphenyl)prop-2-en-1-one; 5378786: (E)-3-(2,3-Dihydrobenzo[b][1,4]dioxin-6-yl)-1-(2-hydroxy-4-methoxyphenyl)prop-2-en-1-one; 5379071: 2',3-Dihydroxy-4,4',6'-trimethoxychalcone; 5380645: 2'-Hydroxy-4'-Methoxychalcone; 5461154: 2',3,4,4',6'-Pentahydroxychalcone; 5467477: 4,4'-Dihydroxychalcone; 5468164: 4-[(E)-3-(3,4-Dihydroxyphenyl)prop-2-enoyl]benzonitrile; 5468166: (E)-3-(4-Dimethylaminophenyl)-1-(4-hydroxyphenyl)prop-2-en-1-one; 5468276: 3-(1,3-Benzodioxol-5-yl)-1-(4-hydroxyphenyl)-2-propen-1-one; 5469051: (4-(3-(4-Methoxyphenyl)-3-oxo-1-propenyl)phenoxy)acetic acid; 5471280: 2',4'-Dimethoxy-3,4-dihydroxychalcone; 5472106: N-[4-[(E)-3-(3-Ethoxy-4-hydroxyphenyl)prop-2-enoyl]phenyl]-2-methyl-5-nitrobenzenesulfonamide; 5472409: (E)-3-(3,4-Dichlorophenyl)-1-(2-hydroxy-4,6-dimethoxyphenyl)prop-2-en-1-one; 5472697: Rhuschalcone I; 5472698: Rhuschalcone III; 5472699: Rhuschalcone IV; 5472700: Rhuschalcone II; 5472701: Rhuschalcone VI; 5706840: 1-(4-Chlorophenyl)-3-(3-hydroxyphenyl)-2-propen-1-one; 5706859: 2-[3-(4-Nitrophenyl)acryloyl]-benzenecarboxylic acid; 5708656: 4-[3-(2-Hydroxyphenyl)-3-oxoprop-1-enyl]benzonitrile; 5708669: 3-(3,4-Dihydro-2H-1,5-benzodioxepin-7-yl)-1-[2-hydroxy-4-(methoxymethoxy)phenyl]prop-2-en-1-one; 5708870: 1-(2-Hydroxy-4-methylphenyl)-3-phenylprop-2-en-1-one; 5708883: 1-[4-(Benzyloxy)-2-hydroxyphenyl]-3-phenylprop-2-en-1-one; 5708895: 3-(3-Chlorophenyl)-1-(2-hydroxyphenyl)prop-2-en-1-one; 5708900: (2E)-3-(3,4-Dichlorophenyl)-1-(4-hydroxyphenyl)prop-2-en-1-one; 5708902: 1-(4-Chlorophenyl)-3-(3-hydroxy-4-methoxyphenyl)prop-2-en-1-one; 5708903: 1-(4-Chlorophenyl)-3-(4-hydroxy-3-methoxyphenyl)prop-2-en-1-one; 5709141: 1-[4-(Benzyloxy)-2-hydroxyphenyl]-3-(4-methoxyphenyl)prop-2-en-1-one; 5709227: 1-(2-Hydroxyphenyl)-3-(4-isopropylphenyl)prop-2-en-1-one; 5709244: 3-(3,4-Dihydro-2H-1,5-benzodioxepin-7-yl)-1-(2-hydroxyphenyl)prop-2-en-1-one; 5709254: 1-(4-Chloro-2-hydroxyphenyl)-3-(2,3-dihydro-1,4-benzodioxin-6-yl)prop-2-en-1-one; 5709255: 3-(2,3-Dihydro-1,4-benzodioxin-6-yl)-1-(2-hydroxy-6-methoxyphenyl)prop-2-en-1-one; 5709262: 1-(2-Hydroxy-4-methoxyphenyl)-3-(3-hydroxy-4-methoxyphenyl)prop-2-en-1-one; 5709263: (E)-1-(2-Hydroxy-4-methoxyphenyl)-3-(3-hydroxyphenyl)prop-2-en-1-one; 5709315: 1-(2-Hydroxyphenyl)-3-(3-nitro-phenyl)prop-2-en-1-one; 5709317: 1-(2-Hydroxy-6-methoxyphenyl)-3-(4-hydroxyphenyl)prop-2-en-1-one; 5709318: 2',3,4-Trihydroxychalcone; 5709337: 1-[2-(Benzyloxy)phenyl]-3-(3-hydroxy-4-methoxyphenyl)prop-2-en-1-one; 5709339: 3-(1,3-Benzodioxol-5-yl)-1-(2-hydroxyphenyl)prop-2-en-1-one; 5709439: (2E)-1-(2-Chlorophenyl)-3-(4-hydroxyphenyl)prop-2-en-1-one; 5711223: 2',4'-Dihydroxy-4-methoxychalcone; 5712116: 3,4-Dimethoxy-2'-hydroxychalcone; 5712162: (E)-3-(4-Chlorophenyl)-1-(4-hydroxyphenyl)prop-2-en-1-one; 5712192: 2-(4-Cinnamoylphenoxy) acetic acid; 5712196: 2-(4-[3-(4-Chlorophenyl)acryloyl]phenoxy)acetic acid; 5718241: (2E)-4-Oxo-4-(4-[(1 E)-3-oxo-3-phenylprop-1-enyl]phenylamino)but-2-enoic acid; 5718243: 1,3-Dioxo-2-[4-(3-oxo-3-phenyl-1-propenyl)phenyl]-5-isoindolinecarboxylic acid; 5720326: (E)-1-(4-Hydroxyphenyl)-3-[4-(1H-1,2,3-triaziren-1-yl)phenyl]-2-propen-1-one; 5725793: 2-[2-[[4-[(E)-3-Oxo-3-phenylprop-1-enyl]phenyl]carbamoyl]phenyl]benzoic acid; 5725966: 1,3-Dioxo-2-3-[(1 E)-3-oxo-3-phenylprop-1-en-1-yl]phenyl-2,3-dihydro-1H-isoindole-5-carboxylic acid; 5728928: (2E)-3-(4-Fluorophenyl)-1-(4-hydroxyphenyl)prop-2-en-1-one; 5729102: (2E)-3-[3-(1H-Benzotriazol-1-ylmethyl)-4-methoxyphenyl]-1-(4-hydroxyphenyl)prop-2-en-1-one; 5729203: 3-3-[(4-Fluorophenoxy)methyl]-4-methoxyphenyl-1-(4-hydroxyphenyl)-2-propen-1-one; 5729206: (2E)-3-4-[(2-Chlorobenzyl)oxy]-3-ethoxyphenyl-1-(4-hydroxy-phenyl)prop-2-en-1-one; 5729209: 4-Bromo-4'-hydroxychalcone; 5729327: (2E)-1-(4-Hydroxyphenyl)-3-(4-methylphenyl)prop-2-en-1-one; 5729350: (E)-3-[3-[(4-Chlorophenoxy)methyl]-4-methoxyphenyl]-1-(4-hydroxyphenyl)prop-2-en-1-one; 5732220: 2-(4-Fluoro-trans-cinnamoyl)benzoic acid; 5736268: (2E)-1-(2-Hydroxy-4-methoxyphenyl)-3-(4-methylphenyl)prop-2-en-1-one; 5736791: (2E)-1-(2-Hydroxyphenyl)-3-4-methoxy-3-[(4-nitrophenoxy)methyl]phenylprop-2-en-1-one; 5736989: N-[4-(5-[(1 E)-3-(2-Hydroxyphenyl)-3-oxoprop-1-en-1-yl]-2-methoxybenzyloxy)phenyl]acetamide; 5737064: (2E)-1-(2-Hydroxyphenyl)-3-4-methoxy-3-[(3-methyl-4-nitrophenoxy)methyl]phenylprop-2-en-1-one; 5743235: 2',3-Dihydroxy-4-methoxychalcone; 5743475: 2'-Hydroxy-6'-methoxychalcone; 5743627: 4'-(Dimethylamino)-2'-hydroxychalcone; 5744241: 3-(Dimethylamino)-2'-hydroxychalcone; 5749456: (2E)-1-(4-Chloro-2-hydroxyphenyl)-3-(3,4-dihydro-2H-1,5-benzo-dioxepin-7-yl)prop-2-en-1-one; 5749931: 4-[(1,3,5,7-Tetraoxo-2,6-bis4-[(1E)-3-oxo-3-phenylprop-1-en-1-yl]phenyl-1,2,3,5,6,7-hexahydropyrrolo[3,4-f]isoindol-4-yl)carbonyl]benzoic acid; 5766641: 1-(4-Hydroxy-phenyl)-3-(4-methoxy-3-morpholin-4-ylmethylphenyl)-propenone; 5781212: 2-(4-[(1E)-3-(2-Hydroxyphenyl)-3-oxoprop-1-enyl]phenyl(carboxymethyl)amino)acetic acid; 5790283: 4-[(E)-3-(3-Ethoxy-4-hydroxyphenyl)prop-2-enoyl]benzonitrile; 5796033: 3-[4-(Dimethylamino)phenyl]-1-(2-hydroxy-4-methylphenyl)-2-propene-1-one; 5796314: (E)-1-(4-Hydroxyphenyl)-3-[4-(4-methylphenyl)sulfanyl-3-nitro-phenyl]prop-2-en-1-one; 5807609: 4-[(E)-3-(4-Bromophenyl)-3-oxoprop-1-enyl] benzoic acid; 5813585: (2E)-3-(3-Hydroxyphenyl)-1-(4-methoxyphenyl)prop-2-en-1-one; 5815007: 2',4'-Dihydroxy-4-(dimethylamino)chalcone; 5816230: (2E)-3-(3,4-Dihydro-2H-1,5-benzodioxepin-7-YL)-1-(2-hydroxy-4-methylphenyl)prop-2-EN-1-one; 5816456: 4',6'-Dimethoxy-4-fluoro-2'-hydroxychalcone; 5816637: (E)-3-[4-(Dimethylamino)-3-nitro-phenyl]-1-(4-hydroxyphenyl) prop-2-en-1-one; 5822393: (E)-1-(4-Bromophenyl)-3-(4-hydroxyphenyl)prop-2-en-1-one; 5822497: (E)-3-(4-Chlorophenyl)-1-(2-hydroxy-4-methoxyphenyl)prop-2-en-1-one; 5823311: (2E)-1-(4-Hydroxyphenyl)-3-(3-nitrophenyl)prop-2-en-1-one; 5831509: 3,3"-(1,4-Phenylene)bis (4'-hydroxyacrylophenone); 5840229: 2'-Hydroxy-3-methoxychalcone; 5841830: (2E)-3-3-[(2,3-Dimethylphenoxy)methyl]-4-methoxyphenyl-1-(4-hydroxyphenyl) prop-2-en-1-one; 5848939: (E)-1-[4-(5,6-Dimethyl-1,3-dihydroisoindol-2-yl)phenyl]-3-(4-hydroxyphenyl)prop-2-en-1-one; 5850845: 2-[4-[(E)-3-(4-Iodophenyl)-3-oxoprop-1-enyl]phenoxy]acetic acid; 5855221: (E)-4-(3-(2,4-Dimethoxyphenyl)-3-oxoprop-1-en-1-yl)benzoic acid; 5863850: 3-(4-Hydroxyphenyl)-1-(4-morpholin-4-ylphenyl)prop-2-en-1-one; 5868565: 2-[4-[(E)-3-[4-(Difluoromethoxy)phenyl]-3-oxoprop-1-enyl] phenoxy]acetic acid; 5869607: 2'-Hydroxy-4,4'-bis(benzyloxy)chalcone; 5871882: (E)-1-(4-Hydroxyphenyl)-3-(4-morpholin-4-ylphenyl)prop-2-en-1-one; 5872465: (E)-1-(4-Ethoxy-2-hydroxyphenyl)-3-(3-ethoxy-4-methoxyphenyl)prop-2-en-1-one; 5873359: (2E)-3-3-[(2-Cyclohexylphenoxy)methyl]-4-methoxyphenyl-1-(4-hydroxyphenyl)prop-2-en-1-one; 5879763: 4-Hydroxycordoin; 5883189: (2E)-3-3-[(1H-Benzimidazol-2-ylsulfanyl)methyl]-4-methoxyphenyl-1-(4-hydroxyphenyl)prop-2-en-1-one; 5897251: (E)-3-(4-Fluorophenyl)-1-(2-hydroxy-4-methoxy-phenyl)prop-2-en-1-one; 5908537: 3-(1,3-Benzodioxol-5-yl)-1-(2-hydroxy-4-methoxy-phenyl)-2-propen-1-one; 5917946: (E)-3-(3-Hydroxy-4-methoxyphenyl)-1-[2-hydroxy-6-methoxy-4-[3,4,5-trihydroxy-6-[(3,4,5-trihydroxy-6-methyloxan-2-yl)oxymethyl]oxan-2-yl]oxyphenyl]prop-2-en-1-one; 5918862: (2E)-1-(2-Hydroxy-4-methoxyphenyl)-3-(2,3,4,5-tetrahydro-1,6-benzodioxocin-8-YL)prop-2-EN-1-one; 5925522: (2E)-3-(4-Azidophenyl)-1-(4-hydroxyphenyl)prop-2-en-1-one; 5927890: (2E)-3-(4-Hydroxyphenyl)-1-(4-methoxy-phenyl) prop-2-en-1-one; 5930244: (E)-3-(3,4-Dimethoxyphenyl)-1-(4-hydroxyphenyl)prop-2-en-1-one; 5935211: 3-(3-(Benzyloxy)-4-methoxyphenyl)-1-(2-hydroxy-4,6-dimethoxyphenyl)-2-propen-1-one; 5948326: 2-[4-[(E)-3-(4-Bromophenyl)-3-oxoprop-1-enyl]phenoxy]acetic acid; 5950123: (E)-1-(4-Cyclohexylphenyl)-3-(3-hydroxy-4-methoxyphenyl)prop-2-en-1-one; 5953346: 4-[(E)-3-Oxo-3-(4-phenylphenyl)prop-1-enyl]benzoic acid; 5953558: 2-[4-[(E)-3-(4-Tert-butylphenyl)-3-oxoprop-1-enyl]phenoxy]acetic acid; 5953849: 2',4'-Dihydroxy-3,4-dimethoxychalcone; 5955473: 4,2'-Dihydroxy-3,4',6'-trimethoxychalcone; 5956581: 4-[(E)-3-(4-Morpholin-4-ylphenyl)-3-oxoprop-1-enyl]benzoic acid; 5957603: (2E)-3-3-[(2,4-Dichlorophenoxy)methyl]-4-methoxyphenyl-1-(2-hydroxyphenyl)prop-2-en-1-one; 5959012: (E)-3-(3-Hydroxyphenyl)-1-(4-morpholin-4-ylphenyl)prop-2-en-1-one; 5961410: Derricidin; 5961745: 4',6'-Dimethoxy-2'-hydroxy-4-methylchalcone; 5962574: (2E)-1-(4-Hydroxyphenyl)-3-(3-methoxy-4-pentyloxyphenyl)prop-2-en-1-one; 5963651: 4-Chloro-4',6'-dimeth-oxy-2'-hydroxychalcone; 5965043: (E)-1-[4-[4,5-Dihydroxy-6-(hydroxymethyl)-3-(3,4,5-trihydroxy-6-methyloxan-2-yl)oxyoxan-2-yl]oxy-2, 6-dihydroxyphenyl]-3-(3-hydroxy-4-methoxyphenyl)prop-2-en-1-one; 5966422: 2-[4-[(E)-3-Oxo-3-(4-phenylphenyl)prop-1-enyl]phenoxy]acetic acid; 5968397: (E)-3-(3-Bromophenyl)-1-(2-hydroxy-4,6-dimethoxy-phenyl)prop-2-en-1-one; 5972385: 4-(Hydroxycarbonyl)-4'-methoxychalcone; 5973634: 4',6'-Dimethoxy-4-dimethylamino-2'-hydroxychalcone; 5973690: (E)-3-(4-Hydroxy-3-methoxyphenyl)-1-(2-hydroxyphenyl)prop-2-en-1-one; 5974179: 4-[(E)-3-Oxo-3-(p-tolyl)prop-1-enyl] benzoic acid; 5975937: 4-Benzyloxy-2'-hydroxy-3,4',6'-trimethoxychalcone; 5975988: (E)-1-(4-Hydroxyphenyl)-3-[4-[(4-methyl-1,2,4-triazol-3-yl)sulfanyl]-3-nitro-phenyl]prop-2-en-1-one; 5977228: (E)-3-[4-(Difluoromethoxy)-3-methoxyphenyl]-1-(4-hydroxy-phenyl)prop-2-en-1-one; 5981188: 4-(2-Benzoylvinyl)benzoic acid; 5986673: 4-Hydroxy-2',4',6'-trimethoxychalcone; 5987347: 3-Hydroxy-2',4,4',6'-tetramethoxychalcone; 5988917: [4-[3-(4-Chlorophenyl)-3-oxo-1-propenyl]phenoxy]acetic acid; 5989511: (E)-3-(3-Hydroxy-phenyl)-1-(4-pyrrolidin-1-ylsulfonylphenyl)prop-2-en-1-one; 5991539: 2-[4-[(E)-3-[4-(Azepan-1-ylsulfonyl)phenyl]-3-oxoprop-1-enyl]phenoxy]acetic acid; 5992399: (E)-1-(2-Chlorophenyl)-3-(3-hydroxy-4-methoxyphenyl)prop-2-en-1-one; 5994055: (E)-1-[4-(Azepan-1-ylsulfonyl)phenyl]-3-(3,4-dihydroxyphenyl)prop-2-en-1-one; 5996034: 4-[(E)-3-(4-Chlorophenyl)-3-oxo-prop-1-enyl]benzoic acid; 6008023: 4-[(2E)-3-Phenyl-2-propenoyl]phenylacetic acid; 6018209: Methyl 4-[[4-[(E)-3-(4-hydroxyphenyl)-3-oxoprop-1-enyl]-2-methoxyphenoxy]methyl]benzoate; 6020416: (E)-3-(4-Hydroxyphenyl)-1-(2-methoxyphenyl) prop-2-en-1-one; 6027568: 3-Fluoro-2'-hydroxychalcone; 6032438: 1-(2-Hydroxyphenyl)-3-[4-methoxy-3-(4-morpholinylmethyl)phenyl]-2-propen-1-one; 6036384: (E)-3-(2,3-Dihydro-1,4-benzodioxin-6-yl)-1-[2-hydroxy-4,6-bis(methoxymethoxy)phenyl]prop-2-en-1-one; 6040156: (2E)-3-(2,3-Dihydro-1,4-benzodioxin-6-yl)-1-(2-hydroxy-4-methylphenyl)prop-2-en-1-one; 6043161: (E)-1-[2-Hydroxy-4-(2-hydroxyethoxy)phenyl]-3-(3-methoxyphenyl) prop-2-en-1-one; 6043348: (E)-3-(3,4-Dimethoxyphenyl)-1-[2-hydroxy-4-(2-hydroxyethoxy)phenyl]prop-2-en-1-one; 6051368: 4-[(1 E)-3-Oxo-3-phenyl-1-propenyl]phenoxyacetic acid; 6054415: (E)-3-(3,4-Dihydro-2H-1,5-benzodioxepin-7-yl)-1-(2-hydroxy-4-methoxyphenyl) prop-2-en-1-one; 6054919: 4-[(E)-3-(4-Fluorophenyl)-3-oxoprop-1-enyl]benzoic acid; 6063903: 4',6'-Dimethoxy-2'-hydroxy-3-nitrochalcone; 6065112: 4-[(E)-3-Oxo-3-(4-pyrro-lidin-1-ylsulfonylphenyl)prop-1-enyl]benzoic acid; 6065444: (2E)-3-(2,3-Dihydro-1,4-benzo-dioxin-6-yl)-1-(4-hydroxyphenyl)prop-2-en-1-one; 6070796: 2-[4-[(E)-3-(4-Morpholin-4-ylphenyl)-3-oxoprop-1-enyl]phenoxy]acetic acid; 6070899: 3,4'-Dimethoxy-2'-hydroxychalcone; 6073054: (E)-3-(3-Hydroxy-4-methoxyphenyl)-1-(4-morpholin-4-ylphenyl)prop-2-en-1-one; 6083790: 4-[(E)-3-[4-(Difluoromethoxy)phenyl]-3-oxoprop-1-enyl]benzoic acid; 6084133: alpha,alpha'-(1,4-Phenylenedimethylidyne)bis(2'-hydroxyacetophenone); 6090017: (Z)-1-[2,4-Dihydroxy-6-[3,4,5-trihydroxy-6-(hydroxymethyl)oxan-2-yl]oxyphenyl]-3-(4-hydroxyphenyl)prop-2-en-1-one; 6115220: 2-[4-[(E)-3-(2,4-Dichlorophenyl)-3-oxoprop-1-enyl]phenoxy]acetic acid; 6123336: (E)-1-[2-Hydroxy-4-[3,4,5-trihydroxy-6-(hydroxymethyl)oxan-2-yl]oxyphenyl]-3-[4-hydroxy-3-[3,4,5-tri hydroxy-6-(hydroxymethyl)oxan-2-yl]oxyphenyl]prop-2-en-1-one; 6123886: (E)-3-(3-Hydroxyphenyl)-1-(4-methylphenyl)prop-2-en-1-one; 6123887: 4-Hydroxy-4'-methylchalcone; 6123889: 4'-Hydroxy-3-methoxychalcone; 6123890: 2-Propen-1-one, 3-(4-hydroxy-3-methoxyphenyl)-1-phenyl-; 6123891: (2E)-3-(4-Ethoxyphenyl)-1-(4-hydroxyphenyl)prop-2-en-1-one; 6123893: 3-Methoxy-4-hydroxy-4'-methylchalcone; 6140247: 1-(4-Aminophenyl)-3-(4-hydroxyphenyl)prop-2-en-1-one; 6141233: (2E)-3-3-[(1,3-Benzothiazol-2-ylsulfanyl)methyl]-4-methoxyphenyl-1-(4-hydroxyphenyl)prop-2-en-1-one; 6144076: 4'-Hydroxy-4-methoxy-2'-methylchalcone; 6144622: 1-(4-Hydroxyphenyl)-3-(4-isopropylphenyl)prop-2-en-1-one; 6144859: 4-[(E)-3-(2-Bromophenyl)-3-oxoprop-1-enyl]benzoic acid; 6149177: (E)-3-(4-Chloro-3-nitro-phenyl)-1-(4-hydroxyphenyl)prop-2-en-1-one; 6151074: 2-[4-[(E)-3-(2,4-Dimethoxyphenyl)-3-oxoprop-1-enyl]phenoxy]acetic acid; 6153741: 4-[(E)-3-(3-Hydroxyphenyl)prop-2-enoyl]-N,N-dimethylbenzenesulfonamide; 6155227: 4-[(E)-3-(4-Nitrophenyl)-3-oxo-prop-1-enyl]benzoic acid; 6166005: 2-[4-[(E)-3-Oxo-3-(4-pyrrolidin-1-ylsulfonylphenyl)prop-1-enyl]phenoxy]acetic acid; 6166490: (E)-3-(4-Hydroxyphenyl)-1-(4-morpholin-4-ylsulfonylphenyl)prop-2-en-1-one; 6167427: [5-[(E)-3-(2-Hydroxy-4-methoxyphenyl)-3-oxoprop-1-enyl]-2-methoxyphenyl]acetate; 6168803: (E)-1-[4-[[2-(Furan-2-yl)-7,8-dihydroxy-4,4a,6,7,8,8a-hexahydropyrano[3,2-d][1,3]dioxin-6-yl]oxy]phenyl]-3-phenylprop-2-en-1-one; 6168899: N-[2-(Furan-2-yl)-8-hydroxy-6-[4-[(E)-3-phenylprop-2-enoyl]phenoxy]-4,4a,6,7,8,8a-hexahydropyrano[3,2-d][1,3]dioxin-7-yl]acetamide; 6171839: Methyl 4-[(E)-3-(4-hydroxyphenyl)-3-oxoprop-1-enyl]benzoate; 6171842: (E)-1-(2,4-Dimethoxyphenyl)-3-(3-hydroxyphenyl)prop-2-en-1-one; 6171844: (E)-3-(4-Hydroxy-3-methoxyphenyl)-1-(4-methoxyphenyl)prop-2-en-1-one; 6171845: Chalcone, 4-hydroxy-2',4'-dimethoxy-; 6171848: (E)-3-(3-Hydroxyphenyl)-1-(4-phenylphenyl)prop-2-en-1-one; 6171849: Biphenyl-4-yl(p-hydroxystyryl)ketone; 6171851: 1-(4-Bromophenyl)-3-(3-hydroxyphenyl)prop-2-ene-1-one; 6171852: (E)-1-(2,4-Dimethoxy-phenyl)-3-(4-hydroxy-3-methoxyphenyl)prop-2-en-1-one; 6172473: (E)-1-(2-Hydroxy-phenyl)-3-(4-phenylmethoxyphenyl)prop-2-en-1-one; 6173967: 2-[2-[[3-[(E)-3-Oxo-3-phenylprop-1-enyl]phenyl]carbamoyl]phenyl]benzoic acid; 6182853: (2E)-3-(2,3-Dihydro-1,4-benzodioxin-6-yl)-1-(2-hydroxyphenyl)prop-2-en-1-one; 6183614: 2-trans-Cinnamoyl-benzoic acid; 6208825: 3-[3-(4-Nitro-3,5-dimethyl-1H-pyrazol-1-ylmethyl)-4-methoxy-phenyl]-1-(2-hydroxyphenyl)-2-propen-1-one; 6212819: 2-[4-[(E)-3-(4-Bromophenyl)prop-2-enoyl]phenoxy]propanoic acid; 6212877: (E)-1-(2,4-Dichlorophenyl)-3-(4-hydroxy-3-nitrophenyl)prop-2-en-1-one; 6213056: (E)-1-(4-Hydroxyphenyl)-3-[3-methoxy-4-(2-methyl-propoxy)phenyl]prop-2-en-1-one; 6213059: 2-[4-[(E)-3-(4-Ethylphenyl)prop-2-enoyl]phenoxy]propanoic acid; 6213240: (E)-3-(4-Hydroxy-3-nitro-phenyl)-1-(4-methoxyphenyl) prop-2-en-1-one; 6213956: (2E)-1-(4-Hydroxyphenyl)-3-(4-nitro-phenyl)prop-2-en-1-one; 6213959: (E)-1-(4-Hydroxyphenyl)-3-[4-(trifluoromethyl)phenyl]prop-2-en-1-one; 6213960: (E)-3-[4-(Difluoromethoxy)phenyl]-1-(4-hydroxyphenyl)prop-2-en-1-one; 6213961: (E)-1-(4-Hydroxyphenyl)-3-[3-(trifluoromethyl)phenyl]prop-2-en-1-one; 6213963: Chembl4459634; 6213964: 4'-Hydroxy-3-methylchalcone; 6213967: Chembl4589531; 6214318: 2-[4-[(E)-3-(4-Hydroxyphenyl)-3-oxoprop-1-enyl]-2-methoxyphenoxy]acetonitrile; 6214587: (E)-1-(4-Bromophenyl)-3-(4-hydroxy-3-nitro-phenyl)prop-2-en-1-one; 6214589: (E)-3-(4-Hydroxy-3-nitro-phenyl)-1-(4-methylphenyl)prop-2-en-1-one; 6214638: (E)-1-[4-(Difluoromethoxy)phenyl]-3-(4-hydroxy-3-nitro-phenyl)prop-2-en-1-one; 6214644: (E)-3-(4-Hydroxy-3-nitro-phenyl)-1-(4-morpholin-4-ylphenyl)prop-2-en-1-one; 6214698: (E)-3-(4-Hydroxy-3-nitro-phenyl)-1-(4-iodophenyl)prop-2-en-1-one; 6215114: (E)-1-(4-Hydroxyphenyl)-3-(4-methoxy-3-propoxyphenyl)prop- 2-en-1-one; 6215435: (E)-3-(3-Ethoxy-4-hydroxyphenyl)-1-(4-pyrrolidin-1-ylsulfonylphenyl)prop-2-en-1-one; 6215861: 4-[(E)-3-[4-(5,6-Dihydro-4H-1,3-thiazin-2-ylamino)phenyl]-3-oxoprop-1-enyl]benzoic acid; 6216278: (E)-1-[4-(Azepan-1-yl)phenyl]-3-(3-hydroxy-4-methoxyphenyl)prop-2-en-1-one; 6217472: 4-[[4-[(E)-3-(4-Butoxyphenyl)prop-2-enoyl]phenyl]sulfonylamino]benzoic acid; 6218676: 4-Hydroxy-4'-tert-butylchalcone; 6219088: (E)-3-(4-Hydroxy-3-nitro-phenyl)-1-[4-(3-methylbutoxy)phenyl]prop-2-en-1-one; 6219128: (E)-1-(4-Hydroxyphenyl)-3-(3-phenoxyphenyl)prop-2-en-1-one; 6222909: (E)-3-(2,3-Dihydro-1,4-benzodioxin-6-yl)-1-(2,4-dihydroxyphenyl)prop-2-en-1-one; 6223756: N,N-Diethyl-2-[4-[(E)-3-(3-hydroxyphenyl)prop-2-enoyl]phenoxy]acetamide; 6229071: Chembl4579602; 6229072: Chembl4450005; 6229073: (2E)-1-(4-Ethoxyphenyl)-3-(4-hydroxyphenyl)prop-2-en-1-one; 6252068: (E)-1-(4-Bromophenyl)-3-(3-hydroxy-4-methoxyphenyl)prop-2-en-1-one; 6253344: Helichrysetin; 6254442: 2-[[4-[(E)-3-(4-Methoxy-carbonylphenyl)prop-2-enoyl]phenyl]sulfonylamino]propanoic acid; 6255516: 3-[4-(Benzyloxy)-3-methoxyphenyl]-1-(4-hydroxyphenyl)-2-propen-1-one; 6266711: (E)-3-(4-Hydroxy-3-methoxyphenyl)-1-(4-phenylphenyl)prop-2-en-1-one; 6266712: (E)-1-(4-Bromophenyl)-3-(4-hydroxy-3-methoxyphenyl)prop-2-en-1-one; 6269064: (E)-1-(4-Hydroxyphenyl)-3-[4-(N-methylanilino)-3-nitro-phenyl]prop-2-en-1-one; 6271214: 2-[4-[(E)-3-(2-Bromophenyl)-3-oxoprop-1-enyl]phenoxy]acetic acid; 6271397: (2E)-3-(3-[4-Chloro-5-methyl-2-(methylethyl)phenoxy]methyl-4-methoxyphenyl)-1-(2-hydroxyphenyl)prop-2-en-1-one; 6280129: 2-[4-[(E)-3-(4-Nitrophenyl)-3-oxoprop-1-enyl]phenoxy]acetic acid; 6280485: (E)-1-(4-Hydroxyphenyl)-3-[3-methoxy-4-[[3-(trifluoromethyl)phenyl]methoxy]phenyl]prop-2-en-1-one; 6285343: (E)-1-(4-Hydroxyphenyl)-3-(3-nitro-4-piperidin-1-ylphenyl)prop-2-en-1-one; 6293081: 2',4-Dihydroxy-4',6'-dimethoxychalcone; 6302502: 4-[(Z)-3-[4-(Dimethylsulfamoyl)phenyl]-3-oxoprop-1-enyl]benzoic acid; 6304694: 2-[[4-[(E)-3-(4-Chlorophenyl)prop-2-enoyl]phenyl]sulfonylamino]propanoic acid; 6307302: 4-[(E)-3-(2,4-Dichlorophenyl)-3-oxoprop-1-enyl]benzoic acid; 6310055: 2-[4-[(E)-3-(4-Methylphenyl)-3-oxoprop-1-enyl]phenoxy]acetic acid; 6310616: (E)-1-[2-Hydroxy-4-[3,4,5-trihydroxy-6-(hydroxymethyl)oxan-2-yl]oxyphenyl]-3-phenylprop-2-en-1-one; 6311508: 4-[(E)-3-(4-Cyanophenyl)-3-oxoprop-1-enyl]benzoic acid; 6311652: 4-[3-Oxo-3-(4-tert-butylphenyl)-1-propenyl]benzoic acid; 6320124: Benzoic acid, 4-[(1E)-3-(2-hydroxyphenyl)-3-oxo-1-propen-1-yl]-; 6365770: 6-Cinnamoyl-m-toluic acid; 6366782: Salicylic acid, 5-(2-(2,4-dihydroxybenzoyl)vinyl)-; 6366787: Salicylic acid, 5-(2-(o-hydroxybenzoyl)vinyl)-; 6372825: 4-[(E)-3-[4-(Diethylsulfa-moyl)phenyl]-3-oxoprop-1-enyl]benzoic acid; 6377410: 2-[4-[(E)-3-[4-(Dimethylsulfamoyl)phenyl]-3-oxoprop-1-enyl]phenoxy]acetic acid; 6393649: 4-[(E)-3-[4-(Dimethylsulfamoyl)phenyl]-3-oxoprop-1-enyl]benzoic acid; 6434768: 4'-(2-Hydroxy-3-(4-phenylpiperazinyl) propoxy)chalcone; 6435704: 2-(2-Dimethylaminoethoxy)chalcone citrate; 6436550: Hesperidin methylchalcone; 6438092: Homobutein; 6438580: 2',6'-Dihydroxy-4,4'-dimethoxychalcone; 6438866: 4'-Ethoxy-2'-hydroxy-4,6'-dimethoxychalcone; 6440269: 3-[3-Hydroxy-4-[(E)-3-(3-hydroxy-4-methoxyphenyl)prop-2-enoyl]phenoxy]propane-1-sulfonic acid; 6440299: 2-Propen-1-one, 1-(2-hydroxy-4,6-dimethoxyphenyl)-3-(4-(methylthio)phenyl); 6441309: Tomanil; 6441980: 2-Propen-1-one, 1-(4-ethoxy-2-hydroxy-6-methoxyphenyl)-3-(4-(methylthio)phenyl)-; 6441981: 2-Propen-1-one, 1-(4-ethoxy-2-hydroxy-6-methoxyphenyl)-3-(4-hydroxyphenyl)-; 6442365: Acetic acid, (2-(3-(4-(1,1-dimethylethyl)phenyl)-1-oxo-2-propenyl)-5-((3-methyl-2-butenyl)oxy)phenoxy)-; 6442433: Isoliquiritin apioside; 6442911: Benzeneacetic acid, 2-(1-oxo-3-phenyl-2-propen-1-yl)-; 6443577: 2',4,4'-Trihydroxy-6'-methoxychalcone 4'-beta-D-glucopyranoside; 6443801: Cinfenoac; 6444933: 2',4'-Dimethoxy-4-hydroxy-3-nitrochalcone; 6445467: DL-3-(4-Fluorophenyl)-1-(4-(2-hydroxy-3-(4-phenyl-1-piperazinyl)propoxy)phenyl)-2-propen-1-one; 6445484: 1-(4-(2-Hydroxy-3-(4-phenyl-1-piperazinyl)propoxy)phenyl)-3-(4-methoxyphenyl)-2-propen-1-one; 6450488: (E)-1-(2-Hydroxy-4-methoxy-6-methylphenyl)-3-(4-methoxyphenyl)prop-2-en-1-one; 6474264: 2-[2-[[4-[(E)-3-(4-Bromophenyl)prop-2-enoyl]phenyl]carbamoyl]phenyl]benzoic acid; 6474295: Pinocembrin chalcone; 6474668: 4,6'-Dimethoxy-2'-hydroxychalcone; 6474669: (E)-1-(2,4-Diethoxy-6-hydroxy-phenyl)-3-phenyl-prop-2-en-1-one; 6474671: 2'-Hydroxy-4-methoxy-6'-Fluorochalcone; 6474674: 2'-Hydroxy-4-methoxy-4'-Fluorochalcone; 6474678: 2'-Hydroxy-4-methoxy-4'-Chlorochalcone; 6474679: 2'-Hydroxy-4'-chlorochalcone; 6474680: 2'-Hydroxy-4'-bromochalcone; 6474682: 2'-Hydroxy-4-methoxy-4'-Bromochalcone; 6474685: 2'-Hydroxy-4'-iodochalcone; 6474686: (E)-1-(2-Hydroxyphenyl)-3-(3-iodophenyl)prop-2-en-1-one; 6474689: (E)-1-(2-Hydroxyphenyl)-3-(4-iodophenyl)prop-2-en-1-one; 6474690: 2'-Hydroxy-4'-methoxy-3-iodochalcone; 6474693: 2'-Hydroxy-3-acetylaminochalcone; 6474694: (E)-3-(3-Aminophenyl)-1-(2-hydroxyphenyl) prop-2-en-1-one; 6474895: (E)-3-(3,4-Dihydroxyphenyl)-1-(4-hydroxyphenyl)prop-2-en-1-one; 6474896: 3,4-Dihydroxychalcone; 6474973: (E)-1-[2,4-Dihydroxy-6-[[(2R,3S,4R,6R)-3,4,6-trihydroxyoxan-2-yl]methoxy]phenyl]-3-(4-hydroxyphenyl)prop-2-en-1-one; 6475718: (E)-1-[2-Hydroxy-4,6-bis(methoxymethoxy)phenyl]-3-phenylprop-2-en-1-one; 6475719: (E)-1-[2-Hydroxy-4,6-bis(methoxymethoxy)phenyl]-3-[4-(methoxymethoxy)phenyl]prop-2-en-1-one; 6475721: (E)-3-[3,4-Bis(methoxymethoxy)phenyl]-1-[2-hydroxy-4,6-bis(methoxymethoxy)phenyl]prop-2-en-1-one; 6475724: Licuroside; 6508040: (E)-1-[4-[2-(Diethylamino) ethoxy]phenyl]-3-phenylprop-2-en-1-one;2-hydroxypropane-1,2,3-tricarboxylic acid; 6526201: (E)-1-[2,4-Dihydroxy-6-[3,4,5-trihydroxy-6-(hydroxymethyl)oxan-2-yl]oxyphenyl]-3-(4-hydroxyphenyl)prop-2-en-1-one; 6537040: Isoliquiritigenin 4'-methyl ether; 6603886: Lopac-1-3766; 6636248: 3-(1,3-Benzodioxol-5-yl)-1-(2-hydroxy-4,6-dimethoxyphenyl)prop-2-en-1-one; 6708743: 1-[2-Hydroxy-4-[(2S,3R,4S,5S,6R)-3,4,5-trihydroxy-6-(hydroxymethyl) oxan-2-yl]oxyphenyl]-3-phenylprop-2-en-1-one; 6710224: 1-[2,4-Bis(ethoxymethoxy)-6-hydroxyphenyl]-3-phenylprop-2-en-1-one; 6857762: 2',4'-Dihydroxychalcone 4'-glucoside; 6917586: Tephrone; 7065342: 2-[N-(Carboxylatomethyl)-4-[(E)-3-(2-hydroxyphenyl)-3-oxoprop-1-enyl]anilino]acetate; 7067194: (E)-3-(3-Hydroxy-4-methoxyphenyl)-1-phenylprop-2-en-1-one; 7067864: [4-[3-(3,4-Dichlorophenyl)-1-oxo-2-propenyl]phenoxy]-acetic acid; 7116350: 2-[3,5-Dihydroxy-4-(3-phenylprop-2-enoyl)phenoxy]acetate; 7245208: 2-[3,5-Dihydroxy-4-[(Z)-3-phenylprop-2-enoyl]phenoxy]acetate; 7245209: 3,5-Dihydroxy-4-[(2Z)-3-phenylprop-2-enoyl]phenoxyacetic acid; 7315227: (E)-1-(2-Hydroxyphenyl)-3-[4-methoxy-3-(morpholin-4-ium-4-ylmethyl)phenyl]prop-2-en-1-one; 7324870: (Z)-1-(4-Hydroxyphenyl)-3-(4-methoxyphenyl)prop-2-en-1-one; 7324871: (Z)-3-(1,3-Benzodioxol-5-yl)-1-(4-hydroxy-phenyl)prop-2-en-1-one; 7381057: (E)-1-(4-Hydroxyphenyl)-3-[4-methoxy-3-(morpholin-4-ium-4-ylmethyl)phenyl]prop-2-en-1-one; 7514808: N-[4-[(E)-3-(4-Hydroxyphenyl)-3- oxoprop-1-enyl]phenyl]acetamide; 7514810: (E)-3-[4-(Diethylamino)phenyl]-1-(4-hydroxy-phenyl)prop-2-en-1-one; 7514812: 3-Chloro-4'-hydroxychalcone; 7514813: (E)-3-(3-Fluorophenyl)-1-(4-hydroxyphenyl)prop-2-en-1-one; 7514818: (E)-3-(4-Ethylphenyl)-1-(4-hydroxyphenyl)prop-2-en-1-one; 7514821: (E)-3-(4-Butoxy-3-methoxyphenyl)-1-(4-hydroxy-phenyl)prop-2-en-1-one; 7514824: (E)-1-(4-Hydroxyphenyl)-3-naphthalen-2-ylprop-2-en-1-one; 7514826: 1-(4-Hydroxyphenyl)-3-(6-methoxy-2-naphthyl)-2-propen-1-one; 7514832: (E)-1-(4-Hydroxyphenyl)-3-[4-methoxy-3-(2-methylpropoxy)phenyl]prop-2-en-1-one; 7514833: 2-[2-Ethoxy-4-[(E)-3-(4-hydroxyphenyl)-3-oxoprop-1-enyl]phenoxy]-N,N-dimethylacetamide; 7514839: (E)-3-(3-Butoxy-4-methoxyphenyl)-1-(4-hydroxyphenyl)prop-2-en-1-one; 7515078: (E)-1-(2-Bromophenyl)-3-(4-hydroxyphenyl)prop-2-en-1-one; 7515293: (E)-1-[4-(Difluoromethoxy)phenyl]-3-(4-hydroxyphenyl)prop-2-en-1-one; 7528818: (E)-3-(4-Hydroxyphenyl)-1-(4-iodophenyl)prop-2-en-1-one; 7528822: 4-[(1E)-3-(4-Iodophenyl)-3-oxoprop-1-enyl]benzoic acid; 7571772: 4-[(E)-3-Oxo-3-[4-(2-oxopyrrolidin-1-yl)phenyl]prop-1-enyl]benzoic acid; 7571788: 1-[4-[(E)-3-(4-Hydroxy-3-nitro-phenyl)prop-2-enoyl]phenyl]pyrrolidin-2-one; 7638067: 1-[4-[(E)-3-(3-Hydroxy-4-methoxyphenyl)prop-2-enoyl]phenyl]pyrrolidin-2-one; 7729030: (E)-3-(3-Bromophenyl)-1-(2-hydroxyphenyl)prop-2-en-1-one; 7729032: (2E)-3-(3-Bromo-4-methoxyphenyl)-1-(2-hydroxyphenyl)prop-2-en-1-one; 7811834: (2S)-2-[[4-[(E)-3-(4-Chlorophenyl)prop-2-enoyl]phenyl]sulfonylamino]propanoic acid; 7811838: (2R)-2-[[4-[(E)-3-(4-Chlorophenyl)prop-2-enoyl]phenyl]sulfonylamino]propanoic acid; 7811861: (2S)-2-[[4-[(E)-3-(4-Methoxycarbonylphenyl)prop-2-enoyl]phenyl]sulfonylamino]propanoic acid; 7811868: (2R)-2-[[4-[(E)-3-(4-Methoxycarbonylphenyl)prop-2-enoyl]phenyl]sulfonylamino]propanoic acid; 7820470: (E)-3-(3-Ethoxy-4-hydroxyphenyl)-1-phenylprop-2-en-1-one; 7827695: (2E)-1-(4-Ethylphenyl)-3-(4-hydroxy-phenyl)prop-2-en-1-one; 7945669: 2-[4-[(E)-3-(3-Hydroxy-4-methoxyphenyl)prop-2-enoyl]phenoxy]-N,N-dimethylacetamide; 7945865: (E)-3-(3-Hydroxy-4-methoxyphenyl)-1-(4-propoxyphenyl)prop-2-en-1-one; 7945882: (E)-3-(3-Hydroxy-4-methoxyphenyl)-1-(4-propan-2-ylphenyl)prop-2-en-1-one; 7945901: (E)-1-[4-(Dimethylamino)phenyl]-3-(3-hydroxy-4-methoxyphenyl)prop-2-en-1-one; 7946023: (E)-3-(4-Hydroxy-3-nitro-phenyl)-1-phenylprop-2-en-1-one; 7946180: 4-[(E)-3-(4-Hydroxyphenyl)-3-oxo-prop-1-enyl]benzoic Acid; 7946182: (E)-3-(4-Ethoxy-3-methoxyphenyl)-1-(4-hydroxyphenyl)prop-2-en-1-one; 7946194: Methyl 4-[[4-[(E)-3-(4-hydroxyphenyl)-3-oxoprop-1-enyl]phenoxy]methyl]benzoate; 7946199: (E)-3-[4-[(2-Chlorophenyl)methoxy]-3-methoxyphenyl]-1-(4-hydroxy-phenyl)prop-2-en-1-one; 7946214: (E)-3-(4-Ethyl-3-nitro-phenyl)-1-(4-hydroxyphenyl)prop-2-en-1-one; 7946215: 4-[(E)-3-(4-Hydroxyphenyl)-3-oxoprop-1-enyl]-2-nitrophenolate; 7946216: (E)-3-(4-Hydroxy-3-nitro-phenyl)-1-(4-hydroxyphenyl)prop-2-en-1-one; 7946217: (E)-3-(9-Ethylcarbazol-3-yl)-1-(4-hydroxyphenyl)prop-2-en-1-one; 7946227: (E)-1-(4-Hydroxyphenyl)-3-(4-piperidin-1-ylphenyl)prop-2-en-1-one; 7946230: (E)-3-(3-Ethoxy-4-prop-2-ynoxyphenyl)-1-(4-hydroxyphenyl)prop-2-en-1-one; 7946232: N-Ethyl-2-[4-[(E)-3-(4-hydroxyphenyl)-3-oxoprop-1-enyl]-2-methoxyphenoxy]acetamide; 7946235: (E)-3-(4-Hydroxyphenyl)-1-(4-nitro-phenyl)prop-2-en-1-one; 7946850: (E)-1-(4-Fluorophenyl)-3-(4-hydroxy-3-nitro-phenyl)prop-2-en-1-one; 7947034: (E)-1-(2-Bromophenyl)-3-(4-hydroxy-3-nitro-phenyl)prop-2-en-1-one; 7947129: (E)-1-(4-Cyclohexylphenyl)-3-(4-hydroxyphenyl) prop-2-en-1-one; 7967103: (E)-1-(4-Tert-butylphenyl)-3-(3-hydroxy-4-methoxyphenyl)prop-2-en-1-one; 7972544: 4-[(E)-3-Oxo-3-(4-piperidin-1-ylsulfonylphenyl)prop-1-enyl]benzoic acid; 7972582: (E)-3-(3-Hydroxy-4-methoxyphenyl)-1-(4-piperidin-1-ylsulfonylphenyl)prop-2-en-1-one; 7972594: (E)-3-(4-Hydroxy-3-nitro-phenyl)-1-(4-piperidin-1-ylsulfonylphenyl)prop-2-en-1-one; 7972632: 4-[(E)-3-(4-Hydroxyphenyl)prop-2-enoyl]-N,N-dimethylbenzenesulfonamide; 7972676: 4-[(E)-3-(4-Hydroxy-3-nitro-phenyl)prop-2-enoyl]-N,N-dimethylbenzenesulfonamide; 7972957: 2-[4-[(E)-3-(4-Fluorophenyl)prop-2-enoyl]phenoxy]acetic acid; 7972971: 2-[4-[(E)-3-(4-Methoxyphenyl)prop-2-enoyl]phenoxy]acetic Acid; 7972991: 2-[4-[(E)-3-(3-Fluorophenyl)prop-2-enoyl]phenoxy]acetic acid; 7972996: 2-[4-[(E)-3-(4-Phenyl-methoxyphenyl)prop-2-enoyl]phenoxy]acetic acid; 7973005: 2-[4-[(E)-3-(4-Phenyl-phenyl)prop-2-enoyl]phenoxy]acetic acid; 7973015: 2-[4-[(E)-3-(4-Ethylphenyl)prop-2-enoyl]phenoxy]acetic acid; 7973019: 2-[4-[(E)-3-(3-Phenylmethoxyphenyl)prop-2-enoyl]phenoxy]acetic acid; 7973022: 2-[4-[(E)-3-(3-Hydroxy-4-methoxyphenyl)prop-2-enoyl]phenoxy]acetate; 7973023: 2-[4-[(E)-3-(3-Hydroxy-4-methoxyphenyl)prop-2-enoyl]phenoxy]acetic acid; 7973026: 2-[4-[(E)-3-(4-Methoxycarbonylphenyl)prop-2-enoyl]phenoxy]acetic acid; 7973028: 2-[4-[(E)-3-(4-Methoxy-3-phenylmethoxyphenyl)prop-2-enoyl]phenoxy]acetic acid; 7973032: 2-[4-[(E)-3-[3-Methoxy-4-(3-methylbutoxy)phenyl]prop-2-enoyl]phenoxy]acetic acid; 7973036: 2-[4-[(E)-3-[4-(Difluoromethoxy)-3-methoxyphenyl]prop-2-enoyl]phenoxy]acetic acid; 7986207: 4-[(E)-3-(2-Chlorophenyl)-3-oxoprop-1-enyl]benzoic acid; 7986209: (E)-1-(2-Chlorophenyl)-3-(3-hydroxyphenyl)prop-2-en-1-one; 7987680: (2S)-2-[4-[(E)-3-(4-Bromophenyl)prop-2-enoyl]phenoxy]propanoic acid; 7987682: (2R)-2-[4-[(E)-3-(4-Bromophenyl)prop-2-enoyl]phenoxy]propanoic acid; 7991446: (E)-3-(3-Ethoxy-4-methoxyphenyl)-1-(4-hydroxyphenyl)prop-2-en-1-one; 8001940: (E)-1-(4-Hydroxy-phenyl)-3-(3-methoxy-4-prop-2-enoxyphenyl)prop-2-en-1-one; 8002347: (E)-1-(2-Bromophenyl)-3-(3-hydroxy-4-methoxyphenyl)prop-2-en-1-one; 8017729: 4-[(E)-3-(3-Hydroxy-4-methoxyphenyl)prop-2-enoyl]-N,N-dimethylbenzenesulfonamide; 8020519: (E)-1-(2,4-Dimethoxyphenyl)-3-(3-hydroxy-4-methoxyphenyl)prop-2-en-1-one; 8020690: (E)-3-(3-Hydroxy-4-methoxyphenyl)-1-(4-methoxyphenyl)prop-2-en-1-one; 8024128: (2S)-2-[4-[(E)-3-(4-Ethylphenyl)prop-2-enoyl]phenoxy]propanoic acid; 8024133: (2R)-2-[4-[(E)-3-(4-Ethylphenyl)prop-2-enoyl]phenoxy]propanoic acid; 8094817: (E)-3-(3-Hydroxy-4-methoxy-phenyl)-1-(4-methylphenyl)prop-2-en-1-one; 8108341: 2-[4-[(E)-3-(4-Cyclohexylphenyl)-3-oxoprop-1-enyl]phenoxy]acetic acid; 8108440: (E)-1-(2-Bromophenyl)-3-(3-hydroxyphenyl) prop-2-en-1-one; 8108795: (E)-3-(3-Hydroxy-4-methoxyphenyl)-1-(4-nitrophenyl)prop-2-en-1-one; 8108796: (E)-1-(2,4-Dichlorophenyl)-3-(3-hydroxy-4-methoxyphenyl)prop-2-en-1-one; 8116804: (E)-1-(2,4-Difluorophenyl)-3-(3-hydroxy-4-methoxyphenyl)prop-2-en-1-one; 8120255: (E)-3-(3-Hydroxy-4-methoxyphenyl)-1-[4-(2-methylpropoxy)phenyl]prop-2-en-1-one; 8120256: (E)-3-(3-Hydroxyphenyl)-1-[4-(2-methylpropoxy)phenyl]prop-2-en-1-one; 8151449: 4-[(E)-3-[4-(2-Methylpropyl)phenyl]-3-oxoprop-1-enyl]benzoic acid; 8151618: (E)-3-(3-Bromo-4-fluorophenyl)-1-(4-hydroxyphenyl)prop-2-en-1-one; 8151975: 2-[4-[(E)-3-(4-Chloro-3-nitro-phenyl)prop-2-enoyl]phenoxy]acetic acid; 8194522: (E)-1-(4-Fluorophenyl)-3-(3-hydroxy-4-methoxyphenyl)prop-2-en-1-one; 8195910: (E)-1-(4-Fluorophenyl)-3-(3-hydroxyphenyl)prop-2-en-1-one; 8209482:

(E)-3-(3,4-Diethoxyphenyl)-1-(4-ethoxy-2-hydroxyphenyl) prop-2-en-1-one; 8415795: (2S)-2-[[4-[(E)-3-Phenylprop-2-enoyl]phenyl]sulfonylamino]propanoic acid; 8415803: (2S)-2-[[4-[(E)-3-(4-Fluorophenyl)prop-2-enoyl]phenyl] sulfonylamino]propanoic acid; 8415810: (2S)-2-[[4-[(E)-3-(3,4-Dimethoxy-phenyl)prop-2-enoyl]phenyl]sulfonylamino]propanoic acid; 8415821: (2S)-2-[[4-[(E)-3-(3-Methoxyphenyl)prop-2-enoyl]phenyl]sulfonylamino] propanoic acid; 8415825: (2S)-2-[[4-[(E)-3-(4-Methylphenyl)prop-2-enoyl]phenyl]sulfonylamino] propanoic acid; 8415830: (2S)-2-[[4-[(E)-3-(4-Methylsulfanylphenyl)prop-2-enoyl]phenyl]sulfonylamino] propanoic acid; 8415843: (2S)-2-[[4-[(E)-3-(3-Fluorophenyl)prop-2-enoyl]phenyl]sulfonylamino] propanoic acid; 8415943: (2S)-2-[[4-[(E)-3-Naphthalen-2-ylprop-2-enoyl]phenyl]sulfonylamino]propanoic acid; 8417059: 1-[4-[(E)-3-(4-Hydroxyphenyl)prop-2-enoyl]phenyl]pyrrolidin-2-one; 8417062: 1-[4-[(E)-3-(4-Hydroxy-3-methoxyphenyl)prop-2-enoyl]phenyl]pyrrolidin-2-one; 8417066: 1-[4-[(E)-3-(3-Ethoxy-4-hydroxyphenyl)prop-2-enoyl]phenyl]pyrrolidin-2-one; 8417070: 1-[4-[(E)-3-(3-Hydroxyphenyl)prop-2-enoyl]phenyl]pyrrolidin-2-one; 8424018: (E)-1-(2-Chloro-4-fluorophenyl)-3-(4-hydroxyphenyl)prop-2-en-1-one; 8424034: (E)-1-(2-Chloro-4-fluorophenyl)-3-(4-hydroxy-3-methoxyphenyl)prop-2-en-1-one; 8424060: (E)-1-(2-Chloro-4-fluorophenyl)-3-(3-ethoxy-4-hydroxyphenyl)prop-2-en-1-one; 8424070: (E)-1-(2-Chloro-4-fluorophenyl)-3-(3-hydroxyphenyl)prop-2-en-1-one; 8424110: (E)-1-(2-Chloro-4-fluoro-phenyl)-3-(4-hydroxy-3-nitro-phenyl)prop-2-en-1-one; 8424114: 2-[4-[(E)-3-(2-Chloro-4-fluorophenyl)-3-oxoprop-1-enyl] phenoxy]acetic acid; 8424130: 2-[4-[(E)-3-(2-Chloro-4-fluorophenyl)-3-oxoprop-1-enyl]-2-methoxyphenoxy]acetic acid; 8426409: (E)-1-(4-Hydroxyphenyl)-3-[3-methoxy-4-(thiophen-2-ylmethoxy)phenyl]prop-2-en-1-one; 8446017: 4-[[4-[(E)-3-(4-Fluorophenyl)prop-2-enoyl]phenyl]sulfonyl-methylamino]butanoic acid; 8446595: (E)-3-(4-Hydroxyphenyl)-1-(4-methylsulfonylphenyl)prop-2-en-1-one; 8446733: (E)-3-(3-Hydroxyphenyl)-1-(4-methylsulfonylphenyl)prop-2-en-1-one; 8446816: (E)-3-(3-Hydroxy-4-methoxyphenyl)-1-(4-methylsulfonylphenyl)prop-2-en-1-one; 8461968: 5-[4-[(E)-3-(4-Morpholin-4-ylphenyl)prop-2-enoyl]phenyl]furan-2-carboxylic acid; 8545676: (2E)-1-(4-Bromophenyl)-3-4-[(2-hydroxyethyl)(methyl)amino] phenylprop-2-en-1-one; 8545689: (E)-3-[4-[Bis(2-hydroxyethyl)amino]phenyl]-1-(4-bromophenyl)prop-2-en-1-one; 8603848: 4-[(E)-3-(4-Hydroxyphenyl)prop-2-enoyl]-N-(4-methoxyphenyl)benzenesulfonamide; 8603849: 4-[(E)-3-(3-Hydroxyphenyl)prop-2-enoyl]-N-(4-methoxyphenyl)benzenesulfonamide; 8685108: (E)-1-[4-(Dimethylamino)phenyl]-3-(4-hydroxy-3-methoxyphenyl)prop-2-en-1-one; 8685123: 4-[(E)-3-[4-(Dimethylamino)phenyl]-3-oxoprop-1-enyl]benzoic acid; 8685138: (E)-1-[4-(Dimethylamino)phenyl]-3-(3-hydroxyphenyl)prop-2-en-1-one; 8685146: (E)-1-[4-(Dimethylamino)phenyl]-3-(3-ethoxy-4-hydroxyphenyl)prop-2-en-1-one; 8685172: (E)-1-[4-(Dimethylamino)phenyl]-3-(4-hydroxy-3-nitro-phenyl) prop-2-en-1-one; 8685186: 2-[4-[(E)-3-[4-(Dimethylamino) phenyl]-3-oxoprop-1-enyl]phenoxy]acetic acid; 8685501: (E)-3-(4-Hydroxy-3-methoxyphenyl)-1-(4-morpholin-4-ylphenyl)prop-2-en-1-one; 8685514: (E)-3-(3-Ethoxy-4-hydroxyphenyl)-1-(4-morpholin-4-ylphenyl)prop-2-en-1-one; 8685554: 2-[2-Methoxy-4-[(E)-3-(4-morpholin-4-ylphenyl)-3-oxoprop-1-enyl]phenoxy]acetic acid; 8685651: (E)-1-[4-(5,6-Dihydro-4H-1,3-thiazin-2-ylamino)phenyl]-3-(4-hydroxyphenyl)prop-2-en-1-one; 8685663: 1-[4-(5,6-Dihydro-4H-1,3-thiazin-2-ylamino)phenyl]-3-(4-hydroxy-3-methoxyphenyl)prop-2-en-1-one; 8685702: (E)-1-[4-(5,6-Dihydro-4H-1,3-thiazin-2-ylamino)phenyl]-3-(3-hydroxyphenyl)prop-2-en-1-one; 8685710: (E)-1-[4-(5,6-Dihydro-4H-1,3-thiazin-2-ylamino)phenyl]-3-(3-ethoxy-4-hydroxyphenyl)prop-2-en-1-one; 8685722: (E)-1-[4-(5,6-Dihydro-4H-1,3-thiazin-2-ylamino)phenyl]-3-(3-hydroxy-4-methoxyphenyl)prop-2-en-1-one; 8685760: 2-[4-[(E)-3-[4-(5,6-Dihydro-4H-1,3-thiazin-2-ylamino)phenyl]-3-oxoprop-1-enyl]phenoxy]acetic acid; 8727217: 2-[4-[(E)-3-[4-(Dimethylamino)phenyl]prop-2-enoyl]phenoxy]acetic acid; 8727220: 2-[4-[(E)-3-[4-(Diethylamino)phenyl]prop-2-enoyl]phenoxy]acetic acid; 8727225: 2-[4-[(E)-3-(4-Piperidin-1-ylphenyl)prop-2-enoyl]phenoxy]acetic acid; 8727240: (E)-3-(4-Hydroxyphenyl)-1-(4-piperidin-1-ylphenyl)prop-2-en-1-one; 8727246: (E)-3-(3-Hydroxyphenyl)-1-(4-piperidin-1-ylphenyl)prop-2-en-1-one; 8727254: (E)-3-(3-Hydroxy-4-methoxyphenyl)-1-(4-piperidin-1-ylphenyl) prop-2-en-1-one; 8813314: 2-[4-[(E)-3-(4-Hydroxyphenyl) prop-2-enoyl]phenoxy]-N-(2-methylphenyl)acetamide; 8813335: 4-[(E)-3-[4-[2-(2-Methylanilino)-2-oxoethoxy] phenyl]-3-oxoprop-1-enyl]benzoic acid; 8813347: 2-[4-[(E)-3-(3-Hydroxyphenyl)prop-2-enoyl]phenoxy]-N-(2-methylphenyl)acetamide; 8814760: (E)-3-(4-Hydroxyphenyl)-1-[4-(2-morpholin-4-yl-2-oxoethoxy) phenyl]prop-2-en-1-one; 8814805: (E)-3-(3-Hydroxyphenyl)-1-[4-(2-morpholin-4-yl-2-oxoethoxy) phenyl]prop-2-en-1-one; 8814825: (E)-3-(3-Hydroxy-4-methoxyphenyl)-1-[4-(2-morpholin-4-yl-2-oxoethoxy) phenyl]prop-2-en-1-one; 8814831: (E)-3-(4-Hydroxy-3-nitro-phenyl)-1-[4-(2-morpholin-4-yl-2-oxoethoxy)phenyl] prop-2-en-1-one; 8814864: 2-[4-[(E)-3-(4-Hydroxyphenyl) prop-2-enoyl]phenoxy]-N-phenylacetamide; 8814889: 4-[(E)-3-[4-(2-Anilino-2-oxoethoxy)phenyl]-3-oxoprop-1-enyl]benzoic acid; 8814891: 2-[4-[(E)-3-(3-Hydroxyphenyl)prop-2-enoyl]phenoxy]-N-phenylacetamide; 8814901: 2-[4-[(E)-3-(3-Hydroxy-4-methoxyphenyl)prop-2-enoyl] phenoxy]-N-phenylacetamide; 8815006: N,N-Diethyl-2-[4-[(E)-3-(4-hydroxyphenyl) prop-2-enoyl]phenoxy]acetamide; 8826820: (E)-1-(2,4-Difluorophenyl)-3-(4-hydroxyphenyl) prop-2-en-1-one; 8826838: 4-[(E)-3-(2,4-Difluorophenyl)-3-oxoprop-1-enyl]benzoic acid; 8826854: (E)-1-(2,4-Difluorophenyl)-3-(3-ethoxy-4-hydroxyphenyl) prop-2-en-1-one; 8826911: 2-[4-[(E)-3-(2,4-Difluorophenyl)-3-oxoprop-1-enyl]phenoxy]acetic acid; 8826941: 2-[4-[(E)-3-(2,4-Difluorophenyl)-3-oxoprop-1-enyl]-2-methoxyphenoxy]acetic acid; 8826969: (E)-3-(4-Hydroxyphenyl)-1-[4-(2-oxo-2-pyrrolidin-1-ylethoxy) phenyl]prop-2-en-1-one; 8827000: (E)-3-(4-Hydroxy-3-methoxyphenyl)-1-[4-(2-oxo-2-pyrrolidin-1-ylethoxy) phenyl]prop-2-en-1-one; 8827021: 4-[(E)-3-Oxo-3-[4-(2-oxo-2-pyrrolidin-1-ylethoxy)phenyl]prop-1-enyl]benzoic acid; 8827054: (E)-3-(3-Hydroxyphenyl)-1-[4-(2-oxo-2-pyrrolidin-1-ylethoxy)phenyl]prop-2-en-1-one; 8827102: (E)-3-(3-Hydroxy-4-methoxyphenyl)-1-[4-(2-oxo-2-pyrrolidin-1-ylethoxy)phenyl]prop-2-en-1-one; 8827117: (E)-3-(4-Hydroxy-3-nitro-phenyl)-1-[4-(2-oxo-2-pyrrolidin-1-ylethoxy)phenyl]prop-2-en-1-one; 8827156: (E)-3-(4-Hydroxy-phenyl)-1-[4-(2-methylpropoxy)phenyl]prop-2-en-1-one; 8827166: 2-[4-[(E)-3-(4-Hydroxy-phenyl)prop-2-enoyl]phenoxy]-N,N-dimethylacetamide; 8827189: 4-[(E)-3-[4-[2-(Dimethyl-amino)-2-oxoethoxy]phenyl]-3-oxoprop-1-enyl]benzoic acid; 8827211: 2-[4-[(E)-3-(3-Hydroxyphenyl)prop-2-enoyl]phenoxy]-N,N-dimethylacetamide; 8827221: 2-[4-[(E)-3-(3-Ethoxy-4-hydroxyphenyl)prop-2-enoyl]phenoxy]-N,N-dimethylacetamide; 8827248: 2-[4-[(E)-3-(4-Hydroxy-3-nitro-phenyl)prop-2-enoyl]phenoxy]-N,N- dimethylacetamide; 8827981: (E)-1-(2-Ethoxyphenyl)-3-(4-hydroxyphenyl)prop-2-en-1-one; 8828001: 4-[(E)-3-(2-Ethoxyphenyl)-3-oxoprop-1-enyl]benzoic acid; 8828003: (E)-1-(2-Ethoxyphenyl)-3-(3-hydroxyphenyl)prop-2-en-1-one; 8828017: (E)-1-(2-Ethoxyphenyl)-3-(3-hydroxy-4-methoxyphenyl)prop-2-en-1-one; 8828082: 4-[(E)-3-(4-Hydroxyphenyl)prop-2-enoyl]-N-propylbenzenesulfonamide; 8828115: 4-[(E)-3-(3-Hydroxyphenyl)prop-2-enoyl]-N-propylbenzenesulfonamide; 8828139: 4-[(E)-3-(3-Hydroxy-4-methoxyphenyl)prop-2-enoyl]-N-propylbenzenesulfonamide; 8828146: (E)-3-(4-Hydroxyphenyl)-1-(4-propoxyphenyl)prop-2-en-1-one; 8828155: (E)-3-(4-Hydroxy-3-methoxyphenyl)-1-(4-propoxyphenyl)prop-2-en-1-one; 8828158: 4-[(E)-3-Oxo-3-(4-propoxyphenyl)prop-1-enyl]benzoic acid; 8828162: (E)-3-(3-Hydroxyphenyl)-1-(4-propoxyphenyl)prop-2-en-1-one; 8828167: (E)-3-(3-Ethoxy-4-hydroxyphenyl)-1-(4-propoxyphenyl)prop-2-en-1-one; 8828173: (E)-3-(4-Hydroxy-3-nitro-phenyl)-1-(4-propoxyphenyl)prop-2-en-1-one; 8828182: 2-[4-[(E)-3-Oxo-3-(4-propoxyphenyl)prop-1-enyl]phenoxy]acetic acid; 8828515: (E)-3-(4-Hydroxyphenyl)-1-(4-propan-2-ylphenyl)prop-2-en-1-one; 8828521: (E)-3-(4-Hydroxy-3-methoxyphenyl)-1-(4-propan-2-ylphenyl)prop-2-en-1-one; 8828547: 2-[4-[(E)-3-Oxo-3-(4-propan-2-ylphenyl)prop-1-enyl]phenoxy]acetic acid; 8828560: 2-[2-Methoxy-4-[(E)-3-oxo-3-(4-propan-2-ylphenyl) prop-1-enyl]phenoxy]acetic acid; 8829225: Chembl4160709; 8829713: (E)-3-(4-Hydroxy-phenyl)-1-(4-propan-2-yloxyphenyl)prop-2-en-1-one; 8829746: 4-[(E)-3-Oxo-3-(4-propan-2-yloxyphenyl)prop-1-enyl]benzoic acid; 8829748: (E)-3-(3-Hydroxyphenyl)-1-(4-propan-2-yloxyphenyl)prop-2-en-1-one; 8829766: (E)-3-(4-Hydroxy-3-nitro-phenyl)-1-(4-propan-2-yloxyphenyl)prop-2-en-1-one; 8830409: 2-[4-[(E)-3-(3-Hydroxyphenyl)prop-2-enoyl]phenoxy]-N-methylacetamide; 8830461: 2-[4-[(E)-3-(3-Hydroxy-4-methoxyphenyl)prop-2-enoyl]phenoxy]-N-methylacetamide; 8832005: (E)-3-(4-Hydroxyphenyl)-1-(4-propylphenyl) prop-2-en-1-one; 8832011: (E)-3-(3-Hydroxy-4-methoxyphenyl)-1-(4-propylphenyl)prop-2-en-1-one; 8832623: (E)-1-(4-Bromophenyl)-3-(3-ethoxy-4-hydroxyphenyl)prop-2-en-1-one; 8832638: 2-[4-[(E)-3-(4-Bromophenyl)-3-oxoprop-1-enyl]-2-methoxyphenoxy]acetic acid; 8832693: (e)-2-(2-Methoxy-4-(3-oxo-3-phenylprop-1-en-1-yl)phenoxy)acetic acid; 8832733: (E)-3-(3-Ethoxy-4-hydroxyphenyl)-1-(4-methylphenyl)prop-2-en-1-one; 8832758: 2-[2-Meth-oxy-4-[(E)-3-(4-methylphenyl)-3-oxoprop-1-enyl]phenoxy]acetic acid; 8832775: (E)-1-(2,4-Dimethoxyphenyl)-3-(3-ethoxy-4-hydroxyphenyl)prop-2-en-1-one; 8832809: 2-[4-[(E)-3-(2,4-Dimethoxyphenyl)-3-oxoprop-1-enyl]-2-methoxyphenoxy] acetic acid; 8832859: 3,4'-Dihydroxychalcone; 8832860: 3-Ethoxy-4,4'-dihydroxychalcone; 8832865: (E)-3-(3,4-Difluoro-phenyl)-1-(4-hydroxyphenyl)prop-2-en-1-one; 8832871: (E)-1-(4-Hydroxyphenyl)-3-[3-methoxy-4-(2-morpholin-4-yl-2-oxoethoxy)phenyl]prop-2-en-1-one; 8832873: (E)-3-(4-Bromo-3-nitro-phenyl)-1-(4-hydroxyphenyl)prop-2-en-1-one; 8832875: (E)-3-(3-Bromo-4-methoxyphenyl)-1-(4-hydroxyphenyl)prop-2-en-1-one; 8832878: (E)-1-(4-Hydroxyphenyl)-3-(3-methoxy-4-propoxyphenyl)prop-2-en-1-one; 8832889: (E)-3-(3-Ethoxy-4-propoxyphenyl)-1-(4-hydroxyphenyl)prop-2-en-1-one; 8832890: (E)-1-(4-Hydroxyphenyl)-3-(4-methyl-3-nitro-phenyl)prop-2-en-1-one; 8832905: (2S)-2-[2-Ethoxy-4-[(E)-3-(4-hydroxyphenyl)-3-oxoprop-1-enyl]phenyl]-N,N-dimethylpropanamide; 8832906: (2R)-2-[2-Ethoxy-4-[(E)-3-(4-hydroxyphenyl)-3-oxoprop-1-enyl]phenoxy]-N,N-dimethylpropanamide; 8832912: (E)-1-(4-Hydroxyphenyl)-3-(3-prop-2-enoxyphenyl)prop-2-en-1-one; 8832916: Methyl 5-[[4-[(E)-3-(4-hydroxyphenyl)-3-oxoprop-1-enyl]-2-methoxyphenoxy]methyl]furan-2-carboxylate; 8832917: (E)-3-[3-(Difluoromethoxy)-4-methoxyphenyl]-1-(4-hydroxyphenyl)prop-2-en-1-one; 8832922: (E)-3-[4-(Difluoromethoxy)-3-ethoxyphenyl]-1-(4-hydroxyphenyl)prop-2-en-1-one; 8832941: (E)-3-(4-Hydroxy-3-methoxyphenyl)-1-(4-nitro-phenyl)prop-2-en-1-one; 8832946: 3-(3-Hydroxyphenyl)-1-(4-nitro-phenyl)prop-2-en-1-one; 8833019: (E)-1-(4-Chlorophenyl)-3-(4-hydroxy-3-nitro-phenyl)prop-2-en-1-one; 8833038: 2-[4-[(E)-3-(4-Chlorophenyl)-3-oxoprop-1-enyl]-2-methoxyphenoxy]acetic acid; 8833060: (E)-1-(2-Chlorophenyl)-3-(3-ethoxy-4-hydroxyphenyl)prop-2-en-1-one; 8833080: (E)-1-(2-Chlorophenyl)-3-(4-hydroxy-3-nitro-phenyl)prop-2-en-1-one; 8833099: 2-[4-[(E)-3-(2-Chlorophenyl)-3-oxoprop-1-enyl]phenoxy]acetic acid; 8833129: 2-[4-[(E)-3-(2-Chlorophenyl)-3-oxoprop-1-enyl]-2-methoxy-phenoxy]acetic acid; 8853424: (E)-1-(2,6-Difluorophenyl)-3-(4-hydroxyphenyl)prop-2-en-1-one; 8853440: (E)-1-(2,6-Difluorophenyl)-3-(4-hydroxy-3-methoxyphenyl)prop-2-en-1-one; 8853468: 4-[(E)-3-(2,6-Difluorophenyl)-3-oxoprop-1-enyl]benzoic acid; 8853484: (E)-1-(2,6-Difluorophenyl)-3-(3-hydroxyphenyl)prop-2-en-1-one; 8853499: (E)-1-(2,6-Difluorophenyl)-3-(3-ethoxy-4-hydroxyphenyl)prop-2-en-1-one; 8853525: (E)-1-(2,6-Difluorophenyl)-3-(3-hydroxy-4-methoxyphenyl)prop-2-en-1-one; 8853627: (E)-1-(2,6-Difluorophenyl)-3-(4-hydroxy-3-nitro-phenyl)prop-2-en-1-one; 8853672: 2-[4-[(E)-3-(2,6-Difluorophenyl)-3-oxoprop-1-enyl]phenoxy]acetic acid; 8853775: 2-[4-[(E)-3-(2,6-Difluorophenyl)-3-oxoprop-1-enyl]-2-methoxyphenoxy]acetic acid; 8853873: (E)-3-(4-Hydroxyphenyl)-1-[2-(trifluoromethyl)phenyl]prop-2-en-1-one; 8853912: 4-[(E)-3-Oxo-3-[2-(trifluoromethyl)phenyl]prop-1-enyl]benzoic acid; 8853926: (E)-3-(3-Hydroxyphenyl)-1-[2-(trifluoromethyl)phenyl]prop-2-en-1-one; 8853942: (E)-3-(3-Ethoxy-4-hydroxyphenyl)-1-[2-(trifluoromethyl)phenyl]prop-2-en-1-one; 8853951: (E)-3-(3-Hydroxy-4-methoxyphenyl)-1-[2-(trifluoromethyl) phenyl]prop-2-en-1-one; 8853968: (E)-3-(4-Hydroxy-3-nitro-phenyl)-1-[2-(trifluoromethyl)phenyl]prop-2-en-1-one; 8855654: 2-[2-Methoxy-4-[(E)-3-oxo-3-(4-phenylphenyl)prop-1-enyl]phenoxy]acetic acid; 8855762: (1z,2e)-1-(2-Fluorophenyl)-3-(4-hydroxyphenyl)-2-propen-1-one; 8855817: (E)-1-(2-Fluorophenyl)-3-(4-hydroxy-3-methoxyphenyl)prop-2-en-1-one; 8855853: 4-[(E)-3-(2-Fluorophenyl)-3-oxoprop-1-enyl]benzoic acid; 8855869: (E)-1-(2-Fluorophenyl)-3-(3-hydroxyphenyl)prop-2-en-1-one; 8855887: (E)-3-(3-Ethoxy-4-hydroxyphenyl)-1-(2-fluoro-phenyl)prop-2-en-1-one; 8855911: (E)-1-(2-Fluorophenyl)-3-(3-hydroxy-4-methoxyphenyl) prop-2-en-1-one; 8856000: (E)-1-(2-Fluorophenyl)-3-(4-hydroxy-3-nitro-phenyl)prop-2-en-1-one; 8856035: 2-[4-[(E)-3-(2-Fluorophenyl)-3-oxoprop-1-enyl]phenoxy]acetic acid; 8856097: 2-[4-[(E)-3-(2-Fluorophenyl)-3-oxoprop-1-enyl]-2-methoxyphenoxy]acetic acid; 8856159: (E)-1-(4-Fluorophenyl)-3-(4-hydroxy-3-methoxyphenyl)prop-2-en-1-one; 8856169: (E)-3-(3-Ethoxy-4-hydroxyphenyl)-1-(4-fluorophenyl)prop-2-en-1-one; 8856249: 2-[4-[(E)-3-(4-Fluorophenyl)-3-oxoprop-1-enyl]phenoxy]acetic acid; 8856286: 2-[4-[(E)-3-(4-Fluorophenyl)-3-oxoprop-1-enyl]-2-methoxyphenoxy]acetic acid; 8856590: (E)-1-(2-Bromophenyl)-3-(4-hydroxy-3-methoxyphenyl)prop-2-en-1-one; 8856602: (E)-1-(2-Bromophenyl)-3-(3-ethoxy-4-hydroxyphenyl)prop-2-en-1-one; 8856639: 2-[4-[(E)-3-(2-Bromophenyl)-3-oxoprop-1-enyl]-2-methoxyphenoxy]acetic acid; 8856810: (E)-1-(4-Methoxyphenyl)-3-(3-ethoxy-4-hydroxy-phenyl)-2-propene-1-one; 8856879: 2-[2-Methoxy-4-[(E)-3-(4-methoxyphenyl)-3-oxoprop-1-enyl]phenoxy]acetic acid; 8858317: (E)-1-(2,4-Dichlorophenyl)-3-(4-hydroxyphenyl)prop-2-en-1-one; 8858318: (E)-1-(2,4-Dichlorophenyl)-3-(4-hydroxy-3-methoxyphenyl)prop-2-en-1-one; 8858341: (E)-1-(2,4-Dichlorophenyl)-3-(3-hydroxyphenyl)prop-2-en-1-one; 8858343: (E)-1-(2,4-Dichlorophenyl)-3-(3-ethoxy-4-hydroxyphenyl)prop-2-en-1-one; 8858376: 2-[4-[(E)-3-(2,4-Dichlorophenyl)-3-oxoprop-1-enyl]-2-methoxyphenoxy]acetic acid; 8859057: (E)-1-[4-(Difluoromethoxy)phenyl]-3-(4-hydroxy-3-methoxyphenyl)prop-2-en-1-one; 8859064: (E)-1-[4-(Difluoromethoxy)phenyl]-3-(3-hydroxyphenyl)prop-2-en-1-one; 8859068: (E)-1-[4-(Difluoromethoxy)phenyl]-3-(3-ethoxy-4-hydroxyphenyl)prop-2-en-1-one; 8859075: (E)-1-[4-(Difluoromethoxy)phenyl]-3-(3-hydroxy-4-methoxyphenyl)prop-2-en-1-one; 8859115: 2-[4-[(E)-3-[4-(Difluoromethoxy)phenyl]-3-oxoprop-1-enyl]-2-methoxyphenoxy]acetic acid; 8862174: (E)-1-(4-Tert-butylphenyl)-3-(4-hydroxy-3-methoxyphenyl)prop-2-en-1-one; 8862216: 2-[4-[(E)-3-(4-Tert-butylphenyl)-3-oxoprop-1-enyl]-2-methoxyphenoxy]acetic acid; 8862366: (E)-1-[2,4-Bis(difluoromethoxy)phenyl]-3-(4-hydroxyphenyl)prop-2-en-1-one; 8862405: (E)-1-[2,4-Bis(difluoromethoxy)phenyl]-3-(3-hydroxyphenyl)prop-2-en-1-one; 8862425: (E)-1-[2,4-Bis(difluoromethoxy)phenyl]-3-(4-hydroxy-3-nitro-phenyl)prop-2-en-1-one; 9026639: 2-[4-[(E)-3-(4-Hydroxyphenyl)-3-oxoprop-1-enyl]phenoxy]acetonitrile; 9033117: 2-[4-[(E)-3-(3-Fluoro-4-methoxyphenyl)prop-2-enoyl]phenoxy]acetic acid; 9034544: 5-[4-[(E)-3-(4-Methoxyphenyl)prop-2-enoyl]phenyl]furan-2-carboxylic acid; 9034557: 5-[4-[(E)-3-(4-Hydroxy-3-methoxyphenyl)prop-2-enoyl]phenyl]furan-2-carboxylic acid; 9034568: 5-[4-[(E)-3-(3,4-Dimethoxyphenyl)prop-2-enoyl]phenyl]furan-2-carboxylic acid; 9034574: 5-[4-[(E)-3-(3-Methoxyphenyl)prop-2-enoyl]phenyl]furan-2-carboxylic acid; 9034589: 5-[4-[(E)-3-(3-Ethoxy-4-hydroxyphenyl)prop-2-enoyl]phenyl]furan-2-carboxylic acid; 9034593: 5-[4-[(E)-3-(3-Hydroxy-4-methoxyphenyl)prop-2-enoyl]phenyl]furan-2-carboxylic acid; 9067365: (E)-3-(3-Bromo-4-hydroxyphenyl)-1-(4-methoxyphenyl)prop-2-en-1-one; 9067394: (E)-3-(3,4-Dihydroxyphenyl)-1-(4-methoxyphenyl)prop-2-en-1-one; 9100382: 3,3'-(1,3-Phenylene)bis[1-(4-hydroxyphenyl)-2-propen-1-one]; 9115166: (E)-3-(3-Hydroxy-4-methoxyphenyl)-1-[4-(2-oxo-2-piperidin-1-ylethoxy)phenyl]prop-2-en-1-one; 9179205: 2-[4-[(E)-3-(2,3-Dihydro-1,4-benzodioxin-6-yl)prop-2-enoyl]-3-hydroxyphenoxy]acetate; 9179206: 2-[4-[(E)-3-(2,3-Dihydro-1,4-benzodioxin-6-yl)prop-2-enoyl]-3-hydroxyphenoxy]acetic acid; 9184767: (E)-1-(4-Hydroxyphenyl)-3-[4-methoxy-3-[(4-nitro-phenyl)methoxy]phenyl]prop-2-en-1-one; 9320803: N-[4-[(E)-3-(4-Hydroxy-3-methoxyphenyl)prop-2-enoyl]phenyl]acetamide; 9321424: N-[4-[(E)-3-(4-Hydroxy-3-methoxyphenyl)prop-2-enoyl]phenyl]propanamide; 9349528: (2E)-1-(4-Bromophenyl)-3-[4-(2-hydroxyethoxy)phenyl]prop-2-en-1-one; 9438768: 2-[4-[(E)-3-(3,4-Difluorophenyl)prop-2-enoyl]phenoxy]acetic acid; 9447378: 4-[(E)-3-(4-Ethoxyphenyl)-3-oxoprop-1-enyl]benzoic acid; 9447379: (E)-1-(4-Ethoxyphenyl)-3-(3-hydroxyphenyl)prop-2-en-1-one; 9447384: (E)-1-(4-Ethoxy-phenyl)-3-(3-hydroxy-4-methoxyphenyl)prop-2-en-1-one; 9447394: (E)-3-(4-Hydroxyphenyl)-1-(4-piperidin-1-ylsulfonylphenyl)prop-2-en-1-one; 9447396: (E)-3-(4-Hydroxy-3-methoxyphenyl)-1-(4-piperidin-1-ylsulfonylphenyl)prop-2-en-1-one; 9447402: (E)-3-(3-Hydroxyphenyl)-1-(4-piperidin-1-ylsulfonylphenyl)prop-2-en-1-one; 9447405: (E)-3-(3-Ethoxy-4-hydroxyphenyl)-1-(4-piperidin-1-ylsulfonylphenyl)prop-2-en-1-one; 9447434: 2-[4-[(E)-3-(4-Hydroxyphenyl)prop-2-enoyl]phenoxy]acetonitrile; 9447437: 2-[4-[(E)-3-(4-Hydroxy-3-methoxyphenyl)prop-2-enoyl]phenoxy]acetonitrile; 9447452: 2-[4-[(E)-3-(3-Hydroxyphenyl)prop-2-enoyl]phenoxy]acetonitrile; 9447457: 2-[4-[(E)-3-(3-Ethoxy-4-hydroxyphenyl)prop-2-enoyl]phenoxy]acetonitrile; 9447517: 4-[(E)-3-(4-Hydroxy-3-methoxyphenyl)prop-2-enoyl]-N,N-dimethylbenzenesulfonamide; 9447520: 4-[(E)-3-(3-Ethoxy-4-hydroxyphenyl)prop-2-enoyl]-N,N-dimethylbenzenesulfonamide; 9447652: 2-[4-[(E)-3-(4-Hydroxy-3-methoxyphenyl)prop-2-enoyl]phenoxy]acetate; 9447653: 2-[4-[(E)-3-(4-Hydroxy-3-methoxyphenyl)prop-2-enoyl]phenoxy]acetic acid; 9447657: 2-[4-[(E)-3-(3-Bromophenyl)prop-2-enoyl]phenoxy]acetic acid; 9447661: 2-[4-[(E)-3-(3,4-Dimethoxyphenyl)prop-2-enoyl]phenoxy]acetic acid; 9447665: 2-[4-[(E)-3-[4-(Trifluoromethyl)phenyl]prop-2-enoyl]phenoxy]acetic acid; 9447667: 2-[4-[(E)-3-[4-(Difluoromethoxy)phenyl]prop-2-enoyl]phenoxy]acetic acid; 9447669: 2-[4-[(E)-3-(3-Chlorophenyl)prop-2-enoyl]phenoxy]acetic acid; 9447671: 2-[4-[(E)-3-(3-Methoxyphenyl)prop-2-enoyl]phenoxy]acetic acid; 9447673: 2-[4-[(E)-3-(4-Ethoxy-3-methoxyphenyl)prop-2-enoyl]phenoxy]acetic acid; 9447675: 2-[4-[(E)-3-(4-Propan-2-ylphenyl)prop-2-enoyl]phenoxy]acetic acid; 9447693: 2-[4-[(E)-3-(4-Methylphenyl)prop-2-enoyl]phenoxy]acetic acid; 9447696: 2-[4-[(E)-3-(3-Ethoxy-4-hydroxyphenyl)prop-2-enoyl]phenoxy]acetate; 9447697: 2-[4-[(E)-3-(3-Ethoxy-4-hydroxyphenyl)prop-2-enoyl]phenoxy]acetic acid; 9447715: 2-[4-[(E)-3-(3-Ethoxy-4-methoxyphenyl)prop-2-enoyl]phenoxy]acetic acid; 9447717: 2-[4-[(E)-3-(3-Bromo-4-methoxyphenyl)prop-2-enoyl]phenoxy]acetic acid; 9447721: 2-[4-[(E)-3-(4-Propoxyphenyl) prop-2-enoyl]phenoxy]acetic acid; 9447729: 2-[4-[(E)-3-(6-Methoxynaphthalen-2-yl)prop-2-enoyl]phenoxy]acetic acid; 9447741: 2-[4-[(E)-3-(3-Bromo-4-fluorophenyl)prop-2-enoyl]phenoxy]acetic acid; 9447753: 2-[4-[(E)-3-(3-Prop-2-enoxyphenyl)prop-2-enoyl]phenoxy]acetic acid; 9447757: 2-[4-[(E)-3-[3-(Difluoromethoxy)-4-methoxyphenyl]prop-2-enoyl]phenoxy]acetic acid; 9447761: 2-[4-[(E)-3-[4-(Difluoromethoxy)-3-ethoxyphenyl]prop-2-enoyl]phenoxy]acetic acid; 9447927: (E)-3-(4-Hydroxyphenyl)-1-(2-nitro-phenyl)prop-2-en-1-one; 9447949: (E)-3-(3-Hydroxyphenyl)-1-(2-nitro-phenyl)prop-2-en-1-one; 9447967: (E)-3-(3-Hydroxy-4-methoxyphenyl)-1-(2-nitro-phenyl)prop-2-en-1-one; 9448121: N-Benzyl-4-[(E)-3-(4-hydroxyphenyl)prop-2-enoyl]benzenesulfonamide; 9448123: N-Benzyl-4-[(E)-3-(3-hydroxyphenyl)prop-2-enoyl]benzenesulfonamide; 9448129: 4-[(E)-3-(4-Hydroxyphenyl) prop-2-enoyl]-N-methylbenzenesulfonamide; 9448156: 4-[(E)-3-(3-Hydroxyphenyl)prop-2-enoyl]-N-methylbenzenesulfonamide; 9448174: 4-[(E)-3-(3-Hydroxy-4-methoxyphenyl)prop-2-enoyl]-N-methylbenzenesulfonamide; 9448299: 4-[(E)-3-(4-Ethylphenyl)-3-oxoprop-1-enyl]benzoic acid; 9448300: (E)-1-(4-Ethylphenyl)-3-(3-hydroxyphenyl)prop-2-en-1-one; 9448305: (E)-1-(4-Ethylphenyl)-3-(3-hydroxy-4-methoxyphenyl)prop-2-en-1-one; 9448314: Schembl21717729; 9448318: (E)-3-(4-Hydroxy-3-methoxyphenyl)-1-(2-methylphenyl)prop-2-en-1-one; 9448323: 4-[(E)-3-(2-Methylphenyl)-3-oxoprop-1-enyl]benzoic acid; 9448326: 3-Hydroxy-2'-methylchalcone; 9448329: (E)-3-(3-Ethoxy-4-hydroxyphenyl)-1-(2-methylphenyl)prop-2-en-1-one; 9448340: (E)-3-(4-Hydroxy-3-nitro-phenyl)-1-(2-methylphenyl)prop-2-en-1-one; 9448359: 2-[2-Methoxy-4-[(E)-3-(2-methylphenyl)-3-oxoprop-1-enyl]phenoxy]acetic acid; 9448397: (E)-1-(2,4-Dimethylphenyl)-3-(4-hydroxyphenyl)

prop-2-en-1-one; 9448404: 4-[(E)-3-(2,4-Dimethylphenyl)-3-oxoprop-1-enyl]benzoic acid; 9448407: (E)-1-(2,4-Dimethylphenyl)-3-(3-hydroxyphenyl)prop-2-en-1-one; 9448411: (E)-1-(2,4-Dimethylphenyl)-3-(3-ethoxy-4-hydroxyphenyl)prop-2-en-1-one; 9448413: (E)-1-(2,4-Dimethylphenyl)-3-(3-hydroxy-4-methoxyphenyl)prop-2-en-1-one; 9448417: (E)-1-(2,4-Dimethylphenyl)-3-(4-hydroxy-3-nitro-phenyl)prop-2-en-1-one; 9448421: 2-[4-[(E)-3-(2,4-Dimethylphenyl)-3-oxoprop-1-enyl]phenoxy]acetic acid; 9448429: 2-[4-[(E)-3-(2,4-Dimethylphenyl)-3-oxoprop-1-enyl]-2-methoxyphenoxy]acetic acid; 9448435: (E)-3-(4-Hydroxyphenyl)-1-(2,4,6-trimethylphenyl)prop-2-en-1-one; 9448437: (E)-3-(3-Hydroxyphenyl)-1-(2,4,6-trimethylphenyl)prop-2-en-1-one; 9448440: (E)-3-(3-Hydroxy-4-methoxyphenyl)-1-(2,4,6-trimethylphenyl)prop-2-en-1-one; 9448445: (E)-3-(3-Hydroxyphenyl)-1-(4-iodophenyl)prop-2-en-1-one; 9448448: (E)-3-(3-Ethoxy-4-hydroxyphenyl)-1-(4-iodophenyl)prop-2-en-1-one; 9448449: (E)-3-(3-Hydroxy-4-methoxyphenyl)-1-(4-iodophenyl)prop-2-en-1-one; 9448642: N-[(4-Fluorophenyl)methyl]-4-[(E)-3-(4-hydroxyphenyl)prop-2-enoyl]benzenesulfonamide; 9448643: N-[(4-Fluorophenyl)methyl]-4-[(E)-3-(3-hydroxyphenyl)prop-2-enoyl]benzenesulfonamide; 9815118: (E)-1-(2,4-Dichlorophenyl)-3-(3,4-dihydroxyphenyl)prop-2-en-1-one; 9851513: (E)-1-(2,4-Dihydroxyphenyl)-3-(4-hydroxyphenyl)prop-2-en-1-one;(E)-3-[4-hydroxy-2-methoxy-5-(2-methylbut-3-en-2-yl)phenyl]-1-(4-hydroxyphenyl)prop-2-en-1-one; 9876018: (9Ar)-7-(dithiophen-2-ylmethylidene)-5-methyl-1,2,3,4,6,8,9,9a-octahydro-quinolizin-5-ium;2-[5-(3-methylbut-2-enoxy)-2-[(E)-3-[4-(3-methylbut-2-enoxy)phenyl]prop-2-enoyl]phenoxy]acetic acid;bromide; 9878220: 4-(3-Phenylprop-2-enoyl)benzoic acid; 9904479: 2',4',6',3-Tetrahydroxy-4-methoxychalcone; 9907346: 5-[[4-[(E)-3-(3,4-Dihydroxyphenyl)prop-2-enoyl]phenyl]methyl]-1,3-thiazolidine-2,4-dione; 9933354: (E)-1-(2,4-Dihydroxyphenyl)-3-[4-[(3S,4R,5R,6S)-3,4,5-trihydroxy-3,6-bis(hydroxymethyl)oxan-2-yl]oxyphenyl]prop-2-en-1-one; 9971453: (E)-1-(2,4-Dihydroxyphenyl)-3-naphthalen-2-ylprop-2-en-1-one; 9974764: 4-Hydroxy-2',3,4',6'-tetramethoxychalcone; 9984671: (E)-1-[2-Hydroxy-6-[2-hydroxy-3-[3-hydroxy-2-[(E)-3-phenylprop-2-enoyl]phenoxy]propoxy]phenyl]-3-phenylprop-2-en-1-one; 9998389: 2-Methyl-2-[4-[(E)-3-(4-methylsulfanylphenyl)prop-2-enoyl]phenoxy]propanoic acid; 9999627: 2-[4-[(E)-3-(4-Chloro-2-hydroxyphenyl)-3-oxoprop-1-enyl]phenyl]sulfanyl-2-methylpropanoic acid; 10020239: 4-[3-(2,4,6-Trimethoxyphenyl)-3-oxo-1-propenyl]benzoic acid; 10022754: 4-Iodo-2',4',6'-trihydroxychalcone; 10027535: (E)-3-[3,4-Bis(phenylmethoxy)phenyl]-1-(2-hydroxy-4-methoxyphenyl)prop-2-en-1-one; 10030794: (E)-1-[2-[2-Hydroxy-3-[2-[(E)-3-(4-methoxyphenyl)prop-2-enoyl]phenoxy]propoxy]phenyl]-3-(4-methoxyphenyl)prop-2-en-1-one; 10041116: N-[4-[(E)-3-(2-Hydroxy-4-methoxyphenyl)-3-oxoprop-1-enyl]phenyl]acetamide; 10043014: 2-[4-[(E)-3-(2-Hydroxy-phenyl)-3-oxoprop-1-enyl]phenyl]sulfanyl-2-methylpropanoic acid; 10044324: 3-[(E)-3-[2-[(4-Methylpiperazin-1-yl)methyl]phenyl]-3-oxoprop-1-enyl]benzoic acid; 10044536: Propan-2-yl 2-[3-[(E)-3-(2-hydroxyphenyl)-3-oxoprop-1-enyl]phenoxy]-2-methylpropanoate; 10051788: (E)-3-(3,4-Dimethoxyphenyl)-1-[4-[2-hydroxy-3-(4-phenylpiperazin-1-yl)propoxy]phenyl]prop-2-en-1-one; 10052569: (3E,5E)-3,5-Dibenzylidene-1-[4-[(E)-3-(4-hydroxy-phenyl)-3-oxoprop-1-enyl]benzoyl]piperidin-4-one; 10062292: 2-(3-Phenyl-1-oxoallyl) phenoxyacetic acid; 10062573: 4-Chloro 2'-hydroxy-4',6'-dimethylchalcone; 10066116: 2-[4-[(E)-3-(4-Chlorophenyl)prop-2-enoyl]phenoxy]-2-methylpropanoic acid; 10067885: 2-[3-Hydroxy-4-[(E)-3-(4-methylsulfanylphenyl)prop-2-enoyl]phenoxy]-2-methylpropanoic acid; 10088061: 4-Bromo-2'-hydroxy-4',6'-dimethylchalcone; 10089627: 2-Methyl-2-[4-[(E)-3-(4-methylsulfanylphenyl)-3-oxoprop-1-enyl]phenoxy]propanoic acid; 10090415: 2-[4-[(E)-3-(2-Acetyloxyphenyl)-3-oxoprop-1-enyl]phenoxy]-2-methylpropanoic acid; 10090671: 2-[4-[(E)-3-(4-Methoxy-2-sulfanylphenyl)-3-oxoprop-1-enyl]phenoxy]-2-methylpropanoic acid; 10095186: 2',4-Dihydroxy-4'-(beta-D-gluco-pyranosyloxy)-6'-methoxychalcone; 10149901: 4-[(E)-3-(3-Thiophen-2-ylphenyl)prop-2-enoyl]benzoic Acid; 10227083: (E)-3-(1-Benzofuran-5-yl)-1-[2-hydroxy-4-methoxy-6-[[3,4,5-trihydroxy-6-(hydroxymethyl)oxan-2-yl]methyl]phenyl]prop-2-en-1-one; 10245712: 4-[3-Oxo-3-[4-(trimethylsilyl)phenyl]-1-propenyl]benzoic acid; 10246380: 4-[(E)-3-Oxo-3-[4-(5-oxo-2H-oxadiazol-3-ium-3-yl)phenyl]prop-1-enyl]benzoic acid; 10246756: 2-[3-Hydroxy-4-[(E)-3-(3-hydroxyphenyl)prop-2-enoyl]phenoxy]-2-methylpropanoic acid; 10249326: Tert-butyl 2-[4-[(E)-3-(2-hydroxyphenyl)-3-oxoprop-1-enyl]phenoxy]-2-methylpropanoate; 10251436: (E)-1-[2,4-Dihydroxy-6-[(3S,4R,5R,6S)-3,4,5-trihydroxy-6-(hydroxymethyl)oxan-2-yl]oxyphenyl]-3-phenylprop-2-en-1-one; 10257949: (E)-1-[2-Hydroxy-6-[2-hydroxy-3-[3-hydroxy-2-[(E)-3-(4-methoxyphenyl)prop-2-enoyl]phenoxy]propoxy]phenyl]-3-(4-methoxyphenyl)prop-2-en-1-one; 10266434: 3-[4-[(E)-3-(2-Hydroxyphenyl)-3-oxo-1-propenyl]phenyl]propenoic acid; 10270600: (E)-3-[4-[3,4-Dihydroxy-5-(hydroxymethyl)oxolan-2-yl]oxy-3-hydroxyphenyl]-1-phenylprop-2-en-1-one; 10286995: 4-[3E-(4-Methoxy-3-thiophen-2-yl-phenyl)-acryloyl]-benzoic acid; 10316229: (E)-3-(4-Hexoxyphenyl)-1-(2,4,6-trihydroxyphenyl)prop-2-en-1-one; 10316505: 2-[4-[(E)-3-(4-Chlorophenyl)prop-2-enoyl]-3-hydroxyphenoxy]-2-methylpropanoic acid; 10317192: 2-Methyl-2-[4-[(E)-3-(4-methylsulfanylphenyl)prop-2-enoyl]phenyl]sulfanylpropanoic acid; 10318361: 4'-Geranyloxy-4,2'-dihydroxychalcone; 10318965: Propan-2-yl 2-[4-[(E)-3-(4-chloro-2-hydroxyphenyl)-3-oxoprop-1-enyl]phenoxy]-2-methylpropanoate; 10331849: (Z)-1-(2,4-Dihydroxyphenyl)-3-phenylprop-2-en-1-one; 10336486: 2-[3-[(E)-3-(2-Hydroxyphenyl)-3-oxoprop-1-enyl]phenoxy]-2-methylpropanoic acid; 10344152: (E)-1-[4-[3-(4-Acetyl-3-hydroxy-2-propylphenoxy)propoxy]phenyl]-3-phenylprop-2-en-1-one; 10346010: (E)-1-[2-[2-Hydroxy-3-[2-[(E)-3-phenylprop-2-enoyl]phenoxy]propoxy]phenyl]-3-phenylprop-2-en-1-one; 10348506: (E)-1-[2-Hydroxy-6-[2-hydroxy-3-[3-hydroxy-2-[(E)-3-(3-methoxyphenyl)prop-2-enoyl]phenoxy]propoxy]phenyl]-3-(3-methoxyphenyl)prop-2-en-1-one; 10364694: Neoisoliquiritigenin; 10370670: (E)-1-[2-[2-Hydroxy-3-[2-[(E)-3-(3-methoxyphenyl)prop-2-enoyl]phenoxy]propoxy]phenyl]-3-(3-methoxyphenyl)prop-2-en-1-one; 10371291: (E)-1-[2-Hydroxy-4-[(2S,3R,4S,5S,6R)-3,4,5-trihydroxy-6-(hydroxymethyl)oxan-2-yl]oxyphenyl]-3-[4-hydroxy-3-[(2R,3S,4R,5R,6S)-3,4,5-trihydroxy-6-(hydroxymethyl)oxan-2-yl]oxyphenyl]prop-2-en-1-one; 10372091: (E)-3-(3,4-Dimethoxyphenyl)-1-[2,6-dimethoxy-4-[(3R,4S,5S,6R)-3,4,5-trihydroxy-6-[[(2S,3R,4R,5R,6S)-3,4,5-trihydroxy-6-methyloxan-2-yl]oxymethyl]oxan-2-yl]oxyphenyl]prop-2-en-1-one; 10377524: (E)-1-(2-Hydroxy-4,6-dimethylphenyl)-3-phenyl-prop-2-en-1-one; 10382732: 2-[4-[(E)-3-(2,4-Dihydroxyphenyl)-3-oxoprop-1-enyl]phenoxy]-2-methylpropanoic acid; 10386991: (E)-3-(4-Decoxyphenyl)-1-(2,4,6-trihydroxyphenyl)prop-2-en-1-one; 10391191: 2,3,5,6-Tetrachloro-4-[(5-(3-phenyl-3-oxo-1-propenyl)-1,3-benzo-dioxol-2-yl)oxy]phenol; 10395031:

Ethyl 2-[3-[3-[3-(2-ethoxy-2-oxoethoxy)-2-[(E)-3-phenyl-prop-2-enoyl]phenoxy]-2-hydroxypropoxy]-2-[(E)-3-phenylprop-2-enoyl]phenoxy]acetate; 10399428: (E)-1-(2-(18F)Fluoranylphenyl)-3-(4-hydroxyphenyl)prop-2-en-1-one; 10403500: 5-[2-(4-Chlorobenzoyl)vinyl]-2-hydroxybenzoic acid methyl ester; 10404228: (E)-4-Ethoxy-2'-hydroxy-4',6'-dimethoxychalcone; 10405090: 3-[3-(2,4,6-Trimethoxyphenyl)-3-oxo-1-propenyl]benzoic acid; 10406265: (E)-1-(4-Hydroxyphenyl)-3-[3-(4-nitrophenoxy)phenyl]prop-2-en-1-one; 10407693: Propan-2-yl 2-[4-[(E)-3-(2-hydroxyphenyl)-3-oxoprop-1-enyl]phenyl]sulfanyl-2-methylpropanoate; 10409695: Tert-butyl 2-[4-[(E)-3-(4-chloro-2-hydroxyphenyl)-3-oxoprop-1-enyl]phenoxy]-2-methylpropanoate; 10426518: 2-[4-[(E)-3-(2-Hydroxyphenyl)-3-oxoprop-1-enyl]phenoxy]-2-methylpropanoic acid; 10428633: 2-[4-[(E)-3-(4-Chloro-2-hydroxyphenyl)-3-oxoprop-1-enyl]phenoxy]-2-methylpropanoic acid; 10430113: (E)-3-(4-Octoxyphenyl)-1-(2,4,6-trihydroxyphenyl)prop-2-en-1-one; 10446494: Methyl 2-hydroxy-5-(3-oxo-3-phenyl-1-propenyl)benzoate; 10450506: (E)-1-(2,4-Dichlorophenyl)-3-[3-[(dimethylamino)methyl]-4-hydroxyphenyl]prop-2-en-1-one; 10452249: 2-[4-[(2-Thiazolyl) carbamoyl]-trans-cinnamoyl]benzoic acid; 10470623: (E)-3-[4-[(E)-3-(2,4-Dihydroxyphenyl)-3-oxoprop-1-enyl]phenyl]prop-2-enoic acid; 10474186: Propan-2-yl 2-[4-[(E)-3-(2-hydroxy-phenyl)-3-oxoprop-1-enyl]phenoxy]-2-methylpropanoate; 10484055: (E)-3-(3-Hydroxy-4-methoxyphenyl)-1-[2-hydroxy-6-methoxy-4-[(2S,3R,4S,5S,6R)-3,4,5-trihydroxy-6-[[(2S,3R,4R,5R,6S)-3,4,5-trihydroxy-6-methyloxan-2-yl]oxymethyl]oxan-2-yl]oxyphenyl]prop-2-en-1-one; 10491149: 2',4'-Dihydroxy-4-methylchalcone; 10494611: 5-[2-(4-Chlorobenzoyl)vinyl]-2-hydroxybenzoic acid; 10495842: 4-Bromo-2',4'-dihydroxychalcone; 10503760: 2-[3-Hydroxy-4-[(E)-3-[3-[(E)-2-quinolin-2-ylethenyl]phenyl]prop-2-enoyl]phenoxy]acetic acid; 10522436: (E)-3-(4-Chlorophenyl)-1-[2-hydroxy-4-(oxan-2-yloxy)phenyl]prop-2-en-1-one; 10526346: (E)-1-[2-Hydroxy-4-(oxan-2-yloxy)phenyl]-3-[3-(oxan-2-yloxy)phenyl]prop-2-en-1-one; 10531776: 5-[[4-(2,3,4-Trimethoxybenzyl) piperazinocarbonyl]methoxy]-2-[3-(3-hydroxy-4-methoxyphenyl)acryloyl]-1,3-benzenediol; 10540319: 2',4'-Dihydroxy-4-chlorochalcone; 10557220: N-[4-[(E)-3-(4-Hydroxyphenyl) prop-2-enoyl]phenyl]-3-[3-[[4-[(E)-3-(4-hydroxyphenyl)prop-2-enoyl]phenyl]sulfamoyl]benzoyl]benzenesulfonamide; 10575999: (E)-3-(3,4-Dimethoxyphenyl)-1-[2-hydroxy-6-[(2S,3R,4S,5S,6R)-3,4,5-trihydroxy-6-(hydroxymethyl)oxan-2-yl]oxyphenyl]prop-2-en-1-one; 10595346: (E)-1-[2-Hydroxy-4-(oxan-2-yloxy)phenyl]-3-(4-methylsulfanylphenyl)prop-2-en-1-one; 10596175: Schembl21527700; 10597634: 2-(3-(3-(Quinolin-2-ylmethoxy)phenyl) acryloyl)benzoic acid; 10600978: 4-[(E)-3-[4-[[1-(1-Ethoxyethyl)benzimidazol-2-yl]methoxy]phenyl]prop-2-enoyl]-3-hydroxybenzoic acid; 10602905: 4-Iodo-2'-hydroxy-4',6'-bis[(2-methoxyethoxy)methoxy] chalcone; 10612087: 2',4'-Dihydroxy-3-methoxychalcone; 10625574: (2S)-4-Methyl-2-[[(2S)-2-[[4-[(E)-3-oxo-3-phenylprop-1-enyl]benzoyl]amino]-3-phenylpropanoyl]amino]pentanoic acid; 10625896: (e)-3-[3,4-Bis(tetrahydro-2h-pyran-2-yloxy)phenyl]-1-[2-hydroxy-4-(tetrahydro-2h-pyran-2-yloxy)phenyl]prop-2-en-1-one; 10649386: 4-Bromo-2'-hydroxy-4',6'-bis[(2-methoxyethoxy)methoxy] chalcone; 10659647: (e)-3-(4-Hydroxy-3-methoxyphenyl)-1-(4-hydroxyphenyl)prop-2-en-1-one; 10670580: (E)-1-[4-[(2E)-3,7-Dimethylocta-2,6-dienoxy]-2-hydroxyphenyl]-3-[4-(methoxymethoxy)phenyl]prop-2-en-1-one; 10696597: (E)-3-[4-[(2E)-3,7-Dimethylocta-2,6-dienoxy]phenyl]-1-[2-hydroxy-4,6-bis(methoxymethoxy)phenyl]prop-2-en-1-one; 10716790: (E)-3-(4-Methoxy-phenyl)-1-[2-[(2S,3R,4S,5S,6R)-3,4,5-trihydroxy-6-(hydroxymethyl)oxan-2-yl]oxyphenyl]prop-2-en-1-one; 10722190: 2-[2-[[4-[3-(3-Methoxy-4-hydroxyphenyl)acryloyl]phenyl]carbamoyl]phenyl]-5-benzoyl-1H-benzimidazole; 10730593: (E)-4-Hydroxy-3-carboxychalcone; 10735104: 2'-Hydroxy-4-nitro-4',6'-dimethoxychalcone; 10752529: 2',6'-Dihydroxychalcone; 10755967: 4-Chloro-2',4',6'-trihydroxychalcone; 10764001: 2-(3-(4-(Quinolin-2-ylmethoxy)phenyl)acryloyl)benzoic acid; 10765958: 4-Fluoro-2'-hydroxy-4',6'-bis[(2-methoxyethoxy) methoxy]chalcone; 10766649: 4-Chloro-2'-hydroxy-4',6'-bis[(2-methoxyethoxy)methoxy]chalcone; 10771832: N-[4-[(E)-3-(4-Hydroxy-3-methoxyphenyl)prop-2-enoyl]phenyl]-3-[3-[[4-[(E)-3-(4-hydroxy-3-methoxyphenyl)prop-2-enoyl]phenyl]sulfamoyl]benzoyl]benzenesulfonamide; 10778685: 2',4',6'-Trihydroxy-4-fluorochalcone; 10782645: 2'-Hydroxy-6'-(benzyloxy)-trans-chalcone; 10784314: (E)-1-[2-Hydroxy-4-(oxan-2-yloxy)phenyl]-3-(3-methoxyphenyl)prop-2-en-1-one; 10788507: 3-Hydroxy-4-[(E)-3-[4-(quinolin-2-ylmethoxy)phenyl]prop-2-enoyl]benzoic acid; 10793864: (E)-3-[3,4-Bis(phenylmethoxy)phenyl]-1-[2-hydroxy-6-[(2S,3R,4S,5S,6R)-3,4,5-trihydroxy-6-(hydroxymethyl)oxan-2-yl]oxyphenyl]prop-2-en-1-one; 10804786: 3,4-Dichloro-2',4'-dihydroxychalcone; 10806690: 4-Bromo-2',4',6'-trihydroxychalcone; 10808037: (E)-1-[2-Hydroxy-4-(oxan-2-yloxy)phenyl]-3-(4-methoxy-phenyl)prop-2-en-1-one; 10827074: 2',4'-Dihydroxy-4-(methylthio)chalcone; 10836134: 3-Hydroxy-4-[(E)-3-[3-(quinolin-2-ylmethoxy)phenyl]prop-2-enoyl]benzoic acid; 10850872: 3-Fluoro-2',4'-dihydroxy-4-methoxychalcone; 10851171: (E)-1-(2-Hydroxyphenyl)-3-[4-(trifluoromethyl)phenyl]prop-2-en-1-one; 10881804: Kanzonol B; 10886195: 3,4-Bis(benzyloxy)-2'-hydroxy-4',6'-bis(methoxymethoxy)chalcone; 10904626: (Z)-4-[4-[(E)-3-(4-Nitro-phenyl)prop-2-enoyl]anilino]-4-oxobut-2-enoic acid; 10919489: (E)-3-[4-[Tert-butyl(dimethyl) silyl]oxy-3-(3-methylbut-2-enyl)phenyl]-1-[4-[tert-butyl(diphenyl)silyl]oxy-2-hydroxyphenyl]prop-2-en-1-one; 10925972: 4-Hydroxy-2',4'-bis(methoxymethoxy)chalcone; 10926755: 3,3'-m-Phenylenebis[1-(2-hydroxyphenyl)-2-propene-1-one]; 10928605: 2-[4-(2-Hydroxy-2-methylpropanoyl)phenoxy] ethyl 4-[(E)-3-oxo-3-phenylprop-1-enyl]benzoate; 10929313: 3beta-[5-[(E)-3-(2,4-Dihydroxyphenyl)-3-oxo-1-propenyl]-2-hydroxyphenyl]-2,3-dihydro-7-hydroxy-2alpha-(4-hydroxyphenyl)-4H-1-benzopyran-4-one; 10934038: (E)-3-[3-(Hydroxy-methyl)phenyl]-1-(2-hydroxyphenyl)prop-2-en-1-one; 10937434: (2E)-1-[2-Hydroxy-4-(methoxymethoxy)phenyl]-3-(2,2-dimethyl-2H-1-benzopyran-6-yl)-2-propene-1-one; 10938413: 2-[4-[(E)-3-(4-Iodophenyl)prop-2-enoyl]phenoxy]acetic acid; 10940339: (2S,3R)-3-[5-[(E)-3-(2,4-Dihydroxyphenyl)-3-oxoprop-1-enyl]-2-hydroxyphenyl]-5,7-dihydroxy-2-(4-hydroxyphenyl)-2,3-dihydrochromen-4-one; 10947648: (Z)-4-[4-[(E)-3-(4-Methylphenyl) prop-2-enoyl]anilino]-4-oxobut-2-enoic acid; 10948254: (Z)-4-[4-[(E)-3-(4-Chlorophenyl) prop-2-enoyl]anilino]-4-oxobut-2-enoic acid; 10951828: (E)-3-[(2R,3R)-3-(Hydroxymethyl)-2-(3-methoxy-4-phenylmethoxyphenyl)-2,3-dihydro-1,4-benzodioxin-6-yl]-1-(2,4,6-trihydroxy-phenyl)prop-2-en-1-one; 10962273: (E)-3-[[3alpha-(2,4-Dihydroxybenzoyl)-2,3-dihydro-2beta-(4-hydroxyphenyl)benzofuran-5-yl]-1-(2,4-dihydroxyphenyl)-2-propen-1-one; 10981804: (Z)-4-[4-[(E)-3-(3,4-Dimethoxyphenyl)prop-2-enoyl]anilino]-4-oxobut-2-enoic acid; 10983454: (E)-1-[2,6-Dihydroxy-4-[(2S,3R,4S,5S,6R)-3,4,5-trihydroxy-6-(hydroxy-methyl)

oxan-2-yl]oxyphenyl]-3-(3-hydroxy-4-methoxyphenyl) prop-2-en-1-one; 10996051: (E)-3-[(2R,3R)-3-(Hydroxymethyl)-2-(3-methoxy-4-phenylmethoxyphenyl)-2,3-dihydro-1,4-benzodioxin-6-yl]-1-[2,4,6-tris(methoxymethoxy)phenyl]prop-2-en-1-one; 11001152: (E)-3-(3-Bromophenyl)-1-(4-hydroxyphenyl)prop-2-en-1-one; 11016891: 1-[2,6-Dihydroxy-4-(tert-butyldimethylsilyloxy)phenyl]-3-[3-(tert-butyldimethylsilyloxy)-4-methoxyphenyl]-2-propene-1-one; 11022479: Neosakuranetin; 11022960: 4,4'-Dihydroxy-2',6'-dimethoxychalcone; 11035487: (E)-1-(4-Hydroxyphenyl)-3-(4-iodophenyl)prop-2-en-1-one; 11036555: (Z)-4-[4-[(E)-3-(3,4-Dichlorophenyl)prop-2-enoyl]anilino]-4-oxobut-2-enoic acid; 11039724: (E)-3-[[3alpha-[2,4-Bis(methoxymethoxy)benzoyl]-2,3-dihydro-2beta-(4-hydroxyphenyl)benzofuran]-5-yl]-1-[2,4-bis(methoxymethoxy)phenyl]-2-propen-1-one; 11043762: 3-[(E)-3-(2-Hydroxyphenyl)-3-oxoprop-1-enyl]benzoic acid; 11058233: (E)-1-(2-Hydroxy-6-phenylmethoxyphenyl)-3-[4-(methoxymethoxy)phenyl]prop-2-en-1-one; 11070489: (E)-3-(1-Benzofuran-5-yl)-1-[2-hydroxy-4-methyl-6-[(2S,3R,4S,5S,6R)-3,4,5-trihydroxy-6-(hydroxy-methyl)oxan-2-yl]oxyphenyl]prop-2-en-1-one; 11072502: (2S,3R)-3-[5-[(E)-3-(2,4-Dihydroxyphenyl)-3-oxoprop-1-enyl]-2-hydroxyphenyl]-5-hydroxy-2-(4-hydroxyphenyl)-7-[(2S,3R,4S,5S,6R)-3,4,5-trihydroxy-6-(hydroxymethyl)oxan-2-yl]oxy-2,3-dihydrochromen-4-one; 11099271: (Z)-4-Oxo-4-[4-[(E)-3-phenylprop-2-enoyl]anilino]but-2-enoic acid; 11099375: Licoagrochalcone A; 11108740: 4-Butyl-4'-hydroxychalcone; 11110910: (Z)-4-[4-[(E)-3-(4-Methoxyphenyl)prop-2-enoyl]anilino]-4-oxobut-2-enoic acid; 11119617: 2'-Hydroxy-4-(methoxymethoxy)chalcone; 11120015: (E)-3-(4-Butoxyphenyl)-1-(2-hydroxy-phenyl)prop-2-en-1-one; 11133693: (E)-3-(2,2-Dimethylchromen-6-yl)-1-[2-hydroxy-4,6-bis(methoxymethoxy)phenyl]prop-2-en-1-one; 11155014: (E)-But-2-enedioic acid;(E)-3-(4-chlorophenyl)-1-[4-[2-(dimethylamino)ethylamino]phenyl]prop-2-en-1-one; 11174470: 4'-Hydroxy-2',4,6'-trimethoxychalcone; 11175013: (E)-1-(2-Hydroxy-4,6-dimethoxyphenyl)-3-naphthalen-2-ylprop-2-en-1-one; 11175917: 2'-Hydroxy-4-bromo-4',6'-dimethoxychalcone; 11180323: N-[4-[(E)-3-[4-(Dimethylamino)phenyl]prop-2-enoyl]phenyl]-5-[(1,3-dioxoisoindol-2-yl)methyl]-2-hydroxybenzamide; 11196385: 2-[(E)-3-(4-Methylphenyl)prop-2-enoyl]benzoic acid; 11208429: 2-[(2E)-3-(4-Chlorophenyl)prop-2-enoyl]benzoic acid; 11223603: (E)-But-2-enedioic acid;(E)-1-[4-[2-(dimethylamino)ethylamino]phenyl]-3-phenylprop-2-en-1-one; 11227320: [3,5-Dibenzoyloxy-4-[(E)-3-(4-hydroxy-3-methoxyphenyl)prop-2-enoyl]phenyl] benzoate; 11233223: (E)-1-[2-Hydroxy-6-methoxy-4-(methoxymethoxy)phenyl]-3-(4-methoxyphenyl)prop-2-en-1-one; 11233250: [4-[(E)-3-(2-Hydroxy-4,6-dimethoxyphenyl)-3-oxoprop-1-enyl]phenyl] nitrate; 11254611: 2'-Hydroxy-3-(methoxy-methoxy)chalcone; 11257333: 2-[2-Fluoro-4-[(E)-3-(4-methylsulfanylphenyl)-3-oxoprop-1-enyl]phenoxy]-2-methylpropanoic acid; 11266033: 2-[(E)-3-(3-Methoxyphenyl)prop-2-enoyl]benzoic acid; 11271357: (E)-3-(1-Benzofuran-5-yl)-1-[2-hydroxy-4-methoxy-6-[[(2S,3R,4R,5S,6R)-3,4,5-trihydroxy-6-(hydroxymethyl)oxan-2-yl]methyl]phenyl]prop-2-en-1-one; 11318576: 5-[(1,3-Dioxoisoindol-2-yl)methyl]-2-hydroxy-N-[4-[(E)-3-(4-methoxyphenyl) prop-2-enoyl]phenyl]benzamide; 11325630: 6-Hydroxyhexyl 4-[(E)-3-phenylprop-2-enoyl]benzoate; 11340220: 2-(4-Chlorophenyl)-N-[4-[(Z)-3-(4-hydroxy-3-methoxyphenyl)prop-2-enoyl]phenyl]-3-methylbutanamide; 11394654: 4-[(E)-3-(2-Benzoyl-6-hydroxyphenyl)-3-oxoprop-1-enyl]benzoic acid; 11403367: 2'-Hydroxy-4'-(methoxymethoxy)chalcone; 11414851: 2-(4-Methoxy-trans-cinnamoyl)benzoic acid; 11415131: (E)-3-(3,4-Dichloro-phenyl)-1-(2-hydroxyphenyl)prop-2-en-1-one; 11437689: (E)-3-(3-Fluoro-4-hydroxyphenyl)-1-(4-methylsulfanylphenyl)prop-2-en-1-one; 11449431: 2',4'-Dihydroxy-4,6'-dimethoxychalcone; 11467679: 2',2'''-Dihydroxy-4,4''-bis(3-methyl-2-butenyloxy)-alpha,beta-dihydro-3,3''-bichalcone; 11488481: 3-[4-Hydroxy-3-[2-hydroxy-5-[(E)-3-(2-hydroxyphenyl)-3-oxoprop-1-enyl]phenyl]phenyl]-1-(2-hydroxyphenyl)propan-1-one; 11531080: (E)-1-[4-[3-(Butylamino)-2-hydroxypropoxy]phenyl]-3-(4-methoxyphenyl)prop-2-en-1-one; 11532735: (E)-1-(2-Hydroxy-4,6-dimethoxyphenyl)-3-[4-[(2S,3R,4S,5S,6R)-3,4,5-trihydroxy-6-(hydroxy-methyl)oxan-2-yl]oxyphenyl]prop-2-en-1-one; 11537954: (E)-1-[4-[2-Hydroxy-3-(propan-2-ylamino)propoxy]phenyl]-3-(4-methoxyphenyl)prop-2-en-1-one; 11547723: (E)-1-[2-Hydroxy-4-(oxan-2-yloxy)phenyl]-3-[3-(3-methylbut-2-enyl)-4-(oxan-2-yloxy)phenyl]prop-2-en-1-one; 11567157: (E)-1-[4-[3-(Tert-butylamino)-2-hydroxypropoxy]phenyl]-3-(4-methoxyphenyl)prop-2-en-1-one; 11569436: (E)-1-[4-[3-[2-(3,4-Dimethoxyphenyl)ethylamino]-2-hydroxypropoxy]phenyl]-3-(4-methoxyphenyl)prop-2-en-1-one; 11584217: (E)-1-[2-Hydroxy-3-[4-(2-methoxyphenyl)piperazin-1-yl]propoxy]phenyl]-3-(4-methoxyphenyl) prop-2-en-1-one; 11610366: (E)-1-[2-[2-Hydroxy-3-(propan-2-ylamino)propoxy]phenyl]-3-(4-methoxyphenyl)prop-2-en-1-one; 11632387: (E)-1-[4-[2-Hydroxy-3-(2-methylpropylamino) propoxy]phenyl]-3-(4-methoxyphenyl)prop-2-en-1-one; 11648781: (E)-3-(1,3-Benzodioxol-5-yl)-1-[4-[2-hydroxy-3-(4-phenylpiperazin-1-yl)propoxy]phenyl]prop-2-en-1-one; 11661233: (E)-3-(1,3-Benzodioxol-5-yl)-1-[4-[2-hydroxy-3-(2-methylpropylamino)propoxy]phenyl]prop-2-en-1-one; 11668680: Sulfonamide chalcone, 5; 11675992: (E)-1-[4-[3-(Tert-butylamino)-2-hydroxypropoxy]phenyl]-3-(3,4-dimethoxyphenyl)prop-2-en-1-one; 11689504: (E)-1-[2-[3-(Butylamino)-2-hydroxypropoxy]phenyl]-3-(4-methoxyphenyl)prop-2-en-1-one; 11695370: (E)-3-(3,4-Dimethoxyphenyl)-1-(2,4,6-trihydroxyphenyl)prop-2-en-1-one; 11696007: (5Z)-5-[[4-[(E)-3-(2-Hydroxyphenyl)-3-oxoprop-1-enyl]phenyl]methylidene]-1,3-thiazolidine-2,4-dione; 11702353: (E)-1-(2-Hydroxy-4-methoxy-6-propan-2-yloxyphenyl)-3-phenylprop-2-en-1-one; 11731885: 2',4'-Dimethoxy-4-(benzyloxy)-6'-hydroxychalcone; 11737680: 2'-Hydroxy-6'-(methoxymethoxy)chalcone; 11741514: (E)-3-(1,3-Benzodioxol-5-yl)-1-[4-[3-(tert-butylamino)-2-hydroxypropoxy]phenyl]prop-2-en-1-one; 11743626: (E)-1-[2,6-Dihydroxy-4-[3,4,5-trihydroxy-6-(hydroxymethyl)oxan-2-yl]oxyphenyl]-3-(4-hydroxyphenyl) prop-2-en-1-one; 11753910: (E)-3-[4-[3-(4-Acetyl-3-hydroxy-2-propylphenoxy)propoxy]phenyl]-1-phenylprop-2-en-1-one; 11763111: 2'-Hydroxy-4',6'-di(methoxymethoxy)-beta-[2beta-(4-hydroxyphenyl)-3alpha-(hydroxymethyl)-2,3-dihydro-1,4-benzodioxin-6-yl]acrylophenone; 11763664: 2'-Hydroxy-3,4,4',6'-tetrakis(benzyloxy)chalcone; 11785358: 5-[(1,3-Dioxoisoindol-2-yl)methyl]-2-hydroxy-N-[4-[(E)-3-phenylprop-2-enoyl]phenyl]benzamide; 11799784: (E)-1-[2-Hydroxy-6-[(2S,3R,4S,5S,6R)-3,4,5-trihydroxy-6-(hydroxymethyl)oxan-2-yl]oxyphenyl]-3-(4-phenylmethoxyphenyl)prop-2-en-1-one; 11802372: (E)-3-[3,4-Bis(phenylmethoxy)phenyl]-1-[2-hydroxy-4,6-bis(phenylmethoxy)phenyl](113C)prop-2-en-1-one; 11811212: (E)-1-(2-Hydroxy-4-phenylmethoxyphenyl)-3-[4-(methoxymethoxy)phenyl]prop-2-en-1-one; 11813366: (E)-3-[4-[2,4-Dihydroxy-5-[(E)-3-(4-hydroxyphenyl)prop-2-enoyl]phenoxy]phenyl]-1-(2-hydroxy-4-methoxyphenyl)

prop-2-en-1-one; 11818702: 2-(4-Isopropyl-trans-cinnamoyl)benzoic acid; 11950526: (E)-1-(2-Hydroxy-4,6-dimethoxyphenyl)-3-[3-methoxy-4-(2-phenylethyl)phenyl]prop-2-en-1-one; 11972381: (E)-1-(2,4-Dihydroxy-phenyl)-3-[4-[(2S,3R,4S,5R,6R)-3,4,5-trihydroxy-6-(hydroxymethyl)oxan-2-yl]oxyphenyl]prop-2-en-1-one; 11978693: Sodium;5-azido-2-[(E)-3-(4-hydroxyphenyl)prop-2-enoyl]benzenesulfonate; 11978694: 5-Azido-2-[(E)-3-(4-hydroxyphenyl)prop-2-enoyl]bem-zenesulfonic acid; 12044949: (E)-3-(4-Ethoxyphenyl)-1-(2,4,6-trihydroxyphenyl)prop-2-en-1-one; 12076441: 3,3'-[Oxybisethylenebisoxybis(4,1-phenylene)]bis[1-(4-hydroxyphenyl)-2-propene-1-one]; 12085730: (E)-3-[[3beta-(2,4-Dihydroxybenzoyl)-2,3-dihydro-2alpha-(4-hydroxyphenyl)benzofuran]-5-yl]-1-(2,4-dihydroxyphenyl)-2-propen-1-one; 12147208: (E)-1-(2,4-Dihydroxyphenyl)-3-(3-nitrophenyl)prop-2-en-1-one; 12303942: Coreopsin; 12303943: Butein 4'-beta-D-glucoside; 12314458: 2',6'-Dihydroxy-4-methoxychalcone-4'-O-neohesperid; 12323396: (Z)-4'-Hydroxychalcone; 12468043: (E)-1-[2-Hydroxy-4,6-bis(benzyloxy)phenyl]-3-phenyl-2-propene-1-one; 12561204: Chembl4513419; 12561213: 4-Chloro-N-[4-[(E)-3-(4-hydroxyphenyl)prop-2-enoyl]phenyl]benzenesulfonamide; 12566142: Chembl4514458; 12648130: (E)-1-(2-Hydroxyphenyl)-3-(3-phenylmethoxy-phenyl)prop-2-en-1-one; 12648131: (E)-3-(3-Hydroxyphenyl)-1-(2-methoxyphenyl)prop-2-en-1-one; 12681944: (E)-1-(2-Hydroxyphenyl)-3-(4-methoxy-3-phenylmethoxyphenyl)prop-2-en-1-one; 12762653: (E)-3-(4-Ethoxyphenyl)-1-(2-hydroxyphenyl)prop-2-en-1-one; 12791890: (E)-1-(2-Hydroxy-4-methylphenyl)-3-(4-methoxyphenyl)prop-2-en-1-one; 12818405: (E)-1-[2,4-Dihydroxy-6-[(3R,4S,5S,6R)-3,4,5-trihydroxy-6-(hydroxymethyl)oxan-2-yl]oxyphenyl]-3-(4-hydroxyphenyl)prop-2-en-1-one; 12883590: 2',4',6'-Trihydroxychalcone; 13247578: (E)-1-[2-Hydroxy-4-(3-methylbut-2-enoxy)phenyl]-3-[4-(3-methylbut-2-enoxy)phenyl]prop-2-en-1-one; 13396916: E-3-(4-Benzyloxy)-1-(2.4-bisbenzyloxy-6-hydroxy)phenyl)propenone; 13454255: (e)-3-(4'-Diethylaminophenyl)-1-(2-hydroxy phenyl)prop-2-en-1-one; 13605116: 4-[(E)-3-[2-(Carboxymethoxy)-4-(3-methylbut-2-enoxy)phenyl]-3-oxoprop-1-enyl]benzoic acid; 13605124: 2-[4-[(E)-3-[2-(Carboxymethoxy)-4-(3-methylbut-2-enoxy)phenyl]-3-oxoprop-1-enyl]phenoxy]acetic acid; 13605127: 2-[4-[(E)-3-[2-(Carboxy-methoxy)-4-(3-methylbut-2-enoxy)phenyl]-3-oxoprop-1-enyl]-2-methoxyphenoxy]acetic acid; 13605129: 3-[(E)-3-[2-(Carboxymethoxy)-4-(3-methylbut-2-enoxy)phenyl]-3-oxoprop-1-enyl]benzoic acid; 13605131: 4-[(E)-3-[4-(Carboxymethoxy)-2-prop-2-enoxyphenyl]-3-oxoprop-1-enyl]benzoic acid; 13605133: 4-[(E)-3-[2-(Carboxymethoxy)-4-prop-2-enoxy-phenyl]-3-oxoprop-1-enyl]benzoic acid; 13605135: 3-[(E)-3-[2-(Carboxymethoxy)-4-prop-2-enoxyphenyl]-3-oxoprop-1-enyl]benzoic acid; 13605137: 4-[(E)-3-[2-(Carboxymethoxy)-4-hex-5-enoxyphenyl]-3-oxoprop-1-enyl]benzoic acid; 13605139: 4-[(E)-3-[4-But-3-enoxy-2-(carboxymethoxy)phenyl]-3-oxoprop-1-enyl]benzoic acid; 13643054: (E)-3-(4-Hydroxy-phenyl)-1-(2-hydroxy-6-phenylmethoxyphenyl)prop-2-en-1-one; 13643061: (E)-2',6'-Dihydroxy-beta-(4-methoxyphenyl)acrylophenone; 13797325: 2-Hydroxy-5-[(E)-3-(4-hydroxyphenyl)-3-oxoprop-1-enyl]benzoic acid; 13842401: 4'-Hydroxy-2'-methoxychalcone; 13870531: 4,2'-Dihydroxy-4',6'-dimethoxychalcone 4-glucoside; 13870532: 4,2'-Dihydroxy-3,4',6'-trimethoxychalcone 4-glucoside; 13870533: (E)-1-(2-Hydroxy-4,6-dimethoxyphenyl)-3-[3-methoxy-4-[(2S,3R,4S,5S,6R)-3,4,5-trihydroxy-6-(hydroxymethyl)oxan-2-yl]oxyphenyl]prop-2-en-1-one; 13870534: 4,2'-Dihydroxy-4',6'-dimethoxychalcone 4-apiosyl-(1→2)-glucoside; 13870535: (E)-3-[4-[(2S,3R,4S,5S,6R)-3-[(2S,3R,4R)-3,4-Dihydroxy-4-(hydroxy-methyl)oxolan-2-yl]oxy-4,5-dihydroxy-6-(hydroxymethyl)oxan-2-yl]oxyphenyl]-1-(2-hydroxy-4,6-dimethoxyphenyl)prop-2-en-1-one; 13990811: 2',4',6'-Trihydroxy-4-methoxychalcone; 14034811: 1-(4,6-Dimethoxy-2-hydroxyphenyl)-3-(3-methoxyphenyl)-2-propene-1-one; 14068747: 2'-Hydroxy-4-nitro-4'-methoxychalcone; 14126638: 2-[4-[3-(4-Chlorophenyl)-3-oxo-1-propenyl]phenoxy]-2-methylpropionic acid; 14187588: Isoliquiritoside; 14187589: (E)-1-(2,4-Dihydroxyphenyl)-3-[4-[(2R,3R,4S,5S,6R)-3,4,5-trihydroxy-6-(hydroxymethyl)oxan-2-yl]oxyphenyl]prop-2-en-1-one; 14282455: Licuraside; 14282634: 2',6'-Dihydroxy-4'-prenyloxychalcone; 14327425: (E)-3-(4-Hydroxyphenyl)-1-[2-hydroxy-4-[3,4,5-trihydroxy-6-(hydroxymethyl)oxan-2-yl]oxyphenyl]prop-2-en-1-one; 14368089: 2-[3,5-Dimethoxy-2-[(E)-3-(4-methoxyphenyl)prop-2-enoyl]phenoxy]acetic acid; 14376454: Lophirone E; 14376455: Lophirone D; 14384815: (E)-1-[2-Hydroxy-4-(methoxymethoxy)phenyl]-3-[4-(methoxy-methoxy)phenyl]prop-2-en-1-one; 14452789: (E)-2',6'-Dihydroxy-beta-(3-methoxy-4-methoxyphenyl)acrylophenone; 14452792: 2'-Hydroxy-6'-methoxy-4-chlorochalcone; 14452794: (E)-2',6'-Dihydroxy-beta-(4-chlorophenyl)acrylophenone; 14524443: Neosakuranin; 14524444: 2'-(beta-D-Glucopyranosyloxy)-4,6'-dihydroxy-4'-methoxy-chalcone; 14527029: 2'-Hydroxy-6'-methoxy-4'-prenyloxychalcone; 14605653: 4-[(E)-3-Oxo-3-(4-trimethylgermylphenyl)prop-1-enyl]benzoic acid; 14655809: 4-Methoxy-2'-hydroxy-4',6'-bis(methoxymethoxy)-trans-chalcone; 14804610: (E)-1-(2-Hydroxy-4-methylphenyl)-3-(4-phenylmethoxyphenyl)prop-2-en-1-one; 14804615: 2'-Hydroxy-4-(benzyloxy)-4'-methoxychalcone; 14804627: (E)-3-(4-Chlorophenyl)-1-(2-hydroxy-4-methylphenyl)prop-2-en-1-one; 14804628: (E)-1-(4-Chloro-2-hydroxyphenyl)-3-(4-chlorophenyl)prop-2-en-1-one; 14844610: 2-[4-[(Z)-3-Phenylprop-2-enoyl]phenoxy]acetic acid; 14854161: Chalcononaringenin 2',4'-di-O-beta-D-glucoside; 14929337: (E)-3-(1,3-Benzodioxol-5-yl)-1-[2-hydroxy-4-(3-methylbut-2-enoxy)phenyl]prop-2-en-1-one; 14977358: 3,4-Dihydroxy-4'-methylchalcone; 14977360: 2'-Chloro-3,4-dihydroxychalcone; 14977361: (E)-1-(4-Chlorophenyl)-3-(3,4-dihydroxyphenyl)prop-2-en-1-one; 14977362: 3-(3,4-Dihydroxy-phenyl)-1-(4-nitrophenyl)-propenone; 14977365: 2'-Methoxy-3,4-dihydroxychalcone; 14977368: 4'-(Dimethylamino)-3,4-dihydroxychalcone; 14977369: 4'-(Isopropyl-oxy)-3,4-dihydroxychalcone; 14977372: 2',4'-Dimethyl-3,4-dihydroxychalcone; 14977373: 2',6'-Dimethoxy-3,4-dihydroxychalcone; 14977375: 2',4',6'-Trimethyl-3,4-dihydroxychalcone; 14995014: (E)-1-(4-Hydroxyphenyl)-3-[3-(quinolin-2-ylmethoxy)phenyl]prop-2-en-1-one; 15080375: 3-[4-[(E)-3-(Phenyl)-3-oxo-1-propenyl]phenyl]propenoic acid; 15080376: 3-[4-[(E)-3-(4-Bromophenyl)-3-oxo-1-propenyl]phenyl]propenoic acid; 15080377: 3-[4-[(E)-3-(4-Methoxyphenyl)-3-oxo-1-propenyl]phenyl]propenoic acid; 15176577: 4"-(Benzensulfon-amide)-4-hydroxychalcone; 15186772: (E)-1-(2-Hydroxyphenyl)-3-(3-phenoxyphenyl)prop-2-en-1-one; 15186773: (E)-1-(4-Hydroxyphenyl)-3-(4-phenoxyphenyl)prop-2-en-1-one; 15210545: (E)-1-(4-Ethoxy-2-hydroxyphenyl)-3-(4-methylphenyl)prop-2-en-1-one; 15225562: (E)-1-[2-Hydroxy-4,6-bis(phenylmethoxy)phenyl]-3-[4-(2-methoxyethoxy-methoxy)phenyl]prop-2-en-1-one; 15229408: Chembl4537198; 15261543: (E)-3-(2,3-Dihydro-1,4-benzodioxin-6-yl)-1-[2-hydroxy-4-(methoxymethoxy)phenyl]

prop-2-en-1-one; 15434466: 2'-Hydroxy-4',6'-di(methoxymethoxy)-beta-[2alpha-(4-hydroxyphenyl)-3beta-(hydroxymethyl)-2,3-dihydro-1,4-benzodioxin-6-yl]acrylophenone; 15516845: 1-[2-Hydroxy-4-(methoxymethoxy)phenyl]-3-[3-(3-methyl-2-butenyl)-4-(methoxymethoxy)phenyl]-2-propene-1-one; 15570621: N-3-Hydroxy-4-[(2E)-3-phenylprop-2-enoyl]phenylacetamide; 15570622: N-3-Hydroxy-4-[(2E)-3-(4-methoxyphenyl)prop-2-enoyl]phenylacetamide; 15603272: (Z)-1-(2,4-Dihydroxyphenyl)-3-(3,4-dimethoxyphenyl)prop-2-en-1-one; 15603273: (Z)-1-(2,4-Dihydroxyphenyl)-3-(4-hydroxy-3-methoxyphenyl)prop-2-en-1-one; 15603274: (Z)-1-(2,4-Dihydroxyphenyl)-3-(3-hydroxy-4-methoxyphenyl)prop-2-en-1-one; 15604475: (Z)-1-(2,4-Dihydroxyphenyl)-3-(4-methoxyphenyl)prop-2-en-1-one; 15680252: (e)-1-[2-Hydroxy-4-(tetrahydro-2h-pyran-2-yloxy)phenyl]-3-[4-(tetrahydro-2h-pyran-2-yloxy)phenyl]prop-2-en-1-one; 15680254: 2',3,4'-Trihydroxychalcone; 15871533: 2'-Hydroxy-4,4'-bis(tert-butyldiphenylsiloxy)chalcone; 15871534: 2'-Hydroxy-4'-(tert-butyldi-phenylsiloxy)chalcone; 15871535: 2'-Hydroxy-3-propyl-4,4'-bis(tert-butyldiphenylsiloxy) chalcone; 15871536: 2'-Hydroxy-3-propyl-4-(tert-butyldimethylsiloxy)-4'-(tert-butyldi-phenylsiloxy) chalcone; 15945303: N-[4-[(E)-3-(3-Hydroxy-4-methoxyphenyl)acryloyl]phenyl]-4-methyl-benzenesulfonamide; 15945377: (E)-1-(2-Fluoro-4-methoxyphenyl)-3-(3-hydroxy-4-methoxyphenyl)prop-2-en-1-one; 15945389: (E)-1-(4-Hydroxyphenyl)-3-[4-(4-methoxyphenoxy)-3-nitro-phenyl]prop-2-en-1-one; 15986591: [2-Hydroxy-5-[(E)-3-(2-hydroxy-4-methoxyphenyl)-3-oxoprop-1-enyl]phenyl] (E)-3-phenylprop-2-enoate; 15986593: (E)-3-(3,4-Dimethoxyphenyl)-1-(2-hydroxy-4-phenylmethoxyphenyl)prop-2-en-1-one; 15986681: [3-[(E)-3-(2-Hydroxy-4-methoxyphenyl)-3-oxoprop-1-enyl]phenyl] 3,4,5-trimethoxybenzoate; 16066848: 4-[(E)-3-[2-(Cyclohexylmethoxy)-6-hydroxyphenyl]-3-oxoprop-1-enyl]benzenesulfonamide; 16129398: (E)-3-(3-Bromophenyl)-1-(2-hydroxy-6-methoxyphenyl)prop-2-en-1-one; 16131034: Alatachalcone; 16131338: 2-Propen-1-one, 3-(3-((5-(4-(2,4-dihydroxybenzoyl)tetrahydro-5-(4-hydroxyphenyl)-3-((4-hydroxyphenyl)methyl)-2-furanyl)-2,4-dihydroxyphenyl)(2,4-dihydroxyphenyl)methyl)-2-(4-hydroxyphenyl)-5-benzofuranyl)-1-(2,4-dihydroxyphenyl)-, (2alpha(R*(2R*,3R*,5(E))),3alpha,4beta,5alpha)-(+)-; 16148290: Azobechalcone; 16250637: (E)-3-[3-Ethoxy-4-[(6-nitro-4H-1,3-benzodioxin-8-yl)methoxy]phenyl]-1-(4-hydroxyphenyl)prop-2-en-1-one; 16378137: 4-[(E)-3-(4-Hydroxy-phenyl)prop-2-enoyl]benzonitrile; 16457992: 2-[(2E)-3-(4-Carboxyphenyl)prop-2-enoyl]benzoic acid; 16457993: 2-(2E)-3-[4-(Dimethylamino)phenyl]prop-2-enoylbenzoic acid; 16459286: 2-[(2E)-3-(1,3-Benzodioxol-5-yl)prop-2-enoyl]benzoic acid; 16554296: 2-[4-[(E)-3-(4-Butoxyphenyl)prop-2-enoyl]phenoxy]propanoic acid; 16554299: 2-[4-[(E)-3-(4-Butoxy-3-methoxyphenyl)prop-2-enoyl]phenoxy]propanoic acid; 16554300: 2-[4-[(E)-3-(4-Propoxyphenyl)prop-2-enoyl]phenoxy]propanoic acid; 16554301: 2-[4-[(E)-3-[4-[2-[Di(propan-2-yl)amino]-2-oxoethoxy]-3-ethoxyphenyl]prop-2-enoyl]phenoxy]propanoic acid; 16554302: 2-[4-[(E)-3-(4-Methoxy-3-propoxyphenyl)prop-2-enoyl]phenoxy]propanoic acid; 16554303: 2-[4-[(E)-3-(3-Ethoxy-4-prop-2-ynoxyphenyl)prop-2-enoyl]phenoxy]propanoic acid; 16554305: 2-[4-[(E)-3-(3-Butoxy-4-methoxyphenyl)prop-2-enoyl]phenoxy]propanoic acid; 16554306: 2-[4-[(E)-3-[3-(Difluoromethoxy)-4-methoxyphenyl]prop-2-enoyl]phenoxy]propanoic acid; 16554317: 4-[(E)-3-[4-(Azepan-1-yl)phenyl]-3-oxoprop-1-enyl]benzoic acid; 16555413: 4-[(E)-3-[4-(Cyanomethoxy)phenyl]-3-oxoprop-1-enyl]benzoic acid; 16659196: (E)-3-[3-[3-[Di(propan-2-yl)amino]-2-hydroxypropoxy]phenyl]-1-phenylprop-2-en-1-one; 16727514: 2'-Hydroxy-4-(methylthio)chalcone; 16737077: 1-[2-Hydroxy-4-(methoxy-methoxy)phenyl]-3-[4-methoxy-3-(3-methylbut-2-enyl)phenyl]prop-2-en-1-one; 16737078: 1-(2-Hydroxy-4-methoxyphenyl)-3-[4-(methoxymethoxy)-3-(3-methylbut-2-enyl)phenyl]prop-2-en-1-one; 16737167: 1-(2-Hydroxy-4-methoxyphenyl)-3-[4-(3-methylbut-2-enyloxy)phenyl]prop-2-en-1-one; 16738212: 1-(2,4-Dihydroxyphenyl)-3-[4-methoxy-3-(3-methylbut-2-enyl)-phenyl]prop-2-en-1-one; 16738409: 1-(2-Hydroxy-4-methoxyphenyl)-3-[4-methoxy-3-(3-methylbut-2-enyl)phenyl]prop-2-en-1-one; 16738410: (E)-1-(2-Hydroxyphenyl)-3-[4-methoxy-3-(3-methylbut-2-enyl)phenyl]prop-2-en-1-one; 16738421: 3-[4-Hydroxy-3-(3-methylbut-2-enyl)phenyl]-1-(2-hydroxy-4-methoxyphenyl)prop-2-en-1-one; 16738422: 1-(2-Hydroxy-4-methoxyphenyl)-3-[3-(3-methylbut-2-enyl)-phenyl]prop-2-en-1-one; 16750535: Chembl4463371; 16752180: 4-[(E)-3-[4-(Tert-butylsulfamoyl)phenyl]-3-oxoprop-1-enyl]benzoic acid; 16752407: 4-[(E)-3-[4-[(2-Methylpropan-2-yl)oxycarbonylamino]phenyl]-3-oxoprop-1-enyl]benzoic acid; 16753496: (E)-1-[4-[[2-(2-Chlorophenyl)-5-methyl-4H-pyrazol-3-ylidene]amino]phenyl]-3-(3-hydroxy-4-methoxyphenyl)prop-2-en-1-one; 16756130: (E)-1-[2-Hydroxy-4,6-bis(methoxymethoxy)phenyl]-3-(4-phenylmethoxyphenyl)prop-2-en-1-one; 16757866: (E)-1-[2-Hydroxy-4-[(2R)-3,4,5-trihydroxy-6-(hydroxymethyl) oxan-2-yl]oxyphenyl]-3-phenylprop-2-en-1-one; 16758552: (Z)-3-(1,3-Benzodioxol-5-yl)-1-(2-hydroxy-4,6-dimethoxyphenyl)prop-2-en-1-one; 16758559: (Z)-2'-Hydroxychalcone; 16760867: 2-3-[(1,3-Dioxo-2-4-[(E)-3-oxo-3-phenyl-1-propenyl]phenyl-2,3-dihydro-1H-isoindol-5-yl)oxy]phenyl-1,3-dioxo-5-isoindolinecarboxylic acid; 16957940: (E)-3-(2,3-Dihydro-1,4-benzodioxin-6-yl)-1-(4-dodecoxy-2-hydroxyphenyl)prop-2-en-1-one; 16959622: 2-[4-[(E)-3-(3-Nitro-4-propan-2-ylphenyl)prop-2-enoyl]phenoxy]propanoic acid; 16959624: (E)-1-[4-(Azepan-1-yl)phenyl]-3-(4-hydroxy-3-nitro-phenyl)prop-2-en-1-one; 16959637: (E)-1-(4-Hydroxyphenyl)-3-(3-nitro-4-propan-2-ylphenyl)prop-2-en-1-one; 16959782: 2-[4-[(E)-3-(4-Hydroxy-3-nitro-phenyl)prop-2-enoyl]phenoxy]acetonitrile; 17018581: (2E,2'E)-4,4'-(Benzene-1,4-diylbis[(1 E)-3-oxoprop-1-ene-1,3-diyl]benzene-4,1-diylimino)bis(4-oxobut-2-enoic acid); 17018686: 2,2'-(Benzene-1,4-diylbis[(1E)-3-oxoprop-1-ene-1,3-diyl]benzene-4,1-diylcarbamoyl)bis(4-nitrobenzoic acid); 17112380: (2E)-3-3-[(1,3-Benzothiazol-2-ylsulfanyl)methyl]-4-methoxyphenyl-1-(2-hydroxyphenyl)prop-2-en-1-one; 17123894: (2E)-1-(2-Hydroxyphenyl)-3-4-methoxy-3-[(4-nitro-1H-pyrazol-1-yl)methyl]phenylprop-2-en-1-one; 17370530: (E)-3-[3-(1H-Benzimidazol-2-ylsulfanylmethyl)-4-methoxyphenyl]-1-(2-hydroxyphenyl)prop-2-en-1-one; 17391245: 4-[(E)-3-(3-Hydroxy-4-methoxyphenyl)prop-2-enoyl]benzonitrile; 17391246: (E)-3-(3-Hydroxy-4-methoxyphenyl)-1-(4-hydroxyphenyl)prop-2-en-1-one; 17391323: 4-[(E)-3-(4-Hydroxy-3-methoxyphenyl)prop-2-enoyl]benzonitrile; 17391468: 2-[4-[(E)-3-(3-Bromophenyl)prop-2-enoyl]phenoxy]propanoic acid; 17394399: (E)-1-[4-(Dimethylamino)phenyl]-3-(4-hydroxyphenyl)prop-2-en-1-one; 17397204: (E)-3-(4-Hydroxy-3-methoxyphenyl)-1-(4-morpholin-4-ylsulfonylphenyl)prop-2-en-1-one; 17422392: 2-[4-[(E)-3-(4-Morpholin-4-ylphenyl)prop-2-enoyl]phenoxy]acetic acid; 17444011: 4-[(E)-3-(2-Methoxyphenyl)-3-oxoprop-1-enyl]benzoic acid; 17464098: (E)-1-(4-Hydroxyphenyl)-3-(4-methoxy-3-methylphenyl)prop-2-en-1-one; 17486318:

Chembl4545330; 17516541: 4-[(E)-3-(2-Methoxy-4-methylphenyl)-3-oxoprop-1-enyl]benzoic acid; 17545206: (E)-1-[4-(Benzimidazol-1-yl)phenyl]-3-(3-hydroxyphenyl)prop-2-en-1-one; 17558850: 2-[4-[(E)-3-(4-Hydroxy-3-nitrophenyl)prop-2-enoyl]phenoxy]acetic acid; 17563765: (E)-1-(4-Tert-butylphenyl)-3-(4-hydroxy-3-nitro-phenyl)prop-2-en-1-one; 17772794: 2-[4-[(E)-3-Phenylprop-2-enoyl]phenyl]prop-2-enoic acid; 17826043: 7-[(E)-3-Oxo-3-phenylprop-1-enyl]-10H-phenoxazine-1-carboxylic acid; 17860419: 2-(2,4-Diaminophenyl)-2-[4-[(E)-3-(4-fluorophenyl)-3-oxoprop-1-enyl]phenyl]decanedioic acid; 17860436: 5-[4-[4-[(E)-3-Oxo-3-phenylprop-1-enyl]phenoxy]carbonylphenoxy]benzene-1,3-dicarboxylic acid; 17860438: 5-[4-[4-[(E)-3-Oxo-3-phenylprop-1-enyl]phenyl]phenoxy]benzene-1,3-dicarboxylic acid; 17860460: 5-[2-[4-[4-[(E)-3-Oxo-3-phenylprop-1-enyl]phenyl]phenoxy]ethoxy]benzene-1,3-dicarboxylic acid; 17860465: 2-(2,4-Diaminophenyl)-2-[4-[(E)-3-(4-fluorophenyl)-3-oxoprop-1-enyl]phenyl]hexanedioic acid; 17860467: (E)-3-[4-[4-(3,5-Dihydroxyphenoxy)phenyl]phenyl]-1-phenylprop-2-en-1-one; 17860470: 5-[2-[4-[4-[(E)-3-Oxo-3-phenylprop-1-enyl]phenoxy]carbonylphenoxy]ethoxy]benzene-1,3-dicarboxylic acid; 17860498: [4-[(E)-3-Oxo-3-phenylprop-1-enyl]phenyl] 4-(3,5-dihydroxyphenoxy)benzoate; 17860572: (2,4-Diaminophenyl)-2-[4-[(E)-3-(4-fluorophenyl)-3-oxoprop-1-enyl]phenyl]octanedioic acid; 17860608: [4-[(E)-3-Oxo-3-phenylprop-1-enyl]phenyl] 4-[2-(3,5-dihydroxyphenoxy)ethoxy]benzoate; 17860611: (E)-3-[4-[4-[2-(3,5-Dihydroxyphenoxy)ethoxy]phenyl]phenyl]-1-phenylprop-2-en-1-one; 17860631: (E)-3-[4-[6-(3,5-Dihydroxyphenoxy)hexyl]phenyl]-1-phenylprop-2-en-1-one; 17860632: (E)-3-[4-[2-(3,5-Dihydroxyphenoxy)ethyl]phenyl]-1-phenylprop-2-en-1-one; 17860641: 5-[6-[4-[(E)-3-Oxo-3-phenylprop-1-enyl]phenyl]hexoxy]benzene-1,3-dicarboxylic acid; 17860642: 5-[2-[4-[(E)-3-Oxo-3-phenylprop-1-enyl]phenyl]ethoxy]benzene-1,3-dicarboxylic acid; 17939918: 1-[2-Hydroxy-4-(3-methyl-2-butenyloxy) phenyl]-3-[4-(acetylamino)phenyl]-2-propene-1-one; 17939922: 1-[2-Hydroxy-4-(2-methyl-2-propenyloxy)phenyl]-3-[4-(dimethylamino)phenyl]-2-propene-1-one; 18074491: 4-[(E)-3-(3-Hydroxyphenyl)prop-2-enoyl]benzonitrile; 18074503: (E)-3-(3-Hydroxyphenyl)-1-(4-morpholin-4-ylsulfonylphenyl)prop-2-en-1-one; 18076912: (E)-3-(3-Hydroxy-4-methoxyphenyl)-1-(2-methylphenyl)prop-2-en-1-one; 18079609: (E)-1-(2,4-Difluorophenyl)-3-(3-hydroxyphenyl)prop-2-en-1-one; 18079625: (E)-3-(3-Hydroxyphenyl)-1-(4-propan-2-ylphenyl)prop-2-en-1-one; 18083429: 2-[4-[(E)-3-Phenylprop-2-enoyl]phenoxy]propanoic acid; 18083430: 2-[4-[(E)-3-(3-Chlorophenyl)prop-2-enoyl]phenoxy]propanoic acid; 18083431: 2-[4-[(E)-3-(3-Methoxyphenyl)prop-2-enoyl]phenoxy]propanoic acid; 18276714: (E)-1-(4-Cyclohexylphenyl)-3-(3-hydroxyphenyl)prop-2-en-1-one; 18287480: 4-[(E)-3-Oxo-3-(4-propan-2-ylphenyl)prop-1-enyl]benzoic acid; 18288792: (E)-3-(3-Hydroxyphenyl)-1-[4-(3-methylbutoxy)phenyl]prop-2-en-1-one; 18339309: (E)-1-[4-(Hydroxymethoxy)phenyl]-3-phenylprop-2-en-1-one; 18372882: (E)-3-(1,3-Benzodioxol-5-yl)-1-(2-hydroxy-6-methoxy-phenyl)prop-2-en-1-one; 18377985: (E)-1-[4-(6-Hydroxyhexoxy)phenyl]-3-(4-methoxy-phenyl)prop-2-en-1-one; 18377986: (E)-1-[4-(12-Hydroxydodecoxy)phenyl]-3-phenylprop-2-en-1-one; 18377988: (E)-1-[4-(14-Hydroxytetradecoxy)phenyl]-3-phenylprop-2-en-1-one; 18424836: (E)-3-[4-(6-Hydroxyhexyl)phenyl]-1-phenylprop-2-en-1-one; 18628379: (E)-1-(4-Hydroxyphenyl)-3-[4-(2,2,3,3,3-pentafluoropropoxy)phenyl]prop-2-en-1-one; 18679595: (2E)-3-(3,4-Difluorophenyl)-1-(2-hydroxyphenyl)prop-2-en-1-one; 18716581: 1-O-(2-Hydroxyethyl) 5-O-[4-[(E)-3-phenyl-prop-2-enoyl]phenyl] 2,2,4-trimethylpentanedioate; 18888035: N-[8-Hydroxy-2,2-dimethyl-6-[4-[(E)-3-phenylprop-2-enoyl]phenoxy]-4,4a,6,7,8, 8a-hexahydropyrano[3,2-d][1,3]dioxin-7-yl]acetamide; 18888036: N-[8-Hydroxy-2,2-dimethyl-6-[2-[(E)-3-phenylprop-2-enoyl]phenoxy]-4,4a,6,7,8,8a-hexahydropyrano[3,2-d][1,3]dioxin-7-yl]acetamide; 18888037: N-[8-Hydroxy-2,2-dimethyl-6-[4-[(E)-3-oxo-3-phenylprop-1-enyl]phenoxy]-4,4a,6,7,8,8a-hexahydropyrano[3,2-d][1,3]dioxin-7-yl]acetamide; 18888039: N-[6-[4-[(E)-3-(4-Chlorophenyl)-3-oxoprop-1-enyl]phenoxy]-8-hydroxy-2,2-dimethyl-4,4a,6,7,8,8a-hexahydropyrano[3,2-d][1,3]dioxin-7-yl]acetamide; 18888051: 4-[(2E)-3-Phenylprop-2-enoyl]phenyl 2-(acetylamino)-4,6-O-benzylidene-2-deoxyhexopyranoside; 18888052: N-[8-Hydroxy-2-phenyl-6-[2-[(E)-3-phenylprop-2-enoyl]phenoxy]-4,4a,6,7,8, 8a-hexahydropyrano[3,2-d][1,3]dioxin-7-yl]acetamide; 18888053: 4-[(1 E)-3-Oxo-3-phenyl-prop-1-en-1-yl]phenyl 2-(acetylamino)-4,6-O-benzylidene-2-deoxyhexopyranoside; 18888055: N-[6-[4-[(E)-3-(4-Chlorophenyl)-3-oxoprop-1-enyl]phenoxy]-8-hydroxy-2-phenyl-4,4a,6,7,8,8a-hexahydropyrano[3,2-d][1,3]dioxin-7-yl]acetamide; 18888066: N-[2-(Furan-2-yl)-8-hydroxy-6-[2-[(E)-3-phenylprop-2-enoyl]phenoxy]-4,4a,6,7,8,8a-hexahydropyrano[3,2-d][1,3]dioxin-7-yl]acetamide; 18888067: N-[2-(Furan-2-yl)-8-hydroxy-6-[4-[(E)-3-oxo-3-phenylprop-1-enyl]phenoxy]-4,4a,6,7,8,8a-hexahydropyrano[3,2-d][1,3]dioxin-7-yl]acetamide; 18888069: N-[6-[4-[(E)-3-(4-Chlorophenyl)-3-oxoprop-1-enyl]phenoxy]-2-(furan-2-yl)-8-hydroxy-4,4a,6,7,8,8a-hexahydropyrano[3,2-d][1,3]dioxin-7-yl]acetamide; 18888092: 2-[[7-Acetamido-2,2-dimethyl-6-[4-[(E)-3-phenylprop-2-enoyl]phenoxy]-4,4a,6,7,8,8a-hexahydropyrano[3,2-d][1,3]dioxin-8-yl]oxy]propanoic acid; 18888093: 2-[[7-Acetamido-2,2-dimethyl-6-[2-[(E)-3-phenylprop-2-enoyl]phenoxy]-4,4a,6,7,8,8a-hexahydropyrano[3,2-d][1,3]dioxin-8-yl]oxy]propanoic acid; 18888094: 2-[[7-Acetamido-2,2-dimethyl-6-[4-[(E)-3-oxo-3-phenylprop-1-enyl]phenoxy]-4,4a,6,7,8,8a-hexahydropyrano[3,2-d][1,3]dioxin-8-yl]oxy]propanoic acid; 18888096: 2-[[7-Acetamido-6-[4-[(E)-3-(4-chlorophenyl)-3-oxoprop-1-enyl]phenoxy]-2,2-dimethyl-4,4a,6,7,8,8a-hexahydropyrano[3,2-d][1,3]dioxin-8-yl]oxy]propanoic acid; 18888119: 2-[[7-Acetamido-2-phenyl-6-[4-[(E)-3-phenylprop-2-enoyl]phenoxy]-4,4a,6,7,8,8a-hexahydropyrano[3,2-d][1,3]dioxin-8-yl]oxy]propanoic acid; 18888120: 2-[[7-Acetamido-2-phenyl-6-[2-[(E)-3-phenylprop-2-enoyl]phenoxy]-4,4a,6,7,8, 8a-hexahydropyrano[3,2-d][1,3]dioxin-8-yl]oxy]propanoic acid; 18888121: 2-[[7-Acetamido-6-[4-[(E)-3-oxo-3-phenylprop-1-enyl]phenoxy]-2-phenyl-4,4a,6,7,8,8a-hexahydropyrano[3,2-d][1,3]dioxin-8-yl]oxy]propanoic acid; 18888123: 2-[[7-Acetamido-6-[4-[(E)-3-(4-chloro-phenyl)-3-oxoprop-1-enyl]phenoxy]-2-phenyl-4,4a,6,7,8,8a-hexahydropyrano[3,2-d][1,3]dioxin-8-yl]oxy]propanoic acid; 18888146: 2-[[7-Acetamido-2-(furan-2-yl)-6-[4-[(E)-3-phenyl-prop-2-enoyl]phenoxy]-4,4a,6,7,8,8a-hexahydropyrano[3,2-d][1,3]dioxin-8-yl]oxy]propanoic acid; 18888147: 2-[[7-Acetamido-2-(furan-2-yl)-6-[2-[(E)-3-phenylprop-2-enoyl]phenoxy]-4,4a,6,7,8,8a-hexahydropyrano[3,2-d][1,3]dioxin-8-yl]oxy]propanoic acid; 18888148: 2-[[7-Acetamido-2-(furan-2-yl)-6-[4-[(E)-3-oxo-3-phenylprop-1-enyl]phenoxy]-4,4a,6,7,8,8a-hexahydropyrano[3,2-d][1,3]dioxin-8-yl]oxy]propanoic acid; 18888150: 2-[[7-Acetamido-6-[4-[(E)-3-(4-chlorophenyl)-3-oxoprop-1-enyl]phenoxy]-2-(furan-2-yl)-4,4a,6,7,8,8a-hexahydropyrano[3,2-d][1,3]dioxin-8-yl]oxy]propanoic acid; 18888173: 2-[[7-Acetamido-2,2-dimethyl-6-[4-[(E)-3- phenylprop-2-enoyl]phenoxy]-4,4a,6,7,8,8a-hexahydropyrano[3,2-d][1,3]dioxin-8-yl]oxy]acetic acid; 18888174: 2-[[7-Acetamido-2,2-dimethyl-6-[2-[(E)-3-phenylprop-2-enoyl]phenoxy]-4,4a,6,7,8,8a-hexahydropyrano[3,2-d][1,3]dioxin-8-yl]oxy]acetic acid; 18888175: 2-[[7-Acetamido-2,2-dimethyl-6-[4-[(E)-3-oxo-3-phenylprop-1-enyl]phenoxy]-4,4a,6,7,8,8a-hexahydropyrano[3,2-d][1,3]dioxin-8-yl]oxy]acetic acid; 18888177: 2-[[7-Acetamido-6-[4-[(E)-3-(4-chlorophenyl)-3-oxoprop-1-enyl]phenoxy]-2,2-dimethyl-4,4a,6,7,8,8a-hexahydropyrano[3,2-d][1,3]dioxin-8-yl]oxy]acetic acid; 18888200: 2-[[7-Acetamido-2-phenyl-6-[4-[(E)-3-phenylprop-2-enoyl]phenoxy]-4,4a,6,7,8,8a-hexahydropyrano[3,2-d][1,3]dioxin-8-yl]oxy]acetic acid; 18888201: 2-[[7-Acetamido-2-phenyl-6-[2-[(E)-3-phenylprop-2-enoyl]phenoxy]-4,4a,6,7,8,8a-hexahydropyrano[3,2-d][1,3]dioxin-8-yl]oxy]acetic acid; 18888202: 2-[[7-Acetamido-6-[4-[(E)-3-oxo-3-phenylprop-1-enyl]phenoxy]-2-phenyl-4,4a,6,7,8,8a-hexahydropyrano[3,2-d][1,3]dioxin-8-yl]oxy]acetic acid; 18888204: 2-[[7-Acetamido-6-[4-[(E)-3-(4-chlorophenyl)-3-oxoprop-1-enyl]phenoxy]-2-phenyl-4,4a,6,7,8, 8a-hexahydropyrano[3,2-d][1,3]dioxin-8-yl]oxy]acetic acid; 18888227: 2-[[7-Acetamido-2-(furan-2-yl)-6-[4-[(E)-3-phenylprop-2-enoyl]phenoxy]-4,4a,6,7,8,8a-hexahydropyrano[3,2-d][1,3]dioxin-8-yl]oxy]acetic acid; 18888228: 2-[[7-Acetamido-2-(furan-2-yl)-6-[2-[(E)-3-phenylprop-2-enoyl]phenoxy]-4,4a,6,7,8,8a-hexahydropyrano[3,2-d][1,3]dioxin-8-yl]oxy]acetic acid; 18888229: 2-[[7-Acetamido-2-(furan-2-yl)-6-[4-[(E)-3-oxo-3-phenylprop-1-enyl]phenoxy]-4,4a,6,7,8,8a-hexahydropyrano[3,2-d][1,3]dioxin-8-yl]oxy]acetic acid; 18888231: 2-[[7-Acetamido-6-[4-[(E)-3-(4-chlorophenyl)-3-oxoprop-1-enyl]phenoxy]-2-(furan-2-yl)-4,4a,6,7,8,8a-hexahydropyrano[3,2-d][1,3]dioxin-8-yl]oxy]acetic acid; 18989359: (E)-1-(4-Ethoxy-2-hydroxy-6-methylphenyl)-3-(4-methylphenyl)prop-2-en-1-one; 19012005: 1,3-Dimethyl-6-[4-[3-[2-[(E)-3-(4-methylsulfanylphenyl)prop-2-enoyl]phenoxy]propyl]piperazin-1-yl]pyrimidine-2,4-dione;oxalic acid; 19012025: 6-[4-[3-[2-[(E)-3-[4-(Dimethyl-amino)phenyl]prop-2-enoyl]phenoxy]propyl]piperazin-1-yl]-1,3-dimethylpyrimidine-2,4-dione;oxalic acid; 19360851: 3-Amino-2-[(E)-3-(3,4-dimethoxyphenyl)prop-2-enoyl]benzoic acid; 19375128: 2-Hydroxy-3-[4-[(E)-3-naphthalen-2-ylprop-2-enoyl]phenyl]-2H-furan-5-one; 19540603: (E)-3-[3-[(2,4-Difluorophenoxy)methyl]-4-methoxyphenyl]-1-(2,4-dihydroxy-phenyl)prop-2-en-1-one; 19540604: (E)-1-(2,4-Dihydroxyphenyl)-3-[4-methoxy-3-[(4-nitropyrazol-1-yl)methyl]phenyl]prop-2-en-1-one; 19540605: (E)-1-(2,4-Dihydroxyphenyl)-3-(3-methoxy-4-phenylmethoxyphenyl)prop-2-en-1-one; 19540610: 4-[[5-[(E)-3-(2,4-Dihydroxyphenyl)-3-oxoprop-1-enyl]-2-methoxyphenyl]methoxy]benzonitrile; 19540611: (E)-1-(2,4-Dihydroxyphenyl)-3-[4-methoxy-3-[(2,3,4,5,6-pentachlorophenoxy)methyl]phenyl]prop-2-en-1-one; 19540612: (E)-1-(2,4-Dihydroxyphenyl)-3-[4-methoxy-3-[(2-methyl-phenoxy)methyl]phenyl]prop-2-en-1-one; 19540613: (E)-3-[3-[(3-Chlorophenoxy)methyl]-4-methoxyphenyl]-1-(2,4-dihydroxyphenyl)prop-2-en-1-one; 19540614: (E)-3-[3-[(4-Tert-butylphenoxy)methyl]-4-methoxyphenyl]-1-(2,4-dihydroxyphenyl)prop-2-en-1-one; 19540615: (E)-1-(2,4-Dihydroxyphenyl)-3-[3-[(2,6-dimethylphenoxy)methyl]-4-methoxyphenyl]prop-2-en-1-one; 19540616: (E)-1-(2,4-Dihydroxyphenyl)-3-[3-[(4-fluorophenoxy)methyl]-4-methoxyphenyl]prop-2-en-1-one; 19540617: (E)-1-(2,4-Dihydroxyphenyl)-3-[4-methoxy-3-[(4-methoxyphenoxy)methyl]phenyl]prop-2-en-1-one; 19540618: (E)-1-(2,4-Dihydroxyphenyl)-3-[4-methoxy-3-(naphthalen-2-yloxymethyl)phenyl]prop-2-en-1-one; 19540619: (E)-1-(2,4-Dihydroxyphenyl)-3-[3-[(2,3-dimethyl-phenoxy)methyl]-4-methoxyphenyl]prop-2-en-1-one; 19540621: (E)-1-(2,4-Dihydroxy-phenyl)-3-[4-methoxy-3-(quinolin-8-yloxymethyl)phenyl]prop-2-en-1-one; 19540622: (E)-1-(2,4-Dihydroxyphenyl)-3-[3-methoxy-4-(phenylsulfanylmethyl)phenyl]prop-2-en-1-one; 19540623: (E)-1-(2,4-Dihydroxyphenyl)-3-[4-methoxy-3-[(4-methyl-2-nitrophenoxy)methyl]phenyl]prop-2-en-1-one; 19540624: (E)-1-(2,4-Dihydroxyphenyl)-3-[4-methoxy-3-[(2-nitrophenoxy)methyl]phenyl]prop-2-en-1-one; 19540625: (E)-1-(2,4-Dihydroxyphenyl)-3-[4-methoxy-3-[(2,3,4,5,6-pentafluorophenoxy)methyl]phenyl]prop-2-en-1-one; 19540627: 1-(2,4-Dihydroxyphenyl)-3-(4-benzyloxyphenyl)-2-propene-1-one; 19540628: (E)-1-(2,4-Dihydroxyphenyl)-3-(4-pentoxyphenyl)prop-2-en-1-one; 19540631: (E)-1-(2,4-Dihydroxy-phenyl)-3-(4-ethoxyphenyl)prop-2-en-1-one; 19540636: (E)-1-(2,4-Dihydroxyphenyl)-3-[4-(trifluoromethyl)phenyl]prop-2-en-1-one; 19540637: (E)-1-(2,4-Dihydroxyphenyl)-3-[3-[(4-ethylphenoxy)methyl]-4-methoxyphenyl]prop-2-en-1-one; 19540638: (E)-3-[3-[(4-Chloro-3,5-dimethylphenoxy)methyl]-4-methoxyphenyl]-1-(2,4-dihydroxyphenyl)prop-2-en-1-one; 19540639: (E)-3-[3-(Chloromethyl)-4-methoxyphenyl]-1-(2,4-dihydroxyphenyl)prop-2-en-1-one; 19540641: 2',4'-Dihydroxy-4-nitrochalcone; 19540645: (E)-1-(2,4-Dihydroxyphenyl)-3-[4-methoxy-3-(phenoxymethyl)phenyl]prop-2-en-1-one; 19540647: (E)-1-(2,4-Dihydroxyphenyl)-3-[4-methoxy-3-(morpholin-4-ylmethyl)phenyl]prop-2-en-1-one; 19540649: (E)-3-[4-(Diethylamino)phenyl]-1-(2,4-dihydroxyphenyl)prop-2-en-1-one; 19540650: (E)-1-(2,4-Dihydroxyphenyl)-3-[4-methoxy-3-[(4-nitrophenoxy)methyl]phenyl]prop-2-en-1-one; 19540651: (E)-3-[3-[(4-Bromo-3,5-dimethylpyrazol-1-yl)methyl]-4-methoxyphenyl]-1-(2,4-dihydroxyphenyl)prop-2-en-1-one; 19540652: (E)-1-(2,4-Dihydroxyphenyl)-3-(3-fluoro-phenyl)prop-2-en-1-one; 19540655: 4-Fluoro-2',4'-dihydroxychalcone; 19540656: (E)-1-(2,4-Dihydroxyphenyl)-3-[3-[(3,5-dimethylpyrazol-1-yl)methyl]-4-methoxyphenyl]prop-2-en-1-one; 19540658: (E)-1-(2,4-Dihydroxyphenyl)-3-[4-methoxy-3-(thiomorpholin-4-ylmethyl)phenyl]prop-2-en-1-one; 19540664: (E)-3-[3-[(2-Bromo-4-chlorophenoxy)methyl]-4-methoxyphenyl]-1-(2,4-dihydroxyphenyl)prop-2-en-1-one; 19540665: (E)-3-[3-[(4-Bromo-2-chlorophenoxy)methyl]-4-methoxyphenyl]-1-(2,4-dihydroxyphenyl)prop-2-en-1-one; 19540666: (E)-3-[3-[(2,3-Dichlorophenoxy)methyl]-4-methoxyphenyl]-1-(2,4-dihydroxy-phenyl)prop-2-en-1-one; 19540667: (E)-1-(2,4-Dihydroxyphenyl)-3-[4-methoxy-3-[(4-propan-2-ylphenoxy)methyl]phenyl]prop-2-en-1-one; 19540668: (E)-1-(2,4-Dihydroxy-phenyl)-3-[4-methoxy-3-[(2,3,5,6-tetrafluorophenoxy)methyl]phenyl]prop-2-en-1-one; 19540669: (E)-3-[3-[(2-Chloro-4-fluorophenoxy)methyl]-4-methoxyphenyl]-1-(2,4-dihydroxy-phenyl)prop-2-en-1-one; 19540671: 2-[[5-[(E)-3-(2,4-Dihydroxyphenyl)-3-oxoprop-1-enyl]-2-methoxyphenyl]methylsulfanyl]-4-phenyl-6-(trifluoromethyl)pyridine-3-carbonitrile; 19540672: (E)-1-(2,4-Dihydroxyphenyl)-3-[3-[(4-iodophenoxy)methyl]-4-methoxyphenyl]prop-2-en-1-one; 19540673: (E)-1-(2,4-Dihydroxyphenyl)-3-[4-methoxy-3-[[3-(trifluoro-methyl)phenoxy]methyl]phenyl]prop-2-en-1-one; 19540674: (E)-1-(2,4-Dihydroxyphenyl)-3-[3-[(5-fluoro-2-nitrophenoxy)methyl]-4-methoxyphenyl]prop-2-en-1-one; 19540676: (E)-1-(2,4-Dihydroxyphenyl)-3-[4-methoxy-3-(methoxymethyl)phenyl]prop-2-en-1-one; 19540677: 6-(Difluoromethyl)-2-[[5-[(E)-3-(2,4-dihydroxyphenyl)-3-oxoprop-1-enyl]-2-methoxyphenyl]methylsulfanyl]-4-methylpyridine-3-carbonitrile; 19540678: 2-[[5-[(E)-

3-(2,4-Dihydroxy-phenyl)-3-oxoprop-1-enyl]-2-methoxyphenyl]methylsulfanyl]-4-methyl-6-(trifluoromethyl)pyridine-3-carbonitrile; 19540679: 6-(Difluoromethyl)-2-[[5-[(E)-3-(2,4-dihydroxyphenyl)-3-oxoprop-1-enyl]-2-methoxyphenyl]methylsulfanyl]-4-phenylpyridine-3-carbonitrile; 19540681: (E)-3-[3-[(3-Chloro-4-fluorophenoxy)methyl]-4-methoxyphenyl]-1-(2,4-dihydroxyphenyl)prop-2-en-1-one; 19540682: (E)-3-[3-[[4-(Difluoromethyl)-6-methyl-pyrimidin-2-yl]sulfanylmethyl]-4-methoxyphenyl]-1-(2,4-dihydroxyphenyl)prop-2-en-1-one; 19540684: (E)-3-[3-(2,3-Dihydro-1H-inden-5-yloxymethyl)-4-methoxyphenyl]-1-(2,4-dihydroxyphenyl)prop-2-en-1-one; 19540685: (E)-3-[3-[(2-Chlorophenoxy)methyl]-4-methoxyphenyl]-1-(2,4-dihydroxyphenyl)prop-2-en-1-one; 19540686: (E)-1-(2,4-Dihydroxy-phenyl)-3-[4-methoxy-3-[(4-methylphenoxy)methyl]phenyl]prop-2-en-1-one; 19540688: (E)-3-[3-[(4-Bromopyrazol-1-yl)methyl]-4-methoxyphenyl]-1-(2,4-dihydroxyphenyl)prop-2-en-1-one; 19540689: (E)-1-(2,4-Dihydroxyphenyl)-3-[4-methoxy-3-(pyridin-2-ylsulfanylmethyl)phenyl]prop-2-en-1-one; 19540702: (E)-1-(2,4-Dihydroxyphenyl)-3-[3-methoxy-4-[(4-nitro-phenyl)methoxy]phenyl]prop-2-en-1-one; 19540703: (E)-1-(2,4-Dihydroxyphenyl)-3-[4-methoxy-3-(pyrrolidin-1-ylmethyl)phenyl]prop-2-en-1-one; 19540704: (E)-3-[3-[(3-Bromo-phenoxy)methyl]-4-methoxyphenyl]-1-(2,4-dihydroxyphenyl)prop-2-en-1-one; 19540711: (E)-1-(2,4-Dihydroxyphenyl)-3-[3-[(2,5-dimethylphenoxy)methyl]-4-methoxyphenyl]prop-2-en-1-one; 19540712: (E)-1-(2,4-Dihydroxyphenyl)-3-[3-(ethoxymethyl)-4-methoxyphenyl]prop-2-en-1-one; 19540717: (E)-1-(2,4-Dihydroxyphenyl)-3-[3-(2-methylpropoxy)phenyl]prop-2-en-1-one; 19540722: (E)-1-(2,4-Dihydroxyphenyl)-3-[4-methoxy-3-(pyrazol-1-ylmethyl)phenyl]prop-2-en-1-one; 19540727: (E)-3-[4-(Difluoromethoxy)phenyl]-1-(2,4-dihydroxyphenyl)prop-2-en-1-one; 19540729: (E)-1-(2,4-Dihydroxyphenyl)-3-[4-methoxy-3-(2,2,2-trifluoroethoxymethyl)phenyl]prop-2-en-1-one; 19540730: (E)-1-(2,4-Dihydroxy-phenyl)-3-[4-methoxy-3-(2,2,3,3-tetrafluoropropoxymethyl)phenyl]prop-2-en-1-one; 19540734: (E)-3-[4-(Difluoromethoxy)-3-methoxyphenyl]-1-(2,4-dihydroxyphenyl)prop-2-en-1-one; 19540740: (E)-3-[3-[(4-Chloro-2-methylphenoxy)methyl]-4-methoxyphenyl]-1-(2,4-dihydroxyphenyl)prop-2-en-1-one; 19540741: (E)-3-[3-[(4-Chloro-3-methylphenoxy)methyl]-4-methoxyphenyl]-1-(2,4-dihydroxyphenyl)prop-2-en-1-one; 19540743: (E)-3-[3-[(2-Tert-butyl-5-methylphenoxy)methyl]-4-methoxyphenyl]-1-(2,4-dihydroxyphenyl)prop-2-en-1-one; 19540746: (E)-3-[3-[[3,5-Bis(difluoromethyl)pyrazol-1-yl]methyl]-4-methoxyphenyl]-1-(2,4-dihydroxyphenyl)prop-2-en-1-one; 19540747: (E)-1-(2,4-Dihydroxyphenyl)-3-[3-(1,1,2,2-tetrafluoroethoxy)phenyl]prop-2-en-1-one; 19540749: (E)-1-(2,4-Dihydroxyphenyl)-3-[4-methoxy-3-[(3-nitrophenoxy)methyl]phenyl]prop-2-en-1-one; 19540753: (E)-3-[3-[(2-Chloro-4-methylphenoxy)methyl]-4-methoxyphenyl]-1-(2,4-dihydroxyphenyl)prop-2-en-1-one; 19540754: (E)-3-[3-[(2-Chloro-4-nitrophenoxy)methyl]-4-methoxyphenyl]-1-(2,4-dihydroxyphenyl)prop-2-en-1-one; 19540755: (E)-3-[4-[(3,4-Diethoxyphenyl)methoxy]phenyl]-1-(2,4-dihydroxyphenyl)prop-2-en-1-one; 19540756: (E)-3-[3-[(3,4-Diethoxyphenyl)methoxy]phenyl]-1-(2,4-dihydroxyphenyl)prop-2-en-1-one; 19540757: (E)-3-[4-(Difluoro-methoxy)-3-ethoxyphenyl]-1-(2,4-dihydroxyphenyl)prop-2-en-1-one; 19540761: (E)-1-(2,4-Dihydroxyphenyl)-3-[3-[(3,5-dimethyl-4-nitropyrazol-1-yl)methyl]-4-methoxyphenyl]prop-2-en-1-one; 19540768: (E)-3-[3-[(4-Chloro-3,5-dimethylpyrazol-1-yl)methyl]-4-methoxy-phenyl]-1-(2,4-dihydroxyphenyl)prop-2-en-1-one; 19540769: (E)-3-[3-[(2,6-Dichlorophenoxy)methyl]-4-methoxyphenyl]-1-(2,4-dihydroxyphenyl)prop-2-en-1-one; 19540770: (E)-1-(2,4-Dihydroxyphenyl)-3-[4-methoxy-3-[(2,4,5-trichlorophenoxy)methyl]phenyl]prop-2-en-1-one; 19540772: (E)-1-(2,4-Dihydroxyphenyl)-3-[4-methoxy-3-[(3-nitropyrazol-1-yl)methyl]phenyl]prop-2-en-1-one; 19540773: (E)-3-[3-[(4-Chloropyrazol-1-yl)methyl]-4-methoxyphenyl]-1-(2,4-dihydroxyphenyl)prop-2-en-1-one; 19540774: (E)-1-(2,4-Dihydroxyphenyl)-3-[3-[(2-ethoxyphenoxy)methyl]-4-methoxyphenyl]prop-2-en-1-one; 19540775: (E)-1-(2,4-Dihydroxyphenyl)-3-[4-methoxy-3-[(2-prop-2-enylphenoxy)methyl]phenyl]prop-2-en-1-one; 19540776: (E)-1-(2,4-Dihydroxyphenyl)-3-[4-methoxy-3-[(4-phenylphenoxy)methyl]phenyl]prop-2-en-1-one; 19540777: (E)-3-[3-[(2-Benzylphenoxy)methyl]-4-methoxyphenyl]-1-(2,4-dihydroxyphenyl)prop-2-en-1-one; 19540778: (E)-1-(2,4-Dihydroxyphenyl)-3-[4-methoxy-3-[(5-methyl-2-nitrophenoxy)methyl]phenyl]prop-2-en-1-one; 19540780: (e)-3-(4-t-Butylphenyl)-1-(2,4-dihydroxy-phenyl)prop-2-en-1-one; 19540783: (E)-1-(2,4-Dihydroxyphenyl)-3-(4-ethylphenyl)prop-2-en-1-one; 19540784: (E)-3-(3-Chlorophenyl)-1-(2,4-dihydroxyphenyl)prop-2-en-1-one; 19540788: (E)-1-(2,4-Dihydroxy-phenyl)-3-(4-propan-2-yloxyphenyl)prop-2-en-1-one; 19540791: (E)-3-(4-Cyclopentyloxy-3-ethoxyphenyl)-1-(2,4-dihydroxyphenyl)prop-2-en-1-one; 19540793: (E)-1-(2,4-Dihydroxy-phenyl)-3-[4-(2-morpholin-4-ylethoxy)phenyl]prop-2-en-1-one; 19540794: (E)-3-[3-(1,3-Benzodioxol-5-yloxymethyl)-4-methoxyphenyl]-1-(2,4-dihydroxyphenyl)prop-2-en-1-one; 19540798: (E)-3-[3-[[4-Chloro-3,5-bis(difluoromethyl)pyrazol-1-yl]methyl]-4-methoxyphenyl]-1-(2,4-dihydroxyphenyl)prop-2-en-1-one; 19540800: 2-[4-[(E)-3-(2,4-Dihydroxyphenyl)-3-oxoprop-1-enyl]-2-methoxyphenoxy]-N-phenylacetamide; 19540801: 2-[4-[(E)-3-(2,4-Dihydroxyphenyl)-3-oxoprop-1-enyl]-2-ethoxyphenoxy]-N-phenylacetamide; 19540802: (E)-1-(2,4-Dihydroxyphenyl)-3-[3-[(2-fluorophenoxy)methyl]-4-methoxyphenyl]prop-2-en-1-one; 19540804: 2-[4-[(E)-3-(2,4-Dihydroxyphenyl)-3-oxoprop-1-enyl]-2-methoxyphenoxy]-N-(2-methylphenyl)acetamide; 19540805: 2-[4-[(E)-3-(2,4-Dihydroxyphenyl)-3-oxoprop-1-enyl]-2-methoxyphenoxy]-N-(2-methoxyphenyl)acetamide; 19540806: 2-[4-[(E)-3-(2,4-Dihydroxy-phenyl)-3-oxoprop-1-enyl]-2-methoxyphenoxy]-N-(4-methylphenyl)acetamide; 19540807: 2-[4-[(E)-3-(2,4-Dihydroxyphenyl)-3-oxoprop-1-enyl]-2-ethoxyphenoxy]-N-(2-methylphenyl)acetamide; 19540808: 2-[4-[(E)-3-(2,4-Dihydroxyphenyl)-3-oxoprop-1-enyl]-2-ethoxyphenoxy]-N-(2-methoxyphenyl)acetamide; 19540809: 2-[4-[(E)-3-(2,4-Dihydroxyphenyl)-3-oxoprop-1-enyl]-2-ethoxyphenoxy]-N-(4-methylphenyl)acetamide; 19564765: (E)-3-[3-[(2,4-Dichlorophenoxy)methyl]-4-methoxyphenyl]-1-(4-hydroxyphenyl)prop-2-en-1-one; 19564766: (E)-1-(4-Hydroxyphenyl)-3-[4-methoxy-3-[(2,4,6-trichlorophenoxy)methyl]phenyl]prop-2-en-1-one; 19564767: (E)-1-(4-Hydroxyphenyl)-3-[4-methoxy-3-[(3-methyl-4-nitrophenoxy)methyl]phenyl]prop-2-en-1-one; 19564768: (E)-3-[3-[(2-Bromophenoxy)methyl]-4-methoxyphenyl]-1-(4-hydroxyphenyl)prop-2-en-1-one; 19564769: (E)-3-[3-[(4-Chloro-5-methyl-2-propan-2-ylphenoxy)methyl]-4-methoxyphenyl]-1-(4-hydroxyphenyl)prop-2-en-1-one; 19564770: (E)-1-(4-Hydroxyphenyl)-3-[4-methoxy-3-[(2,4,6-tribromophenoxy)methyl]phenyl]prop-2-en-1-one; 19564771: (E)-3-[3-[(4-Bromophenoxy)methyl]-4-methoxy-phenyl]-1-(4-hydroxyphenyl)prop-2-en-1-one; 19564772: (E)-3-[3-[(2,4-Difluorophenoxy)methyl]-4- methoxyphenyl]-1-(4-hydroxyphenyl)prop-2-en-1-one;
19564773: (E)-1-(4-Hydroxyphenyl)-3-[4-methoxy-3-[(4-nitropyrazol-1-yl)methyl]phenyl]prop-2-en-1-one;
19564775: 4-[[5-[(E)-3-(4-Hydroxyphenyl)-3-oxoprop-1-enyl]-2-methoxyphenyl]methoxy]benzonitrile; 19564776: (E)-1-(4-Hydroxyphenyl)-3-[4-methoxy-3-[(2,3,4,5,6-penta-chlorophenoxy)methyl]phenyl]prop-2-en-1-one;
19564777: (E)-1-(4-Hydroxyphenyl)-3-[4-methoxy-3-[(2-methylphenoxy)methyl]phenyl]prop-2-en-1-one;
19564778: (E)-3-[3-[(3-Chlorophenoxy)methyl]-4-methoxyphenyl]-1-(4-hydroxyphenyl)prop-2-en-1-one;
19564779: (E)-3-[3-[(4-Tert-butylphenoxy)methyl]-4-methoxyphenyl]-1-(4-hydroxyphenyl)prop-2-en-1-one;
19564780: (E)-3-[3-[(2,6-Dimethylphenoxy)methyl]-4-methoxyphenyl]-1-(4-hydroxy-phenyl)prop-2-en-1-one;
19564781: (E)-1-(4-Hydroxyphenyl)-3-[4-methoxy-3-[(4-methoxy-phenoxy)methyl]phenyl]prop-2-en-1-one;
19564782: (E)-1-(4-Hydroxyphenyl)-3-[4-methoxy-3-(naphthalen-2-yloxymethyl)phenyl]prop-2-en-1-one;
19564783: (E)-1-(4-Hydroxyphenyl)-3-[4-methoxy-3-(quinolin-8-yloxymethyl)phenyl]prop-2-en-1-one; 19564784: (E)-1-(4-Hydroxyphenyl)-3-[3-methoxy-4-(phenylsulfanylmethyl)phenyl]prop-2-en-1-one; 19564785: (E)-1-(4-Hydroxyphenyl)-3-[4-methoxy-3-[(4-methyl-2-nitrophenoxy)methyl]phenyl]prop-2-en-1-one; 19564786: (E)-1-(4-Hydroxyphenyl)-3-[4-methoxy-3-[(2-nitrophenoxy)methyl]phenyl]prop-2-en-1-one; 19564787: (E)-1-(4-Hydroxyphenyl)-3-[4-methoxy-3-[(2,3,4,5,6-pentafluorophenoxy)methyl]phenyl]prop-2-en-1-one;
19564788: 1-(4-Hydroxy-phenyl)-3-(4-pentyloxy-phenyl)-prop-2-en-1-one; 19564791: (E)-3-[3-[(4-Ethylphenoxy)methyl]-4-methoxyphenyl]-1-(4-hydroxyphenyl)prop-2-en-1-one; 19564792: (E)-3-[3-[(4-Chloro-3,5-dimethylphenoxy)methyl]-4-methoxyphenyl]-1-(4-hydroxyphenyl)prop-2-en-1-one; 19564793: (E)-3-[3-(Chloromethyl)-4-methoxyphenyl]-1-(4-hydroxyphenyl)prop-2-en-1-one; 19564795: (E)-1-(4-Hydroxyphenyl)-3-[4-methoxy-3-(phenoxymethyl)phenyl]prop-2-en-1-one;
19564797: (E)-1-(4-Hydroxyphenyl)-3-[4-methoxy-3-[(4-nitrophenoxy)methyl]phenyl]prop-2-en-1-one; 19564798: (E)-3-[3-[(4-Bromo-3,5-dimethylpyrazol-1-yl)methyl]-4-methoxyphenyl]-1-(4-hydroxyphenyl)prop-2-en-1-one;
19564799: (E)-3-[3-[(3,5-Dimethyl-pyrazol-1-yl)methyl]-4-methoxyphenyl]-1-(4-hydroxyphenyl)prop-2-en-1-one;
19564801: (E)-1-(4-Hydroxyphenyl)-3-[4-methoxy-3-(thiomorpholin-4-ylmethyl)phenyl]prop-2-en-1-one; 19564807: (E)-3-[3-[(2-Bromo-4-chlorophenoxy)methyl]-4-methoxyphenyl]-1-(4-hydroxy-phenyl)prop-2-en-1-one; 19564808: (E)-3-[3-[(4-Bromo-2-chlorophenoxy)methyl]-4-methoxyphenyl]-1-(4-hydroxyphenyl)prop-2-en-1-one; 19564809: (E)-3-[3-[(2,3-Dichlorophenoxy)methyl]-4-methoxyphenyl]-1-(4-hydroxyphenyl)prop-2-en-1-one; 19564810: (E)-1-(4-Hydroxyphenyl)-3-[4-methoxy-3-[(4-propan-2-ylphenoxy)methyl]phenyl]prop-2-en-1-one; 19564811: (E)-1-(4-Hydroxyphenyl)-3-[4-methoxy-3-[(2,3,5,6-tetrafluorophenoxy)methyl]phenyl]prop-2-en-1-one;
19564812: (E)-3-[3-[(2-Chloro-4-fluorophenoxy)methyl]-4-methoxyphenyl]-1-(4-hydroxyphenyl)prop-2-en-1-one;
19564814: 2-[[5-[(E)-3-(4-Hydroxyphenyl)-3-oxoprop-1-enyl]-2-methoxyphenyl]methylsulfanyl]-4-phenyl-6-(trifluoromethyl)pyridine-3-carbonitrile; 19564815: (E)-1-(4-Hydroxyphenyl)-3-[3-[(4-iodophenoxy)methyl]-4-methoxyphenyl]prop-2-en-1-one; 19564816: (E)-1-(4-Hydroxyphenyl)-3-[4-methoxy-3-[[3-(trifluoromethyl)phenoxy]methyl]phenyl]prop-2-en-1-one; 19564817: (E)-3-[3-[(5-Fluoro-2-nitrophenoxy)methyl]-4-methoxyphenyl]-1-(4-hydroxy-phenyl)prop-2-en-1-one; 19564819: (E)-1-(4-Hydroxyphenyl)-3-[4-methoxy-3-(methoxy-methyl)phenyl]prop-2-en-1-one; 19564820: 6-(Difluoromethyl)-2-[[5-[(E)-3-(4-hydroxy-phenyl)-3-oxoprop-1-enyl]-2-methoxyphenyl]methylsulfanyl]-4-methylpyridine-3-carbonitrile; 19564821: 2-[[5-[(E)-3-(4-Hydroxyphenyl)-3-oxoprop-1-enyl]-2-methoxyphenyl]methylsulfanyl]-4-methyl-6-(trifluoromethyl)pyridine-3-carbonitrile;
19564822: 6-(Difluoromethyl)-2-[[5-[(E)-3-(4-hydroxyphenyl)-3-oxoprop-1-enyl]-2-methoxyphenyl]methylsulfanyl]-4-phenyl-pyridine-3-carbonitrile; 19564824: (E)-3-[3-[(3-Chloro-4-fluorophenoxy)methyl]-4-methoxy-phenyl]-1-(4-hydroxyphenyl)prop-2-en-1-one; 19564825: (E)-3-[3-[[4-(Difluoromethyl)-6-methylpyrimidin-2-yl]sulfanylmethyl]-4-methoxyphenyl]-1-(4-hydroxyphenyl)prop-2-en-1-one;
19564827: (E)-3-[3-[(2,3-Dihydro-1H-inden-5-yloxymethyl)-4-methoxyphenyl]-1-(4-hydroxyphenyl)prop-2-en-1-one; 19564828: (E)-3-[3-[(2-Chlorophenoxy)methyl]-4-methoxy-phenyl]-1-(4-hydroxyphenyl)prop-2-en-1-one;
19564829: (E)-1-(4-Hydroxyphenyl)-3-[4-methoxy-3-[(4-methylphenoxy)methyl]phenyl]prop-2-en-1-one;
19564831: (E)-3-[3-[(4-Bromopyrazol-1-yl)methyl]-4-methoxyphenyl]-1-(4-hydroxyphenyl)prop-2-en-1-one;
19564832: (E)-1-(4-Hydroxyphenyl)-3-[4-methoxy-3-(pyridin-2-ylsulfanylmethyl)phenyl]prop-2-en-1-one; 19564844: (E)-1-(4-Hydroxyphenyl)-3-[3-methoxy-4-[(4-nitro-phenyl)methoxy]phenyl]prop-2-en-1-one; 19564845: (E)-1-(4-Hydroxyphenyl)-3-[4-methoxy-3-(pyrrolidin-1-ylmethyl)phenyl]prop-2-en-1-one; 19564846: (E)-3-[3-[(3-Bromophenoxy)methyl]-4-methoxyphenyl]-1-(4-hydroxyphenyl)prop-2-en-1-one; 19564853: (E)-3-[3-[(2,5-Dimethylphenoxy)methyl]-4-methoxyphenyl]-1-(4-hydroxyphenyl)prop-2-en-1-one; 19564854: (E)-3-[3-(Ethoxymethyl)-4-methoxyphenyl]-1-(4-hydroxyphenyl)prop-2-en-1-one; 19564859: (E)-1-(4-Hydroxyphenyl)-3-[3-(2-methylpropoxy)phenyl]prop-2-en-1-one; 19564865: (E)-1-(4-Hydroxyphenyl)-3-[4-methoxy-3-(pyrazol-1-ylmethyl)phenyl]prop-2-en-1-one; 19564869: (E)-1-(4-Hydroxyphenyl)-3-[4-methoxy-3-(2,2,2-trifluoroethoxymethyl)phenyl]prop-2-en-1-one; 19564870: (E)-1-(4-Hydroxyphenyl)-3-[4-methoxy-3-(2,2,3,3-tetrafluoropropoxymethyl)phenyl]prop-2-en-1-one;
19564879: (E)-3-[3-[(4-Chloro-2-methylphenoxy)methyl]-4-methoxyphenyl]-1-(4-hydroxyphenyl)prop-2-en-1-one;
19564880: (E)-3-[3-[(4-Chloro-3-methylphenoxy)methyl]-4-methoxyphenyl]-1-(4-hydroxyphenyl)prop-2-en-1-one;
19564882: (E)-3-[3-[(2-Tert-butyl-5-methylphenoxy)methyl]-4-methoxyphenyl]-1-(4-hydroxyphenyl)prop-2-en-1-one; 19564885: (E)-3-[3-[[3,5-Bis(difluoromethyl)pyrazol-1-yl]methyl]-4-methoxyphenyl]-1-(4-hydroxyphenyl)prop-2-en-1-one; 19564886: (E)-1-(4-Hydroxyphenyl)-3-[3-(1,1,2,2-tetrafluoroethoxy)phenyl]prop-2-en-1-one;
19564887: (E)-1-(4-Hydroxyphenyl)-3-[4-methoxy-3-[(3-nitrophenoxy)methyl]phenyl]prop-2-en-1-one; 19564892: (E)-3-[3-[(2-Chloro-4-methylphenoxy)methyl]-4-methoxyphenyl]-1-(4-hydroxy-phenyl)prop-2-en-1-one; 19564893: (E)-3-[3-[(2-Chloro-4-nitrophenoxy)methyl]-4-methoxyphenyl]-1-(4-hydroxyphenyl)prop-2-en-1-one; 19564894: (E)-3-[4-[(3,4-Diethoxyphenyl) methoxy]phenyl]-1-(4-hydroxyphenyl)prop-2-en-1-one; 19564895: (E)-3-[3-[(3,4-Diethoxy-phenyl)methoxy]phenyl]-1-(4-hydroxyphenyl)prop-2-en-1-one; 19564899: (E)-3-[3-[(3,5-Dimethyl-4-nitropyrazol-1-yl)methyl]-4-methoxyphenyl]-1-(4-hydroxyphenyl)prop-2-en-1-one; 19564905: (E)-3-[3-[(4-Chloro-3,5-dimethylpyrazol-1-yl)methyl]-4-methoxyphenyl]-1-(4-hydroxyphenyl)prop-2-en-1-one; 19564906: (E)-3-[3-[(2,6-Dichlorophenoxy)methyl]-4-methoxyphenyl]-1-(4-hydroxyphenyl)prop-2-en-1-one;

19564907: (E)-1-(4-Hydroxyphenyl)-3-[4-methoxy-3-[(2,4,5-trichlorophenoxy)methyl]phenyl]prop-2-en-1-one; 19564909: (E)-1-(4-Hydroxyphenyl)-3-[4-methoxy-3-[(3-nitropyrazol-1-yl)methyl]phenyl]prop-2-en-1-one; 19564910: (E)-3-[3-[(4-Chloropyrazol-1-yl)methyl]-4-methoxyphenyl]-1-(4-hydroxyphenyl) prop-2-en-1-one; 19564911: (E)-3-[3-[(2-Ethoxyphenoxy)methyl]-4-methoxyphenyl]-1-(4-hydroxyphenyl)prop-2-en-1-one; 19564912: (E)-1-(4-Hydroxyphenyl)-3-[4-methoxy-3-[(2-prop-2-enylphenoxy)methyl]phenyl]prop-2-en-1-one; 19564913: (E)-1-(4-Hydroxyphenyl)-3-[4-methoxy-3-[(4-phenylphenoxy)methyl]phenyl]prop-2-en-1-one; 19564914: (E)-3-[3-[(2-Benzylphenoxy)methyl]-4-methoxyphenyl]-1-(4-hydroxyphenyl)prop-2-en-1-one; 19564915: (E)-1-(4-Hydroxyphenyl)-3-[4-methoxy-3-[(5-methyl-2-nitrophenoxy)methyl]phenyl]prop-2-en-1-one; 19564916: Chembl4218580; 19564922: (E)-1-(4-Hydroxyphenyl)-3-(4-propan-2-yloxyphenyl)prop-2-en-1-one; 19564923: (E)-3-(4-Cyclopentyloxy-3-ethoxyphenyl)-1-(4-hydroxyphenyl)prop-2-en-1-one; 19564925: (E)-1-(4-Hydroxyphenyl)-3-[4-(2-morpholin-4-ylethoxy)phenyl]prop-2-en-1-one; 19564926: (E)-3-[3-(1,3-Benzodioxol-5-yloxymethyl)-4-methoxyphenyl]-1-(4-hydroxyphenyl)prop-2-en-1-one; 19564931: (E)-3-[3-[[4-Chloro-3,5-bis(difluoromethyl)pyrazol-1-yl]methyl]-4-methoxyphenyl]-1-(4-hydroxyphenyl)prop-2-en-1-one; 19564933: 2-[4-[(E)-3-(4-Hydroxyphenyl)-3-oxoprop-1-enyl]-2-methoxyphenoxy]-N-phenylacetamide; 19564934: 2-[2-Ethoxy-4-[(E)-3-(4-hydroxyphenyl)-3-oxoprop-1-enyl]phenoxy]-N-phenylacetamide; 19564935: (E)-3-[3-[(2-Fluorophenoxy)methyl]-4-methoxy-phenyl]-1-(4-hydroxyphenyl)prop-2-en-1-one; 19564937: 2-[4-[(E)-3-(4-Hydroxyphenyl)-3-oxoprop-1-enyl]-2-methoxyphenoxy]-N-(2-methylphenyl)acetamide; 19564938: 2-[4-[(E)-3-(4-Hydroxyphenyl)-3-oxoprop-1-enyl]-2-methoxyphenoxy]-N-(2-methoxyphenyl)acetamide; 19564939: 2-[4-[(E)-3-(4-Hydroxyphenyl)-3-oxoprop-1-enyl]-2-methoxyphenoxy]-N-(4-methylphenyl)acetamide; 19564940: 2-[2-Ethoxy-4-[(E)-3-(4-hydroxyphenyl)-3-oxoprop-1-enyl]phenoxy]-N-(2-methylphenyl)acetamide; 19564941: 2-[2-Ethoxy-4-[(E)-3-(4-hydroxy-phenyl)-3-oxoprop-1-enyl]phenoxy]-N-(2-methoxyphenyl)acetamide; 19564942: 2-[2-Ethoxy-4-[(E)-3-(4-hydroxyphenyl)-3-oxoprop-1-enyl]phenoxy]-N-(4-methylphenyl) acetamide; 19571304: (E)-3-[3-[(4-Chlorophenoxy)methyl]-4-methoxyphenyl]-1-(2,4-dihydroxyphenyl)prop-2-en-1-one; 19571305: (E)-3-[3-[(2,4-Dichlorophenoxy)methyl]-4-methoxyphenyl]-1-(2,4-dihydroxyphenyl)prop-2-en-1-one; 19571306: (E)-1-(2,4-Dihydroxyphenyl)-3-[4-methoxy-3-[(2,4,6-trichlorophenoxy)methyl]phenyl]prop-2-en-1-one; 19571307: (E)-1-(2,4-Dihydroxyphenyl)-3-[4-methoxy-3-[(3-methyl-4-nitrophenoxy)methyl]phenyl]prop-2-en-1-one; 19571308: (E)-3-[3-[(2-Bromophenoxy)methyl]-4-methoxyphenyl]-1-(2,4-dihydroxyphenyl)prop-2-en-1-one; 19571309: (E)-3-[3-[(4-Chloro-5-methyl-2-propan-2-ylphenoxy)methyl]-4-methoxyphenyl]-1-(2,4-dihydroxyphenyl)prop-2-en-1-one; 19571310: (E)-1-(2,4-Dihydroxyphenyl)-3-[4-methoxy-3-[(2,4,6-tribromophenoxy)methyl]phenyl]prop-2-en-1-one; 19571311: (E)-3-[3-[(4-Bromophenoxy)methyl]-4-methoxyphenyl]-1-(2,4-di-hydroxyphenyl)prop-2-en-1-one; 19752453: 5-[[2-[(E)-3-(3,4-Dihydroxyphenyl)prop-2-enoyl]phenyl]methyl]-1,3-thiazolidine-2,4-dione; 19752455: 5-[[4-[(E)-3-(4-Hydroxy-3-methoxyphenyl)prop-2-enoyl]phenyl]methyl]-1,3-thiazolidine-2,4-dione; 19752463: (E)-3-(4-Hydroxy-3-methylphenyl)-1-[2-(1,3-thiazolidin-5-ylmethyl)phenyl]prop-2-en-1-one; 19754533: 5-[[4-[(E)-3-(4-Hydroxyphenyl)prop-2-enoyl]phenyl]methyl]-1,3-thiazolidine-2,4-dione; 19820722: 2-[3,5-Dimethoxy-2-[(E)-3-[4-methoxy-3-(3-methylbutyl)phenyl]prop-2-enoyl]phenoxy]acetic acid; 19824587: (E)-3-(3,4-Dihydroxyphenyl)-1-(4-methylsulfanyl-phenyl)prop-2-en-1-one; 19824606: (E)-3-(3-Hydroxyphenyl)-1-(4-methylsulfanylphenyl) prop-2-en-1-one; 19824634: (E)-3-(4-Hydroxyphenyl)-1-(4-methylsulfanylphenyl)prop-2-en-1-one; 19841724: 4-[(E)-3-[2-(Carboxymethoxy)-4-prop-2-ynoxyphenyl]-3-oxoprop-1-enyl]benzoic acid; 19841729: 2-[4-[(E)-3-[2-(Carboxymethoxy)-4-prop-1-en-2-yloxyphenyl]-3-oxoprop-1-enyl]-2-methoxyphenoxy]acetic acid; 19851293: 4-[(E)-3-[2-[(E)-3-(4-Carboxy-phenyl)prop-2-enoyl]phenyl]-3-oxoprop-1-enyl]benzoic acid; 19898760: (E)-1-[2-(3-Chloro-propoxy)-6-hydroxyphenyl]-3-phenyl-prop-2-en-1-one; 19910192: 2-[5-(3-Methylbut-2-enoxy)-2-[(E)-3-(4-methylphenyl)prop-2-enoyl]phenoxy]acetic acid; 19910194: (E)-3-(4-Hexylphenyl)-1-[2-hydroxy-4-(3-methylbut-2-enoxy)phenyl]prop-2-en-1-one; 19910197: 2-[2-[(E)-3-(4-Hexylphenyl)prop-2-enoyl]-5-(3-methylbut-2-enoxy)phenoxy]acetic acid; 19910199: 2-[5-(3-Methylbut-2-enoxy)-2-[(E)-3-(4-propylphenyl)prop-2-enoyl]phenoxy] acetic acid; 19910200: 2-[5-(3-Methylbut-2-enoxy)-2-[(E)-3-[4-[(E)-oct-1-enyl]phenyl]prop-2-enoyl]phenoxy]acetic acid; 19910201: 2-[2-[(E)-3-(4-Heptylphenyl)prop-2-enoyl]-5-(3-methylbut-2-enoxy)phenoxy]acetic acid; 19910203: 2-[2-[(E)-3-[4-[(E)-Hept-1-enyl]phenyl]prop-2-enoyl]-5-(3-methylbut-2-enoxy)phenoxy]acetic acid; 19910204: (E)-3-(4-Tert-butylphenyl)-1-[2-hydroxy-4-(3-methylbut-2-enoxy)phenyl]prop-2-en-1-one; 19910205: 2-[5-(3-Methylbut-2-enoxy)-2-[(E)-3-(4-prop-2-enylphenyl)prop-2-enoyl]phenoxy]acetic acid; 19910207: 2-[2-[(E)-3-[4-[(E)-Hex-1-enyl]phenyl]prop-2-enoyl]-5-(3-methylbut-2-enoxy)phenoxy]acetic acid; 19968509: 2-[(E)-3-(3,4-Dihydroxyphenyl)prop-2-enoyl]benzoic acid; 19968527: 4-[(E)-3-(3,4-Dihydroxyphenyl)prop-2-enoyl]benzoic acid; 19986357: (E)-1-[2-Hydroxy-4-(oxan-2-yloxy)phenyl]-3-phenylprop-2-en-1-one; 20239583: (E)-1-(2,4-Diethoxy-6-hydroxyphenyl)-3-(4-ethoxyphenyl)prop-2-en-1-one; 20239585: (E)-1-(2-Ethoxy-6-hydroxy-4-methoxyphenyl)-3-(4-ethoxyphenyl)prop-2-en-1-one; 20239602: 5-[3,5-Dimethoxy-2-[(E)-3-(4-methoxyphenyl)prop-2-enoyl]phenoxy]-5-oxopentanoic acid; 20239610: (E)-1-(2-Hydroxy-4,6-dimethoxyphenyl)-3-(4-prop-2-enoxyphenyl)prop-2-en-1-one; 20239618: (E)-1-(2-Ethoxy-6-hydroxy-4-methoxyphenyl)-3-(4-methoxyphenyl)prop-2-en-1-one; 20239619: Unii-V652dmr3ST; 20239620: (E)-1-(2,4-Diethoxy-6-hydroxyphenyl)-3-(4-methoxyphenyl)prop-2-en-1-one; 20239623: (E)-1-(4-Ethoxy-2-hydroxy-6-methoxy-phenyl)-3-(4-ethoxyphenyl)prop-2-en-1-one; 20239626: (E)-3-(4-Aminophenyl)-1-(2-hydroxy-4,6-dimethoxyphenyl)prop-2-en-1-one; 20239629: (E)-3-[4-(Diethylamino)phenyl]-1-(2-hydroxy-4,6-dimethoxyphenyl)prop-2-en-1-one; 20239632: (E)-1-(2-Hydroxy-4-methoxy-6-propoxyphenyl)-3-(4-methoxyphenyl)prop-2-en-1-one; 20239637: (E)-1-(2-Hydroxy-4-methoxy-6-propan-2-yloxyphenyl)-3-(4-methoxyphenyl)prop-2-en-1-one; 20239638: 4-[(E)-3-(2-Hydroxy-4,6-dimethoxyphenyl)-3-oxoprop-1-enyl]benzonitrile; 20239639: (E)-1-(2-Hydroxy-4,6-dimethoxyphenyl)-3-(3-methylsulfanylphenyl)prop-2-en-1-one; 20349439: Sodium;2-[4-[(E)-3-(4-hydroxy-3-methoxyphenyl)prop-2-enoyl]phenoxy]acetic acid; 20349440: 2-[4-[(E)-3-[4-(Carboxymethoxy)phenyl]-3-oxoprop-1-enyl]phenoxy]acetic acid; 20349441: 2-[4-[(E)-3-(3-Methylphenyl)prop-2-enoyl]phenoxy]acetic acid; 20349442: Sodium;2-[4-[(E)-3-(4-methoxyphenyl)prop-2-enoyl]phenoxy]acetic acid; 20349443: Disodium;2-[4-[(E)-3-(4-sulfophenyl)prop-2-enoyl]phenoxy]acetic acid;

20349444: 2-[4-[(E)-3-(4-Sulfophenyl)prop-2-enoyl]phenoxy]acetic acid; 20349445: 3-[(E)-3-[4-(Carboxymethoxy)phenyl]-3-oxoprop-1-enyl]benzoic acid; 20349447: 2-[4-[(E)-3-[4-(Carboxymethoxy)-3-methoxyphenyl]prop-2-enoyl]phenoxy]acetic acid; 20349451: 4-[4-[(E)-3-[4-(Carboxymethoxy)phenyl]-3-oxoprop-1-enyl]phenyl]-2-methyl-3-oxobutanoic acid; 20349453: Disodium;4-[(E)-3-[4-(carboxymethoxy)phenyl]prop-2-enoyl]benzoic acid; 20349454: 4-[(E)-3-[4-(Carboxymethoxy)phenyl]prop-2-enoyl]benzoic acid; 20349458: 3-[(E)-3-(4-Hydroxyphenyl)-3-oxoprop-1-enyl]benzoic acid; 20349461: 2-[4-[(E)-3-[3-(Carboxymethoxy)phenyl]prop-2-enoyl]phenoxy]acetic acid; 20349463: Disodium;4-[(E)-3-(4-carboxyphenyl)-3-oxoprop-1-enyl]benzoic acid; 20349464: 4-[(E)-3-(4-Carboxyphenyl)-3-oxoprop-1-enyl]benzoic acid; 20358291: 2-[2-[(E)-3-[4-(3-Methylbut-2-enoxy)phenyl]prop-2-enoyl]phenoxy]acetic acid; 20358294: 2-[5-(3-Methylbut-2-enoxy)-2-[(E)-3-phenylprop-2-enoyl]phenoxy]acetic acid; 20396142: 2-Methyl-2-[4-[(E)-3-oxo-3-phenylprop-1-enyl]phenoxy]propanoic acid; 20452414: N-[4-[(E)-3-(2-Hydroxyphenyl)-3-oxoprop-1-enyl]phenyl] acetamide; 20542186: [4-[(E)-3-(2-Hydroxy-4,6-dimethoxyphenyl)-3-oxoprop-1-enyl]phenyl] acetate; 20542198: 1-(2-Hydroxy-4,6-dimethoxy-phenyl)-3-(4-methoxymethoxy-phenyl)-propenone; 20542204: (E)-3-(3H-Benzimidazol-5-yl)-1-(2-hydroxy-4,6-dimethoxyphenyl)prop-2-en-1-one; 20643188: 2-Hydroxy-2-methyl-1-[4-[4-oxo-4-[4-[(E)-3-oxo-3-phenylprop-1-enyl]phenyl]butoxy]phenyl]propan-1-one; 20656493: 2-Hydroxy-2-methyl-1-[4-[[2-oxo-2-[4-[(E)-3-oxo-3-phenylprop-1-enyl]phenyl]ethoxy]methoxy]phenyl]propan-1-one; 20659079: 2-[4-(2-Hydroxy-2-methylpropanoyl)phenoxy]ethyl 4-[(E)-3-[4-[2-[4-(2-hydroxy-2-methylpropanoyl)phenoxy]ethoxycarbonyl]phenyl]-3-oxoprop-1-enyl]benzoate; 20659080: 2-[4-(2-Hydroxy-2-methylpropanoyl)phenoxy]ethyl 4-[(E)-3-(4-acetylphenyl)-3-oxoprop-1-enyl]benzoate; 20659086: [4-[1-Hydroxy-4-[4-[(E)-3-oxo-3-phenylprop-1-enyl]benzoyl]cyclohexanecarbonyl]phenyl] 4-[(E)-3-oxo-3-phenylprop-1-enyl]benzoate; 20659087: [4-(1-Hydroxycyclohexanecarbonyl)phenyl] 4-[(E)-3-oxo-3-phenylprop-1-enyl]benzoate; 20659089: 4-[(E)-3-[4-(Hydroperoxymethyl)phenyl]prop-2-enoyl]benzoic acid; 20663786: 2-(2-Cyanopropyl)-4-[[4-[(E)-3-[4-(dimethylamino)phenyl]prop-2-enoyl]phenyl]-hydroperoxymethyl]-N-(hydroxymethyl)-4-methylhexanamide; 20663787: 1-O-(2,2-Dimethyl-4-oxopentyl) 5-O-(2-hydroxyethyl) 2-methyl-4-[2-[4-[(E)-3-phenylprop-2-enoyl]phenyl]butyl] pentanedioate; 20663788: (2,2-Dimethyl-4-oxopentyl) 4-(hydroxymethylcarbamoyl)-2-methyl-6-[4-[(E)-3-phenylprop-2-enoyl]phenyl]octanoate; 20663789: 2-[[4-[(E)-3-(4-Hydroxy-3-methoxyphenyl)prop-2-enoyl]phenyl]carbamoylamino]ethyl 2,2-dimethylbutanoate; 20663790: 2-[[4-[(E)-3-(4-Hydroxy-3-methoxyphenyl) prop-2-enoyl]phenyl]carbamoylamino]ethyl 2-ethyl-7-(hydroxymethylamino)-4-(methoxy-methylcarbamoyl)-2,6-dimethyl-7-oxoheptanoate; 20663791: 2-[[4-[(E)-3-(4-Hydroxyphenyl) prop-2-enoyl]phenoxy]carbonylamino] ethyl 2,2-dimethylbutanoate; 20663792: 2-[[4-[(E)-3-(4-Hydroxyphenyl)prop-2-enoyl]phenoxy]carbonylamino] ethyl 2-ethyl-5-(hydroxymethyl-amino)-2,4-dimethyl-5-oxopentanoate; 20663799: 2-Ethyl-N'-(hydroxymethyl)-N-[4-[(E)-3-(4-hydroxyphenyl)prop-2-enoyl]phenyl]-2,4-dimethylpentanediamide; 20663802: 2-Hydroxyethyl 4-(hydroxymethylcarbamoyl)-6-[[4-[(E)-3-(4-hydroxyphenyl)prop-2-enoyl]phenyl]carbamoyl]-2-methyloctanoate; 20663803: (E)-1-(4-Butan-2-ylphenyl)-3-(4-hydroxyphenyl)prop-2-en-1-one; 20663805: 4-(2-Cyano-2-methylpropyl)-2-[2-[4-[(E)-3-[4-(dimethylamino)phenyl]prop-2-enoyl]phenyl]butyl]-N-(hydroxymethyl)-N'-(methoxymethyl) pentanediamide; 20663806: 4-(2-Cyanopropyl)-N-[4-[(E)-3-[4-(dimethylamino)phenyl]prop-2-enoyl]phenoxy]sulfinyl-2-ethyl-N'-(hydroxymethyl)-2-methylpentanediamide; 20663815: 1-O-Butyl 7-O-[2-[[4-[(E)-3-(3,4-dimethoxyphenyl)prop-2-enoyl]phenyl]carbamoylamino]ethyl]6-ethyl-4-(hydroxymethyl-carbamoyl)-2,2,6-trimethylheptanedioate; 20663819: Butyl 6-[[4-[(E)-3-(3,4-dimethoxyphenyl)prop-2-enoyl]phenyl]-hydroperoxymethyl]-4-(hydroxymethyl-carbamoyl)-2,2,6-trimethyloctanoate; 20663823: Methyl 4-[[4-[(E)-3-(4-hydroxy-3-methoxy-phenyl)prop-2-enoyl]phenyl]carbamoyl]-2,4-dimethylhexanoate; 20663824: Methyl 6-[[4-[(E)-3-(4-hydroxy-3-methoxyphenyl)prop-2-enoyl]phenyl]carbamoyl]-4-(methoxymethyl-carbamoyl)-2,6-dimethyloctanoate; 20663825: 3-N-(Hydroxymethyl)-1,5-dimethyl-1-N-(2-methyl-4-oxopentan-2-yl)-5-N-[4-[(E)-3-phenylprop-2-enoyl]phenyl]heptane-1,3,5-tricarbox-amide; 20663828: N-[4-[(E)-3-(4-Hydroxyphenyl)prop-2-enoyl]phenyl]-2,2-dimethylbutan-amide; 20663830: N-(Hydroxymethyl)-4-[4-[(E)-3-(4-hydroxyphenyl)prop-2-enoyl]phenyl]-2-methylhexanamide; 20670442: (E)-1-[4-(2-Hydroxybutoxy)phenyl]-3-(4-methoxyphenyl) prop-2-en-1-one; 20695778: 1-Amino-4-hydroxy-2-[4-[(E)-3-phenylprop-2-enoyl]phenoxy]anthracene-9,10-dione; 20744658: (E)-1-[4-(Dimethylamino)phenyl]-3-[4-(2-hydroxyethoxy)phenyl]prop-2-en-1-one; 20759532: 4-[4-[(E)-3-Oxo-3-phenylprop-1-enyl]phenoxy]benzoic acid; 20792553: (E)-3-[4-(6-Hydroxyhexoxy)phenyl]-1-[4-(1,1,2,2,3,3,4,4,5,5,6,6,6-tridecafluorohexyl)phenyl]prop-2-en-1-one; 20792554: (E)-3-[4-(6-Hydroxyhexoxy)phenyl]-1-(4-iodophenyl)prop-2-en-1-one; 20838354: 4'-[2-Hydroxy-3-(4-phenylpiperazino)propoxy]chalcone; 20838692: (Z)-3-(3-Hydroxy-4-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one; 20839186: 2-[2-[(E)-3-(4-Chlorophenyl) prop-2-enoyl]phenyl]-2-hydroxypropanoate; 20839187: 2-[2-[(E)-3-(4-Chlorophenyl)prop-2-enoyl]phenyl]-2-hydroxypropanoic acid; 20841129: (E)-3-[4-(Dimethylamino)phenyl]-1-[4-(5-hydroxy-2H-oxadiazol-2-ium-3-yl)phenyl]prop-2-en-1-one; 20841130: Schembl22-645654; 20842109: (E)-3-(3-Aminophenyl)-1-(4-bromo-2-hydroxyphenyl)prop-2-en-1-one; 20981741: 1-(4-Ethoxy-2-hydroxyphenyl)-3-phenylprop-2-en-1-one; 21041598: 2,2-Difluoro-2-[4-[(E)-3-(4-thiophen-2-ylphenyl)prop-2-enoyl]phenyl]sulfanylacetic acid; 21041599: 2-[3E-(4-Methoxy-3-thiophen-2-yl-phenyl)-acryloyl]-benzoic acid; 21041621: 4-[(E)-3-(4-Thiophen-2-ylphenyl)prop-2-enoyl]benzoic acid; 21041622: 4-[3E-4-Fluoro-3-(thiophen-2-yl)-phenyl-acryloyl]-benzoic acid; 21041624: 4-[(E)-3-(4-Pyrimidin-5-ylphenyl) prop-2-enoyl]benzoic acid; 21041625: 4-[3E-(4-Pyrrolidin-1-yl-3-thiophen-2-yl-phenyl)-acryloyl]-benzoic acid; 21041626: 4-[(E)-3-[4-(1,3-Thiazol-2-yl)phenyl]prop-2-enoyl]benzoic acid; 21041633: 4-[(E)-3-Oxo-3-(4-thiophen-2-ylphenyl)prop-1-enyl]benzoic acid; 21117850: 4,2',4',6'-Tetrahydroxy-3-methoxychalcone; 21158481: (2S)-5,7-Dihydroxy-2-(4-hydroxyphenyl)-2,3-dihydrochromen-4-one;(E)-1,3-diphenylprop-2-en-1-one; 21159083: 1-[2,4-Dihydroxy-6-[(2S,3R,4S,5S,6R)-3,4,5-trihydroxy-6-(hydroxymethyl)oxan-2-yl]oxyphenyl]-3-(4-hydroxyphenyl)propan-1-one;(E)-1,3-diphenylprop-2-en-1-one; 21159559: (Z)-1-(2-Hydroxy-4-methoxyphenyl)-3-(4-methoxyphenyl)prop-2-en-1-one; 21160631: (Z)-3-(3,4-Dimethoxyphenyl)-1-(2-hydroxy-4-methoxyphenyl)prop-2-en-1-one; 21362351: (E)-3-(1-Benzofuran-5-yl)-1-[2-[(6- ethyl-3,4,5-trimethyloxan-2-yl)methyl]-6-hydroxy-4-methylphenyl]prop-2-en-1-one; 21362356: (E)-3-(1-Benzofuran-5-yl)-1-[2-hydroxy-4-methyl-6-[[3,4,5-trihydroxy-6-(hydroxymethyl)oxan-2-yl]methyl]phenyl]prop-2-en-1-one; 21362358: (E)-3-(1-Benzofuran-5-yl)-1-[2-methoxy-4-methyl-6-[[3,4,5-trihydroxy-6-(hydroxymethyl) oxan-2-yl]methyl]phenyl]prop-2-en-1-one; 21410447: [3,5-Dibenzoyloxy-4-[(E)-3-(4-hydroxyphenyl)prop-2-enoyl]phenyl] benzoate; 21499386: Bis[3,5-dihydroxy-4-[(E)-3-(4-hydroxyphenyl)prop-2-enoyl]phenyl] hydrogen phosphate; 21528622: (E)-1-[4-(2-Hydroxy-ethoxy)phenyl]-3-phenylprop-2-en-1-one; 21550846: (E)-1-(2,4-Dihydroxyphenyl)-3-[4-[(2S,3S,4S,5R,6S)-3,4,5-trihydroxy-6-(hydroxymethyl)oxan-2-yl]oxyphenyl]prop-2-en-1-one; 21588269: 2-[[2-[[4-[(E)-3-Oxo-3-phenyl-1-propenyl]benzoyl]amino]-3-phenylpropanoyl] amino]-4-methylpentanoic acid; 21588270: 2-[[2-[[4-[(Z)-3-Oxo-3-phenyl-1-propenyl]benzoyl]amino]-3-phenylpropanoyl]amino]-4-methylpentanoic acid; 21722038: (E)-3-(4-Hydroxyphenyl)-1-(2-hydroxy-4-phenylmethoxyphenyl)prop-2-en-1-one; 21729319: 4,2',4'-Trihydroxy-6'-methoxychalcone 4-glucoside; 21769514: (E)-1-(2-Hydroxyphenyl)-3-(2,3,4,5-tetrahydro-1,6-benzodioxocin-8-yl)prop-2-en-1-one; 21770793: (E)-3-[(2R,3R)-2-(Hydroxy-methyl)-3-[3-methoxy-4-(methoxymethoxy)phenyl]-2,3-dihydro-1,4-benzodioxin-6-yl]-1-[2,4,6-tris(methoxymethoxy)phenyl]prop-2-en-1-one; 21787384: 2-Propen-1-one, 1-(2-hydroxyphenyl)-3-(4-methoxyphenyl)-; 21787385: (Z)-3-[4-(Dimethylamino)phenyl]-1-(2-hydroxyphenyl)prop-2-en-1-one; 21821084: (E)-3-(4-Bromo-3-nitro-phenyl)-1-(2-hydroxy-phenyl)prop-2-en-1-one; 21981083: 2-[[4-[(E)-3-(4-Thiophen-2-ylphenyl)prop-2-enoyl]phenyl]carbamoylamino]acetic acid; 21981106: 4-[3-(2-Methoxy-4-thiophen-2-yl-phenyl)-3-oxo-E-propenyl]-benzoic acid; 21999626: (E)-3-[4-(2,5-Dihydroxyphenoxy)phenyl]-1-phenylprop-2-en-1-one; 21999627: 3-[(E)-3-(4-Carboxyphenyl)-3-oxoprop-1-enyl] benzoic acid; 21999640: 2-[4-[(E)-3-Oxo-3-phenylprop-1-enyl]phenoxy]terephthalic acid; 21999642: (E)-3-[4-(2,6-Dihydroxyphenoxy)phenyl]-1-phenylprop-2-en-1-one; 21999645: 4-[(E)-3-Oxo-3-phenylprop-1-enyl]phthalic acid; 21999652: (E)-3-[4-(3,5-Dihydroxyphenoxy)phenyl]-1-phenylprop-2-en-1-one; 21999659: 2-[4-[(E)-3-Oxo-3-phenylprop-1-enyl]phenoxy]benzene-1,3-dicarboxylic acid; 21999662: 4-[4-[(E)-3-Oxo-3-phenylprop-1-enyl]phenoxy] benzene-1,3-dicarboxylic acid; 21999665: 5-[4-[(E)-3-Oxo-3-phenylprop-1-enyl]phenoxy]benzene-1,3-dicarboxylic acid; 21999666: (E)-3-[4-(2,4-Dihydroxyphenoxy)phenyl]-1-phenylprop-2-en-1-one; 22026667: 2-(2,4-Diaminophenyl)-2-[4-[(E)-3-oxo-3-phenylprop-1-enyl]phenyl]decanedioic acid; 22026693: 2-(2,4-Diamino-phenyl)-2-[4-[(E)-3-oxo-3-phenylprop-1-enyl]phenyl]octanedioic acid; 22026732: 6-[4-[(E)-3-Oxo-3-phenylprop-1-enyl]phenoxy]hexanoic acid; 22026762: 2-[4-[(E)-3-Oxo-3-phenylprop-1-enyl]phenyl]-2-(4-prop-1-en-2-ylphenyl)acetic acid; 22026855: 2-(2,4-Diaminophenyl)-2-[4-[(E)-3-oxo-3-phenylprop-1-enyl]phenyl]hexanedioic acid; 22026873: 6-[4-[(E)-3-(4-Fluorophenyl)-3-oxoprop-1-enyl]phenoxy]hexanoic acid; 22026912: 2-(4-Ethenylphenyl)-2-[4-[(E)-3-oxo-3-phenylprop-1-enyl]phenyl]acetic acid; 22087353: (E)-1-(2-Hydroxy-4,6-dimethylphenyl)-3-(4-methylphenyl)prop-2-en-1-one; 22263243: 2-(3,4-Dihydroxyphenyl)-3,5,7-trihydroxychromen-4-one;(E)-1,3-diphenylprop-2-en-1-one; 22297302: (2R,3S)-3-[5-[(E)-3-(2,4-Dihydroxyphenyl)-3-oxoprop-1-enyl]-2-hydroxy-phenyl]-5-hydroxy-2-(4-hydroxy-phenyl)-7-[3,4,5-trihydroxy-6-(hydroxymethyl)oxan-2-yl]oxy-2,3-dihydrochromen-4-one; 22297303: (2S,3R)-3-[5-[(E)-3-(2,4-Dihydroxyphenyl)-3-oxoprop-1-enyl]-2-hydroxyphenyl]-5-hydroxy-2-(4-hydroxyphenyl)-7-[3,4,5-trihydroxy-6-(hydroxymethyl)oxan-2-yl]oxy-2,3-dihydrochromen-4-one; 22297304: 3-[5-[(E)-3-(2,4-Dihydroxyphenyl)-3-oxoprop-1-enyl]-2-hydroxyphenyl]-5-hydroxy-2-(4-hydroxyphenyl)-7-[2-hydroxy-1-(1,3,4-trihydroxybutan-2-yloxy)propoxy]-2,3-dihydrochromen-4-one; 22357698: 4-[4-[(E)-3-Phenylprop-2-enoyl]phenyl]butanoic acid; 22402003: (E)-3-(3,4-Dimethylphenyl)-1-(4-hydroxyphenyl)prop-2-en-1-one; 22486553: (E)-1-(4-Fluorophenyl)-3-[4-(4-hydroxybutoxy)phenyl]prop-2-en-1-one; 22486559: (E)-1-(4-Fluorophenyl)-3-[4-(3-hydroxypropoxy)phenyl]prop-2-en-1-one; 22486560: (E)-3-(4-Fluorophenyl)-1-[4-(3-hydroxypropoxy)phenyl]prop-2-en-1-one; 22486566: (E)-1-(4-Fluorophenyl)-3-[4-(6-hydroxyhexoxy)phenyl]prop-2-en-1-one; 22486567: (E)-1-[4-(6-Hydroxyhexoxy)phenyl]-3-phenylprop-2-en-1-one; 22486574: (E)-3-(4-Fluorophenyl)-1-[4-(4-hydroxybutoxy)phenyl]prop-2-en-1-one; 22486583: (E)-3-(4-Fluorophenyl)-1-[4-(6-hydroxyhexoxy)phenyl]prop-2-en-1-one; 22486587: (E)-3-[4-(6-Hydroxyhexoxy)phenyl]-1-phenylprop-2-en-1-one; 22486588: (E)-1-[4-(3-Hydroxypropoxy)phenyl]-3-phenylprop-2-en-1-one; 22486594: (E)-3-[4-(4-Hydroxybutoxy)phenyl]-1-phenylprop-2-en-1-one; 22486595: (E)-3-[4-(3-Hydroxypropoxy)phenyl]-1-phenylprop-2-en-1-one; 22486596: (E)-1-[4-(4-Hydroxybutoxy)phenyl]-3-phenylprop-2-en-1-one; 22524310: (E)-1-[2,4-Dihydroxy-6-[(2S,3R,4R,5S,6R)-3,4,5-trihydroxy-6-(hydroxymethyl)oxan-2-yl]oxyphenyl]-3-(4-hydroxyphenyl)prop-2-en-1-one; 22524410: CID 22524410; 22605238: (E)-3-[3-Hydroxy-4-[(E)-3-(3-hydroxyphenyl)prop-2-enoyl]phenyl]prop-2-enoic acid; 22605244: 3-[4-[3-(Phenyl)propenoyl]phenyl]propenoic acid; 22607000: (E)-3-[4-(Dimethylamino)phenyl]-1-[4-(2-hydroxyethoxy)phenyl]prop-2-en-1-one; 22673750: (E)-1-(2-Amino-4,6-dimethoxyphenyl)-3-(4-hydroxyphenyl)prop-2-en-1-one; 22819973: N-[(2S,3R,4R,5S,6R)-2-[3,5-Dimethoxy-2-[(E)-3-(4-methoxyphenyl)prop-2-enoyl]phenoxy]-4,5-dihydroxy-6-(hydroxymethyl)oxan-3-yl] acetamide; 22942611: (E)-3-[4-(Hydroperoxymethyl)phenyl]-1-(4-hydroxyphenyl)prop-2-en-1-one; 23089829: (E)-1-(2,4-Diethoxy-6-hydroxy-phenyl)-3-(3,4-diethoxy-phenyl)prop-2-en-1-one; 23103543: 2-[2-[(E)-3-(4-Bromophenyl) prop-2-enoyl]-3-hydroxyphenoxy]acetic acid; 23103544: (E)-1-(2-Hydroxy-6-phenyl-methoxyphenyl)-3-(4-methylphenyl)prop-2-en-1-one; 23103545: 4-[(E)-3-(2-Hydroxy-6-phenylmethoxyphenyl)-3-oxoprop-1-enyl]benzoic acid; 23103551: 2-[2-[(E)-3-(4-Aceta-midophenyl)prop-2-enoyl]-3-hydroxyphenoxy]acetic acid; 23103580: (E)-1-(2-Hydroxy-6-phenylmethoxyphenyl)-3-(3-methylphenyl)prop-2-en-1-one; 23144947: 4'-Hydroxychalcone 4'-glucoside; 23169202: 2-[2-[(E)-3-(4-Tert-butylphenyl)prop-2-enoyl]-5-(3-methylbut-2-enoxy)phenoxy]propanoic acid; 23344827: 4-[(E)-3-(4-Chlorophenyl)prop-2-enoyl] benzoic acid; 23678803: 3-(Hydroxy-4-(3-hydroxy-4-methoxyphenyl)-1-oxo-2-propenyl) phenoxy)-1-propanesulfonic acid monopotassium salt; 23702020: Sodium;bis[3,5-dihydroxy-4-[(E)-3-(4-hydroxyphenyl)prop-2-enoyl]phenyl] phosphate; 23724744: Chalconaringenin 4'-glucoside; 23724745: 2',3,4,4',6'-Pentahydroxychalcone 4'-O-beta-D-glucoside; 23724747: Naringin chalcone; 23730300: 2'-Methoxy-4,4'-diacetoxy-6'-hydroxychalcone; 23806093: (E)-1-[2,4-Bis(ethoxymethoxy)-6-hydroxyphenyl]-3-phenylprop-2-en-1-one; 23930387: [(2R,3R,4S,5R,6S)-3,4,5-Trihydroxy-6-[3-hydroxy-4-[(E)-3-phenylprop-2-enoyl]phenoxy]oxan-2-yl]methyl 3,4,5-trihydroxybenzoate; 24203513: 4-Fluoro-N-4[-3-(4-hydroxy-phenyl)-acryloyl]- phenyl-benzen esulfonamide; 24208742: (2E)-1-(2,4-Dihydroxy-6-methoxyphenyl)-3-(4-hydroxyphenyl)prop-2-en-1-one, hyd rate; 24211943: (E)-1-[4-[(2S,4R,5S)-4,5-Dihydroxy-6-(hydroxymethyl)-3-[(2S,4S,5R)-3,4,5-trihydroxy-6-methyloxan-2-yl]oxyoxan-2-yl]oxy-2,6-dihydroxyphenyl]-3-(4-methoxyphenyl)prop-2-en-1-one; 24234295: (E)-3-(3-Hydroxy-4-methoxyphenyl)-1-(2-methoxy-4-methylphenyl)prop-2-en-1-one; 24238366: (E)-1-(4-Hydroxyphenyl)-3-[4-(trifluoromethoxy)phenyl]prop-2-en-1-one; 24280291: N-4-[(2E)-3-(4-Fluorophenyl)prop-2-enoyl]-3-hydroxyphenylacetamide; 24426073: 4-[(E)-3-[4-[2-(Diethylamino)-2-oxoethoxy]phenyl]-3-oxoprop-1-enyl]benzoic acid; 24426079: N,N-Diethyl-2-[4-[(E)-3-(3-hydroxy-4-methoxyphenyl)prop-2-enoyl]phenoxy]acetamide; 24426240: 2-[4-[(E)-3-(4-Acetamidophenyl)prop-2-enoyl]phenoxy]propanoic acid; 24426242: 2-[4-[(E)-3-(3-Nitrophenyl)prop-2-enoyl]phenoxy]propanoic acid; 24426243: 2-[4-[(E)-3-(4-Nitrophenyl)prop-2-enoyl]phenoxy]propanoic acid; 24426244: 2-[4-[(E)-3-(4-Chlorophenyl)prop-2-enoyl]phenoxy]propanoic acid; 24426246: 2-[4-[(E)-3-(2,3-Dihydro-1,4-benzodioxin-6-yl)prop-2-enoyl]phenoxy]propanoic acid; 24426247: 2-[4-[(E)-3-(4-Fluorophenyl)prop-2-enoyl]phenoxy]propanoic acid; 24426251: 2-[4-[(E)-3-(3,4-Dimethoxyphenyl)prop-2-enoyl]phenoxy]propanoic acid; 24426252: 2-[4-[(E)-3-(4-Methoxyphenyl)prop-2-enoyl]phenoxy]propanoic acid; 24426254: 2-[4-[(E)-3-[4-(Trifluoro-methyl)phenyl]prop-2-enoyl]phenoxy]propanoic acid; 24426255: 2-[4-[(E)-3-[4-(Difluoro-methoxy)phenyl]prop-2-enoyl]phenoxy]propanoic acid; 24426256: 2-[4-[(E)-3-(4-Ethoxy-3-methoxyphenyl)prop-2-enoyl]phenoxy]propanoic acid; 24426259: 2-[4-[(E)-3-(3-Fluoro-phenyl)prop-2-enoyl]phenoxy]propanoic acid; 24426260: 2-[4-[(E)-3-(3-Hydroxyphenyl) prop-2-enoyl]phenoxy]propanoic acid; 24426264: 2-[4-[(E)-3-(4-Chloro-3-nitro-phenyl)prop-2-enoyl]phenoxy]propanoic acid; 24426266: 2-[4-[(E)-3-(4-Cyanophenyl)prop-2-enoyl]phenoxy]propanoic acid; 24426267: 2-[4-[(E)-3-(4-Methylsulfanylphenyl)prop-2-enoyl]phenoxy]propanoic acid; 24426268: 2-[4-[(E)-3-(3-Methylphenyl)prop-2-enoyl]phenoxy]propanoic acid; 24426271: 2-[4-[(E)-3-(3-Hydroxy-4-methoxyphenyl)prop-2-enoyl]phenoxy]propanoic acid; 24426272: 2-[4-[(E)-3-[3-[(4-Methylbenzoyl)amino]phenyl]prop-2-enoyl]phenoxy]propanoic acid; 24426273: 2-[4-[(E)-3-[3-[(4-Methoxybenzoyl)amino]phenyl]prop-2-enoyl]phenoxy]propanoic acid; 24426274: 2-[4-[(E)-3-[4-(Difluoromethoxy)-3-methoxyphenyl]prop-2-enoyl]phenoxy]propanoic acid; 24426278: 2-[4-[(E)-3-(4-Prop-2-enoxyphenyl)prop-2-enoyl]phenoxy]propanoic acid; 24426279: 2-[4-[(E)-3-(3-Ethoxy-4-methoxyphenyl)prop-2-enoyl]phenoxy]propanoic acid; 24426282: 2-[4-[(E)-3-(3-Methoxy-4-prop-2-enoxyphenyl)prop-2-enoyl]phenoxy]propanoic acid; 24426283: 2-[4-[(E)-3-[4-(Methylamino)-3-nitro-phenyl]prop-2-enoyl]phenoxy]propanoic acid; 24426285: 2-[4-[(E)-3-[4-(Cyanomethoxy)-3-methoxyphenyl]prop-2-enoyl]phenoxy]propanoic acid; 24426287: 2-[4-[(E)-3-(4-Methyl-3-nitro-phenyl)prop-2-enoyl]phenoxy]propanoic acid; 24426297: 2-[4-[(E)-3-(3-Bromo-4-fluorophenyl)prop-2-enoyl]phenoxy]propanoic acid; 24426303: 2-[4-[(E)-3-[4-[2-(Ethylamino)-2-oxoethoxy]-3-methoxyphenyl]prop-2-enoyl]phenoxy]propanoic acid; 24426458: N-[3-[(E)-3-(4-Hydroxyphenyl)-3-oxoprop-1-enyl]phenyl]-4-methylbenzamide; 24426459: N-[3-[(E)-3-(4-Hydroxyphenyl)-3-oxoprop-1-enyl]phenyl]-4-methoxybenzamide; 24426460: N-(2-Chlorophenyl)-2-[4-[(E)-3-(4-hydroxyphenyl)-3-oxoprop-1-enyl]-2-methoxyphenoxy]acetamide; 24426461: (E)-1-(4-Hydroxyphenyl)-3-[4-(methylamino)-3-nitro-phenyl]prop-2-en-1-one; 24426554: (E)-3-(3-Hydroxy-4-methoxyphenyl)-1-(4-phenylphenyl)prop-2-en-1-one; 24427000: 4-[(E)-3-[4-[(4-Methylphenyl)sulfonylamino]phenyl]-3-oxoprop-1-enyl]benzoic acid; 24427004: 2-[4-[(E)-3-[4-[(4-Methylphenyl)sulfonylamino]phenyl]-3-oxoprop-1-enyl]phenoxy]acetic acid; 24429240: 2-[4-[(E)-3-(4-Ethoxy-phenyl)-3-oxoprop-1-enyl]phenoxy]acetic acid; 24429258: (E)-3-(3-Hydroxy-4-methoxy-phenyl)-1-(4-pyrrolidin-1-ylsulfonylphenyl)prop-2-en-1-one; 24501647: 2-[4-[(E)-3-Oxo-3-[4-(2-oxopyrrolidin-1-yl)phenyl]prop-1-enyl]phenoxy]acetic acid; 24561831: (E)-3-(3-Hydroxy-phenyl)-1-(2-methoxy-4-methylphenyl)prop-2-en-1-one; 24561845: 2-[4-[(E)-3-(2-Methoxy-4-methylphenyl)-3-oxoprop-1-enyl]phenoxy]acetic acid; 24583012: 2-[4-[(E)-3-(4-Methoxy-3-methylphenyl)prop-2-enoyl]phenoxy]propanoic acid; 24650374: 2-[[4-[(E)-3-[4-(Diethyl-amino)phenyl]prop-2-enoyl]phenyl]sulfonyl-methylamino]acetic acid; 24650375: 2-[[4-[(E)-3-(4-Bromophenyl)prop-2-enoyl]phenyl]sulfonyl-methylamino]acetic acid; 24650378: 2-[[4-[(E)-3-(3,4-Dichlorophenyl)prop-2-enoyl]phenyl]sulfonyl-methylamino]acetic acid; 24650379: 2-[[4-[(E)-3-(4-Butoxyphenyl)prop-2-enoyl]phenyl]sulfonyl-methylamino]acetic acid; 24650380: 2-[Methyl-[4-[(E)-3-(4-propan-2-ylphenyl)prop-2-enoyl]phenyl]sulfonylamino]acetic acid; 24650381: 2-[[4-[(E)-3-(3-Methoxy-4-phenylmethoxyphenyl)prop-2-enoyl]phenyl]sulfonyl-methylamino]acetic acid; 24650382: 2-[Methyl-[4-[(E)-3-(4-phenylmethoxy-phenyl)prop-2-enoyl]phenyl]sulfonylamino]acetic acid; 24650383: 2-[Methyl-[4-[(E)-3-(4-phenylphenyl)prop-2-enoyl]phenyl]sulfonylamino]acetic acid; 24650384: 2-[Methyl-[4-[(E)-3-(3-phenylmethoxyphenyl)prop-2-enoyl]phenyl]sulfonylamino]acetic acid; 24650386: 2-[[4-[(E)-3-(4-Tert-butylphenyl)prop-2-enoyl]phenyl]sulfonyl-methylamino]acetic acid; 24650387: 2-[[4-[(E)-3-[3-Methoxy-4-(3-methylbutoxy)phenyl]prop-2-enoyl]phenyl]sulfonyl-methylamino]acetic acid; 24650389: 2-[[4-[(E)-3-(4-Butoxy-3-methoxyphenyl)prop-2-enoyl]phenyl]sulfonyl-methylamino]acetic acid; 24650390: 2-[Methyl-[4-[(E)-3-(4-propoxyphenyl)prop-2-enoyl]phenyl]sulfonylamino]acetic acid; 24650391: 2-[Methyl-[4-[(E)-3-(4-methyl-3-nitro-phenyl)prop-2-enoyl]phenyl]sulfonylamino]acetic acid; 24650392: 2-[Methyl-[4-[(E)-3-naphthalen-2-ylprop-2-enoyl]phenyl]sulfonylamino]acetic acid; 24650393: 2-[Methyl-[4-[(E)-3-(3-nitro-4-propan-2-ylphenyl)prop-2-enoyl]phenyl]sulfonylamino]acetic acid; 24650397: 2-[[4-[(E)-3-(4-Butoxy-3-ethoxyphenyl)prop-2-enoyl]phenyl]sulfonyl-methylamino]acetic acid; 24650399: 2-[[4-[(E)-3-(3-Bromo-4-fluorophenyl)prop-2-enoyl]phenyl]sulfonyl-methylamino]acetic acid; 24650402: 2-[[4-[(E)-3-(4-Methoxy-3-propoxyphenyl)prop-2-enoyl]phenyl]sulfonyl-methylamino]acetic acid; 24650405: 2-[[4-[(E)-3-(3-Butoxy-4-methoxyphenyl)prop-2-enoyl]phenyl]sulfonyl-methylamino]acetic acid; 24650414: 2-[[4-[(E)-3-[4-[(2-Fluoro-phenyl)methoxy]phenyl]prop-2-enoyl]phenyl]sulfonyl-methylamino]acetic acid; 24650416: 2-[Methyl-[4-[(E)-3-[4-(trifluoromethylsulfanyl)phenyl]prop-2-enoyl]phenyl]sulfonylamino]acetic acid; 24650417: 2-[[4-[(E)-3-(4-Methoxy-3-methylphenyl)prop-2-enoyl]phenyl]sulfonyl-methylamino]acetic acid; 24721139: (E)-3-(4-Hydroxyphenyl)-1-[2-hydroxy-4-[(3R,4S,5S)-3,4,5-trihydroxy-6-(hydroxymethyl)oxan-2-yl]oxyphenyl]prop-2-en-1-one; 24721236: 3,6'-Dimethoxy-2'-hydroxychalcone; 24721580: (Z)-1-(2,6-Dihydroxy-4-methoxyphenyl)-3-phenylprop-2-en-1-one; 24757213: N-(4-(3-(4-Hydroxyphenyl) acryloyl)phenyl)-4-methyl-benzenesulfonamide; 24757297: 4"-(4-Fluorobenzensulfonamide)-4-hydroxychalcone; 24757298: 1-(4-Aminophenyl)-3-(3,4-dihydroxyphenyl)

prop-2-en-1-one; 24757299: Chembl4473242; 24757300: Chembl4532164; 24757301: Chembl4517640; 24757380: Chembl4450319; 24778333: 9-Tert-butyl-2-[(E)-3-(4-hydroxyphenyl)-3-oxoprop-1-enyl]-7,12-dihydro-5H-indolo[3,2-d][1]benzazepin-6-one; 24783506: 4-[(E)-3-[2-(Cyclohexyl-methoxy)-6-hydroxyphenyl]-3-oxoprop-1-enyl] benzoic acid; 24783763: N-[4-[(E)-3-[2-(Cyclohexylmethoxy)-6-hydroxyphenyl]-3-oxoprop-1-enyl]phenyl]acetamide; 24783766: 4-[(E)-3-[2-(Cyclohexylmethoxy)-6-hydroxyphenyl]-3-oxoprop-1-enyl]benzaldehyde; 24783767: 4-[(E)-3-(2-Hydroxy-6-phenylmethoxyphenyl)-3-oxoprop-1-enyl] benzenesulfonamide; 24822290: (E)-3-(3-Bromo-4-phenylmethoxyphenyl)-1-(2-hydroxyphenyl)prop-2-en-1-one; 24822295: (E)-3-(3-Tert-butyl-4-phenylmethoxyphenyl)-1-(2-hydroxyphenyl)prop-2-en-1-one; 24824472: (e)-3-(4-t-Butylphenyl)-1-(2-hydroxyphenyl)prop-2-en-1-one; 24824628: (E)-1-(2-Hydroxyphenyl)-3-[4-phenylmethoxy-3-(trifluoromethyl)phenyl]prop-2-en-1-one; 24824629: (E)-1-(2-Hydroxyphenyl)-3-(3-methyl-4-phenylmethoxyphenyl) prop-2-en-1-one; 24824632: (E)-1-(2-Hydroxyphenyl)-3-[3-(trifluoromethyl)phenyl]prop-2-en-1-one; 24827798: (E)-3-(3-Bromo-4-hydroxyphenyl)-1-phenylprop-2-en-1-one; 24828058: (E)-3-(3-Bromo-4-hydroxyphenyl)-1-[4-[(E)-3-(3-bromo-4-hydroxyphenyl)prop-2-enoyl]phenyl]prop-2-en-1-one; 24828069: (E)-3-(3-Fluorophenyl)-1-(2-hydroxy-4-methoxyphenyl)prop-2-en-1-one; 24828193: (E)-3-(3-Fluorophenyl)-1-(2-hydroxy-4,6-dimethoxyphenyl)prop-2-en-1-one; 24835148: 5-[(Z)-3-(2,4-Dihydroxyphenyl)-3-oxoprop-1-enyl]-2-hydroxybenzoic acid; 24836710: (Z)-3-(1,3-Benzodioxol-5-yl)-1-(4-fluoro-2-hydroxyphenyl)prop-2-en-1-one; 24863867: (11As)-8-(3-4-[(E)-3-(2-hydroxyphenyl)-3-oxo-1-propenyl]-2-methoxyphenoxy-propoxy)-7-methoxy-2,5,11a-tetrahydro-1H-benzo[e]pyrrolo[1,2-a][1,4]diazepin-5-one; 24905900: (E)-3-(4-Chlorophenyl)-1-[4-(2-hydroxyethoxy)phenyl]prop-2-en-1-one; 24986059: 2-[(1S)-5-[2-Chloro-4-[(E)-3-oxo-3-phenylprop-1-enyl]phenoxy]-2,3-dihydro-1H-inden-1-yl] acetic acid; 24986270: N-[4-[(E)-3-(3,4-Dihydroxyphenyl) prop-2-enoyl]phenyl]-3-fluorobenzenesulfonamide; 24986271: Chembl4465639; 24986272: Chembl4573131; 24986622: Chembl4465337; 24986623: Chembl4457134; 24986624: Chembl4454009; 24986625: Chembl4450134; 24986627: Chembl4441511; 24986984: Chembl4539374; 24986985: Chembl4466446; 24986986: Chembl4474665; 24986988: Chembl4450936; 24987341: Chembl4476764; 24988450: Chembl4580977; 24988451: 4"-(4-Hydroxyl-ben-zensulfonamide)-4-hydroxychalcone; 24988816: Chembl4555850; 24988821: Chembl4588834; 24988822: Chembl4569122; 24989185: Chembl4584944; 24989186: Chembl4436016; 24989561: Chembl4437356; 24989562: Chembl4516311; 24989564: Chembl4538458; 24989565: Chembl4442277; 24989566: 4"-(4-Nitrobenzensulfona-mide)-4-hydroxychalcone; 24989954: Chembl4446021; 24989955: Chembl4454343; 24989956: 4"-(4-Aminoben-zensulfonamide)-4-hydroxychalcone; 24989957: Chembl4458200; 24989958: Chembl4521942; 24989959: [4-[(E)-3-(4-Hydroxyphenyl)prop-2-enoyl]phenyl] 4-methylbenzenesulfonate; 24990330: [4-[(E)-3-(4-Hydroxyphenyl)prop-2-enoyl]phenyl] 4-fluorobenzenesulfonate; 24990331: Chembl4476360; 24990332: [4-[(E)-3-(4-Hydroxy-phenyl)prop-2-enoyl]phenyl] 4-nitrobenzene-sulfonate; 24990333: [4-[(E)-3-(4-Hydroxy-phenyl)prop-2-enoyl]phenyl] 4-aminobenzenesulfonate; 24990334: [4-[(E)-3-(4-Hydroxy-phenyl)prop-2-enoyl]phenyl] benzenesulfonate; 24990335: Chembl4528725; 24990680: Chembl4459498; 24990681: Chembl4451701; 24991051: Chembl4573075; 24991409: Chembl4471054; 24991762: Chembl4435713; 25021769: 4-Hydroxystyryl phenyl ketone; 25023350: (E)-1-[2-Hydroxy-4-methoxy-6-(methoxymethoxy)phenyl]-3-phenylprop-2-en-1-one; 25023351: 2'-Hydroxy-4'-methoxy-6'-(acetoxy)chalcone; 25112438: (E)-1-(2-Hydroxy-4-propan-2-yloxyphenyl)-3-phenylprop-2-en-1-one; 25113938: (E)-3-[3-[(7-Chloroquinolin-4-yl)amino]phenyl]-1-(4-hydroxyphenyl)prop-2-en-1-one; 25113940: (E)-3-(4-Chlorophenyl)-1-[4-[(7-chloroquinolin-4-yl)amino]phenyl]prop-2-en-1-one;2-hydroxypropane-1,2,3-tricarboxylic acid; 25114158: (E)-1-[4-[(7-Chloroquinolin-4-yl)amino]phenyl]-3-(4-fluorophenyl) prop-2-en-1-one;2-hydroxypropane-1,2,3-tricarboxylic acid; 25114160: (E)-3-[3-[(7-Chloroquinolin-4-yl)amino]phenyl]-1-(4-methoxyphenyl)prop-2-en-1-one; 2-hydroxypropane-1,2,3-tricarboxylic acid; 25114162: (E)-3-[3-[(7-Chloroquinolin-4-yl)amino]phenyl]-1-(2,4-dimethoxyphenyl)prop-2-en-1-one;2-hydroxypropane-1,2, 3-tricarboxylic acid; 25133226: (E)-3-(1,3-Benzodioxol-5-yl)-1-(2,4-dihydroxy-6-methoxyphenyl)prop-2-en-1-one; 25133577: (E)-3-(4-Hydroxy-3-methoxyphenyl)-1-[2-methoxy-4,6-bis(prop-2-enoxy)phenyl]prop-2-en-1-one; 25133927: (E)-3-(4-Hydroxyphenyl)-1-[2-methoxy-4,6-bis (prop-2-enoxy)phenyl]prop-2-en-1-one; 25137474: (E)-3-[3-(6-Azidohexoxy)-4-(methoxymethoxy)phenyl]-1-[2-hydroxy-4,6-bis(methoxymethoxy)phenyl]prop-2-en-1-one; 25148541: (E)-1-(2-Hydroxyphenyl)-3-[4-[4-(2-methoxyphenyl)piperazin-1-yl]phenyl]prop-2-en-1-one; 25148542: (E)-1-(2-Hydroxyphenyl)-3-[4-(4-pyridin-2-ylpiperazin-1-yl)phenyl]prop-2-en-1-one; 25148543: (2e)-1-(2-Hydroxyphenyl)-3-(6-methoxy-2-naphthyl)prop-2-en-1-one; 25170316: (E)-1-[2-Hydroxy-4,6-bis(methoxymethoxy) phenyl]-3-(4-iodophenyl)prop-2-en-1-one; 25172738: (E)-1-(2-Hydroxyphenyl)-3-naphthalen-2-ylprop-2-en-1-one; 25200812: Pentahydroxychalcone,2,4,6,3,4-(SH); 25201046: 1-(4-Hydroxy-2-methoxyphenyl)-3-(4-hydroxyphenyl)prop-2-en-1-one; 25209425: 3-Bromo-2'-hydroxy-4',6'-bis(methoxymethoxy)-trans-chalcone; 25213966: 4-[(E)-3-[4-[[1-(2-Ethoxyethyl)benzimidazol-2-yl]methoxy]phenyl]prop-2-enoyl]-3-hydroxybenzoic acid; 25213967: 4-[(E)-3-[3-[[1-(2-Ethoxyethyl)benzimidazol-2-yl]methoxy]phenyl]prop-2-enoyl]-3-hydroxybenzoic acid; 25256831: 3,4-Dibenzyloxy-2"-hydroxychalcone; 25266037: (E)-3-(4-Hydroxy-3-methoxyphenyl)-1-[4-(trifluoromethyl)phenyl]prop-2-en-1-one; 25266038: (E)-3-(3-Hydroxy-4-methoxyphenyl)-1-[4-(trifluoromethyl)phenyl] prop-2-en-1-one; 25394495: 2-[4-[(E)-3-[4-(Dimethylamino)phenyl]-3-oxoprop-1-enyl]-2-methoxyphenoxy]acetic acid; 25470133: (E)-1-(4-Hydroxyphenyl)-3-[4-(1,3-thiazol-4-ylmethoxy)phenyl] prop-2-en-1-one; 25484478: 5-[4-[(E)-3-(4-Acetamidophenyl)prop-2-enoyl]phenyl]furan-2-carboxylic acid; 25491363: 4-[(E)-3-[4-(3-Carboxypropoxy)phenyl]-3-oxoprop-1-enyl]benzoic acid; 25495359: 4-[[4-[(E)-3-(4-Cyanophenyl)prop-2-enoyl]phenyl]sulfonylamino]butanoic acid; 25496836: 4-[[4-[(E)-3-(3-Methylphenyl)prop-2-enoyl]phenyl]sulfonylamino]butanoic acid; 25520756: 3-[[4-[(E)-3-(3-Chlorophenyl)prop-2-enoyl]phenyl]sulfonylamino]propanoic acid; 25538253: (E)-3-(3-Hydroxyphenyl)-1-(4-thiophen-2-ylphenyl)prop-2-en-1-one; 25538256: (E)-3-(3-Hydroxy-4-methoxyphenyl)-1-(4-thiophen-2-ylphenyl)prop-2-en-1-one; 25613430: (E)-3-(4-Hydroxyphenyl)-1-(4-thiophen-2-ylphenyl)prop-2-en-1-one; 25624955: 2-[[4-[(E)-3-(4-Chloro-phenyl)prop-2-enoyl] phenyl]sulfonylamino]acetic acid; 25625408: 4-[4-[(E)-3-[3-Fluoro-4-(1,2,4-triazol-1-yl)phenyl]prop-2-enoyl]phenoxy]butanoic acid; 25686002: 2-[2-Ethoxy-4-[(E)-3-(4-hydroxyphenyl)-3-oxoprop-1-enyl]phenoxy]-N-[3-(trifluoromethyl)phenyl]acetamide; 25686197: 2-[4-[(E)-3-[4-(Diethylsulfamoyl)phenyl]-3-oxoprop-1-enyl]-2-methoxyphenoxy]acetic acid; 25694834: 3-[[4-[(E)-3-(3-Ethoxy-4-methoxyphenyl)prop-2-enoyl]phenyl]sulfonylamino]propanoic acid; 25707169: 1-[4-[(E)-3-(3-Ethoxy-4-methoxyphenyl)prop-2-enoyl]phenyl]sulfonylpiperidine-4-carboxylic acid; 25707821: 2-[2-Methoxy-4-[(E)-3-[4-(4-methylpiperidin-1-yl)sulfonylphenyl]-3-oxoprop-1-enyl]phenoxy]acetic acid; 25734982: 4-[4-[(E)-3-(3-Fluoro-4-methoxyphenyl)prop-2-enoyl]phenoxy]butanoic acid; 25756937: 2-[4-[(E)-3-(4-Acetamidophenyl)prop-2-enoyl]phenoxy]acetic acid; 25756939: 2-[4-[(E)-3-[3-[(E)-3-[4-(Carboxymethoxy)phenyl]-3-oxoprop-1-enyl]phenyl]prop-2-enoyl]phenoxy]acetic acid; 25756943: 2-[4-[(E)-3-(4-Nitrophenyl)prop-2-enoyl]phenoxy]acetic acid; 25756951: 2-[4-[(E)-3-(3-Methoxy-4-phenylmethoxyphenyl)prop-2-enoyl]phenoxy]acetic acid; 25756959: 2-[4-[(E)-3-(3-Hydroxyphenyl)prop-2-enoyl]phenoxy]acetic acid; 25756994: 2-[4-[(E)-3-[3-[(2-Chlorobenzoyl)amino]phenyl]prop-2-enoyl]phenoxy]acetic acid; 25756996: 2-[4-[(E)-3-[4-(2-Anilino-2-oxoethoxy)-3-ethoxyphenyl]prop-2-enoyl]phenoxy]acetic acid; 25757021: 2-[4-[(E)-3-(4-Butoxy-3-methoxyphenyl)prop-2-enoyl]phenoxy]acetic acid; 25757023: 2-[4-[(E)-3-(3-Methoxy-4-propoxyphenyl)prop-2-enoyl]phenoxy]acetic acid; 25757025: 2-[4-[(E)-3-(3-Methoxy-4-prop-2-enoxyphenyl)prop-2-enoyl]phenoxy]acetic acid; 25757054: 2-[4-[(E)-3-[4-(Cyanomethoxy)-3-methoxyphenyl]prop-2-enoyl]phenoxy]acetic acid; 25757062: 2-[4-[(E)-3-Naphthalen-2-ylprop-2-enoyl]phenoxy]acetic acid; 25759119: 2-[4-[(E)-3-[4-[2-[Di(propan-2-yl)amino]-2-oxoethoxy]-3-ethoxyphenyl]prop-2-enoyl]phenoxy]acetic acid; 25759595: 4-[4-[(E)-3-Phenylprop-2-enoyl]phenoxy]butanoic acid; 25759615: 4-[4-[(E)-3-[4-(Trifluoro-methyl)phenyl]prop-2-enoyl]phenoxy]butanoic acid; 25759619: 4-[4-[(E)-3-(3-Methoxy-phenyl)prop-2-enoyl]phenoxy]butanoic acid; 25759623: 4-[4-[(E)-3-(4-Ethoxyphenyl)prop-2-enoyl]phenoxy]butanoic acid; 25759625: 4-[4-[(E)-3-(4-Chloro-3-nitro-phenyl)prop-2-enoyl]phenoxy]butanoic acid; 25759629: 4-[4-[(E)-3-(4-Methylphenyl)prop-2-enoyl]phenoxy]butanoic acid; 25759633: 4-[4-[(E)-3-(4-Methylsulfanylphenyl)prop-2-enoyl]phenoxy]butanoic acid; 25759637: 4-[4-[(E)-3-(4-Methoxycarbonylphenyl)prop-2-enoyl]phenoxy]butanoic acid; 25759647: 4-[4-[(E)-3-(3-Bromo-4-methoxyphenyl)prop-2-enoyl]phenoxy]butanoic acid; 25759698: 2-[4-[(E)-3-[3-Methoxy-4-(4-methylphenyl)sulfonyloxyphenyl]prop-2-enoyl]phenoxy]acetic acid; 25759700: 2-[4-[(E)-3-(4-Methoxy-3-propoxyphenyl)prop-2-enoyl]phenoxy]acetic acid; 25759712: 2-[4-[(E)-3-(3-Butoxy-4-methoxyphenyl)prop-2-enoyl]phenoxy]acetic acid; 25760739: (2R)-2-[4-[(E)-3-(4-Nitrophenyl)prop-2-enoyl]phenoxy]propanoic acid; 25760741: (2S)-2-[4-[(E)-3-(4-Nitrophenyl)prop-2-enoyl]phenoxy]propanoic acid; 25760748: (2R)-2-[4-[(E)-3-(2,3-Dihydro-1,4-benzodioxin-6-yl)prop-2-enoyl]phenoxy]propanoic acid; 25760750: (2S)-2-[4-[(E)-3-(2,3-Dihydro-1,4-benzodioxin-6-yl)prop-2-enoyl]phenoxy]propanoic acid; 25760756: (2S)-2-[4-[(E)-3-(4-Methoxyphenyl) prop-2-enoyl]phenoxy]propanoic acid; 25760758: (2R)-2-[4-[(E)-3-(4-Methoxyphenyl)prop-2-enoyl]phenoxy]propanoic acid; 25760776: (2R)-2-[4-[(E)-3-(3-Hydroxyphenyl)prop-2-enoyl]phenoxy]propanoic acid; 25760778: (2S)-2-[4-[(E)-3-(3-Hydroxyphenyl)prop-2-enoyl]phenoxy]propanoic acid; 25760824: (2S)-2-[4-[(E)-3-(3-Hydroxy-4-methoxyphenyl) prop-2-enoyl]phenoxy]propanoic acid; 25760826: (2R)-2-[4-[(E)-3-(3-Hydroxy-4-methoxy-phenyl)prop-2-enoyl]phenoxy]propanoic acid; 25760866: 2-[[4-[(E)-3-(4-Methylsulfanyl-phenyl)prop-2-enoyl]phenyl]sulfonylamino]acetic acid; 25760872: 3-[[4-[(E)-3-(3-Nitrophenyl)prop-2-enoyl]phenyl]sulfonylamino]propanoic acid; 25760874: 3-[[4-[(E)-3-(4-Nitrophenyl)prop-2-enoyl]phenyl]sulfonylamino]propanoic acid; 25760878: 3-[[4-[(E)-3-(4-Bromophenyl)prop-2-enoyl]phenyl]sulfonylamino]propanoic acid; 25760880: 3-[[4-[(E)-3-(4-Chlorophenyl)prop-2-enoyl]phenyl]sulfonylamino]propanoic acid; 25760882: 3-[[4-[(E)-3-(2,3-Dihydro-1,4-benzodioxin-6-yl)prop-2-enoyl]phenyl]sulfonylamino]propanoic acid; 25760884: 3-[[4-[(E)-3-(4-Fluorophenyl)prop-2-enoyl]phenyl]sulfonylamino]propanoic acid; 25760886: 3-[[4-[(E)-3-(3-Bromophenyl)prop-2-enoyl]phenyl]sulfonylamino]propanoic acid; 25760890: 3-[[4-[(E)-3-(4-Methoxyphenyl)prop-2-enoyl]phenyl]sulfonylamino]propanoic acid; 25760892: 3-[[4-[(E)-3-[4-(Trifluoromethyl)phenyl]prop-2-enoyl]phenyl]sulfonylamino]propanoic acid; 25760896: 3-[[4-[(E)-3-(3,4-Dichlorophenyl)prop-2-enoyl]phenyl]sulfonylamino]propanoic acid; 25760898: 3-[[4-[(E)-3-[4-(Difluoromethoxy)phenyl]prop-2-enoyl]phenyl]sulfonylamino]propanoic acid; 25760902: 3-[[4-[(E)-3-(3-Fluorophenyl)prop-2-enoyl]phenyl]sulfonylamino]propanoic acid; 25760904: 3-[[4-[(E)-3-(3-Hydroxyphenyl)prop-2-enoyl]phenyl]sulfonylamino]propanoic acid; 25760908: 3-[[4-[(E)-3-(4-Phenylmethoxy-phenyl)prop-2-enoyl]phenyl]sulfonylamino]propanoic acid; 25760914: 3-[[4-[(E)-3-(4-Chloro-3-nitro-phenyl)prop-2-enoyl]phenyl]sulfonylamino]propanoic acid; 25760916: 3-[[4-[(E)-3-(4-Cyanophenyl)prop-2-enoyl]phenyl]sulfonylamino]propanoic acid; 25760918: 3-[[4-[(E)-3-(4-Methylsulfanylphenyl)prop-2-enoyl]phenyl]sulfonylamino]propanoic acid; 25760922: 3-[[4-[(E)-3-(3-Methylphenyl)prop-2-enoyl]phenyl]sulfonylamino]propanoic acid; 25760924: 3-[[4-[(E)-3-(4-Ethylphenyl)prop-2-enoyl]phenyl]sulfonylamino]propanoic acid; 25760926: 3-[[4-[(E)-3-(3-Phenylmethoxyphenyl)prop-2-enoyl]phenyl]sulfonylamino]propanoic acid; 25760930: 3-[[4-[(E)-3-(3-Hydroxy-4-methoxyphenyl)prop-2-enoyl]phenyl]sulfonylamino]propanoic acid; 25760932: 3-[[4-[(E)-3-(4-Methoxycarbonylphenyl)prop-2-enoyl]phenyl]sulfonylamino]propanoic acid; 25760936: 3-[[4-[(E)-3-(4-Methoxy-3-phenylmethoxyphenyl) prop-2-enoyl]phenyl]sulfonylamino]propanoic acid; 25760938: 3-[[4-[(E)-3-(4-Tert-butylphenyl)prop-2-enoyl]phenyl]sulfonylamino]propanoic acid; 25760948: 3-[[4-[(E)-3-(3-Bromo-4-fluorophenyl)prop-2-enoyl]phenyl]sulfonylamino]propanoic acid; 25761173: 4-[[4-[(E)-3-(3-Hydroxyphenyl)prop-2-enoyl]phenyl]sulfonylamino]benzoic acid; 25762130: 3-[[4-[(E)-3-Phenylprop-2-enoyl]phenyl]sulfonylamino]propanoic acid; 25762134: 3-[[4-[(E)-3-(4-Acetamidophenyl)prop-2-enoyl]phenyl]sulfonylamino]propanoic acid; 25762136: 3-[[4-[(E)-3-[4-(Diethylamino)phenyl]prop-2-enoyl]phenyl]sulfonylamino]propanoic acid; 25762144: 3-[[4-[(E)-3-(4-Morpholin-4-ylphenyl)prop-2-enoyl]phenyl]sulfonylamino]propanoic acid; 25762146: 3-[[4-[(E)-3-(3,4-Dimethoxyphenyl)prop-2-enoyl]phenyl]sulfonylamino]propanoic acid; 25762150: 4-[(E)-3-[4-(2-Carboxyethylsulfamoyl)phenyl]-3-oxoprop-1-enyl]benzoic acid; 25762152: 3-[[4-[(E)-3-(4-Propan-2-ylphenyl)prop-2-enoyl]phenyl]sulfonylamino]propanoic acid; 25762154: 3-[[4-[(E)-3-(3-Methoxy-4-phenylmethoxyphenyl)prop-2-enoyl]phenyl]sulfonylamino]propanoic acid; 25762165: 3-[[4-[(E)-3-(4-Methylphenyl)prop-2-enoyl]phenyl]sulfonylamino]propanoic acid; 25762171: 3-[[4-[(E)-3-(3,4-Difluorophenyl)prop-2-enoyl]phenyl]sulfonylamino]propanoic acid; 25762193: 3-[[4-[(E)-3-Naphthalen-2-ylprop-2-enoyl]phenyl]sulfonylamino]propanoic acid; 25762201: 3-[[4-[(E)-3-(6-Methoxynaphtha-len-2-yl)prop-2-enoyl]phenyl]sulfonylamino]propanoic acid; 25978995: 4-[4-[(E)-3-(3-Cyanophenyl)prop-2-enoyl]phenoxy]butanoic acid; 25979514: 2-[4-[(E)-3-(3-Cyanophenyl) prop-2-enoyl]phenoxy]acetic acid; 25979795: 3-[[4-[(E)-3-(3-Cyanophenyl) prop-2-enoyl]phenyl]sulfonylamino]propanoic acid; 27102909: (E)-1-(2,4-Difluorophenyl)-3-(4-hydroxy-3-nitro-phenyl)prop-2-en-1-one; 27105027: (E)-3-(3-Bromo-4-hydroxyphenyl)-1-[4-(dimethyl-amino)phenyl]prop-2-en-1-one; 27105323: (E)-3-(3-Hydroxy-4-methoxyphenyl)-1-(4-propan-2-yloxyphenyl)prop-2-en-1-one; 27105954: 3-[[4-[(E)-3-(4-Prop-2-enoxyphenyl) prop-2-enoyl]phenyl]sulfonylamino]propanoic acid; 27111868: (E)-3-(3-Bromo-4-hydroxy-phenyl)-1-(4-methylphenyl)prop-2-en-1-one; 27111894: (E)-3-(3-Bromo-4-hydroxyphenyl)-1-(2,4-dimethoxyphenyl)prop-2-en-1-one; 27111978: 2-[2-Ethoxy-4-[(E)-3-(4-hydroxy-phenyl)-3-oxoprop-1-enyl]phenoxy]-N,N-di(propan-2-yl)acetamide; 27111981: (E)-3-(3-Bromo-4-hydroxyphenyl)-1-(4-hydroxyphenyl)prop-2-en-1-one; 27111984: 2-[4-[(E)-3-(4-Hydroxyphenyl)-3-oxoprop-1-enyl]-2-methoxyphenoxy]acetic acid; 27112001: (E)-3-(3-Ethoxy-4-hydroxyphenyl)-1-(4-nitro-phenyl)prop-2-en-1-one; 27112021: (E)-3-(4-Hydroxy-3-nitro-phenyl)-1-(4-nitro-phenyl)prop-2-en-1-one; 27112037: (E)-3-(3-Bromo-4-hydroxy-phenyl)-1-(4-nitro-phenyl)prop-2-en-1-one; 27112078: (E)-3-(3-Bromo-4-hydroxyphenyl)-1-(4-chlorophenyl)prop-2-en-1-one; 27112222: 4-[(E)-3-(4-Hydroxy-3-nitro-phenyl)prop-2-enoyl]benzonitrile; 27112253: 4-[(E)-3-(3-Bromo-4-hydroxyphenyl)prop-2-enoyl]benzonitrile; 27112884: (E)-3-(3-Bromo-4-hydroxyphenyl)-1-(4-fluorophenyl)prop-2-en-1-one; 27128219: (E)-1-[4-(5,6-Dihydro-4H-1,3-thiazin-2-ylamino)phenyl]-3-(4-hydroxy-3-nitro-phenyl)prop-2-en-1-one; 27818393: (E)-3-(3-Fluoro-4-methoxyphenyl)-1-(4-hydroxyphenyl)prop-2-en-1-one; 28021641: 1-[4-[(E)-3-(3-Bromo-4-hydroxyphenyl)prop-2-enoyl]phenyl]pyrrolidin-2-one; 29176726: Chembl4577143; 29217810: 2-[4-[(E)-3-(4-Prop-2-enoxyphenyl)prop-2-enoyl]phenoxy]acetic acid; 29356520: N,N-Diethyl-2-[4-[(E)-3-(4-hydroxy-3-nitro-phenyl)prop-2-enoyl]phenoxy]acetamide; 29403972: (E)-1-(4-Ethoxyphenyl)-3-(4-hydroxy-3-nitro-phenyl) prop-2-en-1-one; 29429630: (2S)-2-[4-[(E)-3-[4-(Methylamino)-3-nitrophenyl]prop-2-enoyl]phenoxy]propanoic acid; 29429635: (2R)-2-[4-[(E)-3-[4-(Methylamino)-3-nitro-phenyl]prop-2-enoyl]phenoxy]propanoic acid; 29939239: (E)-3-(3,4-Dimethoxyphenyl)-1-(2-hydroxy-6-methoxy-4-phenyl-methoxyphenyl)prop-2-en-1-one; 29974243: 3-[3,4-Bis(ethoxy-methoxy)phenyl]-1-[2-hydroxy-4,6-bis(ethoxymethoxy)phenyl]-2-propen-1-one; 30228820: 4-[(E)-3-(3-Bromo-4-hydroxyphenyl)prop-2-enoyl]-N,N-diethylbenzenesulfonamide; 30883998: 4-[4-[(E)-3-(3-Nitrophenyl)prop-2-enoyl]phenoxy]butanoic acid; 30884000: 4-[4-[(E)-3-(4-Nitrophenyl)prop-2-enoyl]phenoxy]butanoic acid; 30884002: 4-[4-[(E)-3-(4-Bromo-phenyl)prop-2-enoyl]phenoxy]butanoic acid; 30884004: 4-[4-[(E)-3-(4-Chlorophenyl)prop-2-enoyl]phenoxy]butanoic acid; 30884006: 4-[4-[(E)-3-(4-Fluorophenyl)prop-2-enoyl]phenoxy]butanoic acid; 30884008: 4-[4-[(E)-3-(3-Bromophenyl)prop-2-enoyl]phenoxy]butanoic acid; 30884010: 4-[4-[(E)-3-(4-Methoxyphenyl)prop-2-enoyl]phenoxy]butanoic acid; 30884014: 4-[4-[(E)-3-(3-Chlorophenyl)prop-2-enoyl]phenoxy]butanoic acid; 30884018: 4-[4-[(E)-3-(3-Fluorophenyl)prop-2-enoyl]phenoxy]butanoic acid; 30884020: 4-[4-[(E)-3-(3-Hydroxyphenyl) prop-2-enoyl]phenoxy]butanoic acid; 30884028: 4-[4-[(E)-3-(4-Cyanophenyl)prop-2-enoyl]phenoxy]butanoic acid; 30884030: 4-[4-[(E)-3-(3-Methylphenyl)prop-2-enoyl]phenoxy]butanoic acid; 30884036: 4-[4-[(E)-3-(3,4-Difluorophenyl)prop-2-enoyl]phenoxy]butanoic acid; 30884056: 4-[4-[(E)-3-(4-Methyl-3-nitro-phenyl)prop-2-enoyl]phenoxy]butanoic acid; 30884220: (E)-1-(4-Ethoxyphenyl)-3-(4-hydroxy-3-methoxyphenyl)prop-2-en-1-one; 30884223: (E)-3-(3-Ethoxy-4-hydroxyphenyl)-1-(4-ethoxyphenyl)prop-2-en-1-one; 30884230: (E)-3-(3-Bromo-4-hydroxyphenyl)-1-(4-ethoxyphenyl)prop-2-en-1-one; 30884281: 2-[4-[(E)-3-(3-Bromo-4-hydroxyphenyl)prop-2-enoyl]phenoxy]acetonitrile; 31323845: 3-[[4-[(E)-3-[4-(Difluoromethoxy)-3-methoxyphenyl]prop-2-enoyl]phenyl]sulfonylamino]propanoic acid; 31323851: 3-[[4-[(E)-3-[4-(Methylamino)-3-nitro-phenyl]prop-2-enoyl]phenyl]sulfonylamino]propanoic acid; 31323853: 3-[[4-[(E)-3-(3-Nitro-4-propan-2-ylphenyl)prop-2-enoyl]phenyl]sulfonylamino]propanoic acid; 31473028: 2-[2-Methoxy-4-[(E)-3-oxo-3-(4-phenyl-methoxyphenyl)prop-1-enyl]phenoxy]acetic acid; 31473593: (E)-3-(3-Ethoxy-4-hydroxyphenyl)-1-(4-propan-2-yloxyphenyl)prop-2-en-1-one; 31473827: 3-[[4-[(E)-3-(4-Butoxyphenyl)prop-2-enoyl]phenyl]sulfonylamino]propanoic acid; 31473842: 3-[[4-[(E)-3-[3-Methoxy-4-(3-methylbutoxy)phenyl]prop-2-enoyl]phenyl]sulfonylamino]propanoic acid; 31473845: 3-[[4-[(E)-3-(4-Butoxy-3-methoxyphenyl)prop-2-enoyl]phenyl]sulfonylamino]propanoic acid; 31473848: 3-[[4-[(E)-3-(3-Methoxy-4-prop-2-enoxyphenyl)prop-2-enoyl]phenyl]sulfonylamino]propanoic acid; 31473851: 3-[[4-[(E)-3-(4-Propoxyphenyl)prop-2-enoyl]phenyl]sulfonylamino]propanoic acid; 31473857: 3-[[4-[(E)-3-(4-Butoxy-3-ethoxy-phenyl)prop-2-enoyl]phenyl]sulfonylamino]propanoic acid; 31473860: 3-[[4-[(E)-3-(4-Methoxy-3-propoxyphenyl)prop-2-enoyl]phenyl]sulfonylamino]propanoic acid; 31473869: 3-[[4-[(E)-3-(3-Butoxy-4-methoxyphenyl)prop-2-enoyl]phenyl]sulfonylamino]propanoic acid; 31577912: (E)-3-(3-Hydroxy-4-methoxyphenyl)-1-(4-methylsulfanylphenyl)prop-2-en-1-one; 32354057: 2-[[4-[(E)-3-(3-Chlorophenyl)prop-2-enoyl]phenyl]sulfonyl-methylamino]acetic acid; 36074208: (E)-3-(4-Hydroxy-3-nitro-phenyl)-1-(4-morpholin-4-ylsulfonylphenyl)prop-2-en-1-one; 36074981: (E)-1-(2,4-Dimethylphenyl)-3-(4-hydroxy-3-methoxyphenyl)prop-2-en-1-one; 36074997: Chembl4168220; 38355910: Dtxsid20904218; 38864605: (E)-1-(4-Hydroxyphenyl)-3-(4-pyrrolidin-1-ylphenyl)prop-2-en-1-one; 39310154: 1-[4-[(E)-3-(4-Hydroxy-3-nitro-phenyl)prop-2-enoyl]phenyl]-3-propan-2-ylurea; 39315921: 1-[4-[(E)-3-(3-Bromo-4-hydroxyphenyl)prop-2-enoyl]phenyl]-3-propan-2-ylurea; 39380339: 3-Hydroxy-4'-tert-butylchalcone; 39381962: (E)-1-(4-Ethylphenyl)-3-(4-hydroxy-3-methoxyphenyl)prop-2-en-1-one; 39384271: (E)-3-(4-Hydroxy-3-methoxyphenyl)-1-(2-methoxyphenyl)prop-2-en-1-one; 39384272: (E)-3-(3-Hydroxy-4-methoxyphenyl)-1-(2-methoxyphenyl)prop-2-en-1-one; 39734996: (2E)-1-[4-(Benzyloxy)-2-hydroxyphenyl]-3-(3-fluorophenyl)prop-2-en-1-one; 39735007: N-4-[(2E)-3-(4-Ethoxyphenyl)prop-2-enoyl]-3-hydroxyphenylacetamide; 39735014: N-3-Hydroxy-4-[(2E)-3-(4-methylphenyl)prop-2-enoyl]phenylacetamide; 39735015: N-4-[(2E)-3-(4-Tert-butylphenyl)prop-2-enoyl]-3-hydroxyphenylacetamide; 39735019: N-3-Hydroxy-4-[(2E)-3-(3-methylphenyl)prop-2-enoyl]phenylacetamide; 40030760: 4-[(E)-3-(4-Methylsulfanylphenyl)-3-oxoprop-1-enyl]benzoic acid; 40030770: (E)-3-(3-Ethoxy-4-hydroxyphenyl)-1-(4-methylsulfanylphenyl)prop-2-en-1-one; 40030782: (E)-3-(4-Hydroxy-3-nitro-phenyl)-1-(4-methylsulfanylphenyl)prop-2-en-1-one; 40030816: (E)-3-(3-Bromo-4-hydroxyphenyl)-1-(4-methylsulfanylphenyl)prop- 2-en-1-one; 40154096: 2-[4-[(E)-3-(3-Cyanophenyl)prop-2-enoyl]phenyl]acetic acid; 40154100: 2-[4-[(E)-3-(4-Ethylphenyl) prop-2-enoyl]phenyl]acetic acid; 40154102: 2-[4-[(E)-3-(4-Ethoxy-3-methoxyphenyl)prop-2-enoyl]phenyl]acetic acid; 40492949: (Z)-3-(3,4-Dihydroxyphenyl)-1-(2-hydroxyphenyl)prop-2-en-1-one; 40604487: (E)-1-(4-Hydroxyphenyl)-3-(4-prop-2-enoxyphenyl)prop-2-en-1-one; 40606299: 2-Chloro-N-[3-[(E)-3-(4-hydroxyphenyl)-3-oxoprop-1-enyl]phenyl]benzamide; 40613624: 2-[4-[(E)-3-(4-Butoxyphenyl)prop-2-enoyl]phenoxy]acetic acid; 41928134: 3-[[4-[(E)-3-[3-[(2,2,2-Trifluoroacetyl)amino]phenyl]prop-2-enoyl]phenyl]sulfonylamino]propanoic acid; 42603440: Arenariumoside III; 42607522: Isoliquiritigenin 4,4'-diglucoside; 42607523: Isoliquiritigenin 2'-glucosyl-(1→4)-rhamnoside; 42607524: Monospermoside; 42607525: Isoliquiritigenin 4'-O-glucoside 4-O-apiofuranosyl-(1'''→2''')-glucoside; 42607526: Isoliquiritigenin 4-O-(5'''-O-p-coumaroyl)-apiofuranosyl-(1'''→2''')-glucoside; 42607527: Isoliquiritigenin 4-O-(5'''-O-feruloyl)-apiofuranosyl-(1'''→2''')-glucoside; 42607543: Butein 3,2'-diglucoside; 42607544: Butein 4'-arabinosyl-(1→4)-galactoside; 42607545: Homobutein 4-glucoside; 42607583: 4,2'-Dihydroxychalcone 4-glucoside; 42607585: 3,4-Dihydroxychalcone 4-beta-L-arabinopyranosyl-(1→4)-galactoside; 42607601: Chalconaringenin 4-glucoside; 42607602: Chalconaringenin 2'-(6''-p-coumarylglucoside); 42607603: Chalconaringenin 2'-xyloside; 42607604: Chalconaringenin 2'-rhamnosyl-(1→4)-xyloside; 42607605: Chalconaringenin 2'-rhamnosyl-(1→4)-glucoside; 42607606: Chalconaringenin 2',4'-di-O-glucoside; 42607607: Chalconaringenin 2'-O-glucoside 4'-O-gentobioside; 42607608: 4,2',6'-Trihydroxy-4'-prenyloxychalcone; 42607611: 3,4,2',4',6'-Pentahydroxychalcone 2'-glucoside; 42607612: 3,4,2',4',6'-Pentahydroxychalcone 4'-glucoside; 42607615: Homoeriodictyolchalcone 2'-glucoside; 42607621: Helichrysin; 42607622: 4,2',4'-Trihydroxy-6'-methoxychalcone 4,4'-di-beta-glucoside; 42607623: Helichrysetin 4,4'-di-O-alpha-glucoside; 42607625: 3,4',6'-Trihydroxy-4,2'-dimethoxychalcone 4'-O-rutinoside; 42607626: 4,2',6'-Trihydroxy-3,4'-dimethoxychalcone; 42607627: 4,2'-Dihydroxy-4',6'-dimethoxychalcone 4-O-(5'''-O-p-cinnamoyl)-apiofuranosyl-(1'''→2''')-glucoside; 42618000: Substituted chalcone, 5b; 42618001: Substituted chalcone, 5e; 42618002: Substituted chalcone, 5n; 42618003: Substituted chalcone, 5c; 42618004: Substituted chalcone, 5d; 42631416: (E)-1-(2,4-Dihydroxyphenyl)-3-(2,2-dimethyl-3,4-dihydrochromen-6-yl)prop-2-en-1-one; 42642669: (E)-1-[2-Hydroxy-6-(isopentyloxy)phenyl]-3-(4-hydroxyphenyl)-2-propene-1-one; 42992366: (E)-3-(3-Hydroxy-4-methoxyphenyl)-1-(4-morpholin-4-ylsulfonylphenyl)prop-2-en-1-one; 42999228: 4-[(E)-3-[4-(1-Carboxyethoxy)phenyl]-3-oxoprop-1-enyl]benzoic acid; 42999229: 2-[4-[(E)-3-(4-Methylphenyl)prop-2-enoyl]phenoxy]propanoic acid; 42999232: 2-[4-[(E)-3-(3,4-Difluorophenyl)prop-2-enoyl]phenoxy]propanoic acid; 42999234: 2-[4-[(E)-3-[3-[(2-Chlorobenzoyl)amino]phenyl]prop-2-enoyl]phenoxy]propanoic acid; 42999235: 2-[4-[(E)-3-[4-(2-Anilino-2-oxoethoxy)-3-ethoxyphenyl]prop-2-enoyl]phenoxy]propanoic acid; 42999238: 3-[[4-[(E)-3-(3-Methoxyphenyl)prop-2-enoyl]phenyl]sulfonylamino]propanoic acid; 42999239: 3-[[4-[(E)-3-[3-[(4-Methylbenzoyl)amino]phenyl]prop-2-enoyl]phenyl]sulfonylamino]propanoic acid; 42999242: 3-[[4-[(E)-3-[3-(Difluoromethoxy)-4-methoxyphenyl]prop-2-enoyl]phenyl]sulfonylamino]propanoic acid; 43068075: 1-[4-[(E)-3-(3-Hydroxyphenyl)prop-2-enoyl]phenyl]-3-propan-2-ylurea; 43068079: 4-[(E)-3-Oxo-3-[4-(propan-2-ylcarbamoylamino)phenyl]prop-1-enyl]benzoic acid; 43071503: 2-[4-[(E)-3-Oxo-3-[4-(propan-2-ylcarbamoylamino)phenyl]prop-1-enyl]phenoxy]acetic acid; 43071511: 2-[2-Methoxy-4-[(E)-3-oxo-3-[4-(propan-2-ylcarbamoylamino)phenyl]prop-1-enyl]phenoxy]acetic acid; 44118898: (Z)-3-(3,4-Dihydro-2H-1,5-benzodioxepin-7-yl)-1-[2-hydroxy-4-(methoxymethoxy)phenyl]prop-2-en-1-one; 44350601: 3-(3,4-Dihydroxy-phenyl)-1-(2-pyridin-3-yl-phenyl)-propenone; 44350602: 3-(3,4-Dihydroxy-phenyl)-1-(2-thiophen-2-yl-phenyl)-propenone; 44350736: 2'-Trifluoromethyl-3,4-dihydroxychalcone; 44356454: Sodium;2-[3,5-dihydroxy-4-[(E)-3-(3-hydroxy-4-methoxyphenyl)prop-2-enoyl]phenoxy]acetate; 44356455: 2-[3,5-Dihydroxy-4-[(E)-3-(3-hydroxy-4-methoxyphenyl)prop-2-enoyl]phenoxy]acetic acid; 44356456: Sodium;2-[3-hydroxy-4-[(E)-3-(3-hydroxy-4-methoxyphenyl)prop-2-enoyl]phenoxy]acetate; 44356457: 2-[3-Hydroxy-4-[(E)-3-(3-hydroxy-4-methoxyphenyl)prop-2-enoyl]phenoxy]acetic acid; 44404712: (E)-3-(3-Methoxy-4-phenylmethoxyphenyl)-1-(2,4,6-trihydroxyphenyl)prop-2-en-1-one; 44404713: (E)-3-[4-(Dimethylamino)phenyl]-1-(2,4,6-trihydroxyphenyl)prop-2-en-1-one; 44421707: 3-[(E)-3-[2-(Cyclohexylmethoxy)-6-hydroxyphenyl]-3-oxoprop-1-enyl]benzoic acid; 44421710: (E)-1-[2-(Cyclohexylmethoxy)-6-hydroxyphenyl]-3-phenylprop-2-en-1-one; 44421711: (E)-3-(4-Chlorophenyl)-1-[2-(cyclohexylmethoxy)-6-hydroxyphenyl]prop-2-en-1-one; 44421717: (E)-3-(4-Aminophenyl)-1-[2-(cyclohexylmethoxy)-6-hydroxyphenyl]prop-2-en-1-one; 44421724: (E)-1-[2-(Cyclohexylmethoxy)-6-hydroxyphenyl]-3-(4-ethylphenyl)prop-2-en-1-one; 44421725: (E)-1-[2-(Cyclohexylmethoxy)-6-hydroxyphenyl]-3-[4-(hydroxymethyl)phenyl]prop-2-en-1-one; 44421735: 4-[(E)-3-Oxo-3-(2-phenylmethoxyphenyl)prop-1-enyl]benzoic acid; 44421762: (E)-1-[2-(Cyclohexylmethoxy)-6-hydroxyphenyl]-3-(4-hydroxy-phenyl)prop-2-en-1-one; 44421763: (E)-1-[2-(Cyclohexylmethoxy)-6-hydroxyphenyl]-3-[4-(methoxymethoxy)phenyl]prop-2-en-1-one; 44421769: (E)-1-[4-(Cyclohexylmethoxy)-2-hydroxyphenyl]-3-(4-hydroxyphenyl)prop-2-en-1-one; 44421771: 4-[(E)-3-(2-Hydroxy-4-phenylmethoxyphenyl)-3-oxoprop-1-enyl]benzoic acid; 44421775: Methyl 4-[(E)-3-[2-(cyclohexylmethoxy)-6-hydroxyphenyl]-3-oxoprop-1-enyl]benzoate; 44421776: 4-[(E)-3-[4-(Cyclohexylmethoxy)-2-hydroxyphenyl]-3-oxoprop-1-enyl]benzoic acid; 44428599: (E)-3-[4-(Hexyloxy)phenyl]-1-(2-hydroxyphenyl)prop-2-en-1-one; 44428600: (E)-1-(2-Hydroxy-phenyl)-3-(4-nonoxyphenyl)prop-2-en-1-one; 44428602: 1-(2-Hydroxyphenyl)-3-(4-amino-phenyl)-2-propene-1-one; 44428603: 2'-Hydroxy-3-methoxy-4-(benzyloxy)chalcone; 44428604: (E)-1-(2-Hydroxyphenyl)-3-(3-iodo-4-methoxyphenyl)prop-2-en-1-one; 44428605: (E)-1-(2-Hydroxyphenyl)-3-(3-iodo-4-phenylmethoxyphenyl)prop-2-en-1-one; 44428614: 3,4,2'-Trihydroxy-4',6'-dimethoxychalcone; 44428615: (E)-1-(4-Butoxy-2-hydroxyphenyl)-3-(4-butoxyphenyl)prop-2-en-1-one; 44429050: (E)-3-(4-Hydroxy-3-methoxyphenyl)-1-(4-trimethylsilylphenyl)prop-2-en-1-one; 44435754: [2-Methoxy-4-[(E)-3-oxo-3-phenylprop-1-enyl]phenyl] (2S,4aS,6aR,6aS,6bR,8aR,10S,12aS,14bR)-10-hydroxy-2,4a,6a,6b,9,9,12a-heptamethyl-13-oxo-3,4,5,6,6a,7,8,8a,10,11,12,14b-dodecahydro-1H-picene-2-carboxylate; 44435756: [2-Methoxy-5-[(E)-3-oxo-3-phenylprop-1-enyl]phenyl](2S,4aS,6aR,6aS,6bR,8aR,10S,12aS,14bR)-10-hydroxy-2,4a,6a,6b,9,9,12a-heptamethyl-13-oxo-3,4,5,6,6a,7,8,8a,10,11,12,14b-dodecahydro-1H-picene-2-carboxylate; 44437282: (E)-3-(4-Hydroxyphenyl)-1-(4-(1251)iodanylphenyl)prop-2-en-1-one; 44439635: (E)-3-[3-[2-Hydroxy-3-(2-methylpropylamino)propoxy]

phenyl]-1-phenylprop-2-en-1-one; 44439636: (E)-3-[3-[3-(Tert-butylamino)-2-hydroxypropoxy]phenyl]-1-phenylprop-2-en-1-one; 44439637: (E)-3-[3-[2-Hydroxy-3-(4-phenylpiperazin-1-yl)propoxy]phenyl]-1-phenylprop-2-en-1-one; 44439638: (E)-3-[3-(2-Hydroxy-3-piperidin-1-ylpropoxy)phenyl]-1-phenylprop-2-en-1-one; 44439639: (E)-3-[3-[3-[4-(2-Chlorophenyl)piperazin-1-yl]-2-hydroxypropoxy]phenyl]-1-phenylprop-2-en-1-one; 44439640: (E)-3-[3-[2-Hydroxy-3-(4-methylpiperazin-1-yl)propoxy]phenyl]-1-phenylprop-2-en-1-one; 44439641: (E)-3-[4-[3-(Tert-butylamino)-2-hydroxy-propoxy]phenyl]-1-phenylprop-2-en-1-one; 44439642: (E)-3-[3-[3-(Diethylamino)propylamino]-2-hydroxypropoxy]phenyl]-1-phenylprop-2-en-1-one; 44439643: (E)-3-[4-[3-[Di(propan-2-yl)amino]-2-hydroxypropoxy]phenyl]-1-phenylprop-2-en-1-one; 44439644: (E)-3-[4-(2-Hydroxy-3-piperidin-1-ylpropoxy)phenyl]-1-phenylprop-2-en-1-one; 44439645: (E)-3-[3-[3-(Cyclohexylamino)-2-hydroxypropoxy]phenyl]-1-phenylprop-2-en-1-one; 44439646: (E)-3-[4-[2-Hydroxy-3-(2-methylpropylamino)propoxy]phenyl]-1-phenylprop-2-en-1-one; 44443986: 4-[(E)-3-[4-(2,5-Dioxopyrrol-1-yl)phenyl]-3-oxoprop-1-enyl]benzoic acid; 44446882: [4-[(E)-3-(4-Hydroxyphenyl)-3-oxoprop-1-enyl]phenyl] 4-methylbenzenesulfonate; 44446886: [4-[(E)-3-(4-Hydroxyphenyl)prop-2-enoyl]phenyl] 4-acetamidobenzenesulfonate; 44454048: (6As)-3-[5-[4-[(E)-3-(2-hydroxyphenyl)-3-oxoprop-1-enyl]-2-methoxyphenoxy]pentoxy]-2-methoxy-6a,7,8,9-tetrahydro-5H-pyrrolo[2,1-c][1,4]benzodia-zepine-6,11-dione; 44454107: (6As)-3-[4-[4-[(E)-3-(2-hydroxyphenyl)-3-oxoprop-1-enyl]-2-methoxyphenoxy]butoxy]-2-methoxy-6a,7,8,9-tetrahydro-5H-pyrrolo[2,1-c][1,4]benzodia-zepine-6,11-dione; 44454262: (6As)-3-[3-[4-[(E)-3-(2-hydroxyphenyl)-3-oxoprop-1-enyl]-2-methoxyphenoxy]propoxy]-2-methoxy-6a,7,8,9-tetrahydro-5H-pyrrolo[2,1-c][1,4]benzodia-zepine-6,11-dione; 44454323: (6As)-3-[5-[4-[(E)-3-(2-hydroxyphenyl)-3-oxoprop-1-enyl]-2-methoxyphenoxy]pentoxy]-2-methoxy-6a,7,8,9-tetrahydropyrrolo[2,1-c][1,4]benzodiazepin-11-one; 44454423: (6As)-3-[4-[4-[(E)-3-(2-hydroxyphenyl)-3-oxoprop-1-enyl]-2-methoxy-phenoxy]butoxy]-2-methoxy-6a,7,8,9-tetrahydropyrrolo[2,1-c][1,4]benzodiazepin-11-one; 44482045: (E)-1-(4-(2-(2-Hydroxyethoxy)ethoxy)phenyl)-3-(4-(dimethylamino)phenyl)prop-2-en-1-one; 44482046: (E)-3-[4-(Dimethylamino)phenyl]-1-[4-[2-[2-(2-hydroxyethoxy)ethoxy]ethoxy]phenyl]prop-2-en-1-one; 44482777: 1-[4-[3-(3-Hydroxyphenyl)prop-2-enoyl]phenyl]pyrrolidin-2-one; 44482842: 3-(3-Hydroxy-4-methoxyphenyl)-1-(4-iodophenyl)prop-2-en-1-one; 44482869: 4-[3-(3-Hydroxyphenyl)prop-2-enoyl]benzonitrile; 44482907: 4-[3-(2-Methoxyphenyl)-3-oxoprop-1-en-1-yl]benzoic acid; 44483039: 3-[3-(4-Hydroxyphenyl)-3-oxoprop-1-enyl]benzonitrile; 44550363: Schembl22667449; 44550364: (E)-1-(2-Hydroxy-4,6-dimethoxyphenyl)-3-(4-methoxy-3-methylphenyl)prop-2-en-1-one; 44573295: (E)-1-(2-Hydroxyphenyl)-3-[4-(trifluoromethoxy)phenyl]prop-2-en-1-one; 44573296: (E)-1-(2-Hydroxyphenyl)-3-(4-biphenylyl)-2-propene-1-one; 44577024: 3-Hydroxyhelichrysetin; 44589166: (E)-3-(3-Bromophenyl)-1-(2,4,6-trihydroxyphenyl)prop-2-en-1-one; 44589167: (E)-3-(1,3-Benzodioxol-5-yl)-1-(2,4,6-trihydroxyphenyl)prop-2-en-1-one; 44593443: (E)-3-(3-Chlorophenyl)-1-(2-hydroxy-4,6-dimethoxyphenyl)prop-2-en-1-one; 44627063: (E)-3-(3,4-Dimethoxyphenyl)-1-[2-hydroxy-6-methoxy-4-[(2S,3R,4S,5S,6R)-3,4,5-trihydroxy-6-(hydroxymethyl)oxan-2-yl]oxyphenyl]prop-2-en-1-one; 44629782: 3-(4-Butylphenyl)-1-(4-hydroxyphenyl)prop-2-en-1-one; 44665732: (E)-1-(4-Fluorophenyl)-3-[4-(3-hydroxy-3-methylbut-1-ynyl)phenyl]prop-2-en-1-one; 44818665: (E)-3-[3-[(E)-3-Oxo-3-phenylprop-1-enyl]phenyl]prop-2-enoic acid; 44818666: (E)-3-(3-(E)-3-[2-(4-Methyl-piperazin-1-yl)-phenyl]-3-oxo-propenyl-phenyl)-acrylic acid trifluoroacetate; 44818667: (E)-3-(3-(E)-3-[2-(4-Methyl-piperazin-1-yl)-phenyl]-3-oxo-propenyl-phenyl)-acrylic acid; 44818843: (E)-3-[3-[(E)-3-[2-[(4-Methylpiperazin-1-yl)methyl]phenyl]-3-oxoprop-1-enyl]phenyl]prop-2-enoic acid; 44818847: (E)-3-[3-[(E)-3-[4-(4-Methylpiperazin-1-yl)phenyl]-3-oxoprop-1-enyl]phenyl]prop-2-enoic acid;2,2,2-trifluoroacetic acid; 44818848: (E)-3-[3-[(E)-3-[4-(4-Methylpiperazin-1-yl)phenyl]-3-oxoprop-1-enyl]phenyl]prop-2-enoic acid; 44818849: (E)-3-[3-[(E)-3-[4-[(4-Methylpiperazin-1-yl)methyl]phenyl]-3-oxoprop-1-enyl]phenyl]prop-2-enoic acid; 44819204: (E)-N-Hydroxy-3-[3-[(E)-3-[2-(4-methylpiperazin-1-yl)phenyl]-3-oxoprop-1-enyl]phenyl]prop-2-enamide;2,2,2-trifluoroacetic acid; 44819205: (E)-N-Hydroxy-3-[3-[(E)-3-[2-[(4-methyl-piperazin-1-yl)methyl]phenyl]-3-oxoprop-1-enyl]phenyl]prop-2-enamide;2,2,2-trifluoroacetic acid; 44819900: (E)-3-[4-[(E)-3-[2-(4-Methylpiperazin-1-yl)phenyl]-3-oxoprop-1-enyl]phenyl]prop-2-enoic acid;hydrochloride; 44819901: (E)-3-[4-[(E)-3-[2-(4-Methylpiperazin-1-yl)phenyl]-3-oxoprop-1-enyl]phenyl]prop-2-enoic acid; 44819902: (E)-3-(4-(E)-3-[2-(4-Methyl-piperazin-1-ylmethyl)-phenyl]-3-oxo-propenyl-phenyl)-acrylic acid bis-hydrochloride; 44819903: (E)-3-[4-[(E)-3-[2-[(4-Methylpiperazin-1-yl)methyl]phenyl]-3-oxoprop-1-enyl]phenyl]prop-2-enoic acid; 44820087: (E)-3-[4-[(E)-3-[4-(4-Methylpiperazin-1-yl)phenyl]-3-oxoprop-1-enyl]phenyl]prop-2-enoic acid; 44820088: (E)-3-[4-[(E)-3-[4-[(4-Methylpiperazin-1-yl)methyl]phenyl]-3-oxoprop-1-enyl]phenyl]prop-2-enoic acid;dihydrochloride; 44820089: (E)-3-[4-[(E)-3-[4-[(4-Methylpiperazin-1-yl)methyl]phenyl]-3-oxoprop-1-enyl]phenyl]prop-2-enoic acid; 45032251: 4-[(2E)-3-Phenylprop-2-enoyl]phenyl 2-(acetylamino)-2-deoxyhexopyranoside; 45032325: (2E)-3-4-[(2-Hydroxyethyl)(methyl)amino]phenyl-1-phenylprop-2-en-1-one; 45041797: (Z)-1-[3,5-Dihydroxy-2-[(Z)-3-phenylprop-2-enoyl]phenyl]-3-phenylprop-2-en-1-one; 45047849: 3-(4-Hydroxy-phenyl)-1-(4-hydroxy-2-(gluco-pyranosyl)-phenyl)-propenone; 45047856: 1-(2-Hydroxy-6-(gluco-pyranosyl)-phenyl)-3-(4-nitro-phenyl)-propenone; 45050852: 2-[3-(4-Chlorophenyl)acryloyl]-3,5-dihydroxyphenyl alpha-L-glucopyranoside; 45100237: (Z)-3-(3,4-Dimethoxyphenyl)-1-(4-hydroxyphenyl)prop-2-en-1-one; 45103349: 2'-Hydroxy-4'-methoxy-6'-(2-methoxyethoxymethoxy)chalcone; 45146292: (2E)-3-[4-(1H-2lambda-4-,1,3-Benzothiadiazol-2-ylmethyl)-3-methoxyphenyl]-1-(4-hydroxyphenyl)prop-2-en-1-one; 45257513: (E)-1-[4-(Diethylamino)-2-hydroxyphenyl]-3-(4-methoxyphenyl)prop-2-en-1-one; 45470843: 4-[(E)-3-Oxo-3-(4-pentoxyphenyl)prop-1-enyl]benzoic acid; 45473144: 2-[[4-[(E)-3-(4-Bromophenyl)prop-2-enoyl]phenyl]sulfonylamino]acetic acid; 45473149: 2-[[4-[(E)-3-(4-Methoxyphenyl)prop-2-enoyl]phenyl]sulfonylamino]acetic acid; 45473156: 2-[[4-[(E)-3-[3-(Trifluoromethyl)phenyl]prop-2-enoyl]phenyl]sulfonylamino]acetic acid; 45474481: 4-[(E)-3-[4-(Carboxymethylsulfamoyl)phenyl]-3-oxoprop-1-enyl]benzoic acid; 45474520: 2-[[4-[(E)-3-(4-Hydroxy-3-nitro-phenyl)prop-2-enoyl]phenyl]sulfonylamino]acetic acid; 45476924: 1-[4-[(E)-3-(4-Ethylphenyl)prop-2-enoyl]phenyl]sulfonylpiperidine-4-carboxylic acid; 45783227: [(2R,3S,4S,5R,6S)-6-[4-[(E)-3-(2,4-Dihydroxyphenyl)-3-oxoprop-1-enyl]phenoxy]-3,4,5-trihydroxyoxan-2-yl] methyl (E)-3-(4-hydroxyphenyl)prop-2-enoate; 45835620: 1-(4-Hydroxyphenyl)-3-[4-(trifluoromethoxy)phenyl]prop- 2-en-1-one; 45835672: 1-[4-(Difluoromethoxy)phenyl]-3-(3-hydroxy-4-methoxyphenyl)prop-2-en-1-one; 45835783: 3-(3,4-Difluorophenyl)-1-(4-hydroxyphenyl) prop-2-en-1-one; 45835786: 1-(4-Hydroxyphenyl)-3-[4-(prop-2-en-1-yloxy)phenyl]prop-2-en-1-one; 45835930: 1-4-[3-(4-Hydroxyphenyl)prop-2-enoyl]phenylpyrrolidin-2-one; 45836000: 2-[4-[3-(2,3-Dihydro-1,4-benzodioxin-6-yl) prop-2-enoyl]phenoxy]propanoic acid; 45836120: 1-(2,4-Dimethoxyphenyl)-3-(3-hydroxy-4-methoxyphenyl)prop-2-en-1-one; 45840787: (E)-3-(4-Hydroxy-3-methoxyphenyl)-1-[2-(trifluoromethyl)phenyl]prop-2-en-1-one; 45848114: 2-[4-[(E)-3-[4-[(2-Methyl-1,3-thiazol-4-yl)methoxy]phenyl]prop-2-enoyl]phenoxy]propanoic acid; 45906857: 2-[4-[(E)-3-(4-Propan-2-yloxyphenyl)prop-2-enoyl]phenoxy] acetic acid; 45907168: (E)-3-(3-Hydroxyphenyl)-1-[4-(trifluoromethyl)phenyl]prop-2-en-1-one; 45910153: 4-[(E)-3-[4-[(1-Methylimidazol-2-yl)methoxy]phenyl]-3-oxoprop-1-enyl]benzoic acid; 45916182: (E)-1-[4-(2-Chloroprop-2-enoxy)phenyl]-3-(3-hydroxy-4-methoxyphenyl) prop-2-en-1-one; 45916183: (E)-1-[4-(2-Chloroprop-2-enoxy)phenyl]-3-(4-hydroxy-3-nitro-phenyl)prop-2-en-1-one; 45933915: 2'-Hydroxy-6'-methyl-3,4-methylenedioxychalcone; 45933920: 2'-Hydroxy-3,4,6'-trimethoxychalcone; 46224961: (E)-1-(2,4-Dihydroxy-6-methoxyphenyl)-3-(4-methylphenyl)prop-2-en-1-one; 46224986: (E)-1-(2,4-Dihydroxy-6-methoxyphenyl)-3-(3-methoxyphenyl)prop-2-en-1-one; 46224987: 3-Methoxyhelichrysetin; 46225018: (E)-1-(2,4-Dihydroxy-6-methoxyphenyl)-3-[4-(trifluoromethyl)phenyl]prop-2-en-1-one; 46225019: (E)-3-(4-Chlorophenyl)-1-(2,4-dihydroxy-6-methoxyphenyl)prop-2-en-1-one; 46225020: (E)-1-(2,4-Dihydroxy-6-methoxyphenyl)-3-(4-fluorophenyl)prop-2-en-1-one; 46232188: (E)-3-[4-[(2S,3R,4S,5S,6R)-3-[(2R,3S,4S)-3,4-Dihydroxy-4-(hydroxymethyl) oxolan-2-yl]oxy-4,5-dihydroxy-6-(hydroxymethyl)oxan-2-yl]oxyphenyl]-1-(2,4-dihydroxy-phenyl)prop-2-en-1-one; 46479606: 3-[4-[(E)-3-(4-Nitrophenyl)-3-oxoprop-1-enyl]phenoxy]propanoic acid; 46486412: (E)-1-(4-Hydroxyphenyl)-3-[4-(pyridin-4-ylmethoxy)phenyl]prop-2-en-1-one; 46500944: 4-[(1,3,5,7-Tetraoxo-2,6-bis4-[(E)-3-phenyl-2-propenoyl]phenyl-1,2,3,5,6,7-hexahydropyrrolo[3,4-f]isoindol-4-yl)carbonyl] benzoic acid; 46501376: 2-[4-[1,3-Dioxo-2-[4-[(E)-3-oxo-3-phenylprop-1-enyl]phenyl]isoindol-5-yl]oxyphenyl]-1,3-dioxoisoin-dole-5-carboxylic acid; 46677873: 2,2,2-Trifluoro-N-[3-[(E)-3-(4-hydroxyphenyl)-3-oxoprop-1-enyl]phenyl]acetamide; 46702570: (E)-1-(2-Hydroxy-4-methoxyphenyl)-3-(4-methoxy-phenyl)(1,2,3-13C3)prop-2-en-1-one; 46735308: 3-(Benzoyloxy)-4-(2Z)-3-[4-(benzoyloxy) phenyl]prop-2-enoyl-5-hydroxyphenyl benzoate; 46742526: 2'-Hydroxy-5-methylchalcone; 46865314: (E)-1-[5-[5-[(E)-3-(2,4-Dihydroxyphenyl)-3-oxoprop-1-enyl]-2-hydroxyphenyl]-2-hydroxy-4-methoxyphenyl]-3-(4-hydroxyphenyl)prop-2-en-1-one; 46873245: (E)-1-(4-Nitrophenyl)-3-[4-[(2S,3R,4R,5S,6R)-3,4,5-trihydroxy-6-(hydroxymethyl)oxan-2-yl]oxyphenyl]prop-2-en-1-one; 46873363: (E)-1-(2-Fluoro-6-hydroxyphenyl)-3-(4-fluorophenyl) prop-2-en-1-one; 46873364: (E)-3-(4-Chlorophenyl)-1-(2-fluoro-6-hydroxyphenyl)prop-2-en-1-one; 46873365: 4-[(E)-3-(2-Fluoro-6-hydroxyphenyl)-3-oxoprop-1-enyl]benzonitrile; 46884175: 3-[2-Hydroxy-3-[4-[[3-[(E)-3-(4-methoxyphenyl)-3-oxoprop-1-enyl] phenoxy]methyl]triazol-1-yl]propoxy]-2,4-dimethyl-2H-thiophen-5-one; 46884176: 3-[3-[4-[[3-[(E)-3-(2,4-Dimethoxyphenyl)-3-oxoprop-1-enyl]phenoxy]methyl] triazol-1-yl]-2-hydroxypropoxy]-2,4-dimethyl-2H-thiophen-5-one; 46884220: 3-[2-Hydroxy-3-[4-[[4-[(E)-3-(4-methoxy-phenyl)-3-oxoprop-1-enyl]phenoxy]methyl] triazol-1-yl]propoxy]-2,4-dimethyl-2H-thiophen-5-one; 46884221: 3-[3-[4-[[4-[(E)-3-(2,4-Dimethoxyphenyl)-3-oxoprop-1-enyl]phenoxy]methyl]triazol-1-yl]-2-hydroxypropoxy]-2,4-dimethyl-2H-thiophen-5-one; 46884223: 3-[2-Hydroxy-3-[4-[[2-[(E)-3-(4-methoxyphenyl)prop-2-enoyl]phenoxy]methyl]triazol-1-yl]propoxy]-2,4-dimethyl-2H-thiophen-5-one; 46884301: 3-[2-Hydroxy-3-[4-[[4-[(E)-3-(4-methoxyphenyl) prop-2-enoyl]phenoxy]methyl] triazol-1-yl]propoxy]-2,4-dimethyl-2H-thiophen-5-one; 46884306: 5-Chloro-1-[2-hydroxy-3-[4-[[3-[(E)-3-(4-methoxyphenyl)-3-oxoprop-1-enyl]phenoxy]methyl]triazol-1-yl]propyl]indole-2,3-dione; 46884307: 5-Chloro-1-[3-[4-[[3-[(E)-3-(2,4-dimethoxyphenyl)-3-oxoprop-1-enyl]phenoxy]methyl]triazol-1-yl]-2-hydroxypropyl]indole-2,3-dione; 46884309: 5-Chloro-1-[2-hydroxy-3-[4-[[4-[(E)-3-(4-methoxyphenyl)-3-oxoprop-1-enyl]phenoxy]methyl] triazol-1-yl]propyl]indole-2,3-dione; 46884310: 5-Chloro-1-[3-[4-[[4-[(E)-3-(2,4-dimethoxyphenyl)-3-oxoprop-1-enyl]phenoxy]methyl]triazol-1-yl]-2-hydroxypropyl] indole-2,3-dione; 46884312: 5-Chloro-1-[2-hydroxy-3-[4-[[2-[(E)-3-(4-methoxyphenyl)prop-2-enoyl]phenoxy] methyl]triazol-1-yl]propyl]indole-2,3-dione; 46884318: 5-Chloro-1-[2-hydroxy-3-[4-[[4-[(E)-3-(4-methoxyphenyl) prop-2-enoyl]phenoxy]methyl]triazol-1-yl]propyl]indole-2, 3-dione; 46886004: (E)-1-(2,4-Dihydroxy-5-[2-hydroxy-5-[(E)-3-oxo-3-phenylprop-1-enyl]phenyl]phenyl]-3-(4-hydroxyphenyl)prop-2-en-1-one; 46919026: (E)-4-(3-(4-(4-Chlorophenoxy)butoxy)phenyl)acryloyl)-3-(cyanomethoxy)benzoic acid; 46932090: (E)-3-[4-[(E)-2-(4-Hydroxy-3-methoxy-phenyl)vinyl]phenyl]-1-(4-methoxy-phenyl)prop-2-en-1-one; 46933475: 2-[2-[(E)-3-(1,3-Benzodioxol-5-yl)prop-2-enoyl]-3,5-dihydroxyphenoxy]ethyl nitrate; 46933476: (E)-3-(1,3-Benzodioxol-5-yl)-1-[2,4-dihydroxy-6-[(4-methyl-5-oxido-1,2,5-oxadiazol-5-ium-3-yl)methoxy]phenyl]prop-2-en-1-one; 46933477: (E)-3-(1,3-Benzodioxol-5-yl)-1-[2,4-dihydroxy-6-[(4-methyl-2-oxido-1,2,5-oxadiazol-2-ium-3-yl)methoxy]phenyl]prop-2-en-1-one; 46933478: 2-[2-[(E)-3-(1,3-Benzodioxol-5-yl)prop-2-enoyl]-3-hydroxy-5-[(4-methyl-5-oxido-1,2,5-oxadiazol-5-ium-3-yl)methoxy] phenoxy]ethyl nitrate; 46933792: 5-O-[2-[2-[(E)-3-(1,3-Benzodioxol-5-yl)prop-2-enoyl]-3,5-dihydroxy-phenoxy] ethyl] 3-O-methyl 2,6-dimethyl-4-(3-nitro-phenyl)-1,4-dihydropyridine-3,5-dicarboxylate; 46933793: 5-O-[2-[2-[(E)-3-(3-Bromophenyl)prop-2-enoyl]-3,5-dihydroxyphenoxy]ethyl]3-O-methyl 2,6-dimethyl-4-(3-nitro-phenyl)-1,4-dihydropyridine-3,5-dicarboxylate; 46933794: 5-O-[2-[3,5-Dihydroxy-2-[(E)-3-(4-hydroxyphenyl)prop-2-enoyl]phenoxy]ethyl] 3-O-methyl 2,6-dimethyl-4-(3-nitro-phenyl)-1,4-dihydropyridine-3,5-dicarboxylate; 46933795: 5-O-[2-[2-[(E)-3-(1,3-Benzodioxol-5-yl)prop-2-enoyl]-5-hydroxyphenoxy]ethyl] 3-O-methyl 2,6-dimethyl-4-(3-nitro-phenyl)-1,4-dihydropyridine-3,5-dicarboxylate; 46934565: (E)-1-(2-Hydroxy-4-phenylmethoxyphenyl)-3-[4-(trifluoromethoxy)phenyl]prop-2-en-1-one; 46934708: (E)-1-(2-Hydroxy-4,6-dimethoxyphenyl)-3-(4-phenylphenyl)prop-2-en-1-one; 46946322: (E)-1-[2-Hydroxy-4-[3-hydroxy-4-[(E)-3-(4-hydroxyphenyl)prop-2-enoyl]-5-methoxyphenoxy]-6-methoxyphenyl]-3-(4-hydroxyphenyl) prop-2-en-1-one; 47037018: 3-[4-[(E)-3-(4-Cyanophenyl)-3-oxoprop-1-enyl]phenoxy]propanoic acid; 47046304: (E)-3-(3-Hydroxy-4-methoxyphenyl)-1-[4-(2-methoxyethoxy) phenyl]prop-2-en-1-one; 47046306: (E)-3-(3-Hydroxyphenyl)-1-[4-(2-methoxyethoxy)phenyl]prop-2-en-1-one; 47046312: (E)-3-(4-Hydroxy-3-nitro-phenyl)-1-[4-(2-methoxyethoxy)phenyl]prop-2-en-1-one; 47046320: 4-[(E)-3-[4-(2-Methoxyethoxy)phenyl]-3-oxoprop-1-enyl]

benzoic acid; 47241266: (E)-3-(3-Ethoxy-phenyl)-1-(4-hydroxyphenyl)prop-2-en-1-one; 47448545: (E)-1-(4-Bromophenyl)-3-(3-chloro-4-hydroxyphenyl)prop-2-en-1-one; 47448548: (E)-3-(3-Chloro-4-hydroxyphenyl)-1-phenylprop-2-en-1-one; 47448552: (E)-3-(3-Chloro-4-hydroxyphenyl)-1-(4-methylphenyl) prop-2-en-1-one; 47448554: (E)-3-(3-Chloro-4-hydroxyphenyl)-1-(4-hydroxyphenyl)prop-2-en-1-one; 47448561: (E)-3-(3-Chloro-4-hydroxyphenyl)-1-(4-chlorophenyl)prop-2-en-1-one; 47448565: 4-[(E)-3-(3-Chloro-4-hydroxyphenyl)prop-2-enoyl]benzonitrile; 47448592: (E)-3-(3-Chloro-4-hydroxyphenyl)-1-(4-fluorophenyl)prop-2-en-1-one; 47448602: (E)-3-(3-Chloro-4-hydroxyphenyl)-1-(4-methoxyphenyl)prop-2-en-1-one; 47448684: (E)-3-(3-Chloro-4-hydroxyphenyl)-1-(4-iodophenyl)prop-2-en-1-one; 47448702: (E)-3-(3-Chloro-4-hydroxy-phenyl)-1-(4-methylsulfanylphenyl)prop-2-en-1-one; 49651501: 3-(3-Hydroxyphenyl)-1-[4-(trifluoromethyl)phenyl]prop-2-en-1-one; 49766193: (E)-3-[4-Hydroxy-3-[4-[(E)-3-[2-hydroxy-4-(methoxymethoxy)phenyl]-3-oxoprop-1-enyl]-2-methoxyphenoxy]phenyl]-1-[2-hydroxy-4-(methoxymethoxy)phenyl]prop-2-en-1-one; 49768249: (E)-1-(2,6-Dihydroxy-4-methoxy-phenyl)-3-phenyl-prop-2-en-1-one; 5,7-dihydroxy-2-phenyl-chromen-4-one; 49779725: beta,beta'-(6,6'-Dihydroxybiphenyl-3,3'-diyl)bis(2',4',6'-trihydroxyacrylophenone); 49787998: beta,beta'-[6,6'-Bis(benzyloxy)biphenyl-3,3'-diyl]bis[2'-hydroxy-4',6'-bis(benzyloxy)acrylophenone]; 49788927: (E)-3-[3,4-Bis(phenylmethoxy)phenyl]-1-[2-hydroxy-4,6-bis(phenylmethoxy)phenyl](1,3-13C2)prop-2-en-1-one; 49824673: 5-[[4-[3-(3,4-Dihydroxyphenyl)prop-2-enoyl]phenyl]methyl]-1,3-thiazolidine-2,4-dione; 49826095: 5-[[4-[3-(4-Hydroxy-3-methoxyphenyl)prop-2-enoyl]phenyl]methyl]-1,3-thiazolidine-2,4-dione; 49829464: 4-[[4-[3-(4-Methoxy-3-methylphenyl)prop-2-enoyl]phenyl]sulfonylmethylamino]butanoic acid; 49846735: 2-[(E)-3-(3,4-Dimethoxyphenyl)prop-2-enoyl]benzoic acid; 49847327: 2-[(E)-3-(2,2-Difluoro-1,3-benzodioxol-5-yl)prop-2-enoyl]benzoic acid; 49847329: 2-[(E)-3-(3-Methoxy-4-prop-2-ynoxyphenyl)prop-2-enoyl]benzoic acid; 49847332: 2-[(E)-3-[4-Methoxy-3-(1,1,2,2-tetrafluoroethoxy)phenyl]prop-2-enoyl]benzoic acid; 49847455: 2-[(E)-3-[4-Methoxy-3-(trifluoromethoxy)phenyl]prop-2-enoyl]benzoic acid; 49848599: 2-[(E)-3-[3-Methoxy-4-(1,1,2,2-tetrafluoroethoxy)phenyl]prop-2-enoyl]benzoic acid; 49848720: 2-[(E)-3-(2,2,3,3-Tetrafluoro-1,4-benzodioxin-6-yl)prop-2-enoyl]benzoic acid; 49849080: 2-[(E)-3-[3,4-Bis(1,1,2,2-tetrafluoroethoxy)phenyl]prop-2-enoyl]benzoic acid; 49849183: 2-[(E)-3-(4-Methoxy-3-prop-2-ynoxyphenyl)prop-2-enoyl]benzoic acid; 49863643: E-2-(2-(3-(4-(4-(4-Chlorophenoxy)butoxy)phenyl)acryloyl)phenoxy)acetic acid; 49864058: 2'-Hydroxy-3,4-dimethoxy-4'-(3-methyl-2-butenyloxy)chalcone; 50742113: 1-[4-[2-Hydroxy-3-[4-(3-oxo-3-phenylprop-1-enyl)phenoxy]propoxy]phenyl]-3-phenylprop-2-en-1-one; 50742115: 3-[4-(3-Chloro-2-hydroxypropoxy)phenyl]-1-phenylprop-2-en-1-one; 50742117: 3-[4-(2-Hydroxy-ethoxy)phenyl]-1-phenylprop-2-EN-1-one; 50905804: (E)-1-(4-Hydroxyphenyl)-3-[3-methoxy-4-[(5-phenyl-1,3,4-oxadiazol-2-yl)methoxy]phenyl]prop-2-en-1-one; 50905805: (E)-3-[4-[[5-(4-Chlorophenyl)-1,3,4-oxadiazol-2-yl]methoxy]-3-methoxyphenyl]-1-(4-hydroxy-phenyl)prop-2-en-1-one; 50905806: (E)-1-(4-Hydroxyphenyl)-3-[3-methoxy-4-[[5-(4-nitro-phenyl)-1,3,4-oxadiazol-2-yl]methoxy]phenyl]prop-2-en-1-one; 50905807: (E)-1-(4-Hydroxyphenyl)-3-[3-methoxy-4-[[5-(4-methylphenyl)-1,3,4-oxadiazol-2-yl]methoxy]phenyl]prop-2-en-1-one; 50906019: (E)-1-(4-Hydroxyphenyl)-3-[3-methoxy-4-[(5-phenyl-methoxy-1,3,4-oxadiazol-2-yl)methoxy]phenyl]prop-2-en-1-one; 50907477: 2-[(5E)-5-[[4-[(E)-3-(4-Methylphenyl)-3-oxoprop-1-enyl]phenyl]methylidene]-4-oxo-2-sulfanylidene-1,3-thiazolidin-3-yl]acetic acid; 50907478: 2-[(5E)-5-[[4-[(E)-3-(2,4-Dimethylphenyl)-3-oxoprop-1-enyl]phenyl]methylidene]-4-oxo-2-sulfanylidene-1,3-thiazolidin-3-yl]acetic acid; 50907688: 2-[(5E)-5-[[4-[(E)-3-(4-Methoxyphenyl)-3-oxoprop-1-enyl]phenyl]methylidene]-4-oxo-2-sulfanylidene-1,3-thiazolidin-3-yl]acetic acid; 50907689: 2-[(5E)-4-Oxo-5-[[4-[(E)-3-oxo-3-phenylprop-1-enyl]phenyl]methylidene]-2-sulfanylidene-1,3-thiazolidin-3-yl]acetic acid; 50907690: 2-[(5E)-5-[[4-[(E)-3-(2-Fluorophenyl)-3-oxoprop-1-enyl]phenyl]methylidene]-4-oxo-2-sulfanylidene-1,3-thiazolidin-3-yl]acetic acid; 50907691: 2-[(5E)-5-[[4-[(E)-3-(4-Fluorophenyl)-3-oxoprop-1-enyl]phenyl]methylidene]-4-oxo-2-sulfanylidene-1,3-thiazolidin-3-yl]acetic acid; 50907692: 2-[(5E)-5-[[4-[(E)-3-(2-Chlorophenyl)-3-oxoprop-1-enyl]phenyl]methylidene]-4-oxo-2-sulfanylidene-1,3-thiazolidin-3-yl]acetic acid; 50907906: 2-[(5E)-5-[[4-[(E)-3-(4-Chlorophenyl)-3-oxoprop-1-enyl]phenyl]methylidene]-4-oxo-2-sulfanylidene-1,3-thiazolidin-3-yl]acetic acid; 50907907: 2-((5e)-5-(4-((e)-3-(2,4-Dichlorophenyl)-3-oxoprop-1-enyl)benzylidene)-4-oxo-2-thioxothiazolidin-3-yl) acetic acid; 50907908: 2-[(5E)-5-[[4-[(E)-3-(2-Bromophenyl)-3-oxoprop-1-enyl]phenyl]methylidene]-4-oxo-2-sulfanylidene-1,3-thiazolidin-3-yl]acetic acid; 50907910: 2-[(5E)-5-[[4-[(E)-3-(4-Bromophenyl)-3-oxoprop-1-enyl]phenyl]methylidene]-4-oxo-2-sulfanylidene-1,3-thiazolidin-3-yl]acetic acid; 50908133: 2-[(5E)-5-[[4-[(E)-3-(4-Nitrophenyl)-3-oxoprop-1-enyl]phenyl]methylidene]-4-oxo-2-sulfa-nylidene-1,3-thiazolidin-3-yl]acetic acid; 50908135: 2-[(5E)-5-[[4-[(E)-3-[4-(Methoxy-methoxy)phenyl]-3-oxoprop-1-enyl]phenyl]methylidene]-4-oxo-2-sulfanylidene-1,3-thiazolidin-3-yl]acetic acid; 50908136: 2-[(5E)-5-[[4-[(E)-3-(4-Acetamidophenyl)-3-oxoprop-1-enyl]phenyl]methylidene]-4-oxo-2-sulfanylidene-1,3-thiazolidin-3-yl]acetic acid; 50941638: (E)-3-(3-Bromo-4-hydroxyphenyl)-1-(2-hydroxy-4,6-dimethoxyphenyl)prop-2-en-1-one; 51063745: 4-[3-(4-Methoxyphenyl)prop-2-enoyl]benzoic acid; 51063746: 4-3-[4-(Trifluoro-methyl)phenyl]prop-2-enoylbenzoic acid; 51063747: 4-[3-(4-Fluoroyphenyl)prop-2-enoyl]benzoic acid; 51063748: 4-3-[4-(Trifluoromethoxy)phenyl]prop-2-enoylbenzoic acid; 51097578: Methyl 2-[4-[(E)-3-(3-hydroxy-4-methoxyphenyl)prop-2-enoyl]phenoxy]acetate; 51097579: Methyl 2-[4-[(E)-3-(3-hydroxyphenyl)prop-2-enoyl]phenoxy]acetate; 51099526: 3-[3-[(E)-3-(4-Hydroxyphenyl)-3-oxoprop-1-enyl]phenoxy]propanoic acid; 51099527: 2-[3-[(E)-3-(4-Cyanophenyl)-3-oxoprop-1-enyl]phenoxy]propanoic acid; 51099528: 3-[3-[(E)-3-(4-Cyanophenyl)-3-oxoprop-1-enyl]phenoxy]propanoic acid; 51100327: 4-[(E)-3-[4-(Methanesulfonamido)phenyl]-3-oxoprop-1-enyl]benzoic acid; 51100594: 4-[(E)-3-[4-[2-(Dimethyl-amino)ethoxy]phenyl]-3-oxoprop-1-enyl]benzoic acid; 51370995: (2E)-1-(4-Chlorophenyl)-3-4-[(2-hydroxyethyl)(methyl)amino]phenylprop-2-en-1-one; 51521382: 2-[4-[(Z)-3-Oxo-3-phenylprop-1-enyl]phenoxy]acetic acid; 51923843: (2S)-2-[4-[(E)-3-[4-[(2-Methyl-1,3-thiazol-4-yl)methoxy]phenyl]prop-2-enoyl]phenoxy]propanoic acid; 51923845: (2R)-2-[4-[(E)-3-[4-[(2-Methyl-1,3-thiazol-4-yl)methoxy]phenyl]prop-2-enoyl]phenoxy]propanoic acid; 52102897: 4-[(E)-3-(3-Bromo-4-hydroxyphenyl)prop-2-enoyl]-N,N-dimethylbenzenesulfonamide; 52198153: (E)-3-(3-Bromo-4-hydroxyphenyl)-1-[4-(2-methoxyethoxy)phenyl]prop-2-en-1-one; 52252565: (E)-3-(3-Hydroxyphenyl)-1-[4-[(1-methylimidazol-2-yl)methoxy]phenyl]prop-2-en-1-one;

52252575: (E)-3-(4-Hydroxy-3-nitro-phenyl)-1-[4-[(1-methyl-imidazol-2-yl)methoxy]phenyl]prop-2-en-1-one; 52253727: 3-[4-[(E)-3-(4-Chlorophenyl)-3-oxoprop-1-enyl]phenoxy]propanoic acid; 52445925: 2-[4-[(E)-3-(3-Bromo-4-hydroxy-phenyl)prop-2-enoyl]phenoxy]-N,N-dimethyl-acetamide; 52446241: (E)-3-(3-Bromo-4-hydroxyphenyl)-1-(4-morpholin-4-ylphenyl)prop-2-en-1-one; 52582245: 1-[4-[(E)-3-(3-Hydroxy-4-methoxyphenyl)prop-2-enoyl]phenyl]-3-propan-2-ylurea; 52614183: 3-[4-[(E)-3-(4-Bromophenyl)-3-oxoprop-1-enyl]phenoxy]propanoic acid; 52614194: 3-[4-[(E)-3-(4-Fluorophenyl)-3-oxoprop-1-enyl]phenoxy]propanoic acid; 52614204: 3-[4-[(E)-3-(4-Methoxyphenyl)-3-oxoprop-1-enyl]phenoxy]propanoic acid; 52643905: (E)-3-(4-Hydroxy-3-nitro-phenyl)-1-[4-(trifluoromethyl)phenyl]prop-2-en-1-one; 52643916: 4-[(E)-3-Oxo-3-[4-(trifluoromethyl)phenyl]prop-1-enyl]benzoic acid; 52643926: (E)-3-(3-Hydroxy-4-methoxy-phenyl)-1-[4-(trifluoromethoxy)phenyl]prop-2-en-1-one; 52643928: (E)-3-(3-Hydroxyphenyl)-1-[4-(trifluoromethoxy)phenyl]prop-2-en-1-one; 52643930: (E)-3-(4-Hydroxy-3-nitro-phenyl)-1-[4-(trifluoromethoxy)phenyl]prop-2-en-1-one; 52643943: 4-[(E)-3-Oxo-3-[4-(trifluoromethoxy)phenyl]prop-1-enyl]benzoic acid; 52694946: 4-[(E)-3-[4-(2-Chloroprop-2-enoxy)phenyl]-3-oxoprop-1-enyl]benzoic acid; 52694948: (E)-1-[4-(2-Chloroprop-2-enoxy)phenyl]-3-(3-hydroxyphenyl)prop-2-en-1-one; 52771849: (E)-3-(3-Chloro-4-hydroxyphenyl)-1-(2,4-dimethoxyphenyl)prop-2-en-1-one; 52771851: (E)-3-(3-Chloro-4-hydroxyphenyl)-1-(4-nitro-phenyl)prop-2-en-1-one; 52771907: (E)-3-(3-Chloro-4-hydroxyphenyl)-1-(4-ethoxyphenyl)prop-2-en-1-one; 52771909: 4-[(E)-3-(3-Chloro-4-hydroxyphenyl)prop-2-enoyl]-N,N-dimethylbenzenesulfonamide; 52771910: 4-[(E)-3-(3-Chloro-4-hydroxyphenyl)prop-2-enoyl]-N,N-diethylbenzenesulfonamide; 52771916: (E)-3-(3-Chloro-4-hydroxyphenyl)-1-(4-piperidin-1-ylphenyl)prop-2-en-1-one; 52771938: 2-[4-[(E)-3-(3-Chloro-4-hydroxyphenyl)prop-2-enoyl]phenoxy]-N,N-dimethylacetamide; 52771940: (E)-3-(3-Chloro-4-hydroxyphenyl)-1-[4-(dimethylamino)phenyl]prop-2-en-1-one; 52771941: (E)-3-(3-Chloro-4-hydroxyphenyl)-1-(4-propan-2-yloxyphenyl)prop-2-en-1-one; 52771951: 1-[4-[(E)-3-(3-Chloro-4-hydroxyphenyl)prop-2-enoyl]phenyl]pyrrolidin-2-one; 52771984: (E)-3-(3-Chloro-4-hydroxyphenyl)-1-[4-(trifluoromethyl)phenyl]prop-2-en-1-one; 52771985: (E)-3-(3-Chloro-4-hydroxyphenyl)-1-[4-(trifluoromethoxy)phenyl]prop-2-en-1-one; 52794012: 3-[3-[(E)-3-(4-Bromophenyl)-3-oxoprop-1-enyl]phenoxy]propanoic acid; 52794018: 3-[3-[(E)-3-Oxo-3-phenylprop-1-enyl]phenoxy]propanoic acid; 52794052: 3-[3-[(E)-3-(4-Nitrophenyl)-3-oxoprop-1-enyl]phenoxy]propanoic acid; 52794058: 3-[3-[(E)-3-(4-Chlorophenyl)-3-oxoprop-1-enyl]phenoxy]propanoic acid; 52794110: 3-[3-[(E)-3-Oxo-3-(4-phenylphenyl)prop-1-enyl]phenoxy]propanoic acid; 52794128: 3-[3-[(E)-3-(4-Fluorophenyl)-3-oxoprop-1-enyl]phenoxy]propanoic acid; 52794158: 3-[3-[(E)-3-(4-Methoxyphenyl)-3-oxoprop-1-enyl]phenoxy]propanoic acid; 52794280: 3-[3-[(E)-3-(4-Tert-butylphenyl)-3-oxoprop-1-enyl]phenoxy]propanoic acid; 52904993: N-[(2S,3R,4R,5S,6R)-4,5-Dihydroxy-6-(hydroxymethyl)-2-[4-[(E)-3-phenylprop-2-enoyl]phenoxy]oxan-3-yl]acetamide; 52938982: (E)-1-[4-[4-[[2-Hydroxy-5-[(E)-3-(4-methoxyphenyl)prop-2-enoyl]phenyl]methyl]piperazin-1-yl]phenyl]-3-(4-methoxyphenyl)prop-2-en-1-one; 52943252: 1-[(2R,4S,5S)-4-[4-[[4-[(E)-3-(2,4-Dimethoxyphenyl)-3-oxoprop-1-enyl]-2-methoxyphenoxy]methyl]triazol-1-yl]-5-(hydroxymethyl)oxolan-2-yl]-5-methylpyrimidine-2,4-dione; 52948108: 1-[(2R,4S,5S)-5-(Hydroxymethyl)-4-[4-[[2-methoxy-4-[(E)-3-(4-methoxyphenyl)-3-oxoprop-1-enyl]phenoxy]methyl]triazol-1-yl]oxolan-2-yl]-5-methylpyrimidine-2,4-dione; 53240337: (E)-3-(4-Hydroxy-3-methoxyphenyl)-1-phenylprop-2-en-1-one;2-(2-hydroxy-5-prop-2-enylphenyl)-4-prop-2-enylphenol; 53243462: (E)-3-[4-[2-(5-Ethylpyridin-2-yl)ethoxy]phenyl]-1-(4-hydroxyphenyl) prop-2-en-1-one; 53248579: (E)-3-[3-[[4-(7-Chloroquinolin-4-yl)piperazin-1-yl]methyl]-4-hydroxyphenyl]-1-(2,4-dimethoxyphenyl)prop-2-en-1-one; 53253743: (E)-1-(4-Bromo-phenyl)-3-[4-[(2S,3R,4R,5S,6R)-3,4,5-trihydroxy-6-(hydroxymethyl)oxan-2-yl]oxyphenyl]prop-2-en-1-one; 53316843: N-[4-[(E)-3-(3,4-Dihydroxyphenyl)prop-2-enoyl]phenyl]acetamide; 53317894: (E)-1-(4-Hydroxyphenyl)-3-[3-methoxy-4-[[5-(phenoxymethyl)-1,3,4-oxadiazol-2-yl]methoxy]phenyl]prop-2-en-1-one; 53318159: N-[4-[(E)-3-(3,4-Dihydroxyphenyl)prop-2-enoyl]phenyl]-3-methylbutanamide; 53318160: (E)-N-(4-(3-(3,4-Dihydroxy-phenyl)acryloyl)phenyl)-3,4-difluorobenzamide; 53318161: (E)-N-(4-(3-(3,4-Dihydroxy-phenyl)acryloyl)phenyl)-2-fluoro-4-(trifluoromethyl)benzamide; 53319502: N-[4-[(E)-3-(3,4-Dihydroxyphenyl)prop-2-enoyl]phenyl]thiophene-2-carboxamide; 53319503: (E)-N-(4-(3-(3,4-Dihydroxyphenyl)acryloyl)phenyl)-2,4-difluorobenzamide; 53320003: (E)-3-(1,3-Benzodioxol-5-yl)-1-[4-[4-[[5-[(E)-3-(1,3-benzodioxol-5-yl)prop-2-enoyl]-2-hydroxyphenyl]methyl]piperazin-1-yl]phenyl]prop-2-en-1-one; 53321308: (E)-1-[4-[4-[[2-Hydroxy-3-methoxy-5-[(E)-3-phenylprop-2-enoyl]phenyl]methyl]piperazin-1-yl]phenyl]-3-phenylprop-2-en-1-one; 53322118: N-[4-[(E)-3-(3,4-Dihydroxyphenyl)prop-2-enoyl]phenyl]adamantane-1-carboxamide; 53322119: N-[4-[(E)-3-(3,4-Dihydroxyphenyl)prop-2-enoyl]phenyl]naphtha-lene-2-carboxamide; 53322120: (E)-N-(4-(3-(3,4-Dihydroxyphenyl)acryloyl)phenyl)-4-methoxybenzamide; 53322601: (E)-3-[4-(3-Chloro-2-hydroxypropoxy)phenyl]-1-(4-methoxyphenyl)prop-2-en-1-one; 53322967: (E)-N-(4-(3-(3,4-Dihydroxyphenyl)acryloyl)phenyl)-2-(thiophen-2-yl)acetamide; 53323458: N-[4-[(E)-3-(3,4-Dihydroxyphenyl)prop-2-enoyl]phenyl]-2-methylpropanamide; 53323459: (E)-N-(4-(3-(3,4-Dihydroxyphenyl)acryloyl)phenyl)-benzamide; 53323937: (E)-1-[4-(3-Chloro-2-hydroxypropoxy)phenyl]-3-(4-methoxyphenyl)prop-2-en-1-one; 53324776: (E)-N-(4-(3-(3,4-Dihydroxyphenyl)acryloyl)-phenyl)-furan-2-carboxamide; 53324777: 3,5-Difluoro-N-[4-[(E)-3-(3-hydroxy-4-methylphenyl)prop-2-enoyl]phenyl]benzamide; 53325258: (E)-1-[4-[4-[[2-Hydroxy-3-methoxy-5-[(E)-3-(4-methoxyphenyl)prop-2-enoyl]phenyl]methyl]piperazin-1-yl]phenyl]-3-(4-methoxyphenyl)prop-2-en-1-one; 53325587: (E)-1-(4-Hydroxyphenyl)-3-(1H-indol-5-yl)prop-2-en-1-one; 53326541: (E)-1-[4-[4-[[2-Hydroxy-5-[(E)-3-phenylprop-2-enoyl]phenyl]methyl]piperazin-1-yl]phenyl]-3-phenylprop-2-en-1-one; 53349594: (Z)-2',4'-Dihydroxy-4-benzoyloxychalcone; 53349595: [3-Benzoyloxy-4-[(E)-3-(4-hydroxyphenyl)prop-2-enoyl]phenyl]benzoate; 53361120: 4-[[(5Z)-2,4-Dioxo-5-[[4-[(E)-3-oxo-3-phenylprop-1-enyl]phenyl]methylidene]-1,3-thiazolidin-3-yl]methyl]benzoic acid; 53361121: 4-[[(5Z)-5-[[4-[(E)-3-(2-Chlorophenyl)-3-oxoprop-1-enyl]phenyl]methylidene]-2,4-dioxo-1,3-thiazolidin-3-yl]methyl]benzoic acid; 53361122: 4-[[(5Z)-5-[[4-[(E)-3-(2-Bromophenyl)-3-oxoprop-1-enyl]phenyl]methylidene]-2,4-dioxo-1,3-thiazolidin-3-yl]methyl]benzoic acid; 53361123: 4-[[(5Z)-5-[[4-[(E)-3-(2-Methoxyphenyl)-3-oxoprop-1-enyl]phenyl]methylidene]-2,4-dioxo-1,3-thiazolidin-3-yl]methyl]benzoic acid; 53377035: Methyl 4-[[[5Z)-5-[[4-[(E)-3-(2-hydroxy-phenyl)-3-oxoprop-1-enyl]phenyl]

methylidene]-2,4-dioxo-1,3-thiazolidin-3-yl]methyl]benzoate; 53377037: Methyl 4-[[(5Z)-5-[[4-[(E)-3-(4-hydroxyphenyl)-3-oxoprop-1-enyl]phenyl]methylidene]-2,4-dioxo-1,3-thiazolidin-3-yl]methyl]benzoate; 53377151: 4-[[(5Z)-5-[[4-[(E)-3-(4-Methylphenyl)-3-oxoprop-1-enyl]phenyl]methylidene]-2,4-dioxo-1,3-thiazolidin-3-yl]methyl]benzoic acid; 53377152: 4-[[(5Z)-5-[[4-[(E)-3-(2,4-Dimethylphenyl)-3-oxoprop-1-enyl]phenyl]methylidene]-2,4-dioxo-1,3-thiazolidin-3-yl]methyl]benzoic acid; 53377153: 4-[[(5Z)-5-[[4-[(E)-3-(2,4-Dichlorophenyl)-3-oxoprop-1-enyl]phenyl]methylidene]-2,4-dioxo-1,3-thiazolidin-3-yl]methyl]benzoic acid; 53377154: 4-[[(5Z)-5-[[4-[(E)-3-(2-Fluorophenyl)-3-oxoprop-1-enyl]phenyl]methylidene]-2,4-dioxo-1,3-thiazolidin-3-yl]methyl]benzoic acid; 53377244: 4-[[(5Z)-5-[[4-[(E)-3-(4-Fluorophenyl)-3-oxoprop-1-enyl]phenyl]methylidene]-2,4-dioxo-1,3-thiazolidin-3-yl]methyl]benzoic acid; 53377246: 4-[[(5Z)-5-[[4-[(E)-3-(4-Chlorophenyl)-3-oxoprop-1-enyl]phenyl]methylidene]-2,4-dioxo-1,3-thiazolidin-3-yl]methyl]benzoic acid; 53377248: 4-[[(5Z)-5-[[4-[(E)-3-(4-Bromophenyl)-3-oxoprop-1-enyl]phenyl]methylidene]-2,4-dioxo-1,3-thiazolidin-3-yl]methyl]benzoic acid; 53377336: 4-[[(5Z)-5-[[4-[(E)-3-(4-Methoxyphenyl)-3-oxoprop-1-enyl]phenyl]methylidene]-2,4-dioxo-1,3-thiazolidin-3-yl]methyl]benzoic acid; 53377337: 4-[[(5Z)-5-[[4-[(E)-3-(2-Hydroxyphenyl)-3-oxoprop-1-enyl]phenyl]methylidene]-2,4-dioxo-1,3-thiazolidin-3-yl]methyl]benzoic acid; 53377338: 4-[[(5Z)-5-[[4-[(E)-3-(4-Hydroxyphenyl)-3-oxoprop-1-enyl]phenyl]methylidene]-2,4-dioxo-1,3-thiazolidin-3-yl]methyl]benzoic acid; 53392991: (E)-N-(4-(3-(3,4-Dihydroxy-phenyl)acryloyl)phenyl)-3,5-difluorobenzamide; 53405565: 1-(2,4-Dihydroxyphenyl)-3-(3-methoxyphenyl)prop-2-en-1-one; 53405585: 3-(3,4-Dimethoxyphenyl)-1-(2-hydroxy-6-methoxyphenyl)prop-2-en-1-one; 53405586: 1-(2-Hydroxy-6-methoxyphenyl)-3-phenylprop-2-en-1-one; 53405667: 1-(2-Hydroxy-6-methoxyphenyl)-3-(3-methoxyphenyl)prop-2-en-1-one; 53405915: 3-(4-Hydroxy-3-methoxyphenyl)-1-(2,4,6-trimethoxyphenyl)prop-2-en-1-one; 53407496: 1-[2,4-Bis(ethoxymethoxy)-6-hydroxyphenyl]-3-[3,4-bis(ethoxymethoxy)phenyl]prop-2-en-1-one; 53425332: 3-[3-(Dimethylamino)phenyl]-1-(2-hydroxyphenyl)prop-2-en-1-one; 53425875: 1-[4-(Dimethylamino)-2-hydroxyphenyl]-3-phenylprop-2-en-1-one; 53437924: Potassium;3-[3-hydroxy-4-[3-(3-hydroxy-4-methoxyphenyl)prop-2-enoyl]phenoxy]propane-1-sulfonate; 53438240: 1-[2,4-Bis(benzyloxy)-6-hydroxyphenyl]-3-(3-fluorophenyl)prop-2-en-1-one; 53465655: (E)-1-(2-Hydroxy-4-methoxyphenyl)-3-[4-(methoxymethoxy)phenyl]prop-2-en-1-one; 53491216: (2E)-3-[4-(Difluoromethoxy)phenyl]-1-(2-hydroxyphenyl)prop-2-en-1-one; 53547139: N-[4-[(E)-3-(3-Hydroxyphenyl)prop-2-enoyl]phenyl]methanesulfonamide; 53547140: N-[4-[(E)-3-(4-Hydroxy-3-methoxyphenyl)prop-2-enoyl]phenyl]methanesulfonamide; 53547165: N-[4-[(E)-3-(3-Hydroxyphenyl)prop-2-enoyl]phenyl]ethanesulfonamide; 53555003: (E)-1-[4-(4-Hydroxypiperidin-1-yl)phenyl]-3-(3-methoxyphenyl)prop-2-en-1-one; 53558981: N-[4-[(E)-3-(3-Hydroxy-4-methoxyphenyl)prop-2-enoyl]phenyl]methanesulfonamide; 53574785: (E)-1-[4-(4-Hydroxypiperidin-1-yl)phenyl]-3-(4-methoxyphenyl)prop-2-en-1-one; 53635528: 4-n-Hexyl-2'-hydroxy-4'-(3-methyl-2-butenyloxy)chalcone; 53644116: 2-[4-[3-(4-Chlorophenyl)-3-oxoprop-1-enyl]phenoxy]-2-methylpropanoic acid; 53646265: 2-Hydroxy-5-[3-(4-hydroxyphenyl)-3-oxoprop-1-enyl]benzoic acid; 53646821: 2-[4-(2-Hydroxy-2-methylpropanoyl)phenoxy]ethyl 4-(3-oxo-3-phenylprop-1-enyl)benzoate; 53650150: 3-(3H-Benzimidazol-5-yl)-1-(2-hydroxy-4,6-dimethoxyphenyl)prop-2-en-1-one; 53654402: 1-(2-Hydroxy-4,6-dimethoxyphenyl)-3-(3-methoxyphenyl)prop-2-en-1-one; 53666884: 1-(4-Ethoxy-2-hydroxy-6-methylphenyl)-3-(4-methylphenyl)prop-2-en-1-one; 53668432: 4-[[4-[3-[4-(Carboxymethoxy)phenyl]-3-oxoprop-1-enyl]phenyl]methoxy]-4-oxobutanoic acid; 53669160: 1-(2-Hydroxy-4,6-dimethoxyphenyl)-3-(4-prop-2-enoxyphenyl)prop-2-en-1-one; 53674348: 3-(4-Ethoxyphenyl)-1-(2-hydroxy-4,6-dimethoxyphenyl)prop-2-en-1-one; 53677577: 2'-Carboxymethoxy-4,4',6'-trimethoxychalcone; 53686620: 1-(4-Hydroxyphenyl)-3-(4-methoxy-3-methylphenyl)prop-2-en-1-one; 53688548: 3-[3-[4-(Carboxymethoxy)phenyl]-3-oxoprop-1-enyl]benzoic acid; 53706448: 2-[2-[3-(4-Tert-butylphenyl)prop-2-enoyl]-5-(3-methylbut-2-enoxy)phenoxy]propanoic acid; 53706894: 4-[3-[4-(Carboxymethoxy)-2-prop-2-enoxyphenyl]-3-oxoprop-1-enyl]benzoic acid; 53709151: N-[4-[3-[4-[(Hydroxy-2-oxo-3H-1,3-thiazol-5-yl)methyl]phenyl]-3-oxoprop-1-enyl]phenyl]acetamide; 53709942: 2-[4-[3-(3-Methoxyphenyl)prop-2-enoyl]phenoxy]acetic acid; 53714521: 1-[4-(14-Hydroxytetradecoxy)phenyl]-3-phenylprop-2-en-1-one; 53730373: 4-[3-[2-(Carboxymethoxy)-4-(3-methylbut-2-enoxy)phenyl]-3-oxoprop-1-enyl]benzoic acid; 53731439: 2'-Carboxymethoxy-4-n-heptyl-4'-(3-methyl-2-butenyloxy)chalcone; 53737293: 3-(3-Hydroxyphenyl)-1-(4-hydroxyphenyl)prop-2-en-1-one; 53742484: 3-(4-Hydroxyphenyl)-1-(2-nitro-phenyl)prop-2-en-1-one; 53753462: 2-[4-[3-(3,4-Dichlorophenyl)prop-2-enoyl]phenoxy]acetic acid; 53755924: 1-[4-(2-Hydroxyethoxy)phenyl]-3-phenylprop-2-en-1-one; 53758472: 4-[3-(4-Hydroxyphenyl)-3-oxoprop-1-en-1-yl]benzoic acid; 53759355: 3-(4-Methoxyphenyl)-1-(2,4,6-trihydroxyphenyl)prop-2-en-1-one; 53761572: 4-Hydroxy-5-[[4-[3-(4-hydroxy-3-methoxyphenyl)prop-2-enoyl]phenyl]methyl]-3H-1,3-thiazol-2-one; 53770211: 1-[2-Hydroxy-4-(oxan-2-yloxy)phenyl]-3-phenylprop-2-en-1-one; 53777486: 3-(3-Fluoro-phenyl)-1-(4-hydroxyphenyl)prop-2-en-1-one; 53782722: 2-Hydroxy-3-[4-(3-naphthalen-2-ylprop-2-enoyl)phenyl]-2H-furan-5-one; 53791120: 2-[5-(3-Methylbut-2-enoxy)-2-[3-(4-propylphenyl)prop-2-enoyl]phenoxy]acetic acid; 53797251: 1-[4-[(2-Hydroxyphenyl)methoxy]phenyl]-3-phenylprop-2-en-1-one; 53801271: (6R,7R)-3-(Acetyloxymethyl)-8-oxo-7-[[2-[[4-(3-oxo-3-phenylprop-1-enyl)benzoyl]amino]-2-phenylacetyl]amino]-5-thia-1-azabicyclo[4.2.0]oct-2-ene-2-carboxylic acid; 53809377: Methyl 4-[[3-hydroxy-4-[3-(4-hydroxyphenyl)prop-2-enoyl]phenyl]carbamoyloxy]benzoate; 53810408: 2'-(4-Carboxybu-tanoyloxy)-4,4',6'-trimethoxychalcone; 53812313: [2-Hydroxy-3-[4-(3-phenylprop-2-enoyl)phenoxy]propyl] 2-methylprop-2-enoate; 53815747: 4-Amino-2'-hydroxy-4',6'-dimethoxychalcone; 53832608: 4-[3-[4-(Dimethylamino)phenyl]prop-2-enoyl]benzoic acid; 53850739: 4-[3-(2-Hydroxy-4,6-dimethoxyphenyl)-3-oxoprop-1-enyl]benzonitrile; 53854152: 2-[4-(2,2-Dimethylpropanoyl)phenoxy]ethyl 4-[(E)-3-oxo-3-phenylprop-1-enyl]benzoate; 2-hydroxy-1-[4-(2-hydroxyethoxy)phenyl]-2-methylpropan-1-one;4-(3-oxo-3-phenylprop-1-enyl)benzoic acid; 53854901: 1-[4-(2-Hydroxybutoxy)phenyl]-3-(4-methoxyphenyl)prop-2-en-1-one; 53862296: 1-(2,4-Diethoxy-6-hydroxyphenyl)-3-(4-ethoxyphenyl)prop-2-en-1-one; 53882184: 2-[4-[3-[4-(Carboxymethoxy)-3-methoxyphenyl]prop-2-enoyl]phenoxy]acetic acid; 53891531: 2-Methyl-2-[4-(3-oxo-3-phenylprop-1-enyl)phenoxy]propanoic acid; 53893700: 2-[3-Hydroxy-4-[3-(2-quinolin-2-ylethenyl)phenyl]prop-2-enoyl]phenoxy]acetic acid; 53903222: 2-[4-[3-(4-Methylphenyl)prop-2-enoyl]

phenoxy]acetic acid; 53904844: 1-(4-Hydroxyphenyl)-3-(3-methyl-4-nitro-phenyl)prop-2-en-1-one; 53906014: 3-(3-Ethoxy-4-hydroxyphenyl)-1-(4-hydroxyphenyl)prop-2-en-1-one; 53906975: (1,4-Dihydroxycyclohexyl)-(4-hydroxyphenyl)methanone;[4-[1-hydroxy-4-[4-[(E)-3-oxo-3-phenylprop-1-enyl]benzoyl]cyclohexanecarbonyl]phenyl] 4-[(E)-3-oxo-3-phenylprop-1-enyl]benzoate;4-[(E)-3-oxo-3-phenylprop-1-enyl]benzoyl chloride; 53917706: 1-(2-Hydroxy-4-methoxy-6-propan-2-yloxyphenyl)-3-(4-methoxyphenyl)prop-2-en-1-one; 53921963: 1-(2-Hydroxyphenyl)-3-(4-methylsulfanylphenyl)prop-2-en-1-one; 53925363: 3-Hydroxy-4-[3-[4-(quinolin-2-ylmethoxy)phenyl]prop-2-enoyl]benzoic acid; 53945448: 2-[4-[3-[3-(Carboxymethoxy)phenyl]prop-2-enoyl]phenoxy]acetic acid; 53948432: 2-[2-[3-[4-(3-Methylbut-2-enoxy)phenyl]prop-2-enoyl]phenoxy]acetic acid; 53958843: 1-[4-(Prop-2-enyloxy)-2-carboxy-ethoxyphenyl]-3-(3-carboxyphenyl)-prop-2-en-1-one; 53962767: 3-[3-(4-Hydroxyphenyl)-3-oxoprop-1-enyl]benzoic acid; 53963166: 4-[3-[2-(Carboxymethoxy)-4-prop-2-ynoxyphenyl]-3-oxoprop-1-enyl]benzoic acid; 53965621: 1-(2,4-Dihydroxyphenyl)-3-(3-fluorophenyl)prop-2-en-1-one; 53966669: 1-(2-Ethoxy-6-hydroxy-4-methoxyphenyl)-3-(4-ethoxyphenyl)prop-2-en-1-one; 53971360: 2-[4-[3-(3-Chlorophenyl)prop-2-enoyl]phenoxy]acetic acid; 53976594: 1-[2-[2-Hydroxy-3-(propylamino)propoxy]-4-phenylmethoxyphenyl]-3-phenylprop-2-en-1-one; 53977293: 2-[2-[3-(4-Hex-1-enylphenyl)prop-2-enoyl]-5-(3-methylbut-2-enoxy) phenoxy]acetic acid; 53982926: 1-(2-Fluorophenyl)-3-(4-hydroxyphenyl)prop-2-en-1-one; 53984932: 4-[3-[3-[[4-(1-Ethoxyethyl)-1H-benzimidazol-2-yl]methoxy]phenyl]prop-2-enoyl]-3-hydroxybenzoic acid; 53987212: 2'-Hydroxy-4',6'-dimethoxy-4-(methoxymethoxy) chalcone; 53992665: 1-[4-(6-Hydroxyhexoxy)phenyl]-3-phenylprop-2-en-1-one; 54000168: 4-Hydroxy-5-[[2-[3-(4-hydroxy-3-methoxyphenyl)prop-2-enoyl]phenyl]methyl]-3H-1,3-thiazol-2-one; 54016776: 2-[4-(2-Hydroxy-2-methylpropanoyl)phenoxy]ethyl 4-[3-[4-[2-[4-(2-hydroxy-2-methylpropanoyl)phenoxy]ethoxycarbonyl]phenyl]-3-oxoprop-1-enyl]benzoate; 54028671: 3-(3-Oxo-3-phenyl-1-propenyl)-benzoic acid; 54057907: 3-(4-Hydroxyphenyl)-1-(4-nitro-phenyl)prop-2-en-1-one; 54073919: 4-(3-(3-(2-Quinolinylmethyloxy)phenyl)-1-oxo-2-propen-1-yl)phenol; 54076687: 4-[3-[4-(Hydroperoxymethyl)phenyl]prop-2-enoyl]benzoic acid; 54078334: 1-(4-Hydroxyphenyl)-3-(3-methoxy-4-methylphenyl)prop-2-en-1-one; 54078463: Formaldehyde;1-(1-hydroxy-4-methylcyclohexyl)ethanone;(E)-3-[4-[(4-methyl-phenoxy)methyl]phenyl]-1-phenylprop-2-en-1-one; 4-[(E)-3-oxo-3-phenylprop-1-enyl]benzaldehyde; 54091858: 4-[3-(4-Chlorophenyl)acryloyl]benzoic acid; 54097644: 4-[3-[2-(Carboxymethoxy)-4-prop-2-enoxyphenyl]-3-oxoprop-1-enyl]benzoic acid; 54101155: 2'-Carboxymethoxy-4-n-hexyl-4'-(3-methyl-2-butenyloxy)chalcone; 54103209: 1-(2-Hydroxy-phenyl)-3-[4-(trifluoromethyl)phenyl]prop-2-en-1-one; 54106084: 1-[2-Hydroxy-4-(oxan-2-yloxy)phenyl]-3-[4-methoxy-3-(oxan-2-yloxy)phenyl]prop-2-en-1-one; 54126965: 4-[3-(4-Methylphenyl)prop-2-enoyl]benzoic acid; 54142928: 2-[4-[3-[4-(Carboxymethoxy)phenyl]-3-oxoprop-1-enyl] phenoxy]acetic acid; 54145184: 3-(4-Hydroxyphenyl)-1-(4-propan-2-ylphenyl)prop-2-en-1-one; 54147825: 2'-(Carboxymethoxy)-4'-(3-methyl-2-butenyloxy)-4-(2-propenyl)chalcone; 54153200: 3-[3,4-Bis(oxan-2-yloxy)phenyl]-1-[2-hydroxy-4-(oxan-2-yloxy)phenyl]prop-2-en-1-one; 54155269: 1-(2-Hydroxy-4,6-bis(oxan-2-yloxy) phenyl]-3-[4-(oxan-2-yloxy)phenyl]prop-2-en-1-one; 54164104: (E)-4-[4-(Hydroperoxymethyl)phenyl]but-3-en-2-one;(E)-3-[4-(hydroperoxymethyl)phenyl]-1-(4-hydroxyphenyl)prop-2-en-1-one;[4-[(E)-3-(4-(hydroperoxymethyl)phenyl]prop-2-enoyl]phenyl] 4-[(E)-3-oxobut-1-enyl]benzoate; 54165323: 1-(2-Hydroxy-4,6-dimethoxyphenyl)-3-(4-propoxyphenyl)prop-2-en-1-one; 54166926: [4-(1-Hydroxycyclohexanecarbonyl)phenyl] 4-(3-oxo-3-phenylprop-1-enyl)benzoate; 54167652: 1-O-Butyl 7-O-[2-[[4-[3-(3,4-dimethoxyphenyl)prop-2-enoyl]phenyl]carbamoylamino]ethyl] 6-ethyl-4-(hydroxymethylcarbamoyl)-2,2,6-trimethylheptanedioate; 54179603: 4,4'-(3-Oxoprop-1-ene-1,3-diyl)dibenzoic acid; 54187774: 2-[3-(3,4-Dihydroxy-phenyl)prop-2-enoyl]benzoic acid; 54189996: 4-[3-(3,4-Dihydroxyphenyl)prop-2-enoyl]benzoic acid; 54190460: 4-[3-[2-(Carboxymethoxy)-4-hex-5-enoxyphenyl]-3-oxoprop-1-enyl]benzoic acid; 54192110: 1-[2-Hydroxy-4-(1,2,2-trifluoroethenyl)phenyl]-3-[4-[3-[2-hydroxy-4-(1,2,2-trifluoroethenyl)phenyl]-3-oxoprop-1-enyl]phenyl]prop-2-en-1-one; 54199694: 2-[4-[3-[2-(Carboxymethoxy)-4-(3-methylbut-2-enoxy)phenyl]-3-oxoprop-1-enyl]phenoxy]acetic acid; 54201141: 3-(3-Chloro-4-nitro-phenyl)-1-(4-hydroxyphenyl)prop-2-en-1-one; 54214492: 3-(4-Acetylphenyl)-1-phenylprop-2-en-1-one;2-[4-(2-hydroxy-2-methylpropanoyl)phenoxy]ethyl 4-[(E)-3-oxo-3-phenylprop-1-enyl]benzoate; 54217023: 4-(4-Cinnamoylphenyl)butyric Acid; 54218200: 1-[4-(3-Hydroxypropoxy)phenyl]-3-phenylprop-2-en-1-one; 54230092: 2-[5-(3-Methylbut-2-enoxy)-2-[3-(4-methylphenyl)prop-2-enoyl]phenoxy]acetic acid; 54238934: 2-[3-[4-(Quinolin-2-ylmethoxy)phenyl]prop-2-enoyl]benzoic acid; 54242231: 3-(3,4-Dimethylphenyl)-1-(4-hydroxyphenyl)prop-2-en-1-one; 54251472: 3-[4-(3-Phenylprop-2-enoyl)phenyl]prop-2-enoic acid; 54278990: 4-[3-(4-Hydroxyphenyl)prop-2-enoyl]benzonitrile; 54280346: 3-[4-(Diethylamino)phenyl]-1-(2-hydroxy-4,6-dimethoxyphenyl)prop-2-en-1-one; 54281601: 1-(2,6-Dihydroxyphenyl)-3-(4-hydroxyphenyl)prop-2-en-1-one; 54281653: 3-(3-Chlorophenyl)-1-(4-hydroxyphenyl)prop-2-en-1-one; 54283012: 3-[4-[Bis(2-hydroxyethyl)amino]phenyl]-1-phenylprop-2-en-1-one; 54288459: 1-[4-(6-Hydroxy-hexoxy)phenyl]-3-(4-methoxyphenyl)prop-2-en-1-one; 54288541: 2'-Hydroxy-4,4'-bis(methoxymethoxy) chalcone; 54293943: (6R,7R)-3-(Acetyloxymethyl)-7-[[2-[[4-[3-(4-chloro-phenyl)prop-2-enoyl]benzoyl]amino]-2-phenylacetyl]amino]-8-oxo-5-thia-1-azabicyclo[4.2.0]oct-2-ene-2-carboxylic acid; 54301504: 3-[3-[2-(Carboxymethoxy)-4-prop-2-enoxyphenyl]-3-oxoprop-1-enyl]benzoic acid; 54303977: 1-[2-Hydroxy-4-(oxan-2-yloxy) phenyl]-3-(4-methoxyphenyl)prop-2-en-1-one; 54307405: 2-[4-[3-[4-(Hydroxymethyl)phenyl]prop-2-enoyl]phenoxy]acetic acid; 54312353: 1-(2-Ethoxy-6-hydroxy-4-methoxy-phenyl)-3-(4-methoxyphenyl)prop-2-en-1-one; 54326512: 1-(4-Ethenylphenyl)-3-(4-hydroxyphenyl)prop-2-en-1-one; 54328977: 1-(2,4-Diethoxy-6-hydroxyphenyl)-3-(4-methoxyphenyl) prop-2-en-1-one; 54335129: 3-(3,4-Difluorophenyl)-1-(2-hydroxyphenyl)-2-propen-1-one; 54341076: 4-Acetylamino-2'-hydroxychalcone; 54347228: 4'-Carboxy-4-carboxymethoxy-chalcone; 54348409: 2'-Hydroxy-4,4'-bis(tetrahydropyranyloxy)chalcone; 54352682: 1-(2-Hydroxy-4-methoxy-6-propoxyphenyl)-3-(4-methoxyphenyl)prop-2-en-1-one; 54359970: 3-(4-Hydroxy-3-methylphenyl)-1-[2-(1,3-thiazolidin-5-ylmethyl)phenyl]prop-2-en-1-one; 54364549: 5-[[2-[3-(3,4-Dihydroxyphenyl)prop-2-enoyl]phenyl]methyl]-4-hydroxy-3H-1,3-thiazol-2-one; 54370360: 3-(4-Ethylphenyl)-1-(4-hydroxyphenyl)prop-2-en-1-one; 54371548: 1-(2,4-Dimethoxy-6-aminophenyl)-3-(4-hydroxyphenyl)-prop-2-en-1-one; 54380952: 2-[4-[3-(3-Methylphenyl)prop-2- enoyl]phenoxy]acetic acid; 54382045: 2-[5-(3-Methylbut-2-enoxy)-2-[3-(4-oct-1-enylphenyl)prop-2-enoyl]phenoxy]acetic acid; 54386652: 4-(2-Carboxyethyl)benzalacetophenone; 54387811: 4-[3-[4-(3-Carboxypropanoyloxy) phenyl]-3-oxoprop-1-enyl]benzoic acid; 54390094: 4-Hydroxy-5-[[4-[3-(4-hydroxyphenyl)prop-2-enoyl]phenyl]methyl]-3H-1,3-thiazol-2-one; 54398527: N-[(2S,3R,4R,5S,6R)-2-[3,5-Dimethoxy-2-[3-(4-methoxyphenyl)prop-2-enoyl]phenoxy]-4,5-dihydroxy-6-(hydroxymethyl) oxan-3-yl]acetamide; 54403936: 3-[3,4-Bis(oxan-2-yloxy)phenyl]-1-(2-hydroxyphenyl)prop-2-en-1-one; 54410089: 1-[4-(12-Hydroxydodecoxy)phenyl]-3-phenylprop-2-en-1-one; 54414270: 2-Hydroxy-5-(3-oxo-3-phenylprop-1-enyl)benzoic acid; 54418486: 3-[4-(Diethylamino)phenyl]-1-(2-hydroxyphenyl)prop-2-en-1-one; 54427904: 4-Hydroxy-5-[[4-(3-phenylprop-2-enoyl)phenyl]methyl]-3H-1,3-thiazol-2-one; 54431244: 3-Hydroxy-4-[3-[3-(quinolin-2-ylmethoxy)phenyl]prop-2-enoyl]benzoic acid; 54432439: 1-(2-Hydroxy-4,6-dimethoxyphenyl)-3-(3-methylsulfanylphenyl)prop-2-en-1-one; 54442229: 1-[4-(Dimethyl-amino)phenyl]-3-(4-hydroxyphenyl)prop-2-en-1-one; 54450021: 3-Hydroxy-4-(3',4'-dihydroxycinnamoyl)-cinnamic acid; 54467749: 2-[3-[3-(Quinolin-2-ylmethoxy)phenyl]prop-2-enoyl]benzoic acid; 54469106: 3-[3,4-Bis[3-(3,4-dihydroxyphenyl)prop-2-enoyl]phenyl]prop-2-enoic acid; 54475120: [4-(4-Hydroxybenzoyl)phenyl] acetate;(3-methoxy-2,3,3a,5,6,6a-hexahydrofuro[3,2-b]furan-6-yl)acetate;[4-[(E)-3-(4-methoxyphenyl)prop-2-enoyl]phenyl]acetate; 54478415: 4-t-Butyl-2'-hydroxy-4'-(3-methyl-2-butenyloxy)chalcone; 54481476: 1-(4-Ethoxy-2-hydroxy-6-methoxyphenyl)-3-(4-ethoxyphenyl)prop-2-en-1-one; 54493201: 1-(4-Carboxyphenyl)-3-phenyl-2-propen-1-one; 54498386: 5-[4-[3-[4-(Carboxymethoxy)phenyl]-3-oxoprop-1-enyl]phenyl]-4-oxopentanoic acid; 54506784: 4-[3-[2-[3-(4-Carboxyphenyl)prop-2-enoyl]phenyl]-3-oxoprop-1-enyl]benzoic acid; 54506937: 5-[[4-[3-(3,4-Dihydroxyphenyl)prop-2-enoyl]phenyl]methyl]-4-hydroxy-3H-1,3-thiazol-2-one; 54509909: 1-(4-Ethylphenyl)-3-(4-hydroxyphenyl)prop-2-en-1-one; 54517723: (2E,6E)-2-[(4-Azidophenyl)methylidene]-4-hydroxy-6-[(4-methylphenyl)methylidene]cyclohexan-1-one;(2E,6E)-2-[(4-azidophenyl)methylidene]-4-methyl-6-[(4-methylphenyl)methylidene]cyclohexan-1-one; (3E,5E)-3-[(4-azidophenyl)methylidene]-5-[(4-methylphenyl)methylidene]-4-oxocyclo-hexane-1-carboxylic acid;(Z)-1-(4-azidophenyl)-3-(4-methylphenyl)prop-2-en-1-one;(2E,6E)-2-[(Z)-3-(4-azidophenyl)prop-2-enylidene]-4-(hydroxymethyl)-6-[(Z)-3-(4-methylphenyl)prop-2-enylidene]cyclohexan-1-one;(2E,6E)-2-[(Z)-3-(4-azidophenyl)prop-2-enylidene]-4-hydroxy-6-[(Z)-3-(4-methylphenyl)prop-2-enylidene]cyclohexan-1-one; 54525987: 4-Hydroxy-5-[[4-[3-3-methoxy-4-(methoxymethoxy)phenyl]prop-2-enoyl]phenyl]methyl]-3H-1,3-thiazol-2-one; 54527074: 2-[3,5-Dimethoxy-2-[3-[4-methoxy-3-(3-methylbutyl)phenyl]prop-2-enoyl]phenoxy]acetic acid; 54528223: 1-O-(2,2-Dimethyl-4-oxopentyl) 5-O-(2-hydroxyethyl) 2-methyl-4-[2-[4-(3-phenylprop-2-enoyl)phenyl]butyl]pentanedioate; 54529107: 3-[3,4-Bis(oxan-2-yloxy)phenyl]-1-[2-hydroxy-4,6-bis(oxan-2-yloxy)phenyl]prop-2-en-1-one; 54529521: 4-Hydroxy-5-[[4-[3-(4-methoxyphenyl)prop-2-enoyl]phenyl]methyl]-3H-1,3-thiazol-2-one; 54529787: [4-[3-(2-Hydroxy-4,6-dimethoxyphenyl)-3-oxoprop-1-enyl]phenyl] acetate; 54538532: 1-[2-Hydroxy-4-(oxan-2-yloxy)phenyl]-3-[3-methoxy-4-(oxan-2-yloxy)phenyl]prop-2-en-1-one; 54541004: 4-Hydroxy-2',4',6'-tribenzoyloxy-chalcone; 54541964: 1-[2-(3-Chloropropoxy)-6-hydroxyphenyl]-3-phenylprop-2-en-1-one; 54545560: 3-(4-Hydroxy-3-methylphenyl)-1-(4-nitro-phenyl)prop-2-en-1-one; 54546100: 2-[2-[3-(4-Hept-1-enylphenyl)prop-2-enoyl]-5-(3-methylbut-2-enoxy)phenoxy]acetic acid; 54553910: 2-Methylidene-4-[4-(3-phenylprop-2-enoyl)phenoxy]butanoic acid; 54556576: 2-[5-(3-Methylbut-2-enoxy)-2-(3-phenylprop-2-enoyl)phenoxy]acetic acid; 54566704: 3-[4-(Dimethylamino)phenyl]-1-[4-(2-hydroxyethoxy)phenyl]prop-2-en-1-one; 54577840: (6As)-3-[[1-[3-[4-[(E)-3-(4-hydroxyphenyl)-3-oxoprop-1-enyl]-2-methoxyphenoxy]propyl]triazol-4-yl]methoxy]-2-methoxy-6a,7,8,9-tetrahydropyrrolo[2,1-c][1,4]benzodiazepin-11-one; 54580130: (E)-1-(2,4-Dihydroxyphenyl)-3-[3-(4-hydroxy-3-methoxyphenyl)-2-(hydroxy-methyl)-2,3-dihydro-1,4-benzodioxin-6-yl]prop-2-en-1-one; 54580526: (E)-1-(2-Hydroxy-4-phenylmethoxyphenyl)-3-[3-[5-[(E)-3-(2-hydroxy-4-phenylmethoxyphenyl)-3-oxoprop-1-enyl]-2-phenylmethoxyphenyl]-4-phenylmethoxyphenyl]prop-2-en-1-one; 54583093: (E)-1-(2,6-Dihydroxyphenyl)-3-[3-(4-hydroxy-3-methoxyphenyl)-2-(hydroxymethyl)-2,3-dihydro-1,4-benzodioxin-6-yl]prop-2-en-1-one; 54583499: (E)-1-(2-Hydroxy-4,6-dimethoxyphenyl)-3-[3-[5-[(E)-3-(2-hydroxy-4,6-dimethoxyphenyl)-3-oxoprop-1-enyl]-2-methoxyphenyl]-4-methoxyphenyl]prop-2-en-1-one; 54586980: (E)-3-[3-(4-Hydroxy-3-methoxyphenyl)-2-(hydroxymethyl)-2,3-dihydro-1,4-benzodioxin-6-yl]-1-(2,4,6-trihydroxyphenyl)prop-2-en-1-one; 54586981: (E)-3-[3-(4-Hydroxy-3-methoxyphenyl)-2-(hydroxymethyl)-2,3-dihydro-1,4-benzodioxin-6-yl]-1-(2-hydroxyphenyl)prop-2-en-1-one; 54601392: (Z)-1-(2-Hydroxyphenyl)-3-(3-methoxyphenyl)prop-2-en-1-one; 54608362: (Z)-1-(2-Hydroxyphenyl)-3-[4-[(Z)-3-(2-hydroxyphenyl)-3-oxoprop-1-enyl]phenyl]prop-2-en-1-one; 54610086: (Z)-3-(4-Hydroxy-3-methoxyphenyl)-1-(2-hydroxyphenyl)prop-2-en-1-one; 54681797: 2-[(E)-3-(4-Carboxy-phenyl)prop-2-enoyl]phenolate; 54684649: 4-[(E)-3-(4-Carboxyphenyl)prop-2-enoyl]phenolate; 54715661: 5-[(E)-3-[4-(5-Carboxyfuran-2-yl)phenyl]-3-oxoprop-1-enyl]-2-methoxyphenolate; 54717071: 4-[(E)-3-[4-(5-Carboxyfuran-2-yl)phenyl]-3-oxoprop-1-enyl]-2-methoxyphenolate; 54717073: 4-[(E)-3-[4-(5-Carboxyfuran-2-yl)phenyl]-3-oxoprop-1-enyl]-2-ethoxyphenolate; 54721306: 2-[(E)-3-(4-Carboxyphenyl)prop-2-enoyl]-3-(cyclohexyl-methoxy)phenolate; 54754558: (E)-3-[3-Hydroxy-4-(piperidin-1-ylmethyl)phenyl]-1-(4-methoxyphenyl)prop-2-en-1-one; 54754674: (E)-3-[3-Hydroxy-4-[(4-methylmorpholin-4-ium-4-yl)methyl]phenyl]-1-(4-methoxyphenyl)prop-2-en-1-one; 54754678: (E)-1-(2-Hydroxy-4-methoxyphenyl)-3-[4-(morpholin-4-ylmethyl)-3-phenylmethoxyphenyl]prop-2-en-1-one; 54754803: (E)-3-[4-[(Dimethylamino)methyl]-3-hydroxyphenyl]-1-(4-methoxyphenyl)prop-2-en-1-one; 54754922: (E)-3-[3-Hydroxy-4-[(4-methylpiperazin-1-yl)methyl]phenyl]-1-(4-methoxyphenyl)prop-2-en-1-one; 54754924: (E)-1-(4-Fluorophenyl)-3-[3-hydroxy-4-[1-(hydroxyamino)ethyl]phenyl]prop-2-en-1-one; 54756466: (E)-3-[3-Hydroxy-4-(morpholin-4-ylmethyl)phenyl]-1-(4-methoxyphenyl)prop-2-en-1-one; 54769564: (E)-1-(2-Hydroxyphenyl)-3-(3-methoxy-4-prop-2-ynoxyphenyl)prop-2-en-1-one; 54769565: (6As)-3-[[1-[3-[4-[(E)-3-(2-hydroxyphenyl)-3-oxoprop-1-enyl]-2-methoxyphenoxy]propyl]triazol-4-yl]methoxy]-2-methoxy-6a,7,8,9-tetrahydropyrrolo[2,1-c][1,4]benzodiazepin-11-one; 54769566: (6As)-3-[[1-[4-[4-[(E)-3-(2-hydroxyphenyl)-3-oxoprop-1-enyl]-2-methoxyphenoxy]butyl]triazol-4-yl]methoxy]-2-methoxy-6a,7,8,9-tetrahydropyrrolo[2,1-c][1,4]benzodiazepin-11-one; 54769567: (6As)-3-[[1-[5-[4-[(E)-

3-(2-hydroxyphenyl)-3-oxoprop-1-enyl]-2-methoxyphenoxy]pentyl]triazol-4-yl]methoxy]-2-methoxy-6a,7,8,9-tetrahydropyrrolo[2,1-c][1,4]benzodiazepin-11-one; 54769774: (6As)-3-[[1-[5-[4-[(E)-3-(4-hydroxyphenyl)-3-oxoprop-1-enyl]-2-methoxy-phenoxy]pentyl]triazol-4-yl]methoxy]-2-methoxy-6a,7,8,9-tetrahydropyrrolo[2,1-c][1,4]benzo-diazepin-11-one; 54769987: (6As)-3-[[1-[4-[4-[(E)-3-(4-hydroxyphenyl)-3-oxoprop-1-enyl]-2-methoxyphenoxy]butyl]triazol-4-yl]methoxy]-2-methoxy-6a,7,8,9-tetrahydropyrrolo[2,1-c][1,4]benzodiazepin-11-one; 54769988: (6As,8S)-8-[4-[[4-[(E)-3-(2-hydroxyphenyl)-3-oxoprop-1-enyl]-2-methoxyphenoxy]methyl]triazol-1-yl]-2,3-dimethoxy-6a,7,8,9-tetrahydropyrrolo[2,1-c][1,4]benzodiazepin-11-one; 54769989: (6As,8S)-8-[4-[[4-[(E)-3-(2-hydroxyphenyl)-3-oxoprop-1-enyl]-2-methoxyphenoxy]methyl]triazol-1-yl]-2-methoxy-3-phenylmethoxy-6a,7,8,9-tetrahydropyrrolo[2,1-c][1,4]benzodiazepin-11-one; 54769991: (E)-3-[4-(3-Azidopropoxy)-3-methoxyphenyl]-1-(2-hydroxyphenyl)prop-2-en-1-one; 54770202: (E)-3-[4-[[1-[(3S,5S)-5-[Bis(ethylsulfanyl)methyl]-1-(4,5-dimethoxy-2-nitrobenzoyl)pyrrolidin-3-yl]triazol-4-yl]methoxy]-3-methoxyphenyl]-1-(2-hydroxyphenyl)prop-2-en-1-one; 54770422: (E)-3-[4-[3-[4-[[4-[(2S)-2-[Bis(ethylsulfanyl)methyl]pyrrolidine-1-carbonyl]-2-methoxy-5-nitrophenoxy]methyl]triazol-1-yl]propoxy]-3-methoxyphenyl]-1-(2-hydroxyphenyl) prop-2-en-1-one; 55353400: 3-[[4-[(E)-3-Quinolin-6-ylprop-2-enoyl]phenyl]sulfonylamino]propanoic acid; 55353459: 2-[[4-[(E)-3-[4-(3-Methylbutoxy)phenyl]prop-2-enoyl]phenyl]sulfonylamino]acetic acid; 55353539: 2-[[4-[(E)-3-(4-Butoxy-3-ethoxyphenyl)prop-2-enoyl]phenyl]sulfonylamino]acetic acid; 55353561: 2-[[4-[(E)-3-(4-Methoxy-3-propoxyphenyl)prop-2-enoyl]phenyl]sulfonylamino]acetic acid; 55353577: 2-[[4-[(E)-3-[3-(Difluoromethoxy)-4-methoxyphenyl]prop-2-enoyl]phenyl]sulfonylamino]acetic acid; 55768948: 3-[[3-[(E)-3-(4-Hydroxyphenyl)-3-oxoprop-1-enyl]phenoxy]methyl]benzonitrile; 55771796: 3-[[4-[(E)-3-[4-(Pyridin-4-ylmethoxy)phenyl]prop-2-enoyl]phenyl]sulfonylamino]propanoic acid; 55771855: 3-[[4-[(E)-3-[4-(2-Carboxyethoxy)phenyl]prop-2-enoyl]phenyl]sulfonylamino]propanoic acid; 55772182: 2-[[4-[(E)-3-[4-(Pyridin-4-ylmethoxy)phenyl]prop-2-enoyl]phenyl]sulfonylamino]acetic acid; 55772241: 2-[[4-[(E)-3-[4-(Pyridin-2-ylmethoxy)phenyl]prop-2-enoyl]phenyl]sulfonylamino]acetic acid; 55772242: 3-[4-[(E)-3-[4-(Carboxy-methylsulfamoyl)phenyl]-3-oxoprop-1-enyl]phenoxy]propanoic acid; 55809449: 3-(3-Hydroxy-4-methoxyphenyl)-1-[4-[(1-methylimidazol-2-yl)methoxy]phenyl]prop-2-en-1-one; 55838857: 3-[[4-[(E)-3-[3-(2-Methoxyethoxy)phenyl]prop-2-enoyl]phenyl]sulfonylamino]propanoic acid; 55839235: 2-[[4-[(E)-3-[3-(2-Methoxyethoxy)phenyl]prop-2-enoyl]phenyl]sulfonylamino]acetic acid; 55882398: 3-[4-[3-[4-(2-Chloroprop-2-enoxy)phenyl]-3-oxoprop-1-enyl]phenoxy]propanoic acid; 55883594: 3-[4-[(E)-3-[4-[(1-Methylimidazol-2-yl)methoxy]phenyl]-3-oxoprop-1-enyl]phenoxy]propanoic acid; 56097259: 3-[[4-[(E)-3-[4-[(5-Methyl-1,2,4-oxadiazol-3-yl)methoxy]phenyl]prop-2-enoyl]phenyl]sulfonylamino]propanoic acid; 56097285: 2-[[4-[(E)-3-[4-[(5-Methyl-1,2,4-oxadiazol-3-yl)methoxy]phenyl]prop-2-enoyl]phenyl]sulfonylamino]acetic acid; 56146881: (E)-3-(3-Chloro-4-hydroxyphenyl)-1-[4-[(1-methylimidazol-2-yl)methoxy]phenyl]prop-2-en-1-one; 56177667: Methyl 2-[4-[(E)-3-(3-bromo-4-hydroxyphenyl)prop-2-enoyl]phenoxy]acetate; 56201040: 2-[3-[(E)-3-Oxo-3-(4-propoxyphenyl)prop-1-enyl]phenoxy]propanoic acid; 56201072: 3-[3-[(E)-3-Oxo-3-[4-(trifluoromethyl)phenyl]prop-1-enyl]phenoxy]propanoic acid; 56201103: 3-[3-[(E)-3-[4-[(1-Methylimidazol-2-yl)methoxy]phenyl]-3-oxoprop-1-enyl]phenoxy]propanoic acid; 56201135: 3-[3-[(E)-3-[4-(Azepan-1-yl)phenyl]-3-oxoprop-1-enyl]phenoxy] propanoic acid; 56201356: 3-[3-[(E)-3-(4-Morpholin-4-ylphenyl)-3-oxoprop-1-enyl]phenoxy]propanoic acid; 56201358: 2-[3-[(E)-3-[4-(Dimethylsulfamoyl)phenyl]-3-oxoprop-1-enyl]phenoxy]propanoic acid; 56201390: 2-[3-[(E)-3-Oxo-3-(4-piperidin-1-ylphenyl)prop-1-enyl]phenoxy]propanoic acid; 56337789: 3-[[4-[(E)-3-[4-[2-(Ethylamino)-2-oxoethoxy]phenyl]prop-2-enoyl]phenyl]sulfonylamino]propanoic acid; 56338429: 2-[[4-[(E)-3-[4-[2-(Ethylamino)-2-oxoethoxy]phenyl]prop-2-enoyl]phenyl]sulfonylamino]acetic acid; 56402357: 2-[[4-[(E)-3-[3-(3-Cyanopropoxy)phenyl]prop-2-enoyl]phenyl]sulfonylamino]acetic acid; 56402619: 3-[[4-[(E)-3-[3-(3-Cyanopropoxy)phenyl]prop-2-enoyl]phenyl]sulfonylamino]propanoic acid; 56521448: 2-[[4-[(E)-3-[4-(1-Cyanoethoxy)phenyl]prop-2-enoyl]phenyl]sulfonylamino]acetic acid; 56521830: 3-[[4-[(E)-3-[4-(1-Cyanoethoxy)phenyl]prop-2-enoyl]phenyl]sulfonylamino]propanoic acid; 56528680: 3-[3-[(E)-3-[4-(Ethylsulfonylamino)phenyl]-3-oxoprop-1-enyl]phenoxy]propanoic acid; 56528790: 3-[4-[(E)-3-[4-(Ethylsulfonylamino)phenyl]-3-oxoprop-1-enyl]phenoxy]propanoic acid; 56528798: 2-[3-[(E)-3-[4-(Ethylsulfonylamino)phenyl]-3-oxoprop-1-enyl]phenoxy]propanoic acid; 56528844: N-[4-[(E)-3-(3-Bromo-4-hydroxyphenyl)prop-2-enoyl]phenyl]ethanesulfonamide; 56636131: 4-O-Methylhelichrysetin; 56641248: 5-[4-[(E)-3-Phenylprop-2-enoyl]phenoxy]pentanoic acid; 56641379: 2,2-Dimethyl-5-[4-[(E)-3-phenylprop-2-enoyl]phenoxy]pentanoic acid; 56781320: 4-[(E)-3-(2-Fluoro-4-hydroxyphenyl)-3-oxoprop-1-enyl]benzonitrile; 56794369: (E)-3-(3-Hydroxy-4-methoxyphenyl)-1-(4-imidazol-1-ylphenyl)prop-2-en-1-one; 56847637: N-[4-[(E)-3-[4-[2-Hydroxyethyl(methyl)amino]phenyl]prop-2-enoyl]phenyl]prop-2-enamide; 56945286: (E)-3-[4-[(E)-2-(4-Hydroxy-3,5-dimethoxy-phenyl)vinyl]phenyl]-1-(4-methoxyphenyl)prop-2-en-1-one; 56945409: (E)-1-[4-[(E)-2-(4-Hydroxy-3,5-dimethoxy-phenyl)vinyl]phenyl]-3-(4-methoxyphenyl)prop-2-en-1-one; 56945506: (E)-1-[4-[(E)-2-(4-Hydroxy-3-methoxy-phenyl)vinyl]phenyl]-3-(4-methoxy-phenyl)prop-2-en-1-one; 56949827: [4-[(E)-3-(4-Chlorophenyl)-3-oxoprop-1-enyl]-2-methoxyphenyl] (2R)-2-amino-3-hydroxypropanoate;hydrochloride; 56949828: [4-[(E)-3-(4-Chlorophenyl)-3-oxoprop-1-enyl]-2-methoxyphenyl] (2R)-2-amino-3-hydroxypropanoate; 56977219: 4-[3-[4-[3-(4-Carboxyphenyl)prop-2-enoyl]phenyl]-3-oxoprop-1-enyl]benzoic acid; 56977941: 3-[3-[4-(2-Carboxy-2-prop-2-enoxyethoxy)phenyl]-3-oxoprop-1-enyl]benzoic acid; 56987523: 3-(4-Hexylphenyl)-1-(2-hydroxy-4-pent-2-en-3-yloxyphenyl)prop-2-en-1-one; 56992521: 2-[5-Pent-2-en-3-yloxy-2-[3-(4-prop-2-enylphenyl)prop-2-enoyl]phenoxy]acetic acid; 57002014: 2-[5-Pent-2-en-3-yloxy-2-[3-(4-propylphenyl)prop-2-enoyl]phenoxy]acetic acid; 57008810: 3-[3-[3-[4-[3-(3,4-Dihydroxyphenyl)prop-2-enoyl]-3-hydroxyphenyl]prop-2-enoyloxy]-4-hydroxyphenyl]prop-2-enoic acid; 57027924: 1-[2-(Hydroxymethyl)phenyl]-3-phenylprop-2-en-1-one; 57028243: 3-(3-Bromophenyl)-1-(2-hydroxyphenyl)prop-2-en-1-one; 57031043: 2-[4-[3-(4-Sulfophenyl)prop-2-enoyl]phenoxy]acetic acid; 57051227: 3-(3-Hydroxy-4-methylphenyl)-1-phenylprop-2-en-1-one; 57058803: 3-(4-Tert-butylphenyl)-1-(2-hydroxy-4-pent-2-en-3-yloxyphenyl)prop-2-en-1-one; 57084666: 1-(4-Hydroxyphenyl)-3-[4-(1,2,2-trifluoroethenoxy)phenyl]prop-2-en-1-one; 57085673: N-[4-[3-[2-Hydroxy-4-(3-methylbut- 2-enoxy)phenyl]-3-oxoprop-1-enyl]phenyl]acetamide; 57091096: 2-[4-[3-(4-Methoxyphenyl)prop-2-enoyl]phenoxy]acetic acid; 57099608: (19S)-19-Ethyl-19-hydroxy-7-(3-oxo-3-phenylprop-1-enyl)-17-oxa-3,13-diazapentacyclo [11.8.0.02,11.04,9.015,20]henicosa-1(21),2(11),3,5,7,9,15 (20)-heptaene-14,18-dione; 57104499: 4-[3-(4-Hydroxyphenyl)-3-oxoprop-1-enyl]-N-pyridin-2-ylbenzenesulfonamide; 57106366: 2-[4-[3-(4-Hydroxy-3-methoxyphenyl)prop-2-enoyl]phenoxy]acetic acid; 57114768: 3-[4-[3-[4-(1,2,2-Trifluoroethenoxy)phenyl] prop-2-enoyl]phenyl]propanoic acid; 57122656: 2-[2-[3-(4-Heptylphenyl)prop-2-enoyl]-5-pent-2-en-3-yloxyphenoxy] acetic acid; 57127865: 2-[2-[3-(4-Hexylphenyl)prop-2-enoyl]-5-pent-2-en-3-yloxyphenoxy]acetic acid; 57131247: 3-[4-[3-[4-[3-[3-(3,4-Dihydroxyphenyl)prop-2-enoyl]-4-hydroxyphenyl]prop-2-enoyloxy]-3-hydroxy-phenyl]prop-2-enoyl]-3-hydroxyphenyl]prop-2-enoic acid; 57133872: N-[(2S,3S,4R,5S,6R)-2-[3,5-Dimethoxy-2-[3-(4-methoxyphenyl)prop-2-enoyl]phenoxy]-4,5-dihydroxy-6-(hydroxymethyl)oxan-3-yl]acetamide; 57135591: 4-3-[4-(3-Carboxypropoxy)phenyl]-3-oxoprop-1-en-1-ylbenzoic acid; 57136946: 2-[4-[3-[2-(Carboxymethoxy)-4-pent-2-en-3-yloxyphenyl]-3-oxoprop-1-enyl]phenoxy]acetic acid; 57142857: 1-(2-Hydroxyphenyl)-3-[3-(trifluoromethyl)phenyl]prop-2-en-1-one; 57157663: 3-[4-[3-(4-Ethoxy-3-hydroxyphenyl)prop-2-enoyl]-3-hydroxyphenoxy]propane-1-sulfonic acid; 57160695: 2-[2-[3-(4-Tert-butylphenyl)prop-2-enoyl]-5-pent-2-en-3-yloxyphenoxy]acetic acid; 57168663: 3-(3,4-Dihydroxyphenyl)-1-[2-hydroxy-4-[3,4,5-trihydroxy-6-(hydroxymethyl)oxan-2-yl]oxyphenyl]prop-2-en-1-one; 57190355: 2-[2-[3-(4-Methylphenyl)prop-2-enoyl]-5-pent-2-en-3-yloxyphenoxy]acetic acid; 57190663: 3-(4-Decyl-3-hydroxyphenyl)-1-phenylprop-2-en-1-one; 57230932: (6R,7R)-3-(Acetyloxymethyl)-7-[[2-[[4-[3-(2-hydroxyphenyl)-3-oxoprop-1-enyl]benzoyl]amino]-2-phenylacetyl]amino]-8-oxo-5-thia-1-azabicyclo[4.2.0]oct-2-ene-2-carboxylic acid; 57235894: 3-[3-Hydroxy-4-[3-(4-methoxy-3-phenylmethoxyphenyl)prop-2-enoyl]phenoxy] propane-1-sulfonic acid; 57244149: (19S)-19-Ethyl-19-hydroxy-6-(3-oxo-3-phenylprop-1-enyl)-17-oxa-3,13-diazapentacyclo[11.8.0.02,11.04,9.015,20]henicosa-1(21),2 (11),3,5,7,9,15(20)-heptaene-14,18-dione; 57245215: 2-[2-[3-(4-Tert-butylphenyl)prop-2-enoyl]-5-pent-2-en-3-yloxyphenoxy]propanoic acid; 57274183: (19S)-10,19-Diethyl-19-hydroxy-7-(3-oxo-3-phenylprop-1-enyl)-17-oxa-3,13-diazapentacyclo[11.8.0.02,11.04,9.015,20] henicosa-1(21),2,4(9),5,7,10,15(20)-heptaene-14,18-dione; 57288989: 2-[5-Pent-2-en-3-yloxy-2-[3-(4-pent-2-en-3-yloxyphenyl)prop-2-enoyl]phenoxy]acetic acid; 57307880: 4-[3-[4-(1,2,2-Trifluoroethenoxy)phenyl]prop-2-enoyl]benzoic acid; 57309627: 2-[4-[3-[4-(1,2,2-Trifluoro-ethenoxy) phenyl]prop-2-enoyl]phenyl]acetic acid; 57310003: (6R, 7R)-3-(Acetyloxymethyl)-8-oxo-7-[[2-phenyl-2-[[4-(3-phenylprop-2-enoyl)benzoyl]amino]acetyl]amino]-5-thia-1-azabicyclo[4.2.0]oct-2-ene-2-carboxylic acid; 57320110: 4-[3-[2-(Carboxymethoxy)-4-pent-2-en-3-yloxyphenyl]-3-oxoprop-1-enyl]benzoic acid; 57340889: Chalcone analog, 1; 57345986: 1-(2,6-Dihydroxyphenyl)-3-(4-methoxyphenyl)prop-2-en-1-one; 57350706: [4-[3-[4-(Dimethylamino) phenyl]prop-2-enoyl]phenyl]-ethylcarbamic acid; 57351806: Ethyl-[4-(3-phenylprop-2-enoyl)phenyl]carbamic acid; 57353506: 3-Methyl-4-(3-phenylprop-2-enoyl) benzoic acid; 57360537: [4-[3-[4-(Diethylamino)phenyl] prop-2-enoyl]phenyl]-ethylcarbamic acid; 57363335: 4-[(E)-3-(4-Methoxyphenyl)prop-2-enoyl]benzoic acid; 57366126: 3-(1,3-Benzodioxol-5-yl)-1-(2-hydroxy-6-methylphenyl)prop-2-en-1-one; 57366131: 2'-Hydroxy-4',6'-dibenzyloxychalcone; 57366150: 4-3-[4-(Trifluoromethyl) phenyl]-prop-2-enoylbenzoic acid; 57366151: 4-3-[4-(Trifluoromethoxy)phenyl]-prop-2-enoylbenzoic acid; 57369901: 1-[2-Hydroxy-4,6-bis(phenylmethoxy)phenyl]-3-(4-phenylmethoxyphenyl)prop-2-en-1-one; 57386326: 4-[(E)-3-(1-Hydroxy-3H-2,1-benzoxaborol-6-yl)prop-2-enoyl]benzoic acid; 57386586: (E)-3-(1-Hydroxy-3H-2,1-benzoxaborol-6-yl)-1-(4-hydroxyphenyl)prop-2-en-1-one; 57386840: (E)-3-(1-Hydroxy-3H-2,1-benzoxaborol-6-yl)-1-(2-hydroxyphenyl)prop-2-en-1-one; 57390110: (E)-3-(1,3-Benzodioxol-5-yl)-1-(2-hydroxy-4-prop-2-enoxyphenyl) prop-2-en-1-one; 57390960: (E)-3-[3-(4-Fluorophenyl) phenyl]-1-(4-hydroxyphenyl)prop-2-en-1-one; 57391242: 1-[2-[(E)-3-(3-Ethoxy-4-hydroxyphenyl)prop-2-enoyl]phenyl]-3-(4-methylphenyl) sulfonylurea; 57391891: (E)-1-(2-Hydroxy-4-prop-2-enoxyphenyl)-3-(4-methoxyphenyl) prop-2-en-1-one; 57392723: (E)-1-(2-Hydroxyphenyl)-3-phenylprop-2-en-1-one;hydrochloride; 57393221: (E)-3-(3, 4-Dichlorophenyl)-1-(2-hydroxy-4-methoxyphenyl)prop-2-en-1-one; 57394736: 1-[2-[(E)-3-(3-Hydroxyphenyl)prop-2-enoyl]phenyl]-3-(4-methylphenyl) sulfonylurea; 57397162: (E)-3-(3-Hydroxy-4-methoxyphenyl)-1-[2-hydroxy-4-(3-methylbut-2-enoxy)phenyl]prop-2-en-1-one; 57398874: 2'-Hydroxy-4'-(allyloxy)chalcone; 57401730: 1-[2-[(E)-3-(4-Hydroxyphenyl)prop-2-enoyl]phenyl]-3-(4-methylphenyl)sulfonylurea; 57403259: (E)-3-(4-Fluorophenyl)-1-(2-hydroxyphenyl)prop-2-en-1-one;hydrochloride; 57403458: 1-[2-[(E)-3-(4-Hydroxy-3-methoxyphenyl)prop-2-enoyl]phenyl]-3-(4-methylphenyl)sulfonylurea; 57473103: 2-[5-(3-Methylbut-2-enoxy)-2-[(Z)-3-[4-(3-methylbut-2-enoxy)phenyl]prop-2-enoyl]phenoxy]acetic acid; 57762858: 2-[2-Methyl-4-[(E)-3-oxo-3-[4-(trifluoromethyl)phenyl]prop-1-enyl]phenoxy]acetic acid; 57762869: 2-[4-[(E)-3-(4-Bromophenyl)-3-oxoprop-1-enyl]-2-tert-butylphenoxy]-2-methylpropanoic acid; 57762874: (E)-1-(4-Bromophenyl)-3-(3-tert-butyl-4-hydroxyphenyl)prop-2-en-1-one; 57762882: 2-Methyl-2-[4-[(E)-3-(4-methylsulfanylphenyl)-3-oxoprop-1-enyl]-2-(trifluoromethyl)phenoxy]propanoic acid; 57762890: 2-[4-[(E)-3-(4-Bromophenyl)-3-oxoprop-1-enyl]-2-(trifluoromethyl) phenoxy]-2-methylpropanoic acid; 57762892: 2-[4-[(E)-3-(4-Bromophenyl)-3-oxoprop-1-enyl]-2-cyclohexylphenoxy]-2-methylpropanoic acid; 57762898: 2-[4-[(E)-3-(4-Hydroxyphenyl)-3-oxoprop-1-enyl]phenoxy]-2-methylpropanoic acid; 57762901: (E)-3-(4-Hydroxy-3-methylphenyl)-1-[4-(trifluoromethyl)phenyl]prop-2-en-1-one; 57762912: (E)-3-[4-Hydroxy-3-(trifluoromethyl)phenyl]-1-(4-methylsulfanylphenyl)prop-2-en-1-one; 57814774: (E)-1-(2-Hydroxy-4,6-dimethylphenyl)-3-[4-[2-[4-[(E)-3-(2-hydroxy-4,6-dimethylphenyl)-3-oxoprop-1-enyl]phenoxy]ethoxy] phenyl]prop-2-en-1-one; 57814778: (E)-1-[2-Hydroxy-4,6-bis(methoxy-methoxy)phenyl]-3-(4-prop-2-enoxyphenyl) prop-2-en-1-one; 57814779: 2'-Hydroxy-4-allyloxy chalcone; 57912226: [2-Benzoyloxy-4-[(E)-3-(2-hydroxyphenyl)-3-oxoprop-1-enyl]phenyl] benzoate; 57979919: 4-(Cyclohexen-1-yl)-2-[4-[(E)-3-phenylprop-2-enoyl]phenoxy]butanoic acid; 57979953: 2-[4-[(E)-3-Phenylprop-2-enoyl]phenoxy]hex-5-enoic acid; 57979973: 4-(Cyclohexen-1-yl)-2-[4-[(E)-3-oxo-3-phenylprop-1-enyl]phenoxy] butanoic acid; 58160241: (E)-1-(2-Hydroxy-4-methylphenyl)-3-[3-(methoxymethoxy)-4-phenylmethoxyphenyl]prop-2-en-1-one; 58194090: 4-[(E)-3-(4-Methylphenyl)prop-2-enoyl]benzoic acid; 58208331: (E)-1-Hydroxy-4-[4-[(E)-3-(4-morpholin-4-ylphenyl)-3-oxoprop-1-enyl]phenyl]but-3-en-2-one; 58208334: (E)-4-[4-[(E)-3-[4-[(4-Acetylpiperazin-1-yl)methyl]phenyl]-3-oxoprop-1- enyl]phenyl]-1-hydroxybut-3-en-2-one; 58208335: (E)-4-[4-[(E)-3-[4-[4-(Dimethylamino)piperidin-1-yl]phenyl]-3-oxoprop-1-enyl]phenyl]-1-hydroxybut-3-en-2-one; 58208337: (E)-1-Hydroxy-4-[4-[(E)-3-[4-[(1-methylpiperidin-4-yl)amino]phenyl]-3-oxoprop-1-enyl]phenyl]but-3-en-2-one; 58208339: (E)-1-Hydroxy-4-[4-[(E)-3-oxo-3-(4-piperazin-1-ylphenyl)prop-1-enyl]phenyl]but-3-en-2-one; 58208341: (E)-1-Hydroxy-4-[4-[(E)-3-[2-(4-methylpiperazin-1-yl)phenyl]-3-oxoprop-1-enyl]phenyl]but-3-en-2-one; 58208342: (E)-1-Hydroxy-4-[4-[(E)-3-oxo-3-[4-(piperazin-1-ylmethyl)phenyl]prop-1-enyl]phenyl]but-3-en-2-one; 58208347: (E)-1-Hydroxy-4-[4-[(E)-3-[4-(4-methylpiperazin-1-yl)phenyl]-3-oxoprop-1-enyl]phenyl]but-3-en-2-one; 58208351: (E)-4-[4-[(E)-3-[4-[[(3S,5R)-4-Acetyl-3,5-dimethyl-piperazin-1-yl]methyl]phenyl]-3-oxoprop-1-enyl]phenyl]-1-hydroxybut-3-en-2-one; 58208352: (E)-4-[4-[(E)-3-[4-(4-Benzoylpiperazin-1-yl)phenyl]-3-oxoprop-1-enyl]phenyl]-1-hydroxybut-3-en-2-one; 58208353: (E)-4-[4-[(E)-3-[4-(4-Ethylpiperazin-1-yl)phenyl]-3-oxoprop-1-enyl]phenyl]-1-hydroxybut-3-en-2-one; 58208354: (E)-1-Hydroxy-4-[4-[(E)-3-[4-[(4-methylpiperazin-1-yl)methyl]phenyl]-3-oxoprop-1-enyl]phenyl]but-3-en-2-one; 58208358: (E)-1-Hydroxy-4-[4-[(E)-3-oxo-3-phenylprop-1-enyl]phenyl]but-3-en-2-one; 58208359: (E)-1-Hydroxy-4-[4-[(E)-3-[4-(1-methylpiperidin-4-yl)phenyl]-3-oxoprop-1-enyl]phenyl]but-3-en-2-one; 58208362: (E)-1-Hydroxy-4-[4-[(E)-3-[2-[(4-methylpiperazin-1-yl)methyl]phenyl]-3-oxoprop-1-enyl]phenyl]but-3-en-2-one; 58208365: (E)-4-[4-[(E)-3-[4-[[(2S,6R)-2,6-Dimethylmorpholin-4-yl]methyl]phenyl]-3-oxoprop-1-enyl]phenyl]-1-hydroxybut-3-en-2-one; 58208366: (E)-1-Hydroxy-4-[4-[(E)-3-[4-[4-(2-methylpropyl)piperazin-1-yl]phenyl]-3-oxoprop-1-enyl]phenyl]but-3-en-2-one; 58208371: 4-[4-[(E)-3-[4-[(E)-4-Hydroxy-3-oxobut-1-enyl]phenyl]prop-2-enoyl]phenyl]-N,N-dimethylpiperazine-1-carboxamide; 58208373: (E)-1-Hydroxy-4-[4-[(E)-3-[4-[4-(methylamino)piperidin-1-yl]phenyl]-3-oxoprop-1-enyl]phenyl]but-3-en-2-one; 58208374: (E)-1-Hydroxy-4-[4-[(E)-3-[4-[methyl-(1-methylpiperidin-4-yl)amino]phenyl]-3-oxoprop-1-enyl]phenyl]but-3-en-2-one; 58208375: (E)-4-[4-[(E)-3-[4-[(4-Benzylpiperazin-1-yl)methyl]phenyl]-3-oxoprop-1-enyl]phenyl]-1-hydroxybut-3-en-2-one; 58208376: (E)-4-[4-[(E)-3-[4-[[4-(Dimethylamino)piperidin-1-yl]methyl]phenyl]-3-oxoprop-1-enyl]phenyl]-1-hydroxybut-3-en-2-one; 58208379: (E)-4-[4-[(E)-3-[4-[(4-Ethylpiperazin-1-yl)methyl]phenyl]-3-oxoprop-1-enyl]phenyl]-1-hydroxybut-3-en-2-one; 58208380: (E)-4-[4-[(E)-3-[4-(4-Acetylpiperazin-1-yl)phenyl]-3-oxoprop-1-enyl]phenyl]-1-hydroxybut-3-en-2-one; 58208381: Ethyl 4-[4-[(E)-3-[4-[(E)-4-hydroxy-3-oxobut-1-enyl]phenyl]prop-2-enoyl]phenyl]piperazine-1-carboxylate; 58208382: (E)-1-Hydroxy-4-[4-[(E)-3-[4-(morpholin-4-ylmethyl)phenyl]-3-oxoprop-1-enyl]phenyl]but-3-en-2-one; 58208383: (E)-1-Hydroxy-4-[4-[(E)-3-[4-(4-methylsulfonylpiperazin-1-yl)phenyl]-3-oxoprop-1-enyl]phenyl]but-3-en-2-one; 58208386: (E)-4-[4-[(E)-3-[4-[[(3R,5S)-3,5-Dimethylpiperazin-1-yl]methyl]phenyl]-3-oxoprop-1-enyl]phenyl]-1-hydroxybut-3-en-2-one; 58321596: 3-[4-(Diphenylamino)phenyl]-1-(2-hydroxyphenyl)-2-propene-1-one; 58379464: (E)-3-(3-Bromophenyl)-1-(2,4-dihydroxy-6-methoxyphenyl)prop-2-en-1-one; 58379476: (E)-1-(2,4-Dihydroxy-6-methoxyphenyl)-3-(3-fluorophenyl)prop-2-en-1-one; 58382892: 3-[4-[(E)-3-(4-Chloro-2-hydroxyphenyl)-3-oxoprop-1-enyl]phenoxy]-3-methylbutan-2-one; 58592127: (E)-1-[2,6-Dihydroxy-4-[(2S,4S,5R)-3,4,5-trihydroxy-6-[[(2R,4S,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 58833437: (E)-3-(4-Hydroxy-3-methylphenyl)-1-phenylprop-2-en-1-one; 58960119: Actinium;(E)-1-(2,4-dihy-droxyphenyl)-3-(3,4-dihydroxyphenyl)prop-2-en-1-one; 58981636: (E)-1-[2-[5-Fluoro-3,4-dihydroxy-6-(hydroxymethyl)oxan-2-yl]oxy-6-hydroxy-4-methylphenyl]-3-(4-methoxy-phenyl)prop-2-en-1-one; 59040731: 3-[4-(Fluoromethoxy)phenyl]-1-(4-hydroxyphenyl)prop-2-en-1-one; 59040734: 3-[4-(Fluoromethoxy)phenyl]-1-[4-(6-hydroxyhexoxy)phenyl]prop-2-en-1-one; 59040737: 1-(4-Hydroxyphenyl)-3-[4-(3,3,3-trifluoropropoxy)phenyl]prop-2-en-1-one; 59071770: 1-[4-(Hydroxymethoxy)phenyl]-3-phenylprop-2-en-1-one; 59214885: 4-Phenyl-2-[4-[(E)-3-phenylprop-2-enoyl]phenoxy]butanoic acid; 59214887: 2-[2-[(Z)-3-(4-Bromophenyl)prop-2-enoyl]phenoxy]-4-[4-(4-chlorophenyl)phenyl]butanoic acid; 59214907: 4-[4-(4-Chlorophenyl)phenyl]-2-[4-[(E)-3-phenylprop-2-enoyl]phenoxy]butanoic acid; 59214942: 2-[2-[(Z)-3-(4-Bromophenyl)prop-2-enoyl]phenoxy]-4-phenylbutanoic acid; 59214950: 2-[4-[(E)-3-Oxo-3-phenylprop-1-enyl]phenoxy]-4-phenylbutanoic acid; 59214958: 4-Phenyl-2-[2-[(E)-3-phenylprop-2-enoyl]phenoxy]butanoic acid; 59215002: 2-[2-[(E)-3-[4-(4-Bromophenyl)phenyl]prop-2-enoyl]phenoxy]-4-phenylbutanoic acid; 59215042: 4-[4-(4-Chlorophenyl)phenyl]-2-[4-[(E)-3-oxo-3-phenylprop-1-enyl]phenoxy]butanoic acid; 59237940: Chembl4563497; 59301216: (Z)-4-[4-[(E)-3-(3,4-Dimethylphenyl)prop-2-enoyl]anilino]-4-oxobut-2-enoic acid; 59343701: (E)-3-(4-Chloro-3-methylphenyl)-1-(4-hydroxyphenyl)prop-2-en-1-one; 59349045: (E)-1-(4-Aminophenyl)-3-(4-hydroxy-3-methylphenyl)prop-2-en-1-one; 59349180: (E)-3-(4-Hydroxy-3-methylphenyl)-1-(4-methylphenyl)prop-2-en-1-one; 59349186: (E)-N-(4-(3-(4-Hydroxy-3-methylphenyl)acryloyl)-3-methylphenyl)acetamide; 59408804: (E)-3-(3-Hydroxy-4-methoxyphenyl)-1-[2-hydroxy-6-methoxy-4-[(2S,4S,5R)-3,4,5-trihydroxy-6-[[(1R,3S,4S)-2,3,4-trihydroxy-5-methylcyclohexyl]oxymethyl]oxan-2-yl]oxyphenyl]prop-2-en-1-one; 59429196: (E)-2',6'-Dihydroxy-4'-methoxy-beta-(3-methoxy-4-methoxyphenyl)acrylophenone; 59481164: (E)-1-[2-Hydroxy-4,6-bis(phenylmethoxy)phenyl]-3-(4-hydroxy-3-methoxyphenyl)prop-2-en-1-one; 59481165: (E)-3-(4-Hydroxy-3-methoxyphenyl)-1-(2-hydroxy-4-methylphenyl)prop-2-en-1-one; 59488070: (E)-3-(4-Hydroxy-3-methoxyphenyl)-1-[4-[(E)-3-(4-hydroxy-3-methoxyphenyl)prop-2-enoyl]phenyl]prop-2-en-1-one; 59512565: (E)-1-[4-[2-Hydroxy-3-(4-phenylpiperazin-1-yl)propoxy]phenyl]-3-(3-methoxy-4-methylphenyl)prop-2-en-1-one; 59536677: (E)-3-(3-Chloro-4-methylphenyl)-1-(4-hydroxyphenyl)prop-2-en-1-one; 59563397: (E)-3-(3,4-Dimethoxyphenyl)-1-(4-hydroxy-2-methoxyphenyl)prop-2-en-1-one; 59576450: (E)-1-[2-Hydroxy-4-(oxan-2-yloxy)phenyl]-3-[4-methoxy-3-(oxan-2-yloxy)phenyl]prop-2-en-1-one; 59846223: 4-[(E)-3-(2-Anilino-4-chlorophenyl)-3-oxoprop-1-enyl]-N-(4-hydroxycyclohexyl)benzamide; 59846250: 4-[(E)-3-(2-Anilino-4-chlorophenyl)-3-oxoprop-1-enyl]-N-(2-hydroxy-2-methylpropyl)benzenesulfonamide; 59846266: 4-[(E)-3-(4-Chloro-2-phenylamino-phenyl)-3-oxo-propenyl]-benzoic acid; 59883545: 1-O-(2-Hydroxyethyl) 5-O-[4-(3-phenylprop-2-enoyl)phenyl] 2,2,4-trimethylpentanedioate; 59917054: (E)-3-(3-Hydroxy-4-nitro-phenyl)-1-phenylprop-2-en-1-one; 59971024: 1-Amino-4-hydroxy-2-[4-(3-phenylprop-2-enoyl) phenoxy]anthracene-9,10-dione; 60162022: (E)-1-(4-Amino-2-hydroxyphenyl)-3-[4-(5-methylthiophen-2-yl)phenyl]prop-2-en-1-one; 60162023: (E)-1-(4-Amino-2-hydroxyphenyl)-3-[4-(5-methylfuran-2-yl)phenyl]prop-2-en-1-one; 60162024: (E)-1-(4-Amino-2-hydroxy-phenyl)-3-(4-ethoxyphenyl)

prop-2-en-1-one; 60210097: (E)-1-[4-[(1-Hexyltriazol-4-yl)methoxy]-2-hydroxyphenyl]-3-phenylprop-2-en-1-one; 60210098: (E)-3-(4-Bromophenyl)-1-[4-[(1-hexyltriazol-4-yl)methoxy]-2-hydroxyphenyl]prop-2-en-1-one; 60210099: (E)-3-(4-Chlorophenyl)-1-[4-[(1-hexyltriazol-4-yl)methoxy]-2-hydroxyphenyl]prop-2-en-1-one; 60210101: (E)-1-[4-[(1-Hexyltriazol-4-yl)methoxy]-2-hydroxyphenyl]-3-(4-methoxyphenyl) prop-2-en-1-one; 60210103: (E)-1-[4-[(1-Benzyltriazol-4-yl)methoxy]-2-hydroxyphenyl]-3-phenylprop-2-en-1-one; 60210104: (E)-1-[4-[(1-Benzyltriazol-4-yl)methoxy]-2-hydroxy-phenyl]-3-(4-methoxyphenyl)prop-2-en-1-one; 60210105: (E)-1-[4-[(1-Benzyltriazol-4-yl)methoxy]-2-hydroxyphenyl]-3-(4-propan-2-ylphenyl)prop-2-en-1-one; 60210106: (E)-3-(4-Bromophenyl)-1-[4-[[1-[(4-bromophenyl)methyl]triazol-4-yl]methoxy]-2-hydroxyphenyl]prop-2-en-1-one; 60217319: N-[4-[(E)-3-(3-Chloro-4-hydroxyphenyl)prop-2-enoyl]phenyl]methanesulfonamide; 60217325: N-[4-[(E)-3-(3-Bromo-4-hydroxyphenyl)prop-2-enoyl]phenyl]methanesulfonamide; 60254351: N-[4-[(E)-3-(3-Chloro-4-hydroxyphenyl)prop-2-enoyl]phenyl]ethanesulfonamide; 60267648: (E)-1-[4-(4-Hydroxypiperidin-1-yl)phenyl]-3-naphthalen-2-ylprop-2-en-1-one; 60267684: (E)-3-(3-Chlorophenyl)-1-[4-(4-hydroxy-piperidin-1-yl)phenyl]prop-2-en-1-one; 60267715: (E)-3-(3-Ethoxyphenyl)-1-[4-(4-hydroxypiperidin-1-yl)phenyl]prop-2-en-1-one; 60267716: (E)-1-[4-(4-Hydroxypiperidin-1-yl)phenyl]-3-(3-methoxy-4-methylsulfanylphenyl)prop-2-en-1-one; 60267747: (E)-3-(3-Bromo-4-fluorophenyl)-1-[4-(4-hydroxypiperidin-1-yl)phenyl]prop-2-en-1-one; 60267748: (E)-1-[4-(4-Hydroxypiperidin-1-yl)phenyl]-3-(3-methoxy-4-propoxyphenyl)prop-2-en-1-one; 60267782: N-[4-[(E)-3-[4-(4-Hydroxypiperidin-1-yl)phenyl]-3-oxoprop-1-enyl]phenyl]acetamide; 60267815: (E)-3-(3,4-Dichlorophenyl)-1-[4-(4-hydroxypiperidin-1-yl)phenyl]prop-2-en-1-one; 60267816: (E)-1-[4-(4-Hydroxypiperidin-1-yl)phenyl]-3-(4-methoxy-3-phenyl-methoxyphenyl)prop-2-en-1-one; 60267849: (E)-1-[4-(4-Hydroxypiperidin-1-yl)phenyl]-3-[4-(trifluoromethylsulfanyl)phenyl]prop-2-en-1-one; 60267850: (E)-1-[4-(4-Hydroxypiperidin-1-yl)phenyl]-3-[4-(trifluoromethyl)phenyl]prop-2-en-1-one; 60267882: (E)-1-[4-(4-Hydroxy-piperidin-1-yl)phenyl]-3-(4-propan-2-yloxyphenyl)prop-2-en-1-one; 60267883: (E)-1-[4-(4-Hydroxypiperidin-1-yl)phenyl]-3-(4-nitro-phenyl)prop-2-en-1-one; 60267915: (E)-3-(3-Bromophenyl)-1-[4-(4-hydroxypiperidin-1-yl)phenyl]prop-2-en-1-one; 60268018: (E)-3-(3-Ethoxy-4-methoxyphenyl)-1-[4-(4-hydroxypiperidin-1-yl)phenyl]prop-2-en-1-one; 60268050: (E)-1-[4-(4-Hydroxypiperidin-1-yl)phenyl]-3-phenylprop-2-en-1-one; 60268087: (E)-3-(4-Fluorophenyl)-1-[4-(4-hydroxypiperidin-1-yl)phenyl]prop-2-en-1-one; 60268124: (E)-1-[4-(4-Hydroxypiperidin-1-yl)phenyl]-3-(3-methoxy-4-phenyl-methoxyphenyl)prop-2-en-1-one; 60268125: (E)-3-(4-Ethoxyphenyl)-1-[4-(4-hydroxypiperidin-1-yl)phenyl]prop-2-en-1-one; 60268160: (E)-3-(3-Hydroxyphenyl)-1-[4-(4-hydroxypiperidin-1-yl)phenyl]prop-2-en-1-one; 60268161: (E)-1-[4-(4-Hydroxypiperidin-1-yl)phenyl]-3-(4-phenylmethoxyphenyl)prop-2-en-1-one; 60318102: (E)-3-[4-(Diethylamino)phenyl]-1-[4-(4-hydroxypiperidin-1-yl)phenyl]prop-2-en-1-one; 60318104: (E)-1-[4-(4-Hydroxypiperidin-1-yl)phenyl]-3-[4-(pyridin-2-ylmethoxy)phenyl]prop-2-en-1-one; 60318143: (E)-3-(4-Tert-butylphenyl)-1-[4-(4-hydroxypiperidin-1-yl)phenyl]prop-2-en-1-one; 60318144: (E)-1-[4-(4-Hydroxypiperidin-1-yl)phenyl]-3-[3-methoxy-4-(3-methylbutoxy)phenyl]prop-2-en-1-one; 60318184: (E)-1-[4-(4-Hydroxy-piperidin-1-yl)phenyl]-3-(4-pentoxyphenyl)prop-2-en-1-one; 60318185: (E)-3-(4-Butoxy-3-methoxyphenyl)-1-[4-(4-hydroxypiperidin-1-yl)phenyl]prop-2-en-1-one; 60318224: (E)-1-[4-(4-Hydroxypiperidin-1-yl)phenyl]-3-(4-methyl-3-nitro-phenyl)prop-2-en-1-one; 60318309: (E)-3-(3-Fluoro-4-methoxyphenyl)-1-[4-(4-hydroxypiperidin-1-yl)phenyl]prop-2-en-1-one; 60318352: (E)-3-(3-Ethoxy-4-propoxyphenyl)-1-[4-(4-hydroxypiperidin-1-yl)phenyl]prop-2-en-1-one; 60318432: (E)-1-[4-(4-Hydroxypiperidin-1-yl)phenyl]-3-[4-(3-methylbutoxy)phenyl]prop-2-en-1-one; 60318518: (E)-3-[4-[(2-Fluorophenyl)methoxy]phenyl]-1-[4-(4-hydroxy-piperidin-1-yl)phenyl]prop-2-en-1-one; 60318561: (E)-1-[4-(4-Hydroxypiperidin-1-yl)phenyl]-3-(4-methoxy-3-methylphenyl)prop-2-en-1-one; 60318562: (E)-3-(3,4-Diethoxyphenyl)-1-[4-(4-hydroxypiperidin-1-yl)phenyl]prop-2-en-1-one; 60318679: (E)-1-[4-(4-Hydroxypiperidin-1-yl)phenyl]-3-[4-[(5-methyl-1,2,4-oxadiazol-3-yl)methoxy]phenyl]prop-2-en-1-one; 60318681: (E)-3-[3-(Difluoromethoxy)-4-methoxyphenyl]-1-[4-(4-hydroxypiperidin-1-yl)phenyl]prop-2-en-1-one; 60318682: 3-[[3-[(E)-3-[4-(4-Hydroxypiperidin-1-yl)phenyl]-3-oxoprop-1-enyl]phenoxy]methyl]benzonitrile; 60318719: N-Ethyl-2-[4-[(E)-3-[4-(4-hydroxypiperidin-1-yl)phenyl]-3-oxoprop-1-enyl]phenoxy]acetamide; 60451233: 3-[4-[(E)-3-(4-Ethoxyphenyl)-3-oxoprop-1-enyl]phenoxy]propanoic acid; 60451298: 3-[4-[(E)-3-[4-(Difluoromethoxy)phenyl]-3-oxoprop-1-enyl]phenoxy]propanoic acid; 60463604: 4-[4-[(E)-3-(3-Ethoxyphenyl)prop-2-enoyl]phenoxy]butanoic acid; 60463619: 4-[4-[(E)-3-(4-Propan-2-yloxyphenyl)prop-2-enoyl]phenoxy]butanoic acid; 60465136: (E)-3-(3-Ethoxy-4-hydroxyphenyl)-1-[4-(trifluoro-methyl)phenyl]prop-2-en-1-one; 60465183: (E)-3-(3-Ethoxy-4-hydroxyphenyl)-1-[4-(2-methoxyethoxy)phenyl]prop-2-en-1-one; 60465195: (E)-3-(3-Ethoxy-4-hydroxyphenyl)-1-[4-(trifluoromethoxy)phenyl]prop-2-en-1-one; 60467294: (E)-3-(3-Bromo-4-hydroxyphenyl)-1-(2,4-difluorophenyl)prop-2-en-1-one; 60470376: 4-[4-[(E)-3-[3-(Trifluoromethyl)phenyl]prop-2-enoyl]phenoxy]butanoic acid; 60527667: (E)-3-(3-Hydroxy-4-methoxyphenyl)-1-[4-[(1-methylimidazol-2-yl)methoxy]phenyl]prop-2-en-1-one; 60529648: 3-[4-[(E)-3-[4-(2-Chloro-prop-2-enoxy)phenyl]-3-oxoprop-1-enyl]phenoxy]propanoic acid; 60529710: (E)-1-[4-(2-Chloroprop-2-enoxy)phenyl]-3-(3-ethoxy-4-hydroxyphenyl)prop-2-en-1-one; 60593512: (E)-3-(3-Chloro-4-hydroxyphenyl)-1-[4-(difluoromethoxy)phenyl]prop-2-en-1-one; 60593519: 2-[4-[(E)-3-(3-Chloro-4-hydroxyphenyl)prop-2-enoyl]phenoxy]acetonitrile; 60593583: (E)-3-(3-Chloro-4-hydroxyphenyl)-1-(2,4-difluorophenyl)prop-2-en-1-one; 60593608: (E)-3-(3-Chloro-4-hydroxyphenyl)-1-(4-morpholin-4-ylphenyl)prop-2-en-1-one; 60593640: (E)-3-(3-Chloro-4-hydroxyphenyl)-1-(4-propoxyphenyl)prop-2-en-1-one; 60593700: 4-[4-[(E)-3-(3-Chloro-4-hydroxyphenyl)prop-2-enoyl]phenoxy]butanoic acid; 60601072: Methyl 2-[4-[(E)-3-(3-chloro-4-hydroxyphenyl)prop-2-enoyl]phenoxy]acetate; 60603161: 3-[3-[(E)-3-[4-(Difluoromethoxy)phenyl]-3-oxoprop-1-enyl]phenoxy]propanoic acid; 66550926: 2-[(E)-3-(4-Cyanophenyl) prop-2-enoyl]benzoic acid; 66553964: (E)-1-[4-[(1-Hexyltriazol-4-yl)methoxy]-2-hydroxy-phenyl]-3-(4-propan-2-ylphenyl)prop-2-en-1-one; 66553965: (E)-1-[4-[(1-Hexyltriazol-4-yl)methoxy]-2-hydroxyphenyl]-3-(4-prop-2-ynoxyphenyl)prop-2-en-1-one; 66554277: (E)-1-[4-[(1-Benzyltriazol-4-yl)methoxy]-2-hydroxyphenyl]-3-(4-chlorophenyl)prop-2-en-1-one; 66554352: (E)-1-[4-[(1-Benzyltriazol-4-yl)methoxy]-2-hydroxyphenyl]-3-(4-prop-2-ynoxyphenyl)prop-2-en-1-one; 66554354: (E)-1-[4-[[1-[(4-Bromophenyl)methyl]triazol-4-yl]methoxy]-2-hydroxyphenyl]-3-phenylprop-2-en-1-one; 66554425: (E)-1-[4-[[1-[(4-Bromophenyl)methyl]triazol-4- yl]methoxy]-2-hydroxyphenyl]-3-(4-propan-2-ylphenyl) prop-2-en-1-one; 66561891: 3,4-Dibromo-1-[4-[(E)-3-(4-hydroxyphenyl)prop-2-enoyl]phenyl]pyrrole-2,5-dione; 66573137: (E)-1-[2-(2-Hexyldecoxy)-6-hydroxyphenyl]-3-(4-hydroxy-phenyl)prop-2-en-1-one; 66573138: (E)-1-[2-[(Z)-Dec-4-enoxy]-6-hydroxyphenyl]-3-(4-hydroxyphenyl) prop-2-en-1-one; 66573139: (E)-3-(4-Hydroxyphenyl)-1-(2-hydroxy-4-tetradecoxyphenyl)prop-2-en-1-one; 66573140: (E)-3-(3-Chloro-4-hydroxyphenyl)-1-(2-decoxy-6-hydroxyphenyl)prop-2-en-1-one; 66573142: (E)-1-(2-Decoxy-6-hydroxyphenyl)-3-(3-hydroxyphenyl)prop-2-en-1-one; 66573244: (E)-1-(2-Decoxy-6-hydroxyphenyl)-3-(4-methoxyphenyl)prop-2-en-1-one; 66573245: (E)-1-(2-Decoxy-6-hydroxyphenyl)-3-(4-methylphenyl)prop-2-en-1-one; 66573246: (E)-1-(2-Decoxy-6-hydroxyphenyl)-3-(3,4-dichlorophenyl)prop-2-en-1-one; 66573247: (E)-1-(2-Hexoxy-6-hydroxyphenyl)-3-(4-hexoxyphenyl)prop-2-en-1-one; 66573248: (E)-1-(2-Hydroxy-6-tetradecoxyphenyl)-3-(4-tetradecoxyphenyl)prop-2-en-1-one; 66573249: (E)-1-(2-Hydroxy-6-tetradecoxyphenyl)-3-[4-(methoxymethoxy) phenyl]prop-2-en-1-one; 66573250: (E)-1-(2-Hexadecoxy-6-hydroxyphenyl)-3-[4-(methoxymethoxy)phenyl]prop-2-en-1-one; 66573251: (E)-1-(2-Hydroxy-6-octadecoxyphenyl)-3-[4-(methoxymethoxy)phenyl]prop-2-en-1-one; 66573252: (E)-1-[2-(2-Hexyldecoxy)-6-hydroxyphenyl]-3-[4-(methoxymethoxy)phenyl]prop-2-en-1-one; 66573253: (E)-1-[2-[(Z)-Dec-4-enoxy]-6-hydroxyphenyl]-3-[4-(methoxymethoxy)phenyl]prop-2-en-1-one; 66573335: (E)-1-(2-Hexoxy-6-hydroxyphenyl)-3-(4-hydroxyphenyl)prop-2-en-1-one; 66573343: (E)-1-(2-Hydroxy-4-tetradecoxyphenyl)-3-[4-(methoxymethoxy) phenyl]prop-2-en-1-one; 66573344: (E)-3-[3-Chloro-4-(methoxymethoxy)phenyl]-1-(2-decoxy-6-hydroxyphenyl) prop-2-en-1-one; 66573346: (E)-1-(2-Decoxy-6-hydroxyphenyl)-3-[3-(methoxymethoxy)phenyl]prop-2-en-1-one; 66573424: (E)-1-(2-Hydroxy-6-octoxyphenyl)-3-(4-hydroxyphenyl)prop-2-en-1-one; 66573425: (E)-1-(2-Decoxy-6-hydroxyphenyl)-3-(4-hydroxyphenyl)prop-2-en-1-one; 66573426: (E)-1-(2-Dodecoxy-6-hydroxyphenyl)-3-(4-hydroxyphenyl)prop-2-en-1-one; 66573427: (E)-3-(4-Hydroxyphenyl)-1-(2-hydroxy-6-tetradecoxyphenyl)prop-2-en-1-one; 66573428: (E)-1-(2-Hexadecoxy-6-hydroxyphenyl)-3-(4-hydroxyphenyl)prop-2-en-1-one; 66573429: (E)-1-(2-Hydroxy-6-octadecoxyphenyl)-3-(4-hydroxyphenyl)prop-2-en-1-one; 66573432: (E)-1-(2-Hexoxy-6-hydroxyphenyl)-3-[4-(methoxymethoxy)phenyl] prop-2-en-1-one; 66573433: (E)-1-(2-Hydroxy-6-octoxyphenyl)-3-[4-(methoxymethoxy)phenyl]prop-2-en-1-one; 66573434: (E)-1-(2-Decoxy-6-hydroxy-phenyl)-3-[4-(methoxymethoxy)phenyl]prop-2-en-1-one; 66573435: (E)-1-(2-Dodecoxy-6-hydroxyphenyl)-3-[4-(methoxymethoxy) phenyl]prop-2-en-1-one; 66607829: 1,3-Diphenyl-prop-2-en-1-one;(2S)-5-hydroxy-2-(3-hydroxy-4-methoxyphenyl)-7-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxy-2,3-dihydrochromen-4-one; 66631140: CID 66631140; 66657135: 3-(3,4-Dihydro-2H-1,5-benzodioxepin-7-yl)-1-[2-hydroxy-4-(methoxymethyl)phenyl]prop-2-en-1-one; 66687732: (2S)-5,7-Dihydroxy-2-(4-hydroxyphenyl)-2,3-dihydrochromen-4-one;1,3-diphenylprop-2-en-1-one; 66688099: Quercetin chalcone; 66690004: 5,7-Dihydroxy-2-phenyl-2,3-dihydrochromen-4-one;1,3-diphenylprop-2-en-1-one; 66704313: 4-[(E)-3-(4-Chlorophenyl)prop-2-enoyl]-3-propan-2-yloxybenzoic acid; 66704352: 4-[(E)-3-(4-Methylsulfanylphenyl)prop-2-enoyl]-3-propan-2-ylsulfanylbenzoic acid; 66704360: 4-[(E)-3-(4-Methylsulfanylphenyl)prop-2-enoyl]-3-propan-2-yloxybenzoic acid; 66738877: Formaldehyde;3-(4-hydroxy-3-methoxyphenyl)-1-(4-hydroxyphenyl)prop-2-en-1-one; 66738878: 3-(4-Hydroxy-3-methoxyphenyl)-1-(4-hydroxyphenyl)prop-2-en-1-one; 66751582: 2',4,4'-Trihydroxy-3-prenylchalcone; 66752003: (E)-1-(5-Hydroxy-2-methylphenyl)-3-(4-methoxyphenyl)prop-2-en-1-one;(E)-1-(4-hydroxy-2-methylphenyl)-3-(3,4,5-trimethoxyphenyl)prop-2-en-1-one; 66815801: 4-[3-(2-Anilino-4-chlorophenyl)-3-oxoprop-1-enyl]-N-(4-hydroxycyclohexyl)benzamide; 66815807: 4-[3-(2-Anilino-4-chlorophenyl)-3-oxoprop-1-enyl]benzoic acid; 66815809: 4-[3-(2-Anilino-4-chlorophenyl)-3-oxoprop-1-enyl]-N-(2-hydroxy-2-methylpropyl)benzenesulfonamide; 66912770: 4'-Glucosyloxychalkon; 66921303: 2-[2-(3-Phenylprop-2-enoyl)phenoxy]acetic acid; 66934289: (E)-3-(4-(Benzyloxy)-3-(methoxymethoxy)phenyl)-1-(2-hydroxy-4-(methoxymethoxy)phenyl)prop-2-en-1-one; 66934290: 1-[2-Hydroxy-4-(methoxymethoxy)phenyl]-3-[3-(methoxymethoxy)-4-phenylmethoxyphenyl]prop-2-en-1-one; 66971639: (E)-1-(2,5-Dihydroxyphenyl)-3-phenylprop-2-en-1-one;(E)-1,3-diphenylprop-2-en-1-one; 66992093: (E)-3-[2-Methoxy-4-[(E)-3-oxo-3-phenylprop-1-enyl]phenyl]prop-2-enoic acid; 66992094: 3-[2-Methoxy-4-(3-oxo-3-phenyl-propenyl)-phenyl]-acrylic acid; 66992213: Methyl 4-[3-[4-(3-amino-2-hydroxy-3-oxoprop-1-enyl)phenyl]prop-2-enoyl]benzoate; 67016309: Benzoic acid, 4-[3-(4-fluoro-phenyl)-1-oxo-2-propenyl]-; 67045809: 4-[3-Oxo-3-(4-pentoxyphenyl)prop-1-enyl]benzoic acid; 67045824: 4-[(E)-3-(4-Pentoxyphenyl)prop-2-enoyl]benzoic acid; 67045825: 4-[3-(4-Pentoxyphenyl)prop-2-enoyl] benzoic acid; 67049116: (E)-3-[4-[(E)-3-Oxo-3-(4-piperazin-1-ylphenyl)prop-1-enyl]phenyl]prop-2-enoic acid; hydrochloride; 67049117: (E)-3-[4-[(E)-3-Oxo-3-(4-piperazin-1-ylphenyl)prop-1-enyl]phenyl]prop-2-enoic acid; 67049119: 3-[4-[3-Oxo-3-(4-piperazin-1-ylphenyl) prop-1-enyl]phenyl]prop-2-enoic acid; 67049368: (E)-3-(4-(E)-3-[4-(1-Methyl-piperidin-4-ylmethyl)-phenyl]-3-oxo-propenyl-phenyl)-acrylic acid hydrochloride; 67049369: (E)-3-[4-[(E)-3-[4-[(1-Methylpiperidin-4-yl)methyl]phenyl]-3-oxoprop-1-enyl]phenyl]prop-2-enoic acid; 67049374: 3-[4-[3-[4-[(1-Methylpiperidin-4-yl)methyl]phenyl]-3-oxoprop-1-enyl]phenyl]prop-2-enoic acid; 67049,375: (E)-3-[4-[(E)-3-[4-(4-Methylsulfonylpiperazin-1-yl)phenyl]-3-oxoprop-1-enyl]phenyl]prop-2-enoic acid; 67049,377: 3-[4-[3-[4-(4-Methylsulfonylpiperazin-1-yl)phenyl]-3-oxoprop-1-enyl]phenyl]prop-2-enoic acid; 67049433: (E)-3-4-[(E)-3-(4-Hydroxymethylphenyl)-3-oxo-propenyl]-phenyl-acrylic acid; 67049437: 3-[4-[3-[4-(Hydroxymethyl)phenyl]-3-oxoprop-1-enyl]phenyl]prop-2-enoic acid; 67049446: CID 67049446; 67049447: (e)-3-4-[(e)-3-(4-Hydroxymethylphenyl)-3-oxo-propenyl]-phenyl-acrylic acid potassium salt; 67049502: (E)-3-(4-(E)-3-[4-(4-Isobutyl-piperazin-1-yl)-phenyl]-3-oxo-propenyl-phenyl)-acrylic acid; 67049503: 3-[4-[3-[4-[4-(2-Methylpropyl) piperazin-1-yl]phenyl]-3-oxoprop-1-enyl]phenyl]prop-2-enoic acid; 67049536: (E)-3-(4-(E)-3-[4-(4-Acetyl-piperazin-1-yl)-phenyl]-3-oxo-propenyl-phenyl)-acrylic acid; 67049539: 3-[4-[3-[4-(4-Acetylpiperazin-1-yl)phenyl]-3-oxoprop-1-enyl]phenyl]prop-2-enoic acid; 67049551: 3-[4-[3-[4-[(4-Methylpiperazin-1-yl)methyl] phenyl]-3-oxoprop-1-enyl]phenyl]prop-2-enoic acid; 67049577: (E)-3-(4-(E)-3-[4-(1-Methyl-piperidin-4-yl)-phenyl]-3-oxo-propenyl-phenyl)-acrylic acid trifluoro acetate; 67049578: (E)-3-[4-[(E)-3-[4-(1-Methyl-piperidin-4-yl)phenyl]-3-oxoprop-1-enyl]phenyl]prop-2-enoic acid; 67049603: (E)-3-[4-[(E)-3-[4-[(2-Methylpropan-2-yl) oxycarbonyl]piperazin-1-yl]phenyl]-3-oxoprop-1-enyl]phenyl]prop-2-enoic acid; 67049680: 3-[4-[3-[2-[(4-Methylpiperazin-1-yl)methyl]phenyl]-3-oxoprop-1-enyl]phenyl]prop-2-enoic acid; 67049685: (E)-3-(4-(E)-3-[4-(4-Carbamoyl-piperazin-1-yl)-phenyl]-3-oxo-propenyl-phenyl)-acrylic acid hydrochloride; 67049686: (E)-3-[4-[(E)-3-[4-(4-Carbamoylpiperazin-1-yl)phenyl]-3-oxoprop-1-enyl]phenyl] prop-2-enoic acid; 67049690: 3-[4-[3-[4-(4-Carbamoylpiperazin-1-yl)phenyl]-3-oxoprop-1-enyl]phenyl]prop-2-enoic acid; 67049776: CID 67049776; 67049881: (E)-3-(4-(E)-3-[4-(1-Methyl-piperidin-4-ylamino)-phenyl]-3-oxo-propenyl-phenyl)-acrylic acid trifluoroacetate; 67049882: (E)-3-(4-(E)-3-[4-(1-Methyl-piperidin-4-ylamino)-phenyl]-3-oxo-propenyl-phenyl)-acrylic acid; 67049,884: 3-[4-[3-[4-[(1-Methylpiperidin-4-yl)amino]phenyl]-3-oxoprop-1-enyl] phenyl]prop-2-enoic acid; 67049913: (E)-3-(4-(E)-3-[4-(4-Benzoyl-piperazin-1-yl)-phenyl]-3-oxo-propenyl-phenyl)-acrylic acid hydrochloride; 67049914: (E)-3-(4-(E)-3-[4-(4-Benzoyl-piperazin-1-yl)-phenyl]-3-oxo-propenyl-phenyl)-acrylic acid; 67049,916: 3-[4-[3-[4-(4-Benzoylpiperazin-1-yl)phenyl]-3-oxoprop-1-enyl]phenyl]prop-2-enoic acid; 67049920: (E)-3-[4-[(E)-3-[4-(4-Acetylpiperazin-1-yl)phenyl]-3-oxoprop-1-enyl]phenyl]prop-2-enoic acid;hydrochloride; 67050,037: 3-[4-[3-[2-(4-Methylpiperazin-1-yl)phenyl]-3-oxoprop-1-enyl]phenyl]prop-2-enoic acid; 67062410: (E)-1-(2,4-Dihydroxyphenyl)-3-(4-hydroxyphenyl)prop-2-en-1-one;1,3-diphenylprop-2-en-1-one; 67064976: (2S)-2-(3,4-Dihydroxyphenyl)-5,7-dihydroxy-2,3-dihydrochromen-4-one;1,3-diphenylprop-2-en-1-one; 67110965: 1-(2,4-Dihydroxy-6-methoxyphenyl)-3-[4-hydroxy-3-(3-methylbut-2-enyl)phenyl]prop-2-en-1-one; 67127,303: 3-(4-Hydroxyphenyl)-1-[4-(hexyloxy) phenyl]-2-propene-1-one; 67127304: 4-Hydroxy-4'-hexyloxy-chalcone; 67128,786: 3-[3-Hydroxy-4-[(2R,3R,4S,5S,6R)-3,4,5-trihydroxy-6-(hydroxymethyl)oxan-2-yl]oxyphenyl]-1-(2,4,6-trihydroxyphenyl)prop-2-en-1-one; 67135230: 4-Acetylamino-2'-(carboxymethoxy)-6'-hydroxychalcone; 67135884: 1-(2-Hydroxy-6-phenylmethoxyphenyl)-3-(3-methylphenyl) prop-2-en-1-one; 67136297: 1-(2-Hydroxy-6-phenylmethoxyphenyl)-3-phenylprop-2-en-1-one; 67136312: 4-Bromo-2'-(carboxymethoxy)-6'-hydroxychalcone; 67136326: 2'-Benzyloxy-6'-hydroxy-4-methylchalcone; 67136457: 2'-Benzyloxy-4-carboxy-6'-hydroxychalcone; 67218270: 3-(4-Chlorophenyl)-1-(2,4-dihydroxy-6-methoxyphenyl)prop-2-en-1-one; 67218403: (E)-1-[2-Hydroxy-6-methoxy-4-(methoxymethyl)phenyl]-3-phenylprop-2-en-1-one; 67218405: 1-[2-Hydroxy-6-methoxy-4-(methoxymethyl)phenyl]-3-phenylprop-2-en-1-one; 67218501: 1-(2,4-Dihydroxy-6-methoxyphenyl)-3-(4-hydroxy-3-methoxyphenyl)prop-2-en-1-one; 67287389: (E)-3-(4-Bromophenyl)-1-(2-hydroxy-4-methoxyphenyl) prop-2-en-1-one; 67287393: 3-(4-Bromophenyl)-1-(2-hydroxy-4-methoxyphenyl)prop-2-en-1-one; 67321621: 1-[4-(6-Hydroxyhexoxy)phenyl]-3-(4-iodophenyl)prop-2-en-1-one; 67321622: 3-[4-(6-Hydroxyhexoxy)phenyl]-1-(4-iodophenyl)prop-2-en-1-one; 67332480: 1-(4-Fluorophenyl)-3-(4-hydroxy-3-methoxyphenyl)prop-2-en-1-one; 67332656: (4S)-5-Amino-5-oxo-4-[[4-[(E)-3-oxo-3-phenylprop-1-enyl]benzoyl]amino]pentanoic acid; 67332664: (2S)-5-Amino-5-oxo-2-[[4-[(E)-3-oxo-3-phenylprop-1-enyl]benzoyl]amino]pentanoic acid; 67345734: 3-(1,3-Benzodioxol-5-yl)-1-(2,4-dihydroxy-6-methoxyphenyl)prop-2-en-1-one; 67346714: 1-(2,4-Dihydroxy-6-methoxyphenyl)-3-[4-(trifluoromethyl)phenyl]prop-2-en-1-one; 67347049: 3-(4-Hydroxy-3-methoxyphenyl)-1-[2-methoxy-4,6-bis(prop-2-enoxy)phenyl]prop-2-en-1-one; 67347437: 1-(2,4-Dihydroxy-6-methoxyphenyl)-3-(3-methoxyphenyl)prop-2-en-1-one; 67347571: 1-(2,4-Dihydroxy-6-methoxyphenyl)-3-(4-fluorophenyl)prop-2-en-1-one; 67348991: 1-(2,4-Dihydroxy-6-methoxyphenyl)-3-(4-methylphenyl)prop-2-en-1-one; 67349208: 3-(4-Hydroxyphenyl)-1-[2-methoxy-4,6-bis(prop-2-enoxy)phenyl]prop-2-en-1-one; 67363797: 3-[3-[3-[4-[(4-Methylpiperazin-1-yl)methyl]phenyl]-3-oxoprop-1-enyl]phenyl]prop-2-enoic acid; 67364122: 3-[3-[3-[4-(4-Methylpiperazin-1-yl)phenyl]-3-oxoprop-1-enyl]phenyl]prop-2-enoic acid; 67364186: 3-[3-[3-[2-(4-Methylpiperazin-1-yl)phenyl]-3-oxoprop-1-enyl]phenyl] prop-2-enoic acid; 67422441: 1-(2-Decyl-6-hydroxyphenyl)-3-phenylprop-2-en-1-one; 67483920: 3-[[4-[(E)-3-(4-Cyclohexylphenyl)-3-oxoprop-1-enyl]benzoyl]amino]propanoic acid; 67483921: 3-(4-(3-(4-Cyclohexylphenyl)-3-oxopropenyl)benzoylamino)propionic acid; 67499641: 2-Methyl-4-[(E)-3-oxo-3-phenylprop-1-enyl]benzoic acid; 67499645: 2-Methyl-4-(3-oxo-3-phenylprop-1-enyl)benzoic acid; 67541349: 2-Propen-1-one, 3-[4-(hexyloxy)phenyl]-1-(2-hydroxyphenyl)-; 67541390: (E)-1-(4-Hexoxy-2-hydroxyphenyl)-3-(4-methylphenyl)prop-2-en-1-one; 67541392: 1-(4-Hexoxy-2-hydroxy-phenyl)-3-(4-methylphenyl)prop-2-en-1-one; 67541633: [3-Hydroxy-4-[(E)-3-(4-methoxy-phenyl)prop-2-enoyl]phenyl] hexanoate; 67541634: [3-Hydroxy-4-[3-(4-methoxy-phenyl)prop-2-enoyl]phenyl] hexanoate; 67542275: (E)-3-(3-Hexoxyphenyl)-1-(2-hydroxy-phenyl)prop-2-en-1-one; 67542277: 3-(3-Hexoxyphenyl)-1-(2-hydroxyphenyl)prop-2-en-1-one; 67547622: 3-[3,4-Bis[3-(4-hydroxyphenyl)prop-2-enoyl]phenyl]prop-2-enoic acid; 67566248: 2'-(beta-D-Glucopyranosyloxy)-6'-hydroxy-3-(5-benzo[b]furanyl)acrylophenone; 67709757: (E)-1,3-Diphenylprop-2-en-1-one;prop-2-enoic acid; 67739310: Cyclohexyl 2-methylprop-2-enoate; [4-[3-(4-methylphenyl)prop-2-enoyl]phenyl] prop-2-enoate;prop-2-enoic acid; 67741943: (E)-3-(4-Hydroxy-3-methylphenyl)-1-(4-nitro-phenyl)prop-2-en-1-one; 67800343: 4-[4-[(E)-3-(4-Methylphenyl)prop-2-enoyl]phenyl]butanoic acid; 67800345: 4-[4-[3-(4-Methylphenyl)prop-2-enoyl]phenyl]butanoic acid; 67800880: 4-[4-[(E)-3-(4-Butyl-phenyl)prop-2-enoyl]phenyl]butanoic acid; 67800882: 4-[4-[3-(4-Butylphenyl)prop-2-enoyl]phenyl] butanoic acid; 67802076: 4-[4-[(E)-3-(4-Chlorophenyl)prop-2-enoyl]phenyl]butanoic acid; 67802078: 4-[4-[3-(4-Chlorophenyl)prop-2-enoyl]phenyl]butanoic acid; 67802475: 4-[4-[(E)-3-(4-Butoxyphenyl)prop-2-enoyl]phenyl]butanoic acid; 67802477: 4-[4-[3-(4-Butoxyphenyl)prop-2-enoyl]phenyl]butanoic acid; 67802527: 4-[4-[(E)-3-(4-Fluoro-phenyl)prop-2-enoyl]phenyl]butanoic acid; 67802530: 4-[4-[3-(4-Fluorophenyl)prop-2-enoyl]phenyl] butanoic acid; 67802633: 4-[4-[(E)-3-(3-Fluorophenyl)prop-2-enoyl]phenyl]butanoic acid; 67802634: 4-[4-[3-(3-Fluorophenyl)prop-2-enoyl]phenyl]butanoic acid; 67832902: 2-[2-[3-[4-[(E)-Hex-1-enyl]phenyl]prop-2-enoyl]-5-(3-methylbut-2-enoxy) phenoxy]acetic acid; 67832917: 2-[2-[3-[4-[(E)-Hept-1-enyl]phenyl]prop-2-enoyl]-5-(3-methylbut-2-enoxy)phenoxy]acetic acid; 67833746: 2'-Carboxymethoxy-4'-(3-methyl-2-butenyloxy)-4-(1-(E)-octenyl)chalcone; 67854198: (E)-1-(2,4-Dihydroxyphenyl)-3-(4-hydroxyphenyl)prop-2-en-1-one;(E)-1-(2-hydroxyphenyl)-3-phenylprop-2-en-1-one; 68016719: (E)-3-[4-[2-Hydroxyethyl(methyl)amino]phenyl]-1-(4-nitro-phenyl)prop-2-en-1-one; 6843,825: (E)-3-(4-Bromophenyl)-1-[4-(hydroxymethyl)-2-methoxy-6-methylphenyl] prop-2-en-1-one; 68043901: (E)-3-(4-Bromophenyl)-1-[4-(hydroxymethyl)-2-iodo-6-methoxyphenyl]prop-2-en-1-one; 68100801: 4-[(E)-3-(4-Hydroxyphenyl)prop-2-enoyl] benzoic acid; 68146597: (E)-1-[4-(2,3-Dihydroxypropoxy)-2-hydroxyphenyl]-3-(3-hydroxy-4-methoxyphenyl)prop-2-en-1-one; 68152989: 2-[2-Fluoro-4-[(E)-3-(4- methylphenyl)-3-oxoprop-1-enyl]phenoxy]-2-methylpropanoic acid; 68189962: (E)-3-[4-[[4-[4-(1-Hydroxy-6-methoxyhexyl)phenyl]phenyl]methyl]phenyl]-1-phenylprop-2-en-1-one; 68189963: [6-Hydroxy-6-[[4-[(E)-3-oxo-3-phenylprop-1-enyl]phenyl]methyl]phenyl] hexyl] acetate; 68189964: [6-Hydroxy-6-[4-[4-[2-[4-[(E)-3-oxo-3-phenylprop-1-enyl]phenoxy]ethoxy]phenyl]phenyl] hexyl] acetate; 68189965: (E)-3-[4-[4-(1-Hydroxy-2-methoxyethyl)phenyl]phenyl]-1-phenylprop-2-en-1-one; 68189966: (E)-3-[4-[4-(1-Hydroxy-6-methoxyhexyl)phenyl]phenyl]-1-phenylprop-2-en-1-one; 68189967: [6-Hydroxy-6-[4-[4-[[4-[(E)-3-oxo-3-phenylprop-1-enyl]phenyl] methyl]phenyl]phenyl]hexyl] acetate; 68189968: (E)-3-[4-[[4-(1-Hydroxy-5-methoxypentyl)phenyl]methyl]phenyl]-1-phenylprop-2-en-1-one; 68190688: (E)-1-[4-[(17-Ethyl-10,13-dimethyl-2,3,4,5,6,7,8,9,11,12,14,15,16,17-tetradecahydro-1H-cyclopenta[a]phenanthren-3-yl)oxy] phenyl]-3-(4-hydroxyphenyl)prop-2-en-1-one; 68201233: (E)-3-[4-(4-Hydroxyphenyl)phenyl]-1-phenylprop-2-en-1-one; 68248595: (E)-3-[4-(Hydroxymethyl)phenyl]-1-(4-methoxyphenyl)prop-2-en-1-one; 68327564: 2-[3-(4-Cyanophenyl)prop-2-enoyl]benzoic acid; 68372294: (E)-3-[4-Butoxy-3-(methoxymethoxy)phenyl]-1-[2-hydroxy-4-(methoxymethoxy)phenyl]prop-2-en-1-one; 68374379: 1-[2-(1-Hydroxyethyl)phenyl]-3-[6-(4-phenyl-N-(4-phenylphenyl)anilino)naphthalen-2-yl]prop-2-en-1-one; 68384415: (2R)-2-(2-Phenylethyl)-4-[2-[(E)-3-phenylprop-2-enoyl]phenyl]butanoic acid; 68422642: (E)-1-[4-[[(8R,9S,10S,13R,14S,17R)-10,13-Dimethyl-17-[(2R)-6-methylheptan-2-yl]-2,3,4,5,6,7,8,9,11,12,14,15,16,17-tetradecahydro-1H-cyclopenta[a]phenanthren-3-yl]oxy] phenyl]-3-(4-hydroxyphenyl)prop-2-en-1-one; 68422643: 1-[4-[[(10S,13R,17R)-10,13-Dimethyl-17-[(2R)-6-methylheptan-2-yl]-2,3,4,5,6,7,8,9,11,12,14,15,16,17-tetradecahydro-1H-cyclopenta[a]phenanthren-3-yl]oxy]phenyl]-3-(4-hydroxyphenyl)prop-2-en-1-one; 68422644: 1-[4-[[(8R,9S,10S,13R,14S,17R)-10,13-Dimethyl-17-[(2R)-6-methylheptan-2-yl]-2,3,4,5,6,7,8,9,11,12,14,15,16,17-tetradecahydro-1H-cyclopenta[a]phenanthren-3-yl]oxy] phenyl]-3-(4-hydroxyphenyl)prop-2-en-1-one; 68424726: 3-[4-[[(10R,13R,17R)-10,13-Dimethyl-17-[(2R)-6-methylheptan-2-yl]-2,3,4,7,8,9,11,12,14,15,16,17-dodecahydro-1H-cyclopenta[a]phenanthren-3-yl]oxy]phenyl]-1-(4-hydroxyphenyl)prop-2-en-1-one; 68425469: 1-[4-[[(10R,13R,17R)-10,13-Dimethyl-17-[(2R)-6-methylheptan-2-yl]-2,3,4,7,8,9,11,12,14,15, 16,17-dodecahydro-1H-cyclopenta[a] phenanthren-3-yl]oxy]phenyl]-3-(4-hydroxyphenyl) prop-2-en-1-one; 68425827: (E)-3-[4-[[(8R,9S,10S,13R,14S,17R)-10,13-Dimethyl-17-[(2R)-6-methylheptan-2-yl]-2,3,4,5,6,7,8,9,11,12,14,15,16,17-tetradecahydro-1H-cyclopenta [a]phenanthren-3-yl]oxy]phenyl]-1-(4-hydroxyphenyl) prop-2-en-1-one; 68425830: 3-[4-[[(10S,13R,17R)-10,13-Dimethyl-17-[(2R)-6-methylheptan-2-yl]-2,3,4,5,6,7,8,9, 11,12,14,15,16,17-tetradecahydro-1H-cyclopenta[a] phenanthren-3-yl]oxy]phenyl]-1-(4-hydroxyphenyl)prop-2-en-1-one; 68425832: 3-[4-[[(8R,9S,10S,13R,14S,17R)-10, 13-Dimethyl-17-[(2R)-6-methylheptan-2-yl]-2,3,4,5,6,7,8, 9,11,12,14,15,16,17-tetradecahydro-1H-cyclopenta[a] phenanthren-3-yl]oxy]phenyl]-1-(4-hydroxyphenyl)prop-2-en-1-one; 68452316: 2-[3-(3,4-Dimethoxyphenyl)prop-2-enoyl]benzoic acid; 68467563: 3-[4-[4-[2-(3,5-Dihydroxyphenoxy)ethoxy]phenyl]phenyl]-1-phenylprop-2-en-1-one; 68468150: Benzene-1,2,4-tricarboxylic acid;1,3-bis(4-hydroxyphenyl)prop-2-en-1-one; 68468794: 5-[4-[4-(3-Oxo-3-phenylprop-1-enyl)phenyl]phenoxy]benzene-1,3-dicarboxylic acid; 68468861: 4-[4,5-Dicarboxy-2-[4-(3-oxo-3-phenylprop-1-enyl)phenoxy]phenyl]-5-[4-(3-oxo-3-phenylprop-1-enyl)phenoxy]phthalic acid; 68469206: 5-[6-[4-[4-(3-Oxo-3-phenylprop-1-enyl)phenoxy] carbonylphenoxy]hexoxy]benzene-1,3-dicarboxylic acid; 68469214: 1-(4-Fluorophenyl)-3-[4-(4-hydroxybutoxy)phenyl]prop-2-en-1-one; 68469299: 5-[6-[4-[4-(3-Oxo-3-phenylprop-1-enyl)phenyl]phenoxy]hexoxy]benzene-1,3-dicarboxylic acid; 68469309: 2-(2,4-Diamino-phenyl)-2-[4-(3-oxo-3-phenylprop-1-enyl)phenyl]decanedioic acid; 68469410: 5-[2-[4-[4-(3-Oxo-3-phenylprop-1-enyl)phenyl] phenoxy]ethoxy]benzene-1,3-dicarboxylic acid; 68469412: 3-[4-[4-[6-(3,5-Dihydroxyphenoxy)hexoxy]phenyl]phenyl]-1-phenylprop-2-en-1-one; 68469442: 6-[4-(3-Oxo-3-phenylprop-1-enyl)phenoxy]hexanoic acid; 68469483: 3-(4-Fluorophenyl)-1-[4-(6-hydroxyhexoxy)phenyl]prop-2-en-1-one; 68469786: 3-[3-(4-Carboxyphenyl)-3-oxoprop-1-enyl] benzoic acid; 68470267: 2-(4-Ethenylphenyl)-2-[4-(3-oxo-3-phenylprop-1-enyl)phenyl]acetic acid; 68470660: 2-(2,4-Diaminophenyl)-2-[4-(3-oxo-3-phenylprop-1-enyl)phenyl] hexanedioic acid; 68470742: 2-(2,4-Diaminophenyl)-2-[4-[3-(4-fluorophenyl)-3-oxoprop-1-enyl]phenyl]octanedioic acid; 68470743: [4-(3-Oxo-3-phenylprop-1-enyl)phenyl] 4-[2-(3,5-dihydroxyphenoxy)ethoxy]benzoate; 68470829: 3,5-Diamino-2-[2-[2-[4-[3-(4-fluorophenyl)-3-oxoprop-1-enyl]phenoxy]ethoxy]ethyl]benzoic acid; 68470958: 3-[4-[4-(3,5-Dihydroxyphenoxy)phenyl]phenyl]-1-phenylprop-2-en-1-one; 68471391: 1-(4-Fluorophenyl)-3-[4-(3-hydroxypropoxy)phenyl]prop-2-en-1-one; 68471496: 3,5-Diamino-2-[2-[2-[4-(3-oxo-3-phenylprop-1-enyl)phenoxy] ethoxy]ethyl]benzoic acid; 68471799: 2-(2,4-Diaminophenyl)-2-[4-(3-oxo-3-phenylprop-1-enyl)phenyl] octanedioic acid; 68471930: 2-(2,4-Diaminophenyl)-2-[4-[3-(4-fluorophenyl)-3-oxoprop-1-enyl]phenyl]hexanedioic acid; 68472098: 3-[4-(6-Hydroxyhexoxy)phenyl]-1-phenylprop-2-en-1-one; 68472192: 4-(3-Hydroxypropyloxy)-chalcone; 68472199: 3-[2,3-Dicarboxy-5-[4-(3-oxo-3-phenylprop-1-enyl)phenoxy]phenyl]-5-[4-(3-oxo-3-phenylprop-1-enyl)phenoxy]phthalic acid; 68472304: Benzene-1,2,4-tricarboxylic acid;3-(3-hydroxyphenyl)-1-(4-hydroxyphenyl)prop-2-en-1-one; 68472723: 3-[2,3-Dicarboxy-6-[4-(3-oxo-3-phenylprop-1-enyl)phenoxy]phenyl]-4-[4-(3-oxo-3-phenylprop-1-enyl)phenoxy]phthalic acid; 68472758: 5-[4-[4-(3-Oxo-3-phenylprop-1-enyl)phenoxy]carbonylphenoxy]benzene-1,3-dicarboxylic acid; 68472815: 4-[3,4-Dicarboxy-2-[4-(3-oxo-3-phenylprop-1-enyl)phenoxy] phenyl]-3-[4-(3-oxo-3-phenylprop-1-enyl)phenoxy]phthalic acid; 68472818: [4-(3-Oxo-3-phenylprop-1-enyl)phenyl] 4-[6-(3,5-dihydroxy-phenoxy)hexoxy]benzoate; 68473142: [4-(3-Oxo-3-phenylprop-1-enyl)phenyl] 4-(3,5-dihydroxyphenoxy)benzoate; 68473163: 2-[4-(3-Oxo-3-phenylprop-1-enyl)phenyl]-2-(4-prop-1-en-2-ylphenyl)acetic acid; 68473206: 3-(4-Fluorophenyl)-1-[4-(3-hydroxypropoxy) phenyl]prop-2-en-1-one; 68473246: 1-(4-Fluorophenyl)-3-[4-(6-hydroxyhexoxy)phenyl]prop-2-en-1-one; 68473256: 3-[2,3-Dicarboxy-4-[4-(3-oxo-3-phenylprop-1-enyl)phenoxy]phenyl]-6-[4-(3-oxo-3-phenylprop-1-enyl)phenoxy] phthalic acid; 68473320: 3-(4-Fluorophenyl)-1-[4-(4-hydroxybutoxy)phenyl]prop-2-en-1-one; 68473424: 5-[2-[4-[4-(3-Oxo-3-phenylprop-1-enyl)phenoxy] carbonylphenoxy]ethoxy]benzene-1,3-dicarboxylic acid; 68473455: 5-[3,4-Dicarboxy-5-[4-(3-oxo-3-phenylprop-1-enyl)phenoxy]phenyl]-3-[4-(3-oxo-3-phenylprop-1-enyl) phenoxy]phthalic acid; 68473486: 2-(2,4-Diaminophenyl)-2-[4-[3-(4-fluorophenyl)-3-oxoprop-1-enyl]phenyl] decanedioic acid; 68474404: 1-[4-(4-Hydroxybutoxy) phenyl]-3-phenylprop-2-en-1-one; 68474457: 6-[4-[3-(4-Fluorophenyl)-3-oxoprop-1-enyl]phenoxy]hexanoic acid; 68494588: 3-(4-Hydroxy-3-methoxyphenyl)-1-(4-iodophenyl)prop-2-en-1-one; 68496061: 3-[4-(Dimethylamino)phenyl]-1-[4-[2-(2-hydroxyethoxy)ethoxy]phenyl]prop-2-en-1-one; 68558475: (E)-1-(2,4-Dihydroxyphenyl)-3-(4-hydroxyphenyl)prop-2-en-1-one;(2S)-7-hydroxy-2-(4-hydroxyphenyl)-2,3-dihydrochromen-4-one; 68586376: 1-[2-Hydroxy-4-(methoxymethoxy)phenyl]-3-[4-(methoxymethoxy)-3-(3-methylbut-2-enyl)phenyl]prop-2-en-1-one; 68587336: 1-(2-Hydroxy-4-methoxyphenyl)-3-[4-(3-methylbut-2-enoxy)phenyl]prop-2-en-1-one; 68588476: CID 68588476; 68589163: CID 68589163; 68589368: CID 68589368; 68589375: 1-(2-Hydroxy-4-methoxyphenyl)-3-[3-(3-methylbut-2-enyl)phenyl]prop-2-en-1-one; 68589960: 1-(2-Hydroxy-4-methoxyphenyl)-3-[4-hydroxy-3-(3-methylbut-2-enyl)phenyl]prop-2-en-1-one; 68590087: 1-(2,4-Dihydroxyphenyl)-3-[4-methoxy-3-(3-methylbut-2-enyl)phenyl]prop-2-en-1-one; 68591024: 1-(2-Hydroxyphenyl)-3-[4-methoxy-3-(3-methylbut-2-enyl)phenyl]prop-2-en-1-one; 68596887: (E)-Tert-butyl 4-((4-(3-(4-hydroxy-3-methylphenyl)acryloyl)-3-methylphenoxy)methyl)piperidine-1-carboxylate; 68596890: Tert-butyl 4-[[4-[3-(4-hydroxy-3-methylphenyl)prop-2-enoyl]-3-methylphenoxy]methyl]piperidine-1-carboxylate; 68599201: (E)-1-(4-Amino-2-methylphenyl)-3-(4-hydroxy-3-methylphenyl)prop-2-en-1-one; 68599205: 1-(4-Amino-2-methylphenyl)-3-(4-hydroxy-3-methylphenyl)prop-2-en-1-one; 68599917: N-[4-[3-(4-Hydroxy-3-methylphenyl)prop-2-enoyl]-3-methylphenyl]acetamide; 68626761: (E)-3-(4-Hydroxy-3-methoxyphenyl)-1-(2-hydroxy-4-phenylmethoxyphenyl)prop-2-en-1-one; 68626762: 3-(4-Hydroxy-3-methoxy-phenyl)-1-(2-hydroxy-4-phenylmethoxyphenyl)prop-2-en-1-one; 68628146: 1-[2-Hydroxy-4,6-bis(phenylmethoxy)phenyl]-3-(4-hydroxy-3-methoxyphenyl)prop-2-en-1-one; 68635613: 6-Oxo-6-[4-(3-oxo-3-phenylprop-1-enyl)phenoxy]-3-[4-(3-oxo-3-phenylprop-1-enyl)phenyl]hexanoic acid; 68643592: 1-[4-[3-(Tert-butylamino)-2-hydroxypropoxy]phenyl]-3-(3,4-dimethoxyphenyl)prop-2-en-1-one; 68643596: 4'-[3-Tert-butylamino-2-hydroxy-propoxy]-3,4-methylenedioxy-chalcone; 68643597: (E)-1-[4-[2-Hydroxy-3-(methylamino)propoxy]phenyl]-3-(4-methoxyphenyl)prop-2-en-1-one; 68643598: 4'-[2-Hydroxy-3-methylamino-propoxy]-4-methoxy-chalcone; 68643601: 1-[4-[3-[2-(3,4-Dimethoxyphenyl)ethylamino]-2-hydroxypropoxy]phenyl]-3-(4-methoxyphenyl)prop-2-en-1-one; 68643626: 3-(1,3-Benzodioxol-5-yl)-1-[4-[2-hydroxy-3-(2-methylpropylamino)propoxy]phenyl]prop-2-en-1-one; 68643628: 4'-[2-Hydroxy-3-iso-propylamino-propoxy]-4-methoxy-chalcone; 68643631: 1-[4-[3-(Tert-butylamino)-2-hydroxypropoxy]phenyl]-3-(4-methoxyphenyl)prop-2-en-1-one; 68643633: 1-[2-[2-Hydroxy-3-(propan-2-ylamino)propoxy]phenyl]-3-(4-methoxyphenyl)prop-2-en-1-one; 68643647: 1-[4-[3-(Butylamino)-2-hydroxypropoxy]phenyl]-3-(4-methoxyphenyl) prop-2-en-1-one; 68643658: 4'-[2-Hydroxy-3-(4-phenylpiperazin-1-yl)-propoxy]-3,4-methylenedioxy-chalcone; 68643663: 4'-[2-Hydroxy-3-4-(2-methoxyphenyl)-piperazin-1-ylpropoxy]-4-methoxy-chalcone; 68643665: 1-[4-[2-Hydroxy-3-(2-methylpropylamino)propoxy]phenyl]-3-(4-methoxyphenyl)prop-2-en-1-one; 68643668: 1-[2-[3-(Butylamino)-2-hydroxy-propoxy]phenyl]-3-(4-methoxyphenyl)prop-2-en-1-one; 68643698: 3,4-Dimethoxy-4'-[2-hydroxy-3-(4-phenylpiperazin-1-yl)-propoxy]-chalcone; 68660252: N-[4-[3-(4-Hydroxy-phenyl)-prop-2-enoyl]phenyl]methanesulfonamide; 68660291: N-[4-[3-(3,4-Dihydroxyphenyl)prop-2-enoyl]phenyl]methanesulfonamide; 68660301: 4-Hydroxy-N-[2-[3-(4-hydroxyphenyl)prop-2-enoyl]phenyl]benzenesulfonamide; 68660304: N-[4-[3-(4-Hydroxyphenyl)prop-2-enoyl]phenyl]benzenesulfonamide; 68660311: 4-Hydroxy-N-[2-[3-(3-hydroxyphenyl)prop-2-enoyl]phenyl]benzenesulfonamide; 68660316: N-[2-[3-(3,4-Dihydroxyphenyl)prop-2-enoyl]phenyl]-3-hydroxybenzenesulfonamide; 68660371: 4-Amino-N-[4-[3-(3,4-dihydroxyphenyl)prop-2-enoyl]phenyl]benzenesulfonamide; 68660372: N-[2-[3-(3,4-Dihydroxyphenyl)prop-2-enoyl]phenyl]-4-methylbenzenesulfonamide; 68660375: N-[4-[3-(4-Hydroxyphenyl)prop-2-enoyl]phenyl]-4-methylbenzenesulfonamide; 68660387: N-[4-[3-(3-Hydroxyphenyl)prop-2-enoyl]phenyl]-4-methylbenzenesulfonamide; 68660393: 3-Hydroxy-N-[4-[3-(4-hydroxyphenyl)prop-2-enoyl]phenyl]benzenesulfonamide; 68660394: N-[4-[3-(3,4-Dihydroxyphenyl)prop-2-enoyl]phenyl]-3-fluorobenzenesulfonamide; 68660398: 4-Fluoro-N-[4-[3-(4-hydroxyphenyl)prop-2-enoyl]phenyl]benzenesulfonamide; 68660400: 4-Hydroxy-N-[4-[3-(4-hydroxyphenyl)prop-2-enoyl]phenyl]benzenesulfonamide; 68660407: N-[4-[3-(3,4-Dihydroxyphenyl)prop-2-enoyl]phenyl]-2-nitrobenzenesulfonamide; 68660434: 4-Hydroxy-N-[4-[3-(3-hydroxyphenyl)prop-2-enoyl]phenyl]benzenesulfonamide; 68660469: N-[4-[3-(3,4-Dihydroxyphenyl)prop-2-enoyl]phenyl]-3-nitrobenzenesulfonamide; 68660472: 3-Hydroxy-N-[2-[3-(4-hydroxyphenyl)prop-2-enoyl]phenyl]benzenesulfonamide; 68660559: N-[4-[3-(3,4-Dihydroxyphenyl)prop-2-enoyl]phenyl]-4-hydroxybenzenesulfonamide; 68660579: N-[4-[3-(3,4-Dihydroxyphenyl)prop-2-enoyl]phenyl]-4-nitrobenzenesulfonamide; 68660582: N-[4-[3-(3,4-Dihydroxyphenyl)prop-2-enoyl]phenyl]-3-hydroxybenzenesulfonamide; 68660589: N-[4-[3-(4-Hydroxyphenyl)prop-2-enoyl]phenyl]-2-nitrobenzenesulfonamide; 68660595: 3-Amino-N-[4-[3-(3,4-dihydroxyphenyl)prop-2-enoyl]phenyl]benzenesulfonamide; 68660598: 3-Amino-N-[4-[3-(4-hydroxyphenyl)prop-2-enoyl]phenyl]benzenesulfonamide; 68660600: 3-Fluoro-N-[4-[3-(4-hydroxyphenyl)prop-2-enoyl]phenyl]benzenesulfonamide; 68660607: N-[4-[3-(4-Hydroxyphenyl)prop-2-enoyl]phenyl]-4-nitrobenzenesulfonamide; 68660609: N-[4-[3-(4-Hydroxyphenyl)prop-2-enoyl]phenyl]-3-nitrobenzenesulfonamide; 68660617: N-[4-[3-(3,4-Dihydroxyphenyl)prop-2-enoyl]phenyl]-2-fluorobenzenesulfonamide; 68660633: 2-Amino-N-[4-[3-(3,4-dihydroxyphenyl)prop-2-enoyl]phenyl]benzenesulfonamide; 68660636: 2-Fluoro-N-[4-[3-(4-hydroxyphenyl)prop-2-enoyl]phenyl]benzenesulfonamide; 68660641: N-[4-[3-(3,4-Dihydroxyphenyl)prop-2-enoyl]phenyl]-4-fluorobenzenesulfonamide; 68660650: N-[4-[3-(3,4-Dihydroxyphenyl)prop-2-enoyl]phenyl]benzenesulfonamide; 68660657: N-[4-[3-(3,4-Dihydroxyphenyl)prop-2-enoyl]phenyl]-4-methylbenzenesulfonamide; 68660668: 2-Amino-N-[4-[3-(4-hydroxyphenyl)prop-2-enoyl]phenyl]benzenesulfonamide; 68660670: 3-Hydroxy-N-[4-[3-(3-hydroxyphenyl)prop-2-enoyl]phenyl]benzenesulfonamide; 68660681: 3-Hydroxy-N-[2-[3-(3-hydroxyphenyl)prop-2-enoyl]phenyl]benzenesulfonamide; 68660690: 4-Amino-N-[4-[3-(4-hydroxyphenyl)prop-2-enoyl]phenyl]benzenesulfonamide; 68660701: N-[2-[3-(3,4-Dihydroxyphenyl)prop-2-enoyl]phenyl]-4-hydroxybenzenesulfonamide; 68660759: N-[2-[3-(4-Hydroxyphenyl)prop-2-enoyl]phenyl]-4-methylbenzenesulfonamide; 68703675: (4S)-5-(Benzylamino)-5-oxo-4-[[4-[(E)-3-oxo-3-phenylprop-1-enyl]benzoyl]amino]pentanoic acid; 68703676: (2S)-5-Amino-2-[benzyl-[4-[(E)-3-oxo-3-phenylprop-1-enyl]benzoyl]amino]-5-oxopentanoic acid; 68743638: (E)-3-[3-[(Dimethylamino)methyl]-4-hydroxyphenyl]-1-[4-(2-methoxyphenyl)-2-(4-methyl-piperazin-1-yl)phenyl]prop-2-en-1-one; 68744113: (E)-1-[4-Bromo-2-(4- methylpiperazin-1-yl)phenyl]-3-[3-[(dimethylamino) methyl]-4-hydroxyphenyl]prop-2-en-1-one; 68744922: 1-[2-[2-(Dimethylamino)ethyl-methylamino]-4-(2-methylphenyl)phenyl]-3-[3-[(dimethylamino)methyl]-4-hydroxyphenyl]prop-2-en-1-one; 68748099: 1-[4-Bromo-2-(4-methylpiperazin-1-yl)phenyl]-3-[3-[(dimethylamino) methyl]-4-hydroxyphenyl]prop-2-en-1-one; 68748626: 3-[3-[(Dimethylamino)methyl]-4-hydroxyphenyl]-1-[4-(2-methoxyphenyl)-2-(4-methylpiperazin-1-yl)phenyl]prop-2-en-1-one; 68766524: (E)-3-[3-(3-Hydroxyoxetan-3-yl)phenyl]-1-[4-(trifluoro-methyl)phenyl]prop-2-en-1-one; 68776702: N-[4-[(E)-3-(4-Hydroxyphenyl)prop-2-enoyl] phenyl]-N-nitrobenzenesulfonamide; 68776703: N-[4-[3-(4-Hydroxyphenyl)prop-2-enoyl]phenyl]-N-nitrobenzenesulfonamide; 68783506: CID 68783506; 68828040: 1-(2,4-Dihydroxy-6-methoxyphenyl)-3-[4-hydroxy-3-(3-methylbut-2-enoxy)phenyl]prop-2-en-1-one; 68828504: N-[2-Hydroxy-5-[(E)-3-oxo-3-phenylprop-1-enyl]phenyl]-4-methylbenzenesulfonamide; 68829020: 3-Hydroxy-N-[2-hydroxy-5-[(E)-3-oxo-3-phenylprop-1-enyl]phenyl]benzenesulfonamide; 68830189: 4-Hydroxy-N-[2-hydroxy-5-[(E)-3-oxo-3-phenylprop-1-enyl]phenyl]benzenesulfonamide; 68831547: N-[2-Hydroxy-4-[(E)-3-oxo-3-phenylprop-1-enyl]phenyl]-4-methylbenzenesulfonamide; 68832582: 4-Hydroxy-N-[2-hydroxy-4-[(E)-3-oxo-3-phenylprop-1-enyl]phenyl]benzenesulfonamide; 68847314: 1-[4-Chloro-2-(N-(2-hydroxy-2-methylpropyl)anilino)phenyl]-3-phenylprop-2-en-1-one; 68858699: 3-[4-Hydroxy-3-(trifluoro-methyl)phenyl]-1-(4-methylsulfanylphenyl)prop-2-en-1-one; 68860196: 1-[4-Trifluoromethylphenyl]-3-[3-methyl-4-hydroxyphenyl]prop-2-en-1-one; 68860729: 2-[2-Methyl-4-[3-oxo-3-[4-(trifluoromethyl)phenyl]prop-1-enyl] phenoxy]acetic acid; 68878007: (E)-1-[4-[(1-Tert-butylpiperidin-4-yl)methoxy]-2-methylphenyl]-3-(4-hydroxy-3-methylphenyl)prop-2-en-1-one; 68935399: 1-[2-Hydroxy-4,6-bis(methoxymethoxy)phenyl]-3-(4-prop-2-enoxyphenyl)prop-2-en-1-one; 68959838: 3-[4-Hydroxy-3-(3-methylbut-2-enyl)phenyl]-1-(2,4,6-trihydroxyphenyl) prop-2-en-1-one; 68976461: [2-[[4-[(E)-3-(4-Morpholin-4-ylphenyl)-3-oxoprop-1-enyl]benzoyl]amino]phenyl]carbamic acid; 68977702: 4-[(E)-3-(3,4-Dichlorophenyl)prop-2-enoyl]benzoic acid; 68977704: 4-[3-(3,4-Dichlorophenyl)-acryloyl]-benzoic acid; 68981934: (2S)-5,7-Dihydroxy-2-(4-hydroxy-3-methoxyphenyl)-2,3-dihydrochromen-4-one;1,3-diphenylprop-2-en-1-one; 68985794: 1-[2-Hydroxy-4-[(3R,4S,5S,6R)-3,4,5-trihydroxy-6-(hydroxymethyl)oxan-2-yl]oxyphenyl]-3-phenylprop-2-en-1-one; 69024291: (E)-1,3-Diphenylprop-2-en-1-one;(E)-3-phenylprop-2-enoic acid; 69052692: 3-(3-Fluoro-4-hydroxyphenyl)-1-(4-methylsulfanylphenyl)prop-2-en-1-one; 69056105: 2-[2-Fluoro-4-[3-(4-methylsulfanylphenyl)-3-oxoprop-1-enyl]phenoxy]-2-methylpropanoic acid; 69090885: 3-Amino-2-[3-(3,4-dimethoxyphenyl)prop-2-enoyl]benzoic acid; 69163689: 4-[3-(4-Thiophen-2-ylphenyl)prop-2-enoyl]benzoic acid; 69163948: 4-[3-(4-Pyrimidin-5-ylphenyl)prop-2-enoyl]benzoic acid; 69164380: 4-[3-[4-(1,3-Thiazol-2-yl)phenyl]prop-2-enoyl]benzoic acid; 69201921: (E)-3-(1-Benzofuran-5-yl)-1-[2-hydroxy-4-methyl-6-[(2R,3R,4S,5S,6R)-3,4,5-trihydroxy-6-(hydroxymethyl)thian-2-yl]oxyphenyl]prop-2-en-1-one; 69201926: 3-(1-Benzofuran-5-yl)-1-[2-hydroxy-4-methyl-6-[(2R,3R,4S,5S,6R)-3,4,5-trihydroxy-6-(hydroxymethyl)thian-2-yl]oxyphenyl]prop-2-en-1-one; 69201931: 3-(1-Benzofuran-5-yl)-1-[2-hydroxy-4-methyl-6-[(2S,3R,4S,5S,6S)-3,4,5-trihydroxy-6-(hydroxymethyl)thian-2-yl] oxyphenyl]prop-2-en-1-one; 69207944: 1-(4-Hydroxy-2,6-dimethoxyphenyl)-3-(4-methoxyphenyl)prop-2-en-1-one; 69209591: 2'-O-Methylhelichrysetin; 69242987: 1-(2,4-Diethoxy-6-hydroxyphenyl)-3-(3,4-diethoxyphenyl)prop-2-en-1-one; 69256468: 7-[(2S,3R,4S,5S,6R)-4,5-Dihydroxy-6-(hydroxymethyl)-3-[(2S,3R,4R,5R,6S)-3,4,5-trihydroxy-6-methyloxan-2-yl]oxyoxan-2-yl]oxy-5-hydroxy-2-(4-hydroxyphenyl)-2,3-dihydrochromen-4-one;1,3-diphenylprop-2-en-1-one; 69263078: 1-(2,4-Dichlorophenyl)-3-(3,4-dihydroxy-phenyl)prop-2-en-1-one; 69304230: 2-Acetamidoacetic acid;4-[2-(4-carbamimidoylphenyl)iminohydrazinyl]benzenecarboximidamide;(E)-1-(2,4-dihydroxyphenyl)-3-(4-hydroxyphenyl)prop-2-en-1-one; 69304239: [3-Hydroxy-4-[(E)-3-(4-hydroxyphenyl)prop-2-enoyl]phenyl] dihydrogen phosphate; 69304756: [(3R,4Ar,5S,6S,6aS,10S,10aR,10bS)-3-ethenyl-6,10,10b-trihydroxy-3,4a,7,7,10a-pentamethyl-1-oxo-5,6,6a,8,9,10-hexahydro-2H-benzo[f]chromen-5-yl] acetate;(E)-1-(2,4-dihydroxyphenyl)-3-(4-hydroxyphenyl) prop-2-en-1-one; 69305154: (E)-1-(2,4-Dihydroxyphenyl)-3-(4-hydroxyphenyl)prop-2-en-1-one;2-(3,4-dihydroxyphenyl)-3,5,7-trihydroxychromen-4-one; 69305874: 2-[4-[(7-Chloroquinolin-4-yl)amino]pentyl-ethylamino]ethanol;[3-hydroxy-4-[(E)-3-(4-hydroxyphenyl)prop-2-enoyl]phenyl] hydrogen sulfate; 69305875: [3-Hydroxy-4-[(E)-3-(4-hydroxyphenyl)prop-2-enoyl]phenyl] hydrogen sulfate; 69350322: (Z)-2-Hydroxy-3-[2-methoxy-4-[(E)-3-oxo-3-phenylprop-1-enyl]phenyl]prop-2-enamide; 69350328: 2-Hydroxy-3-[2-methoxy-4-(3-oxo-3-phenylprop-1-enyl) phenyl]prop-2-enamide; 69361249: 3-Hydroxy-3-[2-methoxy-4-(3-oxo-3-phenylprop-1-enyl)phenyl]prop-2-enamide; 69411807: (E)-3-(3-Amino-4-hydroxyphenyl)-1-phenylprop-2-en-1-one; 69455300: (E)-3-(4-Fluorophenyl)-1-(4-hydroxyphenyl)prop-2-en-1-one;1-(4-hydroxyphenyl) ethanone; 69531301: 3-[4-(4-Hydroxybutoxy)phenyl]-1-phenylprop-2-en-1-one; 69586605: 6-[2,4-Diamino-3-[4-[3-(4-fluorophenyl)-3-oxoprop-1-enyl]phenyl]phenoxy]-6-oxohexanoic acid; 69587062: 10-[2,4-Diamino-3-[4-[3-(4-fluorophenyl)-3-oxoprop-1-enyl]phenyl]phenoxy]-10-oxodecanoic acid; 69588116: 8-[2,4-Diamino-3-[4-[3-(4-fluorophenyl)-3-oxoprop-1-enyl]phenoxy]phenoxy]-8-oxooctanoic acid; 69606321: 3-[(Z)-3-[2-[(4-Methylpiperazin-1-yl)methyl]phenyl]-3-oxoprop-1-enyl] benzoic acid; 69606323: 3-[3-[2-[(4-Methylpiperazin-1-yl) methyl]phenyl]-3-oxoprop-1-enyl]benzoic acid; 69606393: 1-(2,4-Dichlorophenyl)-3-[3-[(dimethylamino)methyl]-4-hydroxyphenyl]prop-2-en-1-one; 69645788: 4-[3-(4-Pyrrolidin-1-yl-3-thiophen-2-ylphenyl)prop-2-enoyl]benzoic acid; 69645793: 4-[3-(3-Thiophen-2-ylphenyl)prop-2-enoyl]benzoic acid; 69645823: 4-[3-(4-Methoxy-3-thiophen-2-ylphenyl)prop-2-enoyl]benzoic acid; 69645847: 2-[3-(4-Methoxy-3-thiophen-2-ylphenyl) prop-2-enoyl]benzoic acid; 69645855: 4-[3-(2-Methoxy-4-thiophen-2-ylphenyl)-3-oxoprop-1-enyl]benzoic acid; 69645856: 2,2-Difluoro-2-[4-[3-(4-thiophen-2-ylphenyl)prop-2-enoyl]phenyl] sulfanylacetic acid; 69645880: 4-[3-Oxo-3-(4-thiophen-2-ylphenyl)prop-1-enyl]benzoic acid; 69645885: 4-[3-(4-Fluoro-3-thiophen-2-ylphenyl)prop-2-enoyl]benzoic acid; 69646125: (E)-3-(2,3-Dihydroxyphenyl)-1-(2-hydroxyphenyl)prop-2-en-1-one;(E)-3-(3,4-dihydroxyphenyl)-1-(2,4,6-trihydroxyphenyl)prop-2-en-1-one;(E)-1,3-diphenylprop-2-en-1-one; 69727701: 7-(3-Oxo-3-phenylprop-1-enyl)-10H-phenoxazine-1-carboxylic acid; 69772946: (E)-3-(3-Fluoro-4-methoxyphenyl)-1-(2-hydroxy-4-methoxyphenyl)prop-2-en-1-one; 69779627: 1-[2-Hydroxy-4-(2-methylprop-2-enoxy)phenyl]-3-(3-methoxyphenyl)prop-2-en-1-one; 69779628: 3-[4-(Dimethylamino)phenyl]-1-[2-hydroxy-4-(2-methylprop-2-enoxy)phenyl]prop-2-en-1-one;

69808174: 7-[(2S,3R,4S,5S,6R)-4,5-Dihydroxy-6-(hydroxymethyl)-3-[(2S,3R,4R,5R,6S)-3,4,5-trihydroxy-6-methyloxan-2-yl]oxyoxan-2-yl]oxy-5-hydroxy-2-(3-hydroxy-4-methoxyphenyl)-2,3-dihydrochromen-4-one;1,3-diphenylprop-2-en-1-one; 69947976: 4-[3-[4-[[4-(1-Ethoxyethyl)-1H-benzimidazol-2-yl]methoxy]phenyl]prop-2-enoyl]-3-hydroxybenzoic acid; 69949074: 4-[(E)-3-[3-[[1-(1-Ethoxyethyl)benzimidazol-2-yl]methoxy]phenyl]prop-2-enoyl]-3-hydroxybenzoic acid;hydrochloride; 69949075: 4-[(E)-3-[3-[[1-(1-Ethoxyethyl)benzimidazol-2-yl]methoxy]phenyl]prop-2-enoyl]-3-hydroxybenzoic acid; 69949078: 4-[3-[3-[[4-(1-Ethoxyethyl)-1H-benzimidazol-2-yl]methoxy]phenyl]prop-2-enoyl]-3-hydroxybenzoic acid; hydrochloride; 69964018: (E)-1-[2-Hydroxy-4-(hydroxymethyl)-6-methoxyphenyl]-3-(4-methylphenyl)prop-2-en-1-one; 70059272: 3-[(E)-3-Oxo-3-phenylprop-1-enyl]benzoic acid; 70140753: (E)-3-[3-Hydroxy-2-[(E)-3-phenylprop-2-enoyl]phenyl]prop-2-enoic acid; 70149986: 1-[2-Hydroxy-4-(3-methylbut-2-enoxy)phenyl]-3-(4-methylsulfanyl-phenyl)prop-2-en-1-one; 70150173: 1-[2-Hydroxy-4-(2-methylprop-2-enoxy)phenyl]-3-phenylprop-2-en-1-one; 70150249: 1-[2-Hydroxy-4-(3-methylbut-2-enoxy)phenyl]-3-[4-(trifluoromethyl)phenyl]prop-2-en-1-one; 70150438: 1-[2-Hydroxy-4-(3-methylbut-2-enoxy)phenyl]-3-(4-methylphenyl)prop-2-en-1-one; 70150554: 1-[2-Hydroxy-4-(3-methylbut-2-enoxy)phenyl]-3-(3-nitro-phenyl)prop-2-en-1-one; 70150561: 3-(4-Fluorophenyl)-1-[2-hydroxy-4-(3-methylbut-2-enoxy)phenyl]prop-2-en-1-one; 70151183: 3-(4-Bromophenyl)-1-[2-hydroxy-4-(2-methylprop-2-enoxy)phenyl]prop-2-en-1-one; 70155043: 3-(1,3-Benzodioxol-5-yl)-1-(2-hydroxy-6-methoxyphenyl)prop-2-en-1-one; 70171973: 3-[4-(6-Hydroxy-hexyl)phenyl]-1-phenylprop-2-en-1-one; 70204631: Azane;2-[5-(3-methylbut-2-enoxy)-2-[(E)-3-[4-(3-methylbut-2-enoxy)phenyl]prop-2-enoyl]phenoxy]acetic acid; 70228191: 3-[4-(2,4-Dihydroxyphenoxy)phenyl]-1-phenylprop-2-en-1-one; 70228192: 3-[4-(3,5-Dihydroxy-phenoxy)phenyl]-1-phenylprop-2-en-1-one; 70229781: 5-[4-(3-Oxo-3-phenylprop-1-enyl)phenoxy]benzene-1,3-dicarboxylic acid; 70229783: 2-[4-(3-Oxo-3-phenylprop-1-enyl)phenoxy]benzene-1,3-dicarboxylic acid; 70229786: 3-[4-(2,5-Dihydroxyphenoxy)phenyl]-1-phenylprop-2-en-1-one; 70229898: 4-(3-Oxo-3-phenylprop-1-enyl)phthalic acid; 70230340: 3-[4-(2,6-Dihydroxyphenoxy)phenyl]-1-phenylprop-2-en-1-one; 70230478: 4-[4-(3-Oxo-3-phenylprop-1-enyl)phenoxy]benzene-1,3-dicarboxylic acid; 70231086: 2-[4-(3-Oxo-3-phenylprop-1-enyl)phenoxy]terephthalic acid; 70289934: (E)-1-(2,4-Dihydroxy-phenyl)-3-(3,4-dihydroxyphenyl)prop-2-en-1-one;(E)-1-(2,4-dihydroxyphenyl)-3-(4-hydroxy-3-methoxyphenyl)prop-2-en-1-one; 70348329: 1-[4-(4-Hydroxybut-3-enoxy)phenyl]-3-phenylprop-2-en-1-one; 70360460: CID 70360460; 70379287: (E)-3-(4-Decylsulfanyl-phenyl)-1-(2,6-dihydroxyphenyl)prop-2-en-1-one; 70379292: 3-(4-Decylsulfanylphenyl)-1-(2,6-dihydroxyphenyl)prop-2-en-1-one; 70379437: (E)-1-(4-Decylsulfanylphenyl)-3-(4-hydroxyphenyl)prop-2-en-1-one; 70379449: (E)-1-(4-Decylsulfanylphenyl)-3-(3-hydroxyphenyl)prop-2-en-1-one; 70379566: 3-(4-Decylsulfanylphenyl)-1-(4-hydroxyphenyl)prop-2-en-1-one; 70379585: (E)-3-(4-Decylsulfanylphenyl)-1-(2,4-dihydroxyphenyl)prop-2-en-1-one; 70379588: 3-(4-Decylsulfanylphenyl)-1-(2,4-dihydroxyphenyl)prop-2-en-1-one; 70387654: 4-[(E)-3-[4-[(E)-3-(4-Carboxyphenyl)prop-2-enoyl]phenyl]-3-oxoprop-1-enyl]benzoic acid; 70390346: 4-[3-[4-But-3-enoxy-2-(carboxy-methoxy)phenyl]-3-oxopropanoyl]benzoic acid; 70449031: 3-[(E)-3-[2-(1-Carboxyethoxy)-4-prop-2-enoxy-phenyl]-3-oxoprop-1-enyl]benzoic acid; 70466356: Dihydroxy(oxo)silane;2-[5-(3-methylbut-2-enoxy)-2-[(E)-3-[4-(3-methylbut-2-enoxy)phenyl]prop-2-enoyl]phenoxy]acetic acid; 70481136: (E)-1-(2-Hydroxy-6-methoxy-4-methylsulfanylphenyl)-3-(4-methoxyphenyl)prop-2-en-1-one; 70481141: 1-(2-Hydroxy-6-methoxy-4-methylsulfanyl-phenyl)-3-(4-methoxyphenyl)prop-2-en-1-one; 70482122: (E)-1-(2-Hydroxy-6-methoxy-4-propoxyphenyl)-3-(4-methoxyphenyl)prop-2-en-1-one; 70482125: 1-(2-Hydroxy-6-methoxy-4-propoxyphenyl)-3-(4-methoxyphenyl)prop-2-en-1-one; 70520352: (E)-3-[2-[(E)-3-Phenylprop-2-enoyl]phenyl]prop-2-enoic acid; 70558520: (E)-1-(2-Hydroxy-6-methoxy-4-propan-2-yloxyphenyl)-3-(4-methoxyphenyl)prop-2-en-1-one; 70558521: 1-(2-Hydroxy-6-methoxy-4-propan-2-yloxyphenyl)-3-(4-methoxyphenyl)prop-2-en-1-one; 70578201: 1-[2-Hydroxy-4-(3-methylbut-2-enoxy)phenyl]-3-[4-(3-methylbut-2-enoxy)phenyl]prop-2-en-1-one; 70584879: (E)-3-[4-[Bis(2-hydroxyethyl)amino]phenyl]-1-phenylprop-2-en-1-one; 70588545: CID 70588545; 70588576: CID 70588576; 70588692: CID 70588692; 70588806: CID 70588806; 70588808: Sodium;2-[4-[3-(4-hydroxy-3-methoxyphenyl)prop-2-enoyl]phenoxy]acetate; 70588818: CID 70588818; 70588913: 3-[[4-[(E)-3-[4-(Carboxy-methoxy)phenyl]-3-oxoprop-1-enyl]phenyl]methoxy]-2-methyl-3-oxopropanoic acid; 70590305: 2-[4-[3-[4-(Carboxymethoxy)phenyl]-3-oxoprop-1-enyl]phenyl]-2-propanoyloxy-acetic acid; 70596419: 4-[(Z)-3-Oxo-3-phenylprop-1-enyl]benzoic acid; 70596457: 3-[4-[(Z)-3-Oxo-3-phenylprop-1-enyl]phenyl]propanoic acid; 70599421: Sodium;(6R,7R)-3-(acetyloxymethyl)-7-[[2-[[4-[3-(2-hydroxyphenyl)-3-oxoprop-1-enyl]benzoyl]amino]-2-phenylacetyl]amino]-8-oxo-5-thia-1-azabicyclo[4.2.0]oct-2-ene-2-carboxylate; 70599948: (6R,7R)-3-(Acetyloxymethyl)-7-[[2-[[4-[3-(4-methoxyphenyl)-3-oxoprop-1-enyl]benzoyl]amino]-2-phenylacetyl]amino]-8-oxo-5-thia-1-azabicyclo[4.2.0]oct-2-ene-2-carboxylic acid; 70639145: (E)-1-(2,4-Dihydroxyphenyl)-3-(3-methoxy-4-methylphenyl)prop-2-en-1-one; 70677321: (E)-1-[4-(Acridin-9-ylamino)phenyl]-3-(4-hydroxyphenyl)prop-2-en-1-one; 70677326: (E)-1-[4-(Acridin-9-ylamino)phenyl]-3-(4-hydroxy-3-methoxyphenyl)prop-2-en-1-one; 70681502: (Z)-1-[2,4-Dihydroxy-6-[(2S,3S,4S,5S,6S)-3,4,5-trihydroxy-6-(hydroxy-methyl)oxan-2-yl]oxyphenyl]-3-(4-hydroxyphenyl)prop-2-en-1-one; 70682832: (2S)-2-[(5Z)-5-[[4-[(E)-3-(4-Bromophenyl)-3-oxoprop-1-enyl]phenyl]methylidene]-4-oxo-2-sulfanylidene-1,3-thiazolidin-3-yl]-3-phenylpropanoic acid; 70682833: (2S)-2-[(5Z)-5-[[4-[(E)-3-(4-Methylphenyl)-3-oxoprop-1-enyl]phenyl]methylidene]-4-oxo-2-sulfanylidene-1,3-thiazolidin-3-yl]-3-phenylpropanoic acid; 70682834: (2S)-2-[(5Z)-5-[[4-[(E)-3-(2-Methoxyphenyl)-3-oxoprop-1-enyl]phenyl]methylidene]-4-oxo-2-sulfanylidene-1,3-thiazolidin-3-yl]-3-phenylpropanoic acid; 70684908: (2S)-2-[(5Z)-5-[[4-[(E)-3-(2,4-Dimethylphenyl)-3-oxoprop-1-enyl]phenyl]methylidene]-4-oxo-2-sulfanylidene-1,3-thiazolidin-3-yl]-3-phenylpropanoic acid; 70685837: (E)-1-(2,4-Dihydroxyphenyl)-3-(3-phenylmethoxyphenyl)prop-2-en-1-one; 70687060: (2S)-2-[(5Z)-5-[[4-[(E)-3-(4-Fluorophenyl)-3-oxoprop-1-enyl]phenyl]methylidene]-4-oxo-2-sulfanylidene-1,3-thiazolidin-3-yl]-3-phenylpropanoic acid; 70688259: 2-[(5Z)-5-[[4-[(E)-3-(2,4-Dichlorophenyl)-3-oxoprop-1-enyl]phenyl]methylidene]-4-oxo-2-sulfanylidene-1,3-thiazolidin-3-yl]acetic acid; 70689150: (2S)-2-[(5Z)-5-[[4-[(E)-3-(2-Chlorophenyl)-3-oxoprop-1-enyl]phenyl]methylidene]-4-oxo-2-sulfanylidene-1,3-thiazolidin-3-yl]-3-phenylpropanoic acid; 70689151: (2S)-2-[(5Z)-5-[[4-[(E)-3-(2-Bromophenyl)-3-oxoprop-1-enyl]phenyl]methylidene]-4-oxo-2-sulfanylidene-1,3-thiazolidin-3-yl]-3-phenylpropanoic acid; 70690260: (E)-1-[2-(3-Hexylundecoxy)-6-hydroxyphenyl]-3-(4-hydroxyphenyl)prop-2-en-1-one; 70690264: (E)-3-(4-Hydroxyphenyl)-1-[2-hydroxy-6-[(Z)-undec-5-enoxy]phenyl]prop-2-en-1-one; 70690265: (E)-1-(2-Hexoxy-6-hydroxyphenyl)-3-(4-pentoxyphenyl)prop-2-en-1-one; 70690266: (E)-1-(2-Hydroxy-6-tetradecoxyphenyl)-3-(4-tridecoxyphenyl)prop-2-en-1-one; 70691243: (2S)-2-[(5Z)-5-[[4-[(E)-3-(4-Methoxyphenyl)-3-oxoprop-1-enyl]phenyl]methylidene]-4-oxo-2-sulfanylidene-1,3-thiazolidin-3-yl]-3-phenylpropanoic acid; 70693354: (2S)-2-[(5Z)-4-Oxo-5-[[4-[(E)-3-oxo-3-phenylprop-1-enyl]phenyl]methylidene]-2-sulfa-nylidene-1,3-thiazolidin-3-yl]-3-phenylpropanoic acid; 70697464: (2S)-2-[(5Z)-5-[[4-[(E)-3-(2-Fluorophenyl)-3-oxoprop-1-enyl]phenyl]methylidene]-4-oxo-2-sulfa-nylidene-1,3-thiazolidin-3-yl]-3-phenylpropanoic acid; 70697465: (2S)-2-[(5Z)-5-[[4-[(E)-3-(4-Chlorophenyl)-3-oxoprop-1-enyl]phenyl]methylidene]-4-oxo-2-sulfa-nylidene-1,3-thiazolidin-3-yl]-3-phenylpropanoic acid; 70697466: (2S)-2-[(5Z)-5-[[4-[(E)-3-(2,4-Dichlorophenyl)-3-oxoprop-1-enyl]phenyl]methylidene]-4-oxo-2-sulfa-nylidene-1,3-thiazolidin-3-yl]-3-phenylpropanoic acid; 70697468: (2S)-2-[(5Z)-5-[[4-[(E)-3-(4-Acetamidophenyl)-3-oxoprop-1-enyl]phenyl]methylidene]-4-oxo-2-sulfa-nylidene-1,3-thiazolidin-3-yl]-3-phenylpropanoic acid; 71311831: Chalcone 4 hydrate; 71315334: (E)-1-[2-[2-Hydroxy-3-(propylamino)propoxy]phenyl]-3-phenylprop-2-en-1-one;hydrochloride; 71315335: Desphenethyl-(E)-styrylpropafenone; 71315336: (2E)-Dehydro Propafenone-d5 Hydrochloride; 71315337: (E)-1-[2-[1,1,2,3,3-Pentadeuterio-2-hydroxy-3-(propylamino)propoxy]phenyl]-3-phenylprop-2-en-1-one; 71334603: 2-Propen-1-one, 1-[2-hydroxy-4-(methoxymethoxy)phenyl]-3-phenyl-; 71339600: 2-Propen-1-one, 1-(2,4-dihydroxyphenyl)-3-(4-nitro-phenyl)-; 71341596: 2-Propenoic acid, 3-[4-[3-(2-hydroxyphenyl)-3-oxo-1-propenyl]phenyl]-; 71344504: 2-Propen-1-one, 1-(2,4-dihydroxyphenyl)-3-[4-(trifluoromethyl)phenyl]-; 71347268: 4-3-[4-(Hexyloxy)phenyl]-3-oxoprop-1-EN-1-YLbenzoic acid; 71361874: 1-(2,4-Dihydroxyphenyl)-3-(3-hydroxyphenyl) prop-2-en-1-one; 71364942: 3-(3-Bromophenyl)-1-(4-hydroxyphenyl)prop-2-en-1-one; 71373574: 3-[3-(2,6-Dihydroxyphenyl)-3-oxoprop-1-en-1-yl]benzoic acid; 71374904: 3-(3,4-Dihydroxyphenyl)-1-(4-nitro-phenyl)prop-2-en-1-one; 71384582: 2-[3-(4-Chlorophenyl) acryloyl]benzoic acid; 71384587: 2-[3-(3-Nitrophenyl)acryloyl]benzoic acid; 71384594: 2-3-[4-(Dimethylamino)phenyl]acryloylbenzoic acid; 71385222: 4-[3-(4-Bromophenyl)acryloyl]benzoic acid; 71385900: 2-[3-(3-Methylphenyl)acryloyl]benzoic acid; 71385901: 2-[3-(4-Hydroxyphenyl)acryloyl]benzoic acid; 71400059: 1-(2-Chlorophenyl)-3-(3-hydroxyphenyl) prop-2-en-1-one; 71400150: 2-[3-(3-Hydroxyphenyl)acryloyl]benzoic acid; 71418851: 1,3-Bis4-[(11-hydroxyundecyl)oxy]phenylprop-2-en-1-one; 71439175: 1-[4-[2-Hydroxy-3-(4-phenylpiperazin-1-yl)propoxy]phenyl]-3-phenylprop-2-en-1-one; 71441201: 1-(2-Hydroxy-phenyl)-3-[4-(methoxymethoxy)phenyl]prop-2-en-1-one; 71442332: 1-(4-Hydroxy-2-methoxyphenyl)-3-phenylprop-2-en-1-one; 71444293: 2-Propen-1-one, 3-(3-hydroxy-4-methoxyphenyl)-1-phenyl-; 71450449: 2-Methyl-2-[4-[3-[4-[(E)-3-phenylprop-2-enoyl]phenoxy]propyl]phenoxy]propanoic acid; 71452277: 2-Methyl-2-[4-[[4-[(E)-3-phenylprop-2-enoyl]phenoxy]methyl]phenoxy]propanoic acid; 71454762: (5Z)-5-[[4-[(E)-3-(2,4-Dihydroxy-phenyl)-3-oxoprop-1-enyl]phenyl]methylidene]-1,3-thiazolidine-2,4-dione; 71455811: 2-Methyl-2-[4-[2-[4-[(E)-3-phenylprop-2-enoyl]phenoxy]ethyl]phenoxy]propanoic acid; 71456745: 2-[4-[(E)-3-Oxo-3-(2-prop-2-enoxyphenyl)prop-1-enyl]phenoxy]acetic acid; 71461947: (5Z)-5-[[4-[(E)-3-(4-Hydroxyphenyl)-3-oxo-prop-1-enyl]phenyl]methylidene]-1,3-thiazolidine-2,4-dione; 71491269: (E)-1-[4-[2-(2,4-Difluorophenyl)-2-hydroxy-3-(1,2,4-triazol-1-yl)propoxy]phenyl]-3-phenylprop-2-en-1-one; 71491270: (E)-1-[4-[2-(2,4-Difluorophenyl)-2-hydroxy-3-(1,2,4-triazol-1-yl)propoxy]phenyl]-3-(4-methoxyphenyl)prop-2-en-1-one; 71491337: (E)-3-(4-Chlorophenyl)-1-[4-[2-(2,4-difluorophenyl)-2-hydroxy-3-(1,2,4-triazol-1-yl)propoxy]phenyl]prop-2-en-1-one; 71491340: (E)-1-[4-[2-(2,4-Difluorophenyl)-2-hydroxy-3-(1,2,4-triazol-1-yl)propoxy]phenyl]-3-(4-octoxyphenyl)prop-2-en-1-one; 71491400: (E)-1-[4-[2-(4-Fluorophenyl)-2-hydroxy-3-(1,2,4-triazol-1-yl)propoxy]phenyl]-3-(4-methoxyphenyl) prop-2-en-1-one; 71491401: (E)-1-[4-[2-(4-Bromophenyl)-2-hydroxy-3-(1,2,4-triazol-1-yl)propoxy]phenyl]-3-(4-methoxyphenyl)prop-2-en-1-one; 71491402: (E)-3-(4-Chloro-phenyl)-1-[4-[2-(4-fluorophenyl)-2-hydroxy-3-(1,2,4-triazol-1-yl)propoxy]phenyl]prop-2-en-1-one; 71491404: (E)-1-[4-[2-(2,4-Difluorophenyl)-2-hydroxy-3-(1,2,4-triazol-1-yl)propoxy]phenyl]-3-naphthalen-2-ylprop-2-en-1-one; 71491466: (E)-3-[4-[2-(2,4-Difluorophenyl)-2-hydroxy-3-(1,2,4-triazol-1-yl)propoxy]phenyl]-1-(4-methoxyphenyl)prop-2-en-1-one; 71491467: (E)-3-[4-[2-(2,4-Difluorophenyl)-2-hydroxy-3-(1,2,4-triazol-1-yl)propoxy]phenyl]-1-(4-methylphenyl)prop-2-en-1-one; 71491510: (E)-1-(2,4-Dichlorophenyl)-3-[4-[2-(2,4-difluorophenyl)-2-hydroxy-3-(1,2,4-triazol-1-yl)propoxy]phenyl]prop-2-en-1-one; 71491511: (E)-3-[4-[2-(2,4-Difluorophenyl)-2-hydroxy-3-(1,2,4-triazol-1-yl)propoxy]-3-methoxyphenyl]-1-(4-methoxyphenyl)prop-2-en-1-one; 71491512: (E)-3-[4-[2-(2,4-Difluorophenyl)-2-hydroxy-3-(1,2,4-triazol-1-yl)propoxy]phenyl]-1-(4-octoxyphenyl) prop-2-en-1-one; 71491610: (E)-3-(4-Chlorophenyl)-1-[4-[(2S)-2-(2,4-difluorophenyl)-2-hydroxy-3-(1,2,4-triazol-1-yl)propoxy]phenyl]prop-2-en-1-one; 71491654: (E)-1-[4-[(2R)-2-(2,4-Difluoro-phenyl)-2-hydroxy-3-(1,2,4-triazol-1-yl)propoxy]phenyl]-3-(4-methoxyphenyl)prop-2-en-1-one; 71491655: (E)-1-[4-[(2S)-2-(2,4-Difluorophenyl)-2-hydroxy-3-(1,2,4-triazol-1-yl)propoxy]phenyl]-3-(4-methoxyphenyl)prop-2-en-1-one; 71497045: (E)-1-(2-Hydroxyphenyl)-3-(4-methoxyphenyl)prop-2-en-1-one;5-[[4-[2-[methyl(pyridin-2-yl)amino]ethoxy]phenyl]methyl]-1,3-thiazolidine-2,4-dione; 71500411: 2-[[4-[(E)-3-Phenylprop-2-enoyl]phenyl]carbamoyl]benzoic acid; 71500412: 2-[[4-[(E)-3-(4-Chlorophenyl)prop-2-enoyl]phenyl]carbamoyl]benzoic acid; 71500413: 2-[[4-[(E)-3-(4-Methoxyphenyl)prop-2-enoyl]phenyl]carbamoyl]benzoic acid; 71512719: Chembl4291326; 71540134: (E)-1-(4-Chloro-2-hydroxyphenyl)-3-(3-chlorophenyl)prop-2-en-1-one; 71547235: (E)-3-(3-Chlorophenyl)-1-[2-hydroxy-4-(3-methylbut-2-enoxy)phenyl]prop-2-en-1-one; 71589851: (E)-N-(4-(3-(3,4-Dihydroxyphenyl)acryloyl)phenyl)-1-adamantylamide; 71597852: 4'-Hydroxy-2',6'-dimethoxychalcone; 71624621: (E)-3-(3-Bromo-4-methoxyphenyl)-1-(2,4-dihydroxyphenyl) prop-2-en-1-one; 71624622: (E)-3-(3-Bromo-4-methoxyphenyl)-1-(2-hydroxy-4-methoxyphenyl)prop-2-en-1-one; 71624735: (E)-3-(4-Fluorophenyl)-1-(4-hydroxy-2-methoxyphenyl) prop-2-en-1-one; 71624736: (E)-1-(2,4-Dihydroxyphenyl)-3-(4-pyrrolidin-1-ylphenyl)prop-2-en-1-one; 71652420: Ethyl 3-hydroxy-4-[(E)-3-(4-octoxyphenyl)prop-2-enoyl]benzoate; 71652580: Ethyl 4-[(E)-3-(4-dodecoxyphenyl)prop-2-enoyl]-3-hydroxybenzoate; 71652744: 3-(Carboxymethoxy)-4-[(E)-3-(4-octoxyphenyl)prop-2-enoyl] benzoic acid; 71652745: 3-(Carboxymethoxy)-4-[(E)-3-(4-dodecoxyphenyl)prop-2-enoyl]benzoic acid; 71652746:

3-(Carboxymethoxy)-4-[(E)-3-[3-[4-(4-chlorophenoxy)butoxy]phenyl]prop-2-enoyl]benzoic acid; 71652899: Ethyl 4-[(E)-3-[3-[4-(4-chlorophenoxy)butoxy]phenyl]prop-2-enoyl]-3-hydroxybenzoate; 71698302: (E)-1-(4-Bromo-2-hydroxyphenyl)-3-[4-(trifluoromethyl)phenyl]prop-2-en-1-one; 71699753: Flavonid, 5c; 71724448: (E)-1-(2-Hydroxyphenyl)-3-(4-methoxy-3-propan-2-ylphenyl)prop-2-en-1-one; 71724607: Chembl4291338; 71749251: (2E)-1-(2-Hydroxyphenyl)-3-(phenyl-d5)-2-propen-1-one; 71817310: (E)-1-(4-Amino-2-hydroxyphenyl)-3-(4-ethoxy-3-methoxyphenyl)prop-2-en-1-one; 71817311: (E)-1-(4-Amino-2-hydroxyphenyl)-3-(4-propan-2-ylphenyl)prop-2-en-1-one; 71817312: (E)-1-(4-Amino-2-hydroxyphenyl)-3-(4-ethylphenyl)prop-2-en-1-one; 71817313: (E)-1-(4-Amino-2-hydroxy-phenyl)-3-(4-phenylphenyl)prop-2-en-1-one; 71817314: (E)-1-(4-Amino-2-hydroxyphenyl)-3-(3-phenoxyphenyl)prop-2-en-1-one; 71817454: (E)-1-(4-Amino-2-hydroxyphenyl)-3-naphthalen-2-ylprop-2-en-1-one; 71817455: (E)-1-(4-Amino-2-hydroxyphenyl)-3-(1,3-benzo-dioxol-5-yl)prop-2-en-1-one; 71819498: (E)-1-(4-Amino-2-hydroxyphenyl)-3-(4-methyl-sulfanylphenyl)prop-2-en-1-one; 71819499: (E)-1-(4-Amino-2-hydroxyphenyl)-3-(3-methoxyphenyl)prop-2-en-1-one; 71819500: (E)-1-(4-Amino-2-hydroxyphenyl)-3-(4-fluoro-phenyl)prop-2-en-1-one; 71819501: (E)-1-(4-Amino-2-hydroxyphenyl)-3-(4-chloro-phenyl)prop-2-en-1-one; 71821315: 3-(3-Bromo-4-methoxyphenyl)-1-(2-hydroxyphenyl)prop-2-en-1-one; 71821332: 3-(3-Chloro-4-fluoro-phenyl)-1-(2-hydroxyphenyl)prop-2-en-1-one; 71877012: 2-4-[3-(4-Fluoro-2-methylphenyl)-3-oxoprop-1-en-1-yl]-2-nitrophenoxyacetic acid; 71877015: 2-4-[3-(2,4-Difluoro-phenyl)-3-oxoprop-1-en-1-yl]-2-nitrophenoxyacetic acid; 71893876: 1-(4-Hydroxyphenyl)-3-4-[(1-methyl-1H-imidazol-2-yl)methoxy]phenylprop-2-en-1-one; 71900716: 4-[3-(2-Methoxy-4-methylphenyl)-3-oxoprop-1-en-1-yl]benzoic acid; 71902880: 4-[3-(2,4-Dimethylphenyl)-3-oxoprop-1-en-1-yl]benzoic acid; 71902887: 2-4-[3-(3-Hydroxy-4-methoxyphenyl)prop-2-enoyl]phenoxyacetonitrile; 71903100: 2-[4-(3-4-[(2,4-Dichlorophenyl)methoxy]-3-methoxyphenylprop-2-enoyl)phenoxy]propanoic acid; 71903102: 4-[3-(2-Ethoxyphenyl)-3-oxoprop-1-en-1-yl]benzoic acid; 71937000: 4-3-Oxo-3-[4-(2-oxo-1,3-oxazolidin-3-yl)phenyl]prop-1-en-1-ylbenzoic acid; 71944853: 1-(4-Fluorophenyl)-3-[4-(3-hydroxy-3-methylbut-1-ynyl)phenyl]prop-2-en-1-one; 71944916: 3-[3-(1H-Benzimidazol-2-ylsulfanylmethyl)-4-methoxyphenyl]-1-(2-hydroxy-phenyl)prop-2-en-1-one; 71951161: 2-[[4-[3-[4-[3-[4-[(2-Carboxy-5-nitrobenzoyl)amino]phenyl]-3-oxoprop-1-enyl]phenyl]prop-2-enoyl]phenyl]carbamoyl]-4-nitrobenzoic acid; 71951164: 1-(4-Bromophenyl)-3-[4-[2-hydroxyethyl(methyl)amino]phenyl]prop-2-en-1-one; 71951167: 4-[4-[3-[4-[3-[4-(3-Carboxyprop-2-enoylamino)phenyl]-3-oxoprop-1-enyl]phenyl]prop-2-enoyl]anilino]-4-oxobut-2-enoic acid; 71963834: N-[(2S,3R,4R,5S,6R)-4,5-Dihydroxy-6-(hydroxymethyl)-2-[4-(3-phenylprop-2-enoyl)phenoxy]oxan-3-yl]acetamide; 71966630: Methyl 5-[3-(4-chlorophenyl)-3-oxoprop-1-enyl]-2-hydroxybenzoate; 71966631: Methyl 2-hydroxy-5-(3-oxo-3-phenylprop-1-enyl)benzoate; 71966632: 5-[3-(4-Chloro-phenyl)-3-oxoprop-1-enyl]-2-hydroxybenzoic acid; 71966801: 2-[4-[3-(2,3-Dihydro-1,4-benzodioxin-6-yl)prop-2-enoyl]-3-hydroxyphenoxy]acetic acid; 72027034: 3-(4-Hydroxy-3-nitro-phenyl)-1-[4-(2-methoxyethoxy)phenyl]prop-2-en-1-one; 72027039: 3-(3-Hydroxy-phenyl)-1-[4-(2-methoxyethoxy)phenyl]prop-2-en-1-one; 72027064: 3-(3-Hydroxy-4-methoxyphenyl)-1-[4-(trifluoromethyl)phenyl]prop-2-en-1-one; 72027891: 2-[4-[3-(4-Ethylphenyl)prop-2-enoyl]phenyl]acetic acid; 72027951: 1-[4-[3-(3-Hydroxyphenyl)prop-2-enoyl]phenyl]-3-propan-2-ylurea; 72032053: 2-[4-[3-[4-[(2-Methyl-1,3-thiazol-4-yl)methoxy]phenyl]prop-2-enoyl]phenoxy]propanoic acid; 72034125: 1-(2,4-Dimethylphenyl)-3-(3-hydroxy-4-methoxyphenyl)prop-2-en-1-one; 72034171: 2-[4-[3-(3,4-Difluorophenyl)prop-2-enoyl]phenoxy]acetic acid; 72034195: 4-[3-(3-Hydroxy-4-methoxyphenyl)prop-2-enoyl]-N,N-dimethyl-benzenesulfonamide; 72034212: 1-(4-Ethoxyphenyl)-3-(3-hydroxy-4-methoxy-phenyl)prop-2-en-1-one; 72034214: 1-(4-Ethoxyphenyl)-3-(4-hydroxy-3-methoxyphenyl) prop-2-en-1-one; 72034375: 1-[4-(5,6-Dihydro-4H-1,3-thiazin-2-ylamino)phenyl]-3-(4-hydroxy-3-nitro-phenyl)prop-2-en-1-one; 72034517: 2-[4-[3-(4-Cyclohexylphenyl)-3-oxoprop-1-enyl]phenoxy]acetic acid; 72034523: 3-(3-Ethoxy-4-hydroxyphenyl)-1-(4-fluorophenyl) prop-2-en-1-one; 72034546: 3-(4-Hydroxy-3-methoxyphenyl)-1-[2-(trifluoromethyl)phenyl]prop-2-en-1-one; 72034570: 2-[2-Ethoxy-4-[3-(4-hydroxyphenyl)-3-oxoprop-1-enyl]phenoxy]-N-[3-(trifluoromethyl)phenyl]acetamide; 72034571: 1-(4-Hydroxyphenyl)-3-naphthalen-2-ylprop-2-en-1-one; 72034574: 2-Chloro-N-[3-[3-(4-hydroxyphenyl)-3-oxoprop-1-enyl]phenyl]benzamide; 72034575: 3-(4-Ethoxy-3-methoxyphenyl)-1-(4-hydroxyphenyl) prop-2-en-1-one; 72034581: 3-(3-Ethoxy-4-hydroxyphenyl)-1-(4-methylphenyl)prop-2-en-1-one; 72034613: 4-[[4-[3-(4-Cyanophenyl)prop-2-enoyl]phenyl]sulfonylamino]butanoic acid; 72034614: 3-[[4-[3-(4-Tert-butylphenyl)prop-2-enoyl]phenyl]sulfonylamino]propanoic acid; 72034615: 3-[[4-[3-(3-Hydroxyphenyl)prop-2-enoyl]phenyl]sulfonylamino]propanoic acid; 72034616: 4-[3-[4-(2-Carboxyethylsulfamoyl)phenyl]-3-oxoprop-1-enyl]benzoic acid; 72034617: 3-[[4-[3-(3-Chlorophenyl)prop-2-enoyl]phenyl]sulfonylamino] propanoic acid; 72034631: 2-[[4-[3-(4-Methylsulfanylphenyl)prop-2-enoyl]phenyl]sulfonylamino]acetic acid; 72034647: 3-(3-Bromo-4-hydroxyphenyl)-1-[4-(dimethylamino)phenyl]prop-2-en-1-one; 72034651: 1-[4-(Dimethylamino)phenyl]-3-(3-hydroxy-4-methoxyphenyl)prop-2-en-1-one; 72034654: 4-[3-[4-(Dimethylamino)phenyl]-3-oxoprop-1-enyl]benzoic acid; 72034666: 1-[4-(Azepan-1-yl)phenyl]-3-(4-hydroxy-3-nitro-phenyl)prop-2-en-1-one; 72034670: 3-(3-Hydroxy-4-methoxyphenyl)-1-(4-propan-2-ylphenyl)prop-2-en-1-one; 72034674: 3-(4-Hydroxy-3-methoxyphenyl)-1-(4-propan-2-ylphenyl)prop-2-en-1-one; 72034682: 3-(4-Hydroxy-3-methoxyphenyl)-1-(4-propoxyphenyl)prop-2-en-1-one; 72034684: 2-[4-[3-(3-Hydroxy-4-methoxyphenyl)prop-2-enoyl]phenoxy] propanoic acid; 72034743: 2-[4-[3-(4-Hydroxy-3-nitrophenyl)prop-2-enoyl]phenoxy]-N,N-dimethylacetamide; 72034749: 2-[4-[3-(3-Hydroxyphenyl)prop-2-enoyl]phenoxy]-N,N-dimethylacetamide; 72034751: 4-[3-[4-[2-(Dimethylamino)-2-oxoethoxy]phenyl]-3-oxoprop-1-enyl]benzoic acid; 72034783: 2-[4-[3-(3-Hydroxy-4-methoxyphenyl)prop-2-enoyl]phenoxy]-N-phenylacetamide; 72043596: 1-[4-(4-Hydroxypiperidin-1-yl)phenyl]-3-(3-methoxyphenyl)prop-2-en-1-one; 72043597: 1-[4-(4-Hydroxypiperidin-1-yl)phenyl]-3-(4-methoxyphenyl)prop-2-en-1-one; 72044706: N-4-[3-(3-Hydroxyphenyl)prop-2-enoyl]phenylethane-1-sulfonamide; 72045380: N-4-[3-(4-Hydroxy-3-methoxyphenyl)prop-2-enoyl]phenylmethanesulfonamide; 72045988: 4-(3-4-[2-(Dimethyl-amino)ethoxy]phenyl-3-oxoprop-1-en-1-yl)benzoic acid; 72046099: N-4-[3-(3-Hydroxy-4-methoxyphenyl)prop-2-enoyl]phenylmethanesulfonamide; 72046104: N-4-[3-(3-Hydroxy-phenyl)prop-2-enoyl]phenylmethanesulfonamide; 72046107: 4-[3-(4-Methanesulfon-amidophenyl)-3-oxoprop-1-en-1-yl]benzoic acid; 72046267: 3-3-[3-

(4-Cyanophenyl)-3-oxoprop-1-en-1-yl]phenoxypropanoic acid; 72046268: 2-3-[3-(4-Cyanophenyl)-3-oxoprop-1-en-1-yl]phenoxypropanoic acid; 72046269: 3-3-[3-(4-Hydroxyphenyl)-3-oxoprop-1-en-1-yl]phenoxypropanoic acid; 72046521: Methyl 2-4-[3-(3-hydroxyphenyl)prop-2-enoyl]phenoxyacetate; 72046522: Methyl 2-4-[3-(3-hydroxy-4-methoxyphenyl)prop-2-enoyl]phenoxyacetate; 72048896: 1-4-[(2-Chloroprop-2-en-1-yl)oxy]phenyl-3-(4-hydroxy-3-nitro-phenyl)prop-2-en-1-one; 72048897: 1-4-[(2-Chloroprop-2-en-1-yl)oxy]phenyl-3-(3-hydroxy-4-methoxyphenyl)prop-2-en-1-one; 72050103: 3-(3-Hydroxyphenyl)-1-4-[(1-methyl-1H-imidazol-2-yl)methoxy]phenylprop-2-en-1-one; 72050104: 4-(3-4-[(1-Methyl-1H-imidazol-2-yl)methoxy]phenyl-3-oxoprop-1-en-1-yl)benzoic acid; 72050480: 4-3-[4-(2-Methoxyethoxy)phenyl]-3-oxoprop-1-en-1-ylbenzoic acid; 72050486: 3-(3-Hydroxy-4-methoxyphenyl)-1-[4-(2-methoxyethoxy)phenyl]prop-2-en-1-one; 72050885: 2-(4-3-[4-(Propan-2-yloxy)phenyl]prop-2-enoylphenoxy)acetic acid; 72051743: 3-4-[3-(4-Cyanophenyl)-3-oxoprop-1-en-1-yl]phenoxypropanoic acid; 72052386: 2-4-[3-(4-Ethoxy-3-methoxyphenyl)prop-2-enoyl]phenylacetic acid; 72052388: 2-4-[3-(3-Cyanophenyl)prop-2-enoyl]phenylacetic acid; 72055491: 1-(4-Hydroxyphenyl)-3-4-[(1,3-thiazol-4-yl)methoxy]phenylprop-2-en-1-one; 72055837: 2-[[4-[3-(3-Chlorophenyl)prop-2-enoyl]phenyl]sulfonyl-methylamino]acetic acid; 72056157: 4-(4-3-[3-Fluoro-4-(1H-1,2,4-triazol-1-yl)phenyl]prop-2-enoylphenoxy)butanoic acid; 72056835: 3-(3-Hydroxy-4-methoxyphenyl)-1-[4-(thiophen-2-yl)phenyl]prop-2-en-1-one; 72056836: 3-(3-Hydroxyphenyl)-1-[4-(thiophen-2-yl)phenyl]prop-2-en-1-one; 72056838: 3-(4-Hydroxyphenyl)-1-[4-(thiophen-2-yl)phenyl]prop-2-en-1-one; 72058376: 2-4-[3-(3-Cyanophenyl)prop-2-enoyl]phenoxyacetic acid; 72061471: 3-(3-Hydroxy-4-methoxyphenyl)-1-(2-methoxy-4-methylphenyl)prop-2-en-1-one; 72065131: 2-(4-3-Oxo-3-[4-(2-oxopyrrolidin-1-yl)phenyl]prop-1-en-1-ylphenoxy)acetic acid; 72065135: 1-4-[3-(3-Hydroxy-4-methoxyphenyl)prop-2-enoyl]phenylpyrrolidin-2-one; 72065140: 1-4-[3-(3-Ethoxy-4-hydroxyphenyl)prop-2-enoyl]phenylpyrrolidin-2-one; 72065145: 1-4-[3-(4-Hydroxy-3-methoxyphenyl)prop-2-enoyl]phenylpyrrolidin-2-one; 72067622: 4-3-Oxo-3-[4-(2-oxo-pyrrolidin-1-yl)phenyl]prop-1-en-1-ylbenzoic acid; 72068381: 5-4-[3-(3-Hydroxy-4-methoxy-phenyl)prop-2-enoyl]phenylfuran-2-carboxylic acid; 72068382: 5-4-[3-(4-Acetamidophenyl)prop-2-enoyl]phenylfuran-2-carboxylic acid; 72068461: 1-[4-(1H-1,3-Benzodiazol-1-yl)phenyl]-3-(3-hydroxyphenyl)prop-2-en-1-one; 72077807: 4-[3-(2-Methylphenyl)-3-oxoprop-1-en-1-yl]benzoic acid; 72077894: 3-(3-Hydroxyphenyl)-1-[4-(piperidin-1-yl)phenyl]prop-2-en-1-one; 72077908: 4-3-[4-(2-Methylpropyl)phenyl]-3-oxoprop-1-en-1-ylbenzoic acid; 72077973: 2-[4-(3-3-Methoxy-4-[(4-methylbenzenesulfonyl)oxy]phenylprop-2-enoyl) phenoxy] acetic acid; 72077974: 2-4-[3-(4-Hydroxy-3-nitro-phenyl)prop-2-enoyl]phenoxyacetic acid; 72077975: 2-4-[3-(3-Methoxy-4-propoxyphenyl)prop-2-enoyl]phenoxyacetic acid; 72077978: 2-4-[3-(4-Chloro-3-nitro-phenyl)prop-2-enoyl]phenoxyacetic acid; 72077979: 2-4-[3-(4-Nitrophenyl)prop-2-enoyl]phenoxyacetic acid; 72077980: 2-4-[3-(4-Acetamidophenyl)prop-2-enoyl]phenoxyacetic acid; 72078014: 2-4-[3-(4-Ethoxy-3-methoxyphenyl)prop-2-enoyl]phenoxyacetic acid; 72078016: 2-4-[3-(3,4-Dimethoxyphenyl) prop-2-enoyl]phenoxyacetic acid; 72078017: 2-(4-3-[4-(Morpholin-4-yl)phenyl]prop-2-enoylphenoxy) acetic acid; 72078089: 2-(4-3-[4-(Diethylsulfamoyl)phenyl]-3-oxoprop-1-en-1-yl-2-methoxyphenoxy)acetic acid; 72078122: 1-(4-Ethoxyphenyl)-3-(3-hydroxyphenyl)prop-2-en-1-one; 72078159: 2-[2-Methoxy-4-(3-4-[(4-methylpiperidin-1-yl)sulfonyl]phenyl-3-oxoprop-1-en-1-yl)phenoxy]acetic acid; 72078161: 3-(3-Hydroxy-4-methoxyphenyl)-1-[4-(piperidine-1-sulfonyl)phenyl]prop-2-en-1-one; 72078271: 3-(4-Hydroxy-3-methoxyphenyl)-1-[4-(morpholine-4-sulfonyl)phenyl]prop-2-en-1-one; 72078867: 1-(2-Fluoro-4-methoxy-phenyl)-3-(hydroxy-4-methoxyphenyl)prop-2-en-1-one; 72078870: 2-(4-3-[4-(4-Methylben-zenesulfonamido)phenyl]-3-oxoprop-1-en-1-ylphenoxy)acetic acid; 72078871: N-4-[3-(3-Hydroxy-4-methoxyphenyl)prop-2-enoyl]phenyl-4-methylbenzene-1-sulfonamide; 72078942: 1-(4-Tert-butylphenyl)-3-(4-hydroxy-3-nitro-phenyl)prop-2-en-1-one; 72078960: 1-(4-Tert-butylphenyl)-3-(3-hydroxy-4-methoxyphenyl)prop-2-en-1-one; 72079157: 3-(3-Ethoxy-4-hydroxyphenyl)-1-[4-(morpholin-4-yl)phenyl]prop-2-en-1-one; 72079162: 3-(4-Hydroxy-3-methoxyphenyl)-1-[4-(morpholin-4-yl)phenyl]prop-2-en-1-one; 72079485: 3-(3-Ethoxy-4-hydroxyphenyl)-1-(4-methoxyphenyl)prop-2-en-1-one; 72079530: 1-(4-Fluoro-phenyl)-3-(3-hydroxyphenyl)prop-2-en-1-one; 72079537: 1-(4-Fluorophenyl)-3-(3-hydroxy-4-methoxyphenyl)prop-2-en-1-one; 72079658: 3-(3-Hydroxy-4-methoxyphenyl)-1-[2-(trifluoro-methyl)phenyl]prop-2-en-1-one; 72079679: 4-[3-(3-Hydroxy-4-methoxyphenyl)prop-2-enoyl]benzonitrile; 72079687: 4-[3-(4-Hydroxy-3-methoxyphenyl)prop-2-enoyl]benzonitrile; 72079706: 4-[3-(2-Chlorophenyl)-3-oxoprop-1-en-1-yl]benzoic acid; 72079716: 3-(3-Hydroxy-4-methoxyphenyl)-1-(4-nitrophenyl)prop-2-en-1-one; 72079718: 3-[4-(Difluoromethoxy)-3-ethoxyphenyl]-1-(4-hydroxyphenyl)prop-2-en-1-one; 72079719: 3-[3-(Difluoro-methoxy)-4-methoxyphenyl]-1-(4-hydroxyphenyl)prop-2-en-1-one; 72079723: 2-2-Ethoxy-4-[3-(4-hydroxyphenyl)-3-oxoprop-1-en-1-yl]phenoxy-N,N-dimethylacetamide; 72079724: 3-(3-Bromo-4-fluorophenyl)-1-(4-hydroxyphenyl)prop-2-en-1-one; 72079729: 1-(4-Chloro-phenyl)-3-(3-ethoxy-4-hydroxyphenyl)prop-2-en-1-one; 72079734: 3-(4-Hydroxy-3-methoxy-phenyl)-1-(4-nitro-phenyl)prop-2-en-1-one; 72079737: 1-(4-Hydroxyphenyl)-3-(6-methoxy-naphthalen-2-yl)prop-2-en-1-one; 72079738: 3-3-Ethoxy-4-[(6-nitro-2,4-dihydro-1,3-benzodioxin-8-yl)methoxy]phenyl-1-(4-hydroxyphenyl)prop-2-en-1-one; 72079740: 1-(4-Hydroxyphenyl)-3-[4-(4-methoxyphenoxy)-3-nitro-phenyl]prop-2-en-1-one; 72079743: 3-(3-Ethoxy-4-methoxyphenyl)-1-(4-hydroxyphenyl)prop-2-en-1-one; 72079747: 3-(3-Hydroxy-4-methoxyphenyl)-1-(4-hydroxyphenyl)prop-2-en-1-one; 72079752: 1-(4-Hydroxyphenyl)-3-3-[3-(4-hydroxyphenyl)-3-oxoprop-1-en-1-yl]phenylprop-2-en-1-one; 72079753: N-4-[3-(4-Hydroxyphenyl)-3-oxoprop-1-en-1-yl]phenylacetamide; 72079796: 3-(3-Hydroxy-4-methoxy-phenyl)-1-(4-methylphenyl)prop-2-en-1-one; 72079850: 1-4-[3-(3-Ethoxy-4-methoxy-phenyl)prop-2-enoyl]benzenesulfonylpiperidine-4-carboxylic acid; 72079852: 1-4-[3-(4-Ethylphenyl)prop-2-enoyl]benzenesulfonylpiperidine-4-carboxylic acid; 72079893: 4-4-[3-(3-Hydroxyphenyl)prop-2-enoyl]benzenesulfonamidobenzoic acid; 72079912: 4-4-[3-(3-Methylphenyl)prop-2-enoyl]benzenesulfonamidobutanoic acid; 72079914: 3-4-[3-(3-Ethoxy-4-methoxyphenyl)prop-2-enoyl]benzenesulfonamidopropanoic acid; 72079915: 3-(4-3-[4-(Propan-2-yl)phenyl]prop-2-enoylbenzenesulfonamido)propanoic acid; 72079917: 3-4-[3-(4-Nitrophenyl)prop-2-enoyl]benzenesulfonamidopropanoic acid; 72079918: 3-4-[3-(3-Nitrophenyl)prop-2-enoyl]benzenesulfonamidopropanoic acid; 72080023: 2-(4-3-[4-(Dimethyl-amino)phenyl]-3-oxoprop-1-en-1-yl-2-methoxyphenoxy)acetic acid; 72080035: 1-[4-(Dimethylamino)phenyl]-3-(3-ethoxy-4-hydroxyphenyl)

prop-2-en-1-one; 72080036: 1-[4-(Dimethylamino)phenyl]-3-(3-hydroxyphenyl)prop-2-en-1-one; 72080040: 1-[4-(Dimethyl-amino)phenyl]-3-(4-hydroxy-3-methoxyphenyl)prop-2-en-1-one; 72080102: 4-3-[4-(Azepan-1-yl)phenyl]-3-oxoprop-1-en-1-ylbenzoic acid; 72080175: 2-(4-3-[4-(Methylsulfanyl)phenyl]prop-2-enoylphenoxy)propanoic acid; 72080177: 2-4-[3-(3-Hydroxyphenyl)prop-2-enoyl]phenoxypropanoic acid; 72080178: 2-4-[3-(3-Chlorophenyl)prop-2-enoyl]phenoxypropanoic acid; 72080179: 2-4-[3-(4-Methoxyphenyl)prop-2-enoyl]phenoxypropanoic acid; 72080181: 2-4-[3-(3-Bromophenyl)prop-2-enoyl]phenoxypropanoic acid; 72080184: 2-4-[3-(4-Nitro-phenyl)prop-2-enoyl]phenoxypropanoic acid; 72080201: 2-(4-3-[4-(Methylamino)-3-nitro-phenyl]prop-2-enoylphenoxy)propanoic acid; 72080380: 2-4-[3-(3-Hydroxy-4-methoxyphenyl)prop-2-enoyl]phenoxy-N,N-dimethylacetamide; 72080393: 3-(3-Hydroxy-4-methoxy-phenyl)-1-[4-(2-methylpropoxy)phenyl]prop-2-en-1-one; 72080406: 1-(2,4-Difluorophenyl)-3-(3-hydroxy-4-methoxyphenyl)prop-2-en-1-one; 72080420: 4-[3-(3-Hydroxyphenyl)prop-2-enoyl]-N-(4-methoxyphenyl)benzene-1-sulfonamide; 72080421: 4-[3-(4-Hydroxyphenyl) prop-2-enoyl]-N-(4-methoxyphenyl)benzene-1-sulfonamide; 72080457: 2-4-[3-(3-Hydroxyphenyl)prop-2-enoyl]phenoxy-N-phenylacetamide; 72080462: 3-(3-Hydroxy-4-methoxyphenyl)-1-4-[2-(morpholin-4-yl)-2-oxoethoxy]phenylprop-2-en-1-one; 72080469: 3-(4-Hydroxyphenyl)-1-4-[2-(morpholin-4-yl)-2-oxoethoxy]phenylprop-2-en-1-one; 72129183: 3-(3-Hydroxy-4-methoxyphenyl)-1-[4-(1H-imidazol-1-yl)phenyl]prop-2-en-1-one; 72138476: 2-4-[3-(2,4-Dichlorophenyl)-3-oxoprop-1-en-1-yl]-2-nitrophenoxyacetic acid; 72140607: 4-[3-(2-Fluoro-4-hydroxyphenyl)-3-oxoprop-1-en-1-yl]benzonitrile; 72142481: 2-[3-[1,3-Dioxo-2-[4-(3-oxo-3-phenylprop-1-enyl)phenyl]isoindol-5-yl]oxyphenyl]-1,3-dioxoisoindole-5-carboxylic acid; 72144048: 4-[1,3,5,7-Tetraoxo-2,6-bis[4-(3-phenylprop-2-enoyl)phenyl]pyrrolo[3,4-f]isoindole-8-carbonyl]benzoic acid; 72160908: 3-[4-(Difluoromethoxy)phenyl]-1-(2-hydroxyphenyl)prop-2-en-1-one; 72160947: 4-[3-(4-Iodophenyl)-3-oxoprop-1-enyl]benzoic acid; 72162305: 1-(4-Chlorophenyl)-3-[4-[2-hydroxyethyl(methyl)amino]phenyl]prop-2-en-1-one; 72162834: 3-[3-(1,3-Benzothiazol-2-ylsulfanylmethyl)-4-methoxy-phenyl]-1-(2-hydroxyphenyl)prop-2-en-1-one; 72166725: N-[8-Hydroxy-6-[4-(3-oxo-3-phenylprop-1-enyl)phenyl-4,4a,6,7,8,8a-hexahydropyrano[3,2-d][1,3]dioxin-7-yl]acetamide; 72166726: N-[8-Hydroxy-2-phenyl-6-[4-(3-phenylprop-2-enoyl)phenoxy]-4,4a,6,7,8,8a-hexahydropyrano[3,2-d][1,3]dioxin-7-yl]acetamide; 72166727: N-[4,5-Dihydroxy-6-(hydroxymethyl)-2-[4-(3-phenylprop-2-enoyl)phenoxy]oxan-3-yl]acetamide; 72167118: 3-[4-[2-Hydroxyethyl(methyl)amino]phenyl]-1-phenylprop-2-en-1-one; 72168246: 1-(4-Bromophenyl)-3-[4-(2-hydroxyethoxy)phenyl]prop-2-en-1-one; 72174031: 1-(2-Hydroxyphenyl)-3-[4-methoxy-3-[(4-nitropyrazol-1-yl)methyl]phenyl]prop-2-en-1-one; 72185396: 2-[3-(1,3-Benzodioxol-5-yl)prop-2-enoyl]benzoic acid; 72185397: 2-[3-(4-Carboxyphenyl)prop-2-enoyl]benzoic acid; 72185425: N-[3-Hydroxy-4-[3-(3-methylphenyl) prop-2-enoyl]phenyl]acetamide; 72185427: N-[4-[3-(4-Tert-butylphenyl)prop-2-enoyl]-3-hydroxyphenyl]acetamide; 72185428: N-[3-Hydroxy-4-[3-(4-methylphenyl)prop-2-enoyl]phenyl]acetamide; 72185429: N-[3-Hydroxy-4-(3-phenylprop-2-enoyl)phenyl]acetamide; 72185432: N-[4-[3-(4-Ethoxyphenyl)prop-2-enoyl]-3-hydroxyphenyl] acetamide; 72185433: N-[3-Hydroxy-4-[3-(4-methoxyphenyl)prop-2-enoyl]phenyl]acetamide; 72185451: 3-(3-Fluorophenyl)-1-(2-hydroxy-4-phenylmethoxyphenyl)prop-2-en-1-one; 72185971: N-[4-[3-(4-Fluorophenyl)prop-2-enoyl]-3-hydroxyphenyl]acetamide; 72205031: Methyl 4-[(E)-3-(2-hydroxy-4-methoxyphenyl)-3-oxoprop-1-enyl]benzoate; 72205032: (E)-1-(2-Hydroxy-4-methoxyphenyl)-3-[4-(pyrrolidine-1-carbonyl)phenyl]prop-2-en-1-one; 72205033: (E)-1-(2-Hydroxy-4-methoxyphenyl)-3-[4-(4-methylpiperazine-1-carbonyl)phenyl]prop-2-en-1-one; 72205034: (E)-1-(2-Hydroxy-4-methoxyphenyl)-3-[4-(piperidine-1-carbonyl)phenyl]prop-2-en-1-one; 72205035: (E)-1-(2-Hydroxy-4-methoxyphenyl)-3-[4-(morpholine-4-carbonyl)phenyl]prop-2-en-1-one; 72205211: 4-[(E)-3-(2-Hydroxy-4-methoxyphenyl)-3-oxoprop-1-enyl]-N-propylbenzamide; 72205212: N-Dodecyl-4-[(E)-3-(2-hydroxy-4-methoxyphenyl)-3-oxoprop-1-enyl]benzamide; 72205213: 4-[(E)-3-(2-Hydroxy-4-methoxyphenyl)-3-oxoprop-1-enyl]-N-(2-phenylethyl)benzamide; 72205214: N-Benzyl-4-[(E)-3-(2-hydroxy-4-methoxy-phenyl)-3-oxoprop-1-enyl]benzamide; 72205215: 4-[(E)-3-(2-Hydroxy-4-methoxyphenyl)-3-oxoprop-1-enyl]-N-methyl-N-phenyl-benzamide; 72205216: N-(2,4-Dimethylphenyl)-4-[(E)-3-(2-hydroxy-4-methoxyphenyl)-3-oxoprop-1-enyl]benzamide; 72205404: 4-[(E)-3-(2-Hydroxy-4-methoxyphenyl)-3-oxoprop-1-enyl]-N-propan-2-ylbenzamide; 72205405: 4-[(E)-3-(2-Hydroxy-4-methoxyphenyl)-3-oxoprop-1-enyl]-N-(2-methoxyphenyl)benzamide; 72205406: 4-[(E)-3-(2-Hydroxy-4-methoxyphenyl)-3-oxoprop-1-enyl]-N-(2-hydroxyphenyl)benzamide; 72205407: 4-[(E)-3-(2-Hydroxy-4-methoxyphenyl)-3-oxoprop-1-enyl]-N-(2-hydroxy-5-nitro-phenyl)benzamide; 72205408: (E)-3-[4-(3-Ethoxypropoxy)-3-methoxyphenyl]-1-(2-hydroxy-4-methoxyphenyl)prop-2-en-1-one; 72205409: (E)-1-(2-Hydroxy-4-methoxyphenyl)-3-[3-methoxy-4-(3-phenoxypropoxy)phenyl]prop-2-en-1-one; 72205410: (E)-3-[3-(2-Ethoxyethoxy)phenyl]-1-(2-hydroxy-4-methoxyphenyl)prop-2-en-1-one; 72205594: (E)-3-[4-(2-Ethoxyethoxy)phenyl]-1-(2-hydroxy-4-methoxyphenyl)prop-2-en-1-one; 72240807: [4-[3-(3,4-Dihydroxyphenyl)prop-2-enoyl]phenyl] 3-fluorobenzenesulfonate; 72296426: 1-(2,6-Dihydroxy-4-methoxyphenyl)-3-(3,4-dimethoxyphenyl)prop-2-en-1-one; 72305591: 3-(4-Hydroxy-3-methoxyphenyl)-1-[4-[3-(4-hydroxy-3-methoxyphenyl)prop-2-enoyl]phenyl]prop-2-en-1-one; 72327089: 3-(3,4-Dimethoxyphenyl)-1-(4-hydroxy-2-methoxyphenyl)prop-2-en-1-one; 72439017: 4-Hydroxy-3-methylchalkon; 72480195: 1-[2-[5-Fluoro-3,4-dihydroxy-6-(hydroxymethyl)oxan-2-yl]oxy-6-hydroxy-4-methylphenyl]-3-(4-methoxyphenyl)prop-2-en-1-one; 72532840: 4-Phenyl-2-[4-(3-phenylprop-2-enoyl)phenoxy]butanoic acid; 72532841: 2-[2-[3-(4-Bromophenyl)prop-2-enoyl]phenoxy]-4-[4-(4-chlorophenyl)phenyl]butanoic acid; 72532842: 4-[4-(4-Chlorophenyl)phenyl]-2-[4-(3-phenylprop-2-enoyl)phenoxy]butanoic acid; 72532845: 2-[2-[3-(4-Bromophenyl)prop-2-enoyl]phenoxy]-4-phenylbutanoic acid; 72532846: 2-[4-(3-Oxo-3-phenylprop-1-enyl)phenoxy]-4-phenylbutanoic acid; 72532847: 4-Phenyl-2-[2-(3-phenylprop-2-enoyl)phenoxy]butanoic acid; 72532854: 2-[2-[3-[4-(4-Bromophenyl)phenyl]prop-2-enoyl]phenoxy]-4-phenylbutanoic acid; 72532860: 4-[4-(4-Chlorophenyl)phenyl]-2-[4-(3-oxo-3-phenylprop-1-enyl)phenoxy]butanoic acid; 72544471: (E)-3-[4-(2-Hydroxyethoxy)-3-methoxyphenyl]-1-[4-(4-methylpiperazin-1-yl)phenyl]prop-2-en-1-one; 72550683: (E)-1-[2-Hydroxy-4,6-bis(prop-2-enoxy)phenyl]-3-(4-prop-2-enoxy-phenyl)prop-2-en-1-one; 72550684: (E)-1-(2,6-Dihydroxy-4-prop-2-enoxyphenyl)-3-(4-prop-2-enoxyphenyl)prop-2-en-1-one; 72684486: N-[4-[3-(3-Chloro-4-hydroxyphenyl)prop-2-enoyl]phenyl]methanesulfonamide; 72684490: N-[4-[3-(3-

Bromo-4-hydroxyphenyl)prop-2-enoyl]phenyl]methanesulfonamide; 72686931: N-[4-[3-(3-Chloro-4-hydroxyphenyl)prop-2-enoyl]phenyl]ethanesulfonamide; 72688372: 1-[4-(4-Hydroxypiperidin-1-yl)phenyl]-3-naphthalen-2-ylprop-2-en-1-one; 72688377: 3-(3-Chlorophenyl)-1-[4-(4-hydroxypiperidin-1-yl)phenyl]prop-2-en-1-one; 72688383: 3-(3-Ethoxyphenyl)-1-[4-(4-hydroxypiperidin-1-yl)phenyl]prop-2-en-1-one; 72688384: 1-[4-(4-Hydroxypiperidin-1-yl)phenyl]-3-(3-methoxy-4-methylsulfanylphenyl)prop-2-en-1-one; 72688390: 3-(3-Bromo-4-fluorophenyl)-1-[4-(4-hydroxypiperidin-1-yl)phenyl]prop-2-en-1-one; 72688391: 1-[4-(4-Hydroxypiperidin-1-yl)phenyl]-3-(3-methoxy-4-propoxyphenyl)prop-2-en-1-one; 72688397: N-[4-[3-[4-(4-Hydroxypiperidin-1-yl)phenyl]-3-oxoprop-1-enyl]phenyl]acetamide; 72688403: 3-(3,4-Dichlorophenyl)-1-[4-(4-hydroxypiperidin-1-yl)phenyl]prop-2-en-1-one; 72688404: 1-[4-(4-Hydroxypiperidin-1-yl)phenyl]-3-(4-methoxy-3-phenylmethoxyphenyl)prop-2-en-1-one; 72688407: 1-[4-(4-Hydroxypiperidin-1-yl)phenyl]-3-[4-(trifluoromethylsulfanyl)phenyl]prop-2-en-1-one; 72688408: 1-[4-(4-Hydroxypiperidin-1-yl)phenyl]-3-[4-(trifluoromethyl)phenyl]prop-2-en-1-one; 72688410: 1-[4-(4-Hydroxypiperidin-1-yl)phenyl]-3-(4-propan-2-yloxyphenyl)prop-2-en-1-one; 72688411: 1-[4-(4-Hydroxypiperidin-1-yl)phenyl]-3-(4-nitro-phenyl)prop-2-en-1-one; 72688413: 3-(3-Bromophenyl)-1-[4-(4-hydroxypiperidin-1-yl)phenyl]prop-2-en-1-one; 72688425: 3-(3-Ethoxy-4-methoxyphenyl)-1-[4-(4-hydroxy-piperidin-1-yl)phenyl]prop-2-en-1-one; 72688429: 1-[4-(4-Hydroxypiperidin-1-yl)phenyl]-3-phenylprop-2-en-1-one; 72688434: 3-(4-Fluorophenyl)-1-[4-(4-hydroxypiperidin-1-yl)phenyl]prop-2-en-1-one; 72688442: 1-[4-(4-Hydroxypiperidin-1-yl)phenyl]-3-(3-methoxy-4-phenylmethoxyphenyl)prop-2-en-1-one; 72688443: 3-(4-Ethoxyphenyl)-1-[4-(4-hydroxypiperidin-1-yl)phenyl]prop-2-en-1-one; 72688449: 3-(3-Hydroxyphenyl)-1-[4-(4-hydroxypiperidin-1-yl)phenyl]prop-2-en-1-one; 72688450: 1-[4-(4-Hydroxypiperidin-1-yl)phenyl]-3-(4-phenylmethoxyphenyl)prop-2-en-1-one; 72692942: 3-[4-(Diethylamino)phenyl]-1-[4-(4-hydroxypiperidin-1-yl)phenyl]prop-2-en-1-one; 72692945: 3-(4-Tert-butylphenyl)-1-[4-(4-hydroxypiperidin-1-yl)phenyl]prop-2-en-1-one; 72692946: 1-[4-(4-Hydroxypiperidin-1-yl)phenyl]-3-[3-methoxy-4-(3-methylbutoxy)phenyl]prop-2-en-1-one; 72692949: 1-[4-(4-Hydroxypiperidin-1-yl)phenyl]-3-(4-pentoxyphenyl)prop-2-en-1-one; 72692950: 3-(4-Butoxy-3-methoxyphenyl)-1-[4-(4-hydroxypiperidin-1-yl)phenyl]prop-2-en-1-one; 72692951: 1-[4-(4-Hydroxypiperidin-1-yl)phenyl]-3-(4-methyl-3-nitro-phenyl)prop-2-en-1-one; 72692958: 3-(3-Fluoro-4-methoxyphenyl)-1-[4-(4-hydroxypiperidin-1-yl)phenyl]prop-2-en-1-one; 72692961: 3-(3-Ethoxy-4-propoxyphenyl)-1-[4-(4-hydroxypiperidin-1-yl)phenyl]prop-2-en-1-one; 72692966: 1-[4-(4-Hydroxypiperidin-1-yl)phenyl]-3-[4-(3-methylbutoxy)phenyl]prop-2-en-1-one; 72692979: 1-[4-(4-Hydroxypiperidin-1-yl)phenyl]-3-(4-methoxy-3-methylphenyl)prop-2-en-1-one; 72692980: 3-(3,4-Diethoxyphenyl)-1-[4-(4-hydroxypiperidin-1-yl)phenyl]prop-2-en-1-one; 72692991: 1-[4-(4-Hydroxypiperidin-1-yl)phenyl]-3-[4-[(5-methyl-1,2,4-oxadiazol-3-yl)methoxy]phenyl]prop-2-en-1-one; 72692993: 3-[3-(Difluoromethoxy)-4-methoxyphenyl]-1-[4-(4-hydroxy-piperidin-1-yl)phenyl]prop-2-en-1-one; 72692994: 3-[[3-[3-[4-(4-Hydroxypiperidin-1-yl)phenyl]-3-oxoprop-1-enyl]phenoxy]methyl]benzonitrile; 72692996: N-Ethyl-2-[4-[3-[4-(4-hydroxypiperidin-1-yl)phenyl]-3-oxoprop-1-enyl]phenoxy]acetamide; 72728334: 1-(2,4-Dihydroxyphenyl)-3-[4-[3,4,5-trihydroxy-6-(hydroxymethyl)oxan-2-yl]oxyphenyl]prop-2-en-1-one; 72729461: 1-[4-[3-[3,4-Dihydroxy-4-(hydroxymethyl)oxolan-2-yl]oxy-4,5-dihydroxy-6-(hydroxymethyl)oxan-2-yl]oxy-2-hydroxyphenyl]-3-(4-hydroxyphenyl)prop-2-en-1-one; 72729466: 1-[2,6-Dihydroxy-4-(3-methylbut-2-enoxy)phenyl]-3-phenylprop-2-en-1-one; 72732169: 1-[2-Hydroxy-4-methoxy-6-[3,4,5-trihydroxy-6-(hydroxymethyl)oxan-2-yl]oxyphenyl]-3-(4-hydroxyphenyl)prop-2-en-1-one; 72739470: 1-(4-Chloro-2-hydroxyphenyl)-3-(4-chlorophenyl)prop-2-en-1-one; 72744564: 3-[4-(3-Oxo-3-phenyl-prop-1-enyl)phenyl]prop-2-enoic acid; 72777985: 3-(1-Benzofuran-5-yl)-1-[2-hydroxy-4-methoxy-6-[[3,4,5-trihydroxy-6-(hydroxymethyl)oxan-2-yl]methyl]phenyl]prop-2-en-1-one; 72952592: 2'-Hydroxy-3,4-dichlorochalcone; 73064893: 3-(3,4-Dimethoxyphenyl)-1-(2,4,6-trihydroxyphenyl)prop-2-en-1-one; 73091009: 3-[3,4-Bis(phenylmethoxy)phenyl]-1-[2-hydroxy-4,6-bis(phenylmethoxy)phenyl]prop-2-en-1-one; 73151306: 1-(2-Hydroxy-4,6-dimethoxyphenyl)-3-[3-methoxy-4-(2-phenylethyl)phenyl]prop-2-en-1-one; 73186038: 3-(4-Hydroxyphenyl)-1-(2-hydroxy-6-phenylmethoxyphenyl)prop-2-en-1-one; 73231237: 4-[3-[2-(Cyclohexylmethoxy)-6-hydroxyphenyl]-3-oxoprop-1-enyl]benzenesulfonamide; 73335325: N-[4-[(E)-3-(3,4-Dihydroxyphenyl)prop-2-enoyl]phenyl]-4-methylpentanamide; 73348135: (E)-1-[2-[(2R)-2-Hydroxy-3-piperidin-1-ylpropoxy]phenyl]-3-phenylprop-2-en-1-one; 73349328: N-[4-[(Z)-3-(4-Hydroxy-3-methoxyphenyl)prop-2-enoyl]phenyl]-2-[[5-(3-nitro-phenyl)-1,3,4-oxadiazol-2-yl]sulfanyl]acetamide; 73349439: 7-[4-[2-[4-[(E)-3-(4-Chlorophenyl)prop-2-enoyl]anilino]-2-oxoethyl]piperazin-1-yl]-1-cyclopropyl-6-fluoro-4-oxoquinoline-3-carboxylic acid; 73349441: 1-Cyclopropyl-6-fluoro-7-[4-[2-[4-[(E)-3-(3-nitro-phenyl)prop-2-enoyl]anilino]-2-oxoethyl]piperazin-1-yl]-4-oxoquinoline-3-carboxylic acid; 73352141: 4-[(E)-3-(2-Hydroxy-4-methoxyphenyl)-3-oxoprop-1-enyl]benzoic acid; 73353956: 1-Cyclopropyl-7-[4-[2-[4-[(E)-3-(3,4-dimethoxyphenyl)prop-2-enoyl]anilino]-2-oxoethyl]piperazin-1-yl]-6-fluoro-4-oxoquinoline-3-carboxylic acid; 73355381: N-[4-[(Z)-3-(4-Hydroxyphenyl)prop-2-enoyl]phenyl]-2-[[5-(3-nitro-phenyl)-1,3,4-oxadiazol-2-yl]sulfanyl]acetamide; 73355494: 7-[4-[2-[4-[(E)-3-(3-Chlorophenyl)prop-2-enoyl]anilino]-2-oxoethyl]piperazin-1-yl]-1-cyclopropyl-6-fluoro-4-oxoquinoline-3-carboxylic acid; 73355495: 1-Cyclopropyl-6-fluoro-7-[4-[2-[4-[(E)-3-(4-methoxyphenyl)prop-2-enoyl]anilino]-2-oxoethyl]piperazin-1-yl]-4-oxoquinoline-3-carboxylic acid; 73357038: 1-Cyclopropyl-6-fluoro-4-oxo-7-[4-[2-oxo-2-[4-[(E)-3-phenylprop-2-enoyl]anilino]ethyl]piperazin-1-yl]quinoline-3-carboxylic acid; 73357039: 7-[4-[2-[4-[(E)-3-(1,3-Benzodioxol-5-yl)prop-2-enoyl]anilino]-2-oxoethyl]piperazin-1-yl]-1-cyclopropyl-6-fluoro-4-oxoquinoline-3-carboxylic acid; 73426319: (E)-1-(4-Chlorophenyl)-3-[4-[4-(2-hydroxyethyl)piperazin-1-yl]phenyl]prop-2-en-1-one; 73426320: (E)-1-(4-Bromophenyl)-3-[4-[4-(2-hydroxyethyl)piperazin-1-yl]phenyl]prop-2-en-1-one; 73454085: 1-(4-Hydroxyphenyl)-3-[4-(2,2,3,3,3-pentafluoropropoxy)phenyl]prop-2-en-1-one; 73612569: 1-(2,4-Dihydroxyphenyl)-3-(4-phenylmethoxyphenyl)prop-2-en-1-one; 73652937: 5-[[2-[3-(3,4-Dihydroxyphenyl)prop-2-enoyl]phenyl]methyl]-1,3-thiazolidine-2,4-dione; 73693177: 2-Hydroxy-2-methyl-1-[4-[[2-oxo-2-[4-(3-oxo-3-phenyl-prop-1-enyl)phenyl]ethoxy]methoxy]phenyl]propan-1-one; 73693419: 2-[4-(2-Hydroxy-2-methylpropanoyl)phenoxy]ethyl 4-[3-(4-acetylphenyl)-3-oxoprop-1-enyl]benzoate; 73693979: 4-(2-Cyano-2-methylpropyl)-2-[2-[4-[3-[4-(dimethylamino)phenyl]prop-2-enoyl]phenyl]butyl]-N-(hydroxymethyl)-N'-(methoxymethyl) pentanediamide; 73693991: Butyl 6-[[4-[3-(3,4-dimethoxyphenyl)prop-2-enoyl]phenyl]-hydroperoxymethyl]-4-(hydroxymethylcarbamoyl)-2,2,6-trimethyloctanoate; 73703415: 1-[4-(Dimethylamino)phenyl]-3-[4-(2-hydroxyethoxy)phenyl]prop-2-en-1-one; 73705014: 4-[4-(3-Oxo-3-phenylprop-1-enyl)phenoxy]benzoic acid; 73710478: 3-[4-(6-Hydroxyhexoxy)phenyl]-1-[4-(1,1,2,2,3,3,4,4,5,5,6,6,6-tridecafluorohexyl)phenyl]prop-2-en-1-one; 73772601: 3-(1-Benzofuran-5-yl)-1-[2-hydroxy-4-methyl-6-[[3,4,5-trihydroxy-6-(hydroxymethyl)oxan-2-yl]methyl]phenyl]prop-2-en-1-one; 73772602: 3-(1-Benzofuran-5-yl)-1-[2-methoxy-4-methyl-6-[[3,4,5-trihydroxy-6-(hydroxymethyl)oxan-2-yl]methyl]phenyl]prop-2-en-1-one; 73857738: 2-[[4-[3-(4-Thiophen-2-ylphenyl)prop-2-enoyl]phenyl]carbamoylamino]acetic acid; 73897405: (E)-1-(2,4-Dihydroxyphenyl)-3-[6-(dimethylamino)naphthalen-2-yl]prop-2-en-1-one; 73897406: (E)-3-(6-Chloronaphthalen-2-yl)-1-(2,4-dihydroxyphenyl)prop-2-en-1-one; 73981690: 3-(4-Hydroxyphenyl)-1-[2-hydroxy-4-[3,4,5-trihydroxy-6-(hydroxymethyl)oxan-2-yl]oxyphenyl]prop-2-en-1-one; 74011493: 3-[4-(Hydroperoxymethyl)phenyl]-1-(4-hydroxy-phenyl)prop-2-en-1-one; 74259754: 1-[4-[4,5-Dihydroxy-6-(hydroxymethyl)-3-(3,4,5-trihydroxy-6-methyloxan-2-yl)oxyoxan-2-yl]oxy-2,6-dihydroxyphenyl]-3-(4-methoxyphenyl) prop-2-en-1-one; 74277265: 2-[4-[3-(4-Ethoxyphenyl)-3-oxoprop-1-enyl]phenoxy]acetic acid; 74326142: 3-(4-Tert-butylphenyl)-1-(2-hydroxyphenyl)prop-2-en-1-one; 74350153: 3-(4-Chlorophenyl)-1-[4-(2-hydroxyethoxy)phenyl]prop-2-en-1-one; 74380226: [4-[3-(4-Hydroxyphenyl)prop-2-enoyl]phenyl] 4-hydroxybenzenesulfonate; 74380290: [4-[3-(3-Hydroxyphenyl)prop-2-enoyl]phenyl] 4-hydroxybenzenesulfonate; 74380291: [4-[3-(4-Hydroxyphenyl)prop-2-enoyl]phenyl] 3-hydroxybenzenesulfonate; 74380292: [4-[3-(3-Hydroxyphenyl)prop-2-enoyl]phenyl] 3-hydroxybenzenesulfonate; 74380294: [4-[3-(3,4-Dihydroxyphenyl)prop-2-enoyl]phenyl] 4-hydroxybenzenesulfonate; 74380362: [4-[3-(3,4-Dihydroxyphenyl)prop-2-enoyl]phenyl] 3-hydroxybenzenesulfonate; 74381096: [4-[3-(4-Hydroxyphenyl)prop-2-enoyl]phenyl] 4-methylbenzenesulfonate; 74381213: [4-[3-(4-Hydroxyphenyl)prop-2-enoyl]phenyl] 4-fluorobenzenesulfonate; 74381214: [4-[3-(4-Hydroxyphenyl)prop-2-enoyl]phenyl] 3-fluorobenzenesulfonate; 74381215: [4-[3-(4-Hydroxyphenyl)prop-2-enoyl]phenyl] 4-nitrobenzenesulfonate; 74381216: [4-[3-(4-Hydroxyphenyl)prop-2-enoyl]phenyl] 4-aminobenzenesulfonate; 74381217: [4-[3-(4-Hydroxyphenyl)prop-2-enoyl]phenyl] benzenesulfonate; 74381218: [4-[3-(4-Hydroxyphenyl)prop-2-enoyl]phenyl] methanesulfonate; 74426869: 1-(2-Hydroxyphenyl)-3-naphthalen-2-ylprop-2-en-1-one; 74601409: 3-(3,4-Dimethoxyphenyl)-1-(2-hydroxy-6-methoxy-4-phenylmethoxyphenyl)prop-2-en-1-one; 74763083: (Z)-3-[4-[2-Hydroxyethyl (methyl)amino]phenyl]-1-(2,4,6-trimethoxyphenyl)prop-2-en-1-one; 74767537: 2',4'-Dihydroxy-6'-methoxy-beta-(3,4-dimethoxyphenyl) acrylophenone; 74767538: (E)-3-(3,4-Dimethoxyphenyl)-1-(4-hydroxy-2,6-dimethoxyphenyl)prop-2-en-1-one; 74835081: 2',4'-Dihydroxy-6'-isopentyloxychalcone; 75026050: 3-(3,4-Dihydroxyphenyl)-1-(2-hydroxy-4,6-dimethoxyphenyl)prop-2-en-1-one; 75210605: [4-[3-(2,4-Dibenzoyloxy-6-hydroxyphenyl)-3-oxoprop-1-enyl]phenyl] benzoate; 75210935: 3-Methyl-2'-hydroxychalcone; 75268514: 1-(4-Bromophenyl)-3-(3-chloro-4-hydroxyphenyl)prop-2-en-1-one; 75268515: 3-(3-Chloro-4-hydroxyphenyl)-1-phenylprop-2-en-1-one; 75268519: 3-(3-Chloro-4-hydroxyphenyl)-1-(4-hydroxyphenyl)prop-2-en-1-one; 75268522: 3-(3-Chloro-4-hydroxyphenyl)-1-(4-chloro-phenyl)prop-2-en-1-one; 75268524: 4-[3-(3-Chloro-4-hydroxyphenyl)prop-2-enoyl]benzonitrile; 75268531: 3-(3-Chloro-4-hydroxyphenyl)-1-(4-fluorophenyl)prop-2-en-1-one; 75268537: 3-(3-Chloro-4-hydroxyphenyl)-1-(4-methoxyphenyl)prop-2-en-1-one; 75268559: 3-(3-Chloro-4-hydroxyphenyl)-1-(4-iodophenyl)prop-2-en-1-one; 75268565: 3-(3-Chloro-4-hydroxyphenyl)-1-(4-methylsulfanylphenyl)prop-2-en-1-one; 75363509: (E)-1-(4-Hydroxy-phenyl)-3-[4-[(1-methylimidazol-2-yl)methoxy]phenyl]prop-2-en-1-one; 75366137: (E)-3-(3,4-Dimethoxyphenyl)-1-(2-hydroxy-4,6-dimethylphenyl)prop-2-en-1-one; 75379083: 2-[(E)-3-[3-[(2,2,2-Trifluoroacetyl)amino]phenyl]prop-2-enoyl]benzoic acid; 75401618: 4-[(E)-3-(2-Bromo-4-methoxyphenyl)-3-oxoprop-1-enyl]benzoic acid; 75405423: 4-[(E)-3-Oxo-3-[4-(2-oxo-1,3-oxazolidin-3-yl)phenyl]prop-1-enyl]benzoic acid; 75427335: 4-[(E)-3-(2-Bromo-4-fluorophenyl)-3-oxoprop-1-enyl]benzoic acid; 75427336: 3-[3-[(E)-3-(2-Bromo-4-fluoro-phenyl)-3-oxoprop-1-enyl]phenoxy]propanoic acid; 75454899: 3-[2-Methoxy-4-[(E)-3-[4-(2-methoxyethoxy)phenyl]-3-oxoprop-1-enyl]phenoxy]propanoic acid; 75458109: 3-[(E)-3-(4-Methoxyphenyl)-3-oxoprop-1-enyl]benzoic acid; 75458975: 2-[4-[(E)-3-[4-[(2,4-Dichloro-phenyl)methoxy]-3-methoxyphenyl]prop-2-enoyl]phenoxy]propanoic acid; 75459133: 2-[4-[(E)-3-(3-Hydroxy-4-methoxyphenyl)prop-2-enoyl]phenoxy]acetonitrile; 75465247: 4-[(E)-3-(2-Hydroxy-4-methylphenyl)-3-oxoprop-1-enyl]benzoic acid; 75511194: (E)-1-(2-Hydroxy-4-methoxyphenyl)-3-quinoxalin-6-ylprop-2-en-1-one; 75533146: 2-[4-[(E)-3-(2,4-Dichloro-phenyl)-3-oxoprop-1-enyl]-2-nitrophenoxy]acetic acid; 75535428: 2-[4-[(E)-3-(2,4-Difluoro-phenyl)-3-oxoprop-1-enyl]-2-nitrophenoxy]acetic acid; 75535430: 2-[4-[(E)-3-(4-Fluoro-2-methylphenyl)-3-oxoprop-1-enyl]-2-nitrophenoxy]acetic acid; 75539265: (2E)-3-(3-Chloro-4-fluorophenyl)-1-(2-hydroxyphenyl)prop-2-en-1-one; 75693187: 3-(3-Bromo-4-hydroxy-phenyl)-1-[4-(2-methoxyethoxy)phenyl]prop-2-en-1-one; 75849654: 2-[4-[3-(3-Bromo-4-hydroxyphenyl)prop-2-enoyl]phenoxy]-N,N-dimethylacetamide; 75921656: 3-(3-Chloro-4-hydroxyphenyl)-1-(2,4-dimethoxyphenyl)prop-2-en-1-one; 75921658: 3-(3-Chloro-4-hydroxyphenyl)-1-(4-nitro-phenyl)prop-2-en-1-one; 75921710: 3-(3-Chloro-4-hydroxyphenyl)-1-(4-ethoxyphenyl)prop-2-en-1-one; 75921712: 4-[3-(3-Chloro-4-hydroxyphenyl)prop-2-enoyl]-N,N-dimethylbenzenesulfonamide; 75921713: 4-[3-(3-Chloro-4-hydroxyphenyl)prop-2-enoyl]-N,N-diethylbenzenesulfonamide; 75921719: 3-(3-Chloro-4-hydroxyphenyl)-1-(4-piperidin-1-ylphenyl)prop-2-en-1-one; 75921743: 2-[4-[3-(3-Chloro-4-hydroxyphenyl)prop-2-enoyl]phenoxy]-N,N-dimethylacetamide; 75921745: 3-(3-Chloro-4-hydroxyphenyl)-1-[4-(dimethylamino)phenyl]prop-2-en-1-one; 75921746: 3-(3-Chloro-4-hydroxyphenyl)-1-(4-propan-2-yloxyphenyl)prop-2-en-1-one; 75921756: 1-[4-[3-(3-Chloro-4-hydroxyphenyl)prop-2-enoyl]phenyl] pyrrolidin-2-one; 75921785: 3-(3-Chloro-4-hydroxyphenyl)-1-[4-(trifluoro-methyl)phenyl]prop-2-en-1-one; 75921786: 3-(3-Chloro-4-hydroxyphenyl)-1-[4-(trifluoromethoxy)phenyl]prop-2-en-1-one; 75941314: 3-[3-[3-(4-Bromophenyl)-3-oxoprop-1-enyl]phenoxy]propanoic acid; 75941318: 3-[3-(3-Oxo-3-phenylprop-1-enyl)phenoxy]propanoic acid; 75941338: 3-[3-[3-(4-Nitrophenyl)-3-oxoprop-1-enyl]phenoxy]propanoic acid; 75941342: 3-[3-[3-(4-Chlorophenyl)-3-oxoprop-1-enyl]phenoxy]propanoic acid; 75941372: 3-[3-[3-Oxo-3-(4-phenylphenyl)prop-1-enyl]phenoxy]propanoic acid; 75941383: 3-[3-[3-(4-Fluorophenyl)-3-oxoprop-1-enyl]phenoxy]propanoic acid;

75941401: 3-[3-[3-(4-Methoxyphenyl)-3-oxoprop-1-enyl]phenoxy]propanoic acid; 75941476: 3-[3-[3-(4-Tert-butylphenyl)-3-oxoprop-1-enyl]phenoxy]propanoic acid; 76010446: N-[4-[3-(3,4-Dihydroxy-phenyl)prop-2-enoyl]phenyl]-2-thiophen-2-ylacetamide; 76187516: 3-[3-Hydroxy-4-(piperidin-1-ylmethyl)phenyl]-1-(4-methoxyphenyl)prop-2-en-1-one; 76187611: 3-[4-[(Dimethylamino)methyl]-3-hydroxyphenyl]-1-(4-methoxyphenyl)prop-2-en-1-one; 76187662: 1-(4-Fluorophenyl)-3-[3-hydroxy-4-[1-(hydroxyamino)ethyl]phenyl]prop-2-en-1-one; 76306720: Methyl 2-[4-[3-(3-bromo-4-hydroxyphenyl)prop-2-enoyl]phenoxy]acetate; 76309469: (E)-3-[3,4-Bis(3-methylbut-2-enoxy)phenyl]-1-[2-hydroxy-6-(3-methylbut-2-enoxy)-4-(2-methylprop-1-enoxy)phenyl]prop-2-en-1-one; 76309470: (E)-3-[4-(Dimethyl-amino)phenyl]-1-[2-hydroxy-6-(3-methylbut-2-enoxy)-4-(2-methylprop-1-enoxy)phenyl]prop-2-en-1-one; 76309471: (E)-3-(4-Bromophenyl)-1-[2-hydroxy-6-(3-methylbut-2-enoxy)-4-(2-methylprop-1-enoxy)phenyl]prop-2-en-1-one; 76309472: (E)-3-(4-Fluorophenyl)-1-[2-hydroxy-6-(3-methylbut-2-enoxy)-4-(2-methylprop-1-enoxy)phenyl]prop-2-en-1-one; 76313247: 2-(1H-Benzimidazol-2-ylsulfanyl)-N-[4-[(E)-3-(4-hydroxy-3-methoxyphenyl)prop-2-enoyl]phenyl]acetamide; 76315186: (E)-3-(4-Methylphenyl)-1-(2,4,6-trihydroxyphenyl) prop-2-en-1-one; 76318835: (E)-3-(3-Chlorophenyl)-1-(2,4,6-trihydroxyphenyl)prop-2-en-1-one; 76322491: (E)-3-(3,4-Dimethylphenyl)-1-(2,4,6-trihydroxyphenyl)prop-2-en-1-one; 76324029: (E)-1-[2-Hydroxy-6-(3-methylbut-2-enoxy)-4-(2-methylprop-1-enoxy)phenyl]-3-(3-nitro-phenyl)prop-2-en-1-one; 76324030: (E)-3-(4-Chlorophenyl)-1-[2-hydroxy-6-(3-methylbut-2-enoxy)-4-(2-methylprop-1-enoxy)phenyl]prop-2-en-1-one; 76324031: (E)-1-[2-Hydroxy-6-(3-methylbut-2-enoxy)-4-(2-methylprop-1-enoxy)phenyl]-3-phenylprop-2-en-1-one; 76327582: (E)-1-[2-Hydroxy-6-(3-methylbut-2-enoxy)-4-(2-methylprop-1-enoxy)phenyl]-3-(4-methoxyphenyl)prop-2-en-1-one; 76333354: (E)-3-(3-Fluorophenyl)-1-(2,4,6-trihydroxyphenyl)prop-2-en-1-one; 76334838: (E)-1-[2-Hydroxy-6-(3-methylbut-2-enoxy)-4-(2-methylprop-1-enoxy)phenyl]-3-[4-(3-methylbut-2-enoxy)phenyl]prop-2-en-1-one; 76334839: (E)-3-(4-Hydroxy-3-methoxyphenyl)-1-[2-hydroxy-6-(3-methylbut-2-enoxy)-4-(2-methylprop-1-enoxy)phenyl]prop-2-en-1-one; 76334840: (E)-1-[2-Hydroxy-6-(3-methylbut-2-enoxy)-4-(2-methylprop-1-enoxy)phenyl]-3-(4-methylphenyl)prop-2-en-1-one; 76334957: 2-(1H-Benzimidazol-2-ylsulfanyl)-N-[4-[(E)-3-(4-hydroxyphenyl)prop-2-enoyl]phenyl]acetamide; 76336275: [(3R,4S,5R)-5-[(2S,3R,4S,5S,6R)-2-[4-[(E)-3-(2,4-Dihydroxyphenyl)-3-oxoprop-1-enyl]phenoxy]-4,5-dihydroxy-6-(hydroxymethyl)oxan-3-yl]oxy-3,4-dihydroxy-oxolan-3-yl]methyl (E)-3-(4-hydroxyphenyl)prop-2-enoate; 76362908: N-[4-[3-(3-Bromo-4-hydroxyphenyl)prop-2-enoyl]phenyl]ethanesulfonamide; 76420570: N-[4-[3-[4-[2-Hydroxyethyl(methyl)amino]phenyl]prop-2-enoyl]phenyl]prop-2-enamide; 76537205: 3-(3-Hydroxy-4-methoxyphenyl)-1-[2-hydroxy-4-(3-methylbut-2-enoxy)phenyl]prop-2-en-1-one; 76694922: 4-(Cyclohexen-1-yl)-2-[4-(3-phenylprop-2-enoyl)phenoxy]butanoic acid; 76694927: 2-[4-(3-Phenylprop-2-enoyl)phenoxy]hex-5-enoic acid; 76694929: 4-(Cyclohexen-1-yl)-2-[4-(3-oxo-3-phenylprop-1-enyl)phenoxy]butanoic acid; 76760224: 1-(2-Hydroxyphenyl)-3-[4-(N-phenylanilino)phenyl]prop-2-en-1-one; 76771507: 3-(3-Bromophenyl)-1-(2,4-dihydroxy-6-methoxyphenyl)prop-2-en-1-one; 76771515: 1-(2,4-Dihydroxy-6-methoxyphenyl)-3-(3-fluorophenyl)prop-2-en-1-one; 76844635: 3-(Acetyloxy)-6-[(acetyloxy)methyl]-2-(4-cinnamoylphenoxy)-5-(3,4,5-tri(acetyloxy)-6-[(acetyloxy)methyl]tetrahydro-2h-pyran-2-yloxy)tetrahydro-2h-pyran-4-ylacetate; 76844636: 3-(Acetyloxy)-6-[(acetyloxy)methyl]-2-[4-(3-oxo-3-phenylprop-1-enyl)phenoxy]-5-(3,4,5-tri(acetyloxy)-6-[(acetyloxy)methyl] tetrahydro-2h-pyran-2-yloxy)tetrahydro-2h-pyran-4-ylacetate; 76863159: 3-(3-Bromo-4-hydroxy-phenyl)-1-(2,4-difluorophenyl)prop-2-en-1-one; 76871184: 3-(3-Chloro-4-hydroxyphenyl)-1-[4-(difluoromethoxy)phenyl]prop-2-en-1-one; 76871190: 2-[4-[3-(3-Chloro-4-hydroxy-phenyl)prop-2-enoyl]phenoxy]acetonitrile; 76871223: 3-(3-Chloro-4-hydroxyphenyl)-1-(2,4-difluorophenyl)prop-2-en-1-one; 76871232: 3-(3-Chloro-4-hydroxyphenyl)-1-(4-morpholin-4-ylphenyl)prop-2-en-1-one; 76871270: 4-[4-[3-(3-Chloro-4-hydroxyphenyl)prop-2-enoyl]phenoxy]butanoic acid; 76877655: Methyl 2-[4-[3-(3-chloro-4-hydroxyphenyl)prop-2-enoyl]phenoxy]acetate; 76878052: 3-[3-[3-[4-(Difluoromethoxy)phenyl]-3-oxoprop-1-enyl]phenoxy]propanoic acid; 76972132: (E)-1-[2-[(2S)-2-Hydroxy-3-(propylamino) propoxy]phenyl]-3-phenylprop-2-en-1-one; 76972133: (E)-1-[2-[(2R)-2-Hydroxy-3-(propylamino)propoxy]phenyl]-3-phenylprop-2-en-1-one; 76972134: (E)-1-[2-[(2R)-2-Hydroxy-3-(propylamino)propoxy]phenyl]-3-phenylprop-2-en-1-one;(E)-1-[2-[(2S)-2-hydroxy-3-(propylamino)propoxy]phenyl]-3-phenylprop-2-en-1-one; 77068273: 2-[3,5-Diacetyloxy-2-(acetyloxymethyl)-6-[4-(3-phenylprop-2-enoyl)phenoxy]oxan-4-yl]acetic acid; 77068287: 2-[5-Acetyloxy-2-(acetyloxymethyl)-6-[4-(3-phenylprop-2-enoyl)phenoxy]-3-[3,4,5-triacetyloxy-6-(acetyloxymethyl)oxan-2-yl]oxyoxan-4-yl]acetic acid; 77134514: 2-[2-[3-(4-Methoxy-phenyl)prop-2-enoyl]phenyl]acetic acid; 77145883: 1-(2-Decoxy-6-hydroxyphenyl)-3-(4-hydroxyphenyl)prop-2-en-1-one; 77145885: 3-(4-Hydroxyphenyl)-1-(2-hydroxy-6-tetradecoxyphenyl)prop-2-en-1-one; 77230454: 2-[3,5-Diacetyloxy-2-(acetyloxymethyl)-6-[4-(3-oxo-3-phenylprop-1-enyl)phenoxy]oxan-4-yl]acetic acid; 77251180: 3-[4-[3-[4-[(2-Methylpropan-2-yl)oxycarbonyl]piperazin-1-yl]phenyl]-3-oxoprop-1-enyl]phenyl]prop-2-enoic acid; 77387166: 3-[4-[2-Hydroxyethyl(methyl)amino]phenyl]-1-(4-nitro-phenyl)prop-2-en-1-one; 77409472: 4-[3-(4-Hydroxyphenyl)prop-2-enoyl]benzoic acid; 77421249: 3-[4-[4-(1-Hydroxy-2-methoxyethyl)phenyl]phenyl]-1-phenylprop-2-en-1-one; 77421250: 3-[4-[4-(1-Hydroxy-6-methoxyhexyl)phenyl]phenyl]-1-phenylprop-2-en-1-one; 77436294: 3-[4-(Hydroxymethyl)phenyl]-1-(4-methoxyphenyl)prop-2-en-1-one; 77461201: N-[4-[(Z)-3-[4-(3-Hydroxynaphthalen-2-yl)phenyl]prop-2-enoyl]phenyl]-2-[[5-(3-nitro-phenyl)-1,3,4-oxadiazol-2-yl]sulfanyl]acetamide; 77633490: 3-[4-[3,4-Dihydroxy-5-(hydroxymethyl)oxolan-2-yl]oxy-3-hydroxyphenyl]-1-phenylprop-2-en-1-one; 77711346: 3-(3-Fluoro-4-methoxyphenyl)-1-(2-hydroxy-4-methoxyphenyl)prop-2-en-1-one; 77751506: 1-[2-Hydroxy-4-(hydroxymethyl)-6-methoxyphenyl]-3-(4-methylphenyl)prop-2-en-1-one; 77911669: 1-(2,4-Dihydroxyphenyl)-3-(3-phenylmethoxyphenyl)prop-2-en-1-one; 77991913: 1-[4-[2-(2,4-Difluorophenyl)-2-hydroxy-3-(1,2,4-triazol-1-yl)propoxy]phenyl]-3-phenylprop-2-en-1-one; 77991914: 1-[4-[2-(2,4-Difluorophenyl)-2-hydroxy-3-(1,2,4-triazol-1-yl)propoxy]phenyl]-3-(4-methoxyphenyl) prop-2-en-1-one; 77991953: 3-(4-Chlorophenyl)-1-[4-[2-(2,4-difluorophenyl)-2-hydroxy-3-(1,2,4-triazol-1-yl)propoxy]phenyl]prop-2-en-1-one; 77991986: 1-[4-[2-(4-Fluorophenyl)-2-hydroxy-3-(1,2,4-triazol-1-yl)propoxy]phenyl]-3-(4-methoxyphenyl)prop-2-en-1-one; 77991987: 1-[4-[2-(4-Bromophenyl)-2-hydroxy-3-(1,2,4-triazol-1-yl)propoxy]phenyl]-3-(4-methoxyphenyl)prop-2-en-1-one; 77991988: 3-(4-Chlorophenyl)-1-[4-[2-(4-fluorophenyl)-2-hydroxy-3-

(1,2,4-triazol-1-yl)propoxy]phenyl]prop-2-en-1-one; 77991990: 1-[4-[2-(2,4-Difluorophenyl)-2-hydroxy-3-(1,2,4-triazol-1-yl)propoxy]phenyl]-3-naphthalen-2-ylprop-2-en-1-one; 77992029: 3-[4-[2-(2,4-Difluorophenyl)-2-hydroxy-3-(1,2,4-triazol-1-yl)propoxy]phenyl]-1-(4-methoxyphenyl)prop-2-en-1-one; 77992030: 3-[4-[2-(2,4-Difluorophenyl)-2-hydroxy-3-(1,2,4-triazol-1-yl)propoxy]phenyl]-1-(4-methylphenyl)prop-2-en-1-one; 77992055: 1-(2,4-Dichlorophenyl)-3-[4-[2-(2,4-difluorophenyl)-2-hydroxy-3-(1,2,4-triazol-1-yl)propoxy]phenyl]prop-2-en-1-one; 77992056: 3-[4-[2-(2,4-Difluorophenyl)-2-hydroxy-3-(1,2,4-triazol-1-yl)propoxy]-3-methoxyphenyl]-1-(4-methoxyphenyl)prop-2-en-1-one; 78127085: 1-(4-Hydroxy-2,6-dimethoxyphenyl)-3-phenylprop-2-en-1-one; 78159407: 2-[4-[2-[2-[4-[4-[4-[3-(2-Hydroxyphenyl)-3-oxoprop-1-enyl]phenoxy]butyl]triazol-1-yl]ethoxy]ethoxy]phenyl]chromen-4-one; 78319151: (E)-3-[4-(2-Hydroxyethoxy)phenyl]-1-(4-(1251)iodanylphenyl)prop-2-en-1-one; 78320751: (E)-1-[4-[[1-[2-(2,4-Difluorophenyl)-2-hydroxy-3-(1,2,4-triazol-1-yl)propyl]triazol-4-yl]methoxy]phenyl]-3-phenylprop-2-en-1-one; 78320752: (E)-1-[4-[[1-[2-(2,4-Difluorophenyl)-2-hydroxy-3-(1,2,4-triazol-1-yl)propyl]triazol-4-yl]methoxy]phenyl]-3-(4-methoxyphenyl)prop-2-en-1-one; 78320753: (E)-1-[4-[[1-[2-(2,4-Difluorophenyl)-2-hydroxy-3-(1,2,4-triazol-1-yl)propyl]triazol-4-yl]methoxy]phenyl]-3-(4-methylphenyl)prop-2-en-1-one; 78321069: (E)-3-[4-[[1-[2-(2,4-Difluorophenyl)-2-hydroxy-3-(1,2,4-triazol-1-yl)propyl]triazol-4-yl]methoxy]phenyl]-1-(4-methoxyphenyl)prop-2-en-1-one; 78321070: (E)-3-[4-[[1-[2-(2,4-Difluorophenyl)-2-hydroxy-3-(1,2,4-triazol-1-yl)propyl]triazol-4-yl]methoxy]phenyl]-1-(4-fluorophenyl)prop-2-en-1-one; 78321392: (E)-3-[4-[[1-[2-(2,4-Difluorophenyl)-2-hydroxy-3-(1,2,4-triazol-1-yl)propyl]triazol-4-yl]methoxy]phenyl]-1-[4-(4-propylpiperazin-1-yl)phenyl]prop-2-en-1-one; 78321393: (E)-1-[4-(4-Butylpiperazin-1-yl)phenyl]-3-[4-[[1-[2-(2,4-difluorophenyl)-2-hydroxy-3-(1,2,4-triazol-1-yl)propyl]triazol-4-yl]methoxy]phenyl]prop-2-en-1-one; 78321394: (E)-3-[4-[[1-[2-(2,4-Difluorophenyl)-2-hydroxy-3-(1,2,4-triazol-1-yl)propyl]triazol-4-yl]methoxy]phenyl]-1-[4-(4-pentylpiperazin-1-yl)phenyl]prop-2-en-1-one; 78321395: (E)-3-[4-[[1-[2-(2,4-Difluorophenyl)-2-hydroxy-3-(1,2,4-triazol-1-yl)propyl]triazol-4-yl]methoxy]phenyl]-1-[4-[(4-methoxyphenyl)methyl]piperazin-1-yl]phenyl]prop-2-en-1-one; 78321706: (E)-1-[4-[2-(2,4-Difluorophenyl)-2-hydroxy-3-(1,2,4-triazol-1-yl)propoxy]phenyl]-3-[4-[[1-[2-(2,4-difluorophenyl)-2-hydroxy-3-(1,2,4-triazol-1-yl)propyl]triazol-4-yl]methoxy]phenyl]prop-2-en-1-one; 78427000: Propan-2-yl (2S)-2-[[[(2R,3R,4R,5R)-5-(2,4-dioxopyrimidin-1-yl)-4-fluoro-3-hydroxy-4-methyloxolan-2-yl]methoxy-[4-[(E)-3-phenylprop-2-enoyl]phenoxy]phosphoryl]amino]propanoate; 78494649: 3-[4-(Diethylamino)phenyl]-1-(4-hydroxyphenyl)prop-2-en-1-one; 78494747: 2-Bromo-phenyl-3-(4-hydroxyphenyl)prop-2-en-1-one; 78574105: (E)-3-(4-Hydroxy-3-nitro-phenyl)-1-phenyl-2-propene-1-one; 78787116: 1-(2,4-Difluorophenyl)-3-(3-ethoxy-4-hydroxyphenyl) prop-2-en-1-one; 84846513: 4-Hydroxy-4'-propyloxy-chalcone; 84848836: (E)-3-(4-Hydroxy-3-nitro-phenyl)-1-(4-chlorophenyl)-2-propene-1-one; 84853930: 3-(4-Hydroxy-phenyl)-1-[2-(trifluoromethyl)phenyl]prop-2-en-1-one; 84854777: 2-Bromophenyl-3-(4-hydroxy-3-methoxyphenyl)prop-2-en-1-one; 84854781: 2-Bromophenyl-3-(3-ethoxy-4-hydroxyphenyl)prop-2-en-1-one; 85064429: 3-(3-Hydroxy-4-methoxyphenyl)-1-(2,4,6-trihydroxyphenyl)prop-2-en-1-one; 85087689: 2-Methyl-2-[4-[3-(4-methylsulfanylphenyl) prop-2-enoyl]phenoxy] propanoic acid; 85088029: 2-[4-[3-(4-Chloro-2-hydroxyphenyl)-3-oxoprop-1-enyl]phenyl]sulfanyl-2-methylpropanoic acid; 85101733: 2-[4-[3-(2-Hydroxyphenyl)-3-oxoprop-1-enyl]phenyl]sulfanyl-2-methylpropanoic acid; 85107844: 2'-Hydroxy-4',6'-dimethyl-4-chlorochalcone; 85108776: 2-[4-[3-(4-Chlorophenyl)prop-2-enoyl]phenoxy]-2-methylpropanoic acid; 85109238: 2-[3-Hydroxy-4-[3-(4-methylsulfanylphenyl)prop-2-enoyl]phenoxy]-2-methylpropanoic acid; 85114252: 2-[3-[3-(2-Hydroxyphenyl)-3-oxoprop-1-enyl]phenoxy]-2-methylpropanoic acid; 85126404: 2'-Hydroxy-4',6'-dimethylchalcone; 85127647: 2-[4-[3-(2,4-Dihydroxyphenyl)-3-oxoprop-1-enyl]phenoxy]-2-methylpropanoic acid; 85139965: 2-[4-[3-(2-Hydroxyphenyl)-3-oxoprop-1-enyl]phenoxy]-2-methylpropanoic acid; 85140498: 2-[4-[3-(4-Chloro-2-hydroxyphenyl)-3-oxoprop-1-enyl]phenoxy]-2-methylpropanoic acid; 85153041: Propan-2-yl 2-[4-[3-(2-hydroxyphenyl)-3-oxoprop-1-enyl]phenoxy]-2-methylpropanoate; 85177930: 2',4'-Dihydroxy-4-chloro chalcone; 85199098: Schembl21527701; 85257122: 3-(4-Chlorophenyl)-1-(2,4,6-trihydroxyphenyl) prop-2-en-1-one; 85302628: 3-[3,4-Bis(phenylmethoxy)phenyl]-1-[2-hydroxy-4,6-bis(methoxymethoxy)phenyl]prop-2-en-1-one; 85405776: 3-(4-Butoxyphenyl)-1-(2-hydroxyphenyl)prop-2-en-1-one; 85425030: 3-(4-Bromophenyl)-1-(2-hydroxy-4,6-dimethoxyphenyl)prop-2-en-1-one; 85442661: 1-(2-Hydroxyphenyl)-3-(3-phenylmethoxy-phenyl)prop-2-en-1-one; 85503051: 1-(2,4-Dihydroxyphenyl)-3-[4-(3-methylbut-2-enoxy)phenyl]prop-2-en-1-one; 85533606: 3-(4-Chlorophenyl)-1-(2-hydroxy-4-methylphenyl)prop-2-en-1-one; 85596497: 1-(4-Hydroxyphenyl)-3-(4-octadecoxyphenyl) prop-2-en-1-one; 85603720: 3-(4-Hexoxyphenyl)-1-(4-hydroxyphenyl)prop-2-en-1-one; 85603736: 3-(4-Decoxyphenyl)-1-(4-hydroxyphenyl)prop-2-en-1-one; 85689682: 2-[4-[3-(3,4-Dihydroxyphenyl)prop-2-enoyl]phenyl]acetic acid; 85689690: 2-[4-[3-(4-Pentoxyphenyl)prop-2-enoyl]phenyl]acetic acid; 85689695: 2-[2-[3-(4-Pentoxyphenyl)prop-2-enoyl]phenyl]acetic acid; 85983261: 1-(4-Chloro-2-hydroxyphenyl)-3-(4-methylphenyl) prop-2-en-1-one; 86039133: 1-[4-(Diethylamino)phenyl]-3-(4-hydroxyphenyl)prop-2-en-1-one; 86273286: 5-[(E)-3-Oxo-3-(2,4,6-trihydroxyphenyl)prop-1-enyl]-1,3-benzodioxol-2-one; 86289291: 2',3,4,4',6'-Pentahydroxychalcone(1-); 86289292: 2',3,4,4',6'-Pentahydroxychalcone 4'-O-beta-D-glucoside(1-); 86289307: 2',4,4',6'-Tetrahydroxychalcone (1-); 86289426: Isoliquiritigenin(1-); 86289435: 2',4,4',6'-Tetrahydroxychalcone 4'-O-beta-D-glucoside(1-); 86291910: (E)-3-(3,4-Dimethoxyphenyl)-1-[4-[(2S,3R,4S,5R,6R)-5-hydroxy-3,4-dimethoxy-6-[[(2R,3R,4R,5R,6S)-3,4,5-trihydroxy-6-methyloxan-2-yl]oxymethyl]oxan-2-yl]oxy-2,6-dimethoxyphenyl]prop-2-en-1-one; 86291911: (E)-1-[4-[(2S,3R,4S,5S,6R)-4,5-Dihydroxy-3-methoxy-6-[[(2R,3R,4R,5R,6S)-3,4,5-trihydroxy-6-methyloxan-2-yl]oxymethyl]oxan-2-yl]oxy-2-hydroxy-6-methoxyphenyl]-3-(3,4-dimethoxyphenyl)prop-2-en-1-one; 86291912: (E)-3-(3,4-Dimethoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one; 86342009: (E)-3-[4-Hydroxy-3-(3-methylbut-3-en-2-yl)phenyl]-1-(4-prop-2-enoxyphenyl)prop-2-en-1-one; 86575187: (E)-1-(2,4-Dihydroxy-phenyl)-3-(4-methoxyphenyl)prop-2-en-1-one; (E)-1-(2-hydroxy-4-methoxy-phenyl)-3-(4-hydroxyphenyl) prop-2-en-1-one; 86641367: (E)-3-[4-[(E)-3-[4-(Hydroxymethyl)phenyl]-3-oxoprop-1-enyl]phenyl]-N-(oxan-2-yloxy)prop-2-enamide; 86654221: 2-Methyl-2-(2-methyl-4-(3-oxo-3-(propylthio)phenyl)prop-1-enyl)phenoxy) propanoic acid; 86807990: N-[4-[(E)-3-(3-Chloro-4- hydroxyphenyl)prop-2-enoyl]phenyl]-2,2,2-trifluoroacetamide; 86953690: (E)-1-[4-(4-Hydroxypiperidin-1-yl)phenyl]-3-[4-[3-(trifluoromethyl)pyrazol-1-yl]phenyl]prop-2-en-1-one; 87086506: 1,3-Diphenylprop-2-en-1-one;1-hydroxynaphthalene-2-sulfonic acid; 87127336: 4-Butyl-2-oxo-6-[(E)-3-oxo-3-phenylprop-1-enyl]chromene-3-carboxylic acid; 87166351: (E)-1-(2-Anilino-4-chlorophenyl)-3-[4-(4-hydroxypiperidin-1-yl)sulfonylphenyl]prop-2-en-1-one; 87166387: (E)-1-(2-Anilino-4-chlorophenyl)-3-[4-(3-hydroxypyrrolidin-1-yl)sulfonylphenyl]prop-2-en-1-one; 87188584: 3-[4-[(2E)-6-Methyl-2-(1,2,2,2-tetrahydroxyethylidene)hept-5-enyl]phenyl]-1-phenylprop-2-en-1-one; 87195752: CID 87195752; 87227907: Methyl 4-[(E)-3-[4-[(Z)-3-amino-2-hydroxy-3-oxoprop-1-enyl]phenyl]prop-2-enoyl]benzoate; 87227908: Methyl 4-[(E)-3-[4-[(Z)-3-amino-1-hydroxy-3-oxoprop-1-en-2-yl]phenyl]prop-2-enoyl]benzoate; 87249277: (E)-3-[4-[(E)-3-Oxo-3-[4-(1-piperidin-4-ylethyl)phenyl]prop-1-enyl]phenyl]prop-2-enoic acid;hydrochloride; 87249278: (E)-3-[4-[(E)-3-Oxo-3-[4-(1-piperidin-4-ylethyl)phenyl]prop-1-enyl]phenyl]prop-2-enoic acid; 87249404: (2Z)-2-[[4-[(E)-3-(4-Bromophenyl)-3-oxoprop-1-enyl]phenyl]methylidene]-3,3-dimethyl-butanoic acid; 87249559: (E)-N-Hydroxy-3-[4-[(E)-3-[4-(1-methylpiperidin-4-yl)phenyl]-3-oxoprop-1-enyl]phenyl]prop-2-enamide;2,2,2-trifluoroacetic acid; 87261582: (E)-1-Phenyl-3-[4-[(E)-4,4,4-trihydroxy-3-methylbut-2-enyl]phenyl]prop-2-en-1-one; 87280470: But-1-ene;(E)-1-(2,4-dihydroxyphenyl)-3-(3,4-dihydroxyphenyl)prop-2-en-1-one; 87307721: (E)-1,3-Diphenylprop-2-en-1-one;(2R,3S,4R,5R)-2,3,4,5,6-pentahydroxyhexanal; 87355628: 1-[4-(6-Hydroxyhexoxy)phenyl]-3-[4-(1,1,2,2,3,3,4,4,5,5,6,6,6-tridecafluorohexyl)phenyl]prop-2-en-1-one; 87371736: (2Z)-3,3-Dimethyl-2-[[3-[(E)-3-[4-[(4-methylpiperazin-1-yl)methyl]phenyl]-3-oxoprop-1-enyl]phenyl]methylidene]butanoic acid; 87372211: (2Z)-3,3-Dimethyl-2-[[3-[(E)-3-[2-[(4-methylpiperazin-1-yl)methyl]phenyl]-3-oxoprop-1-enyl]phenyl]methylidene]butanoic acid; 87436343: (E)-3-(4-Hydroxy-3-methoxyphenyl)-1-[2-methoxy-4-[7-methoxy-3-methyl-5-[(E)-prop-1-enyl]-2,3-dihydro-1-benzofuran-2-yl]phenyl]prop-2-en-1-one; 87436519: (E)-3-(3,4-Dihydroxyphenyl)-1-[2-methoxy-4-[7-methoxy-3-methyl-5-[(E)-prop-1-enyl]-2,3-dihydro-1-benzofuran-2-yl]phenyl]prop-2-en-1-one; 87437197: (E)-3-(4-Hydroxy-phenyl)-1-[2-methoxy-4-[7-methoxy-3-methyl-5-[(E)-prop-1-enyl]-2,3-dihydro-1-benzofuran-2-yl]phenyl]prop-2-en-1-one; 87440301: 2-[3,4-Bis [(E)-3-(4-hydroxyphenyl)prop-2-enoyl]phenyl]prop-2-enoic acid; 87458157: 2-[(Z)-3-(3,4-Dimethoxyphenyl)prop-2-enoyl]benzoic acid; 87463074: 4-[4,5-Dicarboxy-2-[4-[(E)-3-oxo-3-phenylprop-1-enyl]phenoxy]phenyl]-5-[4-[(E)-3-oxo-3-phenylprop-1-enyl]phenoxy]phthalic acid; 87463358: 3-[2,3-Dicarboxy-6-[6-[4-[(E)-3-oxo-3-phenylprop-1-enyl]phenoxy]hexoxy]phenyl]-4-[6-[4-[(E)-3-oxo-3-phenylprop-1-enyl]phenoxy]hexoxy]phthalic acid; 87463380: 4-[4,5-Dicarboxy-2-[6-[4-[(E)-3-(4-fluoro-phenyl)-3-oxoprop-1-enyl]phenoxy]hexoxy]phenyl]-5-[6-[4-[(E)-3-(4-fluorophenyl)-3-oxoprop-1-enyl]phenoxy]hexoxy]phthalic acid; 87463683: 3-[2,3-Dicarboxy-5-[4-[4-[(E)-3-oxo-3-phenylprop-1-enyl]phenyl]phenyl]phenyl]-5-[4-[4-[(E)-3-oxo-3-phenylprop-1-enyl]phenyl]phenoxy] phthalic acid; 87463711: 3-[2,3-Dicarboxy-6-[6-[4-[(E)-3-(4-fluoro-phenyl)-3-oxoprop-1-enyl]phenoxy]hexoxy]phenyl]-4-[6-[4-[(E)-3-(4-fluorophenyl)-3-oxoprop-1-enyl]phenoxy]hexoxy]phthalic acid; 87463768: 3-[2,3-Dicarboxy-5-[6-[4-[(E)-3-oxo-3-phenylprop-1-enyl]phenoxy]hexoxy]phenyl]-5-[6-[4-[(E)-3-oxo-3-phenylprop-1-enyl]phenoxy]hexoxy]phthalic acid; 87463979: 4-[4,5-Dicarboxy-2-[6-[4-[(E)-3-oxo-3-phenylprop-1-enyl]phenoxy]hexoxy]phenyl]-5-[6-[4-[(E)-3-oxo-3-phenylprop-1-enyl]phenoxy]hexoxy]phthalic acid; 87464079: 3-[2,3-Dicarboxy-4-[6-[4-[(E)-3-oxo-3-phenylprop-1-enyl]phenoxy]hexoxy]phenyl]-6-[6-[4-[(E)-3-oxo-3-phenylprop-1-enyl]phenoxy]hexoxy]phthalic acid; 87464132: 3-[2,3-Dicarboxy-5-[4-[(E)-3-oxo-3-phenylprop-1-enyl]phenoxy]phenyl]-5-[4-[(E)-3-oxo-3-phenylprop-1-enyl]phenoxy]phthalic acid; 87464182: 4-[4,5-Dicarboxy-2-[4-[4-[(E)-3-oxo-3-phenylprop-1-enyl]phenyl]phenoxy]phenyl]-5-[4-[4-[(E)-3-oxo-3-phenylprop-1-enyl]phenyl]phenoxy]phthalic acid; 87464391: 3-[2,3-Dicarboxy-6-[4-[(E)-3-oxo-3-phenylprop-1-enyl]phenoxy]phenyl]-4-[4-[(E)-3-oxo-3-phenylprop-1-enyl]phenoxy]phthalic acid; 87464404: 4-[3,4-Dicarboxy-2-[4-[(E)-3-oxo-3-phenylprop-1-enyl]phenoxy]phenyl]-3-[4-[(E)-3-oxo-3-phenylprop-1-enyl]phenoxy]phthalic acid; 87464408: 5-[3,4-Dicarboxy-5-[6-[4-[(E)-3-(4-fluorophenyl)-3-oxoprop-1-enyl]phenoxy]hexoxy]phenyl]-3-[6-[4-[(E)-3-(4-fluorophenyl)-3-oxoprop-1-enyl]phenoxy]hexoxy]phthalic acid; 87464410: 3-[2,3-Dicarboxy-5-[6-[4-[(E)-3-(4-fluorophenyl)-3-oxoprop-1-enyl]phenoxy]hexoxy]phenyl]-5-[6-[4-[(E)-3-(4-fluorophenyl)-3-oxoprop-1-enyl]phenoxy]hexoxy]phthalic acid; 87464441: 5-[3,4-Dicarboxy-5-[4-[(E)-3-oxo-3-phenylprop-1-enyl]phenyl]phenoxy]phenyl]-3-[4-[(E)-3-oxo-3-phenylprop-1-enyl]phenyl]phenoxy]phthalic acid; 87464505: 3-[2,3-Dicarboxy-4-[4-[(E)-3-oxo-3-phenylprop-1-enyl]phenyl]phenyl]-6-[4-[(E)-3-oxo-3-phenylprop-1-enyl]phenoxy]phthalic acid; 87464530: 3-[2,3-Dicarboxy-4-[6-[4-[(E)-3-(4-fluorophenyl)-3-oxoprop-1-enyl]phenoxy]hexoxy]phenyl]-6-[6-[4-[(E)-3-(4-fluorophenyl)-3-oxoprop-1-enyl]phenoxy]hexoxy]phthalic acid; 87464540: 4-[3,4-Dicarboxy-2-[4-[4-[(E)-3-oxo-3-phenylprop-1-enyl]phenyl]phenoxy]phenyl]-3-[4-[4-[(E)-3-oxo-3-phenylprop-1-enyl]phenyl]phenoxy]phthalic acid; 87464557: 5-[3,4-Dicarboxy-5-[4-[(E)-3-oxo-3-phenylprop-1-enyl]phenoxy]phenyl]-3-[4-[(E)-3-oxo-3-phenylprop-1-enyl]phenoxy]phthalic acid; 87464841: 4-[3,4-Dicarboxy-2-[6-[4-[(E)-3-oxo-3-phenylprop-1-enyl]phenoxy]hexoxy]phenyl]-3-[6-[4-[(E)-3-oxo-3-phenylprop-1-enyl]phenoxy]hexoxy]phthalic acid; 87464872: 3-[2,3-Dicarboxy-6-[4-[4-[(E)-3-oxo-3-phenylprop-1-enyl]phenyl]phenoxy]phenyl]-4-[4-[4-[(E)-3-oxo-3-phenylprop-1-enyl]phenyl]phenyl]phthalic acid; 87465195: 4-[3,4-Dicarboxy-2-[6-[4-[(E)-3-(4-fluoro-phenyl)-3-oxoprop-1-enyl]phenoxy]hexoxy]phenyl]-3-[6-[4-[(E)-3-(4-fluorophenyl)-3-oxoprop-1-enyl]phenoxy]hexoxy]phthalic acid; 87465222: 5-[3,4-Dicarboxy-5-[6-[4-[(E)-3-oxo-3-phenylprop-1-enyl]phenoxy]hexoxy]phenyl]-3-[6-[4-[(E)-3-oxo-3-phenylprop-1-enyl]phenoxy]hexoxy]phthalic acid; 87465301: 3-[2,3-Dicarboxy-4-[4-[(E)-3-oxo-3-phenylprop-1-enyl]phenyl]phenoxy]phenyl]-6-[4-[(E)-3-oxo-3-phenylprop-1-enyl]phenyl]phenoxy]phthalic acid; 87534128: [4-[(E)-3-(4-Hydroxyphenyl)prop-2-enoyl]phenyl]methanesulfonic acid; 87559541: (E)-3-[3-[2-(Dimethylamino)ethyl-methylamino]phenyl]-1-(4-hydroxyphenyl) prop-2-en-1-one; 87590341: (E)-1-(2,4-Dihydroxy-6-methoxyphenyl)-3-[4-hydroxy-3-(3-methylbut-2-enoxy) phenyl]prop-2-en-1-one; 87590453: [4-[(E)-3-Oxo-3-phenylprop-1-enyl]phenyl] 3-hydroxybenzenesulfonate; 87590472: [2-Hydroxy-4-[(E)-3-oxo-3-phenylprop-1-enyl] phenyl] 4-hydroxybenzenesulfonate; 87590918: [2-Hydroxy-4-[(E)-3-oxo-3-phenylprop-1-enyl]phenyl] 3-hydroxybenzenesulfonate; 87654954: 4-[4-[(E)-3-[4-[(E)-3-(Hydroxyamino)-3-oxoprop-1-enyl]phenyl]prop-2-enoyl]phenyl]piperazine-1-carboxylic acid; 87728345: (E)-3-(4-Ethoxyphenyl)-1-(2-hydroxy-4-methoxyphenyl)prop-2-en- 1-one; 87732261: (E)-3-(1-Benzofuran-5-yl)-1-[2-hydroxy-4-methyl-6-[(2S,3R,4S,5S,6S)-3,4,5-trihydroxy-6-(hydroxymethyl)thian-2-yl]oxyphenyl]prop-2-en-1-one; 87746693: (E)-3-[4-[(2S,3R,4S,5R)-3,4-Dihydroxy-5-(hydroxymethyl)oxolan-2-yl]oxy-3-hydroxyphenyl]-1-phenylprop-2-en-1-one; 87786771: (E)-3-[4-(Dihydroxymethyl)phenyl]-1-phenylprop-2-en-1-one; 87909736: (E)-3-[3-[(2-Hydroxyethylamino)methyl]phenyl]-1-(4-methoxyphenyl)prop-2-en-1-one; 87909746: (E)-3-[3-[[2-Hydroxyethyl(methyl)amino]methyl]phenyl]-1-(4-methoxyphenyl)prop-2-en-1-one; 87931347: (E)-3-(3,4-Dihydroxyphenyl)-1-(2,4,6-trihydroxyphenyl)prop-2-en-1-one;(E)-1,3-diphenylprop-2-en-1-one;(E)-1-phenyl-3-(2,3,4-trihydroxyphenyl)prop-2-en-1-one; 87941272: 2-[4-[(E)-3-(2,6-Dimethoxyphenyl)-3-oxoprop-1-enyl]-2-thiophen-2-ylphenoxy]-2-methylpropanoic acid; 87964755: 1,3-Diphenylprop-2-en-1-one;3-phenyl-2-sulfanylprop-2-enoic acid; 88020884: Methoxy-[2-[[3-(3-oxo-3-phenylprop-1-enyl)phenoxy]methyl]phenyl]carbamic acid; 88069058: 4-[(E)-3-[4-[[4-(1-Ethoxyethyl)-1H-benzimidazol-2-yl]methoxy]phenyl]prop-2-enoyl]-3-hydroxybenzoic acid; 88076553: [(1S,4R)-4-[2-Amino-6-(cyclopropylamino)purin-9-yl]cyclopent-2-en-1-yl]methanol-phosphono (2S)-2-[[4-[(E)-3-oxo-3-phenylprop-1-enyl]phenyl]methoxyamino]propanoate; 88105079: (E)-1-(4-Chlorophenyl)-3-(3,5-dichloro-2-hydroxyphenyl)prop-2-en-1-one;(E)-1-(4-chlorophenyl)-3-(3,4-dichlorophenyl)prop-2-en-1-one; 88105263: (E)-1-(2-Chlorophenyl)-3-(3,5-dichloro-2-hydroxyphenyl)prop-2-en-1-one;(E)-1-(4-chlorophenyl)-3-(3,5-dichloro-2-hydroxyphenyl)prop-2-en-1-one;(E)-1-(4-chlorophenyl)-3-(3,4-dichlorophenyl)prop-2-en-1-one; 88120587: 1-[4-(6-Hydroxyhexoxy)phenyl]-3-[4-(2,2,3,3,3-pentafluoropropoxy)phenyl]prop-2-en-1-one; 88170145: (E)-3-[3-Hydroxy-4-[(E)-3-phenylprop-2-enoyl]phenyl]prop-2-enoic acid; 88176626: 4-[3-(2-Hydroxy-4-prop-2-ynoxyphenyl)-3-oxoprop-1-enyl]benzonitrile; 88177232: 1-(2-Hydroxy-4-prop-2-ynoxyphenyl)-3-phenylprop-2-en-1-one; 88198968: Benzaldehyde;(E)-1-(2-hydroxyphenyl)-3-phenylprop-2-en-1-one;1-phenyl-ethanone; 88242693: 7,8-Dimethoxy-2-oxabicyclo[2.2.2]octa-1(7),4(8),5-trien-5-ol;(E)-1-(4-methoxyphenyl)-3-phenylprop-2-en-1-one; 88244637: 8-Methoxy-2-oxabicyclo[2.2.2]octa-1(6),4,7-trien-5-ol;(E)-3-(3-methoxyphenyl)-1-phenylprop-2-en-1-one; 88249247: (E)-1-[2-[(2S,3R,4R,5S,6R)-3,4-Dihydroxy-6-(hydroxymethyl)-5-[(2S,3R,4S,5S,6R)-3,4,5-trihydroxy-6-(hydroxymethyl)oxan-2-yl]oxyoxan-2-yl]-6-hydroxyphenyl]-3-(4-methoxyphenyl)prop-2-en-1-one; 88250287: (Z)-1-[2-Hydroxy-6-[(2S,3R,4R,5S,6R)-3,4,5-trihydroxy-6-(hydroxymethyl) oxan-2-yl]phenyl]-3-(4-methylphenyl)prop-2-en-1-one; 88250935: (E)-3-(4-Hydroxyphenyl)-1-[2-phenylmethoxy-6-[(2S,3R,4R,5S,6R)-3,4,5-trihydroxy-6-(hydroxymethyl)oxan-2-yl]phenyl]prop-2-en-1-one; 88251175: Ethyl [4-[(Z)-3-oxo-3-[2-phenylmethoxy-6-[(2S,3R,4R,5S,6R)-3,4,5-trihydroxy-6-(hydroxymethyl)oxan-2-yl]phenyl]prop-1-enyl]phenyl]carbonate; 88261523: 4-[(E)-3-[3-[[4-(1-Ethoxyethyl)-1H-benzimidazol-2-yl]methoxy]phenyl]prop-2-enoyl]-3-hydroxybenzoic acid; 88308414: (19S)-19-Ethyl-19-hydroxy-6-[(E)-3-oxo-3-phenylprop-1-enyl]-17-oxa-3,13-diazapentacyclo[11.8.0.02,11.04,9.015,20]henicosa-1(21),2(11),3,5,7,9,15(20)-heptaene-14,18-dione; 88308877: (19S)-19-Ethyl-19-hydroxy-7-[(E)-3-oxo-3-phenylprop-1-enyl]-17-oxa-3,13-diazapentacyclo[11.8.0.02,11.04, 9.015,20]henicosa-1(21),2(11),3,5,7,9,15 (20)-heptaene-14,18-dione; 88309128: (19S)-10,19-Diethyl-19-hydroxy-7-[(E)-3-oxo-3-phenylprop-1-enyl]-17-oxa-3,13-diazapentacyclo[11.8.0.02,11.04,9.015,20] henicosa-1(21),2,4(9),5,7,10,15(20)-heptaene-14,18-dione; 88331793: (E)-1,3-Diphenylprop-2-en-1-one;(E)-1-(2-hydroxyphenyl)-3-phenylprop-2-en-1-one; 88392270: [4-[3-(4-Methoxy-3-methylphenyl)prop-2-enoyl]phenyl] prop-2-enoate;2-methylprop-2-enoic acid;oxiran-2-ylmethyl 2-methylprop-2-enoate; 88441236: Cyanamide;2-[5-(3-methylbut-2-enoxy)-2-[(E)-3-[4-(3-methylbut-2-enoxy)phenyl]prop-2-enoyl]phenoxy]acetic acid; 88451662: 2-[2-[(E)-3-(4-Tert-butylphenyl)prop-2-enoyl]-5-[(E)-pent-2-en-3-yl]oxyphenoxy]acetic acid; 88451663: 2-[5-[(Z)-Pent-2-en-3-yl]oxy-2-[(E)-3-[4-[(E)-pent-2-en-3-yl]oxyphenyl]prop-2-enoyl]phenoxy]acetic acid; 88451668: 2-[2-[(Z)-3-(4-Hexylphenyl)prop-2-enoyl]-5-[(Z)-pent-2-en-3-yl]oxyphenoxy]acetic acid; 88451675: 2-[2-[(E)-3-[4-[(E)-Hex-1-enyl]phenyl]prop-2-enoyl]-5-[(Z)-pent-2-en-3-yl]oxyphenoxy]acetic acid; 88451686: 2-[4-[(E)-3-[2-(Carboxymethoxy)-4-[(E)-pent-2-en-3-yl]oxyphenyl]-3-oxoprop-1-enyl]phenoxy]acetic acid; 88451693: 2-[2-[(E)-3-[4-[(E)-Hept-1-enyl]phenyl]prop-2-enoyl]-5-[(Z)-pent-2-en-3-yl]oxyphenoxy]acetic acid; 88451715: 2-[5-[(E)-Pent-2-en-3-yl]oxy-2-[(E)-3-(4-prop-2-enylphenyl)prop-2-enoyl]phenoxy]acetic acid; 88451719: 2-[2-[(Z)-3-(4-Heptylphenyl)prop-2-enoyl]-5-[(Z)-pent-2-en-3-yl]oxyphenoxy]acetic acid; 88451770: (E)-3-(4-Hexylphenyl)-1-[2-hydroxy-4-[(Z)-pent-2-en-3-yl]oxyphenyl]prop-2-en-1-one; 88451790: (E)-3-(4-Tert-butylphenyl)-1-[2-hydroxy-4-[(E)-pent-2-en-3-yl]oxyphenyl]prop-2-en-1-one; 88451796: 4-[(E)-3-[2-(Carboxymethoxy)-4-[(E)-pent-2-en-3-yl]oxyphenyl]-3-oxoprop-1-enyl]benzoic acid; 88452305: 2-[2-[(E)-3-[4-[(E)-Oct-1-enyl]phenyl]prop-2-enoyl]-5-[(Z)-pent-2-en-3-yl]oxyphenoxy]acetic acid; 88452309: 2-[5-[(Z)-Pent-2-en-3-yl]oxy-2-[(Z)-3-(4-propylphenyl)prop-2-enoyl]phenoxy]acetic acid; 88452311: 2-[2-[(E)-3-(4-Tert-butyl-phenyl)prop-2-enoyl]-5-[(E)-pent-2-en-3-yl]oxyphenoxy]propanoic acid; 88452312: 2-[2-[(E)-3-(4-Methylphenyl)prop-2-enoyl]-5-[(E)-pent-2-en-3-yl]oxyphenoxy]acetic acid; 88477930: (E)-1,3-Bis(4-hydroxyphenyl)prop-2-en-1-one;(E)-3-(4-hydroxyphenyl)-1-phenylprop-2-en-1-one; 88485612: 5-[[2-[(E)-3-(4-Hydroxy-3-methoxyphenyl)prop-2-enoyl]phenyl]methyl]-1,3-thiazolidine-2,4-dione; 88598216: (E)-1-[4-[(E)-4-Hydroxybut-3-en-2-yl]oxyphenyl]-3-phenylprop-2-en-1-one; 88620506: (E)-3-(4-Decylphenyl)-1-(2,6-dihydroxyphenyl)prop-2-en-1-one; 88620700: 2-Hexylthiolane;(E)-1-(4-hydroxyphenyl)-3-phenylprop-2-en-1-one; 88620716: (E)-3-(4-Decylphenyl)-1-(2,4-dihydroxyphenyl)prop-2-en-1-one; 88627696: 3-[(E)-3-[2-(Carboxymethoxy)-4-[(1 E)-3-methylbuta-1,3-dienoxy]phenyl]-3-oxoprop-1-enyl]benzoic acid; 88628164: 2-[4-[(E)-3-[2-(Carboxymethoxy)-4-[(1 E)-3-methylbuta-1,3-dienoxy]phenyl]-3-oxoprop-1-enyl]-2-methoxyphenoxy]acetic acid; 88628279: 2-[4-[(E)-3-[2-(Carboxymethoxy)-4-[(1 E)-3-methylbuta-1,3-dienoxy]phenyl]-3-oxoprop-1-enyl]phenoxy]acetic acid; 88628406: 4-[(E)-3-[2-(Carboxymethoxy)-4-[(1 E)-3-methylbuta-1,3-dienoxy]phenyl]-3-oxoprop-1-enyl]benzoic acid; 88628544: 2-[5-[(1E)-3-Methylbuta-1,3-dienoxy]-2-[(E)-3-[4-[(1 E)-3-methylbuta-1,3-dienoxy]phenyl]prop-2-enoyl]phenoxy]acetic acid; 88671920: 3-[(E)-3-[4-(2-Carboxy-2-prop-2-enoxyethoxy)phenyl]-3-oxoprop-1-enyl]benzoic acid; 88754252: N-[(2S,3S,4R,5S,6R)-2-[3,5-Dimethoxy-2-[(E)-3-(4-methoxyphenyl)prop-2-enoyl]phenoxy]-4,5-dihydroxy-6-(hydroxymethyl)oxan-3-yl]acetamide; 88766502: 3H-Benzimidazole-5-carbaldehyde;(E)-3-(3H-benzimidazol-5-yl)-1-(2-hydroxy-4,6-dimethoxyphenyl)prop-2-en-1-one; 88772813: (E)-1-[2-Hydroxy-4-[(Z)-pent-2-en-3-yl]oxyphenyl]-3-[4-[(E)-pent-2-en-3-yl]oxyphenyl]prop-2-en-1-one; 88781697: 2-[4-[(E)-3-Phenylprop-2-enoyl]phenoxy]

propanedioic acid; 88784015: CID 88784015; 88784094: 4-[(E)-3-Phenylprop-2-enoyl]benzoic acid;hydrochloride; 88785249: 4-[(E)-3-Oxo-3-phenylprop-1-enyl]benzoic acid; hydrochloride; 88792114: Cadmium(2+);2-[5-(3-methylbut-2-enoxy)-2-[(E)-3-[4-(3-methylbut-2-enoxy)phenyl] prop-2-enoyl]phenoxy]acetic acid;sulfate; 88801700: 2-[5-[(E)-Pent-2-en-3-yl]oxy-2-[(E)-3-phenylprop-2-enoyl] phenoxy]acetic acid; 88802132: 2-[2-[(E)-3-[4-[(E)-Pent-2-en-3-yl]oxyphenyl]prop-2-enoyl]phenoxy]acetic acid; 88803181: 3-[3-Hydroxy-4-[(E)-3-(4-methoxy-3-phenylmethoxyphenyl)prop-2-enoyl]phenoxy]propane-1-sulfonic acid; 88850929: (E)-1,3-Diphenylprop-2-en-1-one;3-hydroxy-4-methoxybenzal-dehyde; 88865784: 5-(2,5-Dioxooxolan-3-yl)-8-[4-[4-[2-hydroxy-2-[4-[(E)-3-oxo-3-phenyl-prop-1-enyl]phenyl]ethoxy]phenyl]phenoxy]-3a,4,5,9b-tetrahydrobenzo[e][2]benzofuran-1,3-dione; 88937952: 2-[(Z)-3-(4-Cyanophenyl)prop-2-enoyl]benzoic acid; 88942522: 4-[3-(4-Hydroxyphenyl)prop-2-enoyl]benzaldehyde; 88944977: (E)-3-[4-(Hydroxyamino)phenyl]-1-(4-hydroxyphenyl)prop-2-en-1-one; 88996461: (E)-1-[4-(Difluoromethyl)phenyl]-3-[4-(6-hydroxyhexoxy)phenyl] prop-2-en-1-one; 89012567: (E)-3-(4-Ethylphenyl)-1-(2-hydroxy-4,6-dimethoxyphenyl)prop-2-en-1-one; 89020946: (E)-1-[4-(3-Amino-2-hydroxypropoxy)phenyl]-3-(1,3-benzodioxol-5-yl)prop-2-en-1-one; 89029862: (E)-1-[4-(Hydroxymethyl)phenyl]-3-(4-methoxy-3-methylphenyl)prop-2-en-1-one; 89032291: (E)-1-(4-Butoxy-2-hydroxyphenyl)-3-(4-hydroxy-3-methoxyphenyl)prop-2-en-1-one; 89032310: (E)-1-(2,4-Dibutoxy-6-hydroxy-phenyl)-3-(4-hydroxy-3-methoxyphenyl)prop-2-en-1-one; 89040667: 4-(1-Carboxy-3-oxopropyl)-7-[[4-[(E)-3-(4-fluorophenyl)-3-oxoprop-1-enyl]phenoxy]methoxy]-1-formyl-1,2,3,4-tetrahydronaphthalene-2-carboxylic acid; 89043374: (E)-3-(3-Hydroxy-4-methoxyphenyl)-1-[2-hydroxy-6-methoxy-4-[(2S,4R,5S)-3,4,5-trihydroxy-6-[[(1R,3S,4S)-2,3,4-trihydroxy-5-methylcyclohexyl]oxymethyl]oxan-2-yl] oxyphenyl]prop-2-en-1-one; 89050027: (E)-1-[4-[(2S,5S)-4,5-Dihydroxy-6-[[(5S)-5,6,7-trihydroxy-4-methylheptan-2-yl]oxymethyl]oxan-2-yl]oxy-2-hydroxy-6-methoxyphenyl]-3-(3-hydroxy-4-methoxyphenyl) prop-2-en-1-one; 89067461: 4-[(E)-3-[4-(1-Hydroxypentyl)phenyl] prop-2-enoyl]benzoic acid; 89068308: (E)-1-[4-(3-Hydroxy-2-methylbut-3-en-2-yl)oxyphenyl]-3-(4-hydroxyphenyl)prop-2-en-1-one; 89068364: 4-[(E)-3-[4-(1-Hydroxypentyl)phenyl]-3-oxoprop-1-enyl]benzoic acid; 89091935: (E)-1-(2,6-Dihydroxy-4-methylphenyl)-3-(4-hydroxyphenyl)prop-2-en-1-one; 89100416: [3-[(E)-3-(4-Hydroxyphenyl)-3-oxoprop-1-enyl]phenyl] (E)-3-phenylprop-2-enoate; 89104241: (E)-1-(2,4-Dibutoxy-6-hydroxyphenyl)-3-(3,4-dibutoxyphenyl)prop-2-en-1-one; 89136954: (E)-1-[4-(Hydroxymethyl)phenyl]-3-(4-hydroxyphenyl)prop-2-en-1-one; 89141541: (E)-3-(4-Butoxyphenyl)-1-(2,4-dibutoxy-6-hydroxyphenyl)prop-2-en-1-one; 89152920: (E)-1-[2-Hydroxy-4,6-bis(2-hydroxyethoxy)phenyl]-3-phenylprop-2-en-1-one; 89166528: 2-[4-[(E)-3-(4-Methylsulfanylphenyl)-3-oxoprop-1-enyl]phenoxy]prop-2-enoic acid; 89166654: 2-[4-[(E)-3-(4-Chloro-2-hydroxyphenyl)-3-oxoprop-1-enyl]phenyl]sulfanyl-prop-2-enoic acid; 89174609: (E)-3-(3,4-Dihydroxyphenyl)-1-(2-methoxy-4-methylphenyl) prop-2-en-1-one; 89219370: (E)-3-(3-Hydroxy-4-methoxyphenyl)-1-[2-hydroxy-6-methoxy-4-[(2S,5S)-3,4,5-tri hydroxy-6-[[(2R,5R)-3,4,5-trihydroxy-6-methyloxan-2-yl]oxymethyl] oxan-2-yl]oxyphenyl]prop-2-en-1-one; 89258670: Hesperidin chalcone; 89287733: (E)-3-[4-[2-(2,4-Difluorophenyl)-2-hydroxy-3-(1H-1,2,4-triazol-5-yl)propoxy]phenyl]-1-(4-methylphenyl)prop-2-en-1-one; 89311948: (E)-3-(4-Hydroxy-3-nitrosophenyl)-1-phenylprop-2-en-1-one; 89325925: (E)-1-(4-Diazenylphenyl)-3-(4-hydroxyphenyl) prop-2-en-1-one; 89325926: N-[4-[(E)-3-(3-Hydroxy-4-nitrosophenyl)prop-2-enoyl]phenyl]benzenesulfonamide; 89335398: (E)-3-(4-Aminophenyl)-1-(4-hydroxyphenyl) prop-2-en-1-one; 89351463: 2-[4-[(E)-3-(4-Hydroxyphenyl)prop-2-enoyl]phenoxy]-2-methylpropanoic acid; 89351468: (E)-1-(2-Hydroxy-4-propan-2-yloxyphenyl)-3-(4-methylphenyl)prop-2-en-1-one; 89351469: 2-Methyl-2-[4-[(E)-3-(4-methylphenyl)-3-oxoprop-1-enyl]phenoxy] propanoic acid; 89351476: (E)-1-(4-Chloro-2-hydroxyphenyl)-3-(4-methylphenyl)prop-2-en-1-one; 89351477: 2-[3-Hydroxy-4-[(E)-3-(4-hydroxyphenyl)prop-2-enoyl]phenoxy]-2-methylpropanoic acid; 89356551: 2-Methyl-2-[4-[(E)-3-(4-methylphenyl)prop-2-enoyl]phenoxy]propanoic acid; 89356554: Methyl 2-[4-[(E)-3-(2-hydroxyphenyl)-3-oxoprop-1-enyl]phenyl]sulfanyl-2-methylpropanoate; 89367090: (E)-1-(2-Ethoxy-4,6-dihydroxyphenyl)-3-(4-ethoxyphenyl)prop-2-en-1-one; 89376287: (E)-1-(2-Hydroxyphenyl)-3-[3-methoxy-4-(3-methylbut-2-enoxy)phenyl]prop-2-en-1-one; 89388596: (E)-3-[4-(8-Hydroxyoctoxy)phenyl]-1-phenylprop-2-en-1-one; 89388701: 4-(2-Hydroxyethoxy)chalcone; 89388725: (E)-3-[4-(Hydroxymethoxy)phenyl]-1-phenylprop-2-en-1-one; 89388738: (E)-1-[4-(8-Hydroxyoctoxy)phenyl]-3-phenylprop-2-en-1-one; 89403194: (E)-3-[4-(Hydroxymethyl) phenyl]-1-phenylprop-2-en-1-one; 89510314: (E)-3-(4-Butoxy-3-nitro-phenyl)-1-(2-hydroxyphenyl)prop-2-en-1-one; 89510367: (E)-3-(3-Butoxy-4-methylphenyl)-1-(2-hydroxyphenyl)prop-2-en-1-one; 89611427: N-Hydroxy-N-[2-[(E)-3-(4-hydroxyphenyl)prop-2-enoyl]phenyl] benzenesulfonamide; 89611428: 2-Hydroxy-N-[2-[(E)-3-(4-hydroxyphenyl)prop-2-enoyl]phenyl]benzenesulfonamide; 89641691: (E)-3-[4-[(4-Hydroxyphenoxy) methoxy]phenyl]-1-phenylprop-2-en-1-one; 89641692: [4-[(E)-3-Oxo-3-phenylprop-1-enyl]phenyl] 4-hydroxybenzoate; 89676052: (E)-1-(4-Aminophenyl)-3-(3-hydroxyphenyl)prop-2-en-1-one; 89731648: 2-[4-[(E)-3-(4-Hydroxyphenyl)-3-oxoprop-1-enyl]-2-methylphenoxy]-2-methylpropanoic acid; 89772095: (E)-1-(4-Aminophenyl)-3-[4-[2-hydroxyethyl(methyl)amino]phenyl]prop-2-en-1-one; 89772098: N-[4-[(E)-3-[4-[2-Hydroxyethyl(methyl)amino]phenyl]prop-2-enoyl]phenyl]-3-iodopropanamide; 89773396: 2,6-Difluoro-N-[4-[(E)-3-[4-[2-hydroxyethyl(methyl)amino]phenyl]prop-2-enoyl]phenyl]-3-methylbenzamide; 89773397: Methyl 4-[4-[(E)-3-[4-[2-hydroxyethyl(methyl)amino]phenyl]prop-2-enoyl]anilino]-4-oxobutanoate; 89773398: 4-Ethyl-N-[4-[(E)-3-[4-[2-hydroxyethyl(methyl)amino]phenyl]prop-2-enoyl]phenyl] benzamide; 89773399: 2,6-Difluoro-N-[4-[(E)-3-[4-[2-hydroxyethyl(methyl)amino]phenyl]prop-2-enoyl]phenyl] benzamide; 89773400: 2-Chloro-6-fluoro-N-[4-[(E)-3-[4-[2-hydroxyethyl(methyl)amino]phenyl]prop-2-enoyl] phenyl]-3-methylbenzamide; 89773401: N-[4-[(E)-3-[4-[2-Hydroxyethyl(methyl)amino]phenyl]prop-2-enoyl]phenyl]-4-methylbenzamide; 89773402: 5-Bromo-N-[4-[(E)-3-[4-[2-hydroxyethyl (methyl)amino]phenyl]prop-2-enoyl] phenyl]pyridine-3-carboxamide; 89773403: 3-Chloro-N-[4-[(E)-3-[4-[2-hydroxyethyl(methyl)amino]phenyl]prop-2-enoyl]phenyl]-1-benzothiophene-2-carboxamide; 89773404: 3-Chloro-2-fluoro-N-[4-[(E)-3-[4-[2-hydroxyethyl(methyl)amino]phenyl]prop-2-enoyl]phenyl]-6-(trifluoromethyl)benzamide; 89773405: N-[4-[(E)-3-[4-[2-Hydroxyethyl(methyl)amino]phenyl]prop-2-enoyl]phenyl]-3-methoxybenzamide; 89773406: N-[4-[(E)-3-[4-[2-Hydroxyethyl(methyl)amino]phenyl]prop-2-enoyl]phenyl] octanamide; 89773407: N-[4-[(E)-3-[4-[2-Hydroxyethyl (methyl)amino]phenyl]prop-2-enoyl]phenyl]-1,2-oxazole-5-carboxamide; 89773408: 2-(2,5-Dimethoxyphenyl)-N-[4-[(E)-3-[4-[2-hydroxyethyl(methyl)amino]phenyl]prop-2-enoyl]phenyl]acetamide; 89773409: N-[4-[(E)-3-[4-[2-Hydroxyethyl(methyl)amino]phenyl]prop-2-enoyl]phenyl] pyridine-3-carboxamide; 89773410: N-[4-[(E)-3-[4-[2-Hydroxyethyl(methyl)amino]phenyl]prop-2-enoyl]phenyl] heptanamide; 89773411: N-[4-[(E)-3-[4-[2-Hydroxyethyl (methyl)amino]phenyl]prop-2-enoyl]phenyl]furan-2-carboxamide; 89773413: N-[4-[(E)-3-[4-[2-Hydroxyethyl (methyl)amino]phenyl]prop-2-enoyl]phenyl]-2,2-dimethylpropanamide; 89773429: 3-Chloro-N-[4-[(E)-3-[4-[2-hydroxyethyl(methyl)amino]phenyl]prop-2-enoyl] phenyl]propanamide; 89773430: 3-Chloro-2-fluoro-N-[4-[(E)-3-[4-[2-hydroxyethyl(methyl)amino]phenyl]prop-2-enoyl]phenyl]benzamide; 89773431: 4-Fluoro-N-[4-[(E)-3-[4-[2-hydroxyethyl(methyl)amino]phenyl]prop-2-enoyl]phenyl]-3-(trifluoromethyl)benzamide; 89773432: N-[4-[(E)-3-[4-[2-Hydroxyethyl (methyl)amino]phenyl]prop-2-enoyl]phenyl]-2-phenoxypropanamide; 89773433: N-[4-[(E)-3-[4-[2-Hydroxyethyl(methyl)amino]phenyl]prop-2-enoyl]phenyl]-5-(3-nitro-phenyl)furan-2-carboxamide; 89773434: 4-Decyl-N-[4-[(E)-3-[4-[2-hydroxyethyl (methyl)amino]phenyl]prop-2-enoyl]phenyl]benzamide; 89773435: 3-Chloro-2-fluoro-N-[4-[(E)-3-[4-[2-hydroxyethyl (methyl)amino]phenyl]prop-2-enoyl]phenyl]-5-(trifluoromethyl)benzamide; 89773436: 2-Fluoro-N-[4-[(E)-3-[4-[2-hydroxyethyl(methyl)amino]phenyl]prop-2-enoyl] phenyl]-3-(trifluoromethyl)benzamide; 89773437: 2-Fluoro-N-[4-[(E)-3-[4-[2-hydroxyethyl(methyl) amino] phenyl]prop-2-enoyl]phenyl]benzamide; 89773439: 2-Chloro-N-[4-[(E)-3-[4-[2-hydroxyethyl(methyl)amino] phenyl]prop-2-enoyl]phenyl]pyridine-3-carboxamide; 89773440: 5-Fluoro-N-[4-[(E)-3-[4-[2-hydroxyethyl (methyl)amino]phenyl]prop-2-enoyl]phenyl]-2-methylbenzamide; 89773441: N-[4-[(E)-3-[4-[2-Hydroxyethyl (methyl)amino]phenyl]prop-2-enoyl]phenyl]thiophene-2-carboxamide; 89773442: N-[4-[(E)-3-[4-[2-Hydroxyethyl (methyl)amino]phenyl]prop-2-enoyl]phenyl] cyclopropanecarboxamide; 89773443: 2-Bromo-N-[4-[(E)-3-[4-[2-hydroxyethyl(methyl)amino]phenyl]prop-2-enoyl] phenyl]benzamide; 89773444: N-[4-[(E)-3-[4-[2-Hydroxyethyl(methyl)amino]phenyl]prop-2-enoyl]phenyl] cyclopentane-carboxamide; 89773445: 2-Chloro-4-fluoro-N-[4-[(E)-3-[4-[2-hydroxyethyl(methyl)amino]phenyl] prop-2-enoyl]phenyl]benzamide; 89773446: N-[4-[(E)-3-[4-[2-Hydroxyethyl(methyl)amino]phenyl]prop-2-enoyl] phenyl]-1-methylpyrrole-2-carboxamide; 89773447: N-[4-[(E)-3-[4-[2-Hydroxyethyl(methyl)amino]phenyl]prop-2-enoyl]phenyl]-2-methylfuran-3-carboxamide; 89773488: 2-(3-Chlorocyclohexa-1,5-dien-1-yl)oxy-N-[4-[(E)-3-[4-[2-hydroxyethyl(methyl)amino]phenyl]prop-2-enoyl]phenyl] acetamide; 89773489: 2,4-Dichloro-5-fluoro-N-[4-[(E)-3-[4-[2-hydroxyethyl(methyl)amino]phenyl]prop-2-enoyl] phenyl]benzamide; 89773490: N-[4-[(E)-3-[4-[2-Hydroxyethyl(methyl)amino]phenyl]prop-2-enoyl]phenyl]-2-methylsulfanylpyridine-3-carboxamide; 89773491: 4-Butoxy-N-[4-[(E)-3-[4-[2-hydroxyethyl(methyl)amino] phenyl]prop-2-enoyl]phenyl]benzamide; 89773492: 3-(2-Chloro-6-fluorophenyl)-N-[4-[(E)-3-[4-[2-hydroxyethyl (methyl)amino]phenyl]prop-2-enoyl]phenyl]-5-methyl-1,2-oxazole-4-carboxamide; 89773493: 3-Bromo-N-[4-[(E)-3-[4-[2-hydroxyethyl(methyl)amino]phenyl]prop-2-enoyl] phenyl]benzamide; 89773494: N-[4-[(E)-3-[4-[2-Hydroxyethyl(methyl)amino]phenyl]prop-2-enoyl]phenyl]-3,5-bis(trifluoromethyl)benzamide; 89773495: 2-Fluoro-N-[4-[(E)-3-[4-[2-hydroxyethyl(methyl)amino]phenyl]prop-2-enoyl]phenyl]-4-(trifluoromethyl)benzamide; 89773496: 3-Fluoro-N-[4-[(E)-3-[4-[2-hydroxyethyl(methyl)amino] phenyl]prop-2-enoyl]phenyl]benzamide; 89773497: N-[4-[(E)-3-[4-[2-Hydroxyethyl(methyl)amino]phenyl]prop-2-enoyl]phenyl]-5-phenylfuran-2-carboxamide; 89773498: 5-Fluoro-N-[4-[(E)-3-[4-[2-hydroxyethyl(methyl)amino] phenyl]prop-2-enoyl]phenyl]-2-(trifluoromethyl)benzamide; 89773501: N-[4-[(E)-3-[4-[2-Hydroxyethyl (methyl) amino]phenyl]prop-2-enoyl]phenyl]-4-propylbenzamide; 89773502: 3-Fluoro-N-[4-[(E)-3-[4-[2-hydroxyethyl (methyl)amino]phenyl]prop-2-enoyl]phenyl]-4-(trifluoromethyl)benzamide; 89773503: N-[4-[(E)-3-[4-[2-Hydroxyethyl(methyl)amino]phenyl]prop-2-enoyl]phenyl]-2-iodobenzamide; 89773504: 3-Chloro-4-fluoro-N-[4-[(E)-3-[4-[2-hydroxyethyl(methyl)amino]phenyl]prop-2-enoyl] phenyl]benzamide; 89773505: N-[4-[(E)-3-[4-[2-Hydroxyethyl(methyl)amino]phenyl]prop-2-enoyl]phenyl]-3-phenylpropanamide; 89773506: N-[4-[(E)-3-[4-[2-Hydroxyethyl(methyl)amino]phenyl]prop-2-enoyl]phenyl]-4-pentylbenzamide; 89773507: 4-Chloro-2,3,5,6-tetrafluoro-N-[4-[(E)-3-[4-[2-hydroxyethyl (methyl)amino] phenyl]prop-2-enoyl]phenyl]benzamide; 89773508: 6-Chloro-N-[4-[(E)-3-[4-[2-hydroxyethyl(methyl)amino] phenyl]prop-2-enoyl]phenyl]hexanamide; 89773509: 2-Ethoxy-N-[4-[(E)-3-[4-[2-hydroxyethyl(methyl)amino] phenyl]prop-2-enoyl]phenyl]benzamide; 89773510: N-[4-[(E)-3-[4-[2-Hydroxyethyl(methyl)amino]phenyl]prop-2-enoyl]phenyl]-4-phenylbenzamide; 89773511: 2,3-Dichloro-N-[4-[(E)-3-[4-[2-hydroxyethyl(methyl)amino] phenyl]prop-2-enoyl]phenyl]benzamide; 89773512: 3,4-Dichloro-N-[4-[(E)-3-[4-[2-hydroxyethyl(methyl)amino] phenyl]prop-2-enoyl]phenyl]benzamide; 89773513: 4-Bromo-N-[4-[(E)-3-[4-[2-hydroxyethyl(methyl)amino] phenyl]prop-2-enoyl]phenyl]benzamide; 89773514: 2-Ethyl-N-[4-[(E)-3-[4-[2-hydroxyethyl(methyl)amino] phenyl]prop-2-enoyl]phenyl]hexanamide; 89773515: 2,4-Difluoro-N-[4-[(E)-3-[4-[2-hydroxyethyl(methyl)amino] phenyl]prop-2-enoyl]phenyl]benzamide; 89773516: 2-Chloro-6-fluoro-N-[4-[(E)-3-[4-[2-hydroxyethyl(methyl) amino]phenyl]prop-2-enoyl]phenyl]benzamide; 89773600: N-[4-[(E)-3-[4-[2-Hydroxyethyl(methyl)amino]phenyl] prop-2-enoyl]phenyl]-4-nonylbenzamide; 89773601: 2-Hydroxy-N-[4-[(E)-3-[4-[methyl(propyl)amino]phenyl]prop-2-enoyl]phenyl]benzamide; 89773602: 6-Chloro-2-fluoro-N-[4-[(E)-3-[4-[2-hydroxyethyl(methyl)amino]phenyl] prop-2-enoyl]phenyl]-3-methylbenzamide; 89773603: N-[4-[(E)-3-[4-[2-Hydroxyethyl(methyl)amino]phenyl] prop-2-enoyl]phenyl]pyrazine-2-carboxamide; 89773606: N-[4-[(E)-3-[4-[2-Hydroxyethyl(methyl)amino]phenyl] prop-2-enoyl]phenyl]-5-(2-nitro-phenyl)furan-2-carboxamide; 89773609: 3-Chloro-2,4-difluoro-N-[4-[(E)-3-[4-[2-hydroxyethyl(methyl)amino]phenyl]prop-2-enoyl]phenyl] benzamide; 89773610: 3,5-Dichloro-N-[4-[(E)-3-[4-[2-hydroxyethyl(methyl)amino]phenyl]prop-2-enoyl]phenyl] benzamide; 89773611: 5-(2-Chloro-5-nitro-phenyl)-N-[4-[(E)-3-[4-[2-hydroxyethyl(methyl)amino]phenyl]prop-2-enoyl]phenyl]furan-2-carboxamide; 89773612: N-[4-[(E)-3-[4-[2-Hydroxyethyl(methyl)amino]phenyl]prop-2-enoyl] phenyl]-3-methylbenzamide; 89773613: 6-Chloro-N-[4-[(E)-3-[4-[2-hydroxyethyl (methyl)amino]phenyl]prop-2-enoyl]phenyl]pyridine-3-carboxamide; 89773616: 2-Chloro-N-[4-[(E)-3-[4-[2-hydroxyethyl(methyl)amino] phenyl]prop-2-enoyl]phenyl]-6-methylpyridine-3-carboxamide; 89773617: 6-Bromo-N-[4-[(E)-3-[4-[2-hydroxyethyl (methyl)amino]phenyl]prop-2-enoyl]phenyl]hexanamide; 89773618: (E)-N-[4-[(E)-3-[4-[2-Hydroxyethyl(methyl) amino]phenyl]prop-2-enoyl]phenyl]but-2-enamide;

89773619: 5-(2,3-Dichlorophenyl)-N-[4-[(E)-3-[4-[2-hydroxyethyl(methyl)amino]phenyl]prop-2-enoyl]phenyl]furan-2-carboxamide; 89773620: N-[4-[(E)-3-[4-[2-Hydroxyethyl(methyl)amino]phenyl]prop-2-enoyl]phenyl]-5-methyl-1,2-oxazole-3-carboxamide; 89773621: N-[4-[(E)-3-[4-[2-Hydroxyethyl(methyl)amino]phenyl]prop-2-enoyl]phenyl]-5-methylfuran-2-carboxamide; 89773622: 3,4,5-Trichloro-N-[4-[(E)-3-[4-[2-hydroxyethyl(methyl)amino]phenyl]prop-2-enoyl]phenyl]thiophene-2-carboxamide; 89773623: N-[4-[(E)-3-[4-[2-Hydroxyethyl(methyl)amino]phenyl]prop-2-enoyl]phenyl]dodecanamide; 89773633: 3-Cyclopentyl-N-[4-[(E)-3-[4-[2-hydroxyethyl(methyl)amino]phenyl]prop-2-enoyl]phenyl]propanamide; 89773634: 5-(2-Fluorophenyl)-N-[4-[(E)-3-[4-[2-hydroxyethyl(methyl)amino]phenyl]prop-2-enoyl]phenyl]furan-2-carboxamide; 89773635: 4-Chloro-N-[4-[(E)-3-[4-[2-hydroxyethyl(methyl)amino]phenyl]prop-2-enoyl]phenyl]benzamide; 89773636: 2-(4-Fluorophenyl)-N-[4-[(E)-3-[4-[2-hydroxyethyl(methyl)amino]phenyl]prop-2-enoyl]phenyl]acetamide; 89773637: 2-[4-[(E)-3-[4-[2-Hydroxyethyl(methyl)amino]phenyl]prop-2-enoyl]phenyl]-1,2-benzoxazol-3-one; 89773638: 2,4,5-Trifluoro-N-[4-[(E)-3-[4-[2-hydroxyethyl(methyl)amino]phenyl]prop-2-enoyl]phenyl]benzamide; 89773639: 4-Fluoro-N-[4-[(E)-3-[4-[2-hydroxyethyl(methyl)amino]phenyl]prop-2-enoyl]phenyl]-2-(trifluoromethyl)benzamide; 89773640: N-[4-[(E)-3-[4-[2-Hydroxyethyl(methyl)amino]phenyl]prop-2-enoyl]phenyl]nonanamide; 89773641: 4-Fluoro-N-[4-[(E)-3-[4-[2-hydroxyethyl(methyl)amino]phenyl]prop-2-enoyl]phenyl]-3-methylbenzamide; 89773668: 4-Bromo-2-fluoro-N-[4-[(E)-3-[4-[2-hydroxyethyl(methyl)amino]phenyl]prop-2-enoyl]phenyl]benzamide; 89773669: 2-Fluoro-N-[4-[(E)-3-[4-[2-hydroxyethyl(methyl)amino]phenyl]prop-2-enoyl]phenyl]-5-iodobenzamide; 89773670: 3-Bromo-2,4,5,6-tetrafluoro-N-[4-[(E)-3-[4-[2-hydroxyethyl(methyl)amino]phenyl]prop-2-enoyl]phenyl]benzamide; 89773671: 2-Cyclopentyl-N-[4-[(E)-3-[4-[2-hydroxyethyl(methyl)amino]phenyl]prop-2-enoyl]phenyl]acetamide; 89773672: 3-Chloro-2,6-difluoro-N-[4-[(E)-3-[4-[2-hydroxyethyl(methyl)amino]phenyl]prop-2-enoyl]phenyl]benzamide; 89773673: 4-Amino-2-chloro-N-[4-[(E)-3-[4-[2-hydroxyethyl(methyl)amino]phenyl]prop-2-enoyl]phenyl]benzamide; 89773674: 2,3-Difluoro-N-[4-[(E)-3-[4-[2-hydroxyethyl(methyl)amino]phenyl]prop-2-enoyl]phenyl]benzamide; 89773675: N-[4-[(E)-3-[4-[2-Hydroxyethyl(methyl)amino]phenyl]prop-2-enoyl]phenyl]-5-methyl-3-phenyl-1,2-oxazole-4-carboxamide; 89773676: 3-Fluoro-N-[4-[(E)-3-[4-[2-hydroxyethyl(methyl)amino]phenyl]prop-2-enoyl]phenyl]-5-(trifluoro-methyl)benzamide; 89773677: (E)-3-[4-[2-Hydroxyethyl(methyl)amino]phenyl]-1-(4-methylphenyl)prop-2-en-1-one; 89773678: N-[4-[(E)-3-[4-[2-Hydroxyethyl(methyl)amino]phenyl]prop-2-enoyl]phenyl]cyclohex-2-ene-1-carboxamide; 89773679: 2-Chloro-3,6-difluoro-N-[4-[(E)-3-[4-[2-hydroxyethyl(methyl)amino]phenyl]prop-2-enoyl]phenyl]benzamide; 89773680: 4-Fluoro-N-[4-[(E)-3-[4-[2-hydroxyethyl(methyl)amino]phenyl]prop-2-enoyl]phenyl]benzamide; 89773681: N-[4-[(E)-3-[4-[2-Hydroxyethyl(methyl)amino]phenyl]prop-2-enoyl]phenyl]-3-methylthiophene-2-carboxamide; 89773682: 2-Fluoro-N-[4-[(E)-3-[4-[2-hydroxyethyl(methyl)amino]phenyl]prop-2-enoyl]phenyl]-6-(trifluoromethyl)benzamide; 89773683: Methyl 5-[4-[(E)-3-[4-[2-hydroxyethyl(methyl)amino]phenyl]prop-2-enoyl]anilino]-5-oxopentanoate; 89773685: 2-Chloro-N-[4-[(E)-3-[4-[2-hydroxyethyl(methyl)amino]phenyl]prop-2-enoyl]phenyl]-5-nitrobenzamide; 89773686: (E)-3-(2-Chlorophenyl)-N-[4-[(E)-3-[4-[2-hydroxyethyl(methyl)amino]phenyl]prop-2-enoyl]phenyl]prop-2-enamide; 89773687: N-[4-[(E)-3-[4-[2-Hydroxyethyl(methyl)amino]phenyl]prop-2-enoyl]phenyl]-4-iodobenzamide; 89773688: N-[4-[(E)-3-[4-[2-Hydroxyethyl(methyl)amino]phenyl]prop-2-enoyl]phenyl]-4-methoxy-3-(trifluoromethyl)benzamide; 89773689: N-[4-[(E)-3-[4-[2-Hydroxyethyl(methyl)amino]phenyl]prop-2-enoyl]phenyl]benzamide; 89773690: 2-(4-Chlorophenoxy)-N-[4-[(E)-3-[4-[2-hydroxyethyl(methyl)amino]phenyl]prop-2-enoyl]phenyl]acetamide; 89773691: 3-Chloro-6-fluoro-N-[4-[(E)-3-[4-[2-hydroxyethyl(methyl)amino]phenyl]prop-2-enoyl]phenyl]-1-benzothiophene-2-carboxamide; 89773692: 2-Ethoxy-N-[4-[(E)-3-[4-[2-hydroxyethyl(methyl)amino]phenyl]prop-2-enoyl]phenyl]naphthalene-1-carboxamide; 89773693: N-[4-[(E)-3-[4-[2-Hydroxyethyl(methyl)amino]phenyl]prop-2-enoyl]phenyl]decanamide; 89773694: 3-Chloro-N-[4-[(E)-3-[4-[2-hydroxyethyl(methyl)amino]phenyl]prop-2-enoyl]phenyl]benzamide; 89773695: N-[4-[(E)-3-[4-[2-Hydroxyethyl(methyl)amino]phenyl]prop-2-enoyl]phenyl]-3-(4-methoxyphenyl)propanamide; 89773696: 2,5-Difluoro-N-[4-[(E)-3-[4-[2-hydroxyethyl(methyl)amino]phenyl]prop-2-enoyl]phenyl]benzamide; 89773697: N-[4-[(E)-3-[4-[2-Hydroxyethyl(methyl)amino]phenyl]prop-2-enoyl]phenyl]-4-methoxybenzamide; 89773698: 4-Butyl-N-[4-[(E)-3-[4-[2-hydroxyethyl(methyl)amino]phenyl]prop-2-enoyl]phenyl]benzamide; 89773699: N-[4-[(E)-3-[4-[2-Hydroxyethyl(methyl)amino]phenyl]prop-2-enoyl]phenyl]cyclohexanecarboxamide; 89773701: N-[4-[(E)-3-[4-[2-Hydroxyethyl(methyl)amino]phenyl]prop-2-enoyl]phenyl]-4-(trifluoromethyl)benzamide; 89773702: [2-[4-[(E)-3-[4-[2-Hydroxyethyl(methyl)amino]phenyl]prop-2-enoyl]anilino]-2-oxoethyl] acetate; 89773703: 2-Chloro-N-[4-[(E)-3-[4-[2-hydroxyethyl(methyl)amino]phenyl]prop-2-enoyl]phenyl]benzamide; 89773704: N-[4-[(E)-3-[4-[2-Hydroxyethyl(methyl)amino]phenyl]prop-2-enoyl]phenyl]-2,3-dimethylbenzamide; 89773705: N-[4-[(E)-3-[4-[2-Hydroxyethyl(methyl)amino]phenyl]prop-2-enoyl]phenyl]pent-4-enamide; 89773714: 4-Acetamido-N-[4-[(E)-3-[4-[2-hydroxyethyl(methyl)amino]phenyl]prop-2-enoyl]phenyl]benzamide; 89773715: 2,3-Difluoro-N-[4-[(E)-3-[4-[2-hydroxyethyl(methyl)amino]phenyl]prop-2-enoyl]phenyl]-4-methylbenzamide; 89773717: 2,3,4,5,6-Pentafluoro-N-[4-[(E)-3-[4-[2-hydroxyethyl(methyl)amino]phenyl]prop-2-enoyl]phenyl]benzamide; 89773718: 2-Chloro-5-fluoro-N-[4-[(E)-3-[4-[2-hydroxyethyl(methyl)amino]phenyl]prop-2-enoyl]phenyl]benzamide; 89773719: N-[4-[(E)-3-[4-[2-Hydroxyethyl(methyl)amino]phenyl]prop-2-enoyl]phenyl]-3,4,5-trimethoxybenzamide; 89773721: 2,4,6-Trifluoro-N-[4-[(E)-3-[4-[2-hydroxyethyl(methyl)amino]phenyl]prop-2-enoyl]phenyl]benzamide; 89773722: N-[4-[(E)-3-[4-[2-Hydroxyethyl(methyl)amino]phenyl]prop-2-enoyl]phenyl]morpholine-4-carboxamide; 89773723: (E)-N-[4-[(E)-3-[4-[2-Hydroxyethyl(methyl)amino]phenyl]prop-2-enoyl]phenyl]-3-phenylprop-2-enamide; 89773869: (E)-1-(2,4-Dihydroxyphenyl)-3-(3,4-dimethylphenyl)prop-2-en-1-one; 89784764: Chembl4291487; 89795082: Chembl4291442; 89894234: (2S)-5,7-Dihydroxy-2-(4-hydroxyphenyl)-2,3-dihydrochromen-4-one;1,3-diphenylprop-2-en-1-one;(2R,3S,4R,5R)-2,3,4,5,6-pentahydroxyhexanal; 89898070: (E)-3-(4-Chlorophenyl)-1-[4-[(2R)-2-(2,4-difluorophenyl)-2-hydroxy-3-(1,2,4-triazol-1-yl)propoxy]phenyl]prop-2-en-1-one; 89900617: (E)-1-[4-[2-(2,4-Difluorophenyl)-2-hydroxy-3-(1,2,4-triazol-1-yl)propoxy]phenyl]-3-(4-methylphenyl)prop-2-en-1-one; 89911614: 2-[(E)-3-(3,4-Dimethylphenyl)prop-2-enoyl]benzoic acid; 89988197: (E)-1-[4-(Hydroxymethyl)phenyl]-3-phenylprop-2-en-1-one; 90090502: (E)-1-[4-(Hydroxymethyl)-2,6-dimethoxyphenyl]-3-[4-methyl-3-(trifluoromethyl)phenyl]prop-2-en-1-one; 90090513: (E)-1-[4-(Hydroxymethyl)phenyl]-3-[4-methyl-3-(trifluoromethyl)phenyl]prop-2-en-1-one; 90090514: (E)-1-[4-(Hydroxymethyl)-2-methoxyphenyl]-3-[4-methyl-3-(trifluoromethyl)phenyl]prop-2-en-1-one; 90090519: (E)-1-[4-(Hydroxymethyl)-2-methoxyphenyl]-3-(4-methylphenyl)prop-2-en-1-one; 90090520: (E)-1-[4-(Hydroxymethyl)phenyl]-3-(4-methylphenyl)prop-2-en-1-one; 90090524: (E)-1-[4-(Hydroxymethyl)-2,6-dimethoxyphenyl]-3-(4-methylphenyl)prop-2-en-1-one; 90123853: (E)-1-(2,4-Dihydroxyphenyl)-3-(3,4-dihydroxyphenyl)prop-2-en-1-one; (E)-1-(4-hydroxyphenyl)-3-phenylprop-2-en-1-one; 90128301: (E)-1-[2-Hydroxy-4,6-bis(phenyl-methoxy)phenyl]-3-[4-[2-[4-[(E)-3-[2-hydroxy-4,6-bis(phenylmethoxy)phenyl]-3-oxoprop-1-enyl]phenoxy]ethoxy]phenyl]prop-2-en-1-one; 90128302: (E)-1-[2-Hydroxy-4,6-bis(methoxymethoxy)phenyl]-3-[4-[2-[4-[(E)-3-[2-hydroxy-4,6-bis(methoxymethoxy)phenyl]-3-oxoprop-1-enyl]phenoxy]ethoxy]phenyl]prop-2-en-1-one; 90128850: 5-(2,5-Dioxooxolan-3-yl)-8-[2-[4-[hydroperoxy-[4-[(E)-3-oxo-3-phenylprop-1-enyl]phenyl]methyl]phenyl]-2-hydroxyethoxy]-3a,4,5,9b-tetrahydrobenzo[e][2]benzofuran-1,3-dione; 90128851: 5-(2,5-Dioxooxolan-3-yl)-8-[6-[4-[hydroperoxy-[4-[(E)-3-oxo-3-phenylprop-1-enyl]phenyl]methyl]phenyl]-6-hydroxy-hexoxy]-3a,4,5,9b-tetrahydrobenzo[e][2]benzofuran-1,3-dione; 90128853: 5-(2,5-Dioxooxolan-3-yl)-8-[6-hydroxy-6-[4-[[4-[(E)-3-oxo-3-phenylprop-1-enyl]phenoxy]methoxy]phenyl]hexoxy]-3a,4,5,9b-tetrahydrobenzo[e][2]benzofuran-1,3-dione; 90128860: 5-(2,5-Dioxooxolan-3-yl)-8-[2-hydroxy-2-[4-[[4-[(E)-3-oxo-3-phenylprop-1-enyl]phenoxy]methoxy]phenyl]ethoxy]-3a,4,5,9b-tetrahydrobenzo[e][2]benzofuran-1,3-dione; 90136149: (E)-3-(3-Hydroxy-4-methoxyphenyl)-1-[2-hydroxy-6-methoxy-4-[(2S,4R,5S)-3,4,5-trihydroxy-6-[[(2R,4S,5R)-3,4,5-trihydroxy-6-methyloxan-2-yl]oxymethyl]oxan-2-yl]oxyphenyl]prop-2-en-1-one; 90136515: (E)-3-[4-[(E)-2-(4-Hydroxy-3-methoxyphenyl)ethenyl]phenyl]-1-(4-propan-2-yloxyphenyl)prop-2-en-1-one; 90185872: (E)-1-(4-Bromophenyl)-3-(3,4-dihydroxyphenyl) prop-2-en-1-one; 90203356: 1,3-Diphenylprop-2-en-1-one;(3R,4S,5S,6R)-6-(hydroxy-methyl)oxane-2,3,4,5-tetrol; 90228063: (E)-1-(2-Hydroxy-6-methoxy-4-methylphenyl)-3-(3-nitro-phenyl)prop-2-en-1-one; 90336909: (E)-1-[2-Hydroxy-6-(methoxymethoxy)-4-methylphenyl]-3-[4-(methoxymethoxy)phenyl]prop-2-en-1-one; 90383482: (E)-1-[4-[2-(2,4-Difluorophenyl)-2-hydroxy-3-(1,2,4-triazol-1-yl)propoxy]phenyl]-3-(4-prop-2-ynoxyphenyl) prop-2-en-1-one; 90383546: (E)-1-[4-[2-(2,4-Difluorophenyl)-2-hydroxy-3-(1,2,4-triazol-1-yl)propoxy]phenyl]-3-[4-[[1-[2-(4-fluorophenyl)-2-hydroxy-3-(1,2,4-triazol-1-yl)propyl]triazol-4-yl]methoxy]phenyl]prop-2-en-1-one; 90401212: Propan-2-yl (2S)-2-[[[(2R,3R,4R,5R)-4-fluoro-3-hydroxy-5-(2-methoxy-2-methyl-6-oxo-1H-pyrimidin-3-yl)-4-methyloxolan-2-yl]methoxy-[4-[(E)-3-phenylprop-2-enoyl]phenoxy]phosphoryl]amino]propanoate; 90441656: (E)-1-(2-Hydroxyphenyl)-3-(3-nitro-4-phenylmethoxyphenyl)prop-2-en-1-one; 90441658: (E)-1-(2-Hydroxyphenyl)-3-(4-nitro-3-phenylmethoxyphenyl)prop-2-en-1-one; 90443593: (E)-3-(3-Butoxy-4-nitro-phenyl)-1-(2-hydroxyphenyl)prop-2-en-1-one; 90459356: (E)-1-(2-Hydroxy-6-(methoxymethoxy)phenyl)-3-(4-methoxy-3-(methoxymethoxy)phenyl)prop-2-en-1-one; 90459743: 3-[(E)-3-[2-Hydroxy-4,6-bis(methoxymethoxy)phenyl]-3-oxoprop-1-enyl]benzoic acid; 90470643: 2-Hydroxy-3-[2-[(E)-3-phenylprop-2-enoyl]phenyl]propanoate; 90470644: 2-Hydroxy-3-[2-[(E)-3-phenylprop-2-enoyl]phenyl]propanoic acid; 90656904: (Z)-3-(3,4-Dihydroxyphenyl)-1-(4-hydroxy-2-methoxyphenyl)prop-2-en-1-one; 90671757: 4-[(E)-3-[4-[(E)-3-(4-Carboxyphenyl)-3-oxoprop-1-enyl]phenyl]prop-2-enoyl]benzoic acid; 90677502: (E)-1-[4-[(2E)-3,7-Dimethylocta-2,6-dienoxy]phenyl]-3-(4-hydroxyphenyl)prop-2-en-1-one; 90681063: (E)-1-[2-Hydroxy-6-(4-methylpentoxy)phenyl]-3-(4-hydroxyphenyl) prop-2-en-1-one; 90681064: (E)-1-(2-Butoxy-6-hydroxyphenyl)-3-(4-hydroxyphenyl)prop-2-en-1-one; 90681065: (E)-1-[2-(3,3-Dimethylbutoxy)-6-hydroxyphenyl]-3-(4-hydroxyphenyl)prop-2-en-1-one; 90681066: (E)-1-[2-Hydroxy-6-(2-methylpropoxy)phenyl]-3-(4-hydroxy-phenyl)prop-2-en-1-one; 90681067: (E)-1-[2-(2-Ethylbutoxy)-6-hydroxyphenyl]-3-(4-hydroxyphenyl)prop-2-en-1-one; 90681068: (E)-1-[2-Hydroxy-6-(3-methylbut-2-enoxy)phenyl]-3-(4-hydroxyphenyl)prop-2-en-1-one; 90681069: (E)-1-[2-(Cyclopentylmethoxy)-6-hydroxyphenyl]-3-(4-hydroxyphenyl)prop-2-en-1-one; 90681070: (E)-1-[2-(2-Cyclopentyl-ethoxy)-6-hydroxyphenyl]-3-(4-hydroxyphenyl)prop-2-en-1-one; 90681071: (E)-1-[2-(2-Cyclohexylethoxy)-6-hydroxyphenyl]-3-(4-hydroxyphenyl) prop-2-en-1-one; 90681072: (E)-1-[2-(1-Adamantylmethoxy)-6-hydroxyphenyl]-3-(4-hydroxyphenyl)prop-2-en-1-one; 90681073: 4-[(E)-3-[2-(3,3-Dimethylbutoxy)-6-hydroxyphenyl]-3-oxoprop-1-enyl]benzoic acid; 90681074: 4-[(E)-3-[2-(3,3-Dimethylbutoxy)-6-hydroxyphenyl]-3-oxoprop-1-enyl]benzenesulfonamide; 90681075: (E)-1-[2-(3,3-Dimethylbutoxy)-6-methoxyphenyl]-3-(4-hydroxyphenyl)prop-2-en-1-one; 90686973: 3-[(E)-3-(4-Bromo-2-fluorophenyl)-3-oxoprop-1-enyl]benzoic acid; 90689593: 3-[3-(4-Bromo-2-fluorophenyl)-3-oxoprop-1-enyl]benzoic acid; 90694811: [4-[3-(4-Hydroxyphenyl)-3-oxoprop-1-enyl]phenyl] pyridine-3-carboxylate; 90736505: 2-Methyl-2-[4-[3-(4-methylsulfanylphenyl)prop-2-enoyl]phenyl]sulfanylpropanoic acid; 90738873: N-[4-[3-(4-Hydroxyphenyl)prop-2-enoyl]phenyl]acetamide; 90767710: 2-[3-(3,4-Dimethylphenyl)prop-2-enoyl]benzoic acid; 90782717: 2-[(1S)-5-[2-Chloro-4-(3-oxo-3-phenylprop-1-enyl)phenoxy]-2,3-dihydro-1H-inden-1-yl]acetic acid; 90813761: 1-(4-Bromophenyl)-3-(3-tert-butyl-4-hydroxyphenyl)prop-2-en-1-one; 90907501: 2-[4-[3-[4-(2,5-Dicarboxybenzoyl)oxyphenyl]-3-oxoprop-1-enyl]phenoxy]carbonylterephthalic acid; 90915225: 3-(4-Dodecoxyphenyl)-1-(2-hydroxyphenyl)prop-2-en-1-one; 90927185: 2-[4-[3-(2,4-Dihydroxyphenyl)-3-oxoprop-1-enyl]-2-methoxyphenoxy]acetic acid; 90936995: 2-[3-Hydroxy-4-[3-(3-hydroxyphenyl)prop-2-enoyl]phenoxy]-2-methylpropanoic acid; 90998593: 3-(3-Bromophenyl)-1-(2-hydroxy-6-methoxyphenyl)prop-2-en-1-one; 91019630: 2-Methyl-2-[4-[3-(4-methylsulfanylphenyl)-3-oxoprop-1-enyl]phenoxy]propanoic acid; 91045607: 2-[4-[3-(4-Bromophenyl)-3-oxoprop-1-enyl]-2-cyclohexylphenoxy]-2-methylpropanoic acid; 91063289: [4-[3-(4-Hydroxyphenyl)prop-2-enoyl]phenyl]methanesulfonic acid; 91104183: (2S)-5-Amino-2-[benzyl-[4-(3-oxo-3-phenylprop-1-enyl)benzoyl]amino]-5-oxopentanoic acid; 91126704: Ethane;(E)-1-(2-hydroxyphenyl)-3-(4-methylphenyl)prop-2-en-1-one; 91135546: 3-[2-Methyl-4-[3-oxo-3-(4-propylsulfanylphenyl)prop-1-enyl]phenoxy]propanoic acid; 91235012: 1,1,1-Trihydroxy-7-methyl-3-[[4-(3-oxo-3-phenylprop-1-enyl)phenyl]methyl]oct-6-en-2-one; 91237232: 3-[4-(3-Hydroxy-1,1-dioxo-2H-1,2,5-thiadiazol-5-yl)-3-phenylmethoxy-phenyl]-1-phenylprop-2-en-1-one; 91240644: 2-[3-(3-Thiophen-2-ylphenyl)prop-2-enoyl]benzoic acid; 91256138: 2-[4-[3-(4-Bromophenyl)-3-oxoprop-1-enyl]-2-(trifluoromethyl)phenoxy]-2-methylpropanoic acid acid; 91259271: 3-[4-[3-[4-(Hydroxymethyl)phenyl]-3-oxoprop-1-enyl]phenyl]-N-(oxan-2-yloxy)prop-2-enamide; 91271827: 2-[3-(4-Methoxy-3-methylphenyl)prop-2-enoyl] benzoic acid; 91291655: 2-[4-[3-(4-Bromophenyl)-3-oxoprop-1-enyl]-2-tert-butylphenoxy]-2-methylpropanoic acid; 91339893: [4-(2,5-Dihydroxy-3,4-dimethylpyrrol-1-yl)phenyl] 4-[4-(3-oxo-3-phenylprop-1-enyl)phenoxy]benzoate; 91345152: 2-Methyl-2-[4-[3-(4-methylsulfanylphenyl)-3-oxoprop-1-enyl]-2-(trifluoromethyl) phenoxy]propanoic acid; 91346739: 4-Hydroxy-4'-decyloxy-chalcone; 91359825: 2-Hydroxy-2-methyl-1-[4-[4-oxo-4-[4-[(E)-3-oxo-3-phenylprop-1-enyl]phenyl]butoxy]phenyl]propan-1-one;2-[4-(2-hydroxy-2-methylpropanoyl)phenoxy]ethyl 4-[(E)-3-oxo-3-phenylprop-1-enyl]benzoate; 91377096: 3-(3,4-Dihydroxyphenyl)-1-[4-hydroxy-2-[(2S,3R,4S,5S,6R)-3,4,5-trihydroxy-6-(hydroxymethyl)oxan-2-yl]peroxyphenyl]prop-2-en-1-one; 91391383: 3-[4-[4-Hydroxy-1,1-dioxo-5-(2-trimethylsilylethyl)-1,2,5-thiadiazol-2-yl]-3-phenylmethoxy-phenyl]-1-phenylprop-2-en-1-one; 91393592: Fluoroethane;3-[4-(fluoromethoxy)phenyl]-1-[4-(6-hydroxyhexoxy)phenyl]prop-2-en-1-one; 91412061: 3-(1-Benzofuran-5-yl)-1-(2-hydroxy-4-methylphenyl)prop-2-en-1-one; 91421601: 2-[4-[3-[3-(2,5-Dicarboxybenzoyl)oxyphenyl]prop-2-enoyl]phenoxy]carbonylterephthalic acid; 91424964: 3-Hydroxy-2-(3-phenylprop-2-enoyl)benzaldehyde; 91435153: 3-(3-Hydroxy-4-methoxyphenyl)-1-[2-hydroxy-6-methoxy-4-[(2S,4R,5S)-3,4,5-trihydroxy-6-[[(1R,3S,4S)-2,3,4-trihydroxy-5-methylcyclohexyl]oxymethyl]oxan-2-yl]oxyphenyl]prop-2-en-1-one; 91435429: 1-(2-Hydroxy-4,6-dimethoxyphenyl)-3-[4-[(2R,3R,4S,5S,6R)-3,4,5-trihydroxy-6-(hydroxymethyl) oxan-2-yl]oxyphenyl]prop-2-en-1-one; 91444588: 3-(4-Decoxyphenyl)-1-(2-hydroxyphenyl) prop-2-en-1-one; 91454387: 1-(2,4-Dihydroxyphenyl)-3-[4-hydroxy-3-[(2S,3R,4S,5S,6R)-3,4,5-trihydroxy-6-(hydroxymethyl)oxan-2-yl]oxyphenyl]prop-2-en-1-one; 91470514: (1,4-Dihydroxycyclohexyl)-(4-hydroxyphenyl)methanone;[4-[1-hydroxy-4-[4-[(E)-3-oxo-3-phenylprop-1-enyl]benzoyl]cyclohexanecarbonyl]phenyl] 4-[(E)-3-oxo-3-phenylprop-1-enyl]benzoate;4-(3-oxo-3-phenylpropyl)benzoyl chloride; 91489245: 2-[4-[3-(4-Chlorophenyl)prop-2-enoyl]-3-hydroxyphenoxy]-2-methylpropanoic acid; 91521627: 1-Azido-2-methoxy-4-(3-methoxy-4-methylphenyl)benzene;3-[(4-azidophenyl)methylidene]-5-[(4-methylphenyl) methylidene]-4-oxocyclohexane-1-carboxylic acid;2-[(4-azidophenyl)methylidene]-6-[(4-methylphenyl) methylidene]-4-trimethylsilylcyclohexan-1-one;(2E,6E)-2-[(Z)-3-(4-azidophenyl)prop-2-enylidene]-4-(hydroxymethyl)-6-[(Z)-3-(4-methylphenyl)prop-2-enylidene]cyclohexan-1-one;(2E,6E)-2-[(Z)-3-(4-azidophenyl)prop-2-enylidene]-4-hydroxy-6-[(Z)-3-(4-methylphenyl)prop-2-enylidene]cyclohexan-1-one;(Z)-1,3-bis(4-azidophenyl) prop-2-en-1-one; 91522557: 1-[2,6-Dihydroxy-4-[(2S,4R,5S)-3,4,5-trihydroxy-6-[[(2R,4S,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 91525355: 3-(4-Hydroxyphenyl)-1-[2-hydroxy-4-[(2S,3R,4R,5S,6R)-3,4,5-trihydroxy-6-(hydroxymethyl)oxan-2-yl]oxyphenyl] prop-2-en-1-one; 91536272: 4,4-Diethoxy-4-hydroxy-3-[4-[3-(2-hydroxyphenyl)-3-oxoprop-1-enyl]phenyl]-3-methylbutanoic acid; 91564428: 1-Azido-2-methoxy-4-(3-methoxy-4-methylphenyl)benzene;3-[(4-azidophenyl) methylidene]-5-[(4-methylphenyl)methylidene]-4-oxocyclo-hexane-1-carboxylic acid;2-[(4-azidophenyl) methylidene]-6-[(4-methylphenyl)methylidene]-4-trimethylsilylcyclohexan-1-one;(Z)-1-(4-azidophenyl)-3-(4-methylphenyl)prop-2-en-1-one;(2E,6E)-2-[(Z)-3-(4-azidophenyl)prop-2-enylidene]-4-(hydroxymethyl)-6-[(Z)-3-(4-methylphenyl)prop-2-enylidene]cyclohexan-1-one; (2E,6E)-2-[(Z)-3-(4-azidophenyl)prop-2-enylidene]-4-hydroxy-6-[(Z)-3-(4-methylphenyl)prop-2-enylidene] cyclohexan-1-one; 91574562: 2-[4-[3-(4-Hydroxyphenyl)-3-oxoprop-1-enyl]phenoxy]-2-methylpropanoic acid; 91609600: Fluoroethane;3-[4-(fluoromethoxy)phenyl]-1-(4-hydroxyphenyl)prop-2-en-1-one; 91649154: 3-[(E)-3-(4-Acetamidophenyl)-3-oxoprop-1-enyl]benzoic acid; 91746158: 2',6'-Dihydroxy-4-methoxychalcone-4'-O-neohesperidoside; 91801214: 1-[4-[(E)-3-[4-[Bis(2-hydroxyethyl)amino]phenyl]prop-2-enoyl]phenyl]-3-[(4-methoxyphenyl)methyl]urea; 91872142: 4',6'-Dimethylchalconaringenin; 91885998: (E)-3-Hydroxy-4-methoxy-2'-(3-fluorophenyl)chalcone; 91939809: 3-(3,4-Dimethoxyphenyl)-1-(2-hydroxy-4,6-dimethylphenyl)prop-2-en-1-one; 91939877: 4-[3-(2-Hydroxy-4-methylphenyl)-3-oxoprop-1-enyl]benzoic acid; 91939878: 4-[3-(2-Hydroxy-4-methoxyphenyl)-3-oxoprop-1-enyl]benzoic acid; 91941727: 1-(2-Hydroxy-4-methoxyphenyl)-3-(quinoxalin-6-yl)prop-2-en-1-one; 91941806: N-4-[3-(3-Chloro-4-hydroxyphenyl)prop-2-enoyl]phenyl-2,2,2-trifluoroacetamide; 91943170: 2-3-[3-(2,2,2-Trifluoroacetamido)phenyl]prop-2-enoylbenzoic acid; 91943206: 4-[3-(2-Bromo-4-fluorophenyl)-3-oxoprop-1-en-1-yl]benzoic acid; 91943207: 3-3-[3-(2-Bromo-4-fluorophenyl)-3-oxoprop-1-en-1-yl]phenoxypropanoic acid; 91944072: 4-[3-(2-Bromo-4-methoxyphenyl)-3-oxoprop-1-en-1-yl]benzoic acid; 91944230: 3-(2-Methoxy-4-3-[4-(2-methoxyethoxy)phenyl]-3-oxoprop-1-en-1-ylphenoxy)propanoic acid; 91944332: 3-[3-(4-Methoxyphenyl)-3-oxoprop-1-en-1-yl]benzoic acid; 92000611: Chalcone 4 (hydrate); 92035639: Propafenone Impurity B (EP/BP/USP); 92132543: (E)-1-[4-[(2S,3R,4S,5S,6R)-6-[[(2R,3R,4R,5R,6S)-3,5-Dihydroxy-4,6-dimethyloxan-2-yl]oxymethyl]-3,4,5-trihydroxyoxan-2-yl]oxy-2-hydroxy-6-methoxyphenyl]-3-(3-hydroxy-4-methoxyphenyl)prop-2-en-1-one; 92222123: (Z)-3-(3-Hydroxyphenyl)-1-phenylprop-2-en-1-one; 92223797: (E)-3-(4-Hydroxyphenyl)-1-[4-hydroxy-2-[(2R,3R,4R,5S,6S)-3,4,5-trihydroxy-6-(hydroxymethyl)oxan-2-yl]oxyphenyl]prop-2-en-1-one; 92223798: (E)-3-(4-Hydroxyphenyl)-1-[4-hydroxy-2-[(2R,3S,4R,5S,6S)-3,4,5-trihydroxy-6-(hydroxymethyl)oxan-2-yl]oxyphenyl]prop-2-en-1-one; 92224287: (Z)-3-(4-Chlorophenyl)-1-[2,4-dihydroxy-6-[(2S,3R,4R,5S,6S)-3,4,5-trihydroxy-6-(hydroxymethyl) oxan-2-yl]oxyphenyl]prop-2-en-1-one; 92224296: (E)-1-[2-Hydroxy-6-[(2R,3R,4R,5S,6S)-3,4,5-trihydroxy-6-(hydroxymethyl)oxan-2-yl]oxyphenyl]-3-(4-nitro-phenyl) prop-2-en-1-one; 92224297: (E)-1-[2-Hydroxy-6-[(2R,3S,4R,5S,6S)-3,4,5-trihydroxy-6-(hydroxymethyl)oxan-2-yl]oxyphenyl]-3-(4-nitro-phenyl)prop-2-en-1-one; 92257332: (Z)-3-(1,3-Benzodioxol-5-yl)-1-(2-hydroxy-4-methoxyphenyl)prop-2-en-1-one; 92281757: (Z)-1-(4-Hydroxyphenyl)-3-[4-[(Z)-3-(4-hydroxyphenyl)-3-oxoprop-1-enyl]phenyl]prop-2-en-1-one; 92338199: (Z)-1-(4-Chlorophenyl)-3-(4-hydroxyphenyl)prop-2-en-1-one; 92339931: (Z)-3-[4-(Dimethylamino)phenyl]-1-(4-hydroxyphenyl)prop-2-en-1-one; 92442249: (Z)-1-(2-Hydroxy-4,6-dimethoxyphenyl)-3-phenylprop-2-en-1-one; 92449532: (Z)-1-(2-Hydroxyphenyl)-3-(4-hydroxyphenyl)prop-2-en-1-one; 92468371: (Z)-1-(2-Hydroxy-4,6-dimethoxyphenyl)-3-(3-hydroxy-4-methoxyphenyl)prop-2-en-1-one; 92468372: (Z)-3-(3,4-Dimethoxyphenyl)-1-(2-hydroxy-4,6-dimethoxyphenyl)prop-2-en-1-one; 92525091: (Z)-3-(4-Hydroxyphenyl)-1-(4-methoxyphenyl)prop-2-en-1-one; 92529819: (Z)-3-(4-Chloro-phenyl)-1-(2-hydroxyphenyl)

prop-2-en-1-one; 92530720: (Z)-1-(2-Hydroxy-4,6-dimethoxy-phenyl)-3-(4-methoxy-3-phenylmethoxyphenyl)prop-2-en-1-one; 92532293: (Z)-3-(1,3-Benzodioxol-5-yl)-1-(2,4-dihydroxyphenyl)prop-2-en-1-one; 92532294: (Z)-1-(2-Hydroxy-4,6-dimethoxyphenyl)-3-(4-methoxyphenyl) prop-2-en-1-one; 92533106: (Z)-1-(2-Hydroxy-phenyl)-3-(3-hydroxyphenyl)prop-2-en-1-one; 92533997: (Z)-1-(2-Hydroxy-4-methoxy-phenyl)-3-phenylprop-2-en-1-one; 92533998: (Z)-1-(2-Hydroxyphenyl)-3-[4-[(E)-3-(2-hydroxyphenyl)-3-oxoprop-1-enyl]phenyl]prop-2-en-1-one; 92842624: (E)-3-(4-Hydroxy-phenyl)-1-[4-hydroxy-2-[(2R,3S,4S,5S,6S)-3,4,5-trihydroxy-6-(hydroxymethyl)oxan-2-yl]oxyphenyl]prop-2-en-1-one; 92842626: (E)-3-(4-Hydroxyphenyl)-1-[4-hydroxy-2-[(2R,3R,4S,5S,6S)-3,4,5-trihydroxy-6-(hydroxymethyl)oxan-2-yl]oxyphenyl]prop-2-en-1-one; 92842678: (E)-1-[2-Hydroxy-6-[(2R,3S,4S,5S,6S)-3,4,5-trihydroxy-6-(hydroxymethyl)oxan-2-yl]oxyphenyl]-3-(4-nitro-phenyl)prop-2-en-1-one; 92842680: (E)-1-[2-Hydroxy-6-[(2R,3R,4S,5S,6S)-3,4,5-trihydroxy-6-(hydroxymethyl)oxan-2-yl]oxyphenyl]-3-(4-nitro-phenyl) prop-2-en-1-one; 92852016: (Z)-3-(3,4-Dimethoxyphenyl)-1-(2-hydroxyphenyl) prop-2-en-1-one; 92852019: (Z)-1-(2,4-Dihydroxy-6-methoxyphenyl)-3-phenylprop-2-en-1-one; 92852039: (Z)-3-(4-Hydroxyphenyl)-1-(2,4,6-trimethoxyphenyl)prop-2-en-1-one; 92855576: (Z)-3-(4-Hydroxy-3-methoxyphenyl)-1-phenylprop-2-en-1-one; 92855761: (Z)-3-(4-Chlorophenyl)-1-(4-hydroxyphenyl)prop-2-en-1-one; 92855831: 4-[(Z)-3-[4-(Carboxy-methoxy)phenyl]-3-oxoprop-1-enyl]benzoic acid; 92857967: (Z)-1-(4-Hydroxyphenyl)-3-[4-[(E)-3-(4-hydroxyphenyl)-3-oxoprop-1-enyl]phenyl]prop-2-en-1-one; 92857991: 2-[4-[(Z)-3-(4-Methoxyphenyl)-3-oxoprop-1-enyl]phenoxy]acetic acid; 92859124: (Z)-3-(3-Chloro-phenyl)-1-(2-hydroxyphenyl) prop-2-en-1-one; 92859128: (Z)-3-(4-Bromophenyl)-1-(2-hydroxyphenyl)prop-2-en-1-one; 92861039: (Z)-1-(4-Fluorophenyl)-3-(4-hydroxyphenyl) prop-2-en-1-one; 92908276: (Z)-1-(4-Chlorophenyl)-3-(3-hydroxyphenyl) prop-2-en-1-one; 92908280: 2-[(Z)-3-(4-Nitrophenyl)prop-2-enoyl]benzoic acid; 92908702: 4-[(Z)-3-(2-Hydroxyphenyl)-3-oxoprop-1-enyl]benzonitrile; 92908729: (Z)-1-(2-Hydroxy-4-methylphenyl)-3-phenylprop-2-en-1-one; 92908731: (Z)-1-(2-Hydroxy-4-phenylmethoxyphenyl)-3-phenylprop-2-en-1-one; 92908741: (Z)-3-(3,4-Dichlorophenyl)-1-(4-hydroxyphenyl)prop-2-en-1-one; 92908742: (Z)-1-(4-Chlorophenyl)-3-(3-hydroxy-4-methoxyphenyl)prop-2-en-1-one; 92908743: (Z)-1-(4-Chlorophenyl)-3-(4-hydroxy-3-methoxyphenyl)prop-2-en-1-one; 92908927: (Z)-1-(2-Hydroxy-4-phenylmethoxyphenyl)-3-(4-methoxyphenyl)prop-2-en-1-one; 92908960: (Z)-3-(3,4-Dihydro-2H-1,5-benzodioxepin-7-yl)-1-(2-hydroxyphenyl)prop-2-en-1-one; 92908966: (Z)-1-(4-Chloro-2-hydroxyphenyl)-3-(2,3-dihydro-1,4-benzodioxin-6-yl)prop-2-en-1-one; 92908967: (Z)-3-(2,3-Dihydro-1,4-benzodioxin-6-yl)-1-(2-hydroxy-6-methoxy-phenyl)prop-2-en-1-one; 92908968: (Z)-1-(2-Hydroxy-4-methoxyphenyl)-3-(3-hydroxy-4-methoxyphenyl)prop-2-en-1-one; 92908969: (Z)-1-(2-Hydroxy-4-methoxyphenyl)-3-(3-hydroxyphenyl)prop-2-en-1-one; 92908981: (Z)-3-(4-Fluorophenyl)-1-(2-hydroxyphenyl) prop-2-en-1-one; 92908994: (Z)-1-(2-Hydroxy-6-methoxyphenyl)-3-(4-hydroxyphenyl)prop-2-en-1-one; 92909038: (Z)-1-(2-Chlorophenyl)-3-(4-hydroxyphenyl)prop-2-en-1-one; 92909373: 2-[4-[(Z)-3-(4-Chlorophenyl)prop-2-enoyl]phenoxy]acetic acid; 92910098: 1,3-Dioxo-2-[4-[(Z)-3-oxo-3-phenylprop-1-enyl]phenyl]isoindole-5-carboxylic acid; 92913569: (Z)-3-[3-(Benzotriazol-1-ylmethyl)-4-methoxyphenyl]-1-(4-hydroxyphenyl)prop-2-en-1-one; 92931357: (Z)-1-(2,4-Dichlorophenyl)-3-(4-hydroxy-3-nitro-phenyl)prop-2-en-1-one; 92932030: (2S)-2-[4-[(Z)-3-(4-Ethylphenyl)prop-2-enoyl]phenoxy]propanoic acid; 92932031: (2R)-2-[4-[(Z)-3-(4-Ethylphenyl)prop-2-enoyl]phenoxy]propanoic acid; 92937839: (Z)-1-(4-Hydroxyphenyl)-3-(3-phenoxyphenyl) prop-2-en-1-one; 92945015: N,N-Diethyl-2-[4-[(Z)-3-(3-hydroxyphenyl)prop-2-enoyl]phenoxy]acetamide; 92945693: (Z)-3-(4-Fluorophenyl)-1-(2-hydroxy-4,6-dimethoxyphenyl)prop-2-en-1-one; 92955585: (Z)-1-(4-Hydroxyphenyl)-3-(3-methoxy-4-phenylmethoxyphenyl)prop-2-en-1-one; 92958678: (Z)-1-(2-Hydroxy-4-phenylmethoxyphenyl)-3-(4-phenylmethoxyphenyl)prop-2-en-1-one; 92959530: (Z)-1-(4-Ethoxy-2-hydroxyphenyl)-3-(3-ethoxy-4-methoxyphenyl)prop-2-en-1-one; 92961508: 2-[4-[(Z)-3-(4-Nitrophenyl)-3-oxoprop-1-enyl]phenoxy]acetic acid; 92963683: (Z)-1-(2-Hydroxy-4,6-dimethoxyphenyl)-3-(4-hydroxyphenyl)prop-2-en-1-one; 92964935: (2S)-2-[[4-[(Z)-3-(4-Chlorophenyl)prop-2-enoyl]phenyl]sulfonylamino]propanoic acid; 92964936: (2R)-2-[[4-[(Z)-3-(4-Chlorophenyl)prop-2-enoyl]phenyl]sulfonylamino]propanoic acid; 93009475: 4-[(Z)-3-[4-(Difluoromethoxy)phenyl]-3-oxoprop-1-enyl]benzoic acid; 93022957: 3-Hydroxy-4'-methyl-cis-chalcone; 93030641: (Z)-1-(4-Aminophenyl)-3-(4-hydroxyphenyl)prop-2-en-1-one; 93030730: (Z)-3-[3-(1,3-Benzothiazol-2-ylsulfanylmethyl)-4-methoxyphenyl]-1-(4-hydroxyphenyl)prop-2-en-1-one; 93032538: (Z)-1-(4-Hydroxyphenyl)-3-(4-propan-2-ylphenyl)prop-2-en-1-one; 93045973: (Z)-3-(4-Hydroxyphenyl)-1-(4-morpholin-4-ylsulfonylphenyl)prop-2-en-1-one; 93046488: [5-[(Z)-3-(2-Hydroxy-4-methoxyphenyl)-3-oxoprop-1-enyl]-2-methoxyphenyl] acetate; 93054566: 2-[(Z)-3-Phenylacryloyl]benzoic acid; 93056580: (E)-3-(4-Chlorophenyl)-1-[2,4-dihydroxy-6-[(2S,3R,4R,5S,6S)-3,4,5-trihydroxy-6-(hydroxymethyl)oxan-2-yl]oxyphenyl]prop-2-en-1-one; 93092790: (Z)-3-[3-[(3,5-Dimethyl-4-nitropyrazol-1-yl)methyl]-4-methoxyphenyl]-1-(2-hydroxyphenyl)prop-2-en-1-one; 93286399: (Z)-3-(4-Chlorophenyl)-1-[2,4-dihydroxy-6-[(2S,3S,4R,5S,6S)-3,4,5-trihydroxy-6-(hydroxy-methyl)oxan-2-yl]oxyphenyl] prop-2-en-1-one; 93286400: (E)-3-(4-Chlorophenyl)-1-[2,4-dihydroxy-6-[(2S,3S,4R,5S,6S)-3,4,5-trihydroxy-6-(hydroxymethyl)oxan-2-yl]oxyphenyl]prop-2-en-1-one; 94186364: 4-[(Z)-3-(4-Morpholin-4-ylphenyl)-3-oxoprop-1-enyl]benzoic acid; 94186369: (Z)-3-(3-Ethoxy-4-hydroxyphenyl)-1-(4-morpholin-4-ylphenyl)prop-2-en-1-one; 94805790: (2S)-2-[3-[(E)-3-(4-Cyanophenyl)-3-oxoprop-1-enyl]phenoxy]propanoic acid; 94805791: (2R)-2-[3-[(E)-3-(4-Cyanophenyl)-3-oxoprop-1-enyl]phenoxy]propanoic acid; 95153520: N-[4-[(Z)-3-(4-Hydroxy-3-methoxyphenyl)prop-2-enoyl]phenyl]methanesulfonamide; 95165054: 2-[4-[(Z)-3-(3,4-Dichlorophenyl)prop-2-enoyl]phenoxy] acetic acid; 95241916: (Z)-3-[4-[(2S)-3-Chloro-2-hydroxypropoxy]phenyl]-1-phenylprop-2-en-1-one; 95241917: (E)-3-[4-[(2S)-3-Chloro-2-hydroxypropoxy]phenyl]-1-phenylprop-2-en-1-one; 95241918: (Z)-3-[4-[(2R)-3-Chloro-2-hydroxypropoxy]phenyl]-1-phenylprop-2-en-1-one; 95241919: (E)-3-[4-[(2R)-3-Chloro-2-hydroxypropoxy]phenyl]-1-phenylprop-2-en-1-one; 95241920: (Z)-3-[4-(2-Hydroxyethoxy)phenyl]-1-phenylprop-2-en-1-one; 95241947: (Z)-1-[4-[(2R)-2-Hydroxy-3-[4-[(Z)-3-oxo-3-phenylprop-1-enyl]phenoxy]propoxy]phenyl]-3-phenylprop-2-en-1-one; 95241949: (E)-1-[4-[(2R)-2-Hydroxy-3-[4-[(Z)-3-oxo-3-phenylprop-1-enyl]phenoxy]propoxy]phenyl]-3-phenylprop-2-en-1-one; 95241953: (E)-1-[4-[(2R)-2-Hydroxy-3-[4-[(E)-3-oxo-3-phenylprop-1-enyl]phenoxy]propoxy]phenyl]-3-phenylprop-2-en-1-one; 95479011: (Z)-3-(4-Butylphenyl)-1-(4-hydroxyphenyl)

prop-2-en-1-one; 96882331: (Z)-3-(3-Hydroxy-4-methoxyphenyl)-1-phenylprop-2-en-1-one; 97303693: (Z)-3-(3-Hydroxyphenyl)-1-(2-phenylmethoxyphenyl)prop-2-en-1-one; 97304558: (Z)-3-(3-Hydroxy-4-methoxyphenyl)-1-(2-phenylmethoxyphenyl)prop-2-en-1-one; 97433495: (Z)-3-(3-Hydroxyphenyl)-1-[4-(2-methoxyethoxy)phenyl]prop-2-en-1-one; 97456120: (Z)-3-(3-Hydroxyphenyl)-1-[4-[(1-methylimidazol-2-yl)methoxy]phenyl]prop-2-en-1-one; 97462456: N-[4-[(Z)-3-(3-Hydroxyphenyl)prop-2-enoyl]phenyl]methanesulfonamide; 97464379: N-[4-[(Z)-3-(3-Hydroxyphenyl)prop-2-enoyl]phenyl]ethanesulfonamide; 97510442: (2S)-2-[4-[(Z)-3-(3-Hydroxyphenyl)prop-2-enoyl]phenoxy]propanoic acid; 97510443: (2R)-2-[4-[(Z)-3-(3-Hydroxyphenyl)prop-2-enoyl]phenoxy]propanoic acid; 97517226: N-[4-[(Z)-3-(3-Hydroxy-4-methoxyphenyl)prop-2-enoyl]phenyl]methanesulfonamide; 97525701: (Z)-1-[4-(4-Hydroxypiperidin-1-yl)phenyl]-3-(4-methoxyphenyl)prop-2-en-1-one; 97525702: (Z)-1-[4-(4-Hydroxypiperidin-1-yl)phenyl]-3-(3-methoxyphenyl)prop-2-en-1-one; 97538418: 4-[(Z)-3-(2-Fluoro-4-hydroxyphenyl)-3-oxoprop-1-enyl]benzonitrile; 97538552: (Z)-3-(3-Hydroxy-4-methoxyphenyl)-1-(4-imidazol-1-ylphenyl)prop-2-en-1-one; 97539352: 2-[4-[(Z)-3-Oxo-3-(4-phenylphenyl)prop-1-enyl]phenoxy]acetic acid; 97539362: 2-[4-[(Z)-3-(3-Hydroxy-4-methoxyphenyl)prop-2-enoyl]phenoxy]acetonitrile; 97539904: (Z)-1-(4-Fluorophenyl)-3-(3-hydroxyphenyl)prop-2-en-1-one; 97540012: 2-[4-[(Z)-3-(3-Cyanophenyl)prop-2-enoyl]phenoxy]acetic acid; 97540682: 3-[4-[(Z)-3-(4-Cyanophenyl)-3-oxoprop-1-enyl]phenoxy]propanoic acid; 97540821: (Z)-3-(3-Hydroxy-4-methoxyphenyl)-1-[4-(2-methoxyethoxy)phenyl]prop-2-en-1-one; 97540826: 4-[(Z)-3-[4-(2-Methoxyethoxy)phenyl]-3-oxoprop-1-enyl]benzoic acid; 97543153: Methyl 2-[4-[(Z)-3-(3-hydroxy-4-methoxyphenyl) prop-2-enoyl]phenoxy]acetate; 97543154: Methyl 2-[4-[(Z)-3-(3-hydroxyphenyl)prop-2-enoyl]phenoxy]acetate; 97543257: (2S)-2-[3-[(Z)-3-(4-Cyanophenyl)-3-oxoprop-1-enyl]phenoxy]propanoic acid; 97543258: (2R)-2-[3-[(Z)-3-(4-Cyanophenyl)-3-oxoprop-1-enyl]phenoxy]propanoic acid; 97543259: 3-[3-[(Z)-3-(4-Cyanophenyl)-3-oxoprop-1-enyl]phenoxy]propanoic acid; 97543456: 4-[(Z)-3-[4-[2-(Dimethylamino)ethoxy]phenyl]-3-oxoprop-1-enyl]benzoic acid; 97545228: (Z)-1-[4-(Azepan-1-ylsulfonyl)phenyl]-3-(3,4-dihydroxyphenyl)prop-2-en-1-one; 97555328: 4-[(Z)-3-[4-(2-Carboxyethylsulfamoyl)phenyl]-3-oxoprop-1-enyl]benzoic acid; 97555329: 3-[[4-[(Z)-3-(3-Hydroxyphenyl)prop-2-enoyl]phenyl]sulfonylamino]propanoic acid; 97555330: 3-[[4-[(Z)-3-(4-Tert-butylphenyl)prop-2-enoyl]phenyl]sulfonylamino]propanoic acid; 97555749: 3-[3-[(Z)-3-(4-Hydroxyphenyl)-3-oxoprop-1-enyl]phenoxy]propanoic acid; 97555790: 4-[(Z)-3-[4-(Methanesulfonamido)phenyl]-3-oxoprop-1-enyl]benzoic acid; 97556068: (Z)-1-[4-(Dimethylamino)phenyl]-3-(3-ethoxy-4-hydroxyphenyl)prop-2-en-1-one; 97556070: 3-[[4-[(Z)-3-(4-Propan-2-ylphenyl)prop-2-enoyl]phenyl]sulfonylamino]propanoic acid; 97558694: (2S)-2-[4-[(Z)-3-(4-Methoxyphenyl)prop-2-enoyl]phenoxy]propanoic acid; 97558695: (2R)-2-[4-[(Z)-3-(4-Methoxyphenyl)prop-2-enoyl]phenoxy]propanoic acid; 97558696: 2-[4-[(Z)-3-(4-Chloro-phenyl)-3-oxoprop-1-enyl]phenoxy]acetic acid; 97558703: 2-[4-[(Z)-3-(4-Acetamidophenyl) prop-2-enoyl]phenoxy]acetic acid; 97631727: (Z)-1-(2-Hydroxyphenyl)-3-[4-methoxy-3-(morpholin-4-ylmethyl)phenyl]prop-2-en-1-one; 97644282: (2S)-2-[4-[(Z)-3-(4-Nitrophenyl) prop-2-enoyl]phenoxy]propanoic acid; 97644283: (2R)-2-[4-[(Z)-3-(4-Nitrophenyl)prop-2-enoyl]phenoxy]propanoic acid; 97644377: 4-[(Z)-3-[4-(Azepan-1-yl)phenyl]-3-oxoprop-1-enyl]benzoic acid; 97644522: 3-[[4-[(Z)-3-(3-Nitrophenyl)prop-2-enoyl]phenyl]sulfonylamino]propanoic acid; 97644523: 3-[[4-[(Z)-3-(4-Nitrophenyl)prop-2-enoyl]phenyl]sulfonylamino]propanoic acid; 97644736: (Z)-1-(4-Hydroxyphenyl)-3-(6-methoxynaphthalen-2-yl)prop-2-en-1-one; 97645563: (Z)-1-(4-Tert-butylphenyl)-3-(3-hydroxy-4-methoxyphenyl)prop-2-en-1-one; 97646697: 2-[4-[(Z)-3-(4-Nitrophenyl)prop-2-enoyl]phenoxy]acetic acid; 97646703: 2-[4-[(Z)-3-[3-Methoxy-4-(4-methylphenyl)sulfonyloxyphenyl]prop-2-enoyl]phenoxy]acetic acid; 97741678: (Z)-3-[3-[(2-Cyclohexylphenoxy)methyl]-4-methoxyphenyl]-1-(4-hydroxyphenyl) prop-2-en-1-one; 97893922: 5-[(Z)-3-(4-Chlorophenyl)-3-oxoprop-1-enyl]-2-hydroxybenzoic acid; 97893923: Methyl 2-hydroxy-5-[(Z)-3-oxo-3-phenylprop-1-enyl]benzoate; 97893924: Methyl 5-[(Z)-3-(4-chlorophenyl)-3-oxoprop-1-enyl]-2-hydroxybenzoate; 97966519: (Z)-1-(4-Fluorophenyl)-3-(4-hydroxy-3-methoxyphenyl)prop-2-en-1-one; 97976025: (Z)-3-(4-Hydroxy-3-nitro-phenyl)-1-[4-(2-methoxyethoxy)phenyl]prop-2-en-1-one; 98040435: (Z)-1-[4-[(2R)-2-Hydroxy-3-[4-[(E)-3-oxo-3-phenylprop-1-enyl]phenoxy]propoxy]phenyl]-3-phenylprop-2-en-1-one; 98052074: (E)-3-(3-Hydroxy-4-methoxyphenyl)-1-[2-hydroxy-6-methoxy-4-[(2S,3S,4S,5R,6R)-3,4,5-trihydroxy-6-[[(2R,3S,4S,5R,6R)-3,4,5-trihydroxy-6-methyloxan-2-yl]oxymethyl]oxan-2-yl]oxyphenyl]prop-2-en-1-one; 98052075: (E)-3-(3-Hydroxy-4-methoxyphenyl)-1-[2-hydroxy-6-methoxy-4-[(2S,3S,4S,5R,6R)-3,4,5-trihydroxy-6-[[(2R,3S,4S,5R,6S)-3,4,5-trihydroxy-6-methyloxan-2-yl]oxymethyl]oxan-2-yl]oxyphenyl]prop-2-en-1-one; 98052076: (E)-3-(3-Hydroxy-4-methoxyphenyl)-1-[2-hydroxy-6-methoxy-4-[(2S,3S,4S,5R,6R)-3,4,5-trihydroxy-6-[[(2R,3S,4S,5S,6R)-3,4,5-trihydroxy-6-methyloxan-2-yl]oxymethyl]oxan-2-yl]oxyphenyl]prop-2-en-1-one; 98052077: (E)-3-(3-Hydroxy-4-methoxy-phenyl)-1-[2-hydroxy-6-methoxy-4-[(2S,3S,4S,5R,6R)-3,4,5-trihydroxy-6-[[(2R,3S,4S,5S,6S)-3,4,5-trihydroxy-6-methyloxan-2-yl]oxymethyl]oxan-2-yl]oxyphenyl]prop-2-en-1-one; 98072666: (E)-1-[4-[(2S,3R,4R,5S,6S)-4,5-Dihydroxy-6-(hydroxymethyl)-3-[(2S,3S,4S,5R,6R)-3,4,5-trihydroxy-6-methyloxan-2-yl]oxyoxan-2-yl]oxy-2,6-dihydroxyphenyl]-3-(4-methoxyphenyl)prop-2-en-1-one; 98072668: (E)-1-[4-[(2S,3R,4R,5S,6S)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 98072669: (E)-1-[4-[(2S,3R,4R,5S,6S)-4,5-Dihydroxy-6-(hydroxymethyl)-3-[(2S,3R,4S,5R,6R)-3,4,5-trihydroxy-6-methyl-oxan-2-yl]oxyoxan-2-yl]oxy-2,6-dihydroxyphenyl]-3-(4-methoxyphenyl)prop-2-en-1-one; 98072671: (E)-1-[4-[(2S,3R,4R,5S,6S)-4,5-Dihydroxy-6-(hydroxymethyl)-3-[(2S,3R,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 98116796: (E)-1-[4-[(2R,3R,4R,5S,6S)-4,5-Dihydroxy-6-(hydroxymethyl)-3-[(2S,3S,4S,5R,6R)-3,4,5-trihydroxy-6-methyloxan-2-yl]oxyoxan-2-yl]oxy-2,6-dihydroxyphenyl]-3-(3-hydroxy-4-methoxyphenyl)prop-2-en-1-one; 98116797: (E)-1-[4-[(2R,3R,4R,5S,6S)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(3-hydroxy-4-methoxyphenyl) prop-2-en-1-one; 98116798: (E)-1-[4-[(2R,3R,4R,5S,6S)-4,5-Dihydroxy-6-(hydroxymethyl)-3-[(2S,3S,4S,5S,6R)-3,4,5-trihydroxy-6-methyloxan-2-yl]oxyoxan-2-yl]oxy-2,6-dihydroxy-phenyl]-3-(3-hydroxy-4-methoxyphenyl)prop-2-en-1-one; 98116799: (E)-1-[4-[(2R,3R,4R,5S,6S)-4,5-Dihydroxy-6-(hydroxymethyl)-3-[(2S,3S,4S,5S,6S)-3,4,5-trihydroxy-6-methyl-oxan-2-yl]

oxyoxan-2-yl]oxy-2,6-dihydroxyphenyl]-3-(3-hydroxy-4-methoxyphenyl)prop-2-en-1-one; 98218659: (Z)-1-(2-Hydroxy-6-methoxyphenyl)-3-phenylprop-2-en-1-one; 98328610: (Z)-4-[4-[(Z)-3-[4-[(E)-3-[4-[[(E)-3-Carboxyprop-2-enoyl]amino]phenyl]-3-oxoprop-1-enyl]phenyl]prop-2-enoyl]anilino]-4-oxobut-2-enoic acid; 98527966: (E)-3-(3-Hydroxy-4-methoxy-phenyl)-1-[2-hydroxy-6-methoxy-4-[(2R,3R,4R,5S,6S)-3,4,5-trihydroxy-6-[[(2R,5S)-5-hydroxyoxan-2-yl]oxymethyl]oxan-2-yl]oxyphenyl]prop-2-en-1-one; 98527968: (E)-3-(3-Hydroxy-4-methoxyphenyl)-1-[2-hydroxy-6-methoxy-4-[(2S,3R,4R,5S,6S)-3,4,5-trihydroxy-6-[[(2R,5S)-5-hydroxyoxan-2-yl]oxymethyl]oxan-2-yl]oxyphenyl]prop-2-en-1-one; 98527969: (E)-3-(3-Hydroxy-4-methoxyphenyl)-1-[2-hydroxy-6-methoxy-4-[(2R,3S,4R,5S,6S)-3,4,5-trihydroxy-6-[[(2R,5S)-5-hydroxyoxan-2-yl]oxymethyl]oxan-2-yl]oxyphenyl]prop-2-en-1-one; 98527970: (E)-3-(3-Hydroxy-4-methoxyphenyl)-1-[2-hydroxy-6-methoxy-4-[(2S,3S,4R,5S,6S)-3,4,5-trihydroxy-6-[[(2R,5S)-5-hydroxyoxan-2-yl]oxymethyl]oxan-2-yl]oxyphenyl]prop-2-en-1-one; 98822160: (Z)-3-(4-Chlorophenyl)-1-(2-hydroxy-4,6-dimethoxyphenyl)prop-2-en-1-one; 98906392: 2-[4-[(Z)-3-Phenylprop-2-enoyl]phenyl]acetic acid; 99615397: 3-[(E)-3-(2-Fluoro-6-morpholin-4-ylphenyl)-3-oxoprop-1-enyl]benzoic acid; 99947316: (E)-3-(4-Hydroxy-phenyl)-1-[4-hydroxy-2-[(2R,3S,4R,5R,6R)-3,4,5-trihydroxy-6-(hydroxymethyl)oxan-2-yl]oxyphenyl]prop-2-en-1-one; 99947328: (E)-1-[2-Hydroxy-6-[(2R,3S,4R,5R,6R)-3,4,5-trihydroxy-6-(hydroxymethyl)oxan-2-yl]oxyphenyl]-3-(4-nitro-phenyl)prop-2-en-1-one; 100675245: 4-[(E)-3-[4-(4-Hydroxypiperidin-1-yl)phenyl]-3-oxoprop-1-enyl]benzoic acid; 100918925: (2Z)-1-[2-Hydroxy-4,6-bis(methoxymethoxy)phenyl]-3-(2,2-dimethyl-2H-1-benzopyran-6-yl)-2-propen-1-one; 100925465: 2',4-Dihydroxy-4',6'-bis[(2-methoxyethoxy)methoxy]chalcone; 100925466: 4-Methoxy-2'-hydroxy-4',6'-bis[(2-methoxyethoxy)methoxy]chalcone; 100925467: 2'-Hydroxy-4',6'-bis[(2-methoxyethoxy)methoxy]chalcone; 100933076: 4-[4-[2-(Decyloxycarbonyl)vinyl]cinnamoyl]benzoic acid; 100958822: 2',3-Dihydroxy-4'-methylchalcone; 100958823: 2',4'-Dihydroxy-4-isopropylchalcone; 100976104: 2',4,4',6'-Tetrahydroxy-3-[(E)-3,7-dimethyl-2,6-octadienyl]chalcone; 101008497: 2',3-Dimethoxy-4,4'-dihydroxychalcone; 101020192: (2E)-1-(2-Nitrophenyl)-3-(3-methoxy-4-hydroxyphenyl)-2-propene-1-one; 101228798: 4-(Dihexadecylamino)-4'-[(8-hydroxy-3,6-dioxaoctane-1-yl)oxy]chalcone; 101228799: 2-[(2S,5R,8S,11S)-5-Benzyl-11-[3-(diaminomethylideneamino)propyl]-8-[4-[[2-[2-[2-[2-[4-[(E)-3-[4-(dihexadecylamino)phenyl]prop-2-enoyl]phenoxy]ethoxy]ethoxy]ethoxy]acetyl]amino]butyl]-3,6,9,12,15-pentaoxo-1,4,7,10,13-pentazacyclopentadec-2-yl]acetic acid; 101270498: 3,3'-[Ethylenebisoxybisethylenebisoxybis(4,1-phenylene)]bis[1-(4-hydroxyphenyl)-2-propene-1-one]; 101389244: 4,4'-Bis[3,5-bis[3,5-bis(benzyloxy)benzyloxy]benzyloxy]-2'-hydroxychalcone; 101393329: 5-[4-[(E)-3-(2-Hydroxyphenyl)-3-oxo-1-propenyl] benzylidene]-2,4-thiazolidinedione; 101406039: 6-(4-Cinnamoylphenoxy)hexyl 4-O-[4-O-(alpha-D-galactopyranosyl)-beta-D-galactopyranosyl]-beta-D-glucopyranoside; 101406040: 6-(4-Cinnamoylphenoxy)hexyl 4-O-[3-O-(alpha-D-galactopyranosyl)-beta-D-galactopyranosyl]-beta-D-glucopyranoside; 101423727: 4-[4-O-(p-Hydroxycinnamoyl)beta-D-gluco-pyranosyloxy]-2',4',6'-trihydroxychalcone; 101423795: 4,4'-Bis(beta-D-gluco-pyranosyloxy)-2'-hydroxychalcone; 101423796: 4'-Diglucosylisoliquiritigenin; 101432745: (E)-3-[4-(Dibutylamino)phenyl]-1-(2-hydroxyphenyl)prop-2-en-1-one; 101432747: (E)-3-[4-(Didodecylamino)phenyl]-1-(2-hydroxy-4-octoxyphenyl)prop-2-en-1-one; 101432749: (E)-3-[4-(Dioctylamino)phenyl]-1-(2-hydroxyphenyl)prop-2-en-1-one; 101432751: (E)-3-[4-(Didodecylamino)phenyl]-1-(2-hydroxyphenyl)prop-2-en-1-one; 101432753: (E)-3-[4-(Dibutylamino)phenyl]-1-(2-hydroxy-4-methoxyphenyl)prop-2-en-1-one; 101432755: (E)-3-[4-(Dioctylamino)phenyl]-1-(2-hydroxy-4-methoxyphenyl)prop-2-en-1-one; 101432757: (E)-3-[4-(Didodecylamino)phenyl]-1-(2-hydroxy-4-methoxyphenyl)prop-2-en-1-one; 101432759: (E)-3-[4-(Dibutylamino)phenyl]-1-(2-hydroxy-4-octoxyphenyl)prop-2-en-1-one; 101432761: (E)-3-[4-(Dioctylamino)phenyl]-1-(2-hydroxy-4-octoxyphenyl)prop-2-en-1-one; 101461144: beta-(4-Ethynylphenyl)-2'-hydroxyacrylophenone; 101483099: 1-Phenyl-3-[2alpha-(4-hydroxyphenyl)-3beta-benzoyl-2,3-dihydrobenzofuran-5-yl]-2-propene-1-one; 101493438: (E)-1-[2-Hydroxy-4,6-bis(benzyloxy)phenyl]-3-(1,3-benzodioxole-5-yl)-2-propene-1-one; 101502235: 3,3'-p-Phenylenebis[1-(2-hydroxy-4-methoxyphenyl)-2-propene-1-one]; 101502236: 3,3'-m-Phenylenebis[1-(2-hydroxy-4-methoxyphenyl)-2-propene-1-one]; 101516215: 2'-Hydroxy-6'-methoxy-4-bromochalcone; 101516216: 2'-Hydroxy-6'-methoxy-4-methylchalcone; 101526067: beta,beta'-(4-Methoxy-1,3-phenylene)bis(2'-hydroxy-4',6'-dimethoxyacrylophenone); 101526070: beta,beta'-[6,6'-Bis(tetrahydro-2H-pyran-2-yloxy)biphenyl-3,3'-diyl]bis[2'-hydroxy-4',6'-bis(tetrahydro-2H-pyran-2-yloxy)acrylophenone]; 101553927: 2'-Hydroxy-4'-fluorochalcone; 101606231: Isoliquiritigenin 4'-O-apioglucoside; 101611732: 4'-[[6-O-(6-Deoxy-alpha-L-mannopyranosyl)-beta-D-gluco-pyranosyl]oxy]-3,6'-dihydroxy-4-methoxychalcone; 101614378: 2-[(E)-3-(4-Hydroxyphenyl)-1-oxo-2-propenyl]-3,5-dihydroxyphenyl 6-deoxy-beta-L-galactopyranoside; 101614379: 2-[(E)-3-(4-Hydroxyphenyl)-1-oxo-2-propenyl]-3,5-dihydroxyphenyl 6-deoxy-beta-L-glucopyranoside; 101614380: 2-[(E)-3-(4-Hydroxyphenyl)-1-oxo-2-propenyl]-3,5-dihydroxyphenyl beta-L-glucopyranoside; 101628655: (E)-3-[3-[(2S,3R,4R)-4-[5-[4-(2,4-Dihydroxybenzoyl)-5-(4-hydroxyphenyl)-3-[(4-hydroxyphenyl)methyl]oxolan-2-yl]-2,4-dihydroxyphenyl]-7-hydroxy-2-(4-hydroxyphenyl)-3,4-dihydro-2H-chromen-3-yl]-4-hydroxyphenyl]-1-(2,4-dihydroxyphenyl)prop-2-en-1-one; 101630348: Azobechalcone A; 101630349: Isolophirachalcone A; 101641374: 3-[4-[3-(4-Bromophenyl)propenoyl]phenyl]propenoic acid; 101641375: 3-[4-[3-(4-Methoxyphenyl)propenoyl]phenyl]propenoic acid; 101643630: (E)-3-[4-(Benzoyloxy) phenyl]-1-[2-hydroxy-4-(6-deoxy-beta-L-gluco-pyranosyloxy) phenyl]-2-propen-1-one; 101643631: (E)-3-[4-(Benzoyloxy)phenyl]-1-[2-acetoxy-4-(6-deoxy-2-O-acetyl-beta-L-gluco-pyranosyloxy)phenyl]-2-propen-1-one; 101668463: 4'-(alpha-L-Rhamnopyranosyloxy)-2'-hydroxy-trans-chalcone; 101668464: 4'-(alpha-L-Rhamnopyranosyloxy)-2'-hydroxy-4-methoxy-trans-chalcone; 101678919: 2'-Hydroxy-4,4'-bis(beta-D-gluco-pyranosyloxy)-6'-methoxychalcone; 101690043: 2'-Hydroxy-4-(tert-butylamino)-trans-chalcone; 101799885: 3-(4-Ethylphenyl)-1-(2-hydroxy-4-methoxyphenyl)-2-propene-1-one; 101807199: (E)-2',4'-Dihydroxy-4-benzoyloxychalcone; 101862112: 2'-Hydroxy-4'-acetoxychalcone; 101862113: 3,4-Dimethoxy-2'-hydroxy-4'-acetoxychalcone; 101875710: (E)-2',4',6'-Trihydroxy-beta-[3,4-bis(benzyloxy)phenyl]acrylophenone; 101881073: 2'-Hydroxy-4,4',6'-trimethoxychalcone-3-yl(2'-hydroxy-4',6'-dimethoxychalcone-4-yl) ether; 101882448: 3'-[3-(2-Hydroxy-4-methoxy-phenyl)-3-oxo-1-propenyl]biphenyl-3-carbaldehyde; 101882449: 3,3'-(Biphenyl-3,3'-diyl)bis[1-(2-hydroxyphenyl)-2-propene-1-one]; 101882450: 2-[3'-[3-

(2-Hydroxyphenyl)-3-oxo-1-propenyl]biphenyl-3-yl]-2H-1-benzopyran-4(3H)-one; 101885308: 2',4'-Dihydroxy-4-piperidinochalcone; 101909197: (5S,5As,8aR,9R)-5-[4-[[4-[(E)-3-(4-fluorophenyl)prop-2-enoyl]phenoxy]methyl]triazol-1-yl]-9-(4-hydroxy-3,5-dimethoxyphenyl)-5a,6,8a,9-tetrahydro-5H-[2]benzofuro[6,5-f][1,3]benzodioxol-8-one; 101911090: (E)-1-[2-Hydroxy-4,6-bis(methoxymethoxy)phenyl]-3-[(2S,3S)-2-(4-hydroxy-3-methoxyphenyl)-3-[tri(propan-2-yl)silyloxymethyl]-2,3-dihydro-1,4-benzodioxin-6-yl]prop-2-en-1-one; 101926994: 4',6'-Dichloro-2'-hydroxychalcone; 101938903: [(3S,4R,5S)-5-[(2S,3R,4S,5S,6R)-2-[4-[(E)-3-(2,4-Dihydroxyphenyl)-3-oxoprop-1-enyl]phenoxy]-4,5-dihydroxy-6-(hydroxymethyl)oxan-3-yl]oxy-3,4-dihydroxyoxolan-3-yl]methyl (E)-3-(4-hydroxy-3-methoxyphenyl)prop-2-enoate; 101938904: [(3S,4R,5S)-5-[(2S,3R,4S,5S,6R)-2-[4-[(E)-3-(2,4-Dihydroxyphenyl)-3-oxoprop-1-enyl]phenoxy]-4,5-dihydroxy-6-(hydroxymethyl)oxan-3-yl]oxy-3,4-dihydroxyoxolan-3-yl]methyl (E)-3-(4-hydroxyphenyl)prop-2-enoate; 101953469: 3-[4-[3-Oxo-3-(2-hydroxy-phenyl)-1-propenyl]phenyl]-7-(diethylamino)-2H-1-benzopyran-2-one; 101959357: 4-(3,4-Dimethoxy-trans-cinnamoyl)-trans-cinnamic acid; 101987876: 2'-Hydroxy-3,4-methylenedioxy-4'-fluorochalcone; 101997458: 3alpha-[5-[(E)-3-(2,4-Dihydroxyphenyl)-3-oxo-1-propenyl]-2-hydroxyphenyl]-2,3-dihydro-7-hydroxy-2beta-(4-hydroxyphenyl)-4H-1-benzopyran-4-one; 102011712: 1-[2-Hydroxy-4-(2-propynyloxy)phenyl]-3-(3-methoxyphenyl)-2-propene-1-one; 102029188: 4-[[4-[3-[4-[Bis[2-[2-(2-methoxyethoxy) ethoxy]ethyl]amino]phenyl]-1-oxo-2-propenyl]phenyl]ethynyl]-2,6-pyridinedicarboxylic acid; 102029203: 4-[[4-[3-[4-[Bis[2-[2-[2-(2-methoxyethoxy)ethoxy]ethoxy]ethyl]amino]phenyl]-1-oxo-2-propenyl]phenyl]ethynyl]-2,6-pyridinedicarboxylic acid; 102033205: 3-[[(2R,3S,4S,5R,6S)-6-[3-[(2S,3R,4S,5S,6R)-3-[(2S,3R,4S,5S,6R)-4,5-Dihydroxy-3-[3-(4-hydroxy-3-methoxyphenyl)prop-2-enoyloxy]-6-(hydroxymethyl)oxan-2-yl]oxy-4,5-dihydroxy-6-[[(E)-3-[4-[(2S,3R,4S,5S,6R)-3,4,5-trihydroxy-6-[3-[4-[3-(4-hydroxy-3-methoxyphenyl)prop-2-enoyl]-3-methoxyphenyl]prop-2-enoyloxymethyl]oxan-2-yl]oxyphenyl]prop-2-enoyl]oxymethyl]oxan-2-yl]oxy-2-(3,4-dihydroxyphenyl)-7-hydroxychromenylium-5-yl]oxy-3,4,5-trihydroxyoxan-2-yl]methoxy]-3-oxopropanoic acid; 102033209: 3-[2-O-(beta-D-Glucopyranosyl)-6-O-[(E)-3-[4-[6-O-[(E)-3-[3-methoxy-4-[(E)-3-(3-methoxy-4-hydroxyphenyl)propenoyl]phenyl]propenoyl]-beta-D-gluco-pyranosyloxy]phenyl]propenoyl]-beta-D-gluco-pyranosyloxy]-5-[6-O-(3-hydroxy-3-oxopropanoyl)-beta-D-gluco-pyranosyloxy]-7-hydroxy-2-(3,4-dihydroxyphenyl)-1-benzopyrylium; 102045785: 4'-(Benzyloxy)-2'-hydroxy-3-methoxychalcone; 102047329: 2'-Hydroxy-4'-(phenylethynyl)-beta-(4-(phenylethynyl)phenyl)acrylophenone; 102072379: 2'-Hydroxy-3-nitro-4'-methoxychalcone; 102072381: 2'-Hydroxy-3-nitro-6'-methoxychalcone; 102072382: 2'-Hydroxy-4-nitro-6'-methoxychalcone; 102081355: 2',3,4',6'-Tetrahydroxychalcone; 102081356: 2',4',6'-Trihydroxy-4-aminochalcone; 102096662: 1,1'-(1,4-Phenylene)bis[(E)-3-[4-(hydroxymethyl)phenyl]-2-propen-1-one]; 102101368: 2'-Hydroxy-3-methoxy-4'-(methoxymethoxy)-4,6'-bis(benzyloxy)chalcone; 102113303: 2'-Hydroxy-4'-(phenylethynyl)-beta-phenylacrylophenone; 102113304: 2'-Hydroxy-beta-(4-(phenylethynyl)phenyl)acrylophenone; 102115846: 2'-Hydroxy-4,4'-bis(alpha-D-gluco-pyranosyloxy)-6'-methoxychalcone; 102121822: 1-[2-Hydroxy-4-(beta-D-gluco-pyranosyloxy)phenyl]-3-(4-hydroxy-3-methoxyphenyl)-2-propene-1-one; 102129485: 4-(2-Hydroxyethoxy)-4'-iodochalcone; 102144548: 2'-Hydroxy-6'-isopropoxy-trans-chalcone; 102145742: 2',3-Bis(beta-D-gluco-pyranosyloxy)-4,4'-dihydroxychalcone; 102156616: 2-[1-[4-[4-[(E)-2-Benzoylethenyl]phenoxy]butyl]-3-cyano-4-[(E)-4-[hexyl(6-hydroxyhexyl)amino]styryl]-5-oxo-2,5-dihydro-1H-pyrrole-2-ylidene]malononitrile; 102160884: 2',4-Dihydroxy-3-benzylchalcone; 102194934: (2S)-3alpha,4',7-Trihydroxy-8-[2-hydroxy-5-[2-(2,4-dihydroxybenzoyl)ethenyl]phenyl]-2,3-dihydroflavone; 102196619: 2'-Hydroxy-4-methoxy-3-nitrochalcone; 102196620: 2'-Hydroxy-6'-nitrochalcone; 102197278: 1-[4-[[3-(9H-Carbazole-4-yloxy)-2-hydroxypropyl]amino]phenyl]-3-phenyl-2-propene-1-one; 102197280: 1-[4-[[3-(9H-Carbazole-4-yloxy)-2-hydroxypropyl]amino]phenyl]-3-(4-chlorophenyl)-2-propene-1-one; 102197281: 1-[4-[[3-(9H-Carbazole-4-yloxy)-2-hydroxypropyl]amino]phenyl]-3-(4-nitro-phenyl)-2-propene-1-one; 102197282: 1-[4-[2-Hydroxy-3-(9H-carbazole-4-yloxy)propylamino]phenyl]-3-(4-methoxyphenyl)-2-propene-1-one; 102197283: 1-[4-[[3-(9H-Carbazole-4-yloxy)-2-hydroxypropyl]amino]phenyl]-3-(3-nitro-4-methoxyphenyl)-2-propene-1-one; 102197284: 1-[4-[[3-(9H-Carbazole-4-yloxy)-2-hydroxypropyl]amino]phenyl]-3-(4-methylphenyl)-2-propene-1-one; 102197286: 1-[4-[[3-(9H-Carbazole-4-yloxy)-2-hydroxypropyl]amino]phenyl]-3-(4-hydroxyphenyl)-2-propene-1-one; 102197287: 1-[4-[[3-(9H-Carbazole-4-yloxy)-2-hydroxypropyl]amino]phenyl]-3-(3,4-dichlorophenyl)-2-propene-1-one; 102202409: 4-[Methyl(2-hydroxyethyl)amino]-4'-[[4-(cyclopentylamino)-6-[(cyclohexyl-methyl)amino]-1,3,5-triazine-2-yl]amino]chalcone; 102202410: 4-[Methyl(2-hydroxyethyl)amino]-4'-[[4-(cyclopentylamino)-6-[(3-phenylpropyl)amino]-1,3,5-triazine-2-yl]amino]chalcone; 102238310: beta-(Benzofuran-5-yl)-2'-hydroxy-6'-(methoxy-methoxy)acrylophenone; 102258102: 4'-(Acetylamino)-4-hydroxychalcone; 102271453: 3-[[2-(4-Hydroxyphenyl)-4-oxo-5,7-dihydroxy-3,4-dihydro-2H-1-benzopyran]-3-yl]-2',4,4'-trihydroxy-trans-chalcone; 102271454: 3-[[2-(4-Hydroxyphenyl)-4-oxo-5-hydroxy-7-(beta-D-gluco-pyranosyloxy)-3,4-dihydro-2H-1-benzopyran]-3-yl]-2',4,4'-trihydroxy-trans-chalcone; 102276352: 4-Hydroxy-4'-acetoxychalcone; 102289865: 3-(9-Ethyl-9H-carbazole-3-yl)-1-(2-hydroxyphenyl)-2-propene-1-one; 102308110: 1-[4-[4-(Hydroxymethyl)-1H-1,2,3-triazole-1-yl]phenyl]-3-[4-(dimethylamino)phenyl]-2-propene-1-one; 102308111: 1-[4-[4-(Hydroxymethyl)-1H-1,2,3-triazole-1-yl]phenyl]-3-(4-methylphenyl)-2-propene-1-one; 102308112: 1-[4-[4-(Hydroxymethyl)-1H-1,2,3-triazole-1-yl]phenyl]-3-(4-methoxyphenyl)-2-propene-1-one; 102308113: 1-[4-[4-(Hydroxymethyl)-1H-1,2,3-triazole-1-yl]phenyl]-3-(4-bromophenyl)-2-propene-1-one; 102308115: 1-[4-[4-(Hydroxymethyl)-1H-1,2,3-triazole-1-yl]phenyl]-3-(4-nitro-phenyl)-2-propene-1-one; 102317735: Glucoisoquiritin apioside; 102320046: 1-[2-[6-O-(1-Oxo-8-hydroxy-5,6-octadiene-1-yl)-beta-D-gluco-pyranosyloxy]-4,6-dihydroxyphenyl]-3-(4-hydroxyphenyl)-2-propene-1-one; 102345187: 4-[3-[4-(4-Hydroxybutoxy)phenyl]acryloyl]benzoic acid; 102345188: 4-[3-[4-[4-(Methacryloyloxy)butoxy]phenyl]acryloyl]benzoic acid; 102366351: [Bis[2-[carboxymethyl[[2-[4-[(E)-3-[4-(dimethylamino)phenyl]propenoyl]phenoxy]ethyl]carbamoylmethyl]amino]ethyl]amino]acetic acid; 102371316: 2'-Hydroxy-3,4,4',6'-tetrakis(benzoyloxy)chalcone; 102387518: 1,3-Bis[4-(2-hydroxyethoxy)phenyl]-2-propene-1-one; 102391102: 3,5-Bis(4-cinnamoylphenoxymethyl)phenol; 102399253: (E)-2',3,4,6'-Tetramethoxy-4'-[[6-O-(alpha-L-rhamnopyranosyl)-beta-D-gluco-pyranosyl]oxy]chalcone; 102399254: (E)-2',3,4,6'-Tetramethoxy-4'-[[2-O-methyl-6-

O-(alpha-L-rhamno-pyranosyl)-beta-D-gluco-pyranosyl]oxy]chalcone; 102422516: 4,4'-Bis(4-carboxyphth-alimidyl)chalcone; 102424805: 3-Bromo-2'-hydroxy-4'-(methoxymethoxy)-trans-chalcone; 102483467: 4-Hydroxy-6-[2-(4-hydroxycinnamoyl)-3,5-dihydroxybenzyl]-2H-pyran-2-one; 102500648: Tomoroside B; 102524713: N-[4-[(E)-3-[4-(2-Hydroxyethylamino)phenyl]prop-2-enoyl]phenyl]prop-2-enamide; 102526347: 4,4'-Bis[2-(2-hydroxyethoxy)ethoxy]chalcone; 102565358: 3-Hydroxy-4-[(2E)-3-(3-hydroxy-4-methoxyphenyl)prop-2-enoyl]-5-methoxy-phenyl 6-O-(5-hydroxytetrahydro-2H-pyran-2-yl)hexopyranoside; 103597753: 1-(4-Hydroxyphenyl)-3-[4-(1,2,4-triazol-1-yl)phenyl]prop-2-en-1-one; 109468534: (E)-3-(3-Fluoro-4-hydroxyphenyl)-1-[4-(4-hydroxypiperidin-1-yl)phenyl]prop-2-en-1-one; 110176570: N-(1-Hydroxy-1-phenylpropan-2-yl)-2-[[(E)-3-phenylprop-2-enoyl]phenoxy]acetamide; 110177162: (E)-4-Hydroxy-4-oxobut-2-enoate;2-[4-[4-[(E)-3-(3-methoxyphenyl)prop-2-enoyl]phenoxy]phenoxy]ethyl-di(propan-2-yl)azanium; 110189037: (E)-3-(4-Hydroxy-phenyl)-1-[4-[(3,4,5-trimethoxyphenyl)methoxy]phenyl]prop-2-en-1-one; 111106376: 3-(3-Fluorophenyl)-1-[4-(4-hydroxypiperidin-1-yl)phenyl]prop-2-en-1-one; 111106377: 3-[3-[4-(4-Hydroxypiperidin-1-yl)phenyl]-3-oxoprop-1-enyl]benzonitrile; 111106380: 1-[4-(4-Hydroxy-piperidin-1-yl)phenyl]-3-(3-methylphenyl)prop-2-en-1-one; 111106381: 3-(3,4-Difluoro-phenyl)-1-[4-(4-hydroxypiperidin-1-yl)phenyl]prop-2-en-1-one; 111337708: 3-(3-Fluoro-4-methylphenyl)-1-[4-(4-hydroxypiperidin-1-yl)phenyl]prop-2-en-1-one; 111337709: 3-(2,3-Dihydro-1-benzofuran-5-yl)-1-[4-(4-hydroxypiperidin-1-yl)phenyl]prop-2-en-1-one; 111337713: 3-(4-Fluoro-3-methylphenyl)-1-[4-(4-hydroxypiperidin-1-yl)phenyl]prop-2-en-1-one; 117590664: Sodium;2-[6-[6-[3-(5-ethyl-5-hydroxy-6-methyloxan-2-yl)-15-hydroxy-3,10,12-trimethyl-4,6,8-trioxadispiro[4.1.57.35]pentadec-13-en-9-yl]-3-hydroxy-4-methyl-5-oxooctan-2-yl]-5-methyloxan-2-yl]butanoate;1-(2-hydroxy-4,6-dimethoxyphenyl)-3-phenylprop-2-en-1-one; 117590676: [4-(Dimethylamino)-2-[[14-ethyl-7,12,13-trihydroxy-4-(5-hydroxy-4-methoxy-4,6-dimethyloxan-2-yl)oxy-3,5,7,9,11,13-hexamethyl-2,10-dioxo-oxacyclotetradec-6-yl]oxy]-6-methyloxan-3-yl] propanoate; dodecyl hydrogen sulfate;1-(2-hydroxy-4,6-dimethoxyphenyl)-3-phenylprop-2-en-1-one; 117590681: 17-Ethynyl-2,18-dimethyl-7-oxa-6-azapentacyclo[11.7.0.02,10.04,8.014,18]icosa-4(8),5,9-trien-17-ol;1-(2-hydroxy-4,6-dimethoxyphenyl)-3-phenylprop-2-en-1-one; 117590688: (10,13-Dimethyl-17-oxo-1,2,3,4,7,8,9,11,12,14,15,16-dodecahydrocyclopenta[a]phenanthren-3-yl)acetate;1-(2-hydroxy-4,6-dimethoxyphenyl)-3-phenylprop-2-en-1-one; 117590703: (10,13-Dimethyl-3-oxo-1,2,6,7,8,9,11,12,14,15,16,17-dodecahydrocyclopenta[a]phenanthren-17-yl) propanoate;1-(2-hydroxy-4,6-dimethoxyphenyl)-3-phenylprop-2-en-1-one; 117590705: 5-[3-(1,3-Benzodioxol-5-yl)-1,3,3a,4,6,6a-hexahydrofuro[3,4-c]furan-6-yl]-1,3-benzodioxole;1-(2-hydroxy-4,6-dimethoxyphenyl)-3-phenylprop-2-en-1-one; 117590713: 2-Butan-2-yl-21',24'-dihydroxy-12'-[5-(5-hydroxy-4-methoxy-6-methyloxan-2-yl)oxy-4-methoxy-6-methyl-oxan-2-yl]oxy-3,11',13',22'-tetramethylspiro[2,3-dihydro-pyran-6,6'-3,7,19-trioxatetracyclo[15.6.1.14, 8.020,24]pentacosa-10,14,16,22-tetraene]-2'-one;1-(2-hydroxy-4,6-dimethoxyphenyl)-3-phenylprop-2-en-1-one; 117590737: 1-(2,4-Dihydroxyphenyl)-2-(4-methoxyphenyl) ethanone;1-(2-hydroxy-4,6-dimethoxyphenyl)-3-phenylprop-2-en-1-one; 117590755: 1,4a-Dimethyl-7-propan-2-yl-2,3,4,9,10,10a-hexahydrophenanthrene-1-carboxamide;1-(hydroxy-4,6-dimethoxyphenyl)-3-phenylprop-2-en-1-one; 117590783: 1-(2-Hydroxy-4,6-dimethoxyphenyl)-3-phenyl-prop-2-en-1-one;phenyl 4-amino-2-hydroxybenzoate; 117590785: 1-[(3,4-Diethoxyphenyl)methyl]-6,7-diethoxy-isoquinoline;1-(2-hydroxy-4,6-dimethoxyphenyl)-3-phenylprop-2-en-1-one;hydrochloride; 117590800: 4-Hexyl-benzene-1,3-diol;1-(2-hydroxy-4,6-dimethoxyphenyl)-3-phenylprop-2-en-1-one; 117590816: 4-[3-(4-Butoxyphenoxy)propyl]morpholine;1-(2-hydroxy-4,6-dimethoxyphenyl)-3-phenylprop-2-en-1-one;hydrochloride; 117590817: 1-(2-Hydroxy-4,6-dimethoxyphenyl)-3-phenyl-prop-2-en-1-one;5-hydroxy-7-methoxy-2-methyl-8-(3-methylbut-2-enyl)chromen-4-one; 117590818: 1-(2-Hydroxy-4,6-dimethoxyphenyl)-3-phenylprop-2-en-1-one;2-[4-[3-[2-(trifluoromethyl) phenothiazin-10-yl]propyl]piperazin-1-yl]ethanol;dihydrochloride; 117590840: Dimethyl 2,6-dimethyl-4-(2-nitro-phenyl)-1,4-dihydropyridine-3,5-dicarboxylate;1-(2-hydroxy-4,6-dimethoxyphenyl)-3-phenylprop-2-en-1-one; 117590888: 1-(2-Hydroxy-4,6-dimethoxy-phenyl)-3-phenylprop-2-en-1-one;methyl N-(6-benzoyl-1H-benzimidazol-2-yl)carbamate; 117590892: 1-(2-Hydroxy-4,6-dimethoxyphenyl)-3-phenyl-prop-2-en-1-one;2-methoxy-5-(1-phenylprop-2-enyl)cyclohexa-2,5-diene-1,4-dione; 117590903: 1-(2-Hydroxy-4,6-dimethoxyphenyl)-3-phenylprop-2-en-1-one;2-(1-phenylprop-2-enyl)cyclohexa-2,5-diene-1,4-dione; 117590942: 1-(2-Hydroxy-4,6-dimethoxyphenyl)-3-phenyl-prop-2-en-1-one;(3-hydroxy-13-methyl-6,7,8,9,11,12,14,15,16,17-decahydrocyclopenta[a]phenanthren-17-yl) propanoate; 117590944: 4,8-Dimethyl-12-methylidene-3,14-dioxatricyclo[9.3.0.02,4]tetradec-7-en-13-one;1-(2-hydroxy-4,6-dimethoxyphenyl)-3-phenylprop-2-en-1-one; 117590954: 2-Amino-4,6-dimethyl-3-oxo-1-N,9-N-bis[3,6,10-trimethyl-2,5,8,12,15-pentaoxo-7,14-di(propan-2-yl)-9-oxa-3,6,13-triazabicyclo[14.3.0]nonadecan-11-yl]phenoxazine-1,9-dicarboxamide;1-(2-hydroxy-4,6-dimethoxyphenyl)-3-phenylprop-2-en-1-one; 117590975: But-2-enedioic acid;1-(2-hydroxy-4,6-dimethoxyphenyl)-3-phenylprop-2-en-1-one;1-methyl-4-(3-methylsulfanyl-5,6-dihydrobenzo[b][1]benzothiepin-5-yl)piperazine; 117590977: 1-(3,7-Dihydroxy-2,2-dimethyl-3,4-dihydro-chromen-6-yl)-2-(5-methoxy-2,2-dimethylchromen-6-yl) ethanone;1-(2-hydroxy-4,6-dimethoxyphenyl)-3-phenyl-prop-2-en-1-one; 117591000: 1-(2-Hydroxy-4,6-dimethoxyphenyl)-3-phenylprop-2-en-1-one;2-methoxy-5-[1-(4-methoxyphenyl) prop-2-enyl]cyclohexa-2,5-diene-1,4-dione; 117591013: But-2-enedioic acid;2-[2-[1-(4-chlorophenyl)-1-phenylethoxy]ethyl]-1-methylpyrrolidine; 1-(2-hydroxy-4,6-dimethoxyphenyl)-3-phenylprop-2-en-1-one; 117591025: Sodium;2-(2,6-dichloro-3-methylanilino)benzoate;1-(2-hydroxy-4,6-dimethoxyphenyl)-3-phenyl-prop-2-en-1-one; 117591030: 3,8-Dimethoxy-2-phenyl-chromen-4-one;1-(2-hydroxy-4,6-dimethoxyphenyl)-3-phenylprop-2-en-1-one; 117591031: 1-(2-Chloroethyl)-3-(4-methylcyclohexyl)-1-nitrosourea;1-(2-hydroxy-4,6-dimethoxyphenyl)-3-phenylprop-2-en-1-one; 117591034: 10-Hydroxy-2,4a,6a,6b,9,9,12a-heptamethyl-13-oxo-3,4,5,6,6a,7,8,8a,10,11,12,14b-dodecahydro-1H-picene-2-carboxylic acid;1-(2-hydroxy-4,6-dimethoxyphenyl)-3-phenylprop-2-en-1-one; 117591045: 4-(3-Carboxybut-2-enyl)-14-hydroxy-6,6,18-trimethyl-21-(3-methylbut-2-enyl)-18-(4-methylpent-3-enyl)-12-oxo-2,5,19-trioxapentacyclo[11.8.0.03,7.03,11.015,20]henicosa-1(13),10,14,16,20-pentaene-4-carboxylic acid;1-(2-hydroxy-4,6-dimethoxyphenyl)-3-phenylprop-2-en-1-one; 117591056: 4-[4-(4-Chlorophenyl)-4-hydroxypiperidin-1-yl]-1-(4-fluorophenyl)butan-1-one;1-(2-hydroxy-4,6-dimethoxyphenyl)-3- phenylprop-2-en-1-one; 117591065: 3-(2-Chloro-5,6-dihydrobenzo[b][1]benzazepin-11-yl)-N,N-dimethylpropan-1-amine;1-(2-hydroxy-4,6-dimethoxyphenyl)-3-phenylprop-2-en-1-one;hydrochloride; 117591079: 16,17-Dimethoxy-6-propan-2-yl-2,7,20-trioxapentacyclo[11.8.0.03,11.04,8.014,19]henicosa-3(11),4(8),9,14,16,18-hexaen-12-one;1-(2-hydroxy-4,6-dimethoxyphenyl)-3-phenylprop-2-en-1-one; 117591095: 1-(2-Hydroxy-4,6-dimethoxyphenyl)-3-phenylprop-2-en-1-one;7-methoxy-2-(3-methoxyphenyl)chromen-4-one; 117591096: 3-(2-Chlorothioxanthen-9-ylidene)-N,N-dimethylpropan-1-amine;1-(2-hydroxy-4,6-dimethoxyphenyl)-3-phenylprop-2-en-1-one;hydrochloride; 117591132: 19-Ethyl-19-hydroxy-17-oxa-3,13diazapentacyclo[11.8.0.02, 11.04, 9.015,20]henicosa-1(21),2,4,6,8,10,15(20)-heptaene-14,18-dione;1-(2-hydroxy-4,6-dimethoxyphenyl)-3-phenylprop-2-en-1-one; 117591159: 3,9-Dimethoxy-6a,11a-dihydro-6H-[1]benzofuro[3,2-c]chromene;1-(2-hydroxy-4,6-dimethoxyphenyl)-3-phenylprop-2-en-1-one; 117591168: 1-(2-Hydroxy-4,6-dimethoxyphenyl)-3-phenylprop-2-en-1-one;2,3,9-trimethoxy-6H-chromeno[3,4-b]chromen-6a-ol; 117591169: 1-(2-Hydroxy-4,6-dimethoxyphenyl)-3-phenylprop-2-en-1-one;2,6,6,9-tetramethylcycloundeca-1,4,8-triene; 117591181: 13-Cyclopent-2-en-1-yltridecanoic acid; 1-(2-hydroxy-4,6-dimethoxyphenyl)-3-phenylprop-2-en-1-one; 117591276: (17-Acetyl-6,10,13-trimethyl-3-oxo-2,8,9,11,12,14,15, 16-octahydro-1H-cyclopenta[a]phenanthren-17-yl)acetate;1-(2-hydroxy-4,6-dimethoxy-phenyl)-3-phenylprop-2-en-1-one; 117591358: 5-Benzyl-2-methyl-3,4-dihydro-1H-pyrido[4,3-b]indole;1-(2-hydroxy-4,6-dimethoxyphenyl)-3-phenylprop-2-en-1-one;naphthalene-1,5-disulfonic acid; 117591375: 1-[4-(1,3-Benzodioxol-5-ylmethyl) piperazin-1-yl]-2-(4-chlorophenoxy)ethanone;1-(2-hydroxy-4,6-dimethoxyphenyl)-3-phenylprop-2-en-1-one;hydrochloride; 117591381: 1-(2-Hydroxy-4,6-dimethoxyphenyl)-3-phenylprop-2-en-1-one;9,20,21,25-tetramethoxy-15,30-dimethyl-7,23-dioxa-15,30-diazaheptacyclo[22.6.2.23,6.18,12.114,18.027,31.022,33] hexatriaconta-3(36),4,6(35), 8,10,12(34),18,20,22(33),24,26,31-dodecaene; 117591449: 1,8-Dihydroxy-3-methylanthracene-9,10-dione;1-(2-hydroxy-4,6-dimethoxyphenyl)-3-phenylprop-2-en-1-one; 117591510: 5,10-Dihydroxy-2,2,6a,6b,9,9,12a-heptamethyl-1,3,4,5,6,6a,7,8,8a,10,11,12, 13,14b-tetradecahydropicene-4a-carboxylic acid;1-(2-hydroxy-4,6-dimethoxyphenyl)-3-phenylprop-2-en-1-one; 117591525: (4-Acetamidophenyl) 2-hydroxybenzoate;1-(2-hydroxy-4,6-dimethoxyphenyl)-3-phenylprop-2-en-1-one; 117591638: 1-(2-Hydroxy-4,6-dimethoxy-phenyl)-3-phenylprop-2-en-1-one;3-methoxy-2-propan-2-ylfuro[3,2-g]chromen-7-one; 117591646: 1-(2-Hydroxy-4,6-dimethoxyphenyl)-3-phenylprop-2-en-1-one; 3-phenyl-diazenylpyridine-2,6-diamine;hydrochloride; 117591656: 11-Hydroxy-17,18-dimethoxy-7,7-dimethyl-2,8,21-trioxapentacyclo[12.8.0.03,12.04,9.015,20]docosa-3 (12),4(9),5,10,15,17, 19-heptaen-13-one;1-(2-hydroxy-4,6-dimethoxyphenyl)-3-phenylprop-2-en-1-one; 117591668: 1-(2-Hydroxy-4,6-dimethoxyphenyl)-3-phenylprop-2-en-1-one;hydroxyurea; 117591679: (2-Hydroxy-4,6-dimethoxyphenyl)-phenylmethanone;1-(2-hydroxy-4,6-dimethoxyphenyl)-3-phenylprop-2-en-1-one; 117591713: 5-(1,3-Benzodioxol-5-yl)-1-piperidin-1-ylpenta-2,4-dien-1-one;1-(2-hydroxy-4,6-dimethoxyphenyl)-3-phenylprop-2-en-1-one; 117591849: 1-(2-Hydroxy-4,6-dimethoxyphenyl)-3-phenylprop-2-en-1-one;7-hydroxy-8-methoxy-3-(4-methoxyphenyl)chromen-4-one; 117591874: 1-(2-Hydroxy-4,6-dimethoxy-phenyl)-3-phenylprop-2-en-1-one;6-hydroxy-7-(3-methylbut-2-enoxy)chromen-2-one; 117591904: 1-(2-Hydroxy-4,6-dimethoxyphenyl)-3-phenylprop-2-en-1-one;5-hydroxy-2,8-dimethyl-6,9-dihydropyrano[3,2-h][1]benzoxepin-4-one; 117592077: 5,7-Dihydroxy-2-phenylchromen-4-one;1-(2-hydroxy-4,6-dimethoxyphenyl)-3-phenylprop-2-en-1-one; 117592092: 1-(2-Hydroxy-4,6-dimethoxyphenyl)-3-phenylprop-2-en-1-one;8-methoxy-4-methyl-1H-quinolin-2-one; 117592309: 1-(2-Hydroxy-4,6-dimethoxyphenyl)-3-phenylprop-2-en-1-one;propan-2-yl N-(3-chlorophenyl)carbamate; 117592430: 1-(2-Hydroxy-4,6-dimethoxyphenyl)-3-phenylprop-2-en-1-one;3-(2-methoxyphenyl)prop-2-enoic acid; 117592534: 1-(2-Hydroxy-4,6-dimethoxyphenyl)-3-phenylprop-2-en-1-one;(3-hydroxy-13-methyl-6,7,8,9,11,12,14,15,16,17-decahydrocyclopenta[a]phenanthren-17-yl)acetate; 117592656: 1-(2-Hydroxy-4,6-dimethoxyphenyl)-3-phenylprop-2-en-1-one;methyl 8,10-dichloro-3,9-dihydroxy-1,4,7-trimethyl-6-oxobenzo[b][1,4]benzodioxepine-2-carboxylate; 117592928: 2-(3,4-Dihydroxyphenyl)-3,7-dihydroxychromen-4-one;1-(2-hydroxy-4,6-dimethoxyphenyl)-3-phenylprop-2-en-1-one; 117592935: 3-(2-Chlorophenothiazin-10-yl)-N,N-dimethylpropan-1-amine;1-(2-hydroxy-4,6-dimethoxyphenyl)-3-phenylprop-2-en-1-one; 117592941: 1-(2-Hydroxy-4,6-dimethoxyphenyl)-3-phenylprop-2-en-1-one;5-[2-(4-hydroxyphenyl)ethenyl]benzene-1,3-diol; 117593139: 5-(3-Formyl-2-hydroxy-4-methoxy-6-methylbenzoyl)oxy-2-hydroxy-3,6-dimethylbenzoic acid;1-(2-hydroxy-4,6-dimethoxyphenyl)-3-phenylprop-2-en-1-one; 117593146: 2-Chloro-N,N-bis(2-chloroethyl)ethanamine;1-(2-hydroxy-4,6-dimethoxyphenyl)-3-phenylprop-2-en-1-one;hydrochloride; 117593260: 6-(Furan-3-yl)-17-hydroxy-1,7,11,15,15-pentamethyl-3-oxapentacyclo[8.8.0.02,4.02,7.011,16]octadeca-12,16-diene-14,18-dione;1-(2-hydroxy-4,6-dimethoxyphenyl)-3-phenylprop-2-en-1-one; 117593283: 1-(2-Hydroxy-4,6-dimethoxyphenyl)-3-phenylprop-2-en-1-one;1-[4-hydroxy-3-(3-methylbut-2-enyl)phenyl]ethanone; 117593500: [6-(Furan-3-yl)-17-hydroxy-1,7,11,15,15-pentamethyl-14,18-dioxo-3-oxapentacyclo[8.8.0.02,4.02,7.011, 16]octadeca-12,16-dien-9-yl] acetate; 1-(2-hydroxy-4,6-dimethoxyphenyl)-3-phenylprop-2-en-1-one; 117593575: N,N-Dimethyl-3-(2-tricyclo[9.4.0.03,8]pentadeca-1(15),3,5,7,9,11,13-heptaenylidene)propan-1-amine;1-(2-hydroxy-4,6-dimethoxyphenyl)-3-phenylprop-2-en-1-one;hydrochloride; 117593581: 2,4-Dihydroxyheptadec-16-enyl acetate;2,4-dihydroxyheptadec-16-ynyl acetate;1-(2-hydroxy-4,6-dimethoxyphenyl)-3-phenylprop-2-en-1-one; 117593593: 1-(2-Hydroxy-4,6-dimethoxyphenyl)-3-phenylprop-2-en-1-one;5-methoxy-2,2-dimethyl-3,4-dihydrochromene-6-carboxylic acid; 117593659: 1-[6-[3-(Dimethylamino) propoxy]-2,2-dimethyl-3a,5,6,6a-tetrahydrofuro[2,3-d][1,3]dioxol-5-yl]ethane-1,2-diol;1-(2-hydroxy-4,6-dimethoxyphenyl)-3-phenylprop-2-en-1-one;hydrochloride; 117593709: 1-(2-Hydroxy-4,6-dimethoxyphenyl)-3-phenylprop-2-en-1-one; 1,4,5,8-tetrahydroxy-2,6-dimethylanthracene-9,10-dione; 117593739: Disodium;[3-[2,3-di(dodecanoyloxy)propoxy-oxidophosphoryl]oxy-2-hydroxypropyl] 2,3-di(dodecanoyloxy)propyl phosphate;1-(2-hydroxy-4,6-dimethoxyphenyl)-3-phenylprop-2-en-1-one; 117593823: 5,6-Dimethoxy-7-(4-methoxyphenyl)-2,2-dimethylpyrano[3,2-g]chromen-8-one;1-(2-hydroxy-4,6-dimethoxy-phenyl)-3-phenylprop-2-en-1-one; 117593849: 1-(2-Hydroxy-4,6-dimethoxyphenyl)-3-phenylprop-2-en-1-one;4-hydroxy-3-(3-methylbut-2-enyl)naphthalene-1,2-dione; 117593892: 3-Carboxy-1-[(3-carboxy-2-hydroxynaphthalen-1-yl) methyl]naphthalen-2-olate;2-[2-(2,5-dimethyl-1-phenylpyrrol-3-yl)ethenyl]-N,N,1-trimethylquinolin-1-ium-6-amine; 1-(2-hydroxy-4,6-dimethoxyphenyl)-3-phenylprop-2-en-1- one; 117594400: 3,3-Diphenyl-N-(1-phenylethyl)propan-1-amine;1-(2-hydroxy-4,6-dimethoxyphenyl)-3-phenylprop-2-en-1-one;hydrochloride; 117594468: 4-[5-(4-Carbamimidoylphenoxy) pentoxy]benzenecarboximidamide;1-(2-hydroxy-4,6-dimethoxyphenyl)-3-phenylprop-2-en-1-one;2-hydroxyethanesulfonic acid; 117594476: 5,7-Dihydroxy-2-methyl-6-(3-methylbut-2-enyl)chromen-4-one;1-(2-hydroxy-4,6-dimethoxyphenyl)-3-phenylprop-2-en-1-one; 117594551: 10,11-Dihydroxy-2,4a,6a,6a,9,14a-hexamethyl-3,4,5,6,8,13,14,14b-octahydro-1H-picene-2-carboxylic acid;1-(2-hydroxy-4,6-dimethoxyphenyl)-3-phenylprop-2-en-1-one; 117594692: 30-Ethyl-33-(1-hydroxy-2-methylhex-4-enyl)-1,4,7,10,12,15,19,25,28-nonamethyl-6,9,18,24-tetrakis(2-methylpropyl)-3,21-di(propan-2-yl)-1,4,7,10,13,16,19,22,25,28,31-undecazacyclotritriacontane-2,5,8,11,14,17,20,23,26,29,32-undecone;1-(2-hydroxy-4,6-dimethoxyphenyl)-3-phenylprop-2-en-1-one; 117594694: Trisodium;1-(2-hydroxy-4,6-dimethoxyphenyl)-3-phenylprop-2-en-1-one; phosphonatoformate; 117594773: [3-[(3-Formamido-2-hydroxybenzoyl)amino]-2,6-dimethyl-4,9-dioxo-8-pentyl-1,5-dioxonan-7-yl] 3-methylbutanoate;1-(2-hydroxy-4,6-dimethoxyphenyl)-3-phenylprop-2-en-1-one; 117594824: 1-(2-Hydroxy-4,6-dimethoxyphenyl)-3-phenylprop-2-en-1-one;O-naphthalen-2-yl N-methyl-N-(3-methylphenyl)carbamothioate; 117594843: 1-(2-Hydroxy-4,6-dimethoxyphenyl)-3-phenylprop-2-en-1-one;(2-hydroxy-4-methoxyphenyl)-(2-hydroxyphenyl)methanone; 117595560: 3,5-Diamino-6-chloro-N-(diaminomethylidene) pyrazine-2-carboxamide;1-(2-hydroxy-4,6-dimethoxyphenyl)-3-phenylprop-2-en-1-one;hydrochloride; 117595642: 1-(2-Hydroxy-4,6-dimethoxyphenyl)-3-phenylprop-2-en-1-one;(4-hydroxyphenyl)acetate; 117595716: 2-Amino-3-(3,4-dihydroxyphenyl)-2-methylpropanoic acid;1-(2-hydroxy-4,6-dimethoxyphenyl)-3-phenylprop-2-en-1-one; 117596063: 1-(2-Hydroxy-4,6-dimethoxyphenyl)-3-phenylprop-2-en-1-one;5-hydroxy-2,8-dimethyl-6,7,8,9-tetrahydropyrano[3,2-h][1]benzoxepin-4-one; 117596210: 1-(2-Hydroxy-4,6-dimethoxyphenyl)-3-phenylprop-2-en-1-one;3-hydroxy-13-methyl-9,11,12,14,15,16-hexahydro-6H-cyclopenta[a]phenanthren-17-one; 117596336: 1-(2-Hydroxy-4,6-dimethoxyphenyl)-3-phenylprop-2-en-1-one;2-[1-[3-(trifluoromethyl)phenyl]propan-2-ylamino]ethyl benzoate; hydrochloride; 117596406: 3-Benzhydryloxy-8-methyl-8-azabicyclo[3.2.1]octane;1-(2-hydroxy-4,6-dimethoxyphenyl)-3-phenylprop-2-en-1-one;sulfuric acid; 117596500: 1-(2-Hydroxy-4,6-dimethoxyphenyl)-3-phenylprop-2-en-1-one;5',7,9,13-tetramethylspiro[5-oxapentacyclo[10.8.0.02,9.04,8.013,18]icos-11-ene-6,2'-oxane]-16-ol; 117596834: 1-(2-Hydroxy-4,6-dimethoxyphenyl)-3-phenylprop-2-en-1-one;3-[(5-nitrofuran-2-yl)methylideneamino]-1,3-oxazolidin-2-one; 117596844: Butyl 4-aminobenzoate; 1-(2-hydroxy-4,6-dimethoxyphenyl)-3-phenylprop-2-en-1-one; 117596857: 2-(3,4-Dihydroxyphenyl)-3,5,7-trihydroxychromen-4-one;1-(2-hydroxy-4,6-dimethoxyphenyl)-3-phenylprop-2-en-1-one; 117596980: But-2-enedioic acid;1-(2-hydroxy-4,6-dimethoxyphenyl)-3-phenylprop-2-en-1-one;1-methyl-4-thioxanthen-9-ylidenepiperidine; 117597041: N,N-Diethyl-1-phenothiazin-10-ylpropan-2-amine;1-(2-hydroxy-4,6-dimethoxyphenyl)-3-phenylprop-2-en-1-one;hydrochloride; 117597170: Ethyl 2,4-dihydroxy-6-methylbenzoate;1-(2-hydroxy-4,6-dimethoxyphenyl)-3-phenylprop-2-en-1-one; 117597197: 1-(2-Hydroxy-4,6-dimethoxyphenyl)-3-phenylprop-2-en-1-one;2-(7-oxo-2,3-dihydrofuro[3,2-g]chromen-2-yl)propan-2-yl benzoate; 117597292: (1,10,11,12,14,23-Hexahydroxy-6,10,19-trimethyl-24-oxa-4-azaheptacyclo[12.12.0.02,11.04,9.015,25.018, 23.019,25]hexacosan-22-yl) 2-methylbut-2-enoate;1-(2-hydroxy-4,6-dimethoxyphenyl)-3-phenylprop-2-en-1-one;sulfuric acid; 117597421: 4-(3-Carboxyprop-2-enoyloxymethyl)-10-formyl-3,9-dihydroxy-1,7-dimethyl-6-oxobenzo[b][1,4]benzodioxepine-2-carboxylic acid;1-(2-hydroxy-4,6-dimethoxyphenyl)-3-phenylprop-2-en-1-one; 117597488: (10a-Methoxy-4,7-dimethyl-6a,8,9,10-tetrahydro-6H-indolo[4,3-fg]quinolin-9-yl)methyl 5-bromopyridine-3-carboxylate;1-(2-hydroxy-4,6-dimethoxyphenyl)-3-phenylprop-2-en-1-one; 117597586: 6-Hepta-1,3-dienyl-3,4-dihydroxy-2-oxocyclohexane-1-carbaldehyde;1-(2-hydroxy-4,6-dimethoxyphenyl)-3-phenylprop-2-en-1-one; 117597674: 1,4-Dihydroxy-5,8-bis[2-(2-hydroxyethylamino)ethylamino]anthracene-9,10-dione;1-(2-hydroxy-4,6-dimethoxyphenyl)-3-phenylprop-2-en-1-one;dihydrochloride; 117597703: 1-(2-Hydroxy-4,6-dimethoxyphenyl)-3-phenylprop-2-en-1-one;4,4,10,13,14-pentamethyl-17-(6-methylhept-5-en-2-yl)-2,3,5,6,7,11,12,15,16,17-decahydro-1H-cyclopenta[a]phenanthren-3-ol; 117597742: 1-(2-Hydroxy-4,6-dimethoxyphenyl)-3-phenylprop-2-en-1-one;(2-hydroxy-4-methoxyphenyl)-phenylmethanone; 117597750: [3-[3,4-Dihydroxy-6-methyl-5-[3,4,5-trihydroxy-6-(hydroxymethyl)oxan-2-yl]oxyoxan-2-yl]oxy-4,5-dihydroxyoxan-2-yl] 10-[3,4-dihydroxy-6-methyl-5-(3,4,5-trihydroxyoxan-2-yl)oxyoxan-2-yl]oxy-5-hydroxy-2,2,6a,6b,9,9,12a-heptamethyl-1,3,4,5,6,6a,7,8,8a,10,11,12,13,14b-tetradecahydropicene-4a-carboxylate;1-(2-hydroxy-4,6-dimethoxyphenyl)-3-phenylprop-2-en-1-one; 117597799: 1-(2-Hydroxy-4,6-dimethoxyphenyl)-3-phenylprop-2-en-1-one;methyl N-(6-phenylsulfanyl-1H-benzimidazol-2-yl)carbamate; 117597848: 1-(2-Hydroxy-4,6-dimethoxyphenyl)-3-phenylprop-2-en-1-one;7H-purin-6-amine; 117597889: [2-(3,4-Dihydroxyphenyl)-5,7-dihydroxy-3,4-dihydro-2H-chromen-3-yl] 3,4,5-trihydroxybenzoate;1-(2-hydroxy-4,6-dimethoxyphenyl)-3-phenylprop-2-en-1-one; 117597928: 1-(2-Hydroxy-4,6-dimethoxyphenyl)-3-phenylprop-2-en-1-one;N-methyl-3-phenyl-3-[4-(trifluoromethyl)phenoxy]propan-1-amine;hydrochloride; 117597933: 1-(2-Hydroxy-4,6-dimethoxyphenyl)-3-phenylprop-2-en-1-one;[6-hydroxy-3,4,5-tris(3-nitropropanoyloxy)oxan-2-yl]methyl 3-nitropropanoate; 117597980: 2,3-Dihydroxy-butanedioic acid;1-(2-hydroxy-4,6-dimethoxyphenyl)-3-phenylprop-2-en-1-one;N,N,2-trimethyl-3-phenothiazin-10-ylpropan-1-amine; 117598041: 1-(2-Hydroxy-4,6-dimethoxy-phenyl)-3-phenylprop-2-en-1-one;4-hydroxy-3-(4-hydroxyphenyl)-5-methoxy-8,8-dimethyl-6-(3-methylbut-2-enyl)pyrano[2,3-h]chromen-2-one; 117598064: 1-(2-Hydroxy-4,6-dimethoxy-henyl)-3-phenylprop-2-en-1-one;propan-2-yl 2-[4-(4-chlorobenzoyl)phenoxy]-2-methylpropanoate; 117598121: 1,3-Diphenylurea;1-(2-hydroxy-4,6-dimethoxyphenyl)-3-phenylprop-2-en-1-one; 117598239: 1-(2-Hydroxy-4,6-dimethoxyphenyl)-3-phenylprop-2-en-1-one; 3,4,5-trihydroxybenzoic acid; 117598292: 3-(3,4-Dimethoxyphenyl)prop-2-enoic acid;1-(2-hydroxy-4,6-dimethoxyphenyl)-3-phenylprop-2-en-1-one; 117598341: 2-(Dimethylamino)ethyl 2-(4-chlorophenoxy)acetate;1-(2-hydroxy-4,6-dimethoxyphenyl)-3-phenylprop-2-en-1-one; hydrochloride; 117631812: (E)-1-(2-(Benzyloxy)-6-hydroxyphenyl)-3-(4-(benzyloxy)-phenyl)-prop-2-en-1-one; 117640199: (E)-3-(3,4-Dibutoxyphenyl)-1-(2-hydroxyphenyl)prop-2-en-1-one; 117640274: (E)-3-(4-Butoxy-3-fluorophenyl)-1-(2,4-dibutoxy-6-hydroxyphenyl)prop-2-en-1-one; 117650753: [4-[(E)-3-Oxo-3-phenylprop-1-enyl]phenyl] hydrogen carbonate; 117669109: N-[4-[(E)-3-[4-[2-Hydroxyethyl(methyl)amino]phenyl]prop-2-enoyl]phenyl]-3-iodobenzamide; 117736549: (E)-1-[2-(1-Hydroxypropan- 2-ylamino)phenyl]-3-phenylprop-2-en-1-one; 117780520: Chembl4288017; 117780532: Chembl4286935; 117780536: Chembl4280122; 117803123: 2-[4-[2-[2-[4-[4-[4-[(E)-3-(2-Hydroxyphenyl)-3-oxoprop-1-enyl]phenoxy]butyl]triazol-1-yl]ethylamino]ethoxy]phenyl]chromen-4-one; 117803124: 2-[4-[2-[2-[4-[4-[4-[(E)-3-(2-Hydroxy-4-methylphenyl)-3-oxoprop-1-enyl]phenoxy]butyl]triazol-1-yl]ethylamino]ethoxy]phenyl]chromen-4-one; 117803142: (E)-1-(2-Hydroxyphenyl)-3-(4-prop-2-ynoxyphenyl)prop-2-en-1-one; 117866951: 2-Methyl-2-[2-methyl-4-[(E)-3-oxo-3-(4-propylsulfanylphenyl)prop-1-enyl]phenoxy]propanoic acid; 117888953: (E)-3-[4-Butoxy-3-(methoxymethoxy)phenyl]-1-(2-hydroxyphenyl)prop-2-en-1-one; 117888964: (E)-3-[3-Butoxy-4-(methoxymethoxy)phenyl]-1-(2-hydroxyphenyl)prop-2-en-1-one; 117898819: (E)-3-[4-Hydroxy-3-(morpholin-4-ylmethyl)phenyl]-1-(4-methoxyphenyl)prop-2-en-1-one; 117906162: (E)-3-[3-Butoxy-4-(morpholin-4-ylmethyl)phenyl]-1-(2-hydroxy-4-methylphenyl)prop-2-en-1-one; 117906389: 5-[(E)-3-(4-Hydroxyphenyl)-3-oxoprop-1-enyl]-2-(morpholin-4-ylmethyl)phenyl] 4-methylbenzenesulfonate; 117957329: (E)-3-(3-Hydroxy-4-methoxyphenyl)-1-[2-hydroxy-6-methoxy-4-[(2S,3S,5S)-3,4,5-trihydroxy-6-[[(2R,4S,5R)-3,4,5-trihydroxy-6-methyloxan-2-yl]oxymethyl]oxan-2-yl]oxyphenyl]prop-2-en-1-one; 118124503: (E)-1-(4-Aminophenyl)-3-[4-[bis(2-hydroxyethyl)amino]phenyl]prop-2-en-1-one; 118124811: 2-[N-(2-Hydroxyethyl)-4-[(E)-3-[4-[(4-methoxyphenyl)methylcarbamoylamino]phenyl]-3-oxoprop-1-enyl]anilino]ethyl acetate; 118353202: (E)-3-[4-(4-Hydroxybenzoyl)phenyl]-1-phenylprop-2-en-1-one; 118353215: Occccoc1=CC=C(C(=O)C2=CC=C(C=C2)C=CC(=O)C2=CC=CC=C2)C=C1; 118353218: Occcccoc1=CC=C(C(=O)C2=CC=C(C(C=CC3=CC=CC=C3)=O)C=C2)C=C1; 118353220:Occccccoc1=CC=C(C(=O)C2=CC=C(C=C2)C=CC(=O)C2=CC=CC=C2)C=C1; 118353230:Occcccccoc1=CC=C(C(=O)C2=CC=C(C(C=CC3=CC=CC=C3)=O)C=C2)C=C1; 118353236: Occcccoc1=CC=C(C(=O)C2=CC=C(C=C2)C=CC(=O)C2=CC=CC=C2)C=C1; 118353242: Occcoc1=CC=C(C(=O)C2=CC=C(C=C2)C=CC(=O)C2=CC=CC=C2)C=C1; 118353247: (E)-1-[4-[4-(Hydroxymethoxy)benzoyl]phenyl]-3-phenylprop-2-en-1-one; 118353250: Occccoc1=CC=C(C(=O)C2=CC=C(C(C=CC3=CC=CC=C3)=O)C=C2)C=C1; 118353251: Occcoc1=CC=C(C(=O)C2=CC=C(C(C=CC3=CC=CC=C3)=O)C=C2)C=C1; 118353258: (E)-1-[4-(4-Hydroxybenzoyl)phenyl]-3-phenylprop-2-en-1-one; 118353260: (E)-3-[4-[4-(Hydroxymethoxy)benzoyl]phenyl]-1-phenylprop-2-en-1-one; 118353265: Occoc1=CC=C(C(=O)C2=CC=C(C=C2)C=CC(=O)C2=CC=CC=C2)C=C1; 118353271: Occcoc1=CC=C(C(=O)C2=CC=C(C(C=CC3=CC=CC=C3)=O)C=C2)C=C1; 118372777: (E)-1-(2-Hydroxyphenyl)-3-[4-(methoxymethoxy)-3-phenylmethoxyphenyl]prop-2-en-1-one; 118372783: (E)-1-(2-Hydroxyphenyl)-3-[3-(methoxymethoxy)-4-phenylmethoxyphenyl]prop-2-en-1-one; 118402202: (E)-3-[4-[[4-(4-Hydroxyphenyl)phenoxy]methoxy]phenyl]-1-phenylprop-2-en-1-one; 118440954: (E)-1-(4-Aminophenyl)-3-[4-(hydroxymethyl)-3-methoxyphenyl]prop-2-en-1-one; 118495971: (E)-1-[2-Hydroxy-4,6-bis(phenylmethoxy)phenyl]-3-(4-methoxyphenyl)prop-2-en-1-one; 118501429: (E)-1-(2-Hydroxy-4-methyl-6-phenylmethoxyphenyl)-3-(4-methoxyphenyl)prop-2-en-1-one; 118503351: (E)-1-(2,4-Dibutoxy-6-hydroxyphenyl)-3-(4-methoxyphenyl)prop-2-en-1-one; 118583285: Propan-2-yl (2S)-2-[[[(2R,3R,4R,5R)-4-fluoro-3-hydroxy-4-methyl-5-(4-methylidene-2-oxopyrimidin-1-yl)oxolan-2-yl]methoxy-[4-[(E)-3-phenylprop-2-enoyl]phenoxy]phosphoryl]amino]propanoate; 118593157: (E)-1-(2,4-Dihydroxyphenyl)-3-(3-hydroxy-4-methylphenyl)prop-2-en-1-one; 118598492: OC1=C(C=CC(=C1)O)C(C=CC1=CC(=C(C=C1)O)F)=O; 118604096: 12-[[4-[(E)-3-[4-(Diethylamino)phenyl]prop-2-enoyl]benzoyl]amino]dodecanoic acid; 118643862: 3,5-Diamino-3-[1-[4-[(E)-3-oxo-3-[4-(4-propylphenyl)phenyl]prop-1-enyl]phenoxy]pentyl]cyclohexa-1,4-diene-1-carboxylic acid; 118643863: 3,5-Diamino-2-[5-[4-[(E)-3-oxo-3-[4-(4-propylphenyl)phenyl]prop-1-enyl]phenoxy]pentyl]benzoic acid; 118643867: 3,5-Diamino-2-[1-[4-[(E)-3-oxo-3-[4-(4-pentylphenyl)phenyl]prop-1-enyl]phenoxy]ethyl]benzoic acid; 118643868: 3,5-Diamino-2-[2-[4-[(E)-3-oxo-3-[4-(4-pentylphenyl)phenyl]prop-1-enyl]phenoxy]ethyl]benzoic acid; 118643869: 3,5-Diamino-3-[1-[4-[(E)-3-oxo-3-[4-(4-pentylphenyl)phenyl]prop-1-enyl]phenoxy]pentyl]cyclohexa-1,4-diene-1-carboxylic acid; 118643870: 3,5-Diamino-2-[5-[4-[(E)-3-oxo-3-[4-(4-pentylphenyl)phenyl]prop-1-enyl]phenoxy]pentyl]benzoic acid; 118643871: 3,5-Diamino-2-[8-[4-[(E)-3-oxo-3-[4-(4-pentylphenyl)phenyl]prop-1-enyl]phenoxy]octyl]benzoic acid; 118643926: (Z)-3-(4-((1-(2-(2,4-Difluorophenyl)-2-hydroxy-3-(1H-1,2,4-triazol-1-yl)propyl)-1H-1,2,3-triazol-4-yl) methoxy)phenyl)-1-(4-(4-(4-methoxybenzyl)piperazin-1-yl)phenyl)prop-2-en-1-one; 118654629: (E)-3-[4-[[1-[2-(2,4-Difluorophenyl)-2-hydroxy-3-(1,2,4-triazol-1-yl)propyl]triazol-4-yl]methoxy]phenyl]-1-[4-(4-methylpiperazin-1-yl)phenyl]prop-2-en-1-one; 118676934: (E)-1-[4-[4-(3-Hydroxypropoxy)benzoyl]phenyl]-3-phenylprop-2-en-1-one; 118676936: (E)-1-[4-[4-(8-Hydroxyoctoxy)benzoyl]phenyl]-3-phenylprop-2-en-1-one; 118676939: (E)-1-[4-[4-(2-Hydroxyethoxy)benzoyl]phenyl]-3-phenylprop-2-en-1-one; 118676948: (E)-3-[4-[4-(2-Hydroxyethoxy)benzoyl]phenyl]-1-phenylprop-2-en-1-one; 118676949: (E)-1-[4-[4-(4-Hydroxybutoxy)benzoyl]phenyl]-3-phenylprop-2-en-1-one; 118676950: (E)-1-[4-[4-(6-Hydroxyhexoxy)benzoyl]phenyl]-3-phenylprop-2-en-1-one; 118676951: (E)-3-[4-[4-(6-Hydroxyhexoxy)benzoyl]phenyl]-1-phenylprop-2-en-1-one; 118676952: (E)-3-[4-[4-(4-Hydroxybutoxy)benzoyl]phenyl]-1-phenylprop-2-en-1-one; 118676960: (E)-3-[4-[4-(8-Hydroxyoctoxy)benzoyl]phenyl]-1-phenylprop-2-en-1-one; 118676967: (E)-3-[4-[4-(3-Hydroxypropoxy)benzoyl]phenyl]-1-phenylprop-2-en-1-one; 118699403: (E)-1-(2,6-Dihydroxy-4-methylphenyl)-3-phenylprop-2-en-1-one; 118712279: (E)-1-(2-Hydroxyphenyl)-3-(4-phenoxyphenyl)prop-2-en-1-one; 118722283: (E)-3-(3-Allyloxyphenyl)-1-(2,4-dihydroxyphenyl)prop-2-en-1-one; 118722284: (E)-3-(4-Allyloxyphenyl)-1-(2,4-dihydroxyphenyl)prop-2-en-1-one; 118725311: (E)-1-[2-(4-Fluorophenyl)phenyl]-3-(4-hydroxy-3-methoxyphenyl)prop-2-en-1-one; 118725312: C1=C(O)C(OC)=CC=C1\C=C\C(=O)C1=CC=CC=C1C1=CC=C(F)C=C1; 118725318: C1=C(O)C(OC)=CC=C1\C=C\C(=O)C1=CC=CC=C1 C1=CC(OC)=C(OC)C(OC)=C1; 118725319: C1=C(O)C(OC)=CC=C1\C=C\C(=O)C1=CC=CC=C1 C1=CC=C(OC)C(OC)=C1OC; 118725711: (2E)-1-(2-Hydroxy-4,6-dimethoxyphenyl)-3-(3-hydroxyphenyl)prop-2-en-1-one; 118733749: (E)-1-(2,4-Dihydroxy-6-methoxyphenyl)-3-(4-nitro-phenyl)prop-2-en-1-one; 118733750: (E)-1-(2,4-Dihydroxy-6-methoxyphenyl)-3-(3-nitro-phenyl)prop-2-en-1-one; 118733751: (E)-3-(3,4-Dihydroxyphenyl)-1-(2,4,6-trimethoxyphenyl)prop-2-en-1-one; 118737942: (1R,2R,4R,9S,17S)-4-[4-[[3-Hydroxy-4-[(E)-3-phenylprop-2-enoyl]phenoxy]methyl]triazol-1-yl]-7,13-diazatetracyclo

[7.7.1.02,7.013,17]heptadecan-6-one; 118737983: (1R,2R, 4R,9S,17S)-4-[4-[[4-[(E)-3-(4-Chlorophenyl)prop-2-enoyl]-3-hydroxyphenoxy]methyl]triazol-1-yl]-7,13-diazatetracyclo[7.7.1.02,7.013,17]heptadecan-6-one; 118737984: (1R,2R,4R,9S,17S)-4-[4-[[4-[(E)-3-(4-Fluoro-phenyl)prop-2-enoyl]-3-hydroxyphenoxy]methyl]triazol-1-yl]-7,13-diazatetracyclo[7.7.1.02,7.013,17]heptadecan-6-one; 118737985: (1R,2R,4R,9S,17S)-4-[4-[[3-Hydroxy-4-[(E)-3-(4-methoxyphenyl)prop-2-enoyl]phenoxy]methyl] triazol-1-yl]-7,13-diazatetracyclo[7.7.1.02,7.013,17] heptadecan-6-one; 118737986: (1R,2R,4R,9S,17S)-4-[4-[[3-Hydroxy-4-[(E)-3-(4-methylphenyl)prop-2-enoyl] phenoxy]methyl]triazol-1-yl]-7,13-diazatetracyclo [7.7.1.02,7.013,17]heptadecan-6-one; 118737987: (1R,2R, 4R,9S,17S)-4-[4-[[4-[(E)-3-(4-Tert-butylphenyl)prop-2-enoyl]-3-hydroxyphenoxy]methyl]triazol-1-yl]-7,13-diazatetracyclo[7.7.1.02,7.013,17]heptadecan-6-one; 118737988: (1R,2R,4R,9S,17S)-4-[4-[[3-Hydroxy-4-[(E)-3-[3-(trifluoromethyl)phenyl]prop-2-enoyl]phenoxy] methyl]triazol-1-yl]-7,13-diazatetracyclo[7.7.1.02,7.013, 17]heptadecan-6-one; 118737989: (1R,2R,4R,9S,17S)-4-[4-[[4-[(E)-3-(3-Chlorophenyl)prop-2-enoyl]-3-hydroxyphenoxy]methyl]triazol-1-yl]-7,13-diazatetracyclo [7.7.1.02,7.013,17]heptadecan-6-one; 118737990: (1R,2R, 4R,9S,17S)-4-[4-[[4-[(E)-3-(3,4-Dichlorophenyl)prop-2-enoyl]-3-hydroxyphenoxy]methyl]triazol-1-yl]-7,13-diazatetracyclo[7.7.1.02,7.013,17]heptadecan-6-one; 118737991: (1R,2R,4R,9S,17S)-4-[4-[[4-[(E)-3-(3,4-Dime-thoxyphenyl)prop-2-enoyl]-3-hydroxyphenoxy]methyl]tri-azol-1-yl]-7,13-diazatetracyclo[7.7.1.02,7.013,17]heptade-can-6-one; 118737996: (E)-1-(2-Hydroxy-4-prop-2-ynoxyphenyl)-3-phenylprop-2-en-1-one; 118737997: (E)-3-(3-Chlorophenyl)-1-(2-hydroxy-4-prop-2-ynoxyphenyl) prop-2-en-1-one; 118737998: (E)-3-(3,4-Dichlorophenyl)-1-(2-hydroxy-4-prop-2-ynoxyphenyl)prop-2-en-1-one; 118886909: (E)-1-(2-Hydroxy-4-methyl-6-phenylmethoxy-phenyl)-3-(4-phenylmethoxyphenyl)prop-2-en-1-one; 118886921: (E)-3-(3-Fluoro-4-phenylmethoxyphenyl)-1-(2-hydroxy-4-methyl-6-phenylmethoxyphenyl)prop-2-en-1-one; 118889192: (E)-1-(2-Butoxy-6-hydroxyphenyl)-3-(4-butoxyphenyl)prop-2-en-1-one; 118909598: (E)-1-(2-Hydroxyphenyl)-3-(1H-indol-5-yl)prop-2-en-1-one; 118967667: (E)-1-(2,4-Dihydroxyphenyl)-3-(4-hydroxy-3-methylphenyl)prop-2-en-1-one; 121388932: (E)-1-(2-Hy-droxyphenyl)-3-(4-sulfanylphenyl)prop-2-en-1-one; 121580466: 3-Hydroxy-4-[(E)-3-(3-methoxy-4-methylsul-fanylphenyl)prop-2-enoyl]benzoic acid; 122149850: 4-[(E)-3-[4-(Difluoromethoxy)phenyl]prop-2-enoyl]-3-hydroxy-benzoic acid; 122185099: (E)-3-[3-Hydroxy-4-(pyrrolidin-1-ylmethyl)phenyl]-1-phenylprop-2-en-1-one; 122185101: (E)-3-[4-Hydroxy-3-[(4-methylpiperazin-1-yl)methyl]phe-nyl]-1-(4-methoxyphenyl)prop-2-en-1-one; 122185102: (E)-3-[3-Hydroxy-4-(pyrrolidin-1-ylmethyl)phenyl]-1-(4-methoxyphenyl)prop-2-en-1-one; 122185103: (E)-3-[4-[(4-Ethylpiperazin-1-yl)methyl]-3-hydroxyphenyl]-1-(4-methoxyphenyl)prop-2-en-1-one; 122185104: (E)-3-[3-[(Dimethylamino)methyl]-4-hydroxyphenyl]-1-(4-methoxyphenyl)prop-2-en-1-one; 122185105: (E)-3-[4-Hydroxy-3-(piperidin-1-ylmethyl)phenyl]-1-[4-(trifluoromethyl)phenyl]prop-2-en-1-one; 122185106: (E)-1-(4-Bromophenyl)-3-[3-hydroxy-4-(piperidin-1-ylmethyl) phenyl]prop-2-en-1-one; 122185107: (E)-1-(4-Ethylphenyl)-3-[3-hydroxy-4-(piperidin-1-ylmethyl) phenyl]prop-2-en-1-one; 122185108: (E)-1-(4-Fluorophenyl)-3-[3-hydroxy-4-(piperidinomethyl)phenyl]-2-propene-1-one; 122185196: (E)-3-[3-Hydroxy-4-(piperidin-1-ylmethyl)phenyl]-1-(4-methylphenyl)prop-2-en-1-one; 122187514: COc1cc(\C=C\C(=O)c2ccc(CI) cc2O)ccc1O; 122191389: (5S,5As,8aR,9R)-9-(4-hydroxy-3,5-dimethoxyphenyl)-5-[4-[[4-[(E)-3-phenylprop-2-enoyl] phenoxy]methyl]triazol-1-yl]-5a,6,8a,9-tetrahydro-5H-[2] benzofuro[6,5-f][1,3]benzodioxol-8-one; 122191390: (5S, 5As,8aR,9R)-9-(4-hydroxy-3,5-dimethoxyphenyl)-5-[4-[[4-[(E)-3-oxo-3-phenylprop-1-enyl]phenoxy]methyl]triazol-1-yl]-5a,6,8a,9-tetrahydro-5H-[2]benzofuro[6,5-f][1,3] benzodioxol-8-one; 122191534: (5S,5As,8aR,9R)-5-[4-[[4-[(E)-3-(3-fluorophenyl)prop-2-enoyl]phenoxy]methyl] triazol-1-yl]-9-(4-hydroxy-3,5-dimethoxy-phenyl)-5a,6,8a, 9-tetrahydro-5H-[2]benzofuro[6,5-f][1,3]benzodioxol-8-one; 122191536: (5S,5As,8aR,9R)-9-(4-hydroxy-3,5-dimethoxyphenyl)-5-[4-[[4-[(E)-3-(3-methylphenyl)prop-2-enoyl]phenoxy]methyl]triazol-1-yl]-5a,6,8a,9-tetrahydro-5H-[2]benzofuro[6,5-f][1,3]benzodioxol-8-one; 122191537: (5S,5As,8aR,9R)-9-(4-hydroxy-3,5-dime-thoxyphenyl)-5-[4-[[4-[(E)-3-(4-methoxyphenyl)prop-2-enoyl]phenoxy]methyl]triazol-1-yl]-5a,6,8a,9-tetrahydro-5H-[2]benzofuro[6,5-f][1,3]benzodioxol-8-one; 122193809: (3E,7E,11 E)-1-[[1-[2-[3-Hydroxy-4-[(E)-3-(4-methoxyphenyl)prop-2-enoyl]phenoxy]ethyl]triazol-4-yl] methyl]-5,5,8,12-tetramethyl-1-azacyclododeca-3,7,11-trien-2-one; 122193810: (3E,7E,11E)-1-[[1-[2-[3-Hydroxy-4-[(E)-3-(3-methoxyphenyl)prop-2-enoyl]phenoxy]ethyl] triazol-4-yl]methyl]-5,5,8,12-tetramethyl-1-azacyclododecan-3,7,11-trien-2-one; 122193813: (3E,7E,11 E)-1-[[1-[2-[3-Hydroxy-4-[(E)-3-(4-methylphenyl)prop-2-enoyl]phenoxy]ethyl]triazol-4-yl]methyl]-5,5,8,12-tetram-ethyl-1-azacyclododeca-3,7,11-trien-2-one; 122193814: (3E,7E,11 E)-1-[[1-[2-[3-Hydroxy-4-[(E)-3-[4-methoxy-3-(3-morpholin-4-ylpropoxy)phenyl]prop-2-enoyl]phenoxy] ethyl]triazol-4-yl]methyl]-5,5,8,12-tetramethyl-1-azacy-clododecan-3,7,11-trien-2-one; 122193815: (3E,7E,11 E)-1-[[1-[2-[3-Hydroxy-4-[(E)-3-(4-propan-2-ylphenyl)prop-2-enoyl]phenoxy]ethyl]triazol-4-yl]methyl]-5,5,8,12-tetramethyl-1-azacyclododeca-3,7,11-trien-2-one; 122223102: 3-[4-(3-Oxo-3-phenyl-1-propenyl)phenoxy] propanoic acid; 122581159: (E)-1-[2-Hydroxy-4-(hy-droxymethyl)-6-methoxyphenyl]-3-(4-methoxyphenyl) prop-2-en-1-one; 122581177: (E)-1-[2-Hydroxy-4-(hydroxymethyl)-6-methoxyphenyl]-3-phenylprop-2-en-1-one; 122688043: FC=1C=C(C=CC=1)C1=C (C=CC=1)C(C=CC1=CC(=C(C=C1) N(C)C)O)=0; 122688045: FC1=CC=C(C=C1)C1=C(C=CC=C1)C(/ C=C/C=1C=CC(=C(C=1)S(=O)(=O)O)O)=O; 122688046: FC=1C=C(C=CC=1)C1=C(C=CC=C1)C(/ C=C/C=1C=CC(=C(C=1)S(=O)(=O)O)O)=O; 122693807: 4-[(E)-3-[2-(3-Fluorophenyl)phenyl]-3-oxo-prop-1-enyl]benzoic acid; 122693810: (E)-1-[2-(3-Fluoro-phenyl)phenyl]-3-(3-hydroxyphenyl)prop-2-en-1-one; 122693811: 3-[(E)-3-[2-(3-Fluorophenyl)phenyl]-3-oxo-prop-1-enyl]benzoic acid; 122707159: (Z)-3-(3,4-Dihy-droxyphenyl)-1-phenylprop-2-en-1-one; 122707388: (Z)-3-(3,4-Dihydroxyphenyl)-1-(4-fluorophenyl)prop-2-en-1-one; 123136113: 1-(2-Hydroxyphenyl)-3-(4-nitro-3-phenyl-methoxyphenyl)prop-2-en-1-one; 123146989: 1-[4-[2-(2,4-Difluorophenyl)-2-hydroxy-3-(1,2,4-triazol-1-yl)propoxy] phenyl]-3-[4-[[1-[2-(2,4-difluorophenyl)-2-hydroxy-3-(1,2, 4-triazol-1-yl)propyl]triazol-4-yl]methoxy]phenyl]prop-2-en-1-one; 123159959: COc1ccc(cc1)C(=O)C=Cc1ccc(O) c(CN2CCOCC2)c1; 123174448: 1-[4-[(2S)-2-(2,4-Difluorophenyl)-2-hydroxy-3-(1,2,4-triazol-1-yl)propoxy] phenyl]-3-(4-methoxyphenyl)prop-2-en-1-one; 123181391: 12-[[4-[3-[4-(Diethylamino)phenyl]prop-2-enoyl]benzoyl] amino]dodecanoic acid; 123188229: COCOc1cc(O)c(C (=O)C=Cc2cccc(c2)C(O)=O)c(OCOC)c1; 123212932:

3-(4-Chlorophenyl)-1-[4-[(2S)-2-(2,4-difluorophenyl)-2-hydroxy-3-(1,2,4-triazol-1-yl)propoxy]phenyl]prop-2-en-1-one; 123217755: 1-[4-[[1-[2-(2,4-Difluorophenyl)-2-hydroxy-3-(1,2,4-triazol-1-yl)propyl]triazol-4-yl]methoxy]phenyl]-3-phenylprop-2-en-1-one; 123228840: Propan-2-yl 2-[[[5-(2,4-dioxopyrimidin-1-yl)-4-fluoro-3-hydroxy-4-methyloxolan-2-yl]methoxy-[4-(3-phenylprop-2-enoyl)phenoxy]phosphoryl]amino]propanoate; 123285621: 2-[4-[2-[2-[4-[4-[4-[3-(2-Hydroxyphenyl)-3-oxoprop-1-enyl]phenoxy]butyl]triazol-1-yl]ethylamino]ethoxy]phenyl]chromen-4-one; 123290077: 2-[4-[2-[2-[4-[4-[4-[3-(2-Hydroxy-4-methylphenyl)-3-oxoprop-1-enyl]phenoxy]butyl]triazol-1-yl]ethylamino]ethoxy]phenyl]chromen-4-one; 123350638: Propan-2-yl (2S)-2-[[[(2R,3R,4R,5R)-5-(2,4-dioxopyrimidin-1-yl)-4-fluoro-3-hydroxy-4-methyloxolan-2-yl]methoxy-[4-(3-phenylprop-2-enoyl)phenoxy]phosphoryl]amino]propanoate; 123370229: 1-[4-(Hydroxymethyl)-2-methoxyphenyl]-3-[3-(trifluoromethyl)phenyl]prop-2-en-1-one; 123401096: 1-[4-[2-(2,4-Difluorophenyl)-2-hydroxy-3-(1,2,4-triazol-1-yl)propoxy]phenyl]-3-(4-prop-2-ynoxyphenyl)prop-2-en-1-one; 123407222: 1-(2-Hydroxyphenyl)-3-[3-(methoxymethoxy)-4-phenylmethoxyphenyl]prop-2-en-1-one; 123441782: 3-[4-(Hydroxymethyl)phenyl]-1-phenylprop-2-en-1-one; 123455428: N-[4-[3-[4-[2-Hydroxyethyl(methyl)amino]phenyl]prop-2-enoyl]phenyl]-3-iodopropanamide; 123496861: 2-[4-[2-[2-[4-[4-[4-[3-(4-Fluoro-2-hydroxyphenyl)-3-oxoprop-1-enyl]phenoxy]butyl]triazol-1-yl]ethoxy]ethoxy]phenyl]chromen-4-one; 123511541: 1-[4-[[1-[2-(2,4-Difluorophenyl)-2-hydroxy-3-(1,2,4-triazol-1-yl)propyl]triazol-4-yl]methoxy]phenyl]-3-(4-methoxyphenyl)prop-2-en-1-one; 123524547: 3-(4-Chlorophenyl)-1-[4-[(2R)-2-(2,4-difluorophenyl)-2-hydroxy-3-(1,2,4-triazol-1-yl)propoxy]phenyl]prop-2-en-1-one; 123529900: 1-[4-[(2R)-2-(2,4-Difluorophenyl)-2-hydroxy-3-(1,2,4-triazol-1-yl)propoxy]phenyl]-3-(4-methoxyphenyl)prop-2-en-1-one; 123533691: 3-(3-Fluoro-4-phenylmethoxyphenyl)-1-[2-hydroxy-4,6-bis(phenylmethoxy)phenyl]prop-2-en-1-one; 123539496: 5-(2,5-Dioxooxolan-3-yl)-8-[2-hydroxy-2-[4-[[4-(3-oxo-3-phenylprop-1-enyl)phenoxy]methoxy]phenyl]ethoxy]-3a,4,5,9b-tetrahydrobenzo[e][2]benzofuran-1,3-dione; 123586893: Propan-2-yl 2-[[[5-(2,4-dioxopyrimidin-1-yl)-4-fluoro-3-hydroxy-4-methyloxolan-2-yl]methoxy-[4-(3-phenylprop-2-enoyl)phenoxy]phosphoryl]amino]acetate; 123590838: 1-(2,4-Dihydroxyphenyl)-3-(3-fluoro-4-hydroxyphenyl)prop-2-en-1-one; 123656569: 3-[4-[[1-[2-(2,4-Difluorophenyl)-2-hydroxy-3-(1,2,4-triazol-1-yl)propyl]triazol-4-yl]methoxy]phenyl]-1-(4-methoxyphenyl)prop-2-en-1-one; 123663653: 1-(2-Hydroxyphenyl)-3-[4-(methoxymethoxy)-3-phenylmethoxyphenyl]prop-2-en-1-one; 123680298: 3-[4-[[1-[2-(2,4-Difluorophenyl)-2-hydroxy-3-(1,2,4-triazol-1-yl)propyl]triazol-4-yl]methoxy]phenyl]-1-(4-fluorophenyl)prop-2-en-1-one; 123681995: 1-[2-[5-Fluoro-3,4-dihydroxy-6-(hydroxymethyl)oxan-2-yl]oxy-6-hydroxy-4-methylphenyl]-3-phenylprop-2-en-1-one; 123701400: 1-[4-(Hydroxymethyl)phenyl]-3-[3-(trifluoromethyl)phenyl]prop-2-en-1-one; 123832466: 1-(4-Bromophenyl)-3-(3,4-dihydroxyphenyl)prop-2-en-1-one; 123861395: 1-[2-Hydroxy-6-(methoxymethoxy)phenyl]-3-[4-methoxy-3-(methoxy-methoxy)phenyl]prop-2-en-1-one; 123882719: 1-[4-(Hydroxymethyl)phenyl]-3-phenylprop-2-en-1-one; 123890224: 3-[4-[[1-[2-(2,4-Difluorophenyl)-2-hydroxy-3-(1,2,4-triazol-1-yl)propyl]triazol-4-yl]methoxy]phenyl]-1-[4-(4-propylpiperazin-1-yl)phenyl]prop-2-en-1-one; 123893497: 1-[4-(Hydroxymethyl)-2,6-dimethoxyphenyl]-3-[3-(trifluoromethyl)phenyl]prop-2-en-1-one; 123966740: 1-[4-[3-[4-[Bis(2-hydroxyethyl)amino]phenyl]prop-2-enoyl]phenyl]-3-[(4-methoxyphenyl)methyl]urea; 123986304: 5-(2,5-Dioxooxolan-3-yl)-8-[6-hydroxy-6-[4-[[4-(3-oxo-3-phenylprop-1-enyl)phenoxy]methoxy]phenyl]hexoxy]-3a,4,5,9b-tetrahydrobenzo[e][2]benzofuran-1,3-dione; 123987644: 1-[4-(Hydroxymethyl)phenyl]-3-(4-hydroxyphenyl)prop-2-en-1-one; 123990909: 5-(2,5-Dioxooxolan-3-yl)-8-[4-[4-[2-hydroxy-2-[4-(3-oxo-3-phenylprop-1-enyl)phenyl]ethoxy]phenyl]phenoxy]-3a,4,5,9b-tetrahydrobenzo[e][2]benzofuran-1,3-dione; 124008552: 1-(4-Aminophenyl)-3-[4-[2-hydroxyethyl(methyl)amino]phenyl]prop-2-en-1-one; 124014447: 2-[4-[2-[2-[4-[4-[4-[3-(2-Hydroxy-4-methylphenyl)-3-oxoprop-1-enyl]phenoxy]butyl]triazol-1-yl]ethoxy]ethoxy]phenyl]chromen-4-one; 124021961: 1-[4-[[1-[2-(2,4-Difluorophenyl)-2-hydroxy-3-(1,2,4-triazol-1-yl)propyl]triazol-4-yl]methoxy]phenyl]-3-(4-methylphenyl)prop-2-en-1-one; 124080645: (E)-3-(4-Bromophenyl)-1-(2,4-difluoro-6-hydroxyphenyl)prop-2-en-1-one; 124080727: (E)-3-(4-Bromophenyl)-1-[4-fluoro-2-hydroxy-6-(2,2,2-trifluoroethoxy)phenyl]prop-2-en-1-one; 124093985: 1,3-Diphenylprop-2-en-1-one;(2S)-7-hydroxy-2-(4-hydroxyphenyl)-2,3-dihydrochromen-4-one; 124140053: (E)-1,3-Diphenylprop-2-en-1-one;naphthalen-1-ol;sulfuric acid; 124351262: (Z)-3-(3,4-Dihydroxyphenyl)-1-(2,4,6-trihydroxyphenyl)prop-2-en-1-one; 124389668: (Z)-3-(4-Hydroxyphenyl)-1-(2,4,6-trihydroxyphenyl)prop-2-en-1-one; 124389896: (Z)-1-(2-Hydroxyphenyl)-3-(4-nitro-phenyl)prop-2-en-1-one; 124406588: (Z)-3-(3,4-Dihydroxyphenyl)-1-(4-hydroxyphenyl)prop-2-en-1-one; 124461562: (E)-3-(4-Hydroxyphenyl)-1-[2-hydroxy-4-[(2R,3S,4R,5R,6S)-3,4,5-trihydroxy-6-(hydroxymethyl)oxan-2-yl]oxyphenyl]prop-2-en-1-one; 124485505: (Z)-1-[4-[(2S)-2-Hydroxy-3-[4-[(E)-3-oxo-3-phenylprop-1-enyl]phenoxy]propoxy]phenyl]-3-phenylprop-2-en-1-one; 124511253: Chembl4213562; 124556809: (Z)-1-(2,6-Dihydroxy-4-methoxyphenyl)-3-(4-methoxy-phenyl)prop-2-en-1-one; 124671816: 2-[2-[(Z)-3-(4-Methoxyphenyl)prop-2-enoyl]phenyl]acetic acid; 124671817: 2-[2-[(E)-3-(4-Methoxyphenyl)prop-2-enoyl]phenyl]acetic acid; 124767910: (E)-1-[4-[(2S)-2-Hydroxy-3-[4-[(Z)-3-oxo-3-phenylprop-1-enyl]phenoxy]propoxy]phenyl]-3-phenylprop-2-en-1-one; 124767911: (Z)-1-[4-[(2S)-2-Hydroxy-3-[4-[(Z)-3-oxo-3-phenylprop-1-enyl]phenoxy]propoxy]phenyl]-3-phenylprop-2-en-1-one; 124767912: (E)-1-[4-[(2S)-2-Hydroxy-3-[4-[(E)-3-oxo-3-phenylprop-1-enyl]phenoxy]propoxy]phenyl]-3-phenylprop-2-en-1-one; 124771192: N-[(2S,3S,4S,5S,6R)-4,5-Dihydroxy-6-(hydroxy-methyl)-2-[4-[(E)-3-phenylprop-2-enoyl]phenoxy]oxan-3-yl]acetamide; 124771193: N-[(2S,3S,4R,5R,6R)-4,5-Dihydroxy-6-(hydroxymethyl)-2-[4-[(E)-3-phenylprop-2-enoyl]phenoxy]oxan-3-yl]acetamide; 124771194: N-[(2S,3S,4S,5R,6R)-4,5-Dihydroxy-6-(hydroxymethyl)-2-[4-[(E)-3-phenylprop-2-enoyl]phenoxy]oxan-3-yl]acetamide; 124771195: N-[(2S,3S,4R,5S,6R)-4,5-Dihydroxy-6-(hydroxymethyl)-2-[4-[(E)-3-phenylprop-2-enoyl]phenoxy]oxan-3-yl]acetamide; 124833409: N-[(2S,4Ar,6S,7S,8S,8aR)-8-hydroxy-6-[4-[(E)-3-oxo-3-phenylprop-1-enyl]phenoxy]-2-phenyl-4,4a,6,7,8,8a-hexahydropyrano[3,2-d][1,3]dioxin-7-yl]acetamide; 124833410: N-[(2S,4Ar,6S,7S,8R,8aR)-8-hydroxy-6-[4-[(E)-3-oxo-3-phenylprop-1-enyl]phenoxy]-2-phenyl-4,4a,6,7,8,8a-hexahydropyrano[3,2-d][1,3]dioxin-7-yl]acetamide; 124833411: N-[(2S,4Ar,6S,7S,8R,8aS)-8-hydroxy-6-[4-[(E)-3-oxo-3-phenylprop-1-enyl]phenoxy]-2-phenyl-4,4a,6,7,8,8a-hexahydropyrano[3,2-d][1,3]dioxin-7-yl]acetamide; 124833412: N-[(2S,4Ar,6S,7S,8S,8aS)-8-hydroxy-6-[4-[(E)-3-oxo-3-phenylprop-1-enyl]phenoxy]-2-phenyl-4,4a,6, 7,8,8a-hexahydropyrano[3,2-d][1,3]dioxin-7-yl]acetamide; 124833434: N-[(2S,4Ar,6S,7S,8S,8aR)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124833435: N-[(2S,4Ar,6S,7S,8R,8aR)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124833436: N-[(2S,4Ar,6S,7S,8R,8aS)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124833437: N-[(2S,4Ar,6S,7S,8S,8aS)-8-hydroxy-2-phenyl-6-[4-[(E)-3-phenylprop-2-enoyl]phenoxy]-4,4a,6,7,8,8a-hexahydropyrano[3,2-d][1,3]dioxin-7-yl]acetamide; 124906456: (E)-3-(3-Hydroxy-4-methoxyphenyl)-1-[2-hydroxy-6-methoxy-4-[(2R,3S,4R,5R,6S)-3,4,5-trihydroxy-6-[[(2S,5R)-5-hydroxyoxan-2-yl]oxymethyl]oxan-2-yl]oxyphenyl]prop-2-en-1-one; 124906457: (E)-3-(3-Hydroxy-4-methoxyphenyl)-1-[2-hydroxy-6-methoxy-4-[(2R,3S,4R,5R,6S)-3,4,5-trihydroxy-6-[[(2S,5S)-5-hydroxyoxan-2-yl]oxymethyl]oxan-2-yl]oxyphenyl]prop-2-en-1-one; 124906458: (E)-3-(3-Hydroxy-4-methoxyphenyl)-1-[2-hydroxy-6-methoxy-4-[(2R,3S,4R,5R,6S)-3,4,5-trihydroxy-6-[[(2R,5R)-5-hydroxyoxan-2-yl]oxymethyl]oxan-2-yl]oxyphenyl]prop-2-en-1-one; 124906459: (E)-3-(3-Hydroxy-4-methoxyphenyl)-1-[2-hydroxy-6-methoxy-4-[(2R,3S,4R,5R,6S)-3,4,5-trihydroxy-6-[[(2R,5S)-5-hydroxyoxan-2-yl]oxymethyl]oxan-2-yl]oxyphenyl]prop-2-en-1-one; 124921909: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4S,5S,6R)-3,4,5-trihydroxy-6-methyloxan-2-yl]oxymethyl]oxan-2-yl]oxyphenyl]prop-2-en-1-one; 124921910: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4S,5R,6R)-3,4,5-trihydroxy-6-methyloxan-2-yl]oxymethyl]oxan-2-yl]oxyphenyl]prop-2-en-1-one; 124925164: 2-[(2S,3R,4R,5R,6R)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 124925165: 2-[(2S,3R,4R,5R,6S)-5-Acetyloxy-2-(acetyloxymethyl)-6-[4-[(Z)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 124925166: 2-[(2S,3R,4R,5R,6S)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 124925167: 2-[(2S,3R,4R,5R,6R)-5-Acetyloxy-2-(acetyloxymethyl)-6-[4-[(Z)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 124925172: 2-[(2S,3R,4R,5R,6R)-3,5-Diacetyloxy-2-(acetyloxymethyl)-6-[4-[(E)-3-oxo-3-phenylprop-1-enyl]phenoxy]oxan-4-yl]acetic acid; 124925173: 2-[(2S,3S,4R,5R,6R)-3,5-Diacetyloxy-2-(acetyloxymethyl)-6-[4-[(E)-3-oxo-3-phenylprop-1-enyl]phenoxy]oxan-4-yl]acetic acid; 124925174: 2-[(2S,3S,4R,5R,6R)-3,5-Diacetyloxy-2-(acetyloxymethyl)-6-[4-[(Z)-3-oxo-3-phenylprop-1-enyl]phenoxy]oxan-4-yl]acetic acid; 124925175: 2-[(2S,3R,4R,5R,6R)-3,5-Diacetyloxy-2-(acetyloxymethyl)-6-[4-[(Z)-3-oxo-3-phenylprop-1-enyl]phenoxy]oxan-4-yl]acetic acid; 124925242: 2-[(2S,3R,4R,5R,6R)-3,5-Diacetyloxy-2-(acetyloxymethyl)-6-[4-[(E)-3-phenylprop-2-enoyl]phenoxy]oxan-4-yl]acetic acid; 124925243: 2-[(2S,3R,4R,5R,6R)-3,5-Diacetyloxy-2-(acetyloxymethyl)-6-[4-[(Z)-3-phenylprop-2-enoyl]phenoxy]oxan-4-yl]acetic acid; 124925244: 2-[(2S,3S,4R,5R,6R)-3,5-Diacetyloxy-2-(acetyloxymethyl)-6-[4-[(Z)-3-phenylprop-2-enoyl]phenoxy]oxan-4-yl]acetic acid; 124925245: 2-[(2S,3S,4R,5R,6R)-3,5-Diacetyloxy-2-(acetyloxymethyl)-6-[4-[(E)-3-phenylprop-2-enoyl]phenoxy]oxan-4-yl]acetic acid; 125027357: (E)-1-[4-[(2S,3S,4R,5S,6R)-4,5-Dihydroxy-6-(hydroxymethyl)-3-[(2S,3R,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 125027358: (E)-1-[4-[(2S,3S,4R,5S,6R)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 125027359: (E)-1-[4-[(2S,3S,4R,5S,6R)-4,5-Dihydroxy-6-(hydroxymethyl)-3-[(2S,3S,4S,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 125027360: (E)-1-[4-[(2S,3S,4R,5S,6R)-4,5-Dihydroxy-6-(hydroxymethyl)-3-[(2S,3R,4S,5R,6R)-3,4,5-trihydroxy-6-methyloxan-2-yl]oxyoxan-2-yl]oxy-2,6-dihydroxyphenyl]-3-(4-methoxyphenyl)prop-2-en-1-one; 125027596: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4R,5R,6R)-3,4,5-trihydroxy-6-methyloxan-2-yl]oxymethyl]oxan-2-yl]oxyphenyl]prop-2-en-1-one; 125027597: (E)-3-(3-Hydroxy-4-methoxyphenyl)-1-[2-hydroxy-6-methoxy-4-[(2R,3S,4R,5R,6S)-3,4,5-trihydroxy-6-[[(2R,3S,4R,5S,6R)-3,4,5-trihydroxy-6-methyloxan-2-yl]oxymethyl]oxan-2-yl]oxyphenyl]prop-2-en-1-one; 125028931: (Z)-3-(4-Chlorophenyl)-1-[2,4-dihydroxy-6-[(2S,3R,4S,5R,6R)-3,4,5-trihydroxy-6-(hydroxymethyl)oxan-2-yl]oxyphenyl]prop-2-en-1-one; 125028932: (E)-3-(4-Chlorophenyl)-1-[2,4-dihydroxy-6-[(2S,3S,4S,5R,6R)-3,4,5-trihydroxy-6-(hydroxymethyl) oxan-2-yl]oxyphenyl]prop-2-en-1-one; 125028933: (Z)-3-(4-Chlorophenyl)-1-[2,4-dihydroxy-6-[(2S,3S,4S,5R,6R)-3,4,5-trihydroxy-6-(hydroxymethyl) oxan-2-yl]oxyphenyl]prop-2-en-1-one; 125028934: (E)-3-(4-Chlorophenyl)-1-[2,4-dihydroxy-6-[(2S,3R,4S,5R,6R)-3,4,5-trihydroxy-6-(hydroxymethyl)oxan-2-yl]oxyphenyl]prop-2-en-1-one; 125029297: (E)-1-[2-Hydroxy-6-[(2R,3S,4S,5R,6R)-3,4,5-trihydroxy-6-(hydroxymethyl)oxan-2-yl]oxyphenyl]-3-(4-nitro-phenyl)prop-2-en-1-one; 125029298: (E)-1-[2-Hydroxy-6-[(2R,3R,4R,5R,6R)-3,4,5-trihydroxy-6-(hydroxymethyl)oxan-2-yl]oxyphenyl]-3-(4-nitro-phenyl)prop-2-en-1-one; 125029299: (E)-1-[2-Hydroxy-6-[(2R,3R,4S,5R,6R)-3,4,5-trihydroxy-6-(hydroxymethyl)oxan-2-yl]oxyphenyl]-3-(4-nitro-phenyl)prop-2-en-1-one; 125029365: (E)-3-(4-Hydroxyphenyl)-1-[4-hydroxy-2-[(2R,3S,4S,5R,6R)-3,4,5-trihydroxy-6-(hydroxymethyl)oxan-2-yl]oxyphenyl]prop-2-en-1-one; 125029366: (E)-3-(4-Hydroxyphenyl)-1-[4-hydroxy-2-[(2R,3R,4S,5R,6R)-3,4,5-trihydroxy-6-(hydroxymethyl)oxan-2-yl]oxyphenyl]prop-2-en-1-one; 125029367: (E)-3-(4-Hydroxyphenyl)-1-[4-hydroxy-2-[(2R,3R,4R,5R,6R)-3,4,5-trihydroxy-6-(hydroxymethyl)oxan-2-yl]oxyphenyl]prop-2-en-1-one; 125032725: 2-[(2S,3R,4R,5S,6S)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 125032726: 2-[(2S,3R,4R,5R,6R)-5-Acetyloxy-2-(acetyloxymethyl)-6-[4-[(E)-3-phenylprop-2-enoyl]phenoxy]-3-[(2S,3S,4R,5S,6S)-3,4,5-triacetyloxy-6-(acetyloxymethyl)oxan-2-yl]oxyoxan-4-yl]acetic acid; 125032834: 2-[(2S,3R,4R,5R,6S)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxy-methyl)oxan-2-yl]oxyoxan-4-yl]acetic acid; 125032835: 2-[(2S,3R,4R,5R,6R)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxymethyl)oxan-2-yl]oxyoxan-4-yl]acetic acid;

125032836: 2-[(2S,3R,4R,5S,6S)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxymethyl)oxan-2-yl]oxyoxan-4-yl]acetic acid; 125032837: 2-[(2S,3R,4R,5S,6R)-5-Acetyloxy-2-(acetyloxymethyl)-6-[4-[(E)-3-oxo-3-phenylprop-1-enyl]phenoxy]-3-[(2S,3S,4R,5S,6S)-3,4,5-triacetyloxy-6-(acetyloxymethyl) oxan-2-yl]oxyoxan-4-yl]acetic acid; 125040471: (E)-3-[4-[(2R,3S,4R,5R,6S)-3-[(2S,3R,4S)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125040472: (E)-3-[4-[(2R,3S,4R,5R,6S)-3-[(2S,3S,4S)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125040473: (E)-3-[4-[(2R,3S,4R,5R,6S)-3-[(2S,3S,4R)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125115470: (Z)-1-[2,4-Dihydroxy-6-[(2S,3R,4S,5R,6R)-3,4,5-trihydroxy-6-(hydroxy-methyl)oxan-2-yl]oxyphenyl]-3-(4-hydroxyphenyl)prop-2-en-1-one; 125115471: (E)-1-[2,4-Dihydroxy-6-[(2S,3S,4S,5R,6R)-3,4,5-trihydroxy-6-(hydroxymethyl)oxan-2-yl]oxyphenyl]-3-(4-hydroxyphenyl)prop-2-en-1-one; 125115472: (Z)-1-[2,4-Dihydroxy-6-[(2S,3S,4S,5R,6R)-3,4,5-trihydroxy-6-(hydroxymethyl)oxan-2-yl]oxyphenyl]-3-(4-hydroxyphenyl)prop-2-en-1-one; 125115473: (E)-1-[2,4-Dihydroxy-6-[(2S,3R,4S,5R,6R)-3,4,5-trihydroxy-6-(hydroxy-methyl)oxan-2-yl]oxyphenyl]-3-(4-hydroxyphenyl)prop-2-en-1-one; 125463410: (E)-3-[4-[(2R,3S,4R,5R,6S)-3-[(2R,3S,4S)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 125737183: (E)-1-[4-(5,6-Dimethyl-1,3-dihydroisoindol-2-yl)phenyl]-3-(4-hydroxy-3-methoxyphenyl)prop-2-en-1-one; 126495513: 4-[3-[4-(4-Aminobenzoyl)oxyphenyl]prop-2-enoyl]benzoic acid; 126495516: 4-[3-[4-(4-Aminocyclohexanecarbonyl)oxyphenyl]prop-2-enoyl]benzoic acid; 126495518: 4-[3-(4-Aminophenyl)prop-2-enoyl]benzoic acid; 126495521: 4-[3-[4-(4-Aminooxybenzoyl)oxyphenyl]prop-2-enoyl]benzoic acid; 126495523: 4-[3-(4-Aminooxyphenyl)prop-2-enoyl]benzoic acid; 126495526: 4-[(E)-3-Oxo-3-[4-(4,4,4-trifluorobutoxy)phenyl]prop-1-enyl]benzoic acid; 126513060: (E)-1-(2,4-Dihydroxy-6-nitrosophenyl)-3-(4-hydroxyphenyl)prop-2-en-1-one; 126550034: (E)-1-(2,4-Dihydroxyphenyl)-3-[4-[4-[(E)-3-(2,4-dihydroxyphenyl)-3-oxoprop-1-enyl]-2-hydroxyphenoxy]phenyl]prop-2-en-1-one; 126550035: (E)-3-[4-[4-[(1S,2R,3R,4S)-2,3-Bis(2,4-dihydroxybenzoyl)-4-(4-hydroxyphenyl)cyclobutyl]-2-hydroxyphenoxy]phenyl]-1-(2-hydroxy-4-methylphenyl)prop-2-en-1-one; 126550037: (E)-3-[4-[4-[(1S,2R,3R,4S)-2,3-Bis(2,4-dihydroxybenzoyl)-4-(4-hydroxyphenyl)cyclobutyl]-2-hydroxyphenoxy]phenyl]-1-(2,4-dihydroxyphenyl)prop-2-en-1-one; 126559375: Schembl20608176; 126606590: (E)-1-(2,4-Dihydroxyphenyl)-3-[4-[2-hydroxy-4-[(E)-3-(2-hydroxy-4-nitrosophenyl)-3-oxoprop-1-enyl]phenoxy]phenyl]prop-2-en-1-one; 126650039: 1-[2,4-Dihydroxy-6-[(2S,3R,4S,5S,6R)-3,4,5-trihydroxy-6-(hydroxy-methyl)oxan-2-yl]oxyphenyl]-3-(4-hydroxyphenyl)propan-1-one;1,3-diphenylprop-2-en-1-one;methylsulfinylmethane; 126803696: 4-3-[4-(4-Hydroxypiperidin-1-yl)phenyl]-3-oxoprop-1-en-1-ylbenzoic acid; 126810523: 3-[3-(4-Acetamidophenyl)-3-oxoprop-1-en-1-yl]benzoic acid; 126811254: 3-Hydroxy-4-3-[3-methoxy-4-(methylsulfanyl) phenyl]prop-2-enoylbenzoic acid; 126821259: 3-3-[2-Fluoro-6-(morpholin-4-yl)phenyl]-3-oxoprop-1-en-1-ylbenzoic acid; 126838087: 4-3-[4-(Difluoromethoxy)phenyl]prop-2-enoyl-3-hydroxybenzoic acid; 127025236: (E)-1-(2,4-Dihydroxyphenyl)-3-[4-[(2E)-3,7-dimethylocta-2,6-dienoxy]phenyl]prop-2-en-1-one; 127029854: (E)-1-(2-Hydroxyphenyl)-3-(1-oxido-2,1,3-benzoxadiazol-1-ium-5-yl)prop-2-en-1-one; 127031392: (E)-3-[3-[[1-(3-Chloro-4-fluorophenyl)triazol-4-yl]methoxy]-4-methoxyphenyl]-1-(2-hydroxy-4,6-dimethoxyphenyl)prop-2-en-1-one; 127031673: (E)-3-[3-[[1-(2,4-Difluorophenyl)triazol-4-yl]methoxy]-4-methoxyphenyl]-1-(2-hydroxy-4,6-dimethoxyphenyl)prop-2-en-1-one; 127031674: (E)-3-[3-[[1-(2-Chlorophenyl)triazol-4-yl]methoxy]-4-methoxyphenyl]-1-(2-hydroxy-4,6-dimethoxyphenyl)prop-2-en-1-one; 127031939: 4-(3-Hydroxyphenyl)-N-[4-[(E)-3-(4-hydroxyphenyl)prop-2-enoyl]phenyl]-6-methyl-2-sulfanylidene-3,4-dihydro-1H-pyrimidine-5-carboxamide; 127031974: (E)-3-[4-[[1-(2-Chloro-4-fluorophenyl)triazol-4-yl]methoxy]-3-methoxyphenyl]-1-(2-hydroxy-4,6-dimethoxyphenyl)prop-2-en-1-one; 127032262: (E)-3-[3-[[1-(4-Chlorophenyl)triazol-4-yl]methoxy]-4-methoxyphenyl]-1-(2-hydroxy-4,6-dimethoxyphenyl)prop-2-en-1-one; 127032263: (E)-3-[3,4-Bis[[1-(2-chloro-4-fluorophenyl)triazol-4-yl]methoxy]phenyl]-1-(2-hydroxy-4,6-dimethoxyphenyl)prop-2-en-1-one; 127032264: (E)-3-[3,4-Bis[[1-(3-chloro-4-fluorophenyl)triazol-4-yl]methoxy]phenyl]-1-(2-hydroxy-4,6-dimethoxyphenyl)prop-2-en-1-one; 127032265: (E)-3-[3,4-Bis[[1-(2,4-difluorophenyl)triazol-4-yl]methoxy]phenyl]-1-(2-hydroxy-4,6-dimethoxyphenyl)prop-2-en-1-one; 127032268: (E)-3-[4-[[1-(3-Chloro-4-fluorophenyl)triazol-4-yl]methoxy]-3-methoxyphenyl]-1-(2-hydroxy-4,6-dimethoxyphenyl) prop-2-en-1-one; 127032269: (E)-3-[4-[[1-(2,4-Difluorophenyl)triazol-4-yl]methoxy]-3-methoxyphenyl]-1-(2-hydroxy-4,6-dimethoxyphenyl)prop-2-en-1-one; 127032270: (E)-3-[4-[[1-(2-Chlorophenyl)triazol-4-yl]methoxy]-3-methoxyphenyl]-1-(2-hydroxy-4,6-dimethoxy-phenyl)prop-2-en-1-one; 127032271: (E)-3-[4-[[1-(4-Chlorophenyl)triazol-4-yl]methoxy]-3-methoxyphenyl]-1-(2-hydroxy-4,6-dimethoxyphenyl)prop-2-en-1-one; 127032569: (E)-3-[3-[[1-(2-Chloro-4-fluorophenyl)triazol-4-yl]methoxy]-4-methoxyphenyl]-1-(2-hydroxy-4,6-dimethoxyphenyl)prop-2-en-1-one; 127032880: (E)-3-[3,4-Bis[[1-(2-chlorophenyl)triazol-4-yl]methoxy]phenyl]-1-(2-hydroxy-4,6-dimethoxyphenyl)prop-2-en-1-one; 127032881: (E)-3-[3,4-Bis[[1-(4-chlorophenyl)triazol-4-yl]methoxy]phenyl]-1-(2-hydroxy-4,6-dimethoxyphenyl) prop-2-en-1-one; 127033132: N-[4-[(E)-3-(4-Hydroxyphenyl)prop-2-enoyl]phenyl]-6-methyl-4-(4-methylphenyl)-2-sulfanylidene-3,4-dihydro-1H-pyrimidine-5-carboxamide; 127033404: 5-Acetyl-4-[[4-[(E)-3-(4-hydroxyphenyl)prop-2-enoyl]anilino]methyl]-3-methyl-6-phenyl-1,6-dihydropyrimidin-2-one; 127033696: 4-(3-Hydroxyphenyl)-6-methyl-N-[4-[(E)-3-(3-nitro-phenyl)prop-2-enoyl]phenyl]-2-sulfanylidene-3,4-dihydro-1H-pyrimidine-5-carboxamide; 127035154: (E)-1-(2,6-Dihydroxyphenyl)-3-(3,4-dihydroxyphenyl)prop-2-en-1-one; 127044450: (E)-3-(4-Bromophenyl)-1-(2,6-dihydroxyphenyl)prop-2-en-1-one; 129192681: (E)-1-[4-(Hydroxymethyl)-2-methoxyphenyl]-3-(4-methoxyphenyl)prop-2-en-1-one; 129220919: FC1=CC=C(OC2=CC=C(C=C$_2$)/C=C/C(=O)C$_2$=C(C=C(C=C2O)O)O)C=C1; 129220937: FC(C1=CC=C(OC2=CC=C(C=C$_2$)/C=C/C(=O)C$_2$=C(C=C(C=C2O)O)O)C=C1)(F)F; 129220962: N1=C(C=C=C1)OC1=CC=C(C=C1)/C=C/C(=O)C1=C(C=C(C=C(C=O0)O)O; 129220981: ClC1=CC=C(OC2=CC=C(C=C$_2$)/C=C/C(=O)C$_2$=C(C=C (C═C2O)O)C═C1; 129220996: FC(C1═CC═C(C═C1)/C═C/C(═O)C1═C(C═C(C═C1O)O)O)(F)F; 129223655: Ethyl N-[4-[(E)-3-[4-[2-hydroxyethyl(methyl)amino]phenyl]prop-2-enoyl]phenyl]carbamate; 129223656: N-[4-[(E)-3-[4-[2-Hydroxyethyl(methyl)amino]phenyl]prop-2-enoyl]phenyl]acetamide; 129223658: 1-[4-[(E)-3-[4-[2-Hydroxyethyl(propyl)amino]phenyl]prop-2-enoyl]phenyl]-3-[(4-methoxyphenyl)methyl]urea; 129229058: [4-[(E)-3-[4-[2-Hydroxyethyl(methyl)amino]phenyl]prop-2-enoyl]phenyl]urea; 129229367: 2,2,2-Trichloroethyl N-[4-[(E)-3-[4-[2-hydroxyethyl(methyl)amino]phenyl]prop-2-enoyl]phenyl]carbamate; 129237072: O(C1═CC═CC═C1)C1═CC═C(C═C1)/C═C/C(═O)C1═C(C═C(C═C0O)O)O; 129237256: (E)-3-[4-[(3E)-Hexa-1,3,5-trien-3-yl]oxyphenyl]-1-(2,4,6-trihydroxyphenyl)prop-2-en-1-one; 129237363: (E)-3-(4-Phenylmethoxyphenyl)-1-(2,4,6-trihydroxyphenyl)prop-2-en-1-one; 129431824: (E)-4-[4-[(Z)-3-[4-[(E)-3-[4-[[(E)-3-Carboxyprop-2-enoyl]amino]phenyl]-3-oxoprop-1-enyl]phenyl]prop-2-enoyl]anilino]-4-oxobut-2-enoic acid; 129431825: (Z)-4-[4-[(E)-3-[4-[(E)-3-[4-[[(E)-3-Carboxyprop-2-enoyl]amino]phenyl]-3-oxoprop-1-enyl]phenyl]prop-2-enoyl]anilino]-4-oxobut-2-enoic acid; 129634465: Chalcone butein; 129647486: 2',4-Dihydroxy-3-methylchalkon; 129647568: 4,4'-Dihydroxy-3-methylchalkon; 129661548: 4'-Hydroxy-2',4-dimethoxychalcone; 129712689: 2'-Hydroxy-4,4',6'-tris(methoxymethyloxy)-3-prenyl-chalcone; 129713301: 3-c-Prenyl-2',4'-dihydroxychalcone; 129731921: 4-3-[4-(3-Ethyl-3-hydroxy-pent-1-ynyl)-phenyl]-3-oxo-propenyl-benzonitrile; 129759987: 2'-Hydroxy-4'-(quinolizidin-1-ylmethyl-oxy)chalcone; 129775442: 2'-Hydroxy-4'-methoxy-4-(tetrahydropyran-2-yloxy)chalcone; 129800054: N-(Styrylcarbonylphenyl)-beta-alanine; 129824183: (e)-3-(3-Hydroxyphenyl)-1-(2-methoxy-4,6-bis(meth-oxymethoxy)phenyl)prop-2-en-1-one; 129826232: 4-Hydroxy-4'-butyloxy-chalcone; 129826492: 4-Hydroxy-4'-nonyloxy-chalcone; 129826497: 4-Hydroxy-4'-octyloxy-chalcone; 129826498: 4-Hydroxy-4'-heptyloxy-chalcone; 129826501: 4-Hydroxy-4'-pentyloxy-chalcone; 129829842: 4'-Benzyloxy-2'-hydroxy-3,4-methylenedioxychalcone; 129829881: 4-Benzyloxy-2'-hydroxy-3,4'-dimethoxychalcone; 129829882: 2'-Hydroxy-4,4'-dimethoxy-3,6'-diprenyloxy chalcone; 129841630: 1-(2-Aminophenyl)-3-(4-hydroxyphenyl)prop-2-en-1-one; 129841654: (e)-1-(2-Aminophenyl)-3-(3,4-dihydroxyphenyl)prop-2-en-1-one; 129841815: (e)-1-(2-Aminophenyl)-3-(4-hydroxyphenyl)prop-2-en-1-one; 129848616: Coumaroyl-benzaldehyde; 129852754: 3-(4-((3,7-Dimethylocta-2,6-dien-1-yl)oxy)-3-methoxyphenyl)-1-(4-hydroxyphenyl)prop-2-en-1-one; 129882371: 4,4'-Dihydroxy-3,2'-dimethoxychalcone; 129882667: 2',4-Dihydroxy-3,4'-dimethoxychalcone; 129883870: (e)-2-(((4-(3-(4-Hydroxy-3-methoxyphenyl)acryloyl)phenyl)amino)methyl)-6-methyl-3-thioxo-3,4-dihydro-1,2,4-triazin-5(2h)-one; 129883927: 4-Bromo-2'-hydroxy-4',6'-diisoprenyloxychalcone; 129883996: 2'-Hydroxy-4',6'-diisoprenyloxychalcone; 129884028: 4-Methoxyl-2'-hydroxy-4',6'-diisoprenyloxychalcone; 129884117: (e)-1-(2,4-Difluorophenyl)-3-(4-hydroxy-3-methoxyphenyl)prop-2-en-1-one; 129884261: 4-(4-[3-(4-Fluorophenyl)prop-2-enoyl]phenylamino)-2-methylidene-4-oxobutanoic acid; 129884347: 4-(4-[3-(4-Bromophenyl)prop-2-enoyl]phenylamino)-2-methylidene-4-oxobutanoic acid; 129884357: 4-(4-[3-(4-Chlorophenyl)prop-2-enoyl]phenylamino)-2-methylidene-4-oxobutanoic acid; 129884431: 4-(4-(3-(4-Isopropylphenyl)acryloyl)phenylamino)-2-methylene-4-oxobutanoic acid; 129884438: 2-Methylidene-4-(4-[3-(4-methylphenyl)prop-2-enoyl]phenylamino)-4-oxobutanoic acid; 129884443: 4-(4-[3-(4-Methoxyphenyl)prop-2-enoyl]phenylamino)-2-methylidene-4-oxobutanoic acid; 129886126: (e)-3-(9-Ethyl-9h-carbazol-3-yl)-1-(2-hydroxy-4-methoxyphenyl)prop-2-en-1-one; 129886140: (e)-1-(4-Ethoxy-2-hydroxyphenyl)-3-(9-ethyl-9h-carbazol-3-yl)prop-2-en-1-one; 129900530: Benzene; iron; 2-[4-[(E)-3-oxo-3-phenyl-prop-1-enyl]phenoxy]acetic acid; 130230733: (E)-1-(2-Hydroxy-6-methoxy-4-methylphenyl)-3-(4-prop-2-enoxyphenyl)prop-2-en-1-one; 130230759: (E)-3-(4-Bromophenyl)-1-(2-hydroxy-6-methoxy-4-methylphenyl) prop-2-en-1-one; 130394862: (E)-1-[4-[(2S,3R,4R,5S,6R)-4,5-Dihydroxy-6-(hydroxymethyl)-3-methyloxan-2-yl]oxy-2,6-dihydroxyphenyl]-3-(4-hydroxyphenyl)prop-2-en-1-one; 130461998: Propan-2-yl (2S)-2-[[[(2R,3R,4R,5R)-4-fluoro-3-hydroxy-4-methyl-5-(2-methylidene-4-oxopyrimidin-1-yl)oxolan-2-yl]methoxy-[4-[(E)-3-phenylprop-2-enoyl]phenoxy]phosphoryl]amino]butanoate; 130462095: Propan-2-yl (2S)-2-[[[(2R,3R,4R,5R)-4-fluoro-3-hydroxy-4-methyl-5-(2-methylidene-4-oxopyrimidin-1-yl)oxolan-2-yl]methoxy-[4-[(E)-3-phenylprop-2-enoyl]phenoxy]phosphoryl]amino]propanoate; 130462096: Propan-2-yl (2S)-2-[[[(E)-[(3R,4R,5R)-5-(2,4-dioxopyrimidin-1-yl)-4-fluoro-3-hydroxy-4-methyloxolan-2-ylidene]methoxy]-[4-[(E)-3-phenylprop-2-enoyl]phenoxy]phosphoryl]amino]propanoate; 131676039: 1-Propanone, 1-[4-[[6-O-(6-deoxy-alpha-L-mannopyranosyl)-beta-D-gluco-pyranosyl]oxy]-2,6-dihydroxyphenyl]-3-(4-methoxyphenyl)-; 131741737: 3-(4-(Hex-5-yn-1-yloxy)phenyl)-1-(2-hydroxyphenyl)prop-2-en-1-one; 131741739: 3-(4-(Hex-5-yn-1-yloxy)phenyl)-1-(2-hydroxy-4-methylphenyl)prop-2-en-1-one; 131751237: Licorice glycoside B; 131751238: Licorice glycoside A; 131801300: (E)-3-(4-Hydroxy-3-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one; 131834436: 6-3,5-Dihydroxy-2-[3-(3-hydroxy-4-methoxyphenyl)prop-2-enoyl]phenoxy-3,4,5-trihydroxyoxane-2-carboxylic acid; 131834437: 6-3,5-Dihydroxy-4-[3-(3-hydroxy-4-methoxyphenyl)prop-2-enoyl]phenoxy-3,4,5-trihydroxyoxane-2-carboxylic acid; 131834438: 3,4,5-Trihydroxy-6-2-methoxy-5-[3-oxo-3-(2,4,6-trihydroxyphenyl)prop-1-en-1-yl]phenoxyoxane-2-carboxylic acid; 131834439: 2-Methoxy-5-[3-oxo-3-(2,4,6-trihydroxy-phenyl)prop-1-en-1-yl]phenyloxidanesulfonic acid; 131834447: 6-3,5-Dihydroxy-2-[3-(4-hydroxyphenyl)prop-2-enoyl]phenoxy-3,4,5-trihydroxyoxane-2-carboxylic acid; 131834448: 6-3,5-Dihydroxy-4-[3-(4-hydroxyphenyl)prop-2-enoyl]phenoxy-3,4,5-trihydroxyoxane-2-carboxylic acid; 131834449: 3,4,5-Trihydroxy-6-4-[3-oxo-3-(2,4,6-trihydroxyphenyl)prop-1-en-1-yl]phenoxyoxane-2-carboxylic acid; 131834450: 4-[3-Oxo-3-(2,4,6-trihydroxy-phenyl)prop-1-en-1-yl]phenyloxidanesulfonic acid; 131834453: 6-[3,5-Dihydroxy-2-(3-phenylprop-2-enoyl)phenoxy]-3,4,5-trihydroxyoxane-2-carboxylic acid; 131834454: 6-[3,5-Dihydroxy-4-(3-phenylprop-2-enoyl)phenoxy]-3,4,5-trihydroxyoxane-2-carboxylic acid; 131836489: 3-(3-Methoxyphenyl)-1-(2,4,6-trihydroxyphenyl)prop-2-en-1-one; 131836668: 6-3,5-Dihydroxy-4-[3-(4-methoxyphenyl)prop-2-enoyl]phenoxy-3,4,5-trihydroxyoxane-2-carboxylic acid; 131837294: 6-2-[3-(3,4-Dihydroxyphenyl)prop-2-enoyl]-3,5-dihydroxy-phenoxy-3,4,5-trihydroxyoxane-2-carboxylic acid; 131837295: 6-4-[3-(3,4-Dihydroxy-phenyl)prop-2-enoyl]-3,5-dihydroxyphenoxy-3,4,5-trihydroxyoxane-2-carboxylic acid; 131837296: 3,4,5-Trihydroxy-6-2-hydroxy-5-[3-oxo-3-(2,4,6-trihydroxyphenyl)prop-1-en-1-yl]phenoxyoxane-2-carboxylic acid; 131837297: 3,4,5-Trihydroxy-6-2-hydroxy-4-[3-oxo-3-(2,4, 6-trihydroxyphenyl)prop-1-en-1-yl]phenoxyoxane-2-carboxylic acid; 131837298: 2-Hydroxy-5-[3-oxo-3-(2,4,6-trihydroxyphenyl)prop-1-en-1-yl]phenyloxidanesulfonic acid; 131838575: 6-4-[(1 E)-3-(5-[(2-4-[3-(2,4-Dihydroxyphenyl)-3-oxoprop-1-en-1-yl]phenoxy-4,5-dihydroxy-6-(hydroxymethyl)oxan-3-yl)oxy]-3,4-dihydroxyoxolan-3-yl-methoxy)-3-oxoprop-1-en-1-yl]phenoxy-3,4,5-trihydroxyoxane-2-carboxylic acid; 131838576: 6-[4-(3-4-[(3-[3,4-Dihydroxy-4-([(2E)-3-(4-hydroxyphenyl)prop-2-enoyl]oxymethyl)oxolan-2-yl]oxy-4,5-dihydroxy-6-(hydroxymethyl)oxan-2-yl)oxy]phenylprop-2-enoyl)-3-hydroxyphenoxy]-3,4,5-trihydroxyoxane-2-carboxylic acid; 131838577: 4-[(1 E)-3-(5-[(2-4-[3-(2,4-Dihydroxyphenyl)-3-oxoprop-1-en-1-yl]phenoxy-4,5-dihydroxy-6-(hydroxymethyl)oxan-3-yl)oxy]-3,4-dihydroxyoxolan-3-ylmethoxy)-3-oxoprop-1-en-1-yl]phenyloxidanesulfonic acid; 131838578: 2-[(2-4-[3-(2,4-Dihydroxyphenyl)-3-oxoprop-1-en-1-yl]phenoxy-4,5-dihydroxy-6-(hydroxy-methyl)oxan-3-yl)oxy]-4-hydroxy-4-([(2E)-3-(4-hydroxyphenyl)prop-2-enoyl]oxymethyl)oxolan-3-yloxidanesulfonic acid; 131838579: 6-[4-(3-4-[(3-[3,4-Dihydroxy-4-(hydroxymethyl)oxolan-2-yl]oxy-4,5-dihydroxy-6-(hydroxymethyl)oxan-2-yl)oxy]phenylprop-2-enoyl)-3-hydroxyphenoxy]-3,4,5-trihydroxyoxane-2-carboxylic acid; 131838580: 6-[2-(3-4-[(3-[3,4-Dihydroxy-4-(hydroxymethyl)oxolan-2-yl]oxy-4,5-dihydroxy-6-(hydroxymethyl)oxan-2-yl)oxy]phenylprop-2-enoyl)-5-hydroxyphenoxy]-3,4,5-trihydroxyoxane-2-carboxylic acid; 131838581: (5-[(2-4-[3-(2,4-Dihydroxyphenyl)-3-oxoprop-1-en-1-yl]phenoxy-4,5-dihydroxy-6-(hydroxymethyl)oxan-3-yl)oxy]-3,4-dihydroxyoxolan-3-ylmethoxy)sulfonic acid; 131838582: 2-[(2-4-[3-(2,4-Dihydroxyphenyl)-3-oxoprop-1-en-1-yl]phenoxy-4,5-dihydroxy-6-(hydroxymethyl)oxan-3-yl)oxy]-4-hydroxy-4-(hydroxymethyl)oxolan-3-yloxidanesulfonic acid; 131839144: 3,4,5-Trihydroxy-6-4-[(2E)-3-phenyl-prop-2-enoyl]phenoxyoxane-2-carboxylic acid; 131839146: 3,4,5-Trihydroxy-6-5-methoxy-2-[(2E)-3-phenylprop-2-enoyl]phenoxy-oxane-2-carboxylic acid; 131839147: 3,4,5-Trihydroxy-6-4-[(1 E)-3-(4-methoxyphenyl)-3-oxoprop-1-en-1-yl]phenoxyoxane-2-carboxylic acid; 131839149: 3,4,5-Trihydroxy-6-3-[(1E)-3-(4-methoxyphenyl)-3-oxoprop-1-en-1-yl]phenoxyoxane-2-carboxylic acid; 131839368: 1-(2,4-Dihydroxyphenyl)-3-[4-hydroxy-3-(4-hydroxy-3-methylbut-2-en-1-yl)phenyl]prop-2-en-1-one; 131839370: 1-(2,4-Dihydroxyphenyl)-3-3-[(3,3-dimethyloxiran-2-yl)methyl]-4-hydroxyphenylprop-2-en-1-one; 131839462: 1-(2,4-Dihydroxy-6-methoxyphenyl)-3-(4-methoxyphenyl)prop-2-en-1-one; 131845707: (E)-3-(3-Fluorophenyl)-1-[2-hydroxy-4,6-bis(phenylmethoxy)phenyl]prop-2-en-1-one; 131885805: 1-(2-Hydroxy-6-methoxy-4-phenylmethoxy-phenyl)-3-phenylprop-2-en-1-one; 132063598: (E)-1-(2,4-Dihydroxy-6-nitrosophenyl)-3-phenylprop-2-en-1-one; 132170441: (E)-1-(2,4-Dihydroxyphenyl)-3-(4-ethyl-3-hydroxyphenyl)prop-2-en-1-one; 132215050: 2-[(E)-3-[3-(Difluoromethoxy)-4-methoxyphenyl]prop-2-enoyl]benzoic acid; 132268870: (E)-3-(9-Ethylcarbazol-3-yl)-1-[2-(hydroxymethyl)phenyl]prop-2-en-1-one; 132277736: (e)-1-(4-((e)-3,3-Dimethyltriaz-1-en-1-yl)phenyl)-3-(4-(((2r,3s,4r,5r,6s)-3,4,5-trihydroxy-6-(hydroxymethyl)tetrahydro-2h-pyran-2-yl)oxy)phenyl)prop-2-en-1-one; 132278102: 2'-[4-(4-Hydroxypiperidinyl)butoxy]-3,4,4',6'-tetramethoxychalcone; 132279066: (e)-1-(4-((e)-3,3-Dimethyltriaz-1-en-1-yl)phenyl)-3-(4-(((3s,4r,5r,6s)-3,4,5-trihydroxy-6-(hydroxymethyl)tetrahydro-2h-pyran-2-yl)oxy)phenyl)prop-2-en-1-one; 132280046: (e)-1-(4-((e)-3,3-Dimethyltriaz-1-en-1-yl)phenyl)-3-(3-methoxy-4-(((2r,3s,4r,5s)-3,4,5-trihydroxytetrahydro-2h-pyran-2-yl)oxy)phenyl)prop-2-en-1-one; 132281092: (e)-1-(4-((e)-3,3-Dimethyltriaz-1-en-1-yl)phenyl)-3-(3-methoxy-4-(((2r,3s,4r,5r, 6s)-3,4,5-trihydroxy-6-(hydroxymethyl)tetrahydro-2h-pyran-2-yl)oxy)phenyl)prop-2-en-1-one; 132281627: (e)-1-(4-((e)-3,3-Dimethyltriaz-1-en-1-yl)phenyl)-3-(4-(((2r,3s,4r,5s)-3,4,5-trihydroxytetrahydro-2h-pyran-2-yl)oxy)phenyl)prop-2-en-1-one; 132281700: 2'-[2-(4-Hydroxypiperidinyl)ethoxy]-3,4,4',6'-tetramethoxychalcone; 132491098: 1-[2-Hydroxy-4-(ethoxymethoxy)phenyl]-3-(4-methylphenyl)-2-propene-1-one; 132491099: 1-[2-Hydroxy-4-fluorophenyl]-3-(4-methylphenyl)-2-propene-1-one; 132499862: 3-[4-(Dimethylamino)phenyl]-1-(2-hydroxy-4-methoxyphenyl)-2-propene-1-one; 132519678: N,N',N'',N'''-[25,26,27,28-Tetrakis[2-[2-[2-(2-methoxyethoxy)ethoxy]ethoxy]ethoxy]pentacyclo[19.3.1.13, 7.19,13.115,19]octacosa-1(25),3,5,7(28),9,11,13(27),15,17,19(26),21,23-dodecaene-5,11,17,23-tetra-yl]tetrakis[4-(3-phenyl-3-oxo-1-propenyl)benzamide]; 132519680: [5,11,17,23,29,35-Hexatert-butyl-39,40-dihydroxy-38,41,42-tris[[4-[(E)-3-oxo-3-phenylprop-1-enyl]benzoyl]oxy]-37-heptacyclo[31.3.1.13,7.19,13.115,19.121,25.127,31]dotetraconta-1(36),3,5,7(42),9,11,13(41),15,17,19(40),21(39),22,24,27(38),28,30,33(37),34-octadeca-enyl] 4-[(E)-3-oxo-3-phenylprop-1-enyl]benzoate; 132521258: 4-(Dimethylamino)-4'-(3-hydroxyazetidine-1-yl)chalcone; 132550010: (E)-1-(2-Hydroxy-4-propargyloxyphenyl)-3-(4-hydroxyphenyl)-2-propene-1-one; 132551015: 3-[6-(Dimethylamino)-2-naphthyl]-1-(4-hydroxyphenyl)-2-propene-1-one; 132551713: 2'-Hydroxy-4'-(2-methylpropoxy)chalcone; 132551714: 2'-Hydroxy-4'-(2-methyl-1-propenyloxy)chalcone; 132551715: 2'-Hydroxy-4'-(crotyloxy)chalcone; 132551716: 2'-Hydroxy-4'-(1-butenyloxy)chalcone; 132551717: 2'-Hydroxy-4'-(1-pentenyloxy)chalcone; 132551718: 2'-Hydroxy-4'-geranylchalcone; 132551719: 2'-Hydroxy-4'-farnesylchalcone; 132551953: 1-[2-(beta-D-Glucopyranosyloxy)-4,6-dihydroxyphenyl]-3-phenyl-2-propene-1-one; 132576293: (E)-4-(Dihydroxyphosphinyl-oxymethoxy)-2',4'-dihydroxychalcone; 132582801: 2',4'-Dihydroxy-beta-(2alpha-(4-hydroxyphenyl)-3beta-hydroxymethyl-2,3-dihydrobenzofuran-5-yl)acrylophenone; 132582802: 2',4'-Dihydroxy-beta-(2alpha-(3-methoxy-4-hydroxyphenyl)1,4-benzodioxin-6-yl)acrylophenone; 132604828: 4-O-Geranylisoliquiritigenin; 132819950: Pyrrolidine-1-carboxylic acid 3-hydroxy-4-[(E)-3-[4-(dimethylamino)phenyl]acryloyl]phenyl ester; 132839041: 4'-(6-O-Galloyl-beta-D-gluco-pyranosyloxy)-2'-hydroxy-4-methoxychalcone; 132839042: 4'-(6-O-Galloyl-beta-D-gluco-pyranosyloxy)-2',4-dihydroxychalcone; 132839043: 4'-(beta-D-Glucopyranosyloxy)-2'-hydroxy-4-methoxychalcone; 132990990: 2'-Hydroxy-4-glucosyl-oxychalcone; 133556548: [(2S,3R,4R,5S,6R)-6-[4-[(E)-3-(2,4-Dihydroxyphenyl)-3-oxoprop-1-enyl]phenoxy]-3,4,5-trihydroxyoxan-2-yl]methyl (E)-3-(4-hydroxyphenyl)prop-2-enoate; 133577796: (E)-1-[2,4-Dihydroxy-6-[(2S)-3,4,5-trihydroxy-6-(hydroxymethyl)oxan-2-yl]oxyphenyl]-3-(4-hydroxyphenyl)prop-2-en-1-one; 133960386: 4-[(E)-3-(4-Hydroxyphenyl)-3-oxoprop-1-enyl]-N-methylbenzamide; 134064181: (E)-3-[4-(3-Chloro-2-hydroxypropoxy)phenyl]-1-phenylprop-2-en-1-one; 134064212: (E)-1-[4-[2-Hydroxy-3-[(E)-3-oxo-3-phenylprop-1-enyl]phenoxy]propoxy]phenyl]-3-phenylprop-2-en-1-one; 134130045: [3-Hydroxy-4-[(E)-3-(4-morpholin-4-ylphenyl)prop-2-enoyl]phenyl]pyrrolidine-1-carboxylate; 134130366: [4-[(E)-3-[4-(Diethylamino)phenyl]prop-2-enoyl]-3-hydroxyphenyl] pyrrolidine-1-carboxylate; 134130439: [4-[(E)-3-[4-(Dimethylamino)phenyl]prop-2-enoyl]-3-hydroxyphenyl] 4-methylpiperazine-1-carboxylate; 134130716: [3-Hydroxy-4-[(E)-3-(4-piperidin-1-ylphenyl)prop-2-enoyl] phenyl] pyrrolidine-1-carboxylate; 134130929: [3-Hydroxy-4-[(E)-3-(4-pyrrolidin-1-ylphenyl)prop-2-enoyl]phenyl] pyrrolidine-1-carboxylate; 134131020: [4-[(E)-3-[4-(Dimethylamino)phenyl]prop-2-enoyl]-3-hydroxyphenyl] 4-benzyl-piperazine-1-carboxylate; 134131068: [4-[(E)-3-[4-(Dimethylamino)phenyl]prop-2-enoyl]-3-hydroxyphenyl] N-ethyl-N-methylcarbamate; 134131214: [4-[(E)-3-[4-(Dimethylamino)phenyl]prop-2-enoyl]-3-hydroxyphenyl] N,N-diethylcarbamate; 134131241: [4-[(E)-3-[4-(Dimethylamino)phenyl]prop-2-enoyl]-3-hydroxyphenyl] piperidine-1-carboxylate; 134131491: [4-[(E)-3-[4-(Dimethylamino)phenyl]prop-2-enoyl]-3-hydroxyphenyl] 4-ethylpiperazine-1-carboxylate; 134131513: [4-[(E)-3-[4-(Dimethylamino)phenyl]prop-2-enoyl]-3-hydroxyphenyl] N,N-dimethylcarbamate; 134131581: [4-[(E)-3-[4-(Dimethylamino)phenyl]prop-2-enoyl]-3-hydroxyphenyl] morpholine-4-carboxylate; 134134040: (E)-1-(4-Hydroxyphenyl)-3-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134135074: (E)-3-(3-Bromophenyl)-1-[2-hydroxy-4-(3-methylbut-2-enoxy)phenyl]prop-2-en-1-one; 134137761: [4-[(E)-3-(4-Hydroxyphenyl)-3-oxoprop-1-enyl]phenyl] N-ethyl-N-methylcarbamate; 134137957: [4-[(E)-3-(4-Hydroxyphenyl)prop-2-enoyl]phenyl] N-ethyl-N-methylcarbamate; 134138288: (E)-3-(3-Ethoxy-4-hydroxyphenyl)-1-[4-[2-[[(1R,4S,5R,8S,9R,10S,12R,13R)-1,5,9-trimethyl-11,14,15,16-tetraoxatetracyclo[10.3.1.04,13.08,13]hexadecan-10-yl]oxy]ethoxy]phenyl]prop-2-en-1-one; 134140335: [2-[(E)-3-(4-Hydroxyphenyl)prop-2-enoyl]phenyl] N-ethyl-N-methylcarbamate; 134145483: (E)-1-[4-(4,5-Dihydro-1,3-oxazol-2-ylmethoxy)phenyl]-3-(4-hydroxyphenyl)prop-2-en-1-one; 134146719: [3-[(E)-3-(4-Hydroxyphenyl)-3-oxoprop-1-enyl]phenyl] N-ethyl-N-methylcarbamate; 134150017: [4-[(E)-3-(4-Hydroxyphenyl)prop-2-enoyl]phenyl] N,N-dimethylcarbamate; 134153138: [4-[(E)-3-(4-Hydroxyphenyl)-3-oxoprop-1-enyl]phenyl] N,N-dimethylcarbamate; 134155703: [2-[(E)-3-(4-Hydroxyphenyl)prop-2-enoyl]phenyl] N,N-dimethylcarbamate; 134157111: (E)-1-[2-Hydroxy-4-(3-methylbut-2-enoxy)phenyl]-3-naphthalen-2-ylprop-2-en-1-one; 134157228: [3-[(E)-3-(4-Hydroxyphenyl)-3-oxoprop-1-enyl]phenyl] N,N-dimethylcarbamate; 134157765: (E)-1-[4-(4,5-Dihydro-1,3-oxazol-2-ylmethoxy)phenyl]-3-(3-hydroxyphenyl)prop-2-en-1-one; 134180365: 4-[(E)-3-(4-Chlorophenyl)-3-oxoprop-1-enyl]-2-methoxybenzoic acid; 134180642: OC1=C(C=C(C=C1)/C=C/C(=O)C1=CC=C(C=C1) OC(F)(F)F)OC; 134180759: OC1=C(C=C(C=C1)/C=C/C(=O)C1=CC=C(C=C1)N1Ccncc1)OC; 134180849: Chembl4166275; 134180938: OC1=C(C=C(C=C1)/C=C/C(=O)C1=CC=C(C(=O)Occ)C=C1)OC; 134383475: (E)-1-(2-Amino-4,6-dihydroxyphenyl)-3-(4-aminophenyl)prop-2-en-1-one; 134525224: (E)-3-(3-Fluoro-4-phenylmethoxyphenyl)-1-[2-hydroxy-4,6-bis(phenylmethoxy)phenyl]prop-2-en-1-one; 134591138: 3-[(E)-3-(2-Hydroxyphenyl)-3-oxoprop-1-enyl]benzonitrile; 134591151: (E)-1-(2-Hydroxy-4,6-dimethoxyphenyl)-3-(3-nitrosophenyl)prop-2-en-1-one; 134591418: (E)-1-(2-Hydroxy-6-methoxyphenyl)-3-(3-nitrosophenyl)prop-2-en-1-one; 134729052: (E)-3-(3-Hydroxy-4-methoxyphenyl)-1-[2-hydroxy-6-methoxy-4-[(2S,3R,4S,5S,6R)-3,4,5-trihydroxy-6-[[(2S,3S,4S,5S,6R)-3,4,5-tri hydroxy-6-methyloxan-2-yl]oxyphenyl]oxan-2-yl]oxyphenyl]prop-2-en-1-one; 134736870: (E)-1-[4-[(2S,3R,4S,5S,6R)-4,5-Dihydroxy-6-(hydroxymethyl)-3-[(2S,3R,4R,5R,6S)-3,4,5-trihydroxy-6-methyloxan-2-yl]oxyoxan-2-yl]oxy-2,6-dihydroxyphenyl]-3-(4-methoxyphenyl)prop-2-en-1-one; 134824106: (e)-3-(2',3'-Dihydrobenzofuran-5-yl)-1-(2-hydroxyphenyl)prop-2-en-1-one; 134824198: (e)-3-(3',4'-Diethoxyphenyl)-1-(2-hydroxy phenyl)prop-2-en-1-one; 134833663: Schembl21527690; 134834435: (E)-1-(2-Hydroxy-4-phenylmethoxyphenyl)-3-(3-iodo-4-phenylmethoxyphenyl) prop-2-en-1-one; 134857443: (E)-3-(4-Hydroxy-3-iodophenyl)-1-(2-hydroxyphenyl)prop-2-en-1-one; 134857994: (E)-3-(3-Hydroxy-4-methoxyphenyl)-1-(2-iodophenyl)prop-2-en-1-one; 135127664: (E)-1-[4-[2-(2,4-Difluorophenyl)-2-hydroxy-3-(1,2,4-triazol-1-yl)propoxy] phenyl]-3-[4-[[1-[2-(2,4-difluorophenyl)-2-hydroxy-3-(1,2,4-triazol-1-yl)propyl]-3-methyl-2H-triazol-4-yl]methoxy] phenyl]prop-2-en-1-one; 135127671: (E)-3-[4-[(Z)-2-Amino-3-[amino-[2-(2,4-difluorophenyl)-2-hydroxy-3-(1,2,4-triazol-1-yl)propyl]amino]prop-2-enoxy]phenyl]-1-[4-(4-propylpiperazin-1-yl)phenyl]prop-2-en-1-one; 135127694: (E)-3-[4-[[3-[2-(2,4-Difluorophenyl)-2-hydroxy-3-(1,2,4-triazol-1-yl)propyl]-1,2-dihydrotriazol-5-yl]methoxy]phenyl]-1-(4-methoxyphenyl)prop-2-en-1-one; 135127698: N-Amino-N-[3-[amino-[(Z)-2-amino-3-[4-[(E)-3-phenylprop-2-enoyl]phenoxy]prop-1-enyl]amino]-2-(2,4-difluorophenyl)-2-hydroxypropyl]methanimidamide; 135188495: (E)-1-(2-Hydroxy-4-methoxyphenyl)-3-[4-(oxan-2-yloxy) phenyl]prop-2-en-1-one; 135304980: (E)-1-(2,6-Dihydroxy-4-methoxyphenyl)-3-(3-methoxyphenyl)prop-2-en-1-one; 135304981: 1-(2,6-Dihydroxy-4-methoxyphenyl)-3-(3-methoxyphenyl)prop-2-en-1-one; 135388109: (E)-1,3-Diphenylprop-2-en-1-one;(E)-1-[2-hydroxy-3-[(2E,5E)-7-hydroxy-3,7-dimethylocta-2,5-dienyl]-4-methoxyphenyl]-3-(4-hydroxyphenyl)prop-2-en-1-one; 135388110: 1,3-Diphenylprop-2-en-1-one;1-[2-hydroxy-3-(7-hydroxy-3,7-dimethylocta-2,5-dienyl)-4-methoxyphenyl]-3-(4-hydroxyphenyl)prop-2-en-1-one; 135406630: 2-(5-Benzoyl-1H-benzimidazol-2-yl)-N-[4-[(E)-3-(4-hydroxy-3-methoxyphenyl)prop-2-enoyl]phenyl]benzamide; 135476578: (E)-1-[4-(5-Hydroxy-2-phenyl-4-phenyldiazenylimidazol-1-yl)phenyl]-3-phenylprop-2-en-1-one; 135570551: 3-(4-Hydroxy-3-methoxyphenyl)-1-(4-((1H-indol-3-ylmethylene)amino)phenyl)-2-propen-1-one; 135671952: (E)-3-(3-Ethoxy-4-hydroxyphenyl)-1-[4-(1H-indol-3-ylmethylideneamino)phenyl]prop-2-en-1-one; 135777786: 3-Hydroxy-4-[[3-[(Z)-3-oxo-3-phenylprop-1-enyl]phenyl]diazenyl]naphthalene-2,7-disulfonate; 135777787: 3-Hydroxy-4-[[3-[(Z)-3-oxo-3-phenylprop-1-enyl]phenyl]diazenyl]naphthalene-2,7-disulfonic acid; 135777788: 5-Amino-4-hydroxy-3-[[3-[(Z)-3-oxo-3-phenylprop-1-enyl]phenyl]diazenyl]naphthalene-2,7-disulfonate; 135777789: 5-Amino-4-hydroxy-3-[[3-[(Z)-3-oxo-3-phenylprop-1-enyl]phenyl]diazenyl]naphthalene-2,7-disulfonic acid; 135777790: 3-Hydroxy-4-[[4-[(Z)-3-oxo-3-phenylprop-1-enyl]phenyl]diazenyl]naphthalene-2,7-disulfonate; 135777791: 3-Hydroxy-4-[[4-[(Z)-3-oxo-3-phenylprop-1-enyl]phenyl]diazenyl]naphthalene-2,7-disulfonic acid; 135802263: (E)-3-[(2R)-3-[(S)-[5-[(2R,3S,4S,5S)-4-(2,4-Dihydroxybenzoyl)-5-(4-hydroxyphenyl)-3-[(4-hydroxyphenyl)methyl]oxolan-2-yl]-2,4-dihydroxyphenyl]-(2,4-dihydroxyphenyl)methyl]-2-(4-hydroxyphenyl)-2,3-dihydro-1-benzofuran-5-yl]-1-(2,4-dihydroxyphenyl)prop-2-en-1-one; 135814142: (2E)-3-(4-Fluorophenyl)-1-(4-[(E)-(4-hydroxyphenyl)methylidene]aminophenyl)prop-2-en-1-one; 136019384: N-[(3-Chlorophenyl) carbamoyl]-5-[[4-[3-[4-[[6-[(3-chlorophenyl)carbamoylcarbamoyl]-2-hydroxynaphthalen-1-yl]diazenyl]phenyl]-3-oxoprop-1-enyl]phenyl]diazenyl]-6-hydroxynaphthalene-2-carboxamide; 136019388: N-[(3-Chlorophenyl)carbamoyl]-

6-hydroxy-5-[[4-[3-[4-[[2-hydroxy-6-[[3-(trifluoromethyl)phenyl]carbamoylcarbamoyl]naphthalen-1-yl]diazenyl]phenyl]-3-oxoprop-1-enyl]phenyl]diazenyl]naphthalene-2-carboxamide; 136028486: [3-(Trifluoromethyl)anilino] (1 E)-N-[[6-hydroxy-5-[[4-[3-[4-[[2-hydroxy-6-[(3-methylphenyl)carbamoylcarbamoyl]naphthalen-1-yl]diazenyl]phenyl]prop-2-enoyl]phenyl]diazenyl]naphthalen-2-yl]methoxy]methanimidate; 136028496: (3-Chloroanilino) (1 E)-N-[[5-[[4-[3-[4-[[6-[(3-chlorophenyl)carbamoylcarbamoyl]-2-hydroxynaphthalen-1-yl]diazenyl]phenyl]prop-2-enoyl]phenyl]diazenyl]-6-hydroxynaphthalen-2-yl]methoxy]methanimidate; 136030653: (E)-1-(4-Hydroxyphenyl)-3-[4-[[5-(2-hydroxyphenyl)-1,3,4-oxadiazol-2-yl]methoxy]-3-methoxyphenyl]prop-2-en-1-one; 136054928: (E)-3-[4-[[5-(2-Hydroxyphenyl)-1,3,4-oxadiazol-2-yl]methoxy]-3-methoxyphenyl]-1-(4-methoxyphenyl)prop-2-en-1-one; 136054930: (E)-3-[4-[[5-(2-Hydroxyphenyl)-1,3,4-oxadiazol-2-yl]methoxy]-3-methoxyphenyl]-1-phenylprop-2-en-1-one; 136066601: 6-Hydroxy-5-[[4-[3-[4-[[2-hydroxy-6-[[3-(trifluoromethyl)phenyl]carbamoylcarbamoyl]naphthalen-1-yl]diazenyl]phenyl]-3-oxoprop-1-enyl]phenyl]diazenyl]-N-[[3-(trifluoromethyl)phenyl]carbamoyl]naphthalene-2-carboxamide; 136186467: [3-(Trifluoromethyl)anilino] (1 E)-N-[[6-hydroxy-5-[[4-[3-[4-[[2-hydroxy-6-[[3-(trifluoromethyl)phenyl]carbamoylcarbamoyl]naphthalen-1-yl]diazenyl]phenyl]prop-2-enoyl]phenyl]diazenyl]naphthalen-2-yl]methoxy]methanimidate; 136492083: 1-[4-[[6-[2-(5-Chlorocyclohexa-1,5-dien-1-yl)ethyl]-2-hydroxynaphthalen-1-yl]diazenyl]phenyl]-3-[4-[[6-[2-(3-chlorophenyl)ethyl]-2-hydroxynaphthalen-1-yl]diazenyl]phenyl]prop-2-en-1-one; 136498254: 1-[4-[[2-Hydroxy-6-[2-[3-(trifluoromethyl)phenyl]ethyl]naphthalen-1-yl]diazenyl]phenyl]-3-[4-[1-[2-hydroxy-6-[2-[3-(trifluoromethyl)phenyl]ethyl]naphthalen-1-yl]ethyl]phenyl]prop-2-en-1-one; 136498255: 1-[4-[[2-Hydroxy-6-[2-[3-(trifluoromethyl)phenyl]ethyl]naphthalen-1-yl]diazenyl]phenyl]-3-[4-[1-[2-hydroxy-6-[2-[3-(trifluoromethyl)phenyl]ethyl]naphthalen-1-yl]ethyl]phenyl]prop-2-en-1-one; 136594542: 3-[4-[[6-[2-(3-Chlorophenyl)ethyl]-2-hydroxynaphthalen-1-yl]diazenyl]phenyl]-1-[4-[[2-hydroxy-6-[2-[3-(trifluoromethyl)phenyl]ethyl]naphthalen-1-yl]diazenyl]phenyl]prop-2-en-1-one; 136621144: N-(3-Chlorophenyl)carbamoyl-6-hydroxy-5-[[4-[3-[4-[(2-hydroxy-7-methyl-6,7-dihydronaphthalen-1-yl)diazenyl]phenyl]-3-oxoprop-1-enyl]phenyl]diazenyl]naphthalene-2-carboxamide; 136629467: [3-(Trifluoromethyl)anilino] N-[[6-hydroxy-5-[[4-[3-[4-[[2-hydroxy-6-[[3-(trifluoromethyl)phenyl]carbamoylcarbamoyl]naphthalen-1-yl]diazenyl]phenyl]prop-2-enoyl]phenyl]diazenyl]naphthalen-2-yl]methoxy]methanimidate; 136634998: (3-Chloroanilino) N-[[5-[[4-[3-[4-[[6-[(3-chlorophenyl)carbamoylcarbamoyl]-2-hydroxy-naphthalen-1-yl]diazenyl]phenyl]prop-2-enoyl]phenyl]diazenyl]-6-hydroxynaphthalen-2-yl]methoxy]methanimidate; 136644056: 1,3-Bis[4-[[2-hydroxy-6-[2-[3-(trifluoromethyl)phenyl]ethyl]naphthalen-1-yl]diazenyl]phenyl]prop-2-en-1-one; 136649597: [3-(Trifluoromethyl)anilino] (1Z)-N-[[6-hydroxy-5-[[4-[3-[4-[[2-hydroxy-6-[(3-methylphenyl) carbamoylcarbamoyl]naphthalen-1-yl]diazenyl]phenyl]prop-2-enoyl]phenyl]diazenyl]naphthalen-2-yl]methoxy]methanimidate; 136660729: 1,3-Bis[4-[[6-[2-(3-chlorophenyl)ethyl]-2-hydroxynaphthalen-1-yl]diazenyl]phenyl]prop-2-en-1-one; 136667062: 3-Hydroxy-4-[[3-[(E)-3-oxo-3-phenylprop-1-enyl]phenyl]diazenyl]naphthalene-2,7-disulfonic acid; 136667063: 3-Hydroxy-4-[[4-[(E)-3-oxo-3-phenylprop-1-enyl]phenyl]diazenyl]naphthalene-2,7-disulfonic acid; 136698774: 6-[3-[3-[4-(3-Phenyl-3-oxo-1-propenyl)phenyl]acryloyl]phenylcarbamoyl]-4-carbamoyl-1,3-benzenedicarboxylic acid; 136715069: 1-(2-Hydroxyphenyl)-3-[4-[(5,10,15,20-tetraphenyl-21 H,23H-porphyrin-7-yl)amino]phenyl]-2-propene-1-one; 136715071: 1-(2-Hydroxyphenyl)-3-[4-[[4-(5,15,20-triphenyl-21H,23H-porphyrin-10-yl)phenyl]amino]phenyl]-2-propene-1-one; 136842617: 8-Hydroxy-7-[[4-[(Z)-3-oxo-3-phenylprop-1-enyl]phenyl]diazenyl]naphthalene-1,3,6-trisulfonic acid; 136842618: 8-Hydroxy-7-[[4-[(E)-3-oxo-3-phenylprop-1-enyl]phenyl]diazenyl]naphthalene-1,3,6-trisulfonic acid; 136896225: 3-(4-Pentoxyphenyl)-1-[4-[(2,4-dihydroxybenzylidene)amino]phenyl]-2-propene-1-one; 136896226: 3-[4-(Heptyloxy)phenyl]-1-[4-[(2,4-dihydroxybenzylidene)amino]phenyl]-2-propene-1-one; 136896227: 3-[4-(Octyloxy)phenyl]-1-[4-[(2,4-dihydroxybenzylidene)amino]phenyl]-2-propene-1-one; 136896228: 3-[4-(Dodecyloxy)phenyl]-1-[4-[(2,4-dihydroxybenzylidene)amino]phenyl]-2-propene-1-one; 136896229: 3-[4-(Tetradecyloxy)phenyl]-1-[4-[(2,4-dihydroxybenzylidene)amino]phenyl]-2-propene-1-one; 136896230: 3-[4-(Hexadecyloxy)phenyl]-1-[4-[(2,4-dihydroxybenzylidene)amino]phenyl]-2-propene-1-one; 136896231: 3-(4-Propoxyphenyl)-1-[4-[(2,4-dihydroxybenzylidene)amino]phenyl]-2-propene-1-one; 136896232: 3-(4-Methoxyphenyl)-1-[4-[(2,4-dihydroxy-alpha-methylbenzylidene)amino]phenyl]-2-propene-1-one; 136896233: 3-[4-(Tetradecyloxy) phenyl]-1-[4-[(2,4-dihydroxy-alpha-methylbenzylidene)amino]phenyl]-2-propene-1-one; 136896234: 3-(4-Propoxyphenyl)-1-[4-[(2,4-dihydroxy-alpha-methylbenzylidene)amino]phenyl]-2-propene-1-one; 136896235: 3-(4-Pentoxyphenyl)-1-[4-[(2,4-dihydroxy-alpha-methylbenzylidene)amino]phenyl]-2-propene-1-one; 136896236: 3-[4-(Heptyloxy)phenyl]-1-[4-[(2,4-dihydroxy-alpha-methylbenzylidene)amino]phenyl]-2-propene-1-one; 136896237: 3-[4-(Octyloxy)phenyl]-1-[4-[(2,4-dihydroxy-alpha-methylbenzylidene)amino]phenyl]-2-propene-1-one; 136896238: 3-(4-Decyloxy)phenyl]-1-[4-[(2,4-dihydroxy-alpha-methyl-benzylidene)amino]phenyl]-2-propene-1-one; 136896239: 3-[4-(Dodecyloxy)phenyl]-1-[4-[(2,4-dihydroxy-alpha-methylbenzylidene)amino]phenyl]-2-propene-1-one; 136901595: N-[3-Benzoyl-4-[3-(4-propoxyphenyl)acryloyl]phenyl]-4-propoxybenzeneacrylamide; 136918925: 5-Amino-4-hydroxy-3-[[3-[(E)-3-oxo-3-phenylprop-1-enyl]phenyl]diazenyl]naphthalene-2,7-disulfonic acid; 137002694: 4,6a,9,10-Tetrahydroxy-6,7-dihydroindeno[2,1-c]chromen-3-one;1-(2-hydroxy-4,6-dimethoxyphenyl)-3-phenylprop-2-en-1-one; 137228796: [2-(4-[3-(4-Fluoro-phenyl)-3-oxo-propenyl]-benzylidene-hydrazono)-4-oxo-thiazolidin-5-yl]-acetic acid; 137318852: FC1=CC(=C(C=C1)C(C=CC1=CC=CC=C1)=O)O; 137321334: (e)-3-(2',3'-Dihydrobenzofuran-5-yl)-1-(4-fluoro-2-hydroxylphenyl)prop-2-en-1-one; 137321347: (e)-3-(4'-Diethylaminophenyl)-1-(4-fluoro-2-hydroxylphenyl) prop-2-en-1-one; 137321365: (e)-3-(3',4'-Diethoxyphenyl)-1-(4-fluoro-2-hydroxyl-phenyl)prop-2-en-1-one; 137326483: 4'-Amino-3-hydroxychalcone; 137331728: 1-[2-Benzyloxy-6-hydroxy-4-methyl phenyl]-3-(phenyl)prop-2-en-1-one; 137333808: (E)-1-[4-[(2R,3R,4R,5R,6R)-3,4-Dihydroxy-6-(hydroxymethyl)-5-[(2S,3S,4R,5R)-3,4,5-trihydroxyoxan-2-yl]oxyoxan-2-yl]oxy-2-hydroxyphenyl]-3-(3,4-dihydroxyphenyl)prop-2-en-1-one; 137378729: Schembl20608174; 137378730: Schembl20608175; 137443814: Schembl20681666; 137552893: (e)-3-(4-Isopropylphenyl)-1-(2,4,6-trihydroxyphenyl)prop-2-en-1-one; 137633925: (E)-1-[4-[3-[2-[(7-Chloroquinolin-4-yl)amino]ethylamino]-2-hydroxypropoxy]phenyl]-3-(3,4-dimethoxyphenyl) prop-2-en-1-one; 137634966: (E)-1-(2,4-Dihydroxyphenyl)-3-[4-[(E)-3-(2,4-dihydroxy-phenyl)-3-oxoprop-1-enyl]phenyl]prop-2-en-1-one; 137636029: (E)-1-(2-Hydroxyphenyl)-3-[3-(trifluoromethoxy)phenyl]prop-2-en-1-one; 137647718: (E)-1-(2,4-Dihydroxyphenyl)-3-[3-[(E)-3-(2,4-dihydroxyphenyl)-3-oxoprop-1-enyl]phenyl] prop-2-en-1-one; 137649096: (E)-1-[4-[3-[2-[(7-Chloroquinolin-4-yl)amino]ethylamino]-2-hydroxypropoxy]phenyl]-3-(4-methoxy-phenyl)prop-2-en-1-one; 137656747: (E)-1-(2-Hydroxyphenyl)-3-[3-methoxy-4-(3-piperidin-1-ylpropoxy)phenyl]prop-2-en-1-one; 137660251: (E)-1-(2,6-Dihydroxyphenyl)-3-(3-methoxyphenyl)prop-2-en-1-one; 137661060: (E)-1-(4-Hydroxyphenyl)-3-[3-(trifluoromethoxy)phenyl]prop-2-en-1-one; 137661679: (E)-3-(4-Prop-2-enoxyphenyl)-1-(2,4,6-trihydroxyphenyl)prop-2-en-1-one; 137662243: 4-[(E)-3-(2-Hydroxy-4,6-dimethoxyphenyl)-3-oxoprop-1-enyl]benzoic acid; 137950492: (e)-3-(4-Fluorophenyl)-1-(2-hydroxy-4-methylphenyl)prop-2-en-1-one; 138107319: (E)-1-(2,4-Dihydroxyphenyl)-3-[4-[(2R,3R,4R,5S,6R)-3,4,5-trihydroxy-6-(hydroxymethyl)oxan-2-yl]oxyphenyl]prop-2-en-1-one; 138114808: 3-[4-[3-[(4R)-3,4-Dihydroxy-4-(hydroxymethyl)oxolan-2-yl]oxy-4,5-dihydroxy-6-(hydroxymethyl)oxan-2-yl]oxyphenyl]-1-(2,4-dihydroxyphenyl)prop-2-en-1-one; 138392310: 2'-Hydroxy-6'-methylchalcone; 138394145: Chalcone picrate; 138454317: (E)-3-(3-Hydroxy-4-methoxy-phenyl)-1-[2-hydroxy-6-methoxy-4-[(3R,4S,5S,6R)-3,4,5-trihydroxy-6-[[(2S,3R,4R,5R,6S)-3,4,5-trihydroxy-6-methyloxan-2-yl]oxymethyl]oxan-2-yl] oxyphenyl]prop-2-en-1-one; 138454590: 4-((1z)-3-(4-((2,6-Dihydroxyphenyl)diazenyl)phenyl)-3-oxoprop-1-en-1-yl) benzaldehyde; 138556479: Schembl20912972; 138570318: Schembl20928265; 138723291: Schembl21101810; 139036268: 2',3,4-Trihydroxy-trans-chalcone; 139051595: CID 139051595; 139059023: 2,5-Diphenylhydroquinone1, 3-diphenyl-2-propen-1-one (½); 139059024: 2,5-Diphenylhydroquinone1-(4-methoxyphenyl)-3-phenyl-2-propen-1-one (½); 139069637: Chalcone 2-bromo-3-hydroxy-1-(4-methylphenyl)-3-[4-(methylthio)phenyl]propan-1-one (1:1) co-crystal; 139076079: E-[4-(beta-D-Allopyranosyloxy)phenyl]-1-(4-chlorophenyl)prop-2-enone ethanol solvate; 139076080: (E)-1-(4-Chlorophenyl)-3-[4-[(2S,3R,4R,5S,6R)-3,4,5-trihydroxy-6-(hydroxymethyl)oxan-2-yl]oxyphenyl]prop-2-en-1-one; 139076232: (E)-1-(4-Decyloxyphenyl)-3-(4-hydroxyphenyl)prop-2-en-1-one; 139076233: (E)-1-(4-Decoxyphenyl)-3-(4-hydroxyphenyl)prop-2-en-1-one; 139076391: (E)-3-(4-Decyloxyphenyl)-1-(2-hydroxyphenyl)prop-2-en-1-one; 139076435: (E)-3-[4-(Decyloxy)phenyl]-1-(4-hydroxyphenyl)prop-2-en-1-one; 139076510: (E)-3-[4-(Dodecyloxy)phenyl]-1-(2-hydroxyphenyl)prop-2-en-1-one; 139076511: (E)-3-(4-Dodecoxyphenyl)-1-(2-hydroxyphenyl)prop-2-en-1-one; 139076717: (E)-3-[4-(Hexyloxy)phenyl]-1-(4-hydroxyphenyl)prop-2-en-1-one; 139077109: (E)-4-(beta-D-Allopyranosyloxy)cinnamyl 4-bromophenyl ketone ethanol solvate; 139078667: (2E)-1-[2-Hydroxy-4-(2-methylpropoxy)phenyl]-3-(4-methylphenyl)prop-2-en-1-one; 139079073: 4-Hydroxy-4'-dimethylaminochalcone; 139080104: (E)-1-[4-(Hexyloxy)phenyl]-3-(3-hydroxy-phenyl)prop-2-en-1-one; 139080105: (E)-1-(4-Hexoxyphenyl)-3-(3-hydroxyphenyl)prop-2-en-1-one; 139080679: (E)-1-(2,4-Dihydroxyphenyl)-3-(4-hydroxyphenyl)prop-2-en-1-one monohydrate; 139082286: (E)-1-[2-Hydroxy-4,6-bis(methoxymethoxy)phenyl]-3-[3-methoxy-4-(methoxymethoxy)phenyl]prop-2-en-1-one; 139082287: CID 139082287; 139085392: (E)-1-(4-Fluorophenyl)3-(4-hydroxy-3-methoxyphenyl)prop-2-en-1-one monohydrate; 139085632: (E)-3-[4-(Difluoromethoxy)-3-hydroxyphenyl]-1-phenylprop-2-en-1-one; 139196782: (E)-1-(4-(Benzyloxy)phenyl)-3-(4-hydroxyphenyl)prop-2-en-1-one; 139202754: (E)-3-[4-(Dimethylamino)phenyl]-1-[4-[(2-hydroxyphenyl)methylideneamino]phenyl]prop-2-en-1-one; 139202973: Isoliquiritigenin-isonicotinamide cocrystal; 139202974: Isoliquiritigenin-nicotinamide cocrystal; 139217467: (E)-1-(2-Hydroxyphenyl)-3-(4-methoxy-3-prop-2-enoxyphenyl)prop-2-en-1-one; 139217469: (E)-1-(2-Hydroxy-4-phenylmethoxy-phenyl)-3-(3-methoxy-4-prop-2-enoxyphenyl)prop-2-en-1-one; 139217470: (E)-1-(2-Hydroxy-4-phenylmethoxyphenyl)-3-(4-methoxy-3-prop-2-enoxyphenyl)prop-2-en-1-one; 139217472: (E)-1-(2-Hydroxy-4-prop-2-enoxyphenyl)-3-(4-methoxy-3-prop-2-enoxyphenyl) prop-2-en-1-one; 139217770: (E)-3-[4-(Benzotriazol-1-yl)phenyl]-1-(2-hydroxyphenyl)prop-2-en-1-one; 139227444: (E)-1-(4-Hydroxyphenyl)-3-[3-methoxy-4-[[3-methyl-4-(2,2,2-trifluoroethoxy)pyridin-2-yl]methoxy]phenyl]prop-2-en-1-one; 139234443: (E)-3-[4-[6-(4-Chlorophenyl)-4-hydroxyoxan-2-yl]phenyl]-1-(4-fluorophenyl)prop-2-en-1-one; 139234445: (E)-1-(4-Bromophenyl)-3-[4-[6-(4-bromophenyl)-4-hydroxyoxan-2-yl]phenyl]prop-2-en-1-one; 139243252: CID 139243252; 139243253: CID 139243253; 139395223: Schembl21251482; 139441377: Schembl21303885; 139602140: 2-Methyl-2-[4-[3-[4-(3-phenylprop-2-enoxy)phenyl]prop-2-enoyl]phenoxy]propanoic acid; 139602143: 2-[4-[3-[4-(Pyridin-2-ylmethoxy)phenyl]prop-2-enoyl]phenyl]acetic acid; 139602169: 2-[4-[3-[4-(3-Phenylprop-2-enoxy)phenyl]prop-2-enoyl]phenyl] acetic acid; 139602176: 2-[4-[3-[3-(3-Phenylprop-2-enoxy)phenyl]prop-2-enoyl]phenyl]acetic acid; 139602178: Methyl 2-[4-[3-(3,4-dihydroxyphenyl)prop-2-enoyl]phenyl] acetate; 139602203: 2-[4-[3-(4-Hydroxy-3-methoxyphenyl)prop-2-enoyl]phenyl]acetic acid; 139602207: 2-[2-[3-[4-(3-Phenylprop-2-enoxy)phenyl]prop-2-enoyl]phenyl]acetic acid; 139604008: 3-(4-Heptylphenyl)-1-[2-hydroxy-4-(3-methylbut-2-enoxy)phenyl]prop-2-en-1-one; 139614739: 1-(4-Hydroxy-2-methylphenyl)-3-(4-phenylmethoxyphenyl)prop-2-en-1-one; 139622156: 2-[5-[[4-[3-(4-Hydroxy-3-methoxyphenyl)prop-2-enoyl]phenyl]methyl]-2,4-dioxo-1,3-thiazolidin-3-yl]acetic acid; 139622157: Tert-butyl 2-[5-[[4-[3-(4-hydroxy-3-methoxyphenyl)prop-2-enoyl]phenyl] methyl]-2,4-dioxo-1,3-thiazolidin-3-yl]acetate; 139651547: 2-[4-(3-Phenylprop-2-enoyl)phenyl]butanoic acid; 139662071: 2-[2-[3-[4-(3-Methylbut-2-enoxy)phenyl]prop-2-enoyl]-5-pent-3-en-2-yloxyphenoxy]acetic acid; 139675949: 1-[2-Hydroxy-6-[(2S,3R,4S,5S,6R)-3,4,5-trihydroxy-6-(hydroxymethyl)oxan-2-yl]oxyphenyl]-3-(4-methoxyphenyl)prop-2-en-1-one; 139675959: Ethyl [4-[3-oxo-3-[2-phenylmethoxy-6-[(2S,3R,4S,5S,6R)-3,4,5-trihydroxy-6-(hydroxymethyl)oxan-2-yl]oxyphenyl]prop-1-enyl]phenyl] carbonate; 139675960: 3-(4-Hydroxyphenyl)-1-[2-phenylmethoxy-6-[(2S,3R,4S,5S,6R)-3,4,5-trihydroxy-6-(hydroxy-methyl)oxan-2-yl]oxyphenyl]prop-2-en-1-one; 139675966: 1-[2-[(2S,3R,4R,5S,6R)-3,4-Dihydroxy-6-(hydroxymethyl)-5-[(2R,3R,4S,5S,6R)-3,4,5-trihydroxy-6-(hydroxymethyl)oxan-2-yl]oxyoxan-2-yl]oxy-6-hydroxyphenyl]-3-(4-methoxyphenyl)prop-2-en-1-one; 139675975: 1-[2-Hydroxy-6-[(2S,3R,4S,5S,6R)-3,4,5-trihydroxy-6-(hydroxymethyl)oxan-2-yl]oxyphenyl]-3-(4-methylphenyl)prop-2-en-1-one; 139675977: 3-[4-(Oxan-2-yloxy)phenyl]-1-[2-phenyl-methoxy-6-[(2S,3R,4S,5S,6R)-3,4,5-trihydroxy-6-(hydroxymethyl)oxan-2-yl]oxyphenyl] prop-2-en-1-one; 139681231: 3-(3-Hydroxyphenyl)-1-(4-octadecoxyphenyl)prop-2-en-1-one; 139681240: 3-(4-Hydroxyphenyl)-1-(4-octadecoxyphenyl)prop-2-en-1-one;

139721318: Methyl 4-[3-(4-cyanophenyl)-3-oxoprop-1-enyl]-2-hydroxybenzoate; 139898983: 3-Hydroxy-2-[3-(4-methylphenyl)prop-2-enoyl]benzoic acid; 139898988: 3-Hydroxy-2-(3-phenylprop-2-enoyl)benzoic acid; 139898992: 2-[3-(4-Chlorophenyl)prop-2-enoyl]-3-hydroxybenzoic acid; 139914786: 4-[3-[4-(2-Methylprop-2-enoyloxy)phenyl]-3-oxoprop-1-enyl]benzoic acid; 139953957: 3-Hydroxy-4-4-[3-(4-nitro-phenyl)prop-2-enoyl]phenyl-2H-chromen-2-one; 140017273: 3-(4-Hydroxyphenyl)-1-(4-phenoxyphenyl)prop-2-en-1-one; 140080041: 3-(4-Butylphenyl)-1-[4-(11-hydroxyundecoxy)phenyl]prop-2-en-1-one; 140107971: 3,5-Diamino-2-[7-[4-[(E)-3-oxo-3-[4-(4-propylphenyl)phenyl]prop-1-enyl]phenoxy]heptyl]benzoic acid; 140107979: 3,5-Diamino-2-[8-[4-[(E)-3-oxo-3-[4-(4-propylphenyl)phenyl]prop-1-enyl]phenoxy]octyl]benzoic acid; 140108010: 3,5-Diamino-2-[2-[4-[(E)-3-oxo-3-[4-(4-propylphenyl)phenyl]prop-1-enyl]phenoxy]ethyl]benzoic acid; 140108012: 3,5-Diamino-2-[3-[4-[(E)-3-oxo-3-[4-(4-pentylphenyl)phenyl]prop-1-enyl]phenoxy]propyl]benzoic acid; 140108013: 3,5-Diamino-2-[11-[4-[(E)-3-oxo-3-[4-(4-pentylphenyl)phenyl]prop-1-enyl]phenoxy]undecyl]benzoic acid; 140108030: 3,5-Diamino-2-[7-[4-[(E)-3-oxo-3-[4-(4-pentylphenyl)phenyl]prop-1-enyl]phenoxy]heptyl]benzoic acid; 140108059: 3,5-Diamino-2-[11-[4-[(E)-3-oxo-3-[4-(4-propylphenyl)phenyl]prop-1-enyl]phenoxy]undecyl]benzoic acid; 140108060: 3,5-Diamino-2-[3-[4-[(E)-3-oxo-3-[4-(4-propylphenyl)phenyl]prop-1-enyl]phenoxy]propyl]benzoic acid; 140108074: 3,5-Diamino-2-[6-[4-[(E)-3-oxo-3-[4-(4-pentylphenyl)phenyl]prop-1-enyl]phenoxy]hexyl]benzoic acid; 140108082: 3,5-Diamino-2-[6-[4-[(E)-3-oxo-3-[4-(4-propylphenyl)phenyl]prop-1-enyl]phenoxy]hexyl]benzoic acid; 140128189: 3-[4-[[2,4-Bis(phenylmethoxy)phenyl]methoxy]-3-phenyl-methoxyphenyl]-1-(2-hydroxyphenyl)prop-2-en-1-one; 140131687: 4-[3-[3-[1-(1H-Benzimidazol-2-yl)-2-ethoxypropoxy]phenyl]prop-2-enoyl]-3-hydroxybenzoic acid; 140131688: 4-[3-[4-[1-(1H-Benzimidazol-2-yl)-2-ethoxypropoxy]phenyl]prop-2-enoyl]-3-hydroxybenzoic acid; 140250432: 3-(3,4-Dimethoxyphenyl)-1-(4-hydroxy-2,6-dimethoxyphenyl)prop-2-en-1-one; 140250433: 1-(2,4-Dihydroxy-6-methoxyphenyl)-3-(3,4-dimethoxyphenyl)prop-2-en-1-one; 140250434: 3-(3,4-Dimethoxyphenyl)-1-[2-hydroxy-4,6-bis(methoxymethoxy)phenyl]prop-2-en-1-one; 140339780: (E)-1-[4-[[3-[1-(1-Hydroxypropylamino)propoxy]phenyl]methoxy]phenyl]-3-phenylprop-2-en-1-one; 140345268: C1=CC(OC=CC(=C)C)=CC=C1C=CC(=O)C1=CC=C(OC=CC(C)=C)C=C1Occ(O)=O; 140426282: (E)-3-(1-Benzofuran-5-yl)-1-[2-hydroxy-4-methyl-6-[[3,4,5-tris(phenylmethoxy)-6-(phenylmethoxymethyl)oxan-2-yl]methyl]phenyl]prop-2-en-1-one; 140440690: Occccccoc(=O)C1=CC=C(C=C1)C=CC(=O)C1=CC=CC=C1; 140493303: [3-(Trifluoromethyl)anilino] (1 E)-N-[[6-hydroxy-5-[[4-[(E)-3-[4-[[2-hydroxy-6-[[3-(trifluoromethyl)phenyl]carbamoylcarbamoyl]naphthalen-1-yl]diazenyl]phenyl]prop-2-enoyl]phenyl]diazenyl]naphthalen-2-yl]methoxy]methanimidate; 140497894: (E)-1-[2,6-Dihydroxy-4-[(2S,4R,5S)-3,4,5-trihydroxy-6-[[(2R,4S,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 140554060: 4-[3-[4-(3-Amino-2-hydroxy-3-oxoprop-1-enyl)phenyl]prop-2-enoyl]benzoic acid; 140556445: C1=C(OC(C)(C)C(O)=O)C(C)=CC(C=CC(=O)C=2C=CC(O)=CC=2)=C1; 140651620: OCOc1ccc(C=CC(=O)c2ccccc2)cc1; 140651621: OCCCCCCCCCOc1ccc(C=CC(=O)c2ccccc2)cc1; 140679316: OCCCCCCCCCCOc1ccc(cc1)C(=O)C=Cc1ccccc1; 141039219: 2-[4-[3-(4-Fluorophenyl)-3-oxoprop-1-enyl]phenyl]-4-phenylbut-3-enoic acid; 141047154: 3-(4-Fluorophenyl)-1-[4-(1-hydroxyhexoxy)phenyl]prop-2-en-1-one; 141124286: (E)-3-(3,4-Dihydroxyphenyl)-1-[2-(2-hydroxyethyl)phenyl]prop-2-en-1-one; 141138732: 4-[3-[4-[3-(Hydroxyamino)-3-oxoprop-1-enyl]phenyl]prop-2-enoyl]benzoic acid; 141139323: 1-(2-Hydroxy-4,6-dimethoxyphenyl)-3-[4-(trifluoromethyl)phenyl]prop-2-en-1-one; 141159324: 1-(2,4-Dihydroxy-6-methoxyphenyl)-3-[4-hydroxy-3-(3-methylbuta-1,3-dienyl)phenyl]prop-2-en-1-one; 141189202: 1-(2,4-Dihydroxyphenyl)-3-[4-hydroxy-3-(3-methylbut-3-enyl)phenyl]prop-2-en-1-one; 141189626: 2-Hydroxy-3-[4-[(E)-3-oxo-3-(4-piperazin-1-ylphenyl)prop-1-enyl]phenyl]prop-2-enamide; 141189643: (E)-1-[4-(Hydroxymethyl)phenyl]-3-(4-prop-2-enylphenyl)prop-2-en-1-one; 141193878: 1-[4-[3-(4-Hydroxy-3-methoxyphenyl)prop-2-enoyl]phenyl]-3-(4-hydroxyphenyl)prop-2-en-1-one; 141193879: 3-(3-Hydroxy-4-methoxyphenyl)-1-[4-[3-(3-hydroxy-4-methoxyphenyl)prop-2-enoyl]phenyl]prop-2-en-1-one; 141193880: 1-(4-Acetylphenyl)-3-(4-hydroxy-3-methoxyphenyl)prop-2-en-1-one; 141193881: 3-(3-Hydroxy-4-methoxyphenyl)-1-[4-[3-(4-hydroxy-3-methoxyphenyl)prop-2-enoyl]phenyl]prop-2-en-1-one; 141193882: 1-[4-[3-(3-Hydroxy-4-methoxyphenyl)prop-2-enoyl]phenyl]-3-(4-hydroxyphenyl)prop-2-en-1-one; 141193885: 1-(4-Acetylphenyl)-3-(3-hydroxy-4-methoxyphenyl)prop-2-en-1-one; 141196094: 1-(2,6-Dihydroxy-4-methylphenyl)-3-phenylprop-2-en-1-one; 141208101: 3-(4-Cyclopentyloxyphenyl)-1-(2,4-dihydroxyphenyl) prop-2-en-1-one; 141251635: 1-[2-(Hydroxymethoxy)-4-(3-methylbutan-2-yloxy)phenyl]-3-[4-(3-methylbutan-2-yloxy)phenyl]prop-2-en-1-one; 141322646: OC1=C(C(C=CC2=CC(=C(C=C_2)OC)I)=O)C(=CC(=C1)OC)OC; 141346140: 4-[(E)-3-[4-Chloro-2-(pyridin-2-ylamino)phenyl]-3-oxoprop-1-enyl]benzoic acid; 141348645: 3-[3-[3-(4-Methylphenyl)-3-oxoprop-1-enyl]phenyl]prop-2-enoic acid; 141379446: (E)-1-[4-[4-[4-(1-Hydroxyethyl)piperazin-1-yl]butoxy]phenyl]-3-[4-(2,6,10-trimethyldodecan-2-ylsulfanyl)phenyl]prop-2-en-1-one; 141410058: 2,2,2-Trifluoro-N-[2-[(E)-3-(4-hydroxy-3-methoxyphenyl)prop-2-enoyl]phenyl]acetamide; 141410061: N-[4-[(E)-3-(4-Hydroxy-3-methoxyphenyl)prop-2-enoyl]phenyl]prop-2-ynamide; 141410064: (E)-1-(4-Aminophenyl)-3-(4-hydroxy-3-methoxyphenyl)prop-2-en-1-one; 141410066: 2,2,2-Trifluoro-N-[2-[(E)-3-(3-hydroxy-4-methoxyphenyl)prop-2-enoyl]phenyl]acetamide; 141444079: (E)-1-[2-(4-Fluorophenyl)phenyl]-3-(4-hydroxyphenyl)prop-2-en-1-one; 141444080: (E)-1-[2-(3-Fluorophenyl)phenyl]-3-(4-hydroxyphenyl)prop-2-en-1-one; 141447441: 1-(2-Chloro-6-fluorophenyl)-3-(4-hydroxyphenyl)prop-2-en-1-one; 141447494: 3-(4-Hydroxyphenyl)-1-[4-(trifluoromethoxy)phenyl]prop-2-en-1-one; 141456329: 2-[4-[(E)-3-(4-Hydroxyphenyl)prop-2-enoyl]phenyl]ethyl-methylcarbamic acid; 141465157: 4-[(E)-3-[3-(Benzotriazol-2-yl)-4-hydroxyphenyl]prop-2-enoyl]benzonitrile; 141465158: (E)-3-[3-(Benzotriazol-2-yl)-4-hydroxyphenyl]-1-[4-(dimethylamino)phenyl]prop-2-en-1-one; 141465159: (E)-3-[3-(Benzotriazol-2-yl)-4-hydroxyphenyl]-1-phenylprop-2-en-1-one; 141465160: (E)-3-[3-(Benzotriazol-2-yl)-4-hydroxyphenyl]-1-(4-methoxyphenyl)prop-2-en-1-one; 141472893: 1-(2-Hydroxy-4,6-dimethoxyphenyl)-3-(4-propan-2-yloxyphenyl)prop-2-en-1-one; 141479930: 3-[4-(Dimethylamino)phenyl]-1-[4-[4-(hydroxymethyl)triazol-1-yl]phenyl]prop-2-en-1-one; 141493362: 1-(2-Hydroxyphenyl)-3-[4-(4-methyl-N-(4-methylphenyl)anilino)phenyl]prop-2-en-1-one; 141513176: (E)-3-[4-

Hydroxy-3-(3-methylbut-2-enyl)phenyl]-1-(4-methoxyphenyl) prop-2-en-1-one; 141536297: 3-[4-(Azetidin-1-yl)phenyl]-1-(2-hydroxyphenyl)prop-2-en-1-one; 141625313: (E)-1-[2-[(E)-1,2-Dihydroxy-3-methylbut-1-enyl]phenyl]-3-phenylprop-2-en-1-one; 141730233: 2-Chloro-N-[4-[(E)-3-(4-hydroxyphenyl)prop-2-enoyl]phenyl]benzenesulfonamide; 141730242: 2-Benzyl-N-[4-[(E)-3-(4-hydroxyphenyl)prop-2-enoyl]phenyl]benzenesulfonamide; 141730246: N-[4-[(E)-3-(4-Hydroxyphenyl)prop-2-enoyl]phenyl]-4-methoxybenzenesulfonamide; 141730251: 4-Bromo-N-[4-[(E)-3-(4-hydroxyphenyl)prop-2-enoyl]phenyl]benzenesulfonamide; 141730252: 4-Tert-butyl-N-[4-[(E)-3-(4-hydroxyphenyl) prop-2-enoyl]phenyl]benzenesulfonamide; 141730257: N-[4-[(E)-3-(4-Hydroxyphenyl)prop-2-enoyl]phenyl]-2-methylbenzenesulfonamide; 141730266: 2-Ethyl-N-[4-[(E)-3-(4-hydroxyphenyl)prop-2-enoyl]phenyl]benzenesulfonamide; 141730270: 2-Bromo-N-[4-[(E)-3-(4-hydroxyphenyl)prop-2-enoyl]phenyl]benzenesulfonamide; 141730272: 4-Ethyl-N-[4-[(E)-3-(4-hydroxyphenyl) prop-2-enoyl]phenyl]benzenesulfonamide; 141730624: (E)-3-(3,4-Dihydroxyphenyl)-1-(4-ethoxyphenyl)prop-2-en-1-one; 141730626: (E)-3-(3,4-Dihydroxy-phenyl)-1-(2-fluorophenyl)prop-2-en-1-one; 141730633: (E)-3-(3,4-Dihydroxyphenyl)-1-(4-fluorophenyl)prop-2-en-1-one; 141736511: 3-[4-(3-Chloropropoxy)phenyl]-1-(2-hydroxyphenyl)prop-2-en-1-one; 141736513: 3-[4-(3-Chloropropoxy)phenyl]-1-(2,6-dihydroxy-phenyl)prop-2-en-1-one; 141737756: 3-(4-Bromo-3-chlorophenyl)-1-(4-hydroxyphenyl)prop-2-en-1-one; 141740800: N-[4-[(E)-3-(4-Hydroxy-3-methoxyphenyl)prop-2-enoyl]phenyl]-3-phenylprop-2-ynamide; 141747998: (2S)-2-[(3S,5Z)-5-[[4-[(E)-3-[4-[(3-Fluorophenyl) methoxy]phenyl]-3-oxoprop-1-enyl]phenyl]methylidene]-1-oxo-3-sulfanyl-1,2,4-thiadiazolidin-2-yl]-3-phenylpropanoic acid; 141747999: (2S)-2-[(3S,5Z)-5-[[4-[(E)-3-[4-[(4-Fluorophenyl)methoxy]phenyl]-3-oxoprop-1-enyl]phenyl]methylidene]-1-oxo-3-sulfanyl-1,2,4-thiadiazolidin-2-yl]-3-phenylpropanoic acid; 141748000: (2S)-2-[(3S,5Z)-5-[[4-[(E)-3-(2,4-Dimethylphenyl)-3-oxoprop-1-enyl]phenyl]methylidene]-1-oxo-3-sulfanyl-1,2,4-thiadiazolidin-2-yl]-3-phenylpropanoic acid; 141748002: (2S)-2-[(3S,5Z)-5-[[4-[(E)-3-(4-Fluorophenyl)-3-oxoprop-1-enyl]phenyl]methylidene]-1-oxo-3-sulfanyl-1,2,4-thiadiazolidin-2-yl]-3-phenylpropanoic acid; 141748003: (2S)-2-[(3S,5Z)-5-[[4-[(E)-3-(4-Chlorophenyl)-3-oxoprop-1-enyl]phenyl]methylidene]-1-oxo-3-sulfanyl-1,2,4-thiadiazolidin-2-yl]-3-phenylpropanoic acid; 141748004: (2S)-2-[(3S,5Z)-5-[[4-[(E)-3-(4-Bromophenyl)-3-oxoprop-1-enyl]phenyl]methylidene]-1-oxo-3-sulfanyl-1,2,4-thiadiazolidin-2-yl]-3-phenylpropanoic acid; 141748005: (2S)-2-[(3S,5Z)-5-[[4-[(E)-3-(2-Fluorophenyl)-3-oxoprop-1-enyl]phenyl]methylidene]-1-oxo-3-sulfanyl-1,2,4-thiadiazolidin-2-yl]-3-phenylpropanoic acid; 141748006: (2S)-2-[(3S,5Z)-5-[[4-[(E)-3-[4-[(2-Chlorophenyl)methoxy]phenyl]-3-oxoprop-1-enyl]phenyl]methylidene]-1-oxo-3-sulfanyl-1,2,4-thiadiazolidin-2-yl]-3-phenylpropanoic acid; 141748008: (2S)-2-[(3S,5Z)-5-[[4-[(E)-3-[4-[(2-Fluorophenyl)methoxy]phenyl]-3-oxoprop-1-enyl]phenyl]methylidene]-1-oxo-3-sulfanyl-1,2,4-thiadiazolidin-2-yl]-3-phenylpropanoic acid; 141748009: (2S)-2-[(3S,5Z)-5-[[4-[(E)-3-(4-Methylphenyl)-3-oxoprop-1-enyl]phenyl]methylidene]-1-oxo-3-sulfanyl-1,2,4-thiadiazolidin-2-yl]-3-phenylpropanoic acid; 141748010: (2S)-2-[(3S,5Z)-5-[[4-[(E)-3-[4-[(4-Chlorophenyl)methoxy]phenyl]-3-oxoprop-1-enyl]phenyl]methylidene]-1-oxo-3-sulfanyl-1,2,4-thiadiazolidin-2-yl]-3-phenylpropanoic acid; 141748011: (2S)-2-[(3S,5Z)-5-[[4-[(E)-3-[4-[(4-Methylphenyl)methoxy]phenyl]-3-oxoprop-1-enyl]phenyl]methylidene]-1-oxo-3-sulfanyl-1,2,4-thiadiazolidin-2-yl]-3-phenylpropanoic acid; 141748012: (2S)-2-[(3S,5Z)-5-[[4-[(E)-3-(2-Methoxyphenyl)-3-oxoprop-1-enyl]phenyl]methylidene]-1-oxo-3-sulfanyl-1,2,4-thiadiazolidin-2-yl]-3-phenylpropanoic acid; 141758186: (E)-1-(4-Fluoro-2-hydroxyphenyl)-3-[4-(4-methyl-N-(4-methylphenyl)anilino)phenyl]prop-2-en-1-one; 141790008: (E)-3-(4-Hydroxyphenyl)-1-(4-nitrosophenyl)prop-2-en-1-one; 141799052: 4-[(E)-3-(4-Hydroxyphenyl)prop-2-enoyl]benzonitrile;methanol; 142079912: 4-[(E)-3-[4-(2-Methoxyethoxymethoxy)phenyl]-3-oxoprop-1-enyl]benzoic acid; 142236837: (E)-3-[3-Hydroxy-4-[3-hydroxy-5-(hydroxymethyl)-4-nitrosooxolan-2-yl]oxyphenyl]-1-phenylprop-2-en-1-one; 142259415: 4-[(E)-3-(3-Amino-4-pyrrolidin-1-ylphenyl)prop-2-enoyl]benzoic acid; 142259429: 4-[(E)-3-(4-Pyrrolidin-1-yl-3-sulfanylphenyl)prop-2-enoyl]benzoic acid; 142259444: 4-[(E)-3-[4-[(2-Methylidenecyclopropylidene)methyl]phenyl]-3-oxoprop-1-enyl]benzoic acid; 142259453: 4-[(E)-3-(3-Amino-4-fluorophenyl)prop-2-enoyl]benzoic acid; 142412259: Ethane;(E)-1-(2-hydroxy-4,6-dimethoxyphenyl)-3-(4-hydroxyphenyl)prop-2-en-1-one; 142412261: (E)-1-(2,6-Dihydroxy-3,4-dimethoxyphenyl)-3-[4-[3-[(E)-3-(2-hydroxy-4,6-dimethoxyphenyl)-3-oxoprop-1-enyl]phenyl]prop-2-en-1-one; 142473988: Schembl21802490; 142535463: (E)-1-(2-Hydroxy-4-methylphenyl)-3-(4-hydroxyphenyl)prop-2-en-1-one; 142644881: 1-(4-But-2-enoxy-2-hydroxyphenyl)-3-(3-methoxyphenyl) prop-2-en-1-one; 142655195: 3-(1-Benzofuran-5-yl)-1-(2-hydroxyphenyl)prop-2-en-1-one; 142686432: 3-(4-Fluorophenyl)-1-[4-(2-hydroxyethenyl)phenyl]prop-2-en-1-one; 142702009: Tert-butyl 4-[[4-[(E)-3-(4-hydroxy-3-methylphenyl)prop-2-enoyl]-3-methyl-phenoxy]methyl]-2H-pyrimidine-1-carboxylate; 142722979: (E)-3-[4-(2,3-Dihydropyrrol-1-yl)phenyl]-1-(2,4-dihydroxyphenyl)prop-2-en-1-one; 142722981: (E)-3-[4-(2,3-Dihydropyrrol-1-yl)phenyl]-1-(4-hydroxyphenyl)prop-2-en-1-one; 142740665: OC1=C(C=CC(=C1)OC)C(\C=C\C1=CC2=CC=CC=C₂C=C1)=O; 142740672: OC1=C(C(=CC=C1)OC)C(\C=C\C1=CC2=CC=CC=C₂C=C1)=O; 142792135: C(C)(C)(C)OC(C(C)(C)OC1=C(C=C(C=C1)C=CC(=O)C1=CC=C(C=C1)O)C)=O; 142836668: (E)-3-[4-(6-Hydroxyhexoxy)phenyl]-1-(4-methylphenyl)prop-2-en-1-one; 142847984: 2-[3-Hydroxy-4-[(E)-3-(3-hydroxyphenyl)prop-2-enoyl]phenoxy]-2-methyl-N-oxopropanamide; 142847993: 2-[3-Hydroxy-4-[(E)-3-(4-methylsulfanylphenyl)prop-2-enoyl]phenoxy]-2-methyl-N-oxopropanamide; 142905619: (E)-1-[2-[3,4-Dihydroxy-6-(hydroxymethyl)-5-methyloxan-2-yl]oxy-6-hydroxy-4-methylphenyl]-3-(4-methoxyphenyl) prop-2-en-1-one; 142905624: Ethane;(E)-1-[2-[5-fluoro-3,4-dihydroxy-6-(hydroxymethyl) oxan-2-yl]oxy-6-hydroxy-4-methylphenyl]-3-(4-methoxyphenyl)prop-2-en-1-one; 142913162: 4-[(E)-3-[3-(2H-Thiopyran-2-yl)phenyl]prop-2-enoyl]benzoic acid; 143128223: Hex-5-enoic acid;(E)-1-(4-hydroxyphenyl)-3-phenylprop-2-en-1-one; 143128286: 2-[2-[(E)-3-[4-(4-Bromophenyl)phenyl]prop-2-enoyl]phenoxy]butanoic acid;(3Z)-4,6-dimethylhepta-1,3,5-triene; 143128287: 2-[2-[(E)-3-[4-(4-Bromophenyl)phenyl]prop-2-enoyl]phenoxy] butanoic acid; 143128302: 2-[2-[4-[(E)-3-Oxo-3-phenylprop-1-enyl]phenoxy]ethyl]-4-phenylbutanoic acid; 143150356: (E)-1-(2,4-Dihydroxyphenyl)-3-(3,4-dimethoxyphenyl)prop-2-en-1-one;ethane; 143186777: (E)-1-[2,6-Dihydroxy-4-[(2S,5S)-3,4,5-trihydroxy-6-[[(2R,5R)-5-hydroxy-6-methyloxan-2-yl]oxymethyl]oxan-2-yl]oxyphenyl]-3-(3-hydroxy-4-methoxyphenyl) prop-2-en-1-one; 143275724: Ethane;(E)-1-[2-hydroxy-4,6-bis (phenylmethoxy)phenyl]-3-(4-phenylmethoxyphenyl)prop-2-en-1-one; 143338501: (E)-1-(4-Hydroxy-2-methoxyphenyl)-3-(4-methoxyphenyl)prop-2-en-1-one; 143338503: Ethane;2-[(E)-3-(3-hydroxy-4-methylphenyl) prop-2-enoyl]-5-nitrosobenzonitrile; 143338504: 2-[(E)-3-(3-Hydroxy-4-methyl phenyl)prop-2-enoyl]-5-nitrosobenzonitrile; 143364358: (E)-1-(2,4-Dimethoxyphenyl)-3-(3-hydroxy-4-nitrosophenyl)prop-2-en-1-one; 143552237: (E)-3-(4-Hydroxy-3-methylphenyl)-1-[4-[(4-methylcyclohexa-1,5-dien-1-yl)sulfanylamino]phenyl]prop-2-en-1-one; 143665489: 3-[2-Ethyl-4-[2-methyl-4-[(E)-3-oxo-3-phenyl-prop-1-enyl]phenoxy]phenyl]propanoic acid; 143723583: Ethane;(E)-1-(2-hydroxy-4-methoxyphenyl)-3-phenylprop-2-en-1-one; 143768291: (E)-3-(1,3-Benzodioxol-5-yl)-1-(2-hydroxy-4-iodophosphanyloxyphenyl)prop-2-en-1-one; 144087667: (E)-1-(2-Hydroxy-6-methoxy-4-methylphenyl)-3-(4-methylphenyl) prop-2-en-1-one; 144107490: 2-[(E)-3-[3,4-Bis(difluoromethoxy)phenyl]prop-2-enoyl] benzoic acid; 144290419: (E)-3-[3-Hydroxy-4-[(4-methylpiperazin-1-yl)methyl]phenyl]-1-(4-hydroxyphenyl)prop-2-en-1-one; 144290425: (E)-3-[3-Hydroxy-4-(morpholin-4-ylmethyl)phenyl]-1-phenylprop-2-en-1-one; 144290430: Dimethylamino-methanethiol;ethane;(E)-3-(3-hydroxyphenyl)-1-(4-methoxyphenyl)prop-2-en-1-one; 144290437: (E)-1-(4-Fluorophenyl)-3-(3-hydroxy-4-methylphenyl) prop-2-en-1-one; 144290439: (E)-3-[3-Hydroxy-4-(morpholin-4-ylmethyl)phenyl]-1-(4-hydroxyphenyl)prop-2-en-1-one; 144324379: 2-Hydroxy-5-[3-(4-methylphenyl)-3-oxoprop-1-enyl]benzaldehyde; 144337027: (E)-3-[4-[2-Hydroxyethyl(methyl)amino]phenyl]-1-[4-(1-hydroxyprop-2-enylamino)phenyl]prop-2-en-1-one; 144346805: (E)-1-(2-Hydroxy-6-methylphenyl)-3-(4-hydroxyphenyl)prop-2-en-1-one; 144452308: (E)-3-[4-(Diethylamino)phenyl]-1-(4-ethenylphenyl)prop-2-en-1-one;(E)-3-(3-hydroxyanilino)-1-phenylprop-2-en-1-one; 144490989: (E)-1-[4-[2-(2,4-Difluorophenyl)-2-hydroxy-3-(1,2,4-triazol-1-yl)propoxy]phenyl]-3-(4-hydroxyphenyl)prop-2-en-1-one; 144528368: (E)-1-(2-Hydroxyphenyl)-3-(4-phenyl-methoxyphenyl)prop-2-en-1-one;(E)-1-(2-iodophenyl)-3-(4-methoxyphenyl)prop-2-en-1-one; 144630565: (E)-1-(4-Bromophenyl)-3-(4-hydroxy-3-methoxyphenyl)prop-2-en-1-one;ethane; 144669715: (E)-1-(2,4-Dihydroxyphenyl)-3-(3-hydroxyphenyl)prop-2-en-1-one;methanol; 144690305: N-Amino-N-[3-[amino-[(Z)-2-amino-3-[4-[(E)-3-oxo-3-[4-(4-propylpiperazin-1-yl)phenyl]prop-1-enyl]phenoxy]prop-1-enyl]amino]-2-(4-fluorophenyl)-2-hydroxypropyl]methanimidamide;ethane; 144690306: N-Amino-N-[3-[amino-[(Z)-2-amino-3-[4-[(E)-3-oxo-3-[4-(4-propylpiperazin-1-yl)phenyl]prop-1-enyl]phenoxy]prop-1-enyl]amino]-2-(4-fluorophenyl)-2-hydroxypropyl]methanimidamide; 144690316: (E)-1-[4-[(Z)-2-Amino-3-[amino-[2-(2,4-difluorophenyl)-2-hydroxy-3-(1,2,4-triazol-1-yl)propyl]amino]prop-2-enoxy]phenyl]-3-(4-methoxyphenyl)prop-2-en-1-one; 145188928: (E)-1-(4-Cyclohexa-1,5-dien-1-ylphenyl)-3-(4-hydroxyphenyl)prop-2-en-1-one; 145196288: (E)-1-[2,6-Dihydroxy-4-(3-methylbut-2-enoxy) phenyl]-3-phenylprop-2-en-1-one;2-[4-[(2E)-3,7-dimethyl-octa-2,6-dienoxy]phenyl]ethanol;(E)-1-[2-hydroxy-4-(3-methylbut-2-enoxy)phenyl]-3-phenylprop-2-en-1-one;3-[4-(3-methylbut-2-enoxy)phenyl]propan-1-ol; 145196292: Buta-1,3-diene;(E)-1-[2,6-dihydroxy-4-(3-methylbut-2-enoxy)phenyl]-3-phenylprop-2-en-1-one;2-[4-[(2E)-3,7-dimethylocta-2,6-dienoxy]phenyl]ethanol; 145196295: (E)-1-[4-[(2E)-3,7-Dimethylocta-2,6-dienoxy]-2-hydroxyphenyl]-3-(4-hydroxyphenyl)prop-2-en-1-one;(E)-1-[2-hydroxy-4-(3-methylbut-2-enoxy)phenyl]-3-(4-hydroxyphenyl)prop-2-en-1-one; 145440670: Schembl22066255; 145508810: (E)-3-[3-[(7-Chloroquinolin-4-yl)amino]phenyl]-1-(4-methoxyphenyl)prop-2-en-1-one;ethane;3-hydroxy-3-methylbutanoic acid; 145512487: 4-[(E)-3-(2-Anilino-4-chlorophenyl)-3-oxoprop-1-enyl]-N-(2-hydroxy-2-methylpropyl)benzenesulfinamide; 145533558: (E)-1-[4-[3,4-Dihydroxy-6-[(1,2,3-trihydroxy-4-methoxypentoxy) methyl]oxan-2-yl]oxy-2-hydroxy-6-methoxyphenyl]-3-(3-hydroxy-4-methoxyphenyl)prop-2-en-1-one; 145534806: (E)-1-(2-Amino-4,6-dihydroxyphenyl)-3-(4-hydroxyphenyl)prop-2-en-1-one; 145629557: 2-[4-[2-[2-[Amino-[(Z)-2-amino-6-[4-[(E)-3-(4-fluoro-2-hydroxyphenyl)-3-oxoprop-1-enyl]phenoxy]hex-1-enyl]amino]ethoxy]ethoxy]phenyl]chromen-4-one; 145721581: (e)-3-(3-Hydroxy-4-phenoxyphenyl)-1-phenylprop-2-en-1-one; 145762605: Occcoc1=CC=C(C=C1)C(C=CC1=CC=C(C=C1)occco)=O; 145851643: FC1=CC=C(C(C=CC2=CC=C(C=C$_2$)Occccccoc=2C=C(C=C(C$_2$C(=O)O)C(=O)O)C$_2$=CC(=C(C(=C$_2$)C(=O)O)C(=O)O)) occccccoc2=CC=C(C=C$_2$)C=CC(=O)C$_2$=CC=C(C=C$_2$)F)=O)C=C1; 145851644: FC1=CC=C(C(C=CC2=CC=C(C=C$_2$)Occccccoc2=CC=C(C(=C2C2=C(C(=CC=C2occcccco c2=CC=C(C=C2)C=CC(=O)C2=CC=C(C=C2)F)C(=O)O)C(=O)O)C(=O)O)=O)C=C1; 145851645: 3-[2,3-Dicarboxy-6-[4-[4-(3-oxo-3-phenylprop-1-enyl)phenyl]phenoxy]phenyl]-4-[4-[4-(3-oxo-3-phenylprop-1-enyl)phenyl]phenoxy]phthalic acid; 145851646: 4-[3,4-Dicarboxy-2-[4-[4-(3-oxo-3-phenylprop-1-enyl)phenyl]phenoxy]phenyl]-3-[4-[4-(3-oxo-3-phenylprop-1-enyl) phenyl]phenoxy]phthalic acid; 145851647: FC1=CC=C(C(C=CC2=CC=C(C=C2)Occccccoc2=C(C=CC(=C2C(=O)O)C(=O)O)C2=C(C(=C(C=C2)C(=O)O)C(=O)O)occccccoc2=CC=C(C=C2)C=CC(=O)C2=CC=C(C=C2)F)=O)C=C1; 145851649: FC1=CC=C(C(C=CC2=CC=C(C=C2)Occccccoc2=C(C(=C(C=C2)C2=C(C(=C(C=C2)occcc ccoc2=CC=C(C=C2)C=CC(=O)C2=CC=C(C=C2)F)C(=O)O)C(=O)O)C(=O)O)C(=O)O)=O)C=C1; 145851650: 5-[3,4-Dicarboxy-5-[4-[4-(3-oxo-3-phenylprop-1-enyl)phenyl]phenoxy]phenyl]-3-[4-[4-(3-oxo-3-phenylprop-1-enyl)phenyl]phenoxy]phthalic acid; 145851651: C1(=CC=C(C=C1)Occccccoc1=C(C(=C(C=C1)C1=C(C(=CC(=C1)occccccoc1=CC=C(C=C 1)C=CC(=O)C1=CC=CC=C1)C(=O)O)C(=O)O)C(=O)O)C(=O)O)C=CC(=O)C1=CC=CC=C1;145851652: C1(=CC=C(C=C1)Occccccoc=1C=C(C=C(C1C(=O)O)C(=O)O)C1=CC=C(C(=C1)C(=O)) C(=O)O)occccccoc1=CC=C(C=C1)C=CC(=O)C1=CC=CC=C1)C=CC(=O)C1=CC=CC=C1; 145851653: C1(=CC=C(C=C1)Occccccoc1=C(C=C(C(=C1)C(=O)O)C(=O)O)C1=C(C=C(C(=C1)C(=O)O)C(=O)O)occccccoc1=CC=C(C=C1)C=CC(=O)C1=CC=CC=C1)C=CC(=O)C1=CC=CC=C1; 145851654: 3-[2,3-Dicarboxy-5-[4-[4-(3-oxo-3-phenylprop-1-enyl)phenyl]phenoxy]phenyl]-5-[4-[4-(3-oxo-3-phenylprop-1-enyl)phenyl]phenoxy]phthalic acid; 145851655: C1(=CC=C(C=C1)Occccccoc=1C=C(C(=C(C1)C1=C(C(=CC(=C1)occccccoc1=CC=C(C=C 1)C=CC(=O)C1=CC=CC=C1)C(=O)O)C(=O)O)C(=O)O)C(=O)O)C=CC(=O)C1=CC=CC=C1;145851656: C1(=CC=C(C=C1)Occccccoc1=CC=C(C(=C1 C1=C(C(=CC=C1occccccoc1=CC=C(C=C1)C=CC(=O)C1=CC=CC=C1)C(=O)O)C(=O)O)C(=O)O)C=CC(=O)C1=CC=CC=C1; 145851657: C1(=CC=C(C=C1)Occccccoc1=C(C(=CC(=C1)C(=O)O)C(=O)O)C1=C(C=C(C(=C1)C(=O)O)C(=O)O)occccccoc1=CC=C(C=C1)C=CC(=O)

C1=CC=CC=C1; 145851658: 4-[4,5-Dicarboxy-2-[4-[4-(3-oxo-3-phenylprop-1-enyl)phenyl]phenoxy]phenyl]-5-[4-[4-(3-oxo-3-phenylprop-1-enyl)phenyl]phenoxy]phthalic acid; 145851659: FC1=CC=C(C(C=CC2=CC=C(C=C$_2$)Occcccoc2=C(C=C(C(=C$_2$)C(=O)O)C(=O)O)C$_2$=C(C =C(C(=C$_2$)C(=O)O)C(=O)O) occccccoc2=CC=C(C=C$_2$)C=CC(=O)C$_2$=CC=C(C=C$_2$)F)=O)C =C1; 145851661: FC1=CC=C(C(C=CC2=CC=C(C=C$_2$)Occcccoc=2C=C(C(=C(C$_2$)C$_2$=C(C(=CC(=C$_2$)occccc ccoc2=CC=C(C=C$_2$)C=CC(=O)C$_2$=CC=C(C=C$_2$)F)C(=O)O)C(=O)O)C(=O)O)C(=O)O)=O)C =C1; 145926096: (e)-3-[4-(6,7-Dimethoxyquinazolin-4-ylamino)phenyl]-1-(4-hydroxyphenyl)prop-2-en-1-one; 145946234: Chembl4300115; 145946780: Chembl4300592; 145947225: Chembl4301419; 145949999: Chembl4175213; 145952390: Chembl4175451; 145955526: Chembl4168923; 145955922: Chembl4167307; 145956615: Chembl4159394; 145968537: Chembl4225431; 145971277: Chembl4177186; 145974105: Chembl4177051; 145974337: Chembl4176784; 145978383: Chembl4207502; 145979043: Chembl4281281; 145979515: Chembl4282171; 145979543: Chembl4282928; 145979633: Chembl4279574; 145980082: Chembl4279501; 145980233: Chembl4283038; 145980242: Chembl4283220; 145980340: Chembl4280208; 145980371: Chembl4280887; 145980496: Chembl4278395; 145981416: Chembl4278755; 145981461: Chembl4280143; 145981635: Chembl4278497; 145982373: Chembl4280685; 145982931: Chembl4276741; 145983406: Chembl4277477; 145984409: Chembl4277291; 145984635: Chembl4276778; 145986463: Chembl4291928; 145987030: Chembl4289218; 145987369: Chembl4291529; 145987506: Chembl4289424; 145987818: Chembl4290841; 145988458: Chembl4290237; 145988594: Chembl4293796; 145988726: Chembl4291897; 145988786: Chembl4293533; 145989233: Chembl4293627; 145989410: Chembl4292605; 145990446: Chembl4286815; 145990570: Chembl4284681; 145990695: Chembl4287574; 145990940: Chembl4287931; 145990983: Chembl4283661; 145991107: Chembl4286407; 145991371: Chembl4287419; 145991826: Chembl4287428; 145991865: Chembl4288121; 145991949: Chembl4284719; 145992130: Chembl4283596; 145992306: Chembl4288042; 145993216: Chembl4283623; 145993232: Chembl4284058; 145993610: Chembl4294716; 145993835: Chembl4294648; 145997574: 2'-Hydroxy-4'-isoprenyloxychalcone; 146125065: 3-[[4-[(E)-3-[4-(1,2,4-Triazol-1-yl)phenyl]prop-2-enoyl]phenyl]sulfonylamino]propanoic acid; 146125597: 3-[[4-[(E)-3-[4-(2,2,2-Trifluoroethoxy)phenyl]prop-2-enoyl]phenyl]sulfonylamino]propanoic acid; 146127162: 4-[4-[(E)-3-(3-Pyrazol-1-ylphenyl)prop-2-enoyl]phenoxy]butanoic acid; 146128605: 3-[3-[(E)-3-[4-(Dimethylcarbamoyl)phenyl]-3-oxoprop-1-enyl]phenoxy]propanoic acid; 146153177: 2-[[4-[(E)-3-(3-Pyridin-2-yloxyphenyl)prop-2-enoyl]phenyl]sulfonylamino]acetic acid; 146153604: 4-[(E)-3-[4-(3-Fluorophenoxy)phenyl]prop-2-enoyl]-3-hydroxybenzoic acid; 146153605: 4-[4-[(E)-3-(4-Fluoro-3-sulfamoylphenyl)prop-2-enoyl]phenoxy]butanoic acid; 146223481: Schembl21527681; 146223484: Schembl21527686; 146223485: Schembl21527687; 146223486: Schembl21527691; 146223495: Schembl21527704; 146223496: Schembl21527705; 146223507: Schembl21527718; 146223508: Schembl21527720; 146310571: Schembl21635208; 146310572: Schembl21635209; 146424658: Schembl21776503; 146424659: Schembl21776504; 146746991: (E)-1-(2,4-Dihydroxyphenyl)-3-[4-[[(2S,4S,6S)-4-hydroxy-6-(hydroxymethyl)piperidin-2-yl]amino]phenyl]prop-2-en-1-one; 146785379: (E)-3-[4-[4-(3,4-Dihydropyridazin-6-yl)butoxy]phenyl]-1-(2-hydroxyphenyl)prop-2-en-1-one; 146801340: Schembl22099471; 146801576: Schembl22099100; 146801598: Schembl22099116; 146838909: [3-Hydroxy-4-[(E)-3-(4-hydroxyphenyl)prop-2-enoyl]phenyl] butanoate; 146840924: (E)-1-[2-Hydroxy-4-(2-methyl-3-nitrosobut-3-en-2-yl)oxyphenyl]-3-(4-hydroxyphenyl)prop-2-en-1-one; 146871220: N-[4-[(E)-3-[4-[2-Hydroxyethyl(methyl)amino]phenyl]prop-2-enoyl]phenyl]undec-10-enamide; 146932022: (E)-1-Phenyl-3-[4-[3,4,5-trihydroxy-6-(hydroxymethyl)oxan-2-yl]oxyphenyl]prop-2-en-1-one; 146932052: 2-(3-Chlorophenoxy)-N-[4-[(E)-3-[4-[2-hydroxyethyl(methyl)amino]phenyl]prop-2-enoyl]phenyl]acetamide; 146946218: Propan-2-yl (2S)-2-[[[(2R,3R,4R,5S)-5-[(2,4-dioxopyrimidin-1-yl)methyl]-4-fluoro-3-hydroxy-4-methyloxolan-2-yl]methoxy-[4-[(E)-3-phenylprop-2-enoyl]phenoxy]phosphoryl]amino]propanoate; 147002266: 2-[3-Amino-4-[(E)-3-(3-hydroxyphenyl)prop-2-enoyl]phenoxy]-2-methylpropanoic acid; 147002979: Schembl22098964; 147014076: [4-[(E)-3-(2-Hydroxy-4-methoxyphenyl)-3-oxoprop-1-enyl]phenyl] acetate; 147017030: Schembl22099192; 147077786: (E)-1-[4-[(2S,5S)-4,5-Dihydroxy-6-[[(2R)-3,4,5-trihydroxy-6-methyl-3,6-dihydro-2H-pyran-2-yl]oxymethyl]oxan-2-yl]oxy-2,6-dihydroxyphenyl]-3-(3-hydroxy-4-methoxy-phenyl)prop-2-en-1-one; 147099639: 4-(1-Methylcyclohexyl)-2-[4-[(E)-3-oxo-3-phenylprop-1-enyl]phenoxy]butanoic acid; 147133641: 2-[4-[(E)-3-[4-[5-[(3S)-3-(2,4-Difluorophenyl)-3-hydroxy-5-(4H-imidazol-4-yl)pentan-2-yl]sulfanyl-1,3-dioxan-2-yl]phenyl]-3-oxoprop-1-enyl]phenyl]acetonitrile; 147147232: (E)-1-(2-Hydroxy-4-methyl-6-nitrosophenyl)-3-(4-nitrosophenyl)prop-2-en-1-one; 147164281: (E)-3-[4-[(E)-4-[3,5-Dihydroxy-4-[(E)-3-phenylprop-2-enoyl]phenoxy]but-2-en-2-yl]iodanuidyl]phenyl]-1-[2-hydroxy-4-(3-methylbut-2-enoxy)phenyl]prop-2-en-1-one; 147187926: Schembl22099007; 147189158: Schembl22099084; 147203135: (E)-1-[2-(2,2-Dihydroxyethoxy)-4-(3-methylbut-2-enoxy)phenyl]-3-[4-(3-methylbut-2-enoxy)phenyl]prop-2-en-1-one; 147246989: (E)-3-(3-Hydroxy-4-methylphenyl)-1-(2,4,6-trihydroxyphenyl)prop-2-en-1-one; 147253564: 5-(4-Fluorophenyl)-N-[4-[(E)-3-[4-[2-hydroxyethyl(methyl)amino]phenyl]prop-2-enoyl]phenyl]furan-2-carboxamide; 147254312: Propan-2-yl 2-[[[(2R,3R,4R,5R)-5-(2,4-dioxopyrimidin-1-yl)-4-fluoro-3-hydroxy-4-methyloxolan-2-yl]methoxy-[4-[(E)-3-phenylprop-2-enoyl]phenoxy]phosphoryl]amino]acetate; 147263410: (E)-3-[4-(4-Bromophenyl)phenyl]-1-(2-hydroxy-phenyl)prop-2-en-1-one; 147558435: Schembl22099485; 147583920: [4-[(E)-3-[4-[(2S,3R,4S,5S,6R)-3,5-Dihydroxy-6-(hydroxymethyl)-4-methyloxan-2-yl]oxyphenyl]prop-2-enoyl]-3-hydroxyphenyl] benzoate; 147608684: Schembl22099087; 147621804: Schembl22099196; 147624365: (E)-3-[4-[4-[(2Z)-1-Hydroxy-2-hydroxyiminohexyl]phenyl]sulfanylphenyl]-1-(2-methoxyphenyl)prop-2-en-1-one; 147648968: 4-Hexyl-N-[4-[(E)-3-[4-[2-hydroxyethyl(methyl)amino]phenyl]prop-2-enoyl]phenyl]benzamide; 147703841: (E)-1-[2-Hydroxy-4-(methoxymethyl)phenyl]-3-(4-nitrosophenyl)prop-2-en-1-one; 147704503:

Schembl22099179; 147734029: 4-[(E)-3-(4-Aminophenyl)-3-oxoprop-1-enyl]benzoic acid; 147741608: Schembl22099065; 147756964: 4-(2-Methylcyclohexyl)-2-[4-[(E)-3-phenylprop-2-enoyl]phenoxy]butanoic acid; 147773085: Schembl22099031; 147782031: (E)-1-(2,4-Dihydroxyphenyl)-3-(4-nitrosophenyl)prop-2-en-1-one; 147788154: (E)-1-[4-(1,1-Dihydroxy-2-methylpropan-2-yl)sulfanylphenyl]-3-(4-methylsulfanylphenyl)prop-2-en-1-one; 147831432: N-[4-[(E)-3-[4-[2-Hydroxyethyl(methyl)amino]phenyl]prop-2-enoyl]phenyl]-5-nitrofuran-2-carboxamide; 147843650: 4-Hexoxy-N-[4-[(E)-3-[4-[2-hydroxyethyl(methyl)amino]phenyl]prop-2-enoyl]phenyl]benzamide; 147852962: (4E,5E)-3-Chloro-4-ethylidene-5-(2-fluoroprop-2-enylidene)-N-[4-[(E)-3-[4-[2-hydroxyethyl(methyl)amino]phenyl]prop-2-enoyl]phenyl]thiophene-2-carboxamide; 147917026: N-[4-[(E)-3-[4-[2-Hydroxyethyl(methyl)amino]phenyl]prop-2-enoyl]phenyl]-2-methoxy-6-methylpyridine-4-carboxamide; 147922616: 4-[(E)-3-(4-Formylphenyl)prop-2-enoyl]benzoic acid; 147924835: 2-Fluoro-N-[4-[(E)-3-[4-[2-hydroxyethyl(methyl)amino]phenyl]prop-2-enoyl]phenyl]-3-methyl-6-(trifluoromethyl)benzamide; 148007746: N-[4-[(E)-3-[4-[2-Hydroxyethyl(methyl)amino]phenyl]prop-2-enoyl]phenyl]butanamide; 148081300: 4-Heptyl-N-[4-[(E)-3-[4-[2-hydroxyethyl(methyl)amino]phenyl]prop-2-enoyl]phenyl]benzamide; 148136488: (E)-1-[4-(Cyclopropylmethoxy)-2-hydroxyphenyl]-3-(4-hydroxyphenyl)prop-2-en-1-one; 148178174: 5-(2,5-Dichlorophenyl)-N-[4-[(E)-3-[4-[2-hydroxyethyl(methyl)amino]phenyl]prop-2-enoyl]phenyl]furan-2-carboxamide; 148186072: N-[4-[(E)-3-[4-[2-Hydroxyethyl(methyl)amino]phenyl]prop-2-enoyl]phenyl]-2-methylbenzamide; 148221582: (E)-1-(4-Hydroxyphenyl)-3-(4-nitrosophenyl)prop-2-en-1-one; 148307711: (E)-1-[4-[(2S,5S)-6-[[(2R,5R)-4,5-Dihydroxy-6-methyloxan-2-yl]oxymethyl]-3,4,5-trihydroxyoxan-2-yl]oxy-2,6-dihydroxyphenyl]-3-(3-hydroxy-4-methoxyphenyl)prop-2-en-1-one; 148338587: [3-Hydroxy-4-[(E)-3-[4-(2-morpholin-4-ylethoxy)phenyl]prop-2-enoyl]phenyl] cyclopentanecarboxylate; 148372990: (E)-3-[4-(Cyclopropylmethoxy)phenyl]-1-(2,4-dihydroxyphenyl)prop-2-en-1-one; 148377373: 4-[(E)-3-(3-Carboxyphenyl)prop-2-enoyl]benzenethiolate; 148377374: 3-[(E)-3-Oxo-3-(4-sulfanylphenyl)prop-1-enyl]benzoic acid; 148479939: (E)-1-[2,6-Dihydroxy-4-[[(1R,4S)-1-hydroxy-2-[[3,4,5-trihydroxy-2-(iodanuidyl)-2H-pyran-6-yl]oxymethyl]-3-oxabicyclo[4.1.0]heptan-4-yl]oxy]phenyl]-3-(3-hydroxy-4-methoxyphenyl)prop-2-en-1-one; 148500358: 5-(4-Chloro-3-nitro-phenyl)-N-[4-[(E)-3-[4-[2-hydroxyethyl(methyl)amino]phenyl]prop-2-enoyl]phenyl]furan-2-carboxamide; 148505382: 2-[4-[(E)-3-(2-Hydroxy-phenyl)-3-oxoprop-1-enyl]phenyl]sulfanyl-2-methylpropanamide; 148524613: 2-[[(Z)-But-2-enyl]amino]-4-[3-[4-[(2,2-dimethyl-1,3-dioxolan-4-yl)methoxy]-2-hydroxyphenyl]-3-oxoprop-1-enyl]benzaldehyde; 148703367: Schembl22099184; 148711420: 3-Hydroxy-5-methoxy-2-[(E)-3-(4-methoxyphenyl)prop-2-enoyl]phenolate; 148748339: (E)-1-(4-Hydroxyphenyl)-3-(4-propylphenyl)prop-2-en-1-one; 148777295: (E)-1-[4-(2,3-Dihydroxypropoxy)phenyl]-3-(4-methoxyphenyl)prop-2-en-1-one; 148818906: (E)-3-[4-(6-Hydroxyhexoxy)phenyl]-1-[4-(trifluoromethyl)phenyl]prop-2-en-1-one; 148819963: Schembl22099446; 148827574: 2-Chloro-N-[4-[(E)-3-[4-[2-hydroxyethyl(methyl)amino]phenyl]prop-2-enoyl]phenyl]-6-methoxypyridine-4-carboxamide; 148832330: (E)-3-(4-Hydroxy-3-nitro-phenyl)-1-(2,4,6-trihydroxyphenyl)prop-2-en-1-one; 148854673: (E)-1-[4-(4-Hydroxyazepan-1-yl)phenyl]-3-(4-hydroxyphenyl)prop-2-en-1-one; 148856248: N-[4-[(E)-3-[4-[2-Hydroxyethyl(methyl)amino]phenyl]prop-2-enoyl]phenyl]formamide; 148896062: (E)-1-(2,4-Dihydroxyphenyl)-3-[4-(3,4,5,6-tetrahydroxyoxan-2-yl)oxyphenyl]prop-2-en-1-one; 148940223: (Z)-1-[4-[[4-[(Z)-1-Hydroxy-3-phenylprop-2-enyl]phenyl]-bis(6-oxobenzo[c][2,1]benzoxaphosphinin-6-yl)methyl]phenyl]-3-phenylprop-2-en-1-one; 148945068: 4-[(Z)-3-(4-Hydroxyphenyl)prop-2-enoyl]benzoic acid; 149030372: 2,4-Dichloro-N-[4-[(E)-3-[4-[2-hydroxyethyl(methyl)amino]phenyl]prop-2-enoyl]phenyl]benzamide; 149074820: 4-Heptoxy-N-[4-[(E)-3-[4-[2-hydroxyethyl(methyl)amino]phenyl]prop-2-enoyl]phenyl]benzamide; 149107648: 2-Bromo-3,4,5,6-tetrafluoro-N-[4-[(E)-3-[4-[2-hydroxyethyl(methyl)amino]phenyl]prop-2-enoyl]phenyl]benzamide; 149137919: 2-Cyclopentyl-N-[4-[(E)-3-[4-[hydroxymethyl-iodanuidyl(methyl)amino]phenyl]prop-2-enoyl]phenyl]acetamide; 149138199: (E)-3-[4-(2-Cyclopentylcyclopentyl)-3-methoxyphenyl]-1-(2-hydroxy-4,6-dimethoxyphenyl)prop-2-en-1-one; 149152888: (E)-1-(2-Amino-6-hydroxy-4-nitrosophenyl)-3-(4-hydroxyphenyl)prop-2-en-1-one; 149164836: 2-[3-Amino-4-[(E)-3-(4-hydroxyphenyl)prop-2-enoyl]phenoxy]-2-methylpropanoic acid; 149346946: Schembl22099465; 149376954: [4-[(E)-3-(4-Hydroxyphenyl)-3-oxoprop-1-enyl]phenyl] acetate; 149402787: (E)-3-(2-Chlorocyclohexen-1-yl)-1-[4-[[2-hydroxy-4-[(E)-3-(4-methoxyphenyl)-3-oxoprop-1-enyl]phenyl]methoxy]phenyl]prop-2-en-1-one; 149410140: Schembl22099097; 149412021: (E)-1-(2,4-Dihydroxyphenyl)-3-[4-[2-(1-hydroxycyclopropyl)propan-2-ylsulfanyl]phenyl]prop-2-en-1-one; 149493092: Schembl22099427; 149532018: 2-(4-Chlorophenyl)-N-[4-[(E)-3-[4-[2-hydroxyethyl(methyl)amino]phenyl]prop-2-enoyl]phenyl]acetamide; 149587711: Schembl22099397; 149625951: 3-(2,3-Dicarboxyphenyl)-6-[6-[4-[3-(4-fluorophenyl)-3-oxoprop-1-enyl]phenoxy]hexoxy]phthalic acid; 149648668: 1-[4-(4-Hydroxyphenyl)phenyl]-3-phenylprop-2-en-1-one; 149720512: 3-[4-[2-[[4-(4-Hydroxybutoxy)phenyl]methyl]-1H-inden-1-yl]phenyl]-1-phenylprop-2-en-1-one; 149742001: 1-(2-Hydroxyphenyl)-3-[3-methoxy-4-(3-methylbutoxy)phenyl]prop-2-en-1-one; 149765466: 1-(2-Hydroxy-4,6-dimethoxyphenyl)-3-[4-[(2-methylpropan-2-yl)oxy]phenyl]prop-2-en-1-one; 149766514: 1-[4-[2-[[4-(6-Hydroxyhexoxy)phenyl]methyl]-1H-inden-1-yl]phenyl]-3-phenylprop-2-en-1-one; 149792104: [3,5-Dihydroxy-4-[3-(4-hydroxyphenyl)prop-2-enoyl]phenyl] phosphate; 149792105: [3,5-Dihydroxy-4-[3-(4-hydroxyphenyl)prop-2-enoyl]phenyl] dihydrogen phosphate; 149850466: 1-(2-Hydroxy-6-methylphenyl)-3-(4-methylphenyl)prop-2-en-1-one; 149872918: 2-[2-[3-[4-(3-Methylbut-2-enoxy)phenyl]prop-2-enoyl]phenyl]acetic acid; 149884737: 3-(4-Ethylphenyl)-1-(2-hydroxyphenyl)prop-2-en-1-one; 149884738: (E)-3-(4-Ethylphenyl)-1-(2-hydroxyphenyl)prop-2-en-1-one; 149931673: 3-[4-(4-Hydroxyoctoxy)phenyl]-1-phenylprop-2-en-1-one; 149936021: 1-(2-Amino-6-hydroxyphenyl)-3-(3-methyl-4-pentylphenyl)prop-2-en-1-one; 149985125: 1-[4-(Azidomethyl)phenyl]-3-(4-hydroxyphenyl) prop-2-en-1-one; 149995296: 2-[4-[3-(2-Chloro-4-ethylphenyl)-3-oxoprop-1-enyl]phenoxy]acetic acid; 150025861: 3-(4-Butylphenyl)-1-(2-hydroxyphenyl) prop-2-en-1-one; 150038066: 1-(4-Azido-2-methylphenyl)-3-(4-hydroxy-3-methylphenyl)prop-2-en-1-one; 150086860: 4-[(E)-3-[2-Hydroxy-6-[[4-(trifluoromethoxy)phenyl]methoxy]phenyl]-3-oxoprop-1-enyl]benzoic acid; 150090782: 3-(2,3-Dicarboxyphenyl)-6-[4-[4-(3-oxo-3-phenylprop-1-enyl)phenoxy]phthalic acid; 150119713: 1-(2-Hydroxyphenyl)-3-(4-propylphenyl) prop-2-en-1-one; 150207749: 3-[4-(4-Hydroxycyclohexyl)phenyl]-1-phenylprop-2-en-1-one; 150334510: 2-[4-[3-(2-Bromo-4-propan-2-yloxyphenyl)-3-oxoprop-1-enyl]phenoxy]acetic acid; 150334954: 1-[4-(9H-Fluoren-1-yl)phenyl]-3-(4-hydroxyphenyl)prop-2-en-1-one; 150342573: (E)-3-(4-Chlorophenyl)-1-[2-hydroxy-6-[[4-(trifluoromethoxy)phenyl]methoxy]phenyl]prop-2-en-1-one; 150367264: 3-[4-[[4-(3,5-Dihydroxyphenoxy)phenyl]methoxy]phenyl]-1-phenylprop-2-en-1-one; 150440079: 2-Azido-2-[4-[3-(4-fluorophenyl)-3-oxoprop-1-enyl]phenyl]acetic acid; 150608317: 1-(4-Fluorophenyl)-3-[4-(1-hydroxyoctoxy)phenyl]prop-2-en-1-one; 150682372: N-[4-[(E)-3-[2-Hydroxy-6-[[4-(trifluoromethoxy)phenyl]methoxy]phenyl]-3-oxoprop-1-enyl]phenyl]acetamide; 150738335: 3-(2,3-Dicarboxyphenyl)-6-hexoxy-4-[4-(3-oxo-3-phenylprop-1-enyl)phenoxy]phthalic acid; 150810261: 3-(4-Chloro-3-hydroxyphenyl)-1-phenylprop-2-en-1-one; 150848169: 3-[4-(Dimethylamino)-3-hydroxyphenyl]-1-[2-(3-fluorophenyl)phenyl]prop-2-en-1-one; 150959328: 4-(3,4-Dicarboxyphenyl)-5-[6-[4-(3-oxo-3-phenylprop-1-enyl)phenoxy]hexoxy]phthalic acid; 151017372: 3-[4-(1-Hydroxypropoxy)phenyl]-1-phenylprop-2-en-1-one; 151026921: (E)-3-(4-Ethylphenyl)-1-[2-hydroxy-6-[[4-(trifluoromethoxy)phenyl]methoxy]phenyl]prop-2-en-1-one; 151027559: 4-(3,4-Dicarboxyphenyl)-5-[4-[4-(3-oxo-3-phenylprop-1-enyl)phenyl]phenoxy]phthalic acid; 151061758: 4-(3,4-Dicarboxyphenyl)-5-[6-[4-[3-(4-fluorophenyl)-3-oxoprop-1-enyl]phenoxy]hexoxy]phthalic acid; 151077564: (E)-1-(2,4-Dihydroxyphenyl)-3-(4-phenylphenyl)prop-2-en-1-one; 151090864: 4-(3,4-Dicarboxyphenyl)-3-[6-[4-[3-(4-fluorophenyl)-3-oxoprop-1-enyl]phenoxy]hexoxy]phthalic acid; 151136229: 3-[4-(1-Hydroxyoctoxy)phenyl]-1-phenylprop-2-en-1-one; 151141215: 2-Methoxy-4-[3-(2-methoxyphenyl)-3-oxoprop-1-enyl]benzoic acid; 151169204: N-[3-(Aminomethyl)-4-[(E)-3-(4-hydroxy-3-methylphenyl)prop-2-enoyl]phenyl]acetamide; 151179261: 5-[4-[[4-(3-Oxo-3-phenylprop-1-enyl)phenoxy]methyl]phenoxy]benzene-1,3-dicarboxylic acid; 151253385: (E)-3-[4-[(E)-3-(2-Azidophenyl)-3-oxoprop-1-enyl]phenyl]prop-2-enoic acid; 151257163: (Z)-2-[4-[8-[4-(3-Oxo-3-phenylprop-1-enyl)phenoxy]octoxy]phenyl]but-2-enedioic acid; 151275664: 3-Hydroxy-2-(3-phenylprop-2-enoyl)benzoyl azide; 151312891: 1-[4-(1-Hydroxypropoxy)phenyl]-3-phenylprop-2-en-1-one; 151341284: 1-(4-Fluorophenyl)-3-[4-(1-hydroxyhexoxy)phenyl]prop-2-en-1-one; 151367495: 2-Hydroxy-4-(3-oxo-3-phenylprop-1-enyl)benzoic acid; 151418796: (E)-1-[2-Hydroxy-6-[[4-(trifluoromethoxy)phenyl]methoxy]phenyl]-3-(4-methoxyphenyl)prop-2-en-1-one; 151431259: 4-[3-Amino-2-[3-(4-cyclohexylphenyl)prop-2-enoyl]phenyl]sulfanylbutanoic acid; 151439285: (E)-3-[4-[(E)-3-(4-Azidophenyl)-3-oxoprop-1-enyl]phenyl]prop-2-enoic acid; 151517670: 1-(4-Hydroperoxy-2-hydroxy-6-phenylmethoxyphenyl)-3-phenylprop-2-en-1-one; 151564097: 1-(2-Hydroxyphenyl)-3-(4-propoxyphenyl)prop-2-en-1-one; 151601448: 1-[4-(1-Hydroxy-butoxy)phenyl]-3-phenylprop-2-en-1-one; 151622408: 2-[2-[3-(4-Nitrophenyl)prop-2-enoyl]phenoxy]acetic acid; 151696736: 2-(4-Ethenylphenyl)-2-[4-[3-(4-fluorophenyl)-3-oxoprop-1-enyl]phenyl]acetic acid; 151720917: 3-(4-Azidophenyl)-1-(2-hydroxyphenyl)prop-2-en-1-one; 151727120: 4-(3,4-Dicarboxyphenyl)-3-[4-(3-oxo-3-phenylprop-1-enyl)phenoxy]phthalic acid; 151757492: 1-[4-(1-Hydroxyhexoxy)phenyl]-3-phenylprop-2-en-1-one; 151772949: 3-(2,3-Dicarboxyphenyl)-6-[4-(3-oxo-3-phenylprop-1-enyl)phenoxy]phthalic acid; 151821781: 4-(3,4-Dicarboxyphenyl)-3-[6-[4-(3-oxo-3-phenylprop-1-enyl)phenoxy]hexoxy]phthalic acid; 151825758: 1-[4-(4-Hydroxycyclohexyl)phenyl]-3-phenylprop-2-en-1-one; 151849519: 1-(2-Azido-6-hydroxy-4-methylphenyl)-3-(1-benzofuran-5-yl)prop-2-en-1-one; 151854329: 3-(2,3-Dicarboxyphenyl)-6-[6-[4-(3-oxo-3-phenylprop-1-enyl)phenoxy]hexoxy]phthalic acid; 151860725: 4-[3-[4-(1-Adamantyl)phenyl]-3-oxoprop-1-enyl]benzoic acid; 151873539: 3-[4-[[4-(3-Hydroxypropoxy)phenyl]-phenylmethyl]phenyl]-1-phenylprop-2-en-1-one; 152069227: 3-[4-(2-Hydroxypropoxy)phenyl]-1-phenylprop-2-en-1-one; 152069379: 3-(4-Azidooxy-3-methylphenyl)-1-(4-hydroxyphenyl)prop-2-en-1-one; 152105784: 1-(4-Fluorophenyl)-3-[4-(8-hydroxyoctoxy)phenyl]prop-2-en-1-one; 152142966: 2-[2-[3-(4-Bromophenyl)prop-2-enoyl]-3-hydroxyphenoxy]-1H-indole-3-carboxylic acid; 152151029: N-Azido-4-[3-(2-hydroxyphenyl)-3-oxoprop-1-enyl]benzamide; 152162472: 1-[2-(Hydroxymethoxy)phenyl]-3-phenylprop-2-en-1-one; 152199234: (E)-3-(4-Chlorophenyl)-1-(2-hydroxy-6-phenylmethoxyphenyl)prop-2-en-1-one; 152199630: [4-[3-(4-Hydroxy-phenyl)prop-2-enoyl]phenyl] nitrate; 152225250: 3-(4-Fluorophenyl)-1-[4-(1-hydroxyoctoxy)phenyl]prop-2-en-1-one; 152270533: 3-(4-Fluorophenyl)-1-[4-(1-hydroxybutoxy)phenyl]prop-2-en-1-one; 152314187: (E)-1-(2-Hydroxy-6-phenylmethoxyphenyl)-3-(4-methoxy-phenyl)prop-2-en-1-one; 152358080: [3-Hydroxy-4-(3-phenylprop-2-enoyl)phenyl]benzoate; 152361179: (E)-3-(4-Ethylphenyl)-1-(2-hydroxy-6-phenylmethoxyphenyl)prop-2-en-1-one; 152369199: 3-[4-[[4-(Hydroxymethoxy)phenyl]-phenylmethyl]phenyl]-1-phenylprop-2-en-1-one; 152376461: 3-[4-(1-Hydroxyhexoxy)phenyl]-1-phenylprop-2-en-1-one; 152385827: (E)-1-(2-Hydroxy-4,6-dimethoxyphenyl)-3-[3-(trifluoromethyl)phenyl]prop-2-en-1-one; 152430818: 1-[4-(2-Hydroxypropoxy)phenyl]-3-phenylprop-2-en-1-one; 152452891: 4-(3,4-Dicarboxyphenyl)-5-[4-(3-oxo-3-phenylprop-1-enyl)phenoxy]phthalic acid; 152470376: 3-[4-[[4-(2-Hydroxyethoxy)phenyl]-phenylmethyl]phenyl]-1-phenylprop-2-en-1-one; 152552653: 4-[3-Amino-2-[3-(4-propan-2-ylphenyl)prop-2-enoyl]phenyl]sulfanylbutanoic acid; 152634930: 4-(3,4-Dicarboxyphenyl)-3-[4-[4-(3-oxo-3-phenylprop-1-enyl)phenyl]phenoxy]phthalic acid; 152638354: 4-[(E)-3-[2-(Cyclohexylmethoxy)phenyl]-3-oxoprop-1-enyl]benzoic acid; 152645185: 2-[4-[3-(4-Chlorophenyl)prop-2-enoyl]-3-methoxy-phenyl]acetic acid; 152649735: 2-Azido-2-[4-(3-oxo-3-phenylprop-1-enyl)phenyl]acetic acid; 152745196:OC(=O)Coc1=CC(OC=CC(=C)C)=CC=C1C(=O)C=CC1=CC=C(occ(=O)C=C 1; 152745197: C1=C(Occ(O)=O)C(OC)=CC(C=CC(=O)C=2C(=CC(OC=CC(C)=C)=CC=2)occ(O)=O)=C1; 152747053:OC(=O)Coc1=CC(OC=CC(=C)C)=CC=C1C(=O)C=CC1=CC=CC(C(O)=O)=C1; 152747054:OC(=O)Coc1=CC(OC=CC(=C)C)=CC=C1C(=O)C=CC1=CC=C(C(O)=O)C=C1; 152781556: C1=C(O)C(OC)=CC(C=CC(=O)C=2C(=CC=CC=2)CC2C(NC(=O)S2)=O)=C1; 152846263: 2-[4-[(E)-3-(2-Amino-4-hydroxyphenyl)-3-oxoprop-1-enyl]phenoxy]-2-methylpropanoic acid; 152879028: (E)-3-(4-Chloro-3-phenylphenyl)-1-[4-[(2R)-2-hydroxypropyl]sulfonylphenyl]prop-2-en-1-one; 152886041: (E)-3-[4-[2-[3-(Hydroxymethyl) buta-1,3-dien-2-yloxy]ethoxy]phenyl]-1-[4-[2-(3-methylbut-1-en-2-yloxy)ethoxy]phenyl]prop-2-en-1-one; 152902528: (E)-1-(2-Hydroxy-4-methoxyphenyl)-3-[4-[(2S,3S,4S,6R)-3,4,5-trihydroxy-6-(hydroxymethyl)oxan-2-yl]oxyphenyl]prop-2-en-1-one; 152913097: (E)-1-[4-[(2S,5S)-6-[[(2R,5R)-4,5-Dihydroxy-6-methyloxan-2-yl]oxymethyl]-4,5-dihydroxyoxan-2-yl]oxy-2,6-dihydroxyphenyl]-3-(3-hydroxy-4-methoxyphenyl)prop-2-en-1-one; 152916824: 4-[(E)-3-(2-Hydroxy-4,6- dimethoxyphenyl)-3-oxoprop-1-enyl]benzaldehyde; 152918013: (E)-3-[3-(Aziridin-1-yl)phenyl]-1-(2-hydroxyphenyl)prop-2-en-1-one; 152972410: Schembl22099054; 153022082: Schembl22099450; 153076249: 4-[(E)-3-[4-[(E)-(2-Methylidenecyclopropylidene)methyl]phenyl]-3-oxoprop-1-enyl]benzoic acid; 153116067: 8-[5-[3-(2,4-Dihydroxyphenyl)-3-oxoprop-1-enyl]-2-hydroxyphenyl]-5,7-dihydroxy-2-(4-hydroxyphenyl)chromen-4-one; 153259545: (E)-1-[4-[(2S,5S)-4,5-Dihydroxy-6-[[(2R)-4-hydroxy-4-(hydroxymethyl)-6-methyloxan-2-yl]methoxymethyl]oxan-2-yl]oxy-2,6-dihydroxyphenyl]-3-(3-hydroxy-4-methoxyphenyl)prop-2-en-1-one; 153499774: (E)-3-(4-Hydroxy-3-methoxyphenyl)-1-(4-isocyanophenyl)prop-2-en-1-one; 153504889: Schembl22107849; 153505278: Schembl22099479; 153505282: Schembl22099378; 153505291: Schembl22099102; 153505297: Schembl22099398; 153505299: Schembl22099193; 153505301: Schembl22099403; 153505309: Schembl22099194; 153505310: Schembl22099092; 153505319: Schembl22099402; 153505322: Schembl22099426; 153505339: Schembl22099434; 153505345: Schembl22099187; 153505361: Schembl22099056; 153505363: Schembl22099492; 153505365: Schembl22099466; 153505370: Schembl22099413; 153505371: Schembl22099472; 153505372: Schembl22099191; 153505373: Schembl22099462; 153505375: Schembl22099410; 153505393: Schembl22099451; 153505394: Schembl22099391; 153505396: Schembl22098946; 153505397: Schembl22099101; 153505407: Schembl22099008; 153505417: Schembl22099438; 153505425: Schembl22099399; 153505430: Schembl22099457; 153505435: Schembl22099481; 153505455: Schembl22099478; 153505463: Schembl22098984; 153505465: Schembl22099459; 153505481: Schembl22099453; 153505494: Schembl22099197; 153505497: Schembl22099396; 153505503: Schembl22099424; 153505504: Schembl22098966; 153505508: Schembl22099188; 153505512: Schembl22099411; 153505513: Schembl22098991; 153505515: Schembl22099189; 153505518: Schembl22099425; 153505549: Schembl22098982; 153505553: Schembl22099409; 153505557: Schembl22099433; 153505560: Schembl22099183; 153505561: Schembl22099474; 153505579: Schembl22099199; 153505582: Schembl22099178; 153505583: Schembl22099430; 153505586: Schembl22099198; 153505588: Schembl22099174; 153505594: Schembl22099010; 153505596: Schembl22099412; 153505597: Schembl22099489; 153505606: Schembl22099182; 153505609: Schembl22098958; 153505613: Schembl22098909; 153505626: Schembl22099483; 153505631: Schembl22099195; 153505634: Schembl22098999; 153505635: Schembl22099437; 153505639: Schembl22099108; 153505641: Schembl22099486; 153505642: Schembl22099420; 153505649: Schembl22099458; 153505653: Schembl22099448; 153505655: Schembl22099032; 153505661: Schembl22099416; 153505665: Schembl22098983; 153505669: Schembl22099028; 153505670: Schembl22099435; 153505672: Schembl22099094; 153505673: Schembl22099190; 153505677: Schembl22099015; 153505696: Schembl22099405; 153505703: Schembl22099083; 153505704: Schembl22099491; 153505709: Schembl22099180; 153505713: Schembl22099439; 153505717: Schembl22099210; 153522609: (E)-1-[2-(2-Aminoethyl)phenyl]-3-(4-hydroxy-3-methoxyphenyl)prop-2-en-1-one; 153522610: (E)-1-[4-(2-Aminoethyl)phenyl]-3-(4-hydroxy-3-methoxyphenyl)prop-2-en-1-one; 153606272: [4-[(E)-3-(4-Hydroxyphenyl)prop-2-enoyl]phenyl] 2-methylprop-2-enoate; 153606276: Schembl22090364; 153802661: C1(=CC=C(C=C1)OC(=O)NC(C(=O)O)C1=CC=CC=C1)C=CC(=O)C1=CC=CC=C1; 153824944: ClC=1C=C(OCC(=O)O)C=CC=1C(C=CC1=CC=C(C=C1)CCC)=O; 153848748: ClC(C(=O)O)OC1=CC=C(C=C1)C(C=CC1=CC=CC=C1)=O; 153859010: 3-[4-[(Z)-3-Oxo-3-phenylprop-1-enyl]phenyl]prop-2-enoic acid; 153905845: C1(=CC(=CC=C1)/C=C/C(=O)C1=C(C(=O)O)C=C(C=C1N)Cl)C1=CC=CC=C1; 153936465: FC=1C(=C(C=CC=1)C1=CC=CC=C1)C(\C=C\C1=CC(=CC=C1)O)=O; 153979935: NC1=CC=C(C(C=CC2=CC=C(C=C2)C(=O)O)=O)C=C1; 154059752: Cc1cc(C=CC(=O)c2ccc(O)cc2)ccc1OC(C)C([O-])=O; 154060913: Oc1cccc(OCc2ccccc2)c1C(=O)C=Cc1ccc(OCc2ccccc2)cc1; 154069104: COc1ccc(CN2CCN(CC2)c2ccc(cc2)C(=O)C=C/c2ccc(OCc3cn(CC(O)(Cn4cncn4)c4ccc(F)c c4F)nn3)cc2)cc1; 154102669: OC1=C(C=C(C=1)C=CC(=O)C1=CC=C(C=C1)Occ=C(C)C)C=C=C(C)C; 154107255: OC1=C(C=CC2=CC=C(C=C2)O)CC=C(C)C)=O)C=CC(=C1)Occ=C(C)C; 154157919: OC1=C(C=CC2=CC=C(C=C2)OCC2=CC=C(C=C2)=O)C=CC(=C1)Cl; 154159872: OC1=C(C(C=CC2=CC=C(C=C2)OC)CC=C(C)C)=O)C=CC(=C1)Occ=C(C)C; 154160970: ClC=1C=C(OCC(=O)O)C=CC1C(C=CC1=CC=CC=C1)=O; 154176545: OC1=C(C(C=CC2=CC=C(C=C2)Occ2=CC=CC=C2)=O)C=CC(=C1)C; 154183216: OC1=C(C(C=CC2=CC=C(C=C2)OC)=O)C(C=CC=C1)Occ1=CC=CC=C1; 154210262: OC1=C(C(C=CC2=CC=C(C=C2)Occ2=CC=CC=C2)=O)C=CC(=C1)OC; 154216482: 5-(2,4-Diaminophenyl)-6-oxo-6-[4-(3-oxo-3-phenylprop-1-enyl)phenoxy]hexanoic acid; 154220780: OC1=CC=C(C(=O)C2=CC=C(C(C=CC3=CC=CC=C3)=O)C=C2)C=C1; 154233148: OC1=C(C(C=CC2=CC=C(C=C2)Occ2=CC=CC=C2)=O)C=CC(=C1)F; 154233650: Ococ1=CC=C(C(=O)C2=CC=C(C(C=CC3=CC=CC=C3)=O)C=C2)C=C1; 154239410: ClC=1C=C(OCC(=O)O)C=CC1C(C=CC1=CC=C(C=C1)Cl)=O; 154246977: C(C)N(C1=CC=C2C=C(C(OC2=C1)=O)C1=CC=C(C=C1)C=CC(=O)C1=C(C=CC=C1)O)C C; 154247977: C(C)C1=CC=C(C=C1)C(=O)C=CC1=CC=C(Occ(=O)O)C=C1; 154249021: OC1=C(C(C=CC2=CC=C(C=C2)Occ2=CC=CC=C2)=O)C=CC(=C1)OC; 154274158: C(=O)(O)Coc1=C(C(C=CC2=CC=C(C=C2)cccc=C)=O)C=CC(=C1)occ=C(C)C; 154281328: 4-[(E)-3-(4-Methylsulfanylphenyl)prop-2-enoyl]benzoic acid; 154296606: C1(=CC=C(C=C1)/C=C/C(=O)C1=C(C(=O)O)C=C(C=C1N)Cl)C1=CC=CC=C1; 154321200: 01C(=CC=C1)C=1C=C(C=CC1)C=CC(=O)C1=C(C=C(C=C1OC)OC)O; 154335615: OC1=C(C(C=CC2=CC=C(C=C2)O)CC=C(C)C)=O)C(=CC=C1)OCC=C(C)C; 154341007: OC1=CC=C(C(=O)C2=CC=C(C=C2)C=CC(=O)C2=CC=CC=C2)C=C1; 154354946: 9-(2,4-Diaminophenyl)-10-oxo-10-[4-(3-oxo-3-phenylprop-1-enyl)phenoxy]decanoic acid; 154370423: C(C)OC(=O)C=CC1=CC=C(C=C1)C=CC(=O)C1=CC=C(C=C1)Occo; 154371747: C(C)N(CC)Ccoc1=CC=C(C=C/C(=O)C2=CC=C(C=C2)O)C=C1; 154374030: Ococ1=CC=C(C(=O)C2=CC=C (C=C₂)C=CC(=O)C₂=CC=CC=C₂)C=C1; 154382441: 7-(2,4-Diaminophenyl)-8-oxo-8-[4-(3-oxo-3-phenylprop-1-enyl)phenoxy]octanoic acid; 154410272: C(C=Cccc)OC1=CC(=C(C=C1)C(C=CC1=CC=C(C=C1)C(=O)O)=O)occ(=O)O; 154410273: C(C=CC)OC1=CC(=C(C=C1)C(C=CC1=CC=C(C=C1)C(=O)O)=O)Occ(=O)O; 154441977: (E)-1-[2,6-Dihydroxy-4-[(2S,5S)-3,4,5-trihydroxy-6-[[(2R,5R)-3,4,5-trihydroxy-6-methyloxan-2-yl]oxymethyl]oxan-2-yl]oxyphenyl]-3-(3-hydroxy-4-methoxyphenyl)prop-2-en-1-one; 154496376: (E)-3-(3,4-Dihydroxyphenyl)-1-[2-hydroxy-4-[(2S,3S,4S,5S,6S)-3,4,5-trihydroxy-6-(hydroxymethyl)oxan-2-yl]oxyphenyl]prop-2-en-1-one; 154496797: (E)-1-[2,4-Dihydroxy-6-[(2S,3S,4S,5S,6R)-3,4,5-trihydroxy-6-(hydroxymethyl)oxan-2-yl]oxyphenyl]-3-(4-hydroxyphenyl)prop-2-en-1-one; 154508922: 3-[2,3-Dicarboxy-4-[4-[4-(3-oxo-3-phenylprop-1-enyl)phenyl]phenoxy]phenyl]-6-[4-[4-(3-oxo-3-phenylprop-1-enyl)phenyl]phenoxy]phthalic acid; 154508934: 5-(2,4-Diaminophenyl)-6-[4-[3-(4-fluorophenyl)-3-oxoprop-1-enyl]phenoxy]-6-oxohexanoic acid; 154508936: 7-(2,4-Diaminophenyl)-8-[4-[3-(4-fluorophenyl)-3-oxoprop-1-enyl]phenoxy]-8-oxooctanoic acid; 154508938: 9-(2,4-Diaminophenyl)-10-[4-[3-(4-fluorophenyl)-3-oxoprop-1-enyl]phenoxy]-10-oxodecanoic acid; 154525706: (Z)-1,3-Bis(4-hydroxyphenyl)prop-2-en-1-one; 154527335: 4-[(E)-3-Oxo-3-[4-[4-[(E)-3-oxobut-1-enyl]benzoyl]phenyl]prop-1-enyl]benzoic acid; 154678309: (E)-3-[3-[[(2S,5S)-4-(2-Hydroxypropan-2-yloxy)-5-[(6-methylpurin-9-yl)methyl]oxolan-2-yl]methoxy]-4-(1-methoxyethenyl)phenyl]-1-[2-(1-phenylmethoxyethenyl)phenyl]prop-2-en-1-one; 154678315: Schembl22343727; 154678322: Schembl22343668; 154678332: 2-[(E)-3-[4-Amino-3-[[(2S,4R,5R)-5-(6-aminopurin-9-yl)-4-hydroxyoxolan-2-yl]methoxy]phenyl]prop-2-enoyl]benzoic acid; 154678350: Schembl22343604; 154678363: Schembl22343544; 154699691: (2S,3S,4S,5R,6S)-3,4,5-Trihydroxy-6-[2-[(E)-3-phenylprop-2-enoyl]phenoxy]oxane-2-carboxylic acid; 154699800: (2S,3S,4S,5R,6S)-3,4,5-Trihydroxy-6-[4-[(E)-3-phenylprop-2-enoyl]phenoxy]oxane-2-carboxylic acid; 154699814: (2S,3S,4S,5R,6S)-3,4,5-Trihydroxy-6-[4-[(E)-3-oxo-3-phenylprop-1-enyl]phenoxy]oxane-2-carboxylic acid; 154710928: (E)-1-(2-Hydroxyphenyl)-3-[4-(phenoxymethyl)phenyl]prop-2-en-1-one; 154730833: Lophirachalcone; 154831693: (E)-3-(3-Hydroxy-4-methoxyphenyl)-1-[2-hydroxy-6-methoxy-4-[(2R,3S,4R,5R,6S)-3,4,5-trihydroxy-6-[[(2S,3S,4S,5S,6R)-3,4,5-trihydroxy-6-methyloxan-2-yl]oxymethyl]oxan-2-yl]oxyphenyl]prop-2-en-1-one; 154931562: Schembl22099006; 154931568: Schembl22099082; 155018381: Schembl22273858; 155046962: Schembl22323623; 155046963: Schembl22323624; 155058758: Schembl22343605; 155058820: Schembl22343702; 155143226: Schembl22465738; 155290122: 2,2-Dichloro-N-((1R,2R)-1,3-dihydroxy-1-(4-(3-phenylacryloyl)phenyl)propan-2-yl)acetamide; 155332050: Schembl22704488; 155332063: Schembl22704501; 155332306: Schembl22704791; 155332507: Schembl22705020; 155488757: Sofalcone-CoA; (Acyl-CoA); [M+H]+; 155510534: Chembl4543178; 155510755: Chembl4434713; 155510974: Chembl4435309; 155511824: Chembl4436420; 155512624: Chembl4437622; 155515176: Chembl4441267; 155515670: Chembl4441838; 155516433: Chembl4443141; 155516490: Chembl4443841; 155517333: Chembl4444748; 155517788: Chembl4445762; 155517977: Chembl4445280; 155518426: Chembl4446815; 155519920: Chembl4448344; 155520070: Chembl4524387; 155520833: Chembl4449688; 155521464: Chembl4450171; 155522174: Chembl4451613; 155522930: Chembl4453455; 155523992: Chembl4454906; 155525182: Chembl4456071; 155525316: Chembl4456222; 155525409: Chembl4457806; 155525799: Chembl4457588; 155527534: Chembl4459528; 155527687: Chembl4460121; 155528707: Chembl4461443; 155528915: Chembl4461873; 155529078: Chembl4462394; 155530670: Chembl4464702; 155530862: Chembl4465191; 155531484: Chembl4466366; 155531521: Chembl4466019; 155531903: Chembl4466811; 155533958: Chembl4469398; 155534584: Chembl4470548; 155536289: Chembl4473200; 155536307: Chembl4473461; 155537289: Chembl4474824; 155537768: Chembl4475829; 155538194: Chembl4476091; 155538460: Chembl4476518; 155538683: Chembl4476735; 155541094: Chembl4517746; 155542211: Chembl4520508; 155542470: Chembl4520772; 155542903: Chembl4522036; 155543722: Chembl4522874; 155544824: Chembl4567417; 155545633: Chembl4529531; 155547171: Chembl4534640; 155548523: Chembl4537240; 155549176: Chembl4538762; 155549201: Chembl4538061; 155550156: Chembl4540199; 155552206: Chembl4546568; 155553953: Chembl4582024; 155554859: Chembl4550996; 155555673: Chembl4552080; 155556670: Chembl4556096; 155556909: Chembl4555992; 155560171: Chembl4565177; 155562436: Chembl4571871; 155563112: Chembl4573295; 155563922: Chembl4574317; 155564123: Chembl4575664; 155564266: Chembl4575971; 155564886: Chembl4578704; 155565612: Chembl4579723; 155566202: Chembl4583837; 155567163: Chembl4586077; 155567296: Chembl4588851; 155568569: Chembl4591934; 155691395: (E)-1-(2-Hydroxy-4-pentadecylphenyl)-3-phenylprop-2-en-1-one; 155725233: Ethane;(E)-1-(4-ethoxy-2-hydroxyphenyl)-3-(4-methylphenyl)prop-2-en-1-one;propan-2-ol; 155803493: 4-(3-(9-Ethyl-9h-carbazol-3-yl)acryloyl)benzoic acid; 155806629: [4-[(E)-3-(3-Hydroxy-4-methoxyphenyl) prop-2-enoyl]phenyl]boronic acid; 155810784: N-[4-(Dimethylamino)phenyl]-2-[4-[(E)-3-(2-hydroxyphenyl)-3-oxoprop-1-enyl]phenyl]acetamide; 155810992: (E)-1-[4-[[4,6-Bis(2-hydroxyethylamino)-1,3,5-triazin-2-yl]amino]phenyl]-3-[4-(trifluoromethyl)phenyl]prop-2-en-1-one; 155812175: 2-[4-[(E)-3-(2-Hydroxyphenyl)-3-oxoprop-1-enyl]phenyl]-N-phenylacetamide; 155814882: 2-[4-[(E)-3-(2-Hydroxyphenyl)-3-oxoprop-1-enyl]phenyl]-N-naphthalen-1-ylacetamide; 155816396: (E)-1-[4-[[4,6-Bis(2-hydroxyethylamino)-1,3,5-triazin-2-yl]amino]phenyl]-3-(4-fluorophenyl)prop-2-en-1-one; 155885851: (2E)-Dehydro Propafenone-[d5] Hydrochloride.

Figure 5:
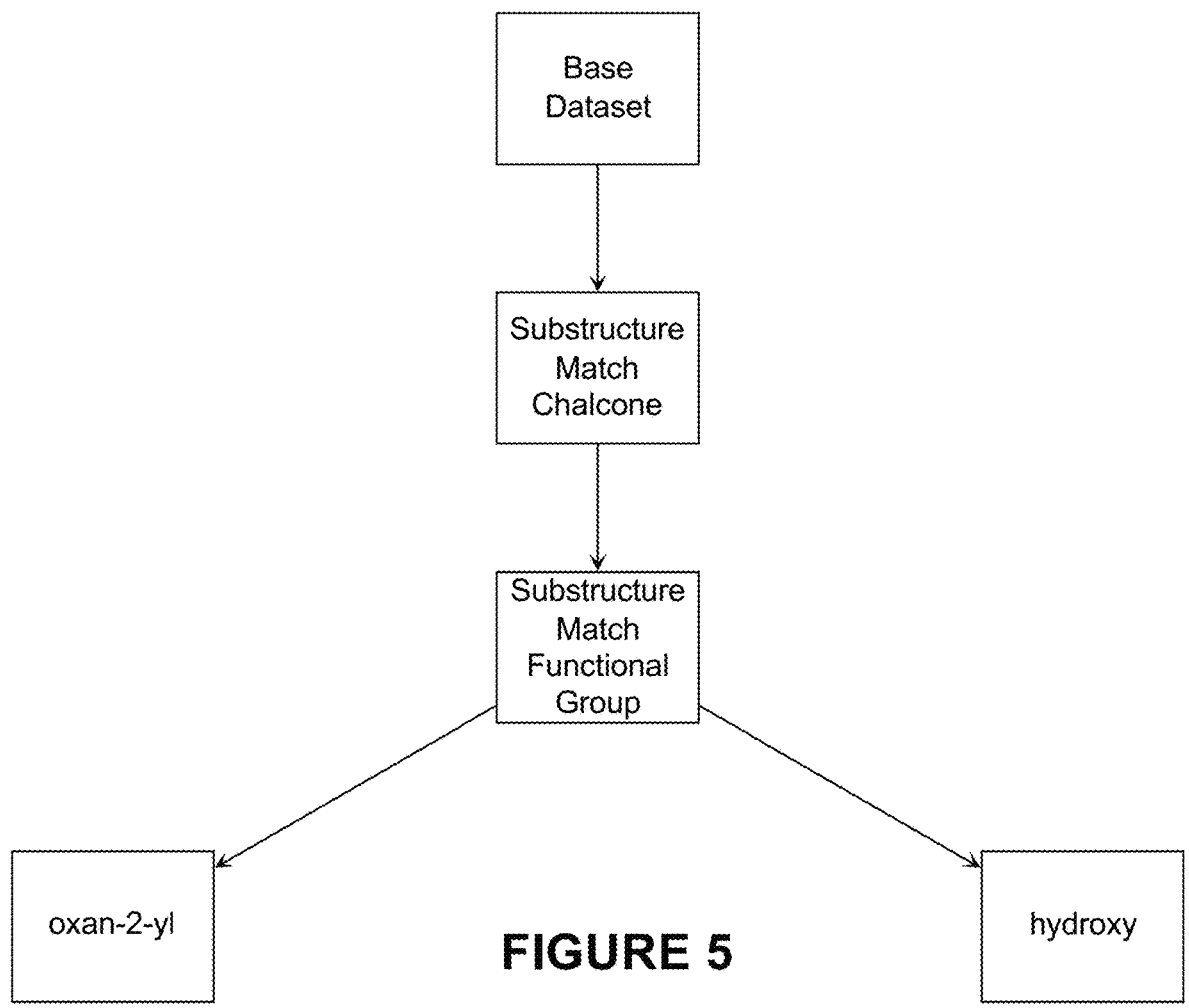
FIG. 5 illustrates pseudocode for searching for and identifying chalcones having a chalcone substructure in a chemical database in accordance with various embodiments of the invention.

Additional examples of compounds of the invention may be found by using substructure matching. The base dataset is formed from various databases such as SciFinder® and PubChem by searching for compounds with the chalcone SMARTS filter "[CD2H1](=[CD2H1]-[cH0]: 1:[cH1]:[cH1]:[cH1]:[cH1]1)-[CD3H0](=[OX1-0])-[cH0]: 2:[cH0](-[OD1H1]):[cH1]:[cH1]:[cH1]:[cH1]2". Then, the compounds with functional groups matching the SMARTS Filter "*~[#6][OH1]" and C1CCOC=,:C1" are extracted from this base dataset. Representative pseudocode for finding some compounds of the invention using substructure matching is illustrated in FIG. 5.

Figure 2N:
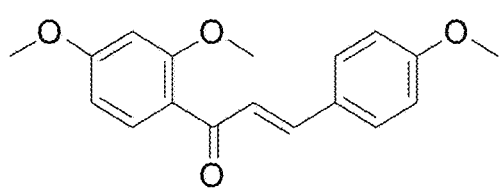
Figure 2Q:
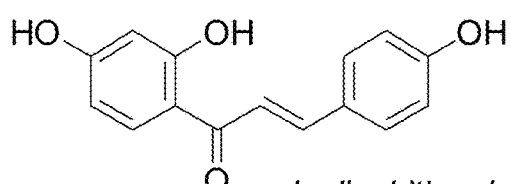
Figure 2P:
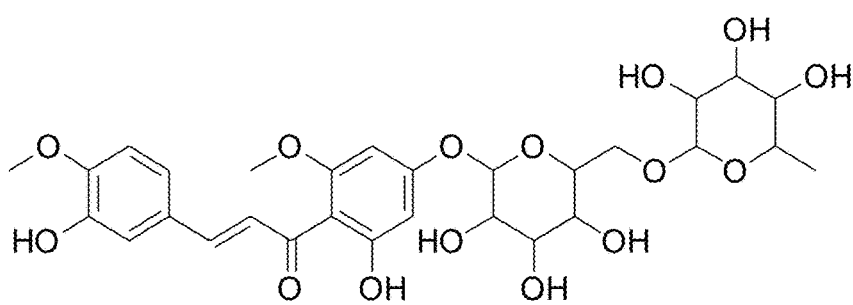

Additional examples of compounds of the invention include compounds that are already in clinical and nutraceutical use, proven to be relatively non-toxic in animal or human studies, and/or clinically approved for use for other indications unrelated to the invention (known as "repurposed" pharmaceuticals). Such compounds include sofalcone (FIG. 2O), metochalcone (FIG. 2N), and hesperidin methyl chalcone (FIG. 2P).

Figure 3:
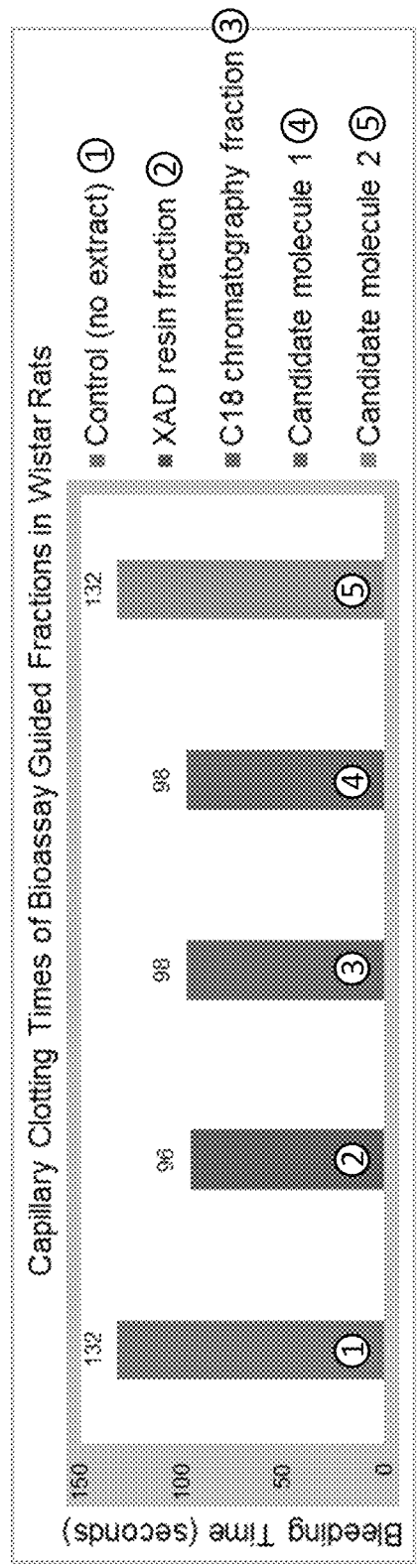
FIG. 3 illustrates a sample result of a capillary blood clotting time study in Wistar rats in accordance with various embodiments of the invention.

During the bioassay-guided fractionation process, blood clotting time was used as a screen for active compounds, and a particular class of compounds known as chalcones was discovered to induce blood coagulation. FIG. 3 illustrates a sample result from an ex vivo capillary clotting assay in Wistar rats in accordance with various embodiments of the invention as described in further detail below. As illustrated, the effect on capillary clotting time of "candidate compound 1" (referred to herein as "HF-2021 a"), was nearly identical to that of the chromatography fractions, suggesting that HF-2021a was the main driver of the reduction in clotting time.

After demonstrating efficacy in the capillary clotting test, HF-2021a was prepared by synthetic methods in the chemistry laboratory. Both the naturally sourced and synthesized samples were studied and shown to be identical by characterization methods such as nuclear magnetic resonance ("NMR") spectroscopy. HF-2021a is illustrated in FIG. 2D where $R_3$=OH, and $R'_2$, $R'_3$, $R'_4$=OCH$_3$.

Figure 4:
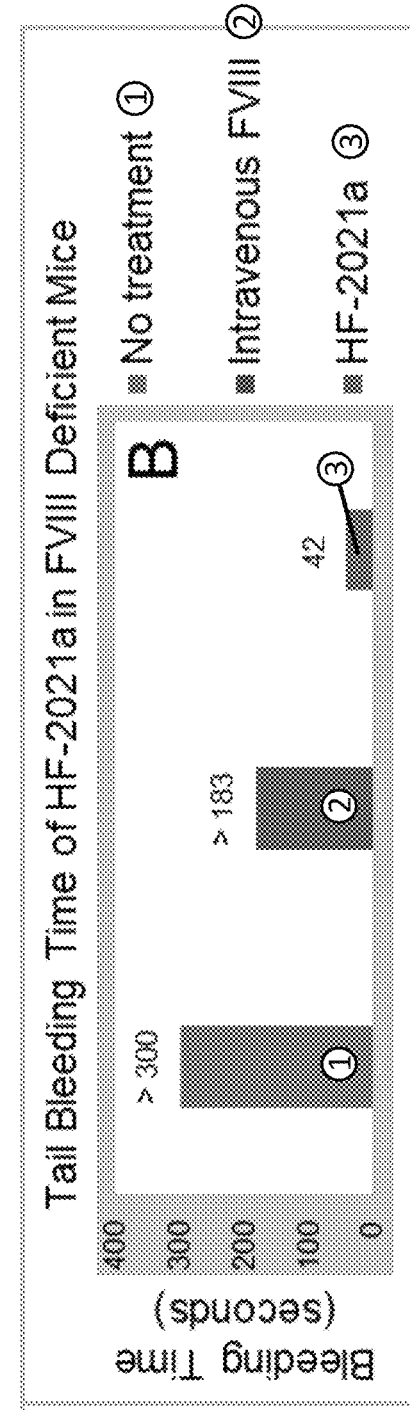
FIG. 4 illustrates a sample result of a tail bleeding study in a FVIII-deficient mouse model in accordance with various embodiments of the invention.

HF-2021a, was then assessed in tail bleeding assay in the B6;129S-F8$^{tm1Kaz}$J FVIII-deficient mouse model (referred to herein as "FVIII-KO mice") for its potential as a hemophilia A therapeutic as described in further detail below. As illustrated in FIG. 4, a reduction in tail bleeding time due to repeated administrations of HF-2021a was also observed in this assay, with the compound outperforming the standard FVIII therapy.

According to various implementations of the invention, the compounds of the invention are chalcones having the general chalcone structure of FIG. 2A. One such chalcone having the chalcone substructure described herein as HF-2021a, is known as 1-(6-Hydroxy-2,3,4-trimethoxyphenyl)-3-(4-hydroxy-phenyl)prop-2-en-1-one (also known as CAS 59567-92-9). Subsequent to the discovery of HF-2021a, another chalcone having the chalcone substructure, flavokawain A (also known as CAS 37951-13-6), a commercial material available in larger quantities, was also demonstrated as an active blood clotting agent in the heparinized blood assay. Flavokawain A, also described herein as HF-2021b, is illustrated in FIG. 2K.

According to various implementations of the invention, the compounds of the invention are selected from a class of chalcones having the chalcone substructure. Bioassay-guided fractionation of the extracts described herein demonstrated the discovery of many individual analog compounds of chalcone. Experiments on various individual analog compounds and extracts are summarized in Table 1.

TABLE 1

Summary of Experiments Using Chalcones as Coagulant Compounds

| Type | Name/CAS | Source of Studies | Summary of Studies |
|---|---|---|---|
| Chalcone | HF-2021a/CAS 59567-92-9 | YewSavin | Normal rat capillary clotting test (ex vivo oral) FVIII deficient mouse tail bleeding test (in vivo oral) Heparinized clotting test (in vitro) |
| | HF-2021b/CAS 3420-72-2 | YewSavin | Heparinized clotting test (in vitro) |
| | HF-2021c/CAS 961-29-5 | YewSavin | FVIII deficient thrombin generation test (in vitro) |
| | HF-2021d/CAS 24292-52-2 | YewSavin | FVIII deficient thrombin generation test (in vitro) |
| | HF-2021e/CAS 64506-49-6 | YewSavin | FVIII deficient thrombin generation test (in vitro) |
| | HF-2021f/CAS 18493-30-6 | YewSavin | FVIII deficient thrombin generation test (in vitro) |
| | HF-2021g/CAS 73692-50-9 | YewSavin | FVIII deficient thrombin generation test (in vitro) |
| | HF-2022a/CAS 644-34-8 | YewSavin | FVIII deficient thrombin generation test (in vitro) |
| Plant Extract | *Chromolaena odorata* | Literature | Normal rat stomach ulcer test (in vivo oral) |
| | *Tridax procumbens* | Literature | Normal rat capillary clotting test (ex vivo oral) |
| | *Typha elephantina* | YewSavin | Normal mouse tail bleeding test (in vivo topical) |

Chalcones having the chalcone substructure are generally well known, and a large variety of derivatives can be readily synthesized to generate compounds with a substructure with desirable properties as would be appreciated.

Synthetic methods for producing many of these compounds are well documented and generally follow a similar three-step method. Chalcones may be synthesized with the Claisen-Schmidt condensation of ketones such as the protected ketone 2,4,6-trimethoxyaceto-phenone and 4-(methoxymethoxy)benzaldehyde substituted at the 3-position with either a proton, hydroxy, or methoxy group. This reaction gives the chalcones of interest, and is typically carried out in polar solvents at about 50-100° C. for several hours with either an acid or base catalyst. Sodium hydride can also be used to drive the reaction.

For example, the chalcone isosakuranetin is prepared using the following scheme:

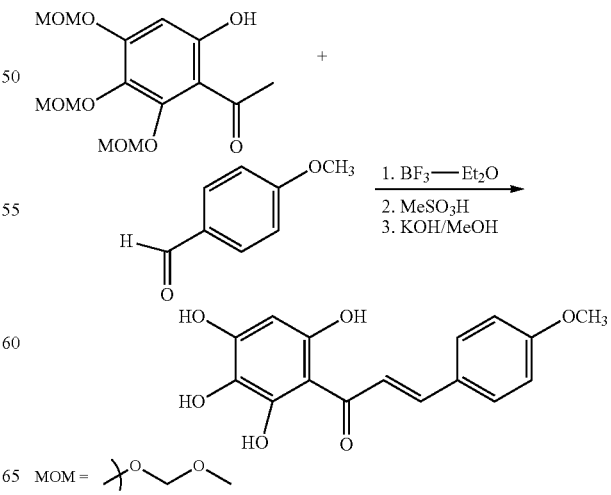

EMBODIMENTS

According to various embodiments of the invention, chalcones having the chalcone substructure are found to induce blood clotting. Experiments described below demonstrate that such chalcones significantly reduced blood clotting time in hemophilia blood and animal models. Experiments described below demonstrate that chalcones used as oral prophylactic agents reduced blood clotting time and increased blood clotting efficiency without any apparent risk of immunogenicity or unwanted blood clots. Experiments described below demonstrate that chalcones reduced the inhibitory activity of antithrombin on thrombin-driven blood clotting, thereby increasing the effectiveness of the thrombin mechanism in clotting blood. Neither the use of chalcones to treat blood clotting disorders nor their impact on inhibitory activity of antithrombin on thrombin-driven blood clotting mechanism were known prior to this invention.

EXAMPLES

Example I: Treatment of Bleeding Disorder with Chalcones in FVIII-KO Mice

The purpose of this experiment was to evaluate the effectiveness of chalcones on tail bleeding time in mice. FVIII-KO mice were divided into three groups of five mice each. Group 1 was a disease control group that received no treatment, group 2 was a standard treatment group that received FVIII therapy injections, and group 3 was a chalcone treatment group that received orally administered HF-2021a once daily for seven days. Following the final oral administration of HF-2021a, all three groups of mice were anesthetized with a ketamine/xylazine injection and placed in a prone position. A distal 10 mm segment of the each mouse's tail was amputated with a scalpel, and the remaining tail stump was immediately immersed in a 50 mL Falcon tube containing isotonic saline pre-warmed in a water bath to 37° C. Each mouse was allowed to bleed freely for 20 minutes even if bleeding ceased, in order to detect any re-bleeding. Bleeding time was determined using a stopwatch. At the end of the 20 minutes, the experiment was terminated to avoid lethality. All animals were then bled additionally to obtain a sufficient amount of blood for determining fibrinogen content. Organs were collected, weighed and preserved for future assays. Table 2 summarizes the results of this experiment.

The summary of results in Tables 1 and 2 show that HF-2021a significantly improved, capillary clotting times, thrombin generation, and tail bleeding times for normal and FVIII-KO mice. Of particular note is the improvement in tail bleeding time for group 3 (the chalcone treatment group), which was superior to that of group 2 (the standard treatment group). The summary of results also suggests that the mode of action of chalcones is likely independent of FVIII.

Figure 1:
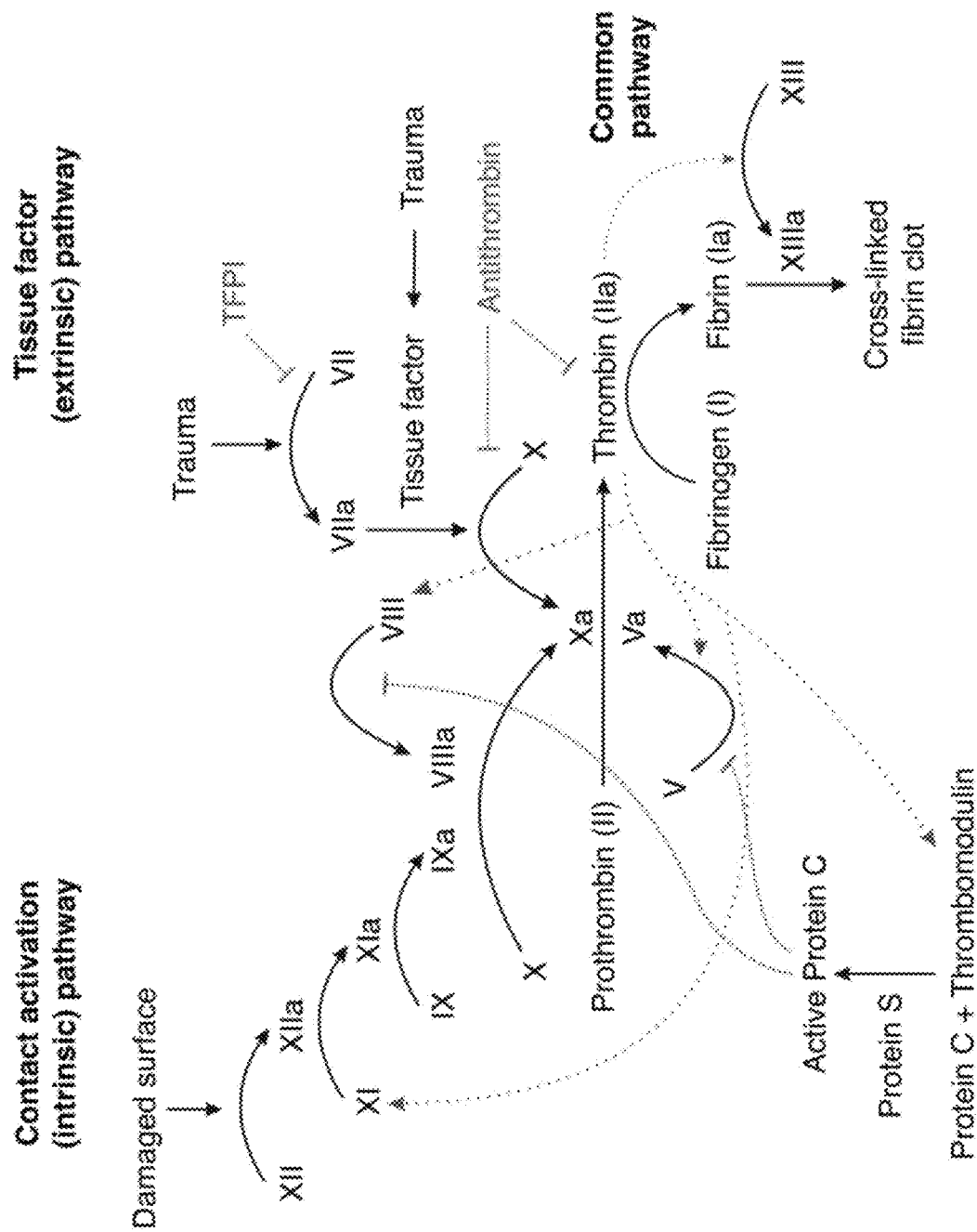
FIG. 1 illustrates various known pathways responsible for initiating "hemostasis."
Figure 6:
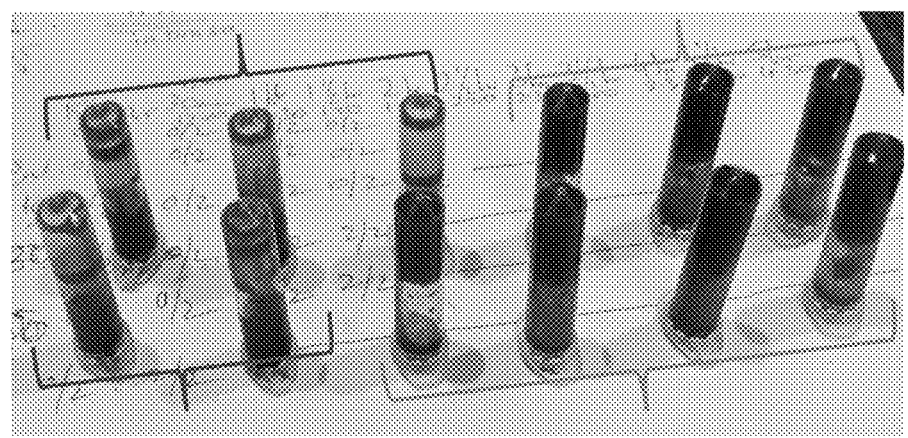
FIG. 6 depicts inverted tubes demonstrating blood samples that clotted versus blood samples that did not clot in accordance with various embodiments of the invention.
Figure 7:
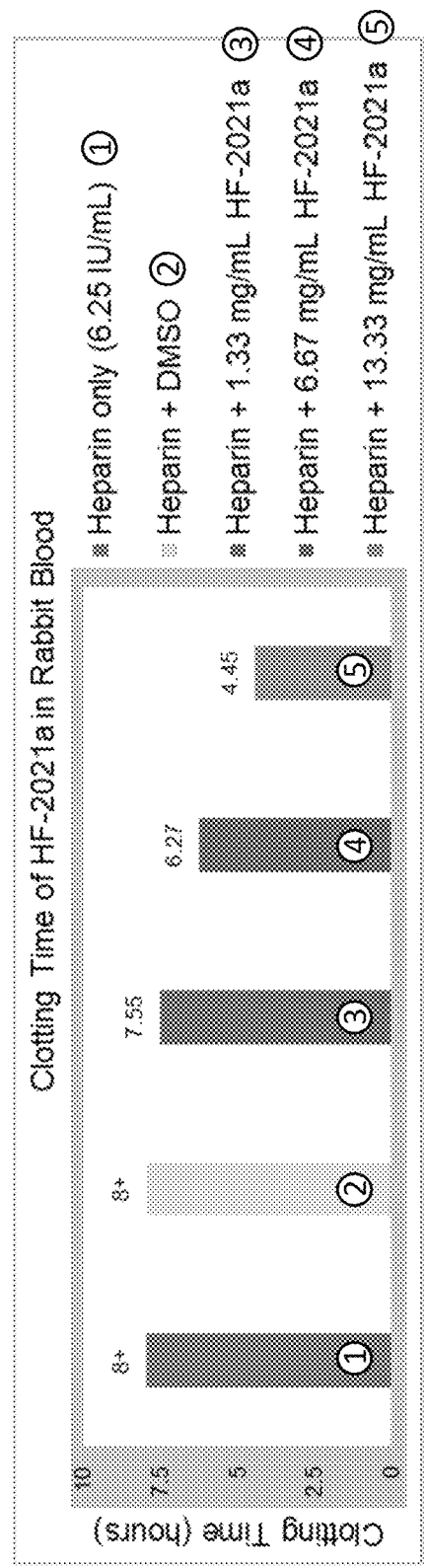
FIG. 7 illustrates blood clotting times for heparinized rabbit blood at various concentrations in accordance with various embodiments of the invention.

Example II: Reversal of Heparin-Induced Inhibition of Blood Clotting by Chalcones The purpose of this experiment was to deduce a potential mechanism of action for chalcones in decreasing blood clotting and bleeding time. First, rabbit blood (200 μL) was added to the anticoagulant drug heparin (1.25 IU) in Eppendorf Tubes®. Varying concentrations of HF-2021a dissolved in a dimethyl sulfoxide ("DMSO") delivery vehicle were then added to these tubes, and the tubes were inverted every 30 minutes to observe the progress of blood clotting. FIG. 6 depicts the inverted tubes to demonstrate that in the samples where the blood had clotted, the clot remained in the upper portion of the tube, while in the samples where the blood had not clotted, the liquid blood was found at the bottom of the tube. FIG. 7 illustrates the blood clotting times for these heparinized rabbit blood samples at varying concentrations of HF-2021a. A dose dependence relationship was observed between increasing concentrations of HF-2021a and decreasing blood clotting times of the heparinized rabbit blood samples. These results suggest that HF-2021a inhibits the activity of antithrombin by disrupting the formation of the heparin-antithrombin complex in rabbit blood samples that are treated with the anticoagulant heparin. In untreated blood that is still inside a human or an animal, heparan sulfate that is found on cellular surfaces plays an equivalent role to heparin by forming a heparan-antithrombin complex and activating antithrombin. Thus, these results also suggest that HF-2021a similarly inhibits the activity of antithrombin in natural untreated blood by disrupting the formation of the naturally occurring heparan-antithrombin complex (see e.g., FIG. 1).

Example III: Thrombin Generation in Healthy and Hemophilic Human Plasma

Thrombin generation is regarded as a significant indicator of the efficiency of blood clotting. Therefore, the thrombin generation assay ("TGA") can be used as a proxy to estimate overall blood clotting efficiency of factor proteins and others

TABLE 2

Blood Clotting Time in Factor VIII Deficient Mice

| Group | Bodyweight (Day 0) | Bodyweight (Day 7) | Bleeding Time (Seconds) | Capillary Clotting Time (Seconds) | Optical Density | Fibrin content (mg/dL) | Survival Rate |
|---|---|---|---|---|---|---|---|
| Factor VIII Deficient | 18.5 (1.1) | 18.6 (1.1) | >300 (0) | 134 (24.1) | 2.2 (0.1) | 189.2 (12.4) | 0/5 after 24 hours |
| Factor VIII Deficient + Intravenous Factor VIII | 18.9 (0.9) | 19.6 (0.4) | >183 (0) | 69.6 (23.9) | 1.4 (0.7) | 179.1 (31.2) | 1/5 after 24 hours |
| Factor VIII Deficient + Oral HF-2021a | 17.4 (1.4) | 18.8 (1.1) | 41.8 (9.7) | 44.6 (13.2) | 0.5 (0.1) | 281.2 (44.1) | 3/5 after 48 hours | agents from observing the clotting of plasma samples. The thrombin generation experiments were run using a microtiter plate fluorometer. Solvent systems consisting of a buffer, a fluorogenic substrate, and eight candidate compounds in inert solvents were added to pre-warmed citrated FVIII-deficient plasma along with tissue factor. The clotting reactions in the plasma-compound mixtures were initiated by adding calcium chloride solution to all the samples, and the fluorescence measurements recorded by the fluorimeter were compared against negative control (FVIII-deficient plasma without compounds or solvent system), vehicle control (FVIII-deficient plasma with solvent system only), and positive control (FVIII-deficient plasma mixed with regular plasma) reference measurements.

Each of the eight candidate compounds was tested via the TGA at three different concentrations. Eight different candidate compounds with a variety of structural features such as a hydroxyl group pattern, a methoxy group, a sugar derivative, and a prenylated chalcone all demonstrated significant activity and dose-dependent behavior in increasing thrombin generation in both healthy and FVIII-deficient human plasma.

Figure 8:
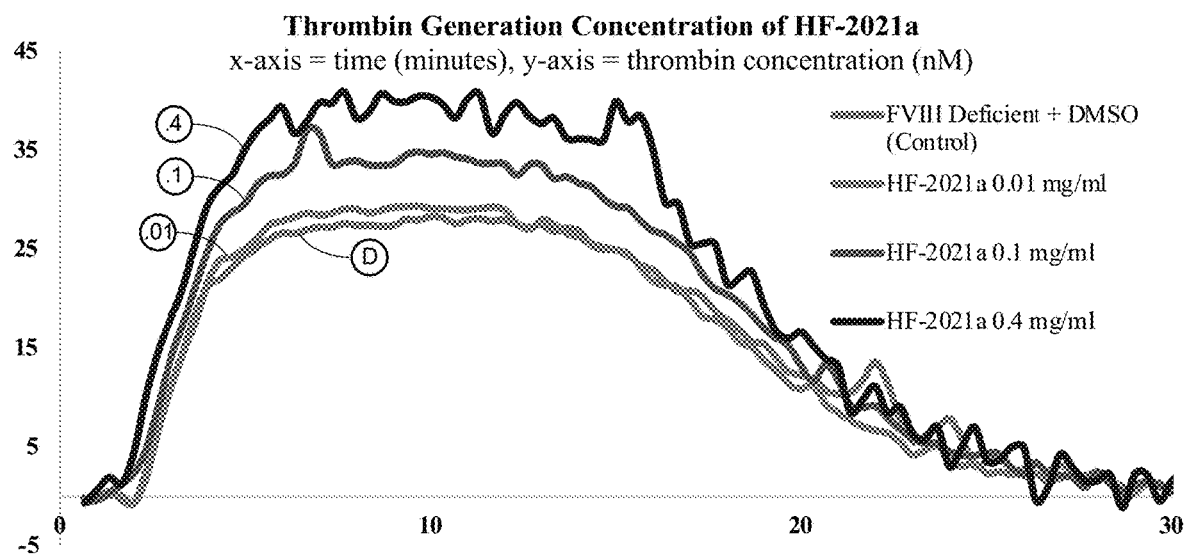
FIG. 8 illustrates thrombin generation for various concentrations of candidate compound 1 (i.e., HF-2021a) in accordance with various embodiments of the invention.
Figure 9:
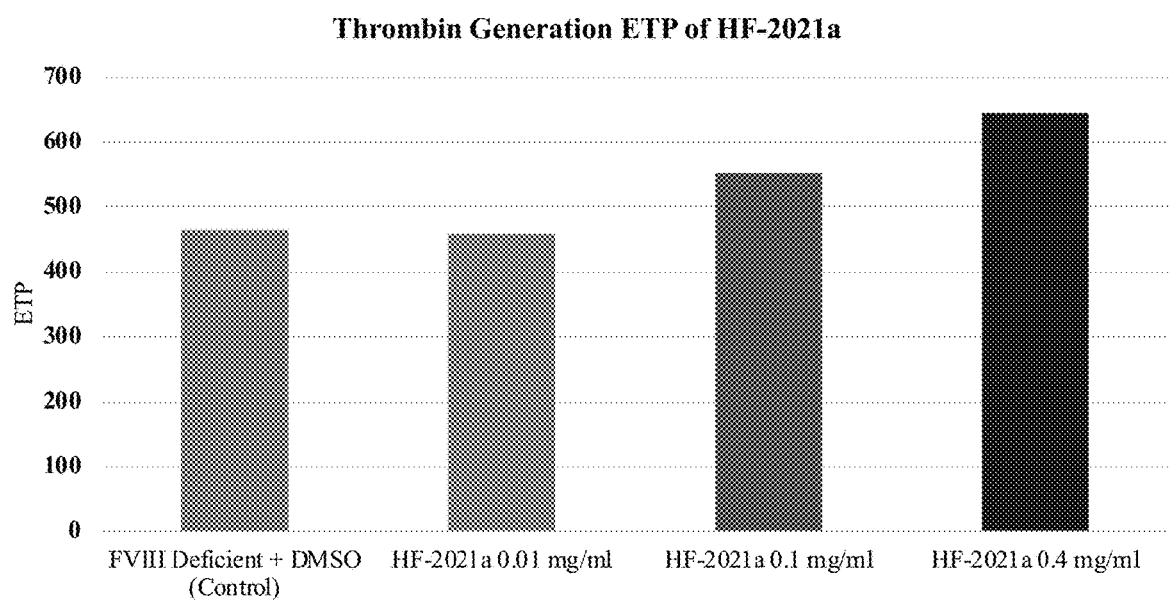
FIG. 9 illustrates a thrombin generation endogenous thrombin potential (ETP) dependence on concentration of candidate compound 1 (i.e., HF-2021a) in accordance with various embodiments of the invention.

FIG. 8 illustrates thrombin generation for various concentrations of candidate compound 1 in accordance with various embodiments of the invention. More particularly, candidate compound 1, also referred to as HF-2021a, is the chalcone 1-(6-hydroxy-2,3,4-trimethoxyphenyl)-3-(4-hydroxy-phenyl)prop-2-en-1-one (also known as CAS 59567-92-9). As illustrated in FIG. 8, the thrombin generation curves of three different concentrations of HF-2021a (namely, 0.01 mg/ml, 0.1 mg/ml, and 0.4 mg/ml) are compared with the thrombin generation curve of FVIII-deficient plasma. FIG. 9 illustrates an observed dose dependence of the thrombin generation ETP on the concentration of HF-2021a.

Figure 10:
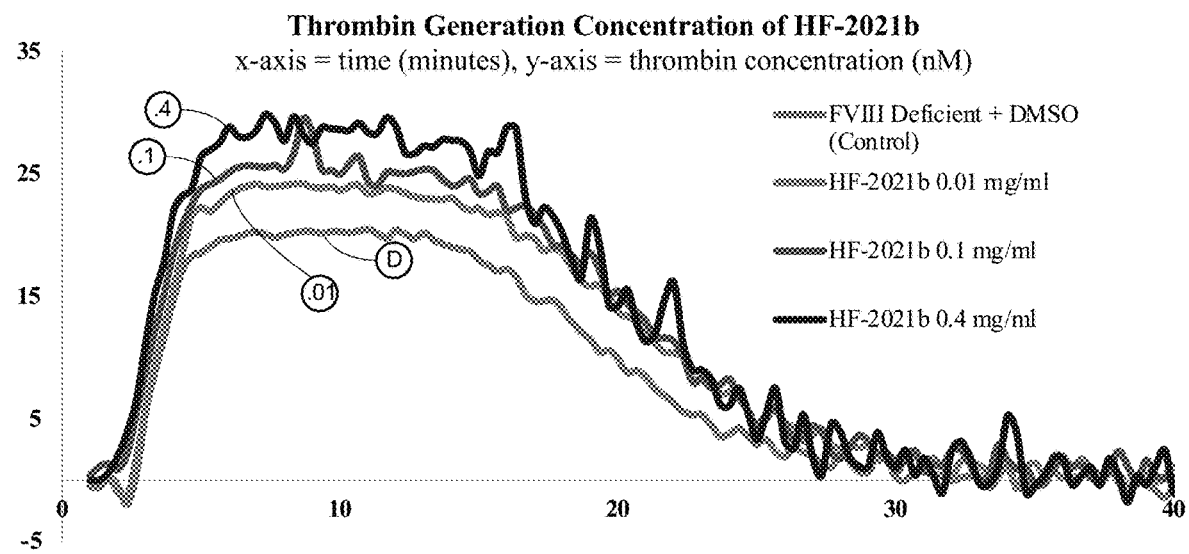
FIG. 10 illustrates thrombin generation for various concentrations of candidate compound 2 (i.e., HF-2021b) in accordance with various embodiments of the invention.
Figure 11:
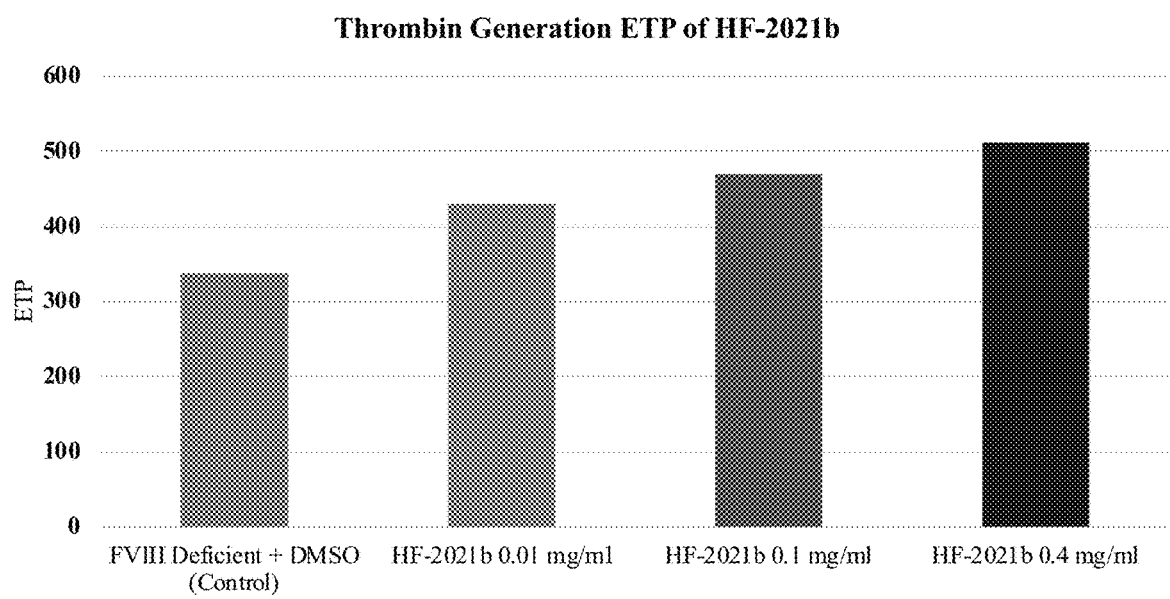
FIG. 11 illustrates a thrombin generation ETP dependence on concentration of candidate compound 2 (i.e., HF-2021b) in accordance with various embodiments of the invention.

FIG. 10 illustrates thrombin generation for various concentrations of candidate compound 2 in accordance with various embodiments of the invention. More particularly, candidate compound 2, also referred to as HF-2021b, is the chalcone 1-(2-hydroxy-4,6-dimethoxyphenyl)-3-(4-methoxyphenyl)prop-2-en-1-one (also known as CAS 37951-13-6 or flavokawain A) and is shown in FIG. 2K. As illustrated in FIG. 10, the thrombin generation curves of three different concentrations of HF-2021b (namely, 0.01 mg/ml, 0.1 mg/ml, and 0.4 mg/ml) are compared with the thrombin generation curve of FVIII-deficient plasma. FIG. 11 illustrates an observed dose dependence of the thrombin generation ETP on the concentration of HF-2021b.

Figure 12:
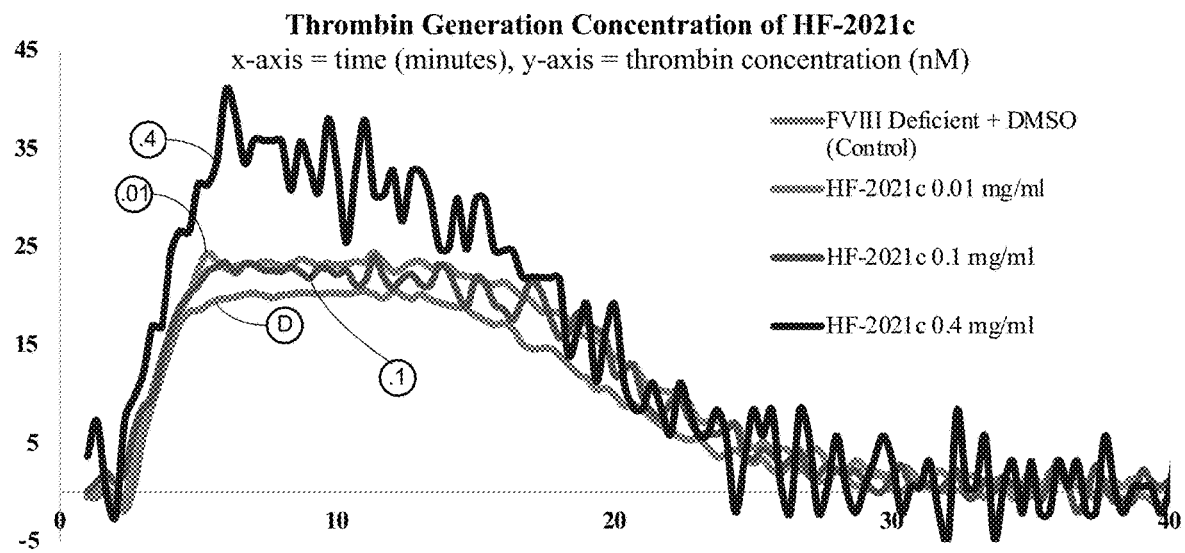
FIG. 12 illustrates thrombin generation for various concentrations of candidate compound 3 (i.e., HF-2021c) in accordance with various embodiments of the invention.
Figure 13:
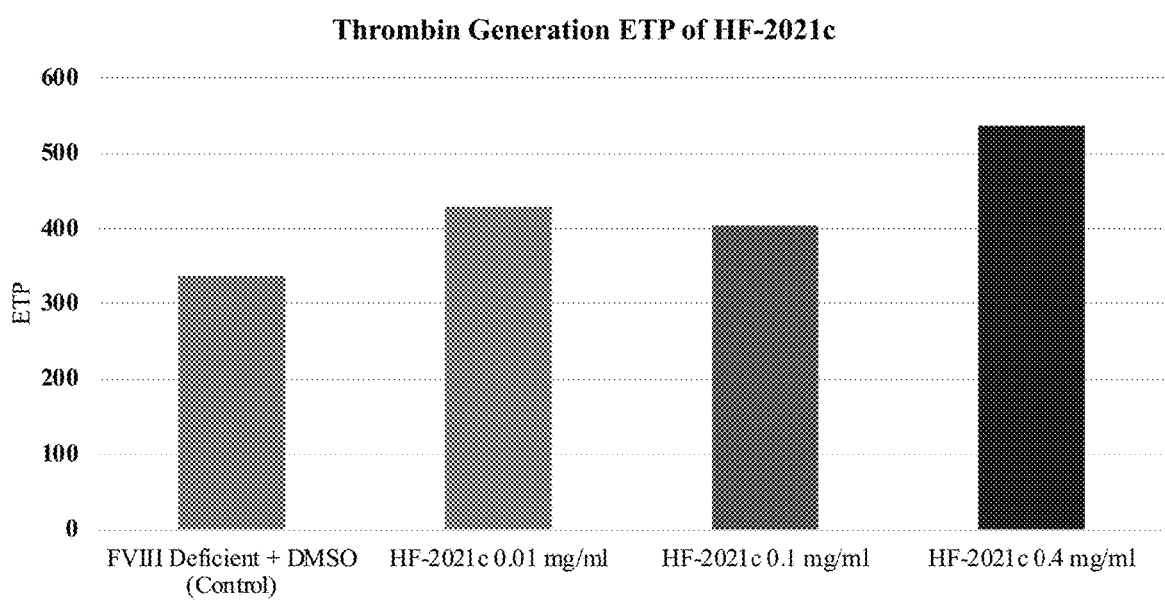
FIG. 13 illustrates a thrombin generation ETP dependence on concentration of candidate compound 3 (i.e., HF-2021c) in accordance with various embodiments of the invention.

FIG. 12 illustrates thrombin generation for various concentrations of candidate compound 3 in accordance with various embodiments of the invention. More particularly, candidate compound 3, also referred to as HF-2021c, is the chalcone (E)-1-(2,4-dihydroxyphenyl)-3-(4-hydroxyphenyl) prop-2-en-1-one (also known as CAS 961-29-5 or isoliquiritigenin) and is shown in FIG. 2Q. As illustrated in FIG. 12, the thrombin generation curves of three different concentrations of HF-2021c (namely, 0.01 mg/ml, 0.1 mg/ml, and 0.4 mg/ml) are compared with the thrombin generation curve of FVIII-deficient plasma. FIG. 13 illustrates an observed dose dependence of the thrombin generation ETP on the concentration of HF-2021c.

Figure 14:
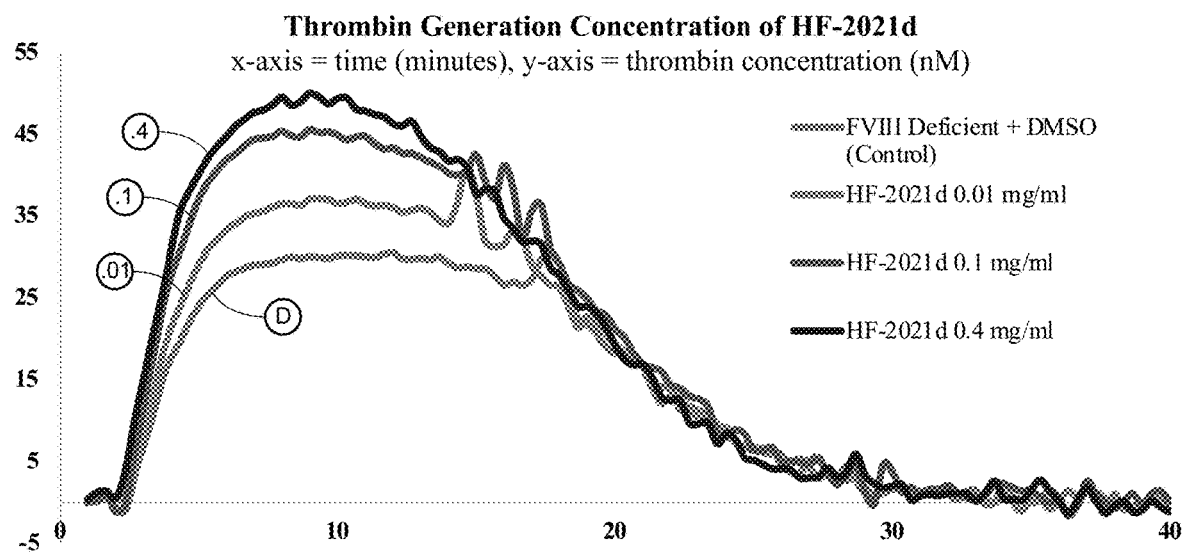
FIG. 14 illustrates thrombin generation for various concentrations of candidate compound 4 (i.e., HF-2021d) in accordance with various embodiments of the invention.
Figure 15:
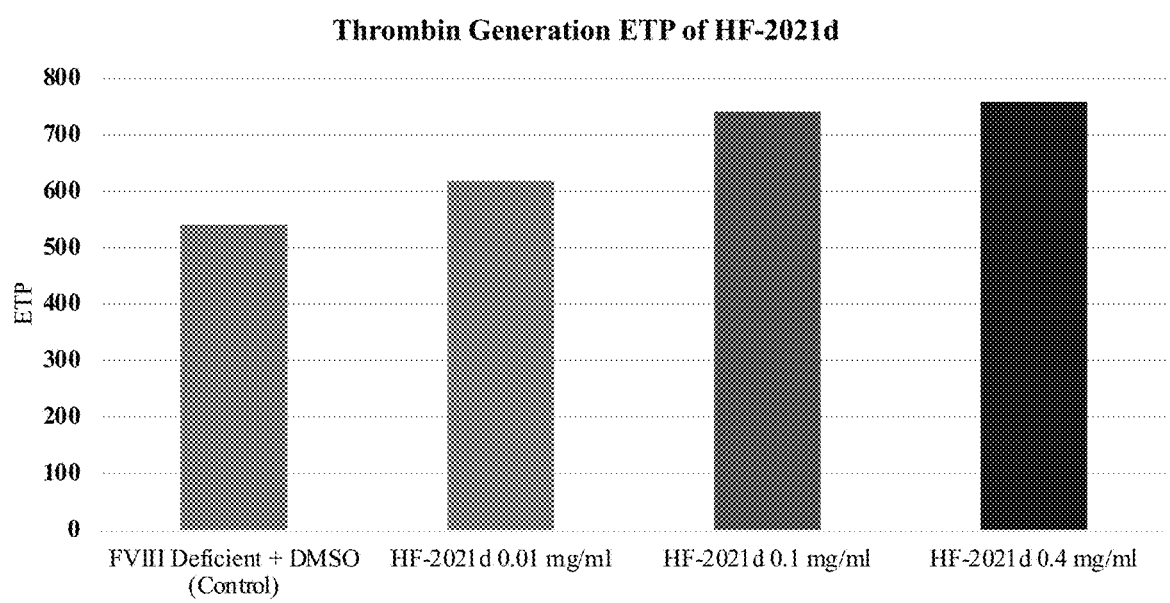
FIG. 15 illustrates a thrombin generation ETP dependence on concentration of candidate compound 4 (i.e., HF-2021d) in accordance with various embodiments of the invention.

FIG. 14 illustrates thrombin generation for various concentrations of candidate compound 4 in accordance with various embodiments of the invention. More particularly, candidate compound 4, also referred to as HF-2021d, is the chalcone (E)-3-(3-hydroxy-4-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl] oxymethyl]oxan-2-yl]oxyphenyl]prop-2-en-1-one (also known as CAS 24292-52-2 or hesperidin methyl chalcone) and is shown in FIG. 2P. As illustrated in FIG. 14, the thrombin generation curves of three different concentrations of HF-2021d (namely, 0.01 mg/ml, 0.1 mg/ml, and 0.4 mg/ml) are compared with the thrombin generation curve of FVIII-deficient plasma. FIG. 15 illustrates an observed dose dependence of the thrombin generation ETP on the concentration of HF-2021d.

Figure 16:
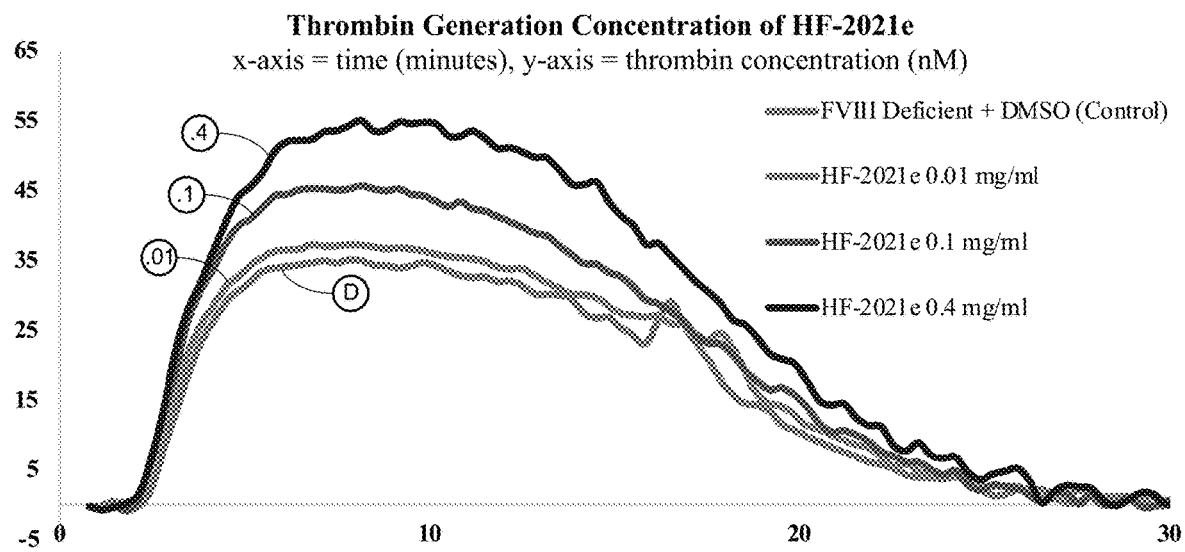
FIG. 16 illustrates thrombin generation for various concentrations of candidate compound 5 (i.e., HF-2021e) in accordance with various embodiments of the invention.
Figure 17:
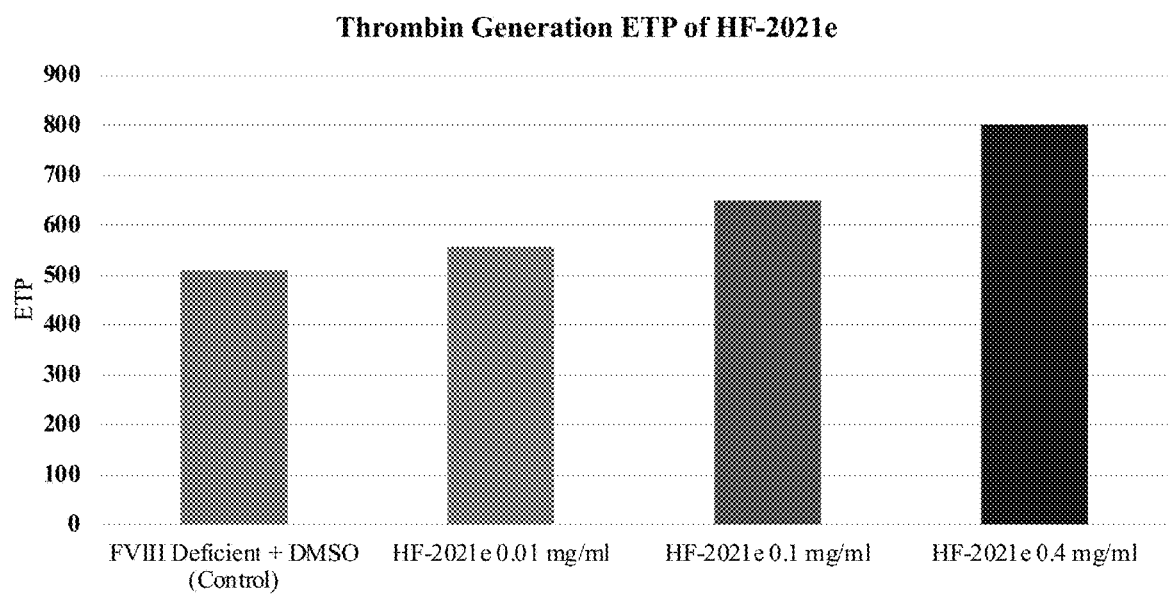
FIG. 17 illustrates a thrombin generation ETP dependence on concentration of candidate compound 5 (i.e., HF-2021e) in accordance with various embodiments of the invention.

FIG. 16 illustrates thrombin generation for various concentrations of candidate compound 5 in accordance with various embodiments of the invention. More particularly, candidate compound 5, also referred to as HF-2021e, is the chalcone 2-[5-(3-methylbut-2-enoxy)-2-[(E)-3-[4-(3-methylbut-2-enoxy)phenyl]prop-2-enoyl]phenoxy]acetic acid (also known as CAS 64506-49-6 or sofalcone) and is shown in FIG. 2O. As illustrated in FIG. 16, the thrombin generation curves of three different concentrations of HF-2021e (namely, 0.01 mg/ml, 0.1 mg/ml, and 0.4 mg/ml) are compared with the thrombin generation curve of FVIII-deficient plasma. FIG. 17 illustrates an observed dose dependence of the thrombin generation ETP on the concentration of HF-2021e.

Figure 18:
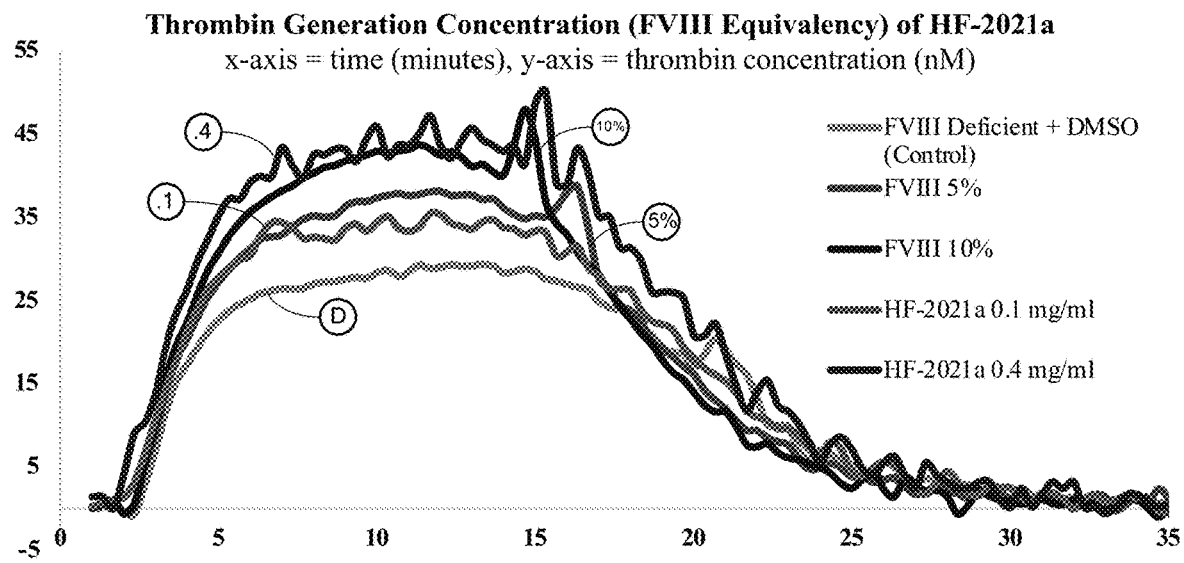
FIG. 18 illustrates a FVIII equivalency of thrombin generation for various concentrations of candidate compound 1 (i.e., HF-2021a) in accordance with various embodiments of the invention.

FIG. 18 illustrates thrombin generation curves for varying concentrations of HF-2021a compared with FVIII-deficient plasma samples containing 5% and 10% of normal FVIII levels. The curve of the 0.4 mg/mL HF-2021a sample (0.4) over the curve of the 10% FVIII sample (10%) indicates that 0.4 mg/ml of HF-2021a generates a thrombin response superior to that of 10% of normal FVIII activity. For perspective, 10% of normal FVIII activity may be sufficient to alleviate symptoms of severe hemophilia A patients from the baseline of elevated and spontaneous bleeding episodes to elevated bleeding during major surgical procedures only. The restoration of 10% of normal FVIII activity by 0.4 mg/ml of HF-2021a suggests that this compound has at least a similar, if not superior, impact on thrombin generation to the FDA-approved antibody drug HEMLIBRA®.

Figure 19:
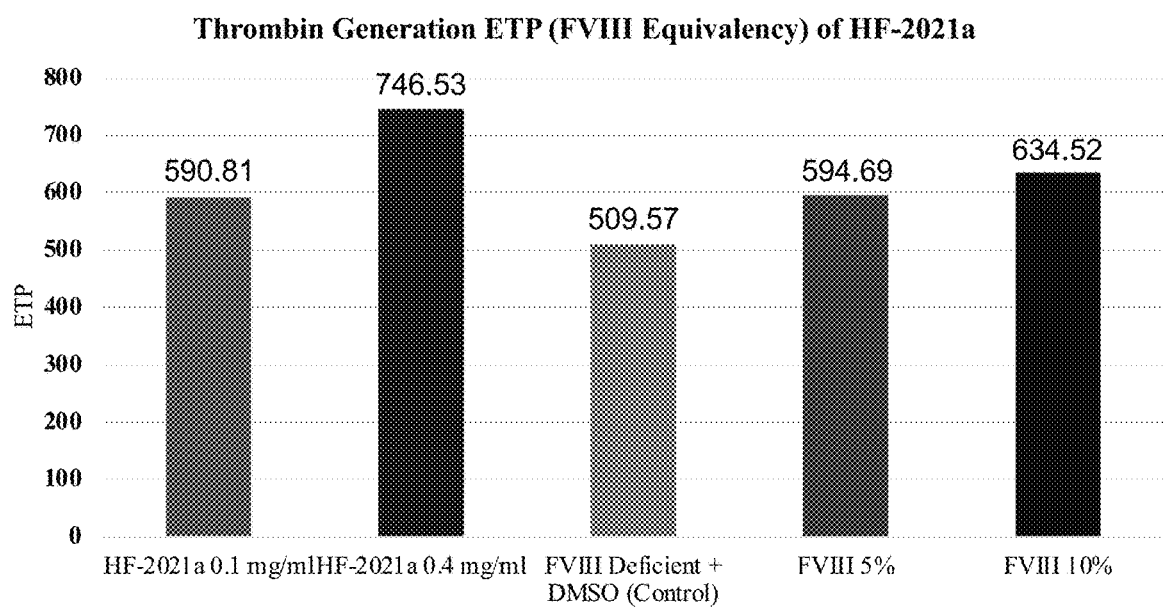
FIG. 19 illustrates a FVIII equivalency of thrombin generation ETP for various concentrations of candidate compound 1 (i.e., HF-2021a) in accordance with various embodiments of the invention.

FIG. 19 illustrates a comparison of thrombin generation ETPs of FIG. 18. The ETPs of these curves support the conclusion that that 0.4 mg/ml of HF-2021a generates a thrombin response at least similar, if not superior, to that of 10% of normal FVIII activity as provided by HEMLIBRA®.

Figure 20:
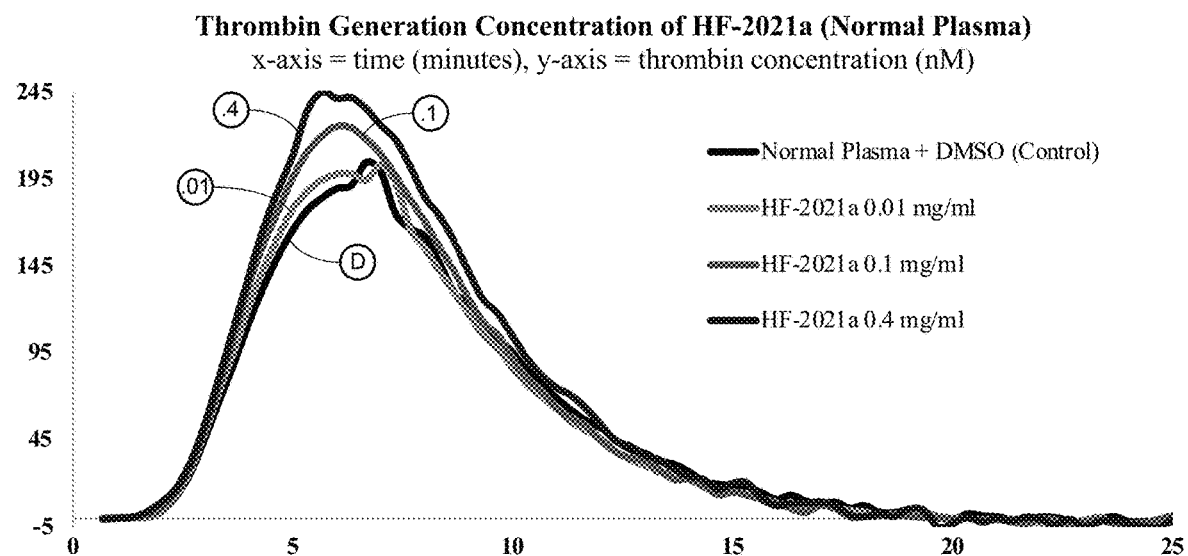
FIG. 20 illustrates thrombin generation for various concentrations of candidate compound 1 (i.e., HF-2021a) in normal plasma in accordance with various embodiments of the invention.

FIG. 20 illustrates thrombin generation curves for varying concentrations of HF-2021a in normal plasma. The thrombin generation curves corresponding to higher concentrations of HF-2021a are elevated over their lower concentration counterparts, suggesting that HF-2021a exhibits a dose dependent response across a broad concentration range which may be an important characteristic for treating bleeding and bleeding disorders with this and similar compounds. The fact that similar responses are found for HF-2021a in normal plasma as compared with FVIII-deficient plasma suggests that there is no confounding variable present in the FVIII-deficient experiments that would lead to elevated thrombin levels in FVIII-deficient plasma but not in normal plasma.

Figure 21:
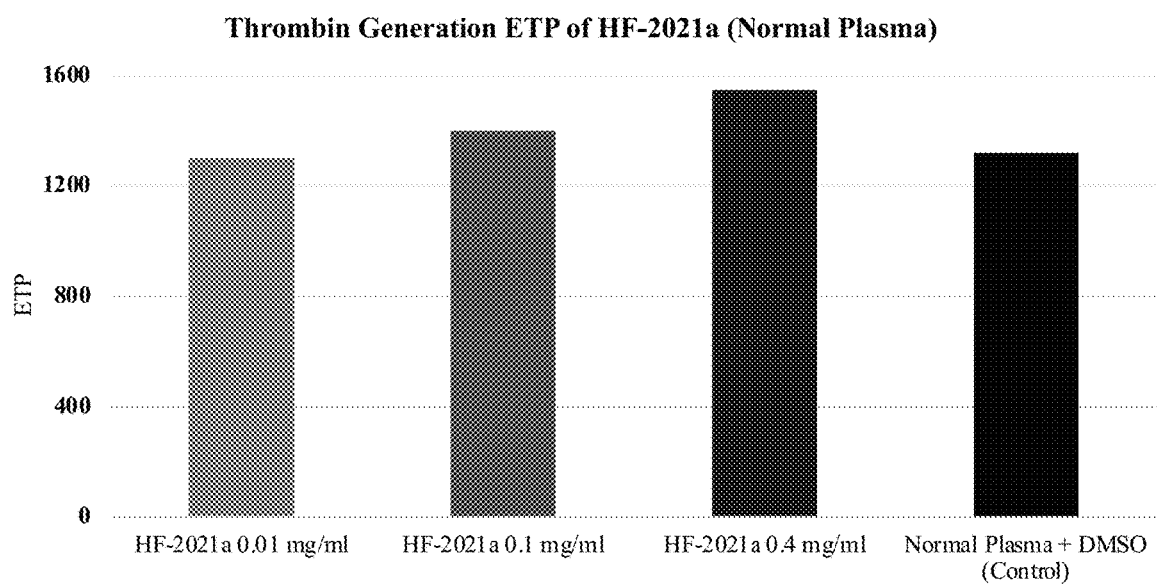
FIG. 21 illustrates a thrombin generation ETP dependence on concentration of candidate compound 1 (i.e., HF-2021a) in normal plasma in accordance with various embodiments of the invention.

FIG. 21 illustrates the thrombin generation ETPs as a function of HF-2021a concentration. Similar to the curves in FIG. 2O, a dose dependent response is also observed in ETP with the increase of compound concentration, which may be an important characteristic for treating bleeding and bleeding disorders.

These results discussed above from HF-2021a thrombin generation experiments and shown in FIGS. 18-21 in conjunction with the thrombin generation curves from other tested compounds indicate that: 1) a wide range of chalcones increase thrombin generation in a dose-dependent manner that may be characteristic of a successful therapy in treating bleeding and bleeding disorders; 2) the magnitude of thrombin generation from these chalcones reflects levels of FVIII that can alleviate hemophilia A symptoms in a clinical setting; and 3) the effect of these chalcones is in the range of an existing FDA-approved drug, HELIMBRA®. The three results described above demonstrate the potential of chalcones of various structures to provide similar, if not superior, benefits to existing treatments for hemophilia A patients in a clinical setting.

Figure 22:
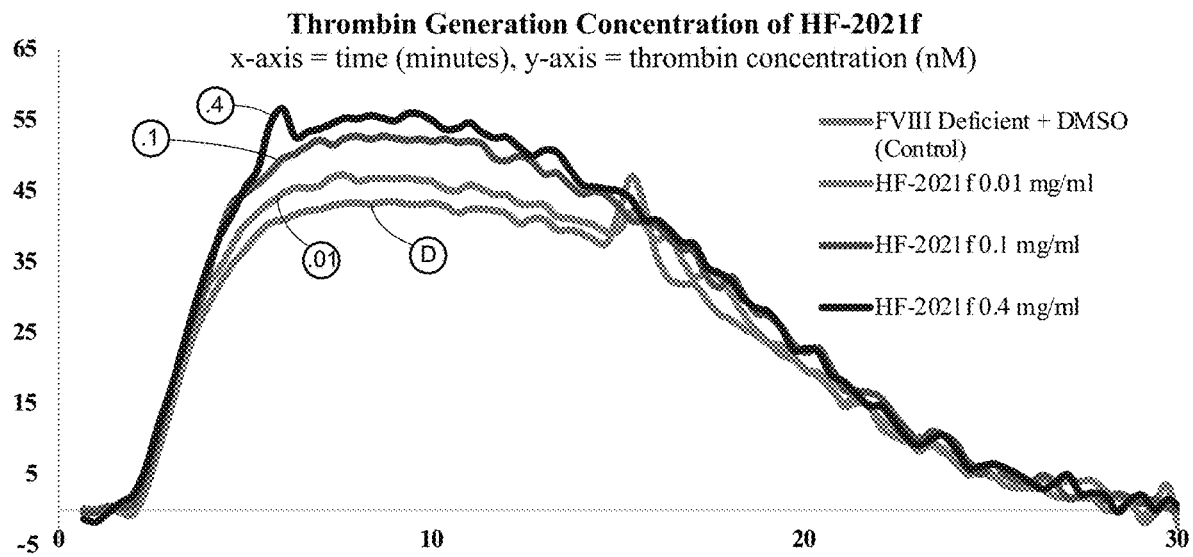
FIG. 22 illustrates thrombin generation for various concentrations of candidate compound 6 (i.e., HF-2021f) in accordance with various embodiments of the invention.
Figure 23:
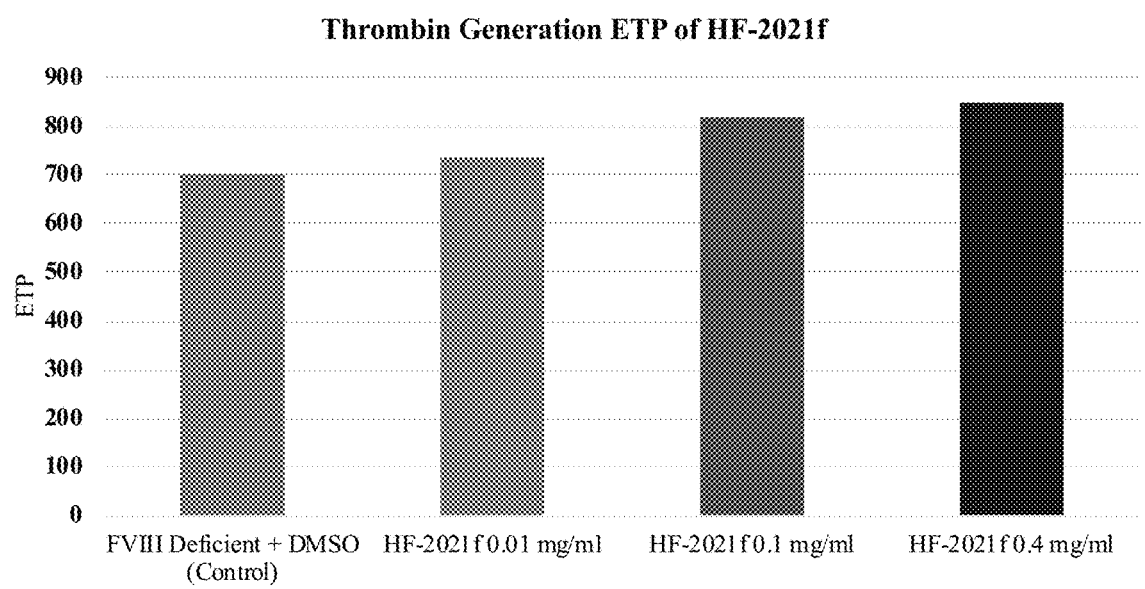
FIG. 23 illustrates a thrombin generation ETP dependence on concentration of compound 6 (i.e., HF-2021f) in accordance with various embodiments of the invention.

FIG. 22 illustrates thrombin generation for various concentrations of candidate compound 6 in accordance with various embodiments of the invention. More particularly, candidate compound 6, also referred to as HF-2021f, is the chalcone 4-methoxyphenyl-3-(2,4-dimethoxyphenyl)-1-oxo-2-propene (also known as CAS 18493-30-6 or metochalcone) and is shown in FIG. 2N. As illustrated in FIG. 22, the thrombin generation curves of three different concentrations of HF-2021f (namely, 0.01 mg/ml, 0.1 mg/ml, and 0.4 mg/ml) are compared with the thrombin generation curve of FVIII-deficient plasma. FIG. 23 illustrates an observed dose dependence of the thrombin generation ETP on the concentration of HF-2021f.

Figure 24:
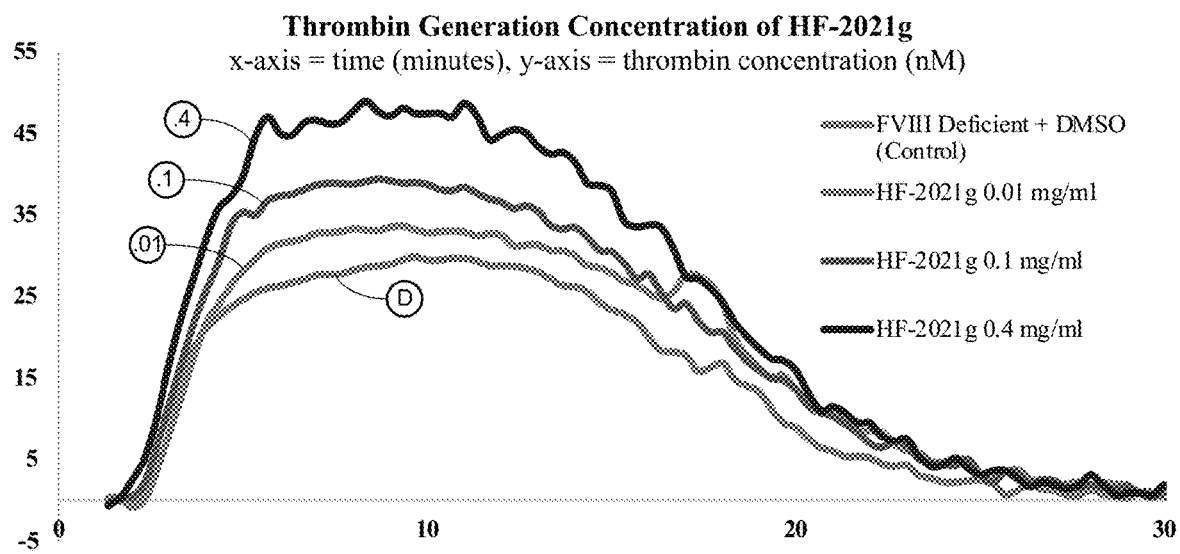
FIG. 24 illustrates thrombin generation for various concentrations of candidate compound 7 (i.e., HF-2021g) in accordance with various embodiments of the invention.
Figure 25:
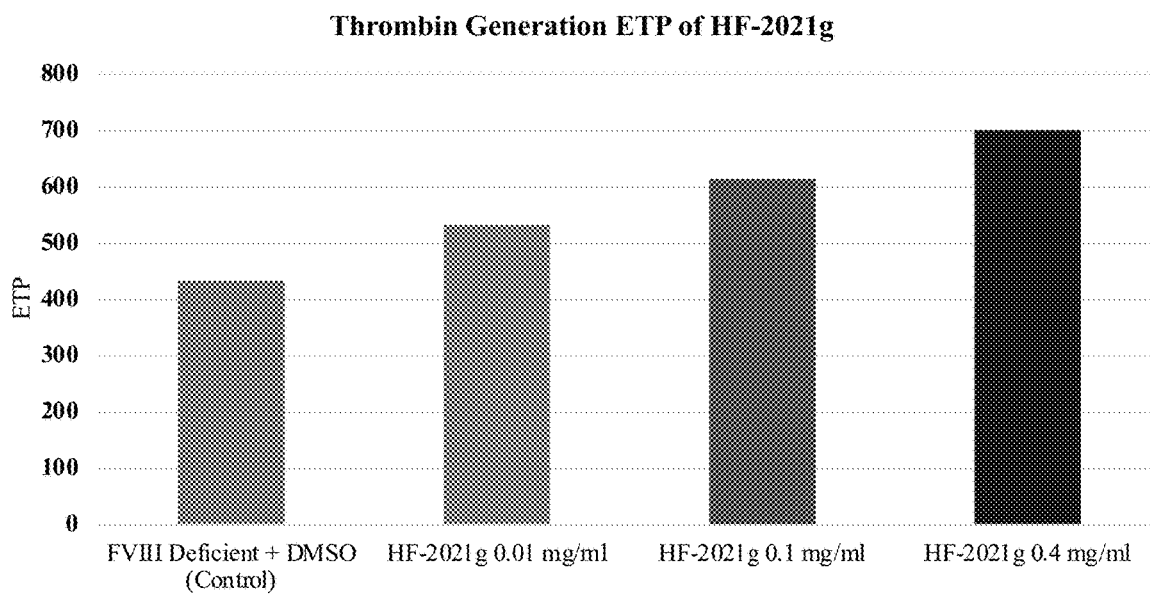
FIG. 25 illustrates a thrombin generation ETP dependence on concentration of candidate compound 7 (i.e., HF-2021g) in accordance with various embodiments of the invention.

FIG. 24 illustrates thrombin generation for various concentrations of candidate compound 7 in accordance with various embodiments of the invention. More particularly, candidate compound 7, also referred to as HF-2021g, is the chalcone (E)-3-(4-hydroxyphenyl)-1-(2,4,6-trihydroxyphenyl)prop-2-en-1-one (also known as CAS 25515-46-2 or naringenin chalcone). As illustrated in FIG. 24, the thrombin generation curves of three different concentrations of HF-2021g (namely, 0.01 mg/ml, 0.1 mg/ml, and 0.4 mg/ml) are compared with the thrombin generation curve of FVIII-deficient plasma. FIG. 25 illustrates an observed dose dependence of the thrombin generation ETP on the concentration of HF-2021g.

Figure 26:
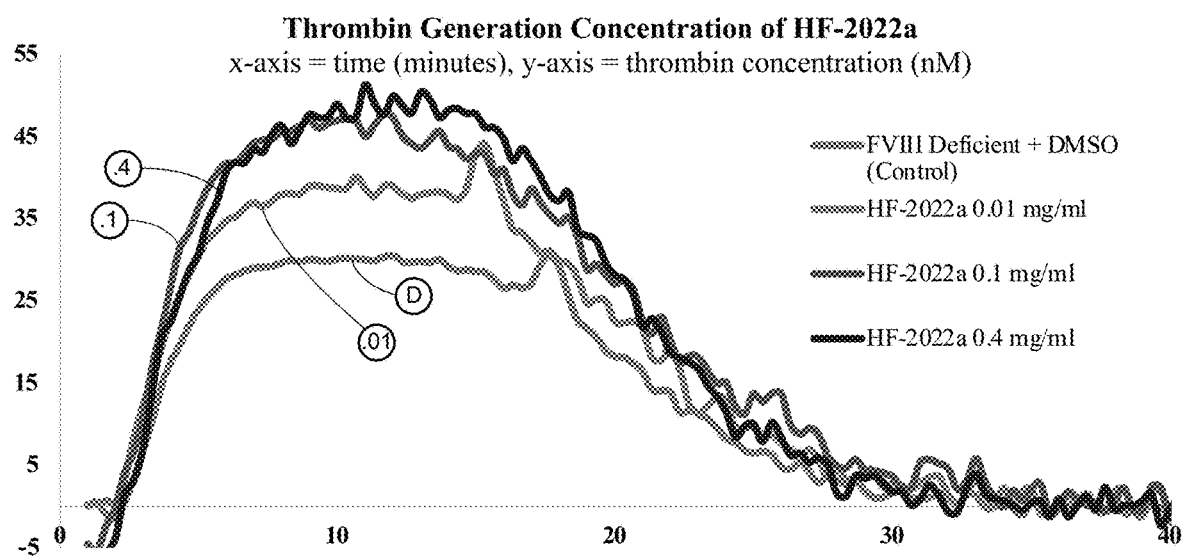
FIG. 26 illustrates thrombin generation for various concentrations of candidate compound 8 (i.e., HF-2022a) in accordance with various embodiments of the invention.
Figure 27:
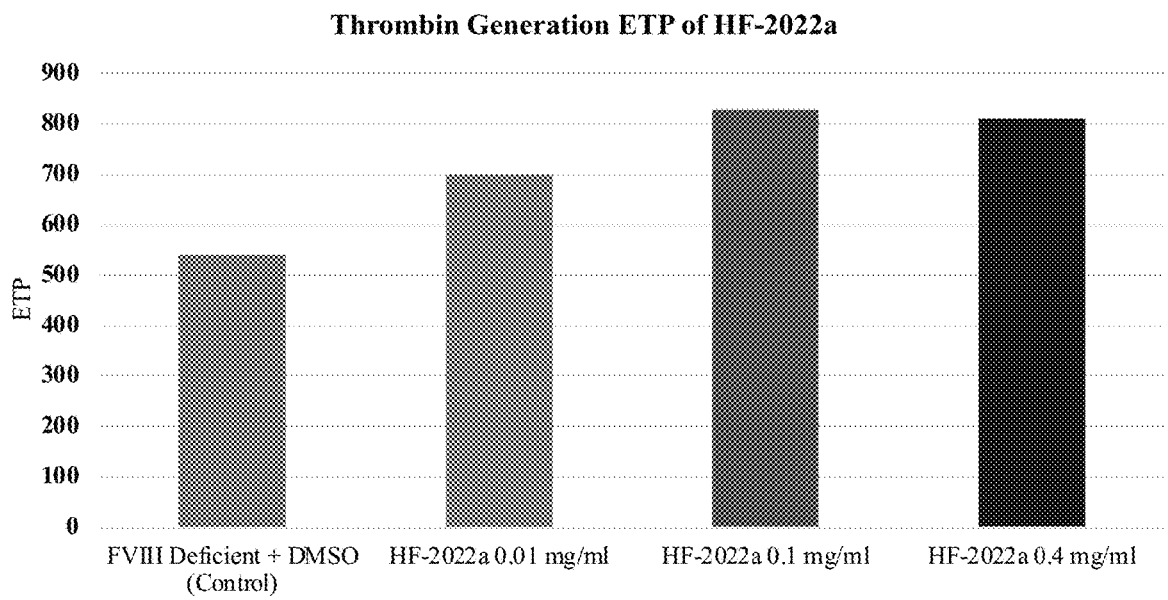
FIG. 27 illustrates a thrombin generation ETP dependence on concentration of candidate compound 8 (i.e., HF-2022a) in accordance with various embodiments of the invention.

FIG. 26 illustrates thrombin generation for various concentrations of candidate compound 8 in accordance with various embodiments of the invention. More particularly, candidate compound 8, also referred to as HF-2022a, is the chalcone 3-(1,3-Benzodioxol-5-yl)-1-phenyl-2-propen-1-one (also known as CAS 644-34-8). As illustrated in FIG. 26, the thrombin generation curves of three different concentrations of HF-2022a (namely, 0.01 mg/ml, 0.1 mg/ml, and 0.4 mg/ml) are compared with the thrombin generation curve of FVIII-deficient plasma. FIG. 27 illustrates an observed dose dependence of the thrombin generation ETP on the concentration of HF-2022a.

Figure 28:
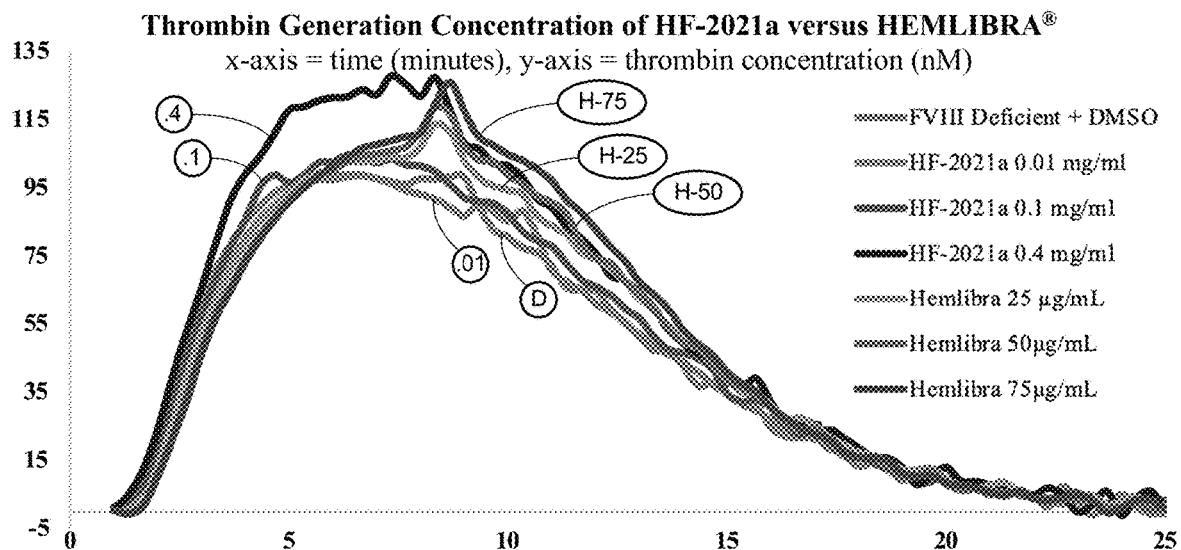
FIG. 28 illustrates a comparison between thrombin generation for various concentrations of candidate compound 1 (i.e., HF-2021a) and various physiological concentrations of HEMLIBRA® in accordance with various embodiments of the invention.
Figure 29:
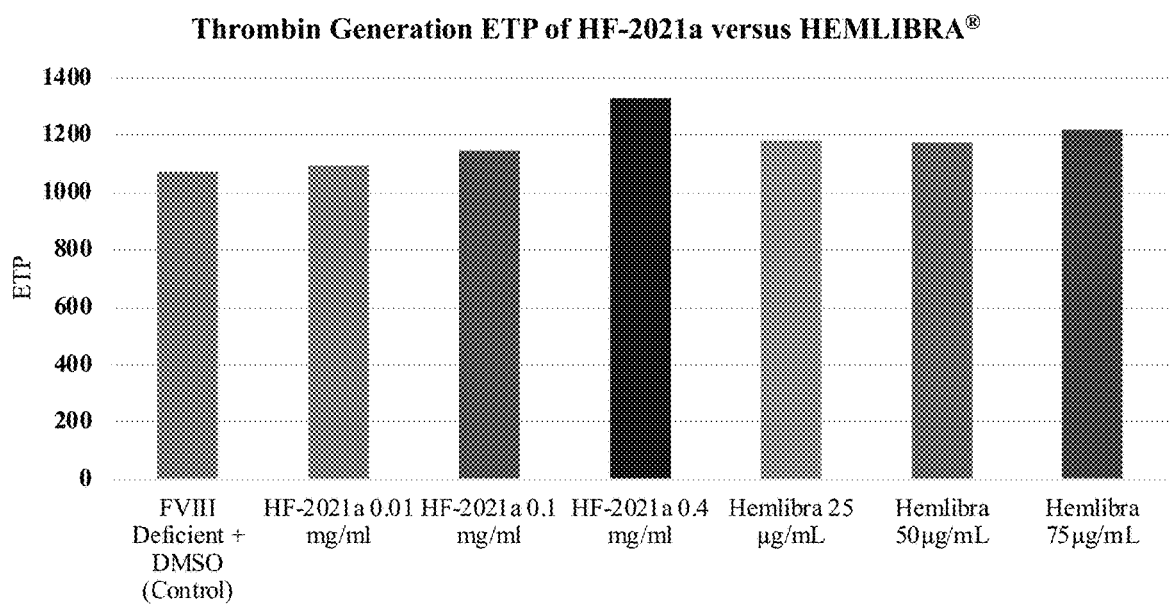
FIG. 29 illustrates a comparison between the thrombin generation ETP of candidate compound 1 (i.e., HF-2021a) and various physiological concentrations of HEMLIBRA® in accordance with various embodiments of the invention.

FIG. 28 illustrates a comparison between thrombin generation for various concentrations of candidate compound 1 (i.e., HF-2021a) and various concentrations of HEMLIBRA® and FIG. 29 illustrates the corresponding ETP data, in accordance with various embodiments of the invention. These comparisons suggest that the highest tested concentration of HF-2021a (i.e., 0.4 mg/ml) provides a slightly larger effect on thrombin concentration and ETP than the highest tested concentration of HEMLIBRA® (i.e., 75 µg/ml). These comparisons also suggest that the second highest tested concentration of HF-2021a (i.e., 0.1 mg/ml) provides comparable effects on thrombin concentration and ETP as any of the concentrations of HEMLIBRA®.

Figure 30:
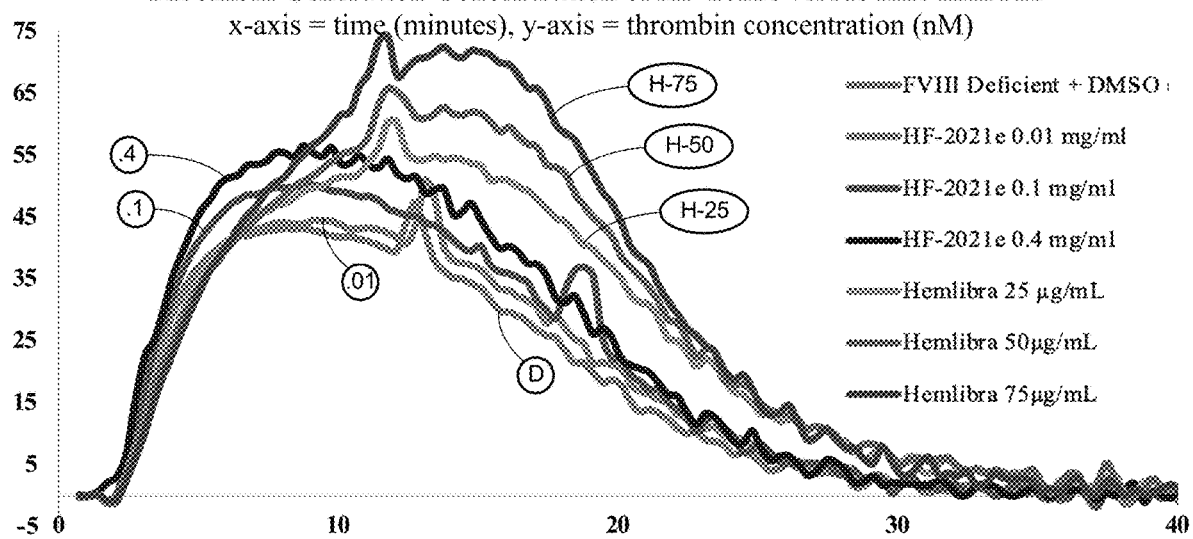
FIG. 30 illustrates a comparison between thrombin generation for various concentrations of candidate compound 5 (i.e., HF-2021e) and various physiological concentrations of HEMLIBRA® in accordance with various embodiments of the invention.
Figure 31:
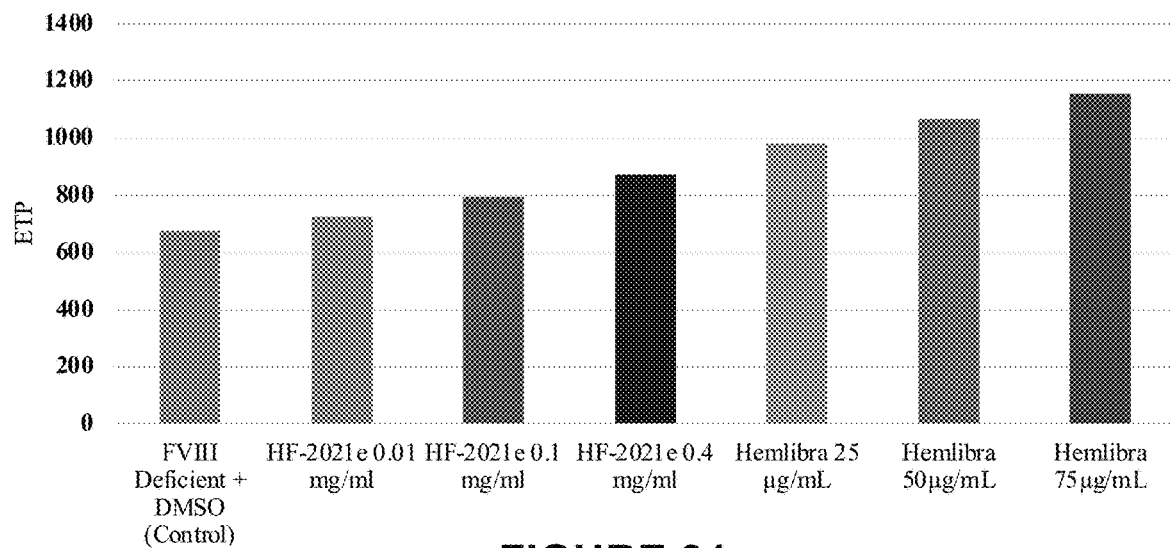
FIG. 31 illustrates a comparison between the thrombin generation ETP of candidate compound 5 (i.e., HF-2021e) and various physiological concentrations of HEMLIBRA® in accordance with various embodiments of the invention.

FIG. 30 illustrates a comparison between thrombin generation for various concentrations of candidate compound 5 (i.e., HF-2021e) and various concentrations of HEMLIBRA® and FIG. 31 illustrates the corresponding ETP data, in accordance with various embodiments of the invention. These comparisons suggest that the highest tested concentration of HF-2021e (i.e., 0.4 mg/ml) provides a slightly lower effect on thrombin concentration and ETP than the lowest tested concentration of HEMLIBRA® (i.e., 25 µg/ml).

Figure 32:
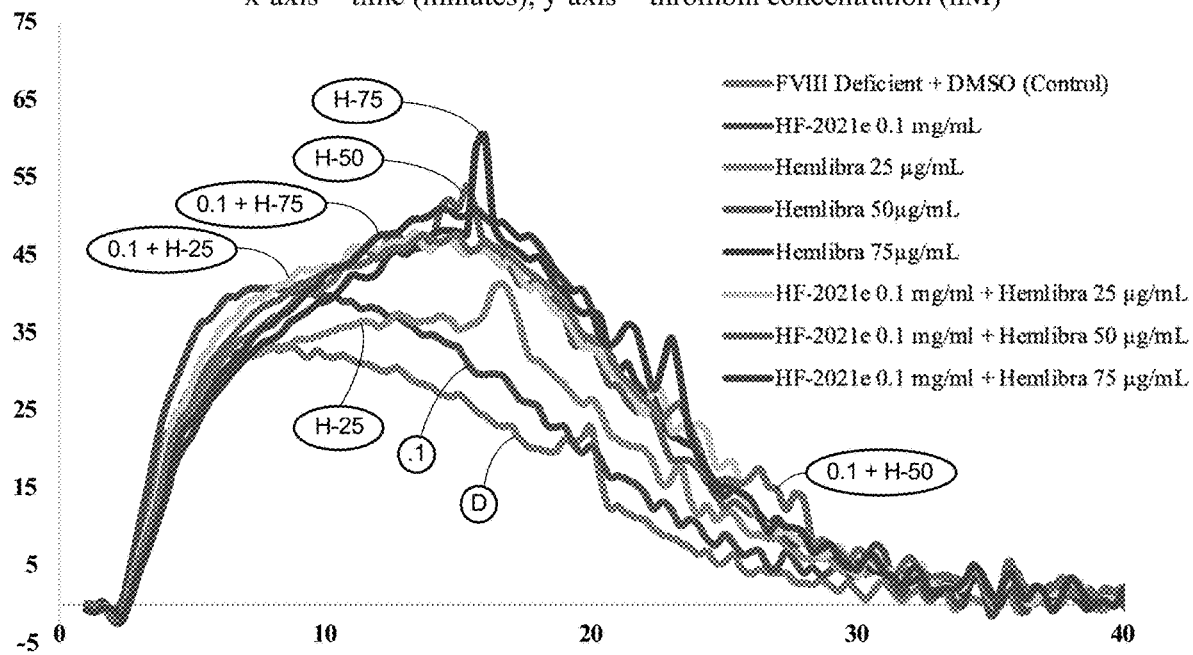
FIG. 32 illustrates a comparison between thrombin generation for candidate compound 5 (i.e., HF-2021e) combined with various physiological concentrations of HEMLIBRA® in accordance with various embodiments of the invention.
Figure 33:
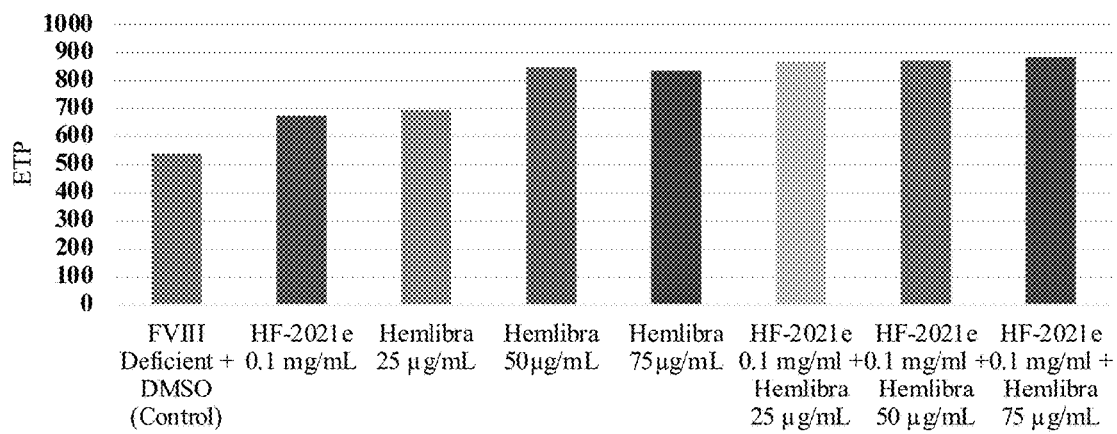
FIG. 33 illustrates a comparison between the thrombin generation ETP of candidate compound 5 (i.e., HF-2021e) combined with various physiological concentrations of HEMLIBRA® in accordance with various embodiments of the invention.

FIG. 32 illustrates a comparison between thrombin generation for candidate compound 5 (i.e., HF-2021e) combined with various concentrations of HEMLIBRA® and FIG. 33 illustrates the corresponding ETP data, in accordance with various embodiments of the invention. These comparisons suggest that the combined dosing of HF-2021e (0.1 mg/mL) with low (25 µg/ml), medium (50 µg/ml), and high (75 µg/ml) concentrations of HEMLIBRA® lead to greater thrombin concentrations and ETPs than any individual dosage of the two drugs by themselves. These comparisons also suggest that a dose of 0.1 mg/ml of HF-2021e and 25 µg/ml of HEMLIBRA® generates slightly more thrombin concentration and ETP than a dose of 75 µg/ml of HEMLIBRA®, suggesting that concurrent use of HF-2021e and HEMLIBRA® might cut the required dose of HEMLIBRA® by 67% while preserving roughly the same thrombin generation capability.

Figure 34:
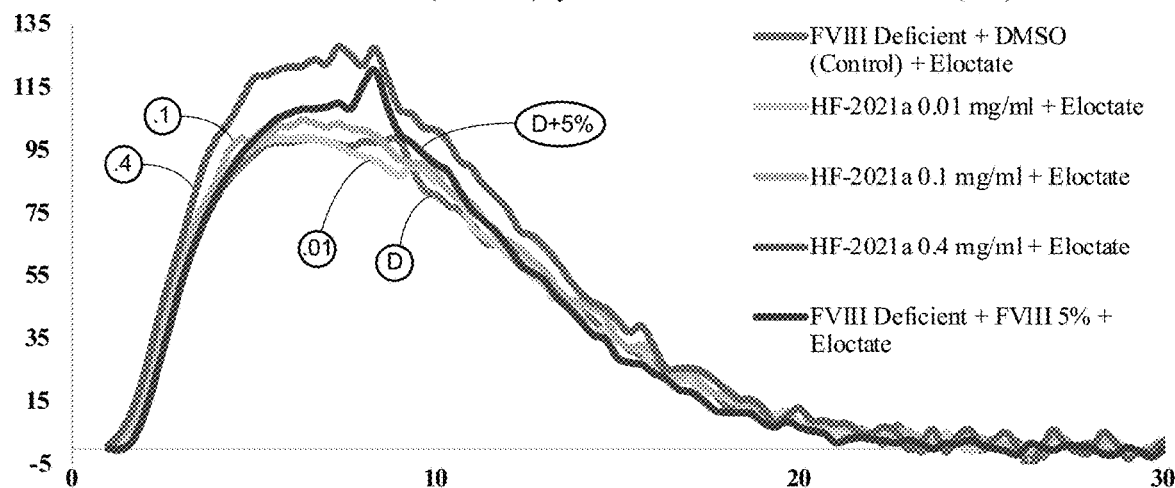
FIG. 34 illustrates thrombin generation for various concentrations of candidate compound 1 (i.e., HF-2021a) combined with a standard dose of efmoroctocog alfa (marketed as ELOCTATE®) in accordance with various embodiments of the invention.
Figure 35:
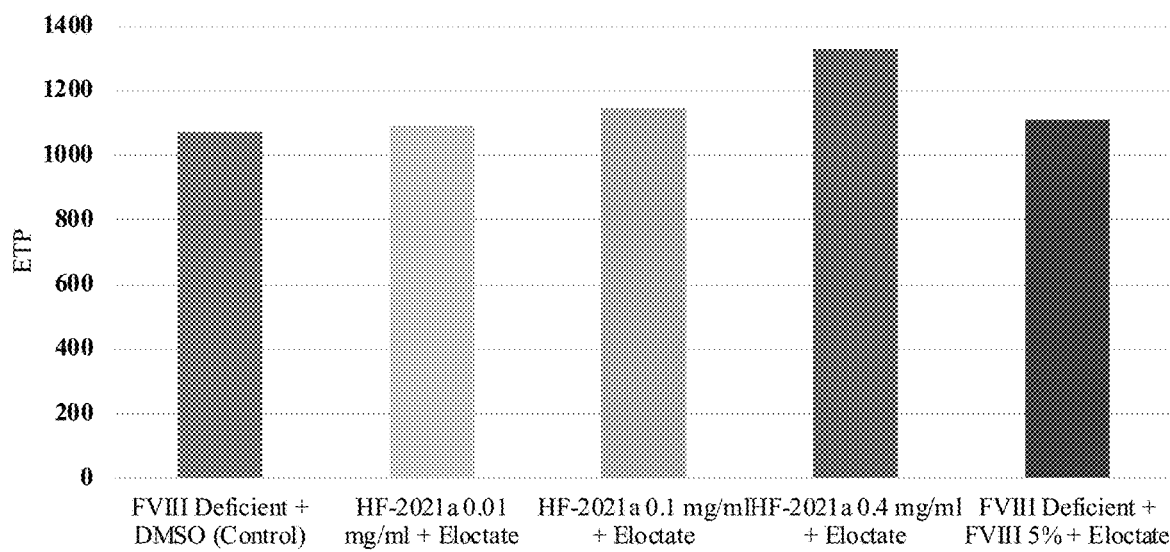
FIG. 35 illustrates the thrombin generation ETP of candidate compound 1 (i.e., HF-2021a) combined with a standard dose of ELOCTATE® in accordance with various embodiments of the invention.

FIG. 34 illustrates a comparison between thrombin generation for candidate compound 1 (i.e., HF-2021a) combined with various concentrations of ELOCTATE® (Efmoroctocog alfa) and FIG. 35 illustrates the corresponding ETP data, in accordance with various embodiments of the invention. For this data, ELOCTATE® was taken by the patient prior to collecting the plasma from the patient. These comparisons suggest that dosing of HF-2021a at all tested concentrations combined with existing ELOCTATE® in the sample lead to greater thrombin concentrations and ETPs than ELOCTATE® by itself.

FIGS. 32-35 indicate that chalcones including, but not limited to, the candidate compound (i.e., HF-2021a, HF-2021e, etc.) provided increased thrombin generation and ETP in the presence of either HEMLIBRA® or ELOCTATE® than these individual drugs alone. This suggests that chalcones, including the candidate compound, may be used as part of a combined therapy with other existing hemophilia drugs. This also suggests that chalcones, including the candidate compound, may act synergistically with other existing hemophilia drugs. This also suggests that chalcones, including the candidate compounds, may significantly reduce the required dosage of other existing hemophilia drugs while achieving similar thrombin generation effects.

While the invention has been described herein in terms of various implementations, it is not so limited and is limited only by the scope of the following claims, as would be apparent to one skilled in the art. These and other implementations of the invention will become apparent upon consideration of the description provided above and the accompanying figures. In addition, various components and features described with respect to one implementation of the invention may be used in other implementations as would be appreciated.

What is claimed:

1. A method for treating hemophilia or Willebrand disease comprising administering a therapeutically effective amount of a composition comprising a chalcone to a subject in need thereof, wherein the chalcone is selected from the group consisting of 1-(6-hydroxy-2,3,4-trimethoxyphenyl)-3-(4-hydroxy-phenyl)prop-2-en-1-one, 1-(2-hydroxy-4,6-dimethoxyphenyl)-3-(4-methoxyphenyl)prop-2-en-1-one, (E)-1-(2,4-dihydroxyphenyl)-3-(4-hydroxyphenyl)prop-2-en-1-one, (E)-3-(3-hydroxy-4-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one, 2-[5-(3-methylbut-2-enoxy)-2-[(E)-3-[4-(3-methylbut-2-enoxy)phenyl]prop-2-enoyl]phenoxy]acetic acid, 4-methoxyphenyl-3-(2,4-dimethoxyphenyl)-1-oxo-2-propene, (E)-3-(4-hydroxyphenyl)-1-(2,4,6-trihydroxyphenyl)prop-2-en-1-one, and 3-(1,3-benzodioxol-5-yl)-1-phenyl-2-propen-1-one.

2. The method of claim 1, wherein administering the therapeutically effective amount of the composition comprises prophylactically administering the therapeutically effective amount of the composition.

3. The method of claim 1, wherein the administering a composition comprising a chalcone comprises administering the chalcone to increase thrombin generation.

4. The method of claim 1, wherein the administering a composition comprising a chalcone comprises administering the chalcone to enhance clotting.

5. The method of claim 1, wherein blood of the subject comprises anti-clotting agents.

6. The method of claim 1, wherein the administering a composition comprising a chalcone comprises administering the chalcone to accelerate clotting.

7. A method for treating hemophilia or Willebrand disease comprising administering a therapeutically effective amount of a composition comprising a chalcone to a subject in need thereof, wherein the blood of the subject is factor deficient blood, wherein the chalcone is selected from the group consisting of 1-(6-hydroxy-2,3,4-trimethoxyphenyl)-3-(4-hydroxy-phenyl)prop-2-en-1-one, 1-(2-hydroxy-4,6-dimethoxyphenyl)-3-(4-methoxyphenyl)prop-2-en-1-one, (E)-1-(2,4-dihydroxyphenyl)-3-(4-hydroxyphenyl)prop-2-en-1-one, (E)-3-(3-hydroxy-4-methoxyphenyl)-1-[2-hydroxy-6-methoxy-4-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxyphenyl]prop-2-en-1-one, 2-[5-(3-methylbut-2-enoxy)-2-[(E)-3-[4-(3-methylbut-2-enoxy)phenyl]prop-2-enoyl]phenoxy]acetic acid, 4-methoxyphenyl-3-(2,4-dimethoxyphenyl)-1-oxo-2-propene, (E)-3-(4-hydroxyphenyl)-1-(2,4,6-trihydroxyphenyl)prop-2-en-1-one, and 3-(1,3-benzodioxol-5-yl)-1-phenyl-2-propen-1-one.

8. The method of claim 7, wherein administering the therapeutically effective amount of the composition comprises prophylactically administering the therapeutically effective amount of the chalcone composition.

9. The method of claim 7, wherein the administering a composition comprising a chalcone comprises administering the chalcone to increase thrombin generation.

10. The method of claim 7, wherein the administering a composition comprising a chalcone comprises administering the chalcone to accelerate clotting.

11. The method of claim 7, wherein blood of the subject comprises anti-clotting agents.

* * * * *